US012708628B2

(12) United States Patent
Feinberg

(10) Patent No.: US 12,708,628 B2
(45) **Date of Patent: *Aug. 18, 2026**

(54) COMPOSITIONS AND METHODS FOR THE TREATMENT OF MOTION SICKNESS AND EMESIS

(71) Applicant: Repurposed Therapeutics, Inc., St. Louis, MO (US)

(72) Inventor: Barry I. Feinberg, St. Louis, MO (US)

(73) Assignee: Repurposed Therapeutics, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/377,510

(22) Filed: Oct. 6, 2023

(65) Prior Publication Data

US 2025/0057854 A1 Feb. 20, 2025

Related U.S. Application Data

(63) Continuation of application No. 18/230,236, filed on Aug. 4, 2023.

(51) Int. Cl.

| | |
|---|---|
| ***A61K 31/5386*** | (2006.01) |
| ***A61K 9/00*** | (2006.01) |
| ***A61K 9/06*** | (2006.01) |
| ***A61K 47/02*** | (2006.01) |
| ***A61K 47/10*** | (2017.01) |
| ***A61K 47/12*** | (2006.01) |
| ***A61K 47/18*** | (2017.01) |
| ***A61K 47/32*** | (2006.01) |

(Continued)

(52) U.S. Cl.
CPC ........ *A61K 31/5386* (2013.01); *A61K 9/0043* (2013.01); *A61K 9/06* (2013.01); *A61K 47/02* (2013.01); *A61K 47/10* (2013.01); *A61K 47/12* (2013.01); *A61K 47/186* (2013.01); *A61K 47/32* (2013.01); *A61P 1/08* (2018.01); *A61P 39/00* (2018.01)

(58) Field of Classification Search
CPC .......... A61K 31/5386; A61K 9/06; A61P 1/08
See application file for complete search history.

(56) References Cited

U.S. PATENT DOCUMENTS

2006/0193784 A1 8/2006 Crooks et al.
2010/0114309 A1 5/2010 de Juan, Jr. et al.
(Continued)

FOREIGN PATENT DOCUMENTS

WO 99/12544 A2 3/1999
WO WO-9912544 A1 * 3/1999 ............. A61K 31/46
WO 2020/123057 A2 6/2020

OTHER PUBLICATIONS

Chemical Store—Polyvinyl Alcohol from https://chemicalstore.com/polyvinyl-alcohol/ (Year: 2020).*
(Continued)

*Primary Examiner* — San Min R Hui
(74) *Attorney, Agent, or Firm* — Venable LLP

(57) ABSTRACT

The present disclosure comprises compositions and methods for the treatment, including one or more of prevention and rescue therapy, of subjects at risk for or suffering from motion sickness, which may include nausea or vomiting/emesis associated with motion. In particular, compositions and methods for nasal administration of scopolamine are provided.

24 Claims, 93 Drawing Sheets

(51) Int. Cl.
*A61P 1/08* (2006.01)
*A61P 39/00* (2006.01)

(56) References Cited

U.S. PATENT DOCUMENTS

2013/0289019 A1 10/2013 Chau
2022/0000881 A1 1/2022 Helton

OTHER PUBLICATIONS

Ahmed, S., et al., Effects of pH and Dose on Nasal Adsorption of Scopolamine Hydrobromide in Human Subjects, Pharmaceutical Research , 2000, 974-977, vol. 17, No. 8.
Akerstedt et al., Subjective and Objective Sleepiness in the Active ildividual, International Journal of Neuroscience, 1990, 29-37, vol. 52.
Allen, L., Scopolamine Hydrobromide 0.25% Ophthalmic Solution IJPC, 2016, 20(4) 326.
Awasthi et al., Space Motion Sickness, An Overview, Ind J. Aerospace Med, 2012, 44-49, 56(2).
Bhargavi, R., et al., Formulation and Evaluation of Scopolamine Nasal In-Situ Gel, Inventi Rapid: NDDS vol. 2015, Issue 2.
Buckey et al., InIntranasal Scopolamine for Motion Sickness. Aviation, Space, and Environmental Medicine,, 2008, 79, 306.
Cao, S-L, et al., Preparation of ion-activated in situ gel systems of scopolamine hydrobromide and evaluation of its antimotion sickness efficacy, Acta Pharmacol. Sin., 28(4):584-590 (2007).
Cheung et al., Various Anti-Motion Sickness Drugs and Core Body Temperature Changes. Aviation, Space, and Environmental Medicine, 2011, 409-415., vol. 82, No. 4.
Chinn, H.I., et al., Prevention and treatment of motion sickness by intranasal medication, Proc. Soc. Exp. Biol. Med., 90(3):666-669 (1955).
Chinn et al., Comparison of Various Drugs Against Airsickness, Journal of Applied Physiology, 1953, 257-259, vol. 6.
Geyer, D.J., et al., The Pharmacokinetics and Efficacy of a Low-Dose, Aqueous, Intranasal Scopolamine Spray, NAMRU-D Report No. 17-104, 2017.
Gibaldi et al., Pharmacokinetics, 1982, 2nd ed. New York: Marcel Dekker.
Gianaros, P.J., et al., A Questionnaire for the Assessment of the Multiple Dimensions of Motion Sickness, Aviat. Space Environ. Med., 2001, 115-119, 72(2).
Gil et al., Scopolamine Patch to Prevent Seasickness: Clinical Response vs. Plasma Concentration in Sailors, Aviation, Space, and Environmental Medicine, 2005, 766-770, 76(8).
GLAXOSMITHKLINEI plc. (Mar. 26, 2013). Transderm Scōp® [package insert]. Parsippany, NJ: GlaxoSmithKline plc. Retrieved from https://dailymed.nlm.nih.gov/dailymed/fda/fdaDrugXsl.cfm?setid=f6fdc88b-ea00-4694-8f21-b8d15dbb339e&type=display.
Golding, J. G. et al., Motion Sickness Susceptibility Fluctuates Through Menstrual Cycle. Aviation, Space, and Environmental Medicine, 2005, 76, 970-973.
Golding, J. F. et al., A motion sickness maximum Around the 0.2 Hz Frequency Range of Horizontal Translational Oscillation. Aviation, Space, and Environmental Medicine, 2001, 72, 188-192.
Golding, J.F., Motion sickness susceptibility questionnaire revised and its relationship to other forms of sickness. Brain Res Bull., 1998. 507-516, 47(5).
Hutchins et al., Clinical Problems in Aviation Medicine Relationship Between Past History of Motion Sickness and Attrition from Flight Training. Aerospace Medicine, 1965, 36, 984-987.
Hyde, R.W., et al., Absorption from nasal mucous membrane, Ann. Otol. Rhinol. Laryngol., 62(4):957-968 (1953).
Kaida et al., Validation of the Karolinska Sleepiness Scale Against Performance and EEG Variables. Clinical Neurophysiology, 2006, 117, 1574-1581, 117.
Kane et al., Identifying and Monitoring Cognitive Deficits in Clinical Populations using Automated Neuropsychological Assessment Metrics (ANAM) Tests. Archives of Clinical Neuropsychology, 2007, S115-S126, 22 Suppl 1.
Klocker et al., Scopolamine Nasal Spray in Motion Sickness: a Randomised, Controlled, and Crossover Study for the Comparison of Two Scopolamine Nasal Sprays With Oral Dimenhydrinate and Placebo. European Journal of Pharmaceutical Sciences, 2001, 227-232, 13.
Lackner, J.R., Motion sickness: more than nausea and vomiting, Exp. Brain Res., 2014, 2493-2510, 232.
Lewandowski et al., A Neuropsychologic-Pharmacodynamic Paradigm for Demonstrating Cognitive Enhancement and Suppression in the Elderly, Archives of Internal Medicine, 1995, 157, 2350-2356.
Matsangas, P., et al., The Effect of Mild Motion Sickness and Sopite Syndrome on Multitasking Cognitive Performance, Human Factors, 2014, 1124-1135, vol. 56, No. 6.
Miller et al., A Provocative Test for Grading Susceptibility to Motion Sickness Yielding a Single Numerical Scale. Acta Otolaryngolica, 1970, 274 Suppl.
Nachum et al., Scopolamine Bioavailability in Combined Oral and Transdermal Delivery. The Journal of Pharmacology and Experimental Therapeutics, 2001, 121-123, 296(1).
Nachum et al., Transdermal Scopolamine For Prevention of Motion Sickness. Clinical Pharmacokinetics and Therapeutic Applications, 2006, 543-566, 45(6).
Parrott, A. C.. Transdermal Scopolamine: a Review of Its Effects Upon Motion Sickness, Psychological Performance, and Physiological Functioning. Aviation, Space, and Environmental Medicine, 1989, 1-9. vol. 60, No. 1.
Putcha et al., Pharmacokinetics and Oral Bioavailability of Scopolamine in Normal Subjects. Pharmaceutical Research, 1989, 481-485, vol. 6, No. 4.
Putcha et al., Bioavailability of Intranasal Scopolamine in Normal Subjects. Journal of Pharmaceutical Sciences, 1996, 899-902, vol. 85, No. 8.
Putcha, L., et al., Pharmacokinetics of Scopolamine Intranasal Gel Formulation (Inscop) During Antiorthostatic Bedrest, NASA Technical Reports Server (2013)(available at https://ntrs.nasa.gov/api/citations/20110011043/downloads/20110011043.pdf).
Putheti, R., et al., Nasal Drug delivery in Pharmaceutical and biotechnology: present and future, e-JST, (2009)—available at https://www.researchgate.net/publication/228559889_Nasal_Drug_delivery_in_Pharmaceutical_and_biotechnology_Present_and_future.
Renner et al., Pharmacokinetics and Pharmacodynamics in Clinical Use of Scopolamine. Therapeutic Drug Monitoring, 2005, 655-665, vol. 27, No. 5.
Russomano, T., et al., Space motion sickness: A common neurovestibular dysfunction in microgravity, Neurology India, 2019, 214-218, vol. 67, Issue 8.
Shoblock, J., et al., Pharmacokinetic Studies of Scopolamine in Human and Rodent for the Establishment of PK-PD Models, Poster, Neuropharmacol. 43:S476-S652, Abst. W113, p. S547 (2017).
Short et al., Initial Construct Validation of frequently Employed ANAM Measures Through Structural Equation Modeling. Archives of Clinical Neuropsychology, 2007, S63-S77, 22(51).
Simmons, R.G., et al., Comparison of oral scopolamine, intranasal scopolamine, and dextroamphetamine as motion sickness countermeasures for young healthy aviation candidates, Aviat. Space, and Environ. Med., 78(3):297—(2007).
Simmons, R.G., et al., A comparison of intranasal and oral scopolamine for motion sickness prevention in military personnel, Namrl Technical Report 08-10 (2008).
Simmons, R.G., et al., Efficacy of intranasal scopolamine gel for motion sickness treatment in aviation candidates, NAMRL Technical Report 09-17 (2009).
Simmons, R.G., et al., The Efficacy of Low-Dose Intranasal Scopolamine for Motion Sickness, Aviation, Space, and Enviromental Med., 81(4):405-412 (2010).
Sprinks et al., Scopolamine (hyoscine) for Preventing and Treating Motion Sickness (Review). Cochrane Database Syst Rev, 2011, 6(10).

(56) References Cited

OTHER PUBLICATIONS

Stankovic, A.S., et al., Intranasal Scopolamine for Motion Sickness, Aerosp. Med. Hum. Perform., 2019, 917-924, vol. 90, No. 11.
Thorne, Throughput: a Simple Performance Index with Desirable Characteristics, Behavior Research Methods, 2006, 569-573, 38(4).
Tonndorf, J., et al., Absorption from nasal mucous membrane: systemic effect of hyoscine following intranasal administration, Ann. Otol. Rhinol. Laryngol., 1953, 630-641, 62(3).
Vaksman, et al., Effect of intranasal scopolamine on reaction time and working memory, Aviat. Space Environ. Med., 79(3):313 (2008).
Weerts, A.P., et al., Intranasal scopolamine affects the semicircular canals centrally and peripherally, J. Appl. Physiol., 2015, 213-218, 119.
Weerts, A.P., et al., Restricted sedation and absence of cognitive impairments after administration of intranasal scopolamine, J. Psychopharmacol., 29(12):1231-1235 (2015).
Wei, Y., et al., Microdialysis pharmacokinetic study of scopolamine in plasma, olfactory bulb and vestibule after Intranasal administration, Drug Deliv., 2016, 263-268, 23(1).
Wood et al., Evaluation of 16 Anti-Motion Sickness Drugs Under Controlled Laboratory Conditions. Aerospace Medicine, 1968, 39, 1341-1344.
Wu, L., Doctoral Dissertation entitled “Clinical Pharmacokinetics of Intranasal Scopolamine for Space Motion Sickness,” College of Pharmacy, University of Houston 2014.
Wu, L, et al., Dose Escalation Pharmacokinetics of Intranasal Scopolamine Gel Formulation, J. Clin. Pharmacol., 2015, 195-203., 55(2).
Scopolamie Hydrobromide, CAS#114-49-8, https://www.biocrick.com/Scopolamine-hydrobromide-BCN1199.html, Jun. 18, 2020.
Marx et al., Multiple (serial) poisoning with scopolamine present in a compounded nose drop preparation, Ceskoslovenska Pediatrie, Abstract, Sep. 1, 1992, 553-555, 47(9).
Treatment of nasal formulations with motion sickness containing scopolamine, Sep. 11, 1998.
Yu-Yun, Tong Laboratory investigation of Scopolaine Hydrobromide Nasal Spray, Jan. 1, 2004, Strait Pharmaceutical Journal.
Hyoscine, EC No. 200-090, CAS No. 51-34-3,.
Nasal in-situ gel of scopolamine with phase change property, Abstract, Feb. 27, 2006.
Li et al., Analysis on brain targeting of scopolamine following intranasal administration by using solid phase extraction and LC/MS assay, Western Pacific Region Index Medicus, Chongqing Medicine , Abstract, 2013;(36):4405-4407.
Intranasal scopolamine hydrobromide: pH affects absorption, Inpharma 1260—Oct. 21, 2000.
Intranasal Scopolamine—INSCOP, This drug, in intranasal form, is an effective treatment for motion sickness., Medical/TB/Topics/Health Medicine-Biotechnology, Jul. 1, 2015.
DPI 386 Nasal Gel for the Prevention of Nausea Associated With Motion Sicknes, Trial Identifier—NCT04219982, DPI-386-07, Jun. 2018-Jan. 2019.
Randomized, Double-Blind, Placebo-Controlled Phase 3 Study of the Safety and Efficacy of Defender Pharmaceuticals Inc, (DPI)-386 Nasal Gel on Ocean-Going Vessels for the Prevention and Treatment of Nausea Associated With Motion Sickness, aval Aeromedical Research Unit, Dayton.
Golding Predicting Individual Differences in Motion Sickness Susceptibility by Questionnare, Personality and Individual Differences, vol. 41, Issue 2, Jul. 2006, pp. 237-246,.
Graybiel et al., Sopite Syndrome: a sometimes sole manifestation of motion sickness. Aviat. Space Environ Med. 1976; Abstract, 47(8): 873-882.
Keshavarz et al., Motion Sickness: current concepts and management. Current Opinion in Neurology, 2022; Abstract, 35 Issue (1):107-112.
Gresty et al., Impact of Vertigo and Spatial disorientation on concurrent cognitive tasks. Ann NY Acad Sci 2009:1164: 263-267, Abstract.
https://go.drugbank.com/drugs/DB00747.
https://www.renpharm.com/nasal-spray-development/ 2002.

* cited by examiner

FIG. 3C - alertness
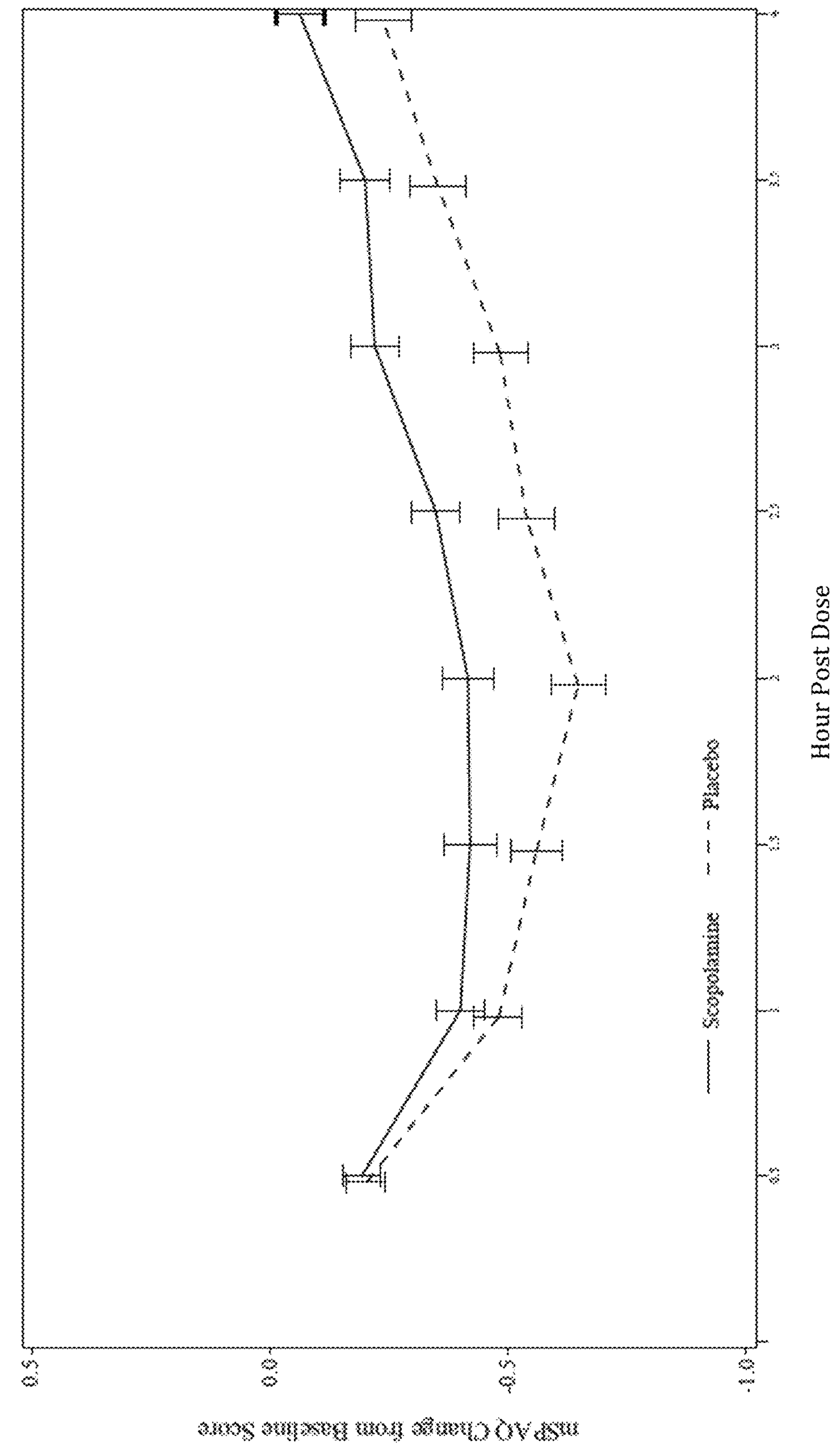

FIG. 3D - balance
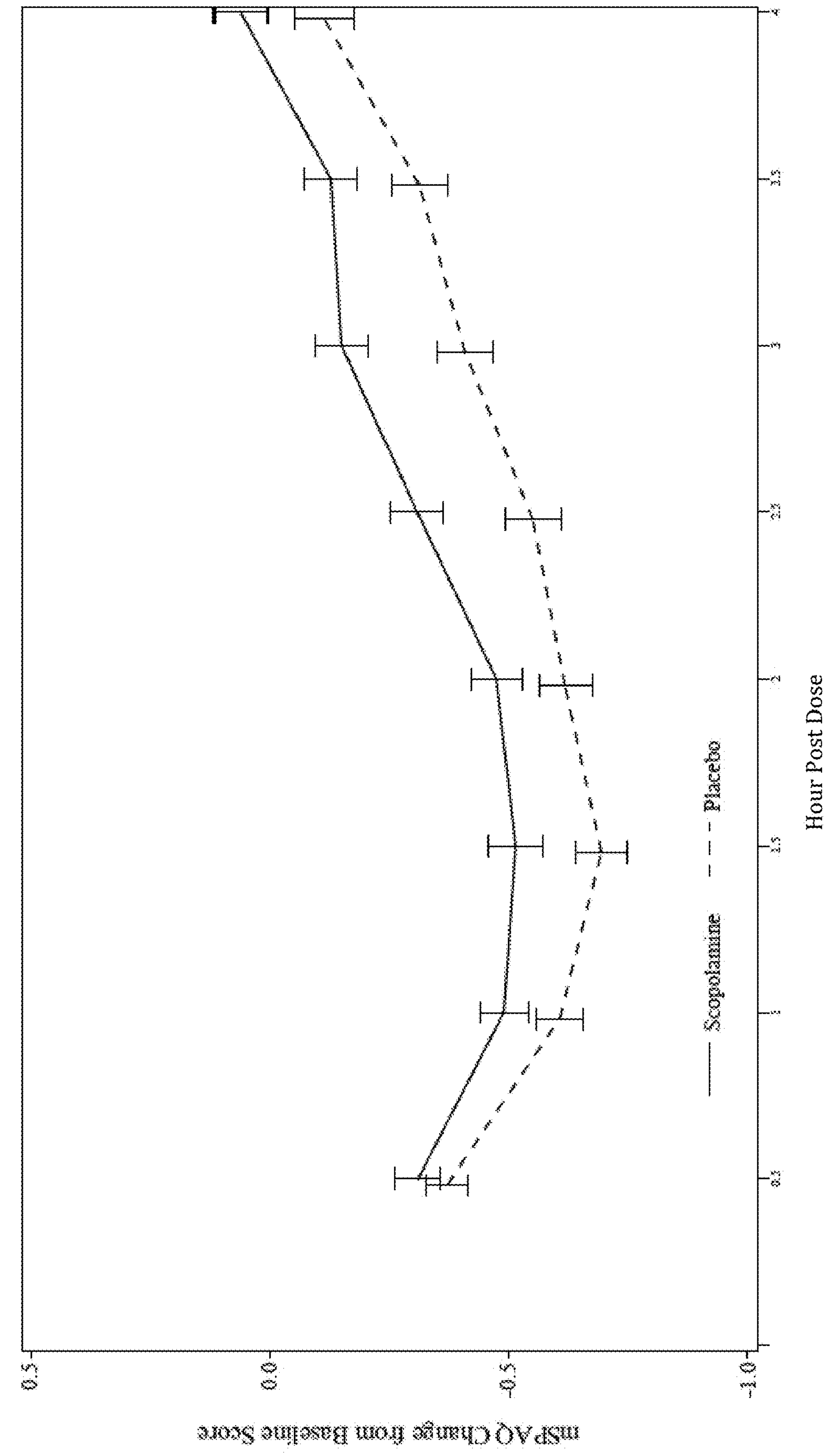

FIG. 3E - concentration
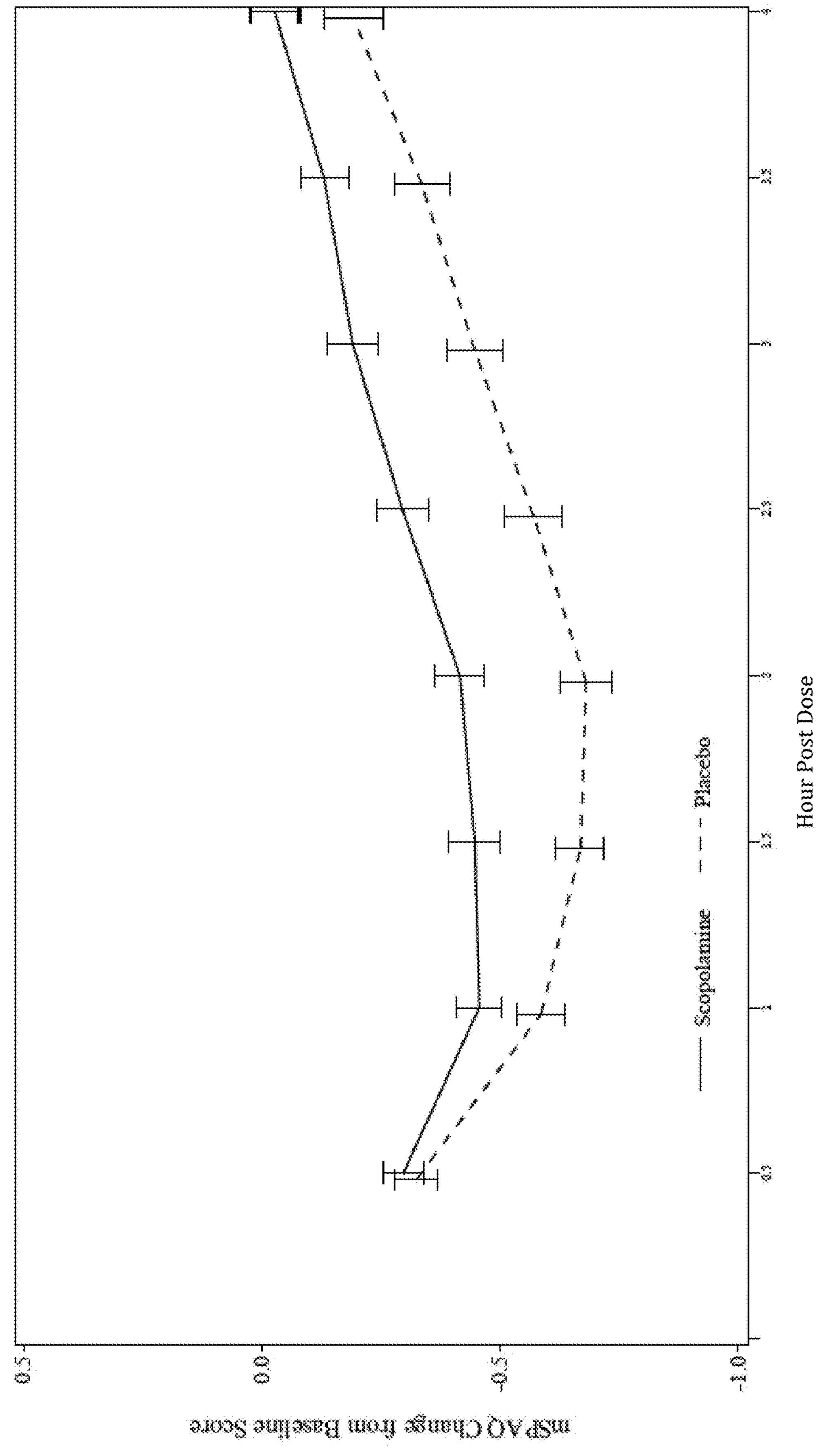

FIG. 3F – hand-eye coordination
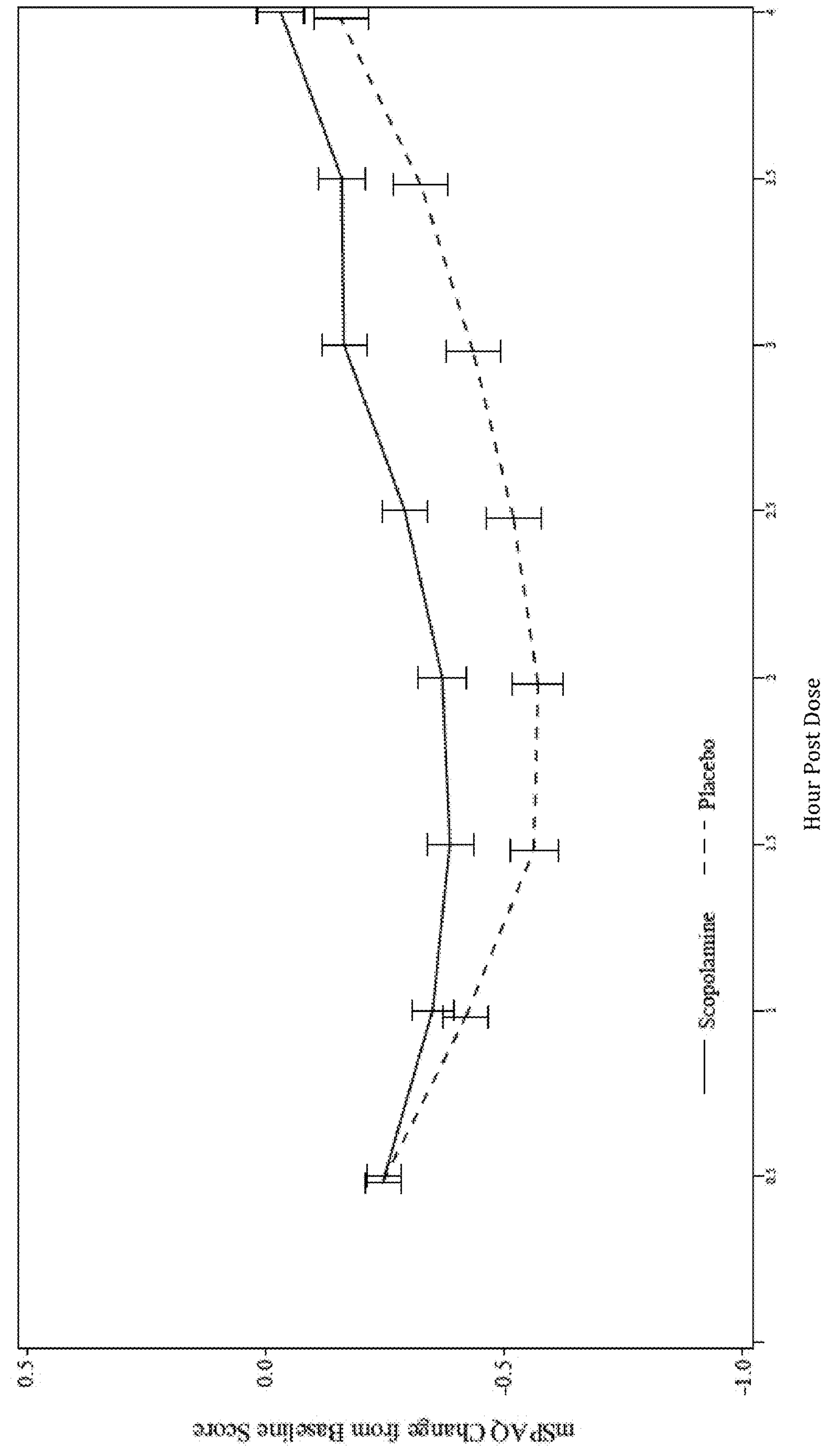

FIG. 3G - mood
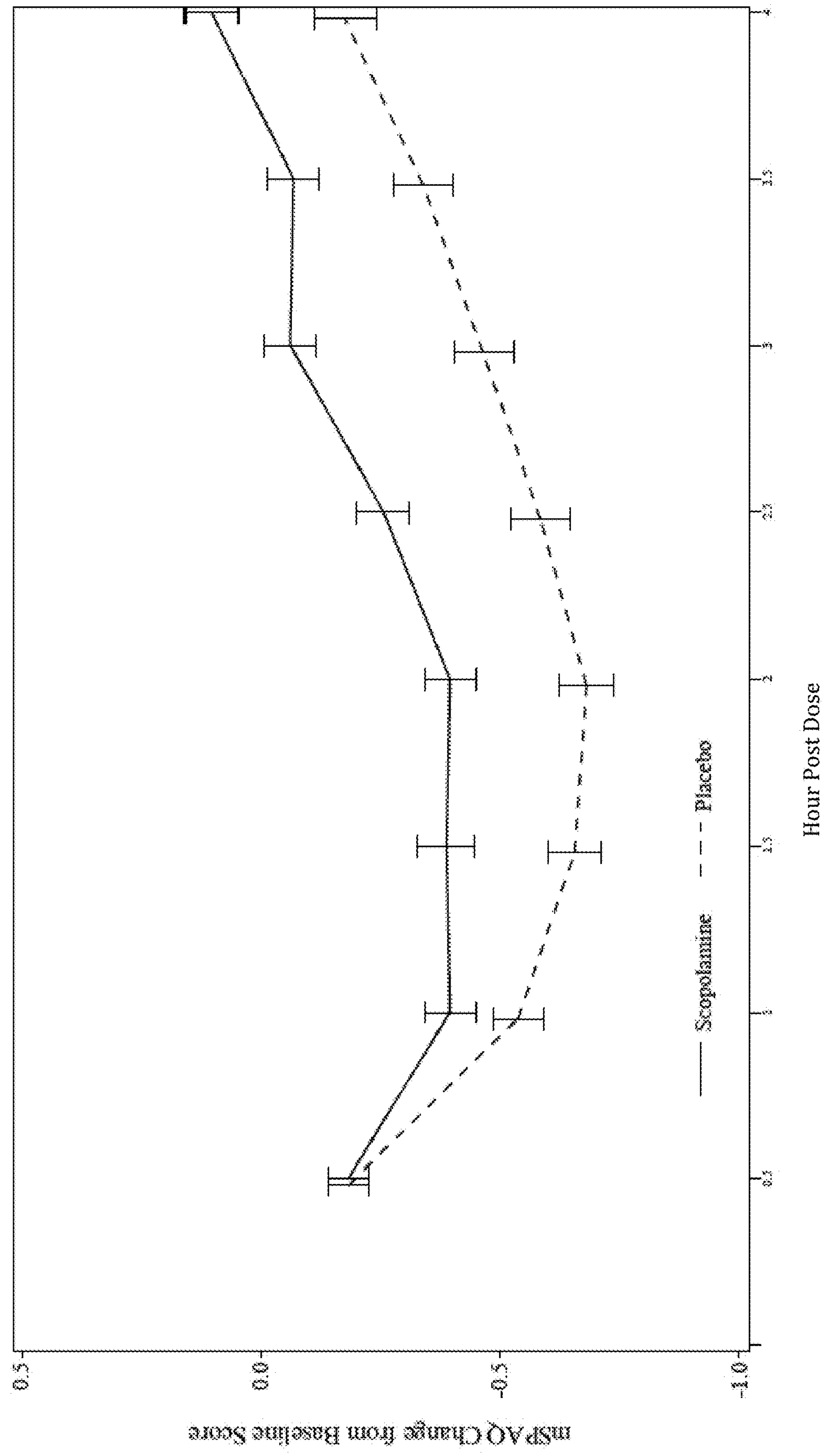

FIG. 3H – reaction time
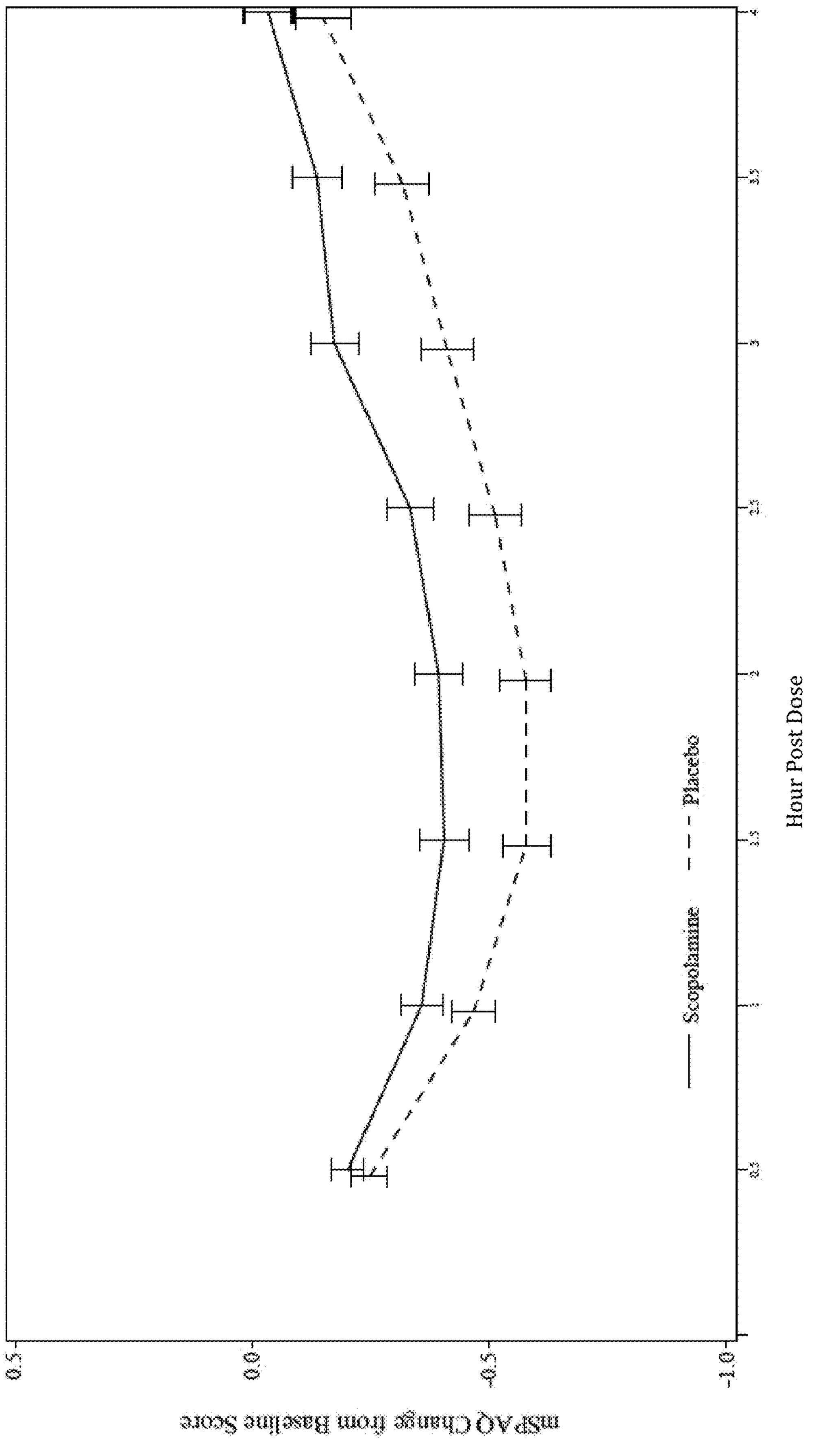

FIG. 3I – overall performance
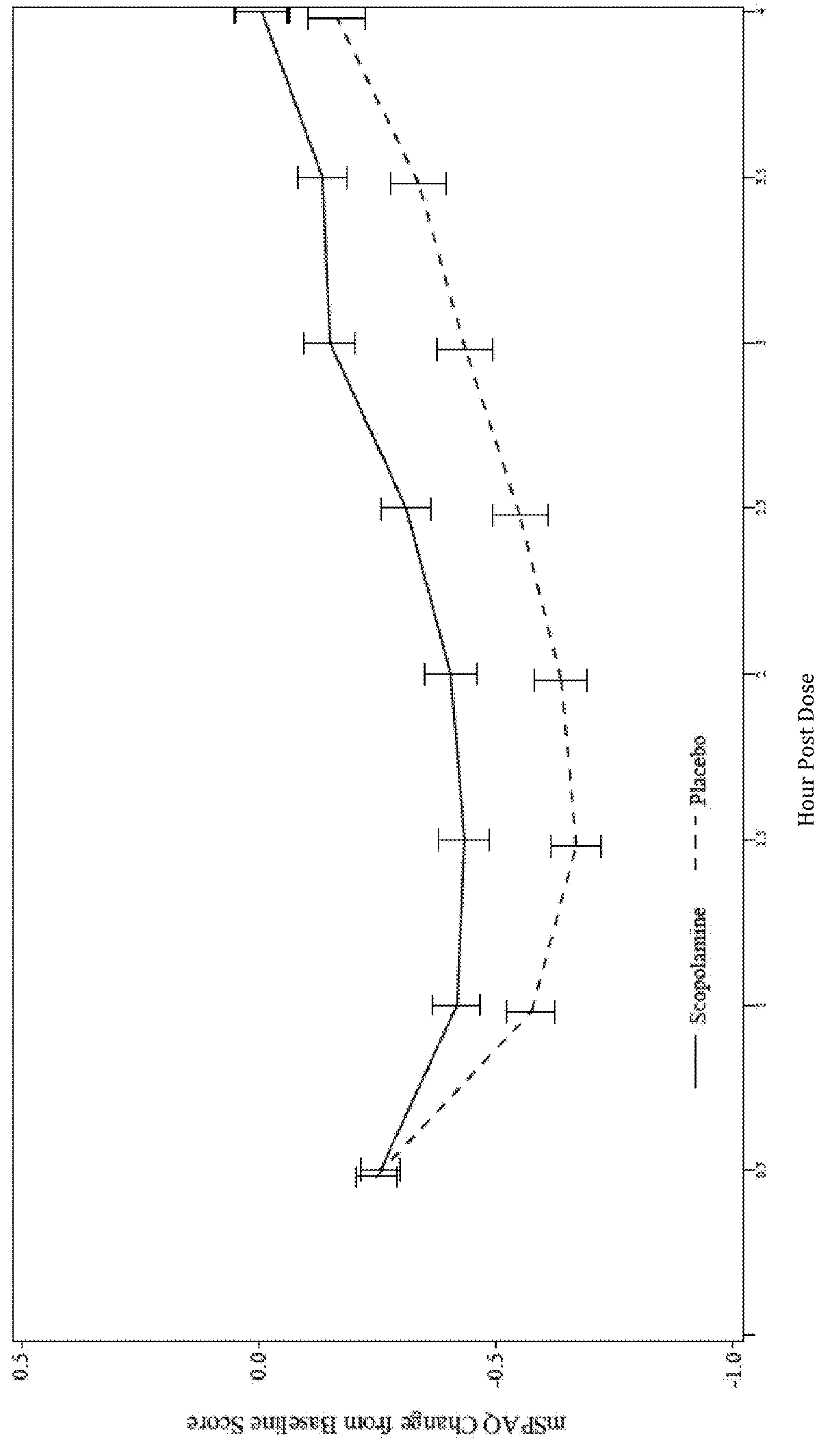

FIG. 3J - memory
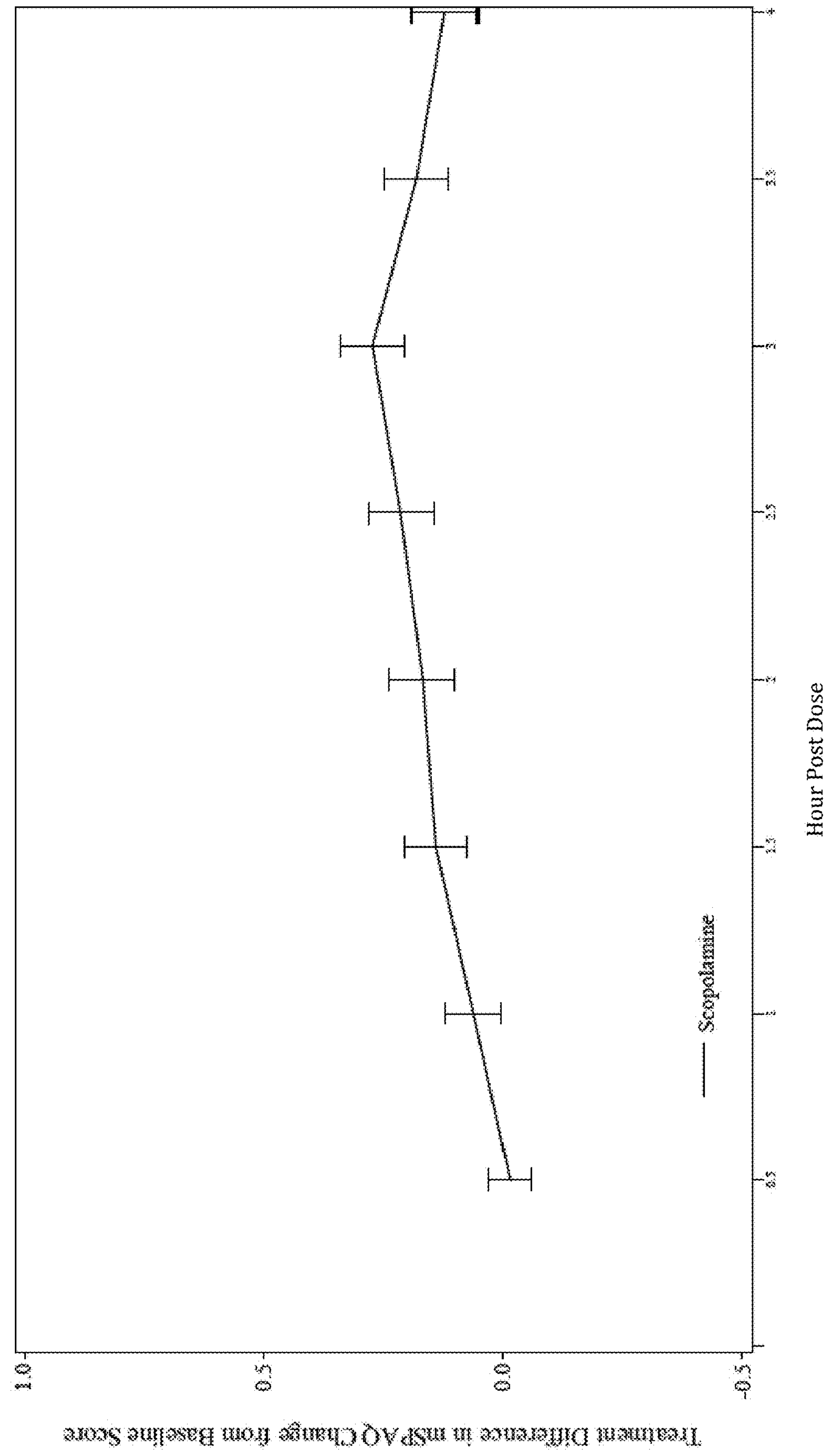

FIG. 3K - alertness
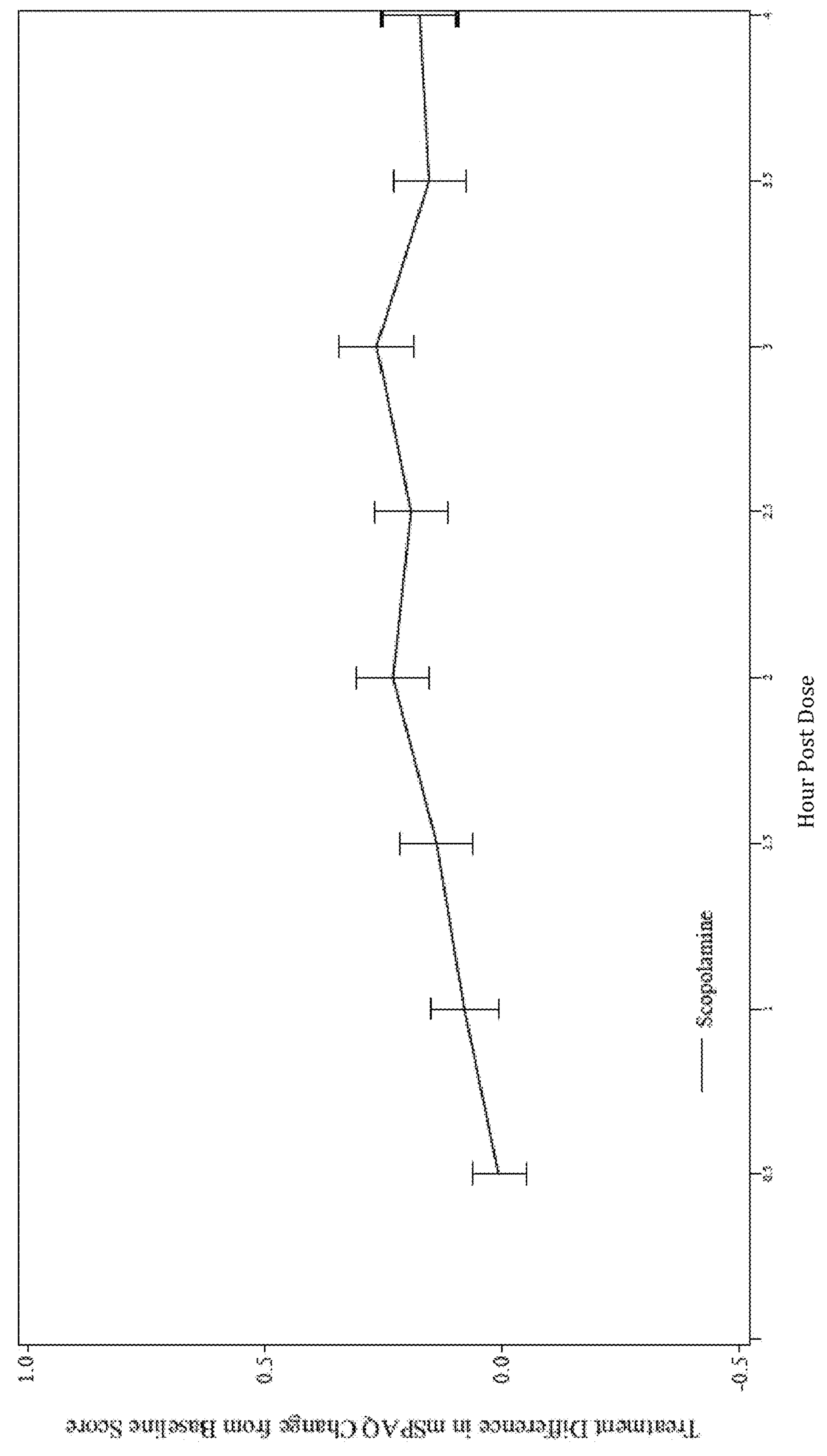

FIG. 3L - balance
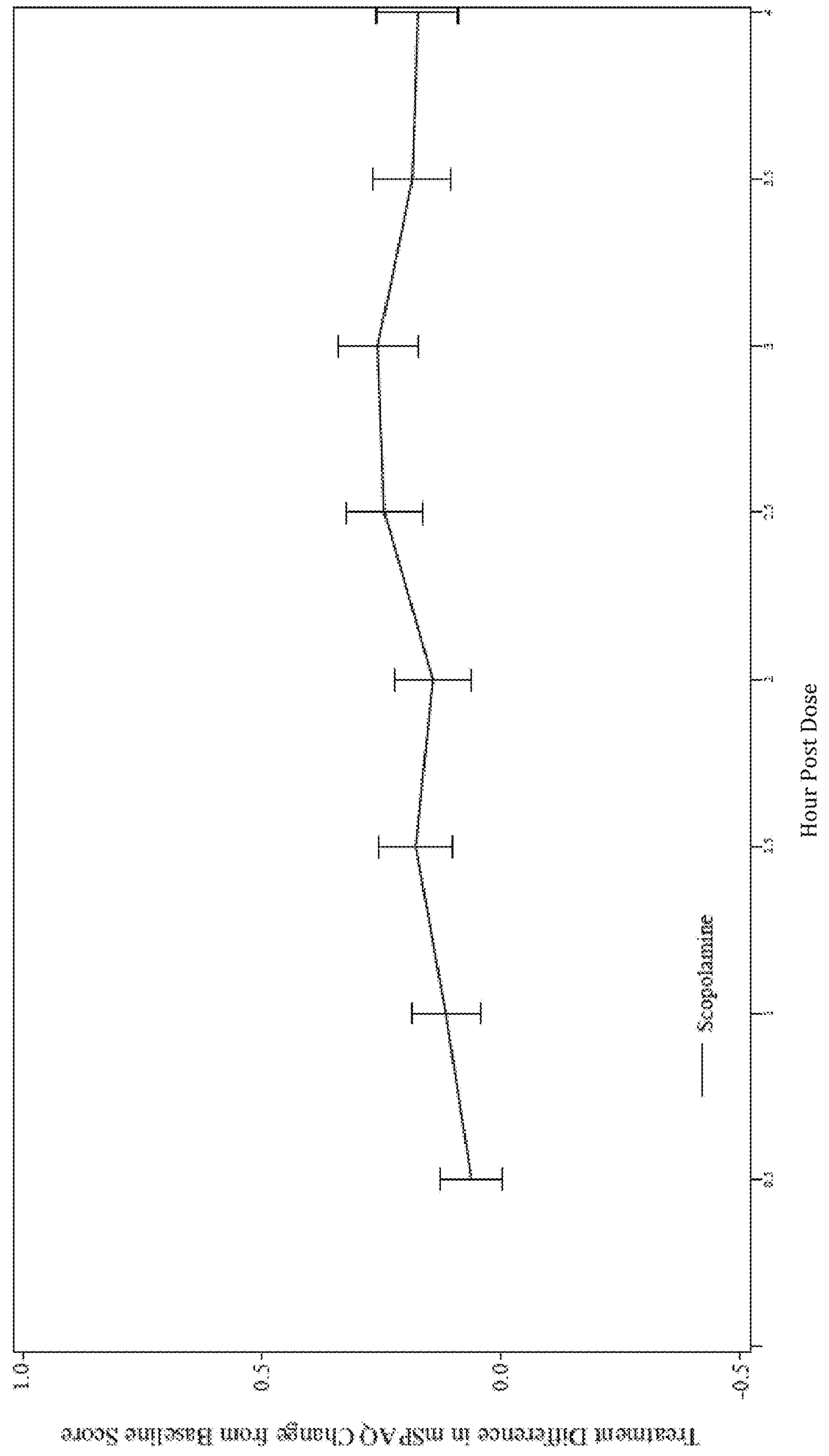

FIG. 3M - concentration
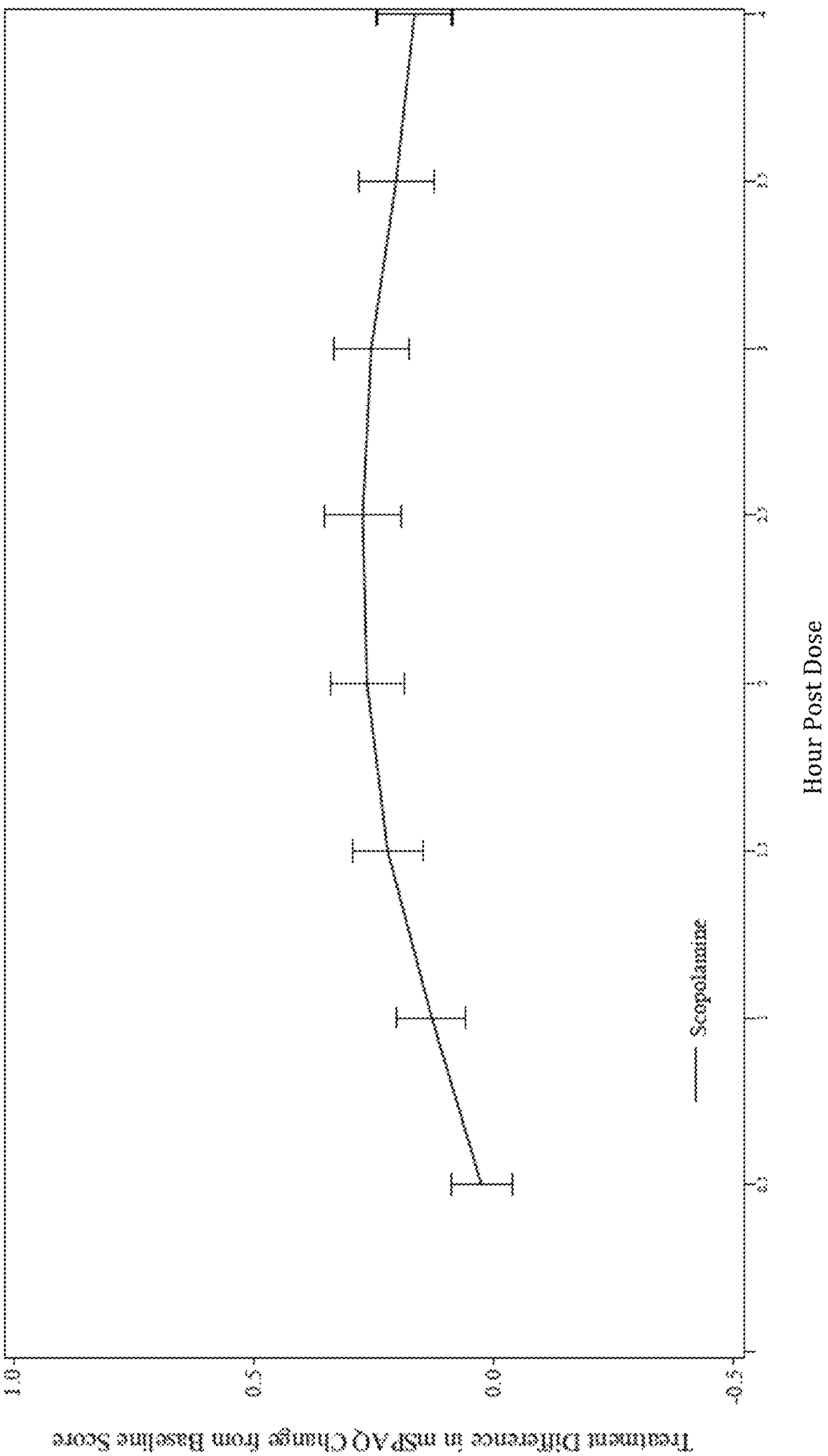

FIG. 3N – hand-eye coordination
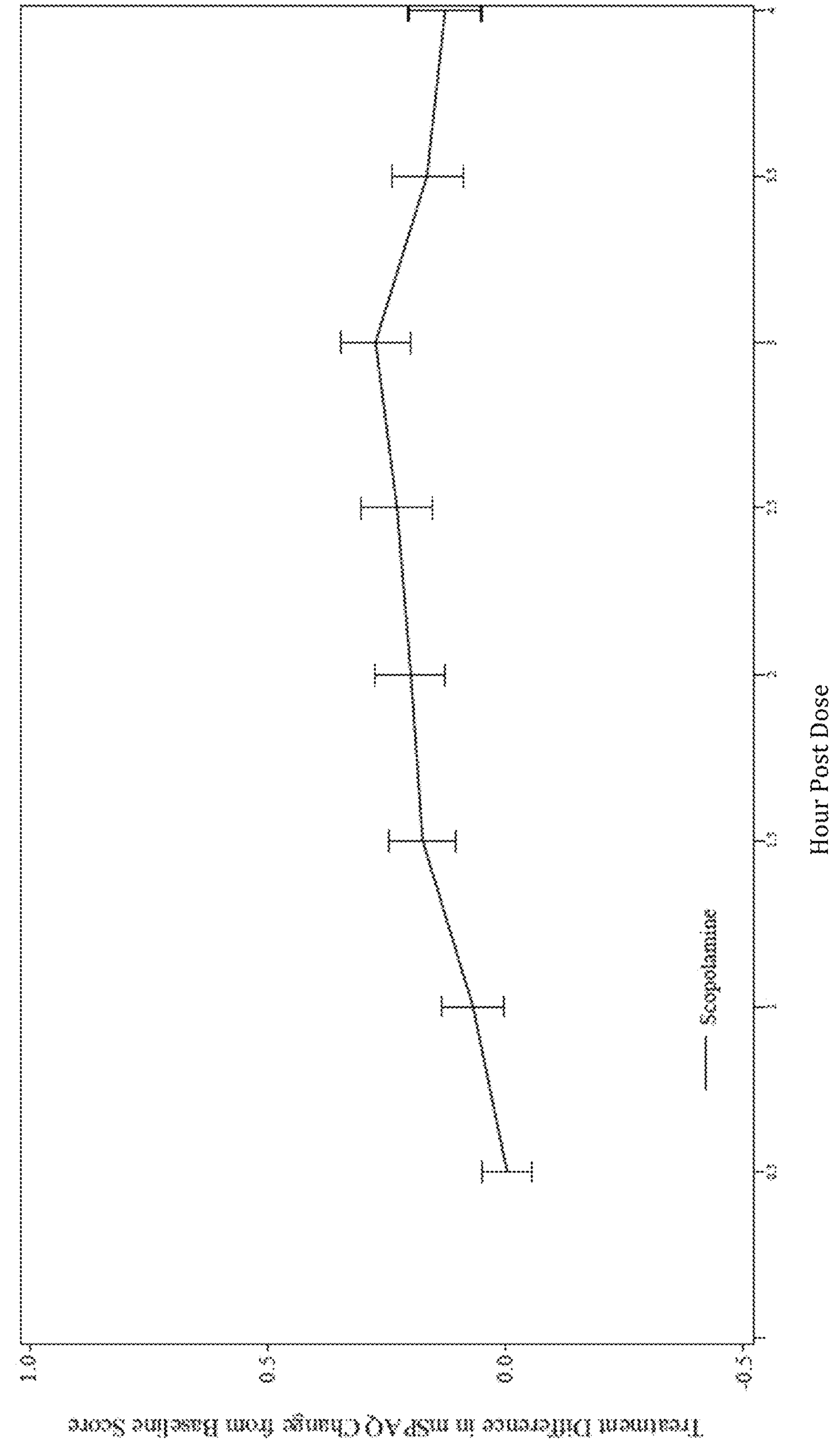

FIG. 3O - mood
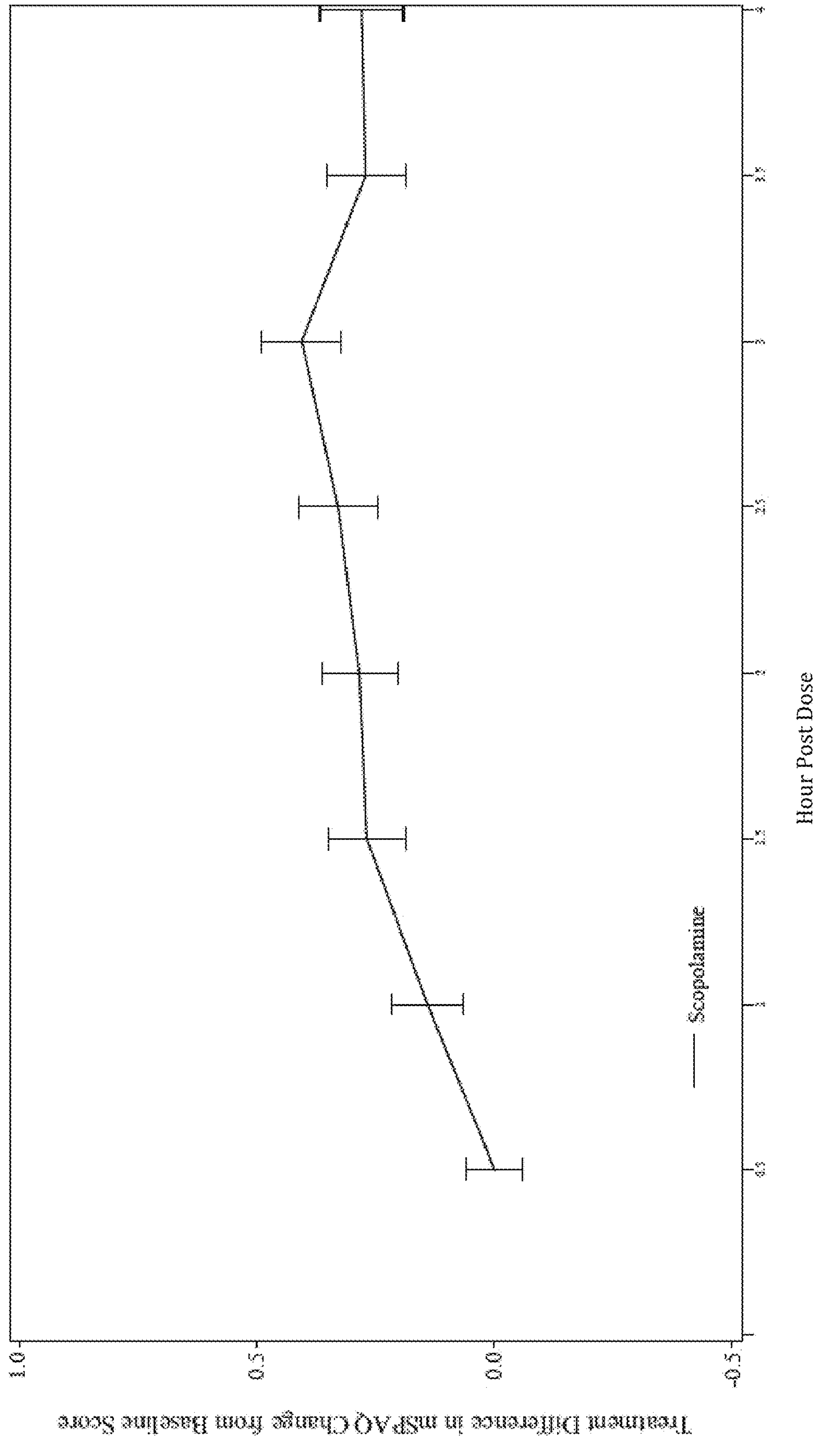

FIG. 3P – reaction timealert
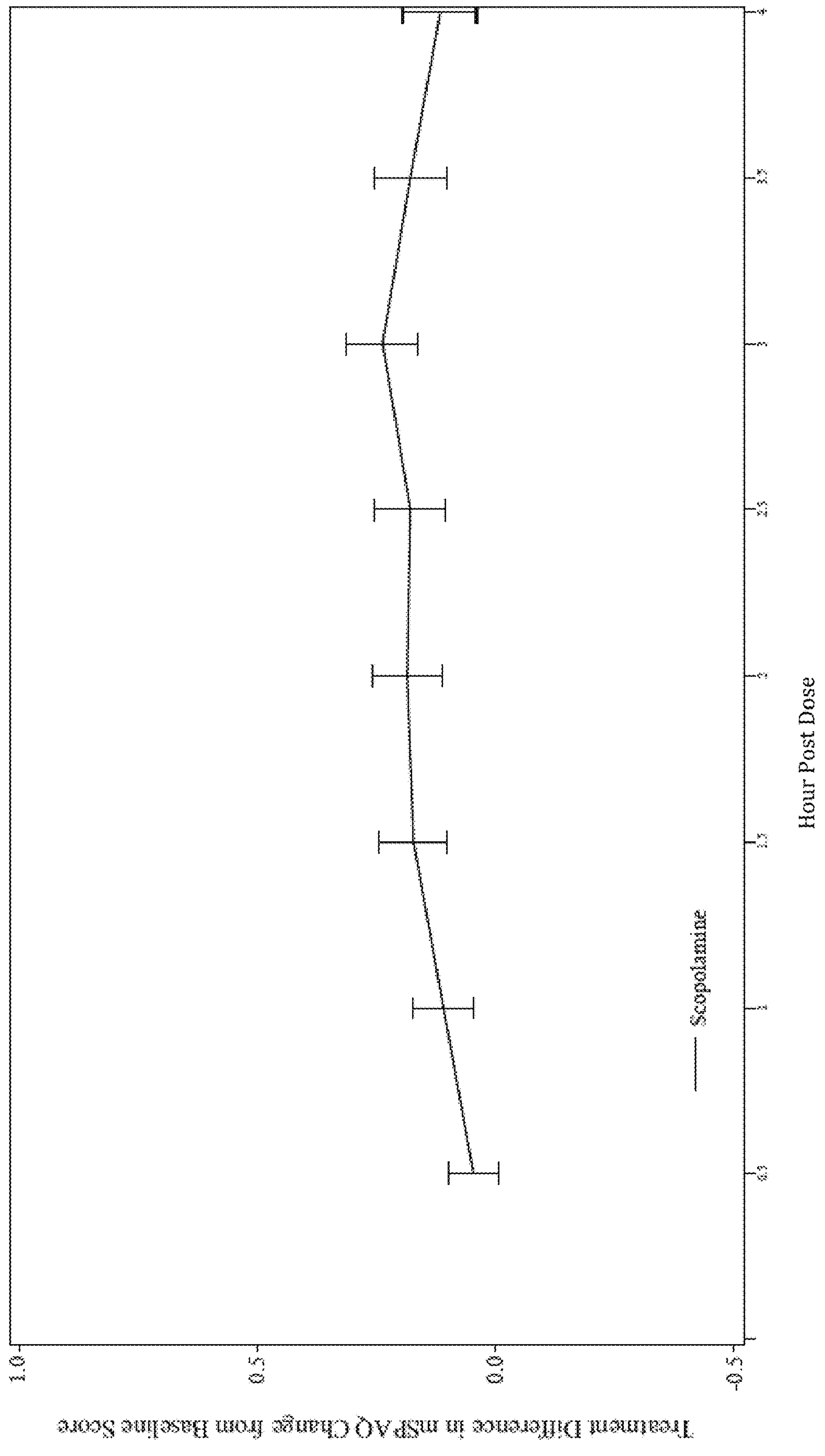

FIG. 4A: Disposition of Subjects
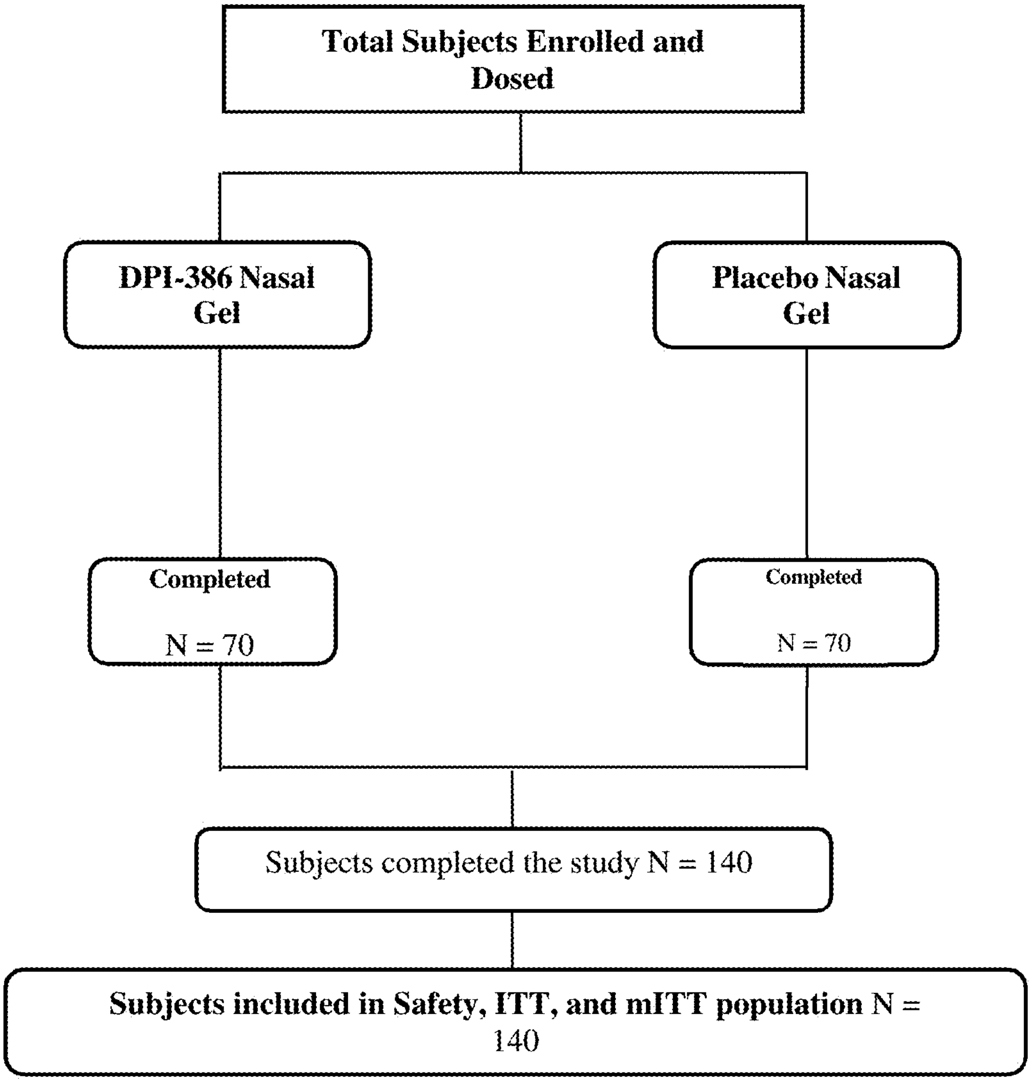

FIG. 4B: Kaplan-Meier Plot of Time to Vomiting or Use of Rescue Medication, ITT Population

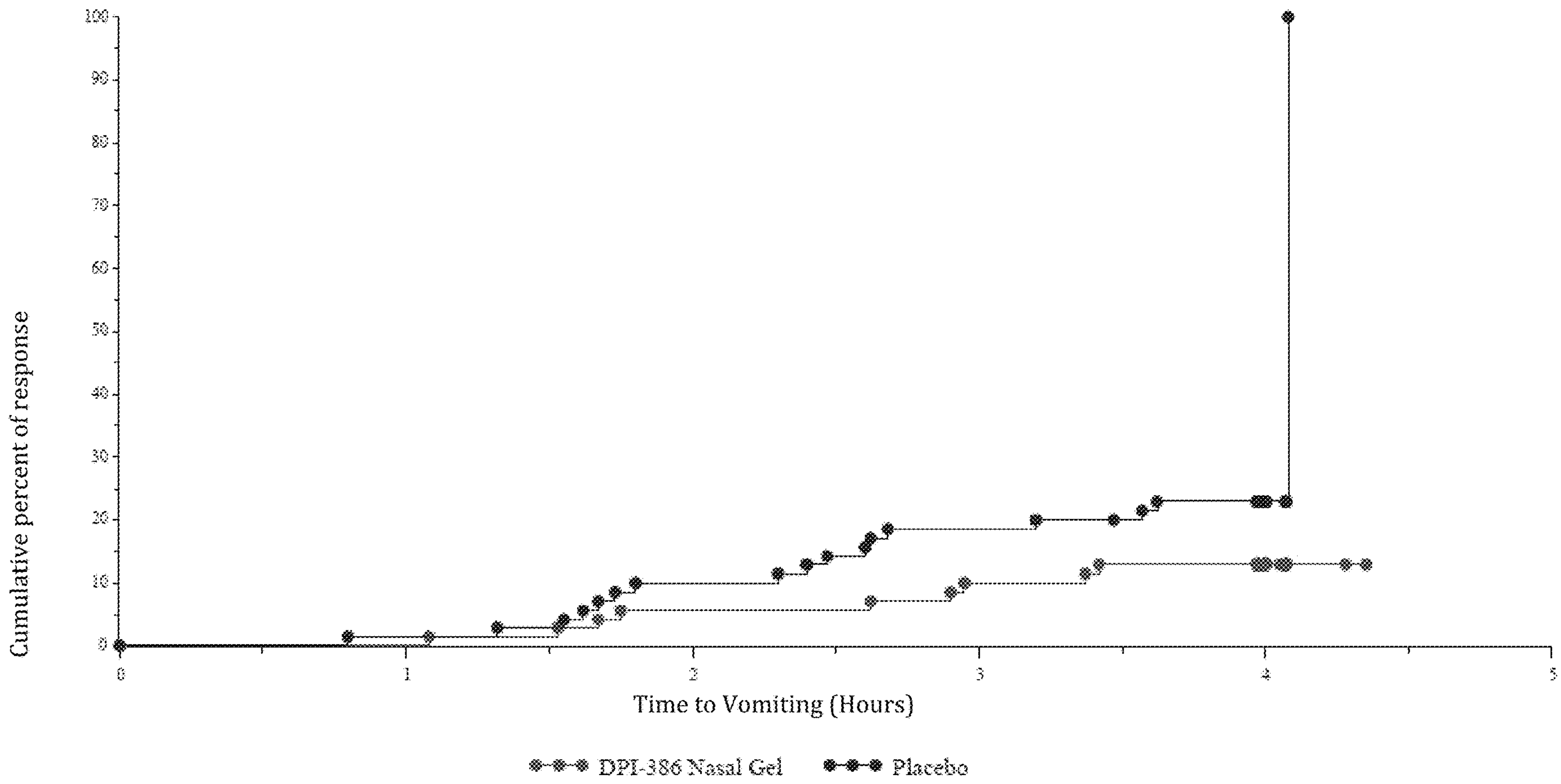

Note: Log Rank P-value=0.0105.
Note: Subjects who reported vomiting or have taken rescue treatment within 4 hours after receiving study drug are considered having the event and time to event is derived as number of hours from the dosing to the earliest time of vomiting or rescue medication use.
The within 4 hours after receiving study drug window is from the time of the first dose to the time of the end of voyage.
Subjects without an event was censored at the time of the end of voyage (approximately 4 hours post dose).
Figure Generation: 26JAN2022 11:39 Program source: f_km.SAS FIG. 4C: Kaplan-Meier Plot of Time to Vomiting or Use of Rescue Medication, Per Protocol Population

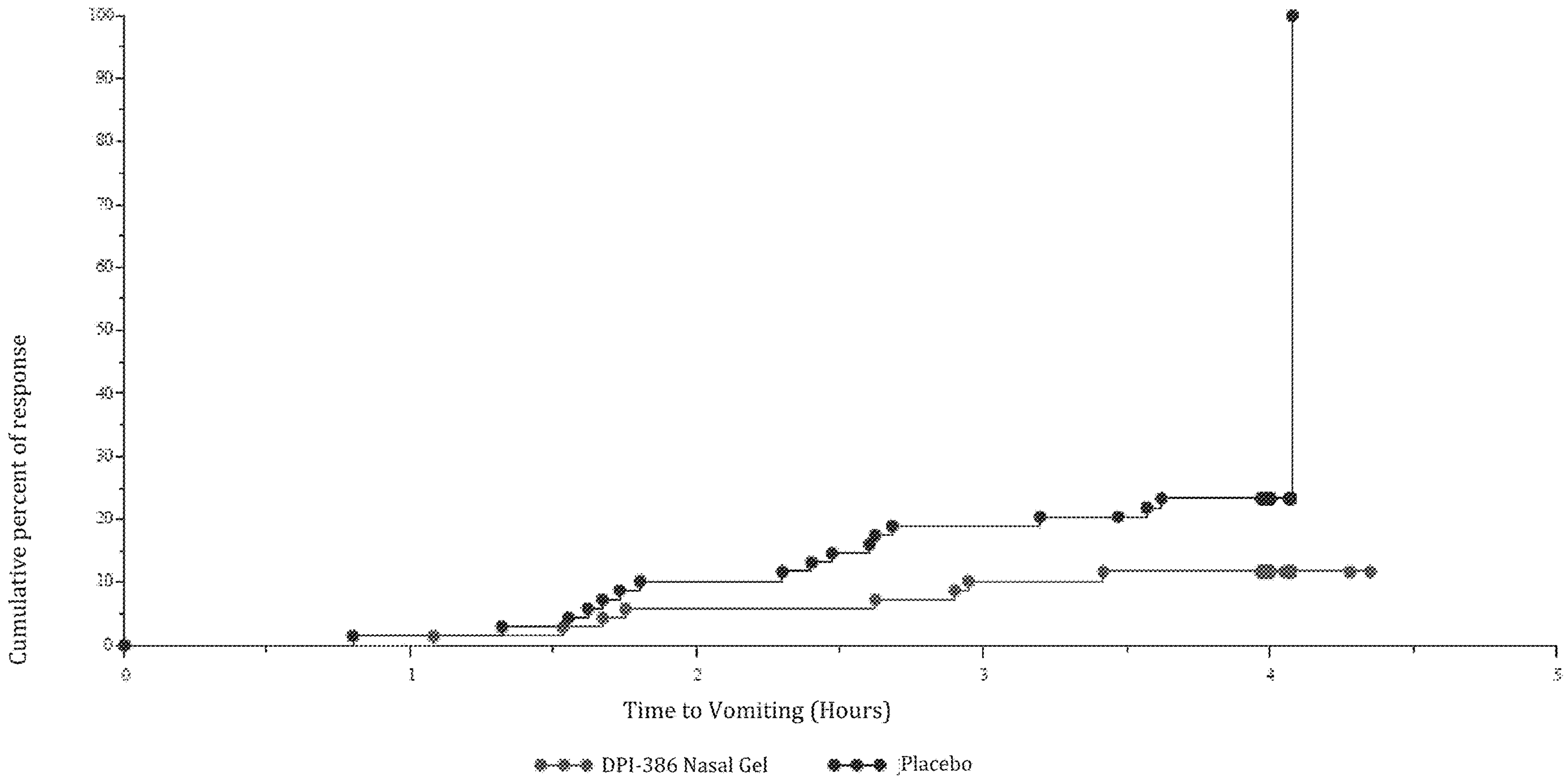

Note: Log Rank P-value=0.0039.
Note: Subjects who reported vomiting or have taken rescue treatment within 4 hours after receiving study drug are considered having the event and time to event is derived as number of hours from the dosing to the earliest time of vomiting or rescue medication use.
The within 4 hours after receiving study drug window is from the time of the first dose to the time of the end of voyage.
Subjects without an event was censored at the time of the end of voyage (approximately 4 hours post dose).
Figure Generation: 26JAN2022 11:39 Program source: f_km.SAS

FIG. 4D: MS-29 Study: Forest Plot of Treatment Difference for Key Efficacy Endpoints (ITT Population)
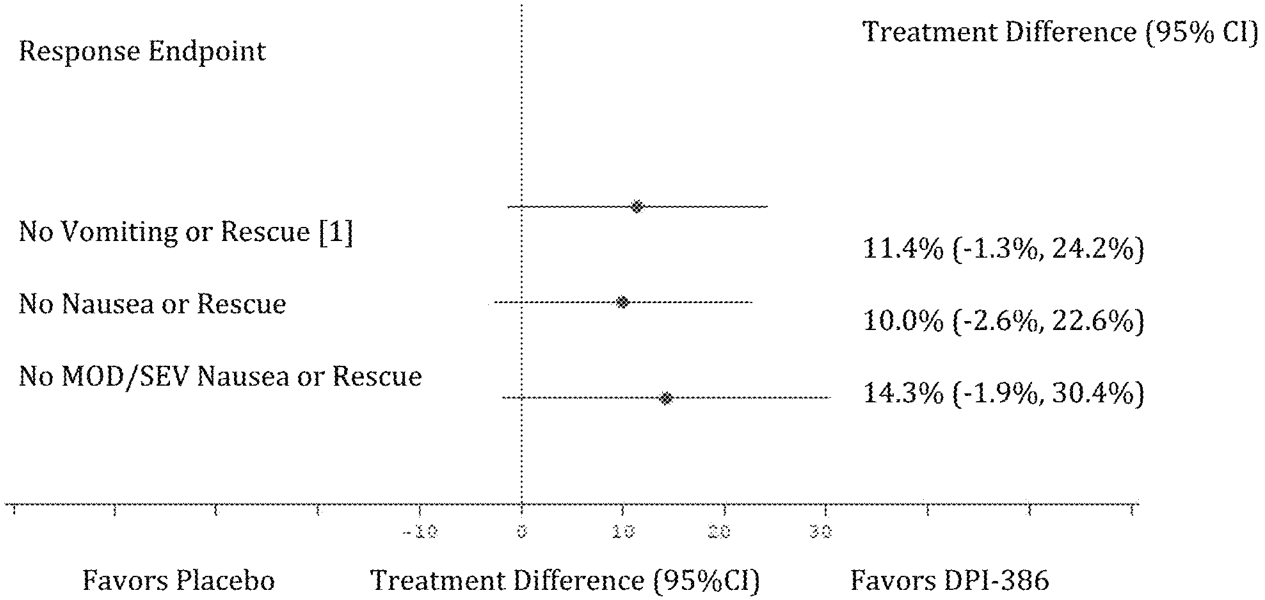
[1] Subjects who did not vomit or use rescue medication were Complete Responders.
Note: MOD/SEV = Moderate or Severe
Abbreviations: CI = confidence interval; ITT = intent-to-treat.

FIG. 4E: MS-29 Study: Forest Plot of Relative Risk or Hazard Ratio for Key Efficacy Endpoints (ITT Population)
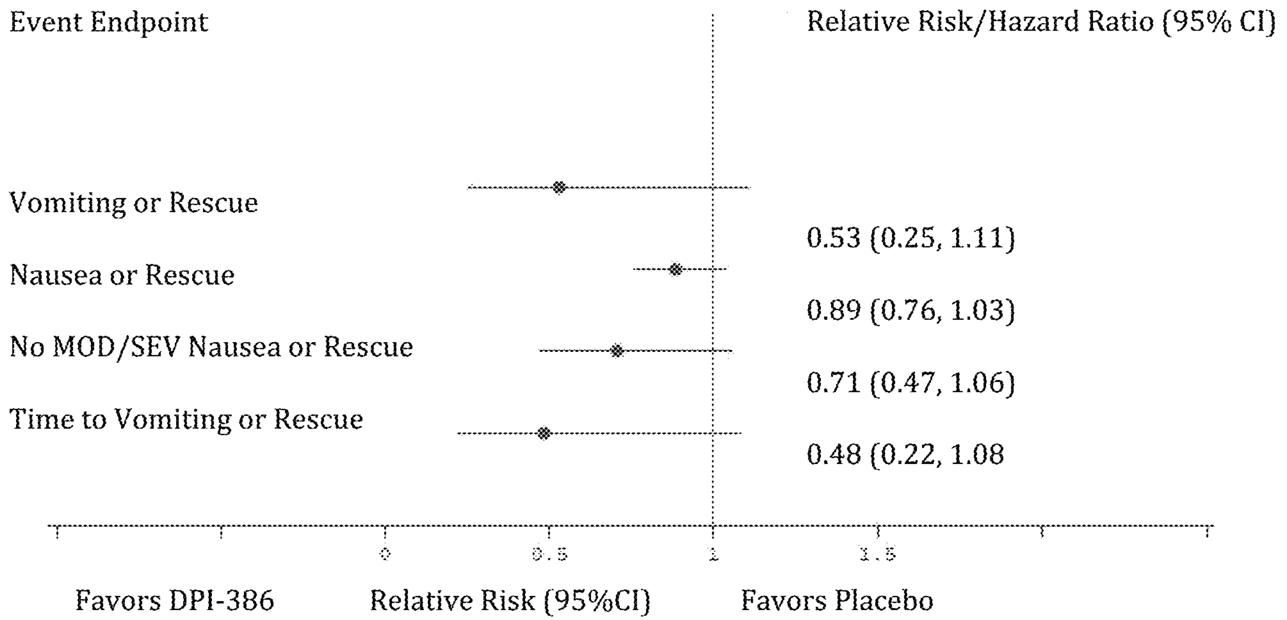
Note: MOD/SEV = Moderate or Severe. Subjects took rescue medication were counted as having an event.
Abbreviations: CI = confidence interval; ITT = intent-to-treat.

Note: mPSAQ Score were assigned as 1=significantly worse,2=somewhat worse,3=no effect,4=somewhat better,5=significantly better.
Analysis was based on MMRM including fixed effects of treatment, visit, baseline score and interaction terms of treatment by visit.
Figure Generation: 26JAN2022 11:39 Program source: f_mmrm_MSPQ.sas Note: mPSAQ Score were assigned as 1=significantly worse,2=somewhat worse,3=no effect,4=somewhat better,5=significantly better.
Analysis was based on MMRM including fixed effects of treatment, visit, baseline score and interaction terms of treatment by visit.
Figure Generation: 26JAN2022 11:39 Program source: f_mmrm_MSPQ.sas Note: mPSAQ Score were assigned as 1=significantly worse,2=somewhat worse,3=no effect,4=somewhat better,5=significantly better.
Analysis was based on MMRM including fixed effects of treatment, visit, baseline score and interaction terms of treatment by visit.
Figure Generation: 26JAN2022 11:39
Program source: f_mmrm_MSPQ.sas Note: mPSAQ Score were assigned as 1=significantly worse,2=somewhat worse,3=no effect,4=somewhat better,5=significantly better.
Analysis was based on MMRM including fixed effects of treatment, visit, baseline score and interaction terms of treatment by visit.
Figure Generation: 26JAN2022 11:39 Program source: f_mmrm_MSPQ.sas Note: mPSAQ Score were assigned as 1=significantly worse,2=somewhat worse,3=no effect,4=somewhat better,5=significantly better.
Analysis was based on MMRM including fixed effects of treatment, visit, baseline score and interaction terms of treatment by visit.
Figure Generation: 26JAN2022 11:39 Program source: f_mmrm_MSPQ.sas

FIG. 4L

Least Squares Mean (SE) Change from Baseline in mPSAQ Reaction Time
ITT Population

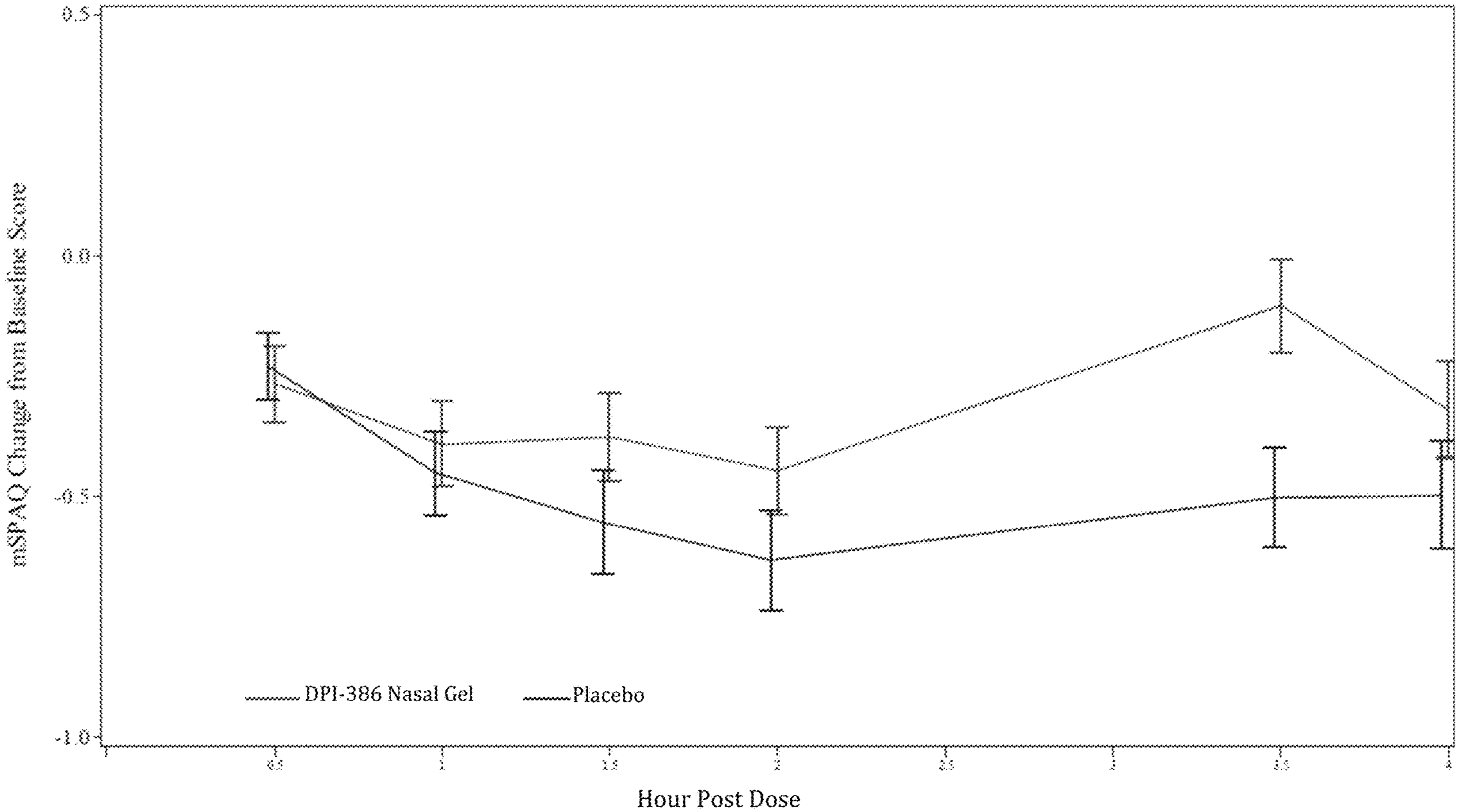

Note: mPSAQ Score were assigned as 1=significantly worse,2=somewhat worse,3=no effect,4=somewhat better,5=significantly better.
Analysis was based on MMRM including fixed effects of treatment, visit, baseline score and interaction terms of treatment by visit.
Figure Generation: 26JAN2022 11:39 Program source: f_mmrm_MSPQ.sas Note: mPSAQ Score were assigned as 1=significantly worse,2=somewhat worse,3=no effect,4=somewhat better,5=significantly better.
Analysis was based on MMRM including fixed effects of treatment, visit, baseline score and interaction terms of treatment by visit.
Figure Generation: 26JAN2022 11:39 Program source: f_mmrm_MSPQ.sas

FIG. 4N: Least Squares Mean (SE) of Treatment Difference from Placebo in Nausea Assessment Score – MMRM, ITT Population

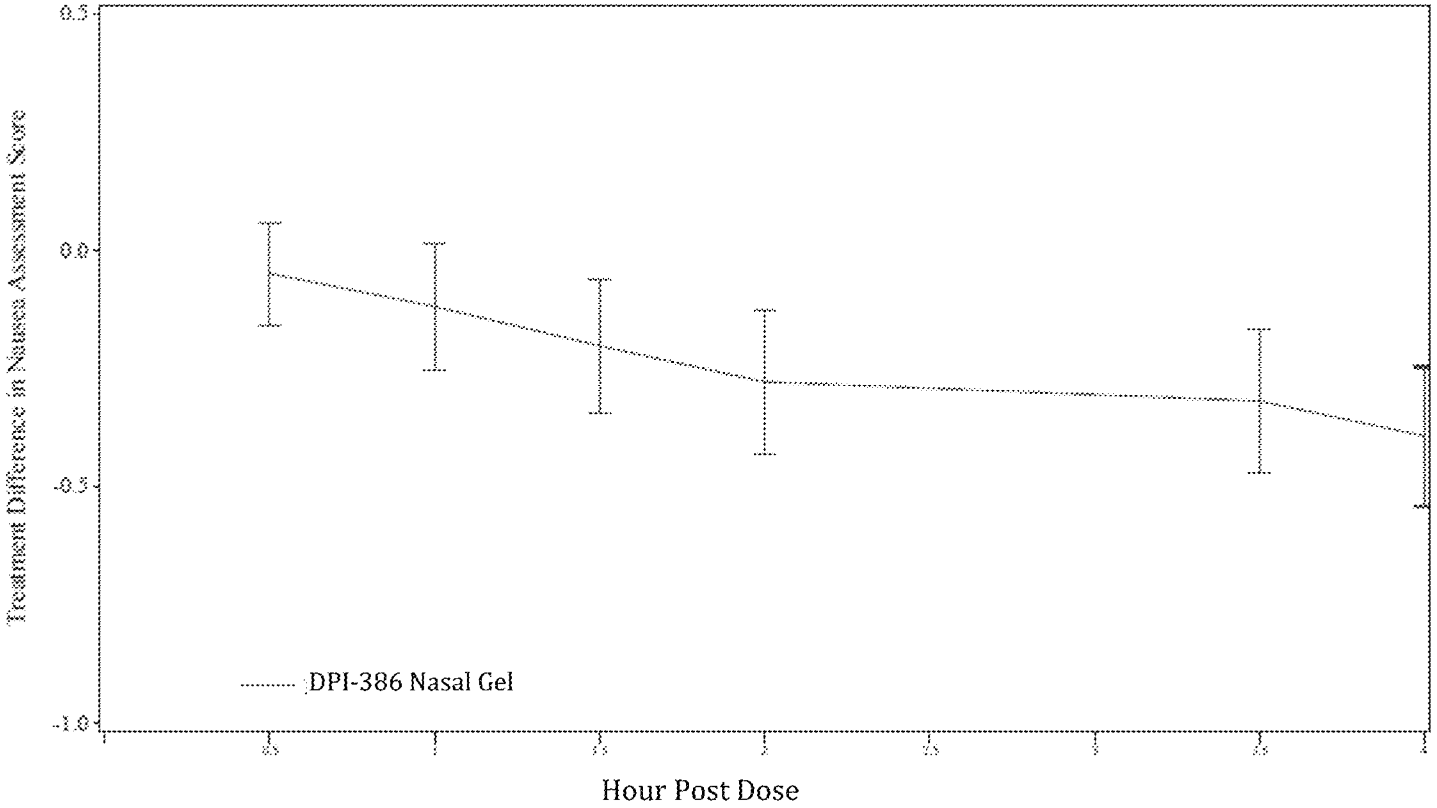

ITT = Intent-to-Treat; MMRM = mixed model for repeated measures; SE = standard error.

Note: Nausea Assessment Score were assigned as following: 0= No symptoms; 1=mild nausea; 2=moderate nausea; 3=severe nausea.

Analysis was based on MMRM including fixed effects of treatment, visit, baseline score and interaction terms of treatment by visit.

FIG. 40: Forest Plot of Between-group Treatment Differences in the Proportions of Subjects without Nausea and without Use of Rescue Medication, Pooled Analysis and By Study, ITT Population
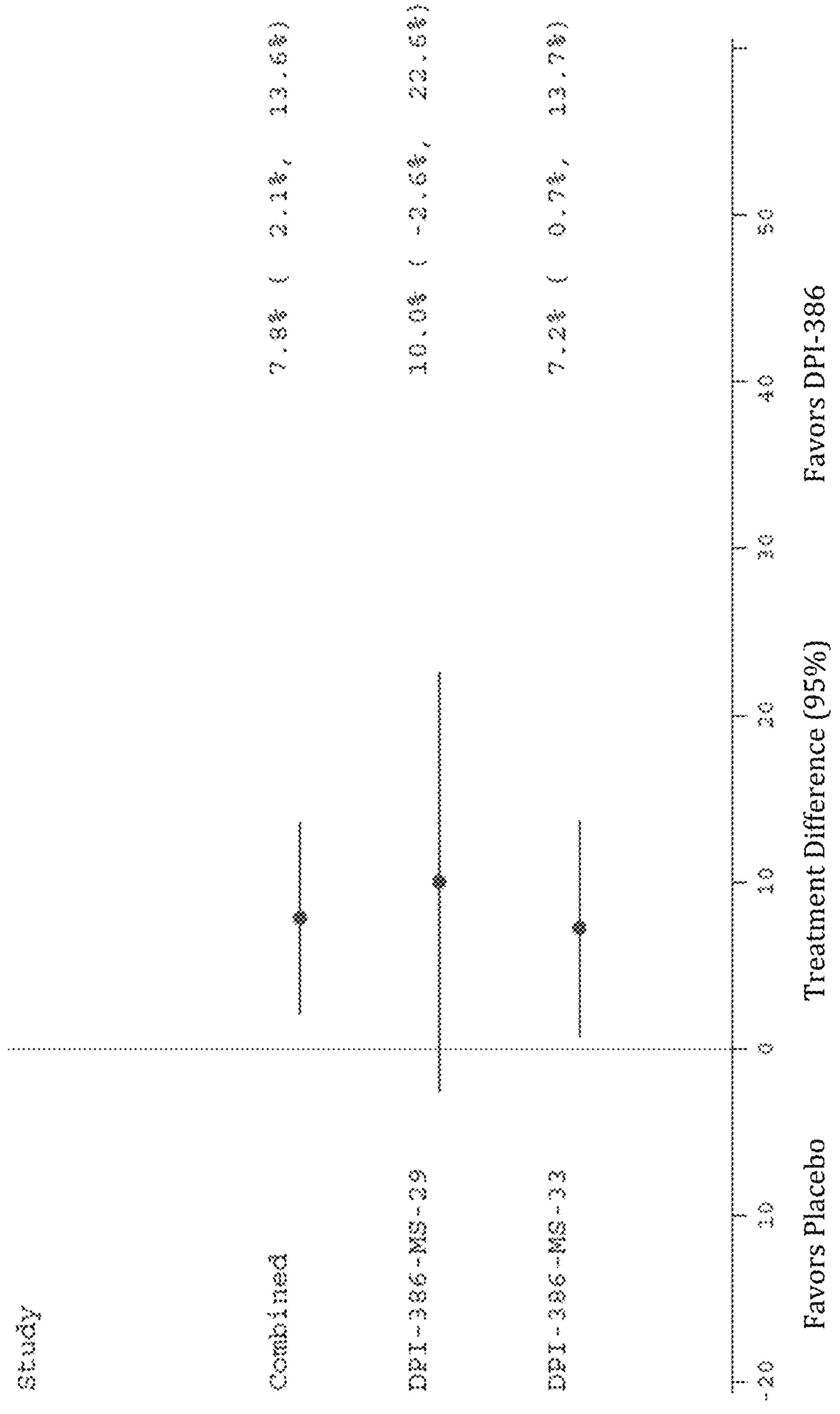

FIG. 4P: Forest Plot of Between-group Treatment Differences in the Proportions of Subjects without Moderate or Severe Nausea and without Use of Rescue Medication, Pooled Analysis and By Study, ITT Population
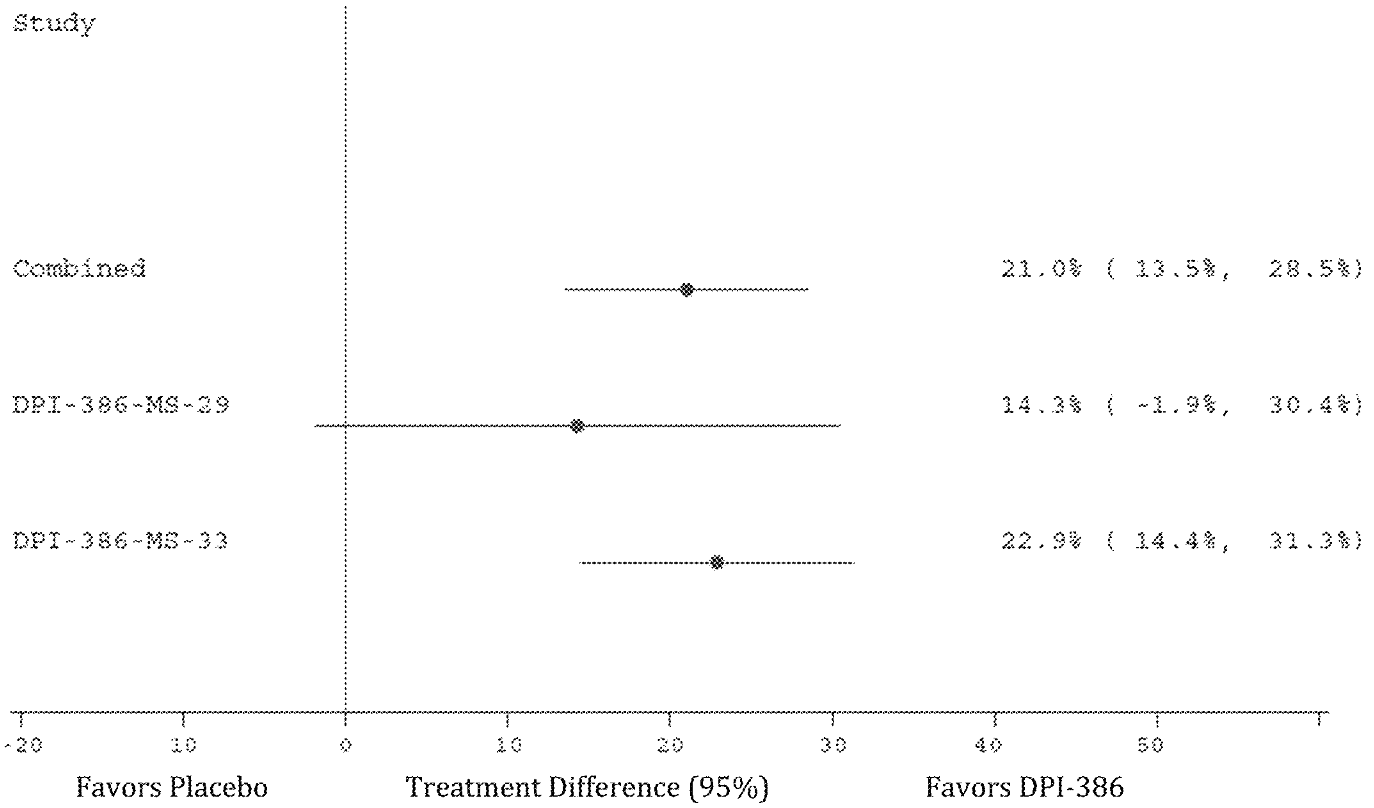

FIG. 4Q: Kaplan-Meier Plot of Time to Vomiting or to Use of Rescue Medication, Pooled Analysis, ITT Population
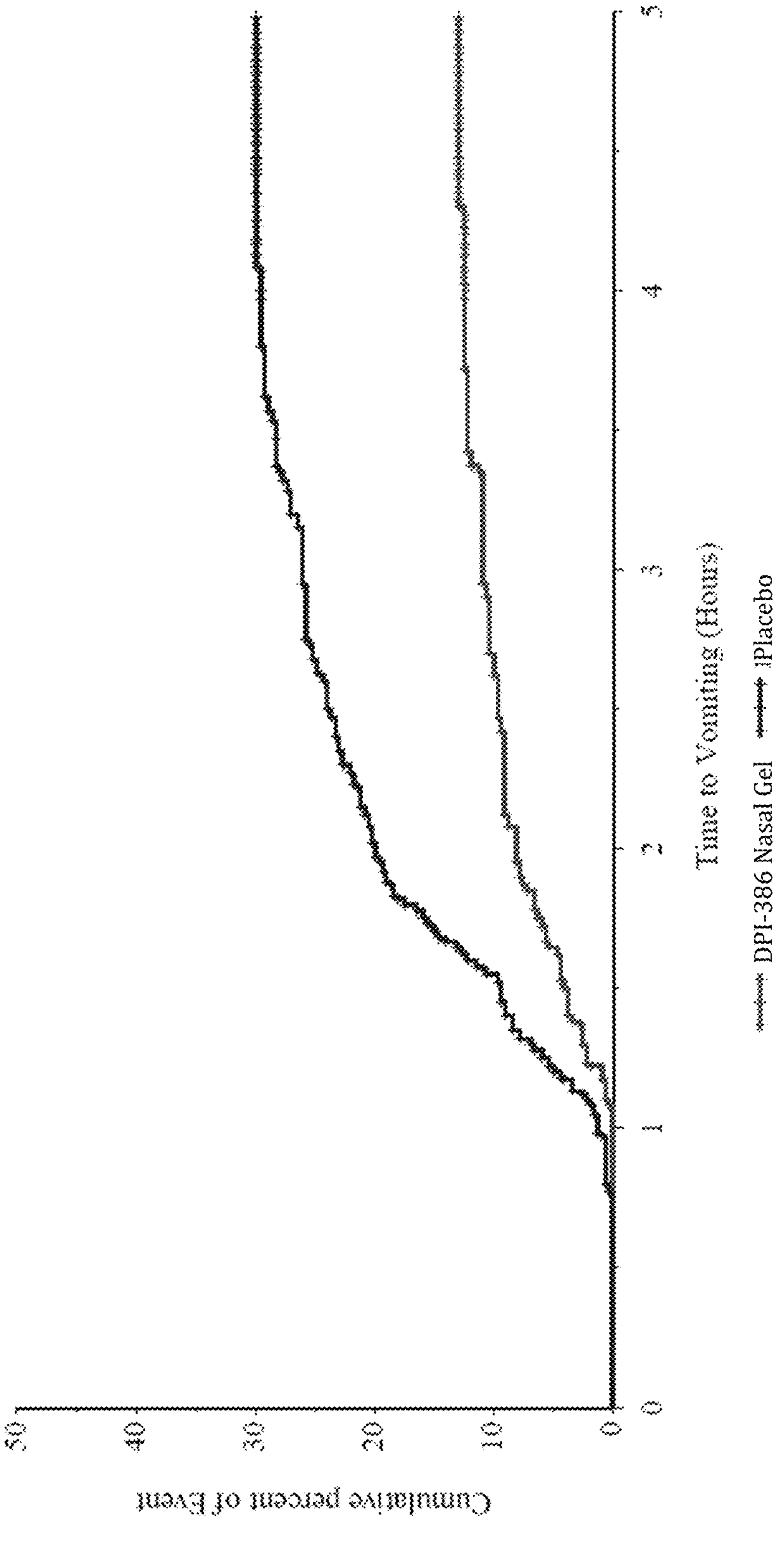
Note: Stratified Log Rank P-value<0.0001.

FIG. 4R: Forest Plot of Hazard Ratios for Time to Vomiting or Use of Rescue Medication, Pooled Analysis and By Study, ITT Population
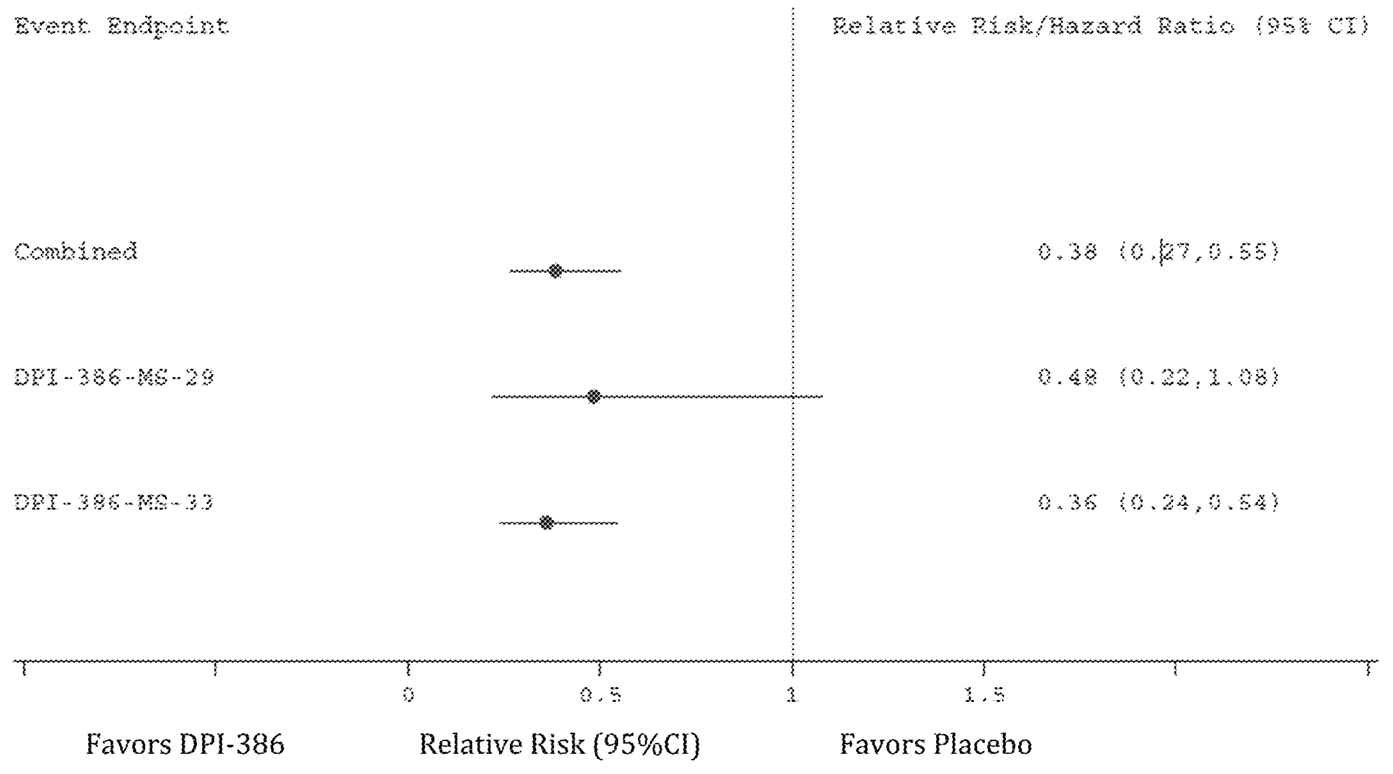

Disposition of Subjects

Kaplan-Meier Plot of Time to the First Use of Rescue Medication, ITT Population

ITT = Intent-to-Treat.

Source: Figure 14.2.1.1

Median Plasma Scopolamine Concentration-Time Profiles following Intranasal Administration of 0.2 mg Twice Daily for 3 Days Source: Figure 14.2.3.1

Comparison of Scopolamine Pharmacokinetic Exposure by Sex Following Intranasal Administration of 0.2 mg Twice Daily Source: Figure 14.2.8.2

Comparison of Scopolamine Pharmacokinetic Exposure by Age Group Following Intranasal Administration of 0.2 mg Twice Daily
Cmax (pg/mL)
AUC0-6 (min*pg/mL)
D2AM <65 Years
D2AM 65-74 Years
D2AM >=75 Years
D3AM <65 Years
D3AM 65-74 Years
D3AM >=75 Years
D4AM <65 Years
D4AM 65-74 Years
D4AM >=75 Years
Source: Figure 14.2.8.3

Box Plot of Subjects with and without ACTS Symptoms and the Day 2 (AM) Scopolamine PK Parameter AUC0-6 (min*pg/mL)

Note: Scopolamine PK Parameters on Day 2 AM from all subjects were used in the analysis.

Source: Figure 14.2.12

Box Plot of Subjects with and without ACTS Symptoms and the Day 2 (AM) Scopolamine PK Parameter AUCt (min*pg/mL)

Note: Scopolamine PK Parameters on Day 2 AM from all subjects were used in the analysis.

Source: Figure 14.2.12

Box Plot of Subjects with and without ACTS Symptoms and the Day 2 (AM) Scopolamine PK Parameter Cmax (pg/mL)

Note: Scopolamine PK Parameters on Day 2 AM from all subjects were used in the analysis.

Source: Figure 14.2.12

FIG. 6B

Summary of Scopolamine PK Parameters
PK Parameter Population

| Treatment | Visit | Statistics | AUC0-inf (min*pg/mL) | AUCt (min*pg/mL) | AUCtau (min*pg/mL) | AUC3d (min*pg/mL) |
|---|---|---|---|---|---|---|
| DPI-386 Nasal Gel | Day 1 / Dose 1 | N | 19 | 20 | 20 | |
| | | Mean | 28347.910 | 26483.861 | 26576.030 | |
| | | STD | 10726.4478 | 10795.5572 | 10821.3537 | |
| | | CV (%) | 37.84 | 40.76 | 40.72 | |
| | | Median | 28378.665 | 24570.815 | 24688.445 | |
| | | Min | 10707.22 | 10119.87 | 10145.65 | |
| | | Max | 52748.94 | 51326.62 | 51326.62 | |
| | | Geom. Mean | 26304.756 | 24424.221 | 24510.571 | |
| | | SD (log) | 0.4146 | 0.4222 | 0.4222 | |
| | | %CVb | 43.31 | 44.18 | 44.17 | |
| | | 95% CI Lower | 21404.03 | 20044.77 | 20115.75 | |
| | | 95% CI Upper | 32327.56 | 29760.51 | 29865.56 | |
| | Day 1 / Dose 2 | N | | 20 | 20 | |
| | | Mean | | 32477.504 | 34278.186 | |
| | | STD | | 17297.1352 | 16436.4306 | |
| | | CV (%) | | 53.26 | 47.95 | |
| | | Median | | 34329.310 | 35868.800 | |
| | | Min | | 4143.57 | 9610.77 | |
| | | Max | | 65833.76 | 65873.52 | |
| | | Geom. Mean | | 26531.983 | 29119.539 | |
| | | SD (log) | | 0.7456 | 0.6648 | |
| | | %CVb | | 86.22 | 74.55 | |
| | | 95% CI Lower | | 18716.64 | 21333.10 | |
| | | 95% CI Upper | | 37610.70 | 39747.98 | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6C

Summary of Scopolamine PK Parameters
PK Parameter Population

| Treatment | Visit | Statistics | AUC %Extrap. (%) | R(AUCtau) | R(AUCtau/AUCinf) | Cmax (pg/mL) |
|---|---|---|---|---|---|---|
| DPI-386 Nasal Gel | Day 1 / Dose 1 | N | 18 | | | 20 |
| | | Mean | 10.189 | | | 176.355 |
| | | STD | 4.4290 | | | 74.2811 |
| | | CV (%) | 43.47 | | | 42.12 |
| | | Median | 8.925 | | | 158.500 |
| | | Min | 5.37 | | | 68.00 |
| | | Max | 21.42 | | | 305.00 |
| | | Geom. Mean | 9.372 | | | 161.471 |
| | | SD (log) | 0.4166 | | | 0.4387 |
| | | %CVb | 43.54 | | | 46.07 |
| | | 95% CI Lower | 7.82 | | | 131.90 |
| | | 95% CI Upper | 11.53 | | | 198.27 |
| | Day 1 / Dose 2 | N | | | | 20 |
| | | Mean | | | | 148.025 |
| | | STD | | | | 72.7054 |
| | | CV (%) | | | | 49.12 |
| | | Median | | | | 154.000 |
| | | Min | | | | 13.20 |
| | | Max | | | | 260.00 |
| | | Geom. Mean | | | | 120.145 |
| | | SD (log) | | | | 0.7972 |
| | | %CVb | | | | 94.23 |
| | | 95% CI Lower | | | | 82.73 |
| | | 95% CI Upper | | | | 174.48 |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6D

Summary of Scopolamine PK Parameters
PK Parameter Population

| Treatment | Visit | Statistics | R(Cmax) | Ctau (pg/mL) | t 1/2 (min) | tmax (min) |
|---|---|---|---|---|---|---|
| DPI-386 Nasal Gel | Day 1 / Dose 1 | N | | 20 | 18 | 20 |
| | | Mean | | 23.565 | 96.928 | 80.000 |
| | | STD | | 23.1594 | 19.7605 | 72.3119 |
| | | CV (%) | | 98.63 | 20.39 | 90.39 |
| | | Median | | 20.050 | 91.425 | 50.000 |
| | | Min | | 5.24 | 67.70 | 20.00 |
| | | Max | | 122.00 | 138.89 | 300.00 |
| | | Geom. Mean | | 21.455 | 95.166 | |
| | | SD (log) | | 0.7842 | 0.1942 | |
| | | %CVb | | 92.18 | 19.61 | |
| | | 95% CI Lower | | 14.86 | 86.40 | |
| | | 95% CI Upper | | 30.97 | 104.82 | |
| | Day 1 / Dose 2 | N | | 18 | | 20 |
| | | Mean | | 4.144 | | 63.000 |
| | | STD | | 3.9212 | | 27.3573 |
| | | CV (%) | | 94.61 | | 43.42 |
| | | Median | | 3.140 | | 60.000 |
| | | Min | | 0.00 | | 30.00 |
| | | Max | | 13.50 | | 120.00 |
| | | Geom. Mean | | 4.953 | | |
| | | SD (log) | | 0.5496 | | |
| | | %CVb | | 59.38 | | |
| | | 95% CI Lower | | 3.55 | | |
| | | 95% CI Upper | | 6.90 | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6E

Summary of Scopolamine PK Parameters
PK Parameter Population

| Treatment | Visit | Statistics | tlag (min) | tlast (min) | CL/F (mL/min) | Vz/F (mL) |
|---|---|---|---|---|---|---|
| DPI-386 Nasal Gel | Day 1 / Dose 1 | N | 20 | 20 | 18 | 18 |
| | | Mean | 1.250 | 355.200 | 6554.336 | 905613.943 |
| | | STD | 2.7506 | 0.8944 | 3100.3017 | 403838.0671 |
| | | CV (%) | 220.05 | 0.25 | 47.30 | 44.59 |
| | | Median | 0.000 | 355.000 | 5567.575 | 851823.965 |
| | | Min | 0.00 | 355.00 | 2995.49 | 369213.12 |
| | | Max | 10.00 | 359.00 | 14756.40 | 1654027.71 |
| | | Geom. Mean | | | 6006.520 | 824671.399 |
| | | SD (log) | | | 0.4146 | 0.4483 |
| | | %CVb | | | 43.31 | 47.18 |
| | | 95% CI Lower | | | 4887.47 | 659873.44 |
| | | 95% CI Upper | | | 7381.79 | 1030626.27 |
| | Day 1 / Dose 2 | N | | 20 | | |
| | | Mean | | 818.250 | | |
| | | STD | | 344.9991 | | |
| | | CV (%) | | 42.16 | | |
| | | Median | | 1065.000 | | |
| | | Min | | 360.00 | | |
| | | Max | | 1065.00 | | |
| | | Geom. Mean | | | | |
| | | SD (log) | | | | |
| | | %CVb | | | | |
| | | 95% CI Lower | | | | |
| | | 95% CI Upper | | | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6F

Summary of Scopolamine PK Parameters
PK Parameter Population

| Treatment | Visit | Statistics | tlag (min) | tlast (min) | CL/F (mL/min) | Vz/F (mL) |
|---|---|---|---|---|---|---|
| DPI-386 Nasal Gel | Day 1 / Dose 1 | N | 20 | 20 | 18 | 18 |
| | | Mean | 1.250 | 359.200 | 6554.336 | 905613.843 |
| | | STD | 2.7506 | 0.8944 | 3100.3017 | 403838.0671 |
| | | CV (%) | 220.05 | 0.25 | 47.30 | 44.59 |
| | | Median | 0.000 | 355.000 | 5567.575 | 851823.965 |
| | | Min | 0.00 | 355.00 | 2995.49 | 369213.12 |
| | | Max | 10.00 | 399.00 | 14756.40 | 1654027.71 |
| | | Geom. Mean | | | 6006.520 | 824671.389 |
| | | SD (log) | | | 0.4146 | 0.4483 |
| | | %CVb | | | 43.31 | 47.18 |
| | | 95% CI Lower | | | 4887.47 | 659873.44 |
| | | 95% CI Upper | | | 7381.79 | 1030626.27 |
| | Day 1 / Dose 2 | N | | 20 | | |
| | | Mean | | 818.250 | | |
| | | STD | | 344.9991 | | |
| | | CV (%) | | 42.16 | | |
| | | Median | | 1065.000 | | |
| | | Min | | 360.00 | | |
| | | Max | | 1065.00 | | |
| | | Geom. Mean | | | | |
| | | SD (log) | | | | |
| | | %CVb | | | | |
| | | 95% CI Lower | | | | |
| | | 95% CI Upper | | | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6G

Summary of Scopolamine PK Parameters
PK Parameter Population

| Treatment | Visit | Statistics | AUC0-inf (min*pg/mL) | AUCt (min*pg/mL) | AUCtau (min*pg/mL) | AUC3d (min*pg/mL) |
|---|---|---|---|---|---|---|
| DPI-386 Nasal Gel | Day 2 / Dose 3 | N | | 18 | 18 | |
| | | Mean | | 21956.761 | 22051.329 | |
| | | STD | | 11363.1951 | 11416.6535 | |
| | | CV (%) | | 51.75 | 51.77 | |
| | | Median | | 22862.370 | 22979.490 | |
| | | Min | | 4048.27 | 4061.35 | |
| | | Max | | 43473.94 | 43698.84 | |
| | | Geom. Mean | | 18545.247 | 18623.926 | |
| | | SD (log) | | 0.6580 | 0.6581 | |
| | | %CVb | | 73.60 | 73.62 | |
| | | 95% CI Lower | | 13370.08 | 13426.07 | |
| | | 95% CI Upper | | 25723.56 | 25834.10 | |
| | Day 2 / Dose 4 | N | | 18 | 18 | |
| | | Mean | | 31181.499 | 31607.131 | |
| | | STD | | 15431.3590 | 14975.8112 | |
| | | CV (%) | | 49.49 | 47.38 | |
| | | Median | | 35840.575 | 35978.870 | |
| | | Min | | 2626.43 | 3441.14 | |
| | | Max | | 50709.94 | 50765.14 | |
| | | Geom. Mean | | 24685.889 | 25908.430 | |
| | | SD (log) | | 0.8653 | 0.7801 | |
| | | %CVb | | 105.56 | 91.53 | |
| | | 95% CI Lower | | 16051.61 | 17577.65 | |
| | | 95% CI Upper | | 37959.87 | 38187.51 | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 030 Transderm Scop data were excluded from the summary due to the transdermal scopolamine patch removed early.
Table Generation: 20APR2022 19:25 Program source: t_adpp.sas

FIG. 6H

Summary of Scopolamine PK Parameters
PK Parameter Population

| Treatment | Visit | Statistics | AUC %Extrap. (%) | R(AUCtau) | R(AUCtau/AUCinf) | Cmax (pg/mL) |
|---|---|---|---|---|---|---|
| DPI-386 Nasal Gel | Day 2 / Dose 3 | N | | | | 18 |
| | | Mean | | | | 140.729 |
| | | STD | | | | 70.9998 |
| | | CV (%) | | | | 50.45 |
| | | Median | | | | 140.500 |
| | | Min | | | | 39.50 |
| | | Max | | | | 285.00 |
| | | Geom. Mean | | | | 121.344 |
| | | SD (log) | | | | 0.5954 |
| | | %CVb | | | | 65.22 |
| | | 95% CI Lower | | | | 90.25 |
| | | 95% CI Upper | | | | 163.15 |
| | Day 2 / Dose 4 | N | | | | 18 |
| | | Mean | | | | 126.889 |
| | | STD | | | | 66.6254 |
| | | CV (%) | | | | 52.51 |
| | | Median | | | | 120.000 |
| | | Min | | | | 26.10 |
| | | Max | | | | 245.00 |
| | | Geom. Mean | | | | 106.274 |
| | | SD (log) | | | | 0.6802 |
| | | %CVb | | | | 76.71 |
| | | 95% CI Lower | | | | 75.77 |
| | | 95% CI Upper | | | | 149.05 |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 61

Summary of Scopolamine PK Parameters
PK Parameter Population

| Treatment | Visit | Statistics | R(Cmax) | Ctau (pg/mL) | t 1/2 (min) | tmax (min) |
|---|---|---|---|---|---|---|
| DPI-386 Nasal Gel | Day 2 / Dose 3 | N | | 18 | | 18 |
| | | Mean | | 23.094 | | 64.278 |
| | | STD | | 15.4163 | | 35.7603 |
| | | CV (%) | | 66.75 | | 55.63 |
| | | Median | | 19.800 | | 60.000 |
| | | Min | | 2.61 | | 15.00 |
| | | Max | | 53.80 | | 122.00 |
| | | Geom. Mean | | 17.764 | | |
| | | SD (log) | | 0.8169 | | |
| | | %CVb | | 97.41 | | |
| | | 95% CI Lower | | 11.83 | | |
| | | 95% CI Upper | | 26.67 | | |
| | Day 2 / Dose 4 | N | | 18 | | 18 |
| | | Mean | | 5.424 | | 69.278 |
| | | STD | | 4.0132 | | 33.8679 |
| | | CV (%) | | 73.99 | | 48.89 |
| | | Median | | 4.995 | | 60.000 |
| | | Min | | 0.00 | | 15.00 |
| | | Max | | 14.00 | | 120.00 |
| | | Geom. Mean | | 5.792 | | |
| | | SD (log) | | 0.4906 | | |
| | | %CVb | | 52.16 | | |
| | | 95% CI Lower | | 4.41 | | |
| | | 95% CI Upper | | 7.60 | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6J

Summary of Scopolamine PK Parameters
PK Parameter Population

| Treatment | Visit | Statistics | tlag (min) | tlast (min) | CL/F (mL/min) | Vz/F (mL) |
|---|---|---|---|---|---|---|
| DPI-386 Nasal Gel | Day 2 / Dose 3 | N | | 19 | | |
| | | Mean | | 355.000 | | |
| | | STD | | 0.0000 | | |
| | | CV (%) | | 0.00 | | |
| | | Median | | 355.000 | | |
| | | Min | | 355.00 | | |
| | | Max | | 355.00 | | |
| | | Geom. Mean | | | | |
| | | SD (log) | | | | |
| | | %CVb | | | | |
| | | 95% CI Lower | | | | |
| | | 95% CI Upper | | | | |
| | Day 2 / Dose 4 | N | | 18 | | |
| | | Mean | | 947.556 | | |
| | | STD | | 270.3808 | | |
| | | CV (%) | | 28.53 | | |
| | | Median | | 1065.000 | | |
| | | Min | | 360.00 | | |
| | | Max | | 1066.00 | | |
| | | Geom. Mean | | | | |
| | | SD (log) | | | | |
| | | %CVb | | | | |
| | | 95% CI Lower | | | | |
| | | 95% CI Upper | | | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6K

Summary of Scopolamine PK Parameters
PK Parameter Population

| Treatment | Visit | Statistics | Cumulative Amount IP Excreted (mg) | Renal Clearance (L/hour) | Cumulative Percent IP Excreted (%) |
|---|---|---|---|---|---|
| DPI-386 Nasal Gel | Day 2 / Dose 3 | N | | | |
| | | Mean | | | |
| | | STD | | | |
| | | CV (%) | | | |
| | | Median | | | |
| | | Min | | | |
| | | Max | | | |
| | | Geom. Mean | | | |
| | | SD (log) | | | |
| | | %CVb | | | |
| | | 95% CI Lower | | | |
| | | 95% CI Upper | | | |
| | Day 2 / Dose 4 | N | | | |
| | | Mean | | | |
| | | STD | | | |
| | | CV (%) | | | |
| | | Median | | | |
| | | Min | | | |
| | | Max | | | |
| | | Geom. Mean | | | |
| | | SD (log) | | | |
| | | %CVb | | | |
| | | 95% CI Lower | | | |
| | | 95% CI Upper | | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:28 Program source: t_adpp.sas

FIG. 6L

Summary of Scopolamine PK Parameters
PK Parameter Population

| Treatment | Visit | Statistics | AUC0-inf (min*pg/mL) | AUCt (min*pg/mL) | AUCtau (min*pg/mL) | AUC38 (min*pg/mL) |
|---|---|---|---|---|---|---|
| DPI-386 Nasal Gel | Day 3 / Dose 5 | N | | 18 | 18 | |
| | | Mean | | 21783.522 | 21884.990 | |
| | | STD | | 9001.4891 | 9035.2459 | |
| | | CV (%) | | 41.32 | 41.29 | |
| | | Median | | 22307.370 | 22396.165 | |
| | | Min | | 7748.94 | 7769.71 | |
| | | Max | | 44921.12 | 45081.97 | |
| | | Geom. Mean | | 19972.866 | 20069.332 | |
| | | SD (log) | | 0.4434 | 0.4432 | |
| | | %CVb | | 46.61 | 46.58 | |
| | | 95% CI Lower | | 16020.47 | 16099.93 | |
| | | 95% CI Upper | | 24900.36 | 25017.39 | |
| | Day 3 / Dose 6 | N | | 18 | 19 | 18 |
| | | Mean | | 32958.855 | 33264.389 | 170740.851 |
| | | STD | | 16811.7049 | 16469.4346 | 57978.0994 |
| | | CV (%) | | 51.01 | 49.51 | 33.96 |
| | | Median | | 35288.235 | 35288.295 | 175169.840 |
| | | Min | | 1546.36 | 1746.76 | 47638.62 |
| | | Max | | 59216.31 | 59216.31 | 268297.26 |
| | | Geom. Mean | | 24771.117 | 25859.227 | 158461.896 |
| | | SD (log) | | 1.0261 | 0.9433 | 0.4378 |
| | | %CVb | | 136.61 | 119.79 | 45.96 |
| | | 95% CI Lower | | 14870.68 | 16176.36 | 127460.70 |
| | | 95% CI Upper | | 41262.96 | 41338.07 | 197003.25 |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6M

Summary of Scopolamine PK Parameters
PK Parameter Population

| Treatment | Visit | Statistics | AUC %Extrap. (%) | R(AUCtau) | R(AUCtau/AUCinf) | Cmax (pg/mL) |
|---|---|---|---|---|---|---|
| DPI-386 Nasal Gel | Day 3 / Dose 5 | N | | 18 | 16 | 18 |
| | | Mean | | 0.996 | 0.929 | 146.694 |
| | | STD | | 0.6375 | 0.5979 | 58.9397 |
| | | CV (%) | | 64.03 | 64.33 | 40.18 |
| | | Median | | 0.910 | 0.835 | 134.500 |
| | | Min | | 0.24 | 0.31 | 63.80 |
| | | Max | | 2.37 | 2.23 | 279.00 |
| | | Geom. Mean | | 0.820 | 0.780 | 135.562 |
| | | SD (log) | | 0.6552 | 0.6052 | 0.4164 |
| | | %CVb | | 73.22 | 66.50 | 43.52 |
| | | 95% CI Lower | | 0.59 | 0.57 | 110.20 |
| | | 95% CI Upper | | 1.14 | 1.08 | 166.75 |
| | Day 3 / Dose 6 | N | | | | 18 |
| | | Mean | | | | 119.472 |
| | | STD | | | | 61.0135 |
| | | CV (%) | | | | 51.07 |
| | | Median | | | | 134.000 |
| | | Min | | | | 11.00 |
| | | Max | | | | 222.00 |
| | | Geom. Mean | | | | 94.408 |
| | | SD (log) | | | | 0.8686 |
| | | %CVb | | | | 105.14 |
| | | 95% CI Lower | | | | 61.29 |
| | | 95% CI Upper | | | | 145.41 |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6N

Summary of Scopolamine PK Parameters
PK Parameter Population

| Treatment | Visit | Statistics | R(Cmax) | Ctau (pg/mL) | t 1/2 (min) | tmax (min) |
|---|---|---|---|---|---|---|
| DPI-386 Nasal Gel | Day 3 / Dose 5 | N | 18 | 18 | 17 | 18 |
| | | Mean | 1.035 | 21.694 | 118.537 | 38.667 |
| | | STD | 0.6977 | 11.7169 | 39.2928 | 18.7303 |
| | | CV (%) | 67.41 | 54.01 | 33.15 | 48.44 |
| | | Median | 0.835 | 19.700 | 109.770 | 40.000 |
| | | Min | 0.36 | 4.35 | 72.48 | 10.00 |
| | | Max | 2.70 | 51.60 | 201.20 | 75.00 |
| | | Geom. Mean | 0.851 | 18.537 | 113.153 | |
| | | SD (log) | 0.6317 | 0.6267 | 0.3069 | |
| | | %CVb | 70.30 | 69.35 | 31.43 | |
| | | 95% CI Lower | 0.62 | 13.57 | 96.64 | |
| | | 95% CI Upper | 1.17 | 25.31 | 132.49 | |
| | Day 3 / Dose 6 | N | | | | 18 |
| | | Mean | | | | 74.167 |
| | | STD | | | | 50.5339 |
| | | CV (%) | | | | 68.14 |
| | | Median | | | | 60.000 |
| | | Min | | | | 15.00 |
| | | Max | | | | 240.00 |
| | | Geom. Mean | | | | |
| | | SD (log) | | | | |
| | | %CVb | | | | |
| | | 95% CI Lower | | | | |
| | | 95% CI Upper | | | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6O

Summary of Scopolamine PK Parameters
PK Parameter Population

| Treatment | Visit | Statistics | tlag (min) | tlast (min) | CL/F (mL/min) | Vz/F (mL) |
|---|---|---|---|---|---|---|
| DPI-386 Nasal Gel | Day 3 / Dose 5 | N | 18 | 18 | 18 | 17 |
| | | Mean | 0.000 | 355.167 | 8679.760 | 1431401.299 |
| | | STD | 0.0000 | 0.3835 | 4244.5716 | 823399.6000 |
| | | CV (%) | | 0.11 | 48.90 | 57.52 |
| | | Median | 0.000 | 355.000 | 7068.380 | 1314408.260 |
| | | Min | 0.00 | 355.00 | 3904.73 | 456311.18 |
| | | Max | 0.00 | 356.00 | 20335.39 | 3657118.47 |
| | | Geom. Mean | | | 7872.709 | 1248112.796 |
| | | SD (log) | | | 0.4432 | 0.5338 |
| | | %CVb | | | 45.58 | 57.42 |
| | | 95% CI Lower | | | 6315.61 | 948549.40 |
| | | 95% CI Upper | | | 9813.71 | 1642281.94 |
| | Day 3 / Dose 6 | N | | 18 | | |
| | | Mean | | 956.667 | | |
| | | STD | | 284.0257 | | |
| | | CV (%) | | 29.69 | | |
| | | Median | | 1080.000 | | |
| | | Min | | 300.00 | | |
| | | Max | | 1080.00 | | |
| | | Geom. Mean | | | | |
| | | SD (log) | | | | |
| | | %CVb | | | | |
| | | 95% CI Lower | | | | |
| | | 95% CI Upper | | | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:29 Program source: t_adpp.sas

FIG. 6P

Summary of Scopolamine PK Parameters
PK Parameter Population

| Treatment | Visit | Statistics | Cumulative Amount IP Excreted (mg) | Renal Clearance (L/hour) | Cumulative Percent IP Excreted (%) |
|---|---|---|---|---|---|
| DPI-386 Nasal Gel | Day 3 / Dose 5 | N | | | |
| | | Mean | | | |
| | | STD | | | |
| | | CV (%) | | | |
| | | Median | | | |
| | | Min | | | |
| | | Max | | | |
| | | Geom. Mean | | | |
| | | SD (log) | | | |
| | | %CVb | | | |
| | | 95% CI Lower | | | |
| | | 95% CI Upper | | | |
| | Day 3 / Dose 6 | N | 19 | 18 | 18 |
| | | Mean | 0.002 | 3.686 | 1.208 |
| | | STD | 0.0011 | 1.2233 | 0.7000 |
| | | CV (%) | 57.87 | 33.19 | 57.95 |
| | | Median | 0.002 | 3.470 | 1.100 |
| | | Min | 0.00 | 1.81 | 0.11 |
| | | Max | 0.00 | 6.08 | 2.76 |
| | | Geom. Mean | 0.001 | 3.495 | 0.951 |
| | | SD (log) | 0.8484 | 0.3403 | 0.8508 |
| | | %CVb | 102.66 | 35.04 | 103.08 |
| | | 95% CI Lower | 0.00 | 2.95 | 0.62 |
| | | 95% CI Upper | 0.00 | 4.14 | 1.45 |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6Q

Summary of Scopolamine PK Parameters
PK Parameter Population

| Treatment | Visit | Statistics | AUC0-inf (min*pg/mL) | AUCt (min*pg/mL) | AUC3d (min*pg/mL) | AUC %Extrap. (%) |
|---|---|---|---|---|---|---|
| Transderm Scop | Dose 1 | N | 1 | 20 | 20 | 3 |
| | | Mean | 444645.870 | 378267.916 | 378186.022 | 43.087 |
| | | STD | | 106430.8222 | 106416.6761 | 22.4912 |
| | | CV (%) | | 28.14 | 28.14 | 52.20 |
| | | Median | 444645.870 | 400451.205 | 400451.205 | 52.310 |
| | | Min | 444645.87 | 108840.49 | 108840.49 | 17.45 |
| | | Max | 444645.87 | 556896.04 | 556896.04 | 59.50 |
| | | Geom. Mean | 444645.870 | 359602.799 | 359527.511 | 37.870 |
| | | SD (log) | | 0.3596 | 0.3595 | 0.6741 |
| | | %CVb | | 37.15 | 37.15 | 75.85 |
| | | 95% CI Lower | | 303903.04 | 303846.18 | 7.10 |
| | | 95% CI Upper | | 425511.29 | 425412.72 | 202.09 |

Note: DFI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6R

Summary of Scopolamine PK Parameters
PK Parameter Population

| Treatment | Visit | Statistics | Cmax (pg/mL) | t 1/2 (min) | tmax (min) | tlag (min) |
|---|---|---|---|---|---|---|
| Transderm Scop | Dose 1 | N | 20 | 3 | 20 | 20 |
| | | Mean | 133.590 | 3722.890 | 1489.200 | 108.000 |
| | | STD | 44.2743 | 2332.6273 | 1279.1812 | 71.7892 |
| | | CV (%) | 33.14 | 62.66 | 86.13 | 66.47 |
| | | Median | 128.600 | 3831.750 | 721.000 | 120.000 |
| | | Min | 61.90 | 1337.68 | 420.00 | 0.00 |
| | | Max | 249.00 | 5999.12 | 4320.00 | 240.00 |
| | | Geom. Mean | 126.868 | 3132.894 | | |
| | | SD (log) | 0.3326 | 0.7703 | | |
| | | %CVb | 34.20 | 90.01 | | |
| | | 95% CI Lower | 108.58 | 462.24 | | |
| | | 95% CI Upper | 148.23 | 21233.46 | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.95.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas

FIG. 6S

Summary of Scopolamine PK Parameters
PK Parameter Population

| Treatment | Visit | Statistics | tlast (min) | CL/F (mL/min) | Vz/F (mL) |
|---|---|---|---|---|---|
| Transderm Scop | Dose 1 | N | 20 | 1 | 1 |
| | | Mean | 4320.850 | 2248.980 | 4340239.300 |
| | | STD | 2.3005 | | |
| | | CV (%) | 0.05 | | |
| | | Median | 4320.000 | 2248.980 | 4340239.300 |
| | | Min | 4320.00 | 2248.98 | 4340239.30 |
| | | Max | 4330.00 | 2248.98 | 4340239.30 |
| | | Geom. Mean | | 2248.980 | 4340239.300 |
| | | SD (log) | | | |
| | | %CVb | | | |
| | | 95% CI Lower | | | |
| | | 95% CI Upper | | | |

Note: DPI-386 Nasal Gel 0.2 mg scopolamine HBr was administered into one nostril twice daily, 6 hours apart within day, for 3 consecutive days.
Note: The scopolamine transdermal system (Transderm Scop) was applied once and delivers 1 mg of scopolamine over 3 days.
Note: Lambda_z related PK parameters were excluded from PK parameter summaries if Rsq < 0.85.
Note: AUCinf, CL/F, and Vz/F were excluded from summary if AUCexp > 30% for nasal gel Dose 1 and Transderm Scop Dose 1.
Note: R(Cmax) = Cmax,Dose5/Cmax,Dose1, R(AUCtau)= AUCtau,Dose5/AUCtau,Dose1, R(AUCtau/AUCinf)= AUCtau,Dose5/AUCinf,Dose1
Note: Subject 020 Transderm Scop data were excluded from the summary due to the transdermal scopolamine patch removed early.
Table Generation: 20APR2022 19:25 Program source: t_adpp.sas Study DPI-386-MS-31 Scopolamine Concentration-Time Profiles (Preliminary Data)

Note: Subject 1004 Period 2 (Nasal Gel), Dose 1, 5 minute concentration (968 pg/mL) was omitted from plot Note: Subject 1004 Period 2 (Nasal Gel), Dose 1, 5 minute concentration (968 pg/mL) was omitted from plot Note: Subject 1004 Period 2 (Nasal Gel), Dose 1, 5 minute concentration (968 pg/mL) was omitted from plot

Study DPI-386-MS-31 Scopolamine AUC3d & Cmax vs Treatment (Preliminary Data)

Note: Subject 1004 Period 2 (Nasal Gel), Dose 1, 5 minute concentration (968 pg/mL) was omitted from plots FIG. 6X Study DPI-386-MS-31 Scopolamine PK Summary

| | DPI-386 Nasal Gel 0.2 mg scopolamine HBr | | | | | | Transdermal Scopolamine (1.0 mg scopolamine) N=21 |
|---|---|---|---|---|---|---|---|
| PK Parameter | Dose 1 (Day 1 AM) N=20 | Dose 2 (Day 1 PM) N=20 | Dose 3 (Day 2 AM) N=18 | Dose 4 (Day 2 PM) N=18 | Dose 5 (Day 3 AM) N=18 | Dose 6 (Day 3 PM) N=18 | |
| AUC3d (pg*min/mL) | - | - | - | - | - | Doses 1-6 171,228 (57,731) | 387,981 (114,700) |
| Tlag (min) | 0 (0, 10) | Not done | Not done | Not done | 0 (0, 0) | Not done | 120 (0, 240) |
| Tmax (min) | 50 (20, 300) | 60 (30, 120) | 60 (15, 120) | 60 (15, 120) | 40 (10, 60) | 60 (15, 240) | 720 (420, 4320) 12 (7, 72) hours |
| Cmax (pg/mL) | 176 (74.0) | 148 (72.7) | 141 (70.8) | 127 (66.6) | 147 (58.9) | 120 (61.0) | 141 (49.9) |
| AUC(0-t) (pg*min/mL) | 26,681 (10,895) | 32,532 (17,458) | 22,044 (11,421) | 31,346 (15,534) | 21,923 (8956) | 32,940 (16,820) | 387,981 (114,700) |
| AUCtau (pg*min/mL) | 26,681 (10,895) | 34,410 (16,487) | 22,044 (11,421) | 31,700 (15,039) | 21,923 (8956) | 33,379 (16,212) | Not done |
| AUC(0-inf) (pg*min/mL) | 28,597 (10,869) [N=18] | Not done | Not done | Not done | Not done | Not done | Not done |
| t1/2 (min) | 95.2 (70.5, 160) [N=18] | Not done | Not done | Not done | 107 (74.9, 210) [N=17] | Not done | Not done |

Cmax, AUC(0-t), AUCtau, AUCinf presented as arithmetic mean (SD

Tlag, Tmax, t1/2 presented as median (minimum, maximum)

FIG. 6Y

Study DPI-386-MS-31 Statistical Comparison of Scopolamine PK

| | Geometric Least Squares Mean (GLSM) | | GLSM Ratio (90% CI) |
|---|---|---|---|
| **PK Parameter** | **DPI-386 Nasal Gel** | **Transdermal Scopolamine** | **DPI-386 Nasal Gel vs. Transdermal Scopolamine** |
| AUC3d (pg*min/mL) | 158,056 | 368,919 | 42.8 (34.4, 53.3) |
| Cmax (pg/mL) | 137.2 | 133.2 | 103.0 (83.8, 126.6) |

Note: A Geometric Mean Ratio of 100 = no difference between treatments

Individual Subject Concentration-Time Profiles (Log-linear Plots)

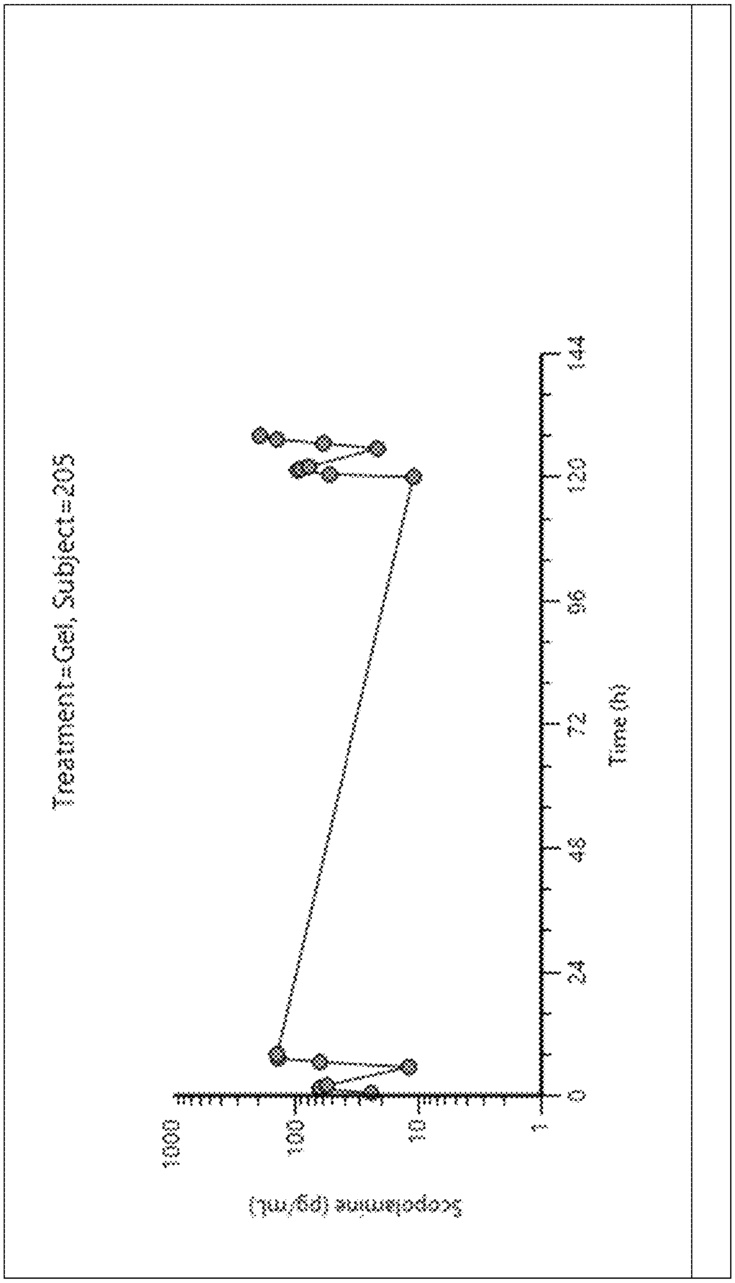
FIG. 6Zii

FIG. 6Ziii
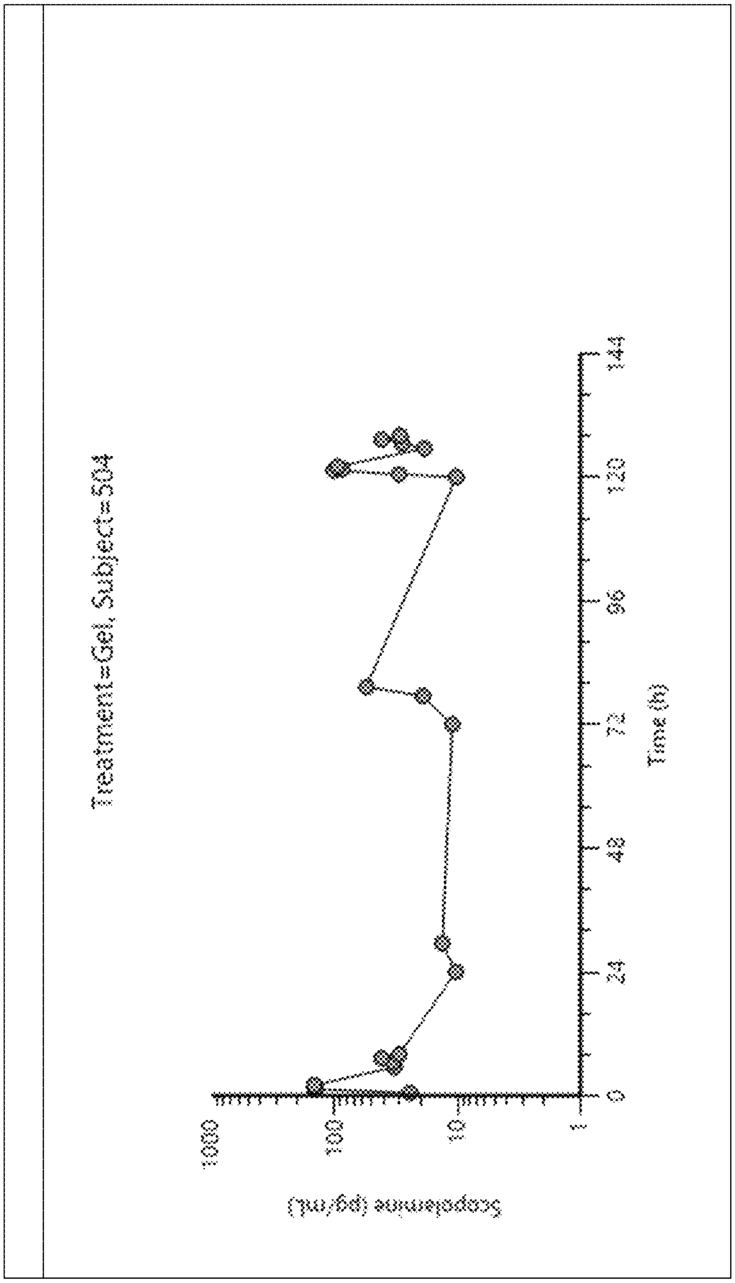

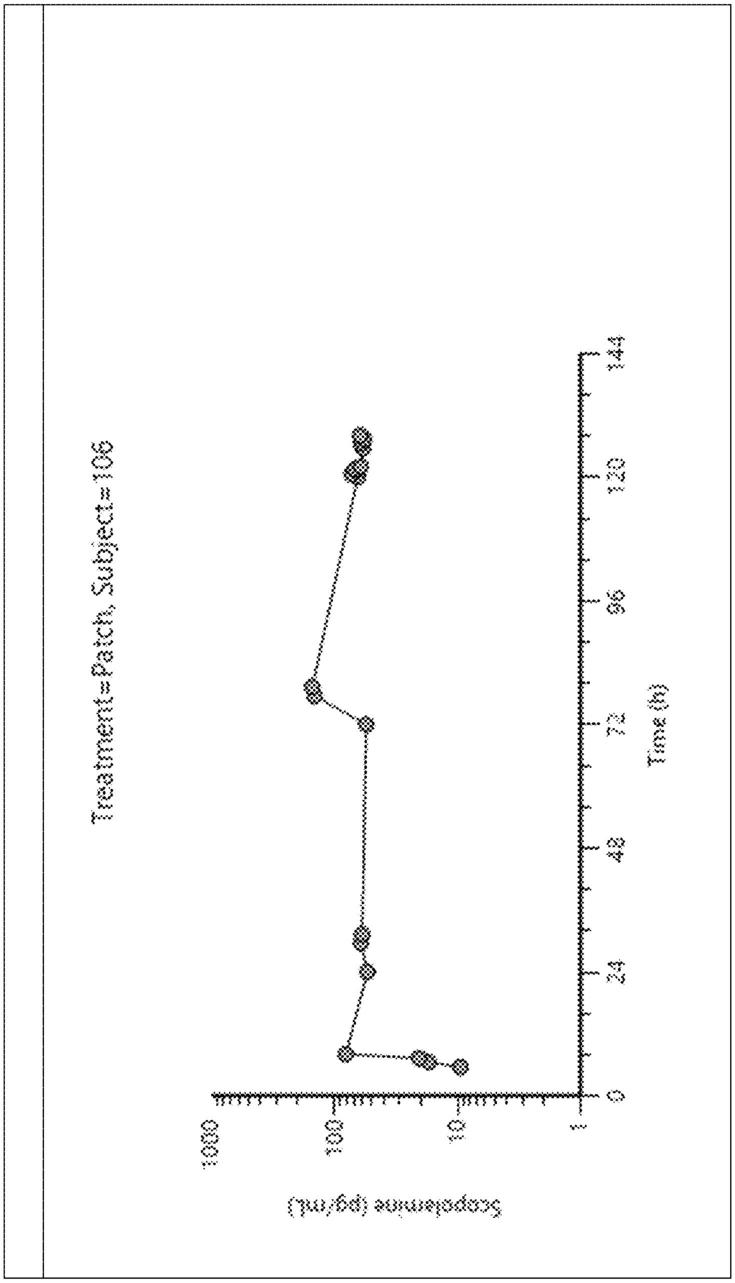
FIG. 6Ziv

FIG. 6Zvi
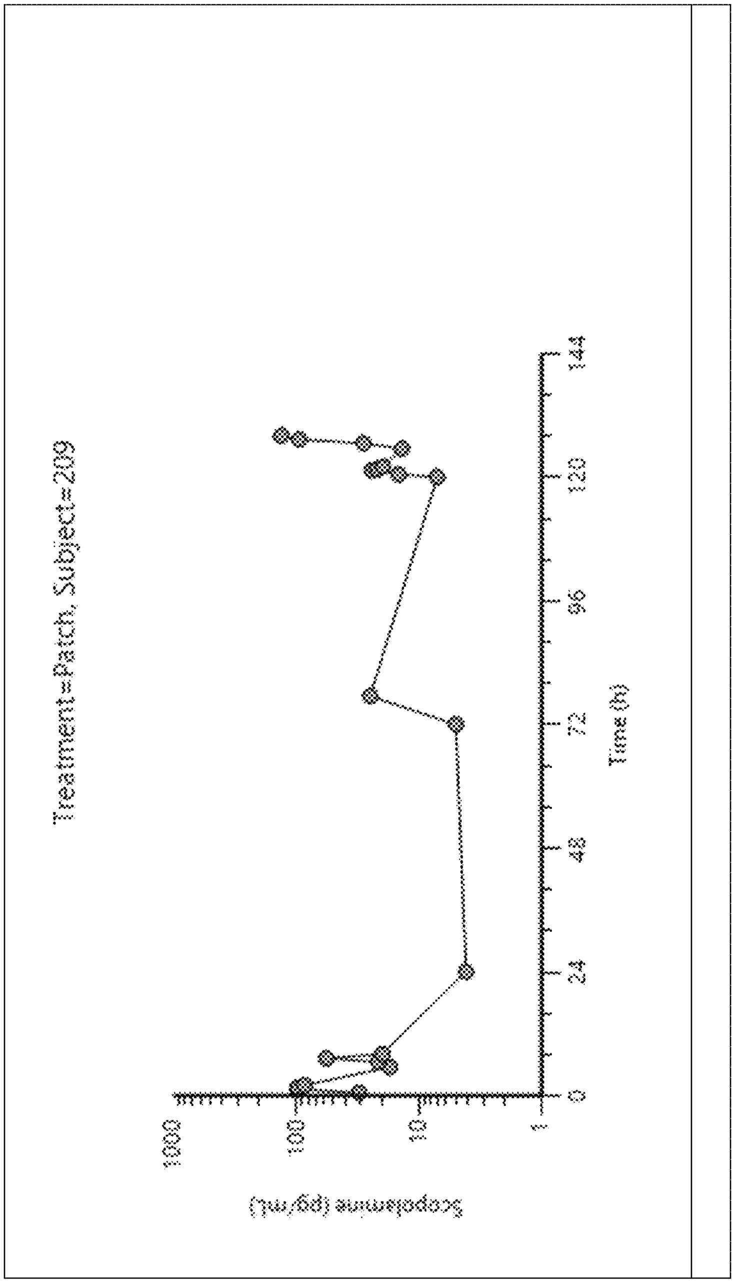

FIG. 6Zvii
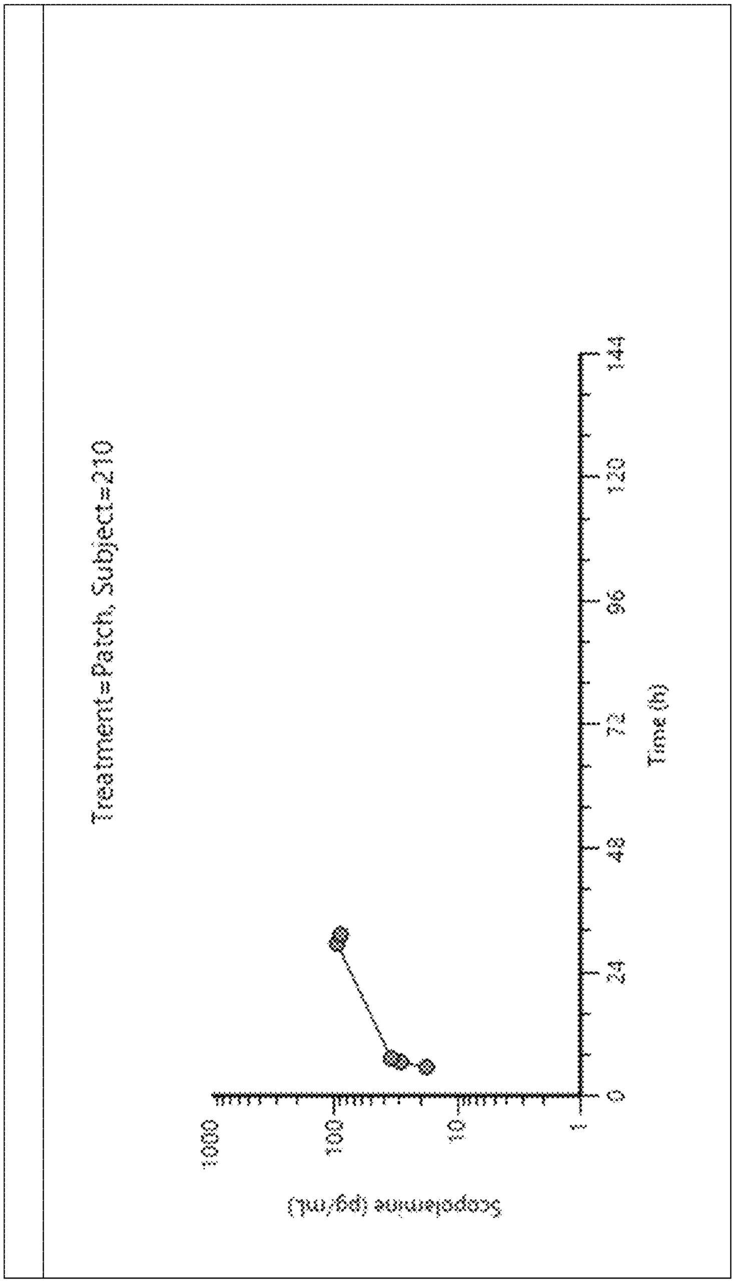

FIG. 6Zviii
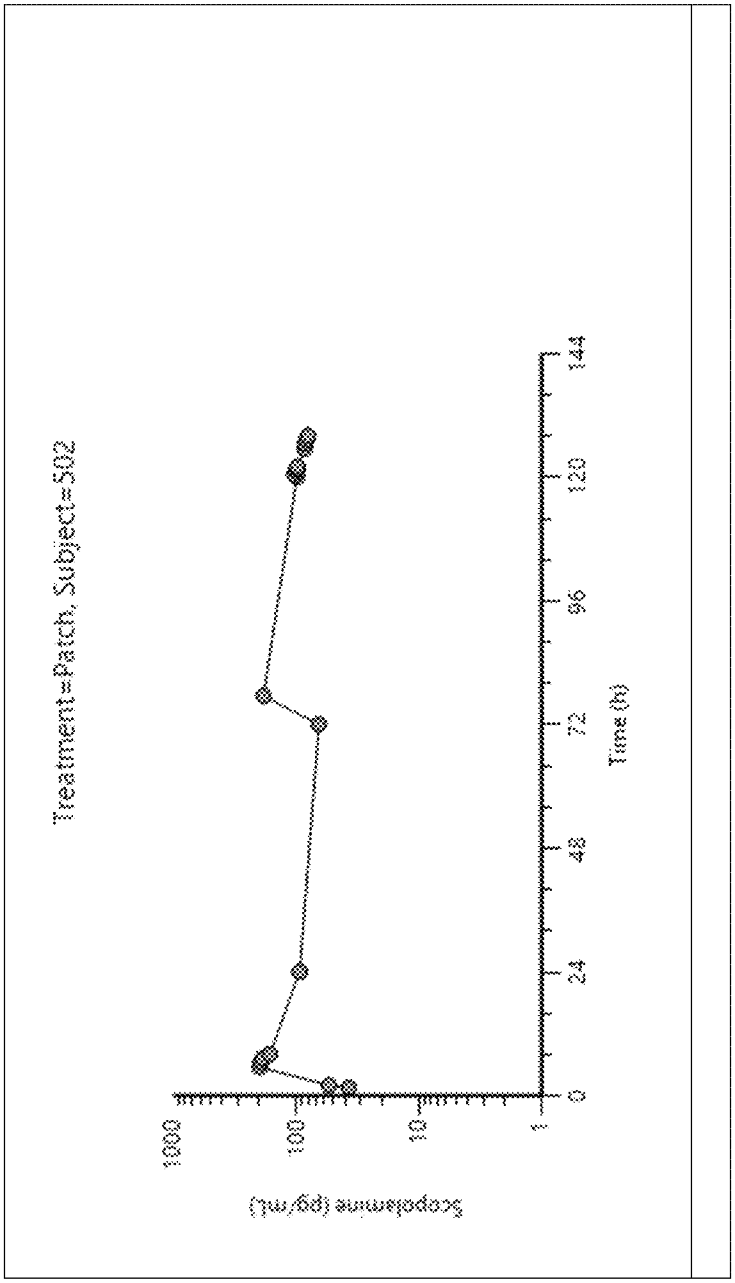

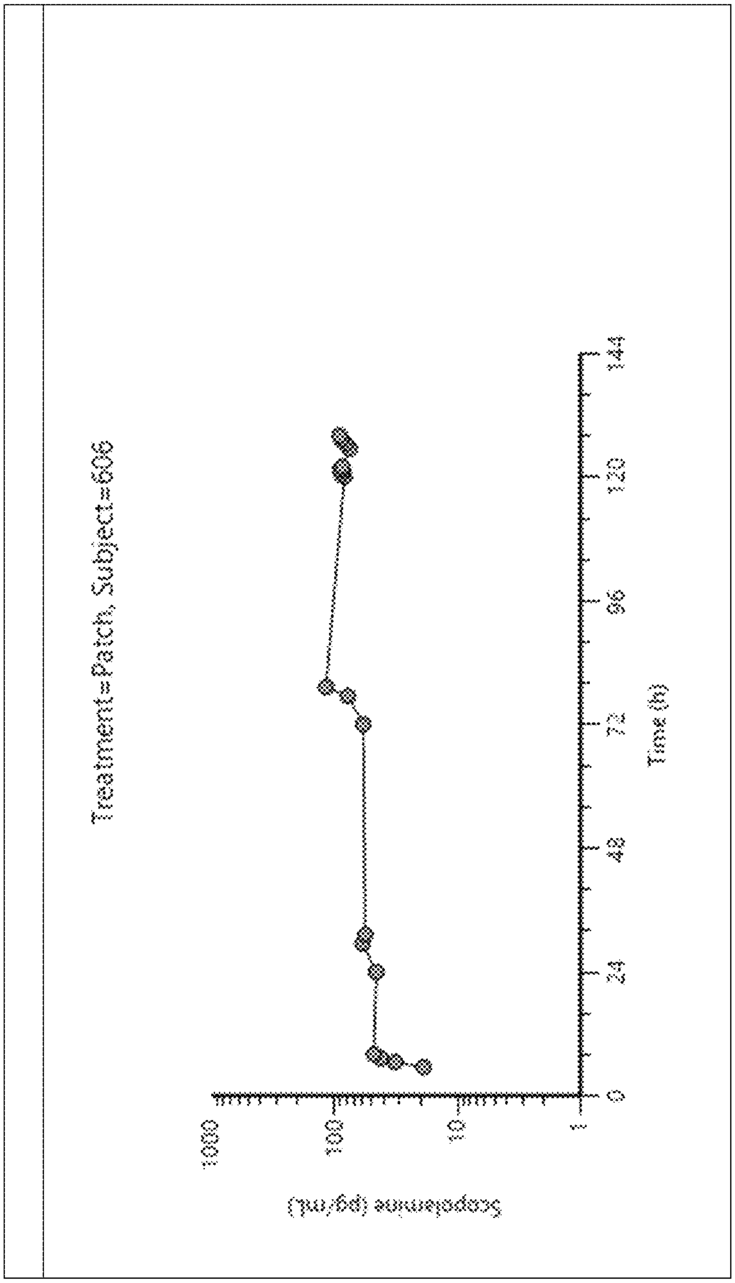
FIG. 6Zix

Mean Concentration-Time Plot of Study 07 Data using Study 31 Formatting

Median Concentration-Time Plot of Study 07 Data using Study 31 Formatting

Mean Concentration-Time Plot of Study 07 Data using Study 31 Formatting – Linear Plot

Mean Concentration-Time Plot of Study 31 Data – Linear Plot

Mean Concentration-Time Plot of Study 31 Data – Log-linear Plot

Linear Plot of Mean Concentration-Time Plot of Study 31 Data with Periods of Time with Gel Concentrations Greater than Patch Identified

FIG. 6GG

Calculation of Time that Gel Concentration is Greater than Patch Concentration over the 72 Hour Sampling Time

| Time2 | Time1 | Duration of Gel>Patch | Total Time | Patch>Gel | %Gel>Patch |
|---|---|---|---|---|---|
| 4.6 | 0 | 4.6 | | | |
| 8.2 | 6.3 | 1.9 | | | |
| 32 | 30.5 | 1.5 | | | |
| 50 | 48.3 | 1.7 | | | |
| 56.6 | 54.6 | 2 | | | |
| | | 11.7 | 72 | 60.3 | 16.3% |

Abbreviations: AE = adverse event; ITT = Intent-to-Treat; mITT = modified Intent-to-Treat; PP = Per Protocol Source: Table 14.1.5

FIG. 8A: Disposition of Subjects
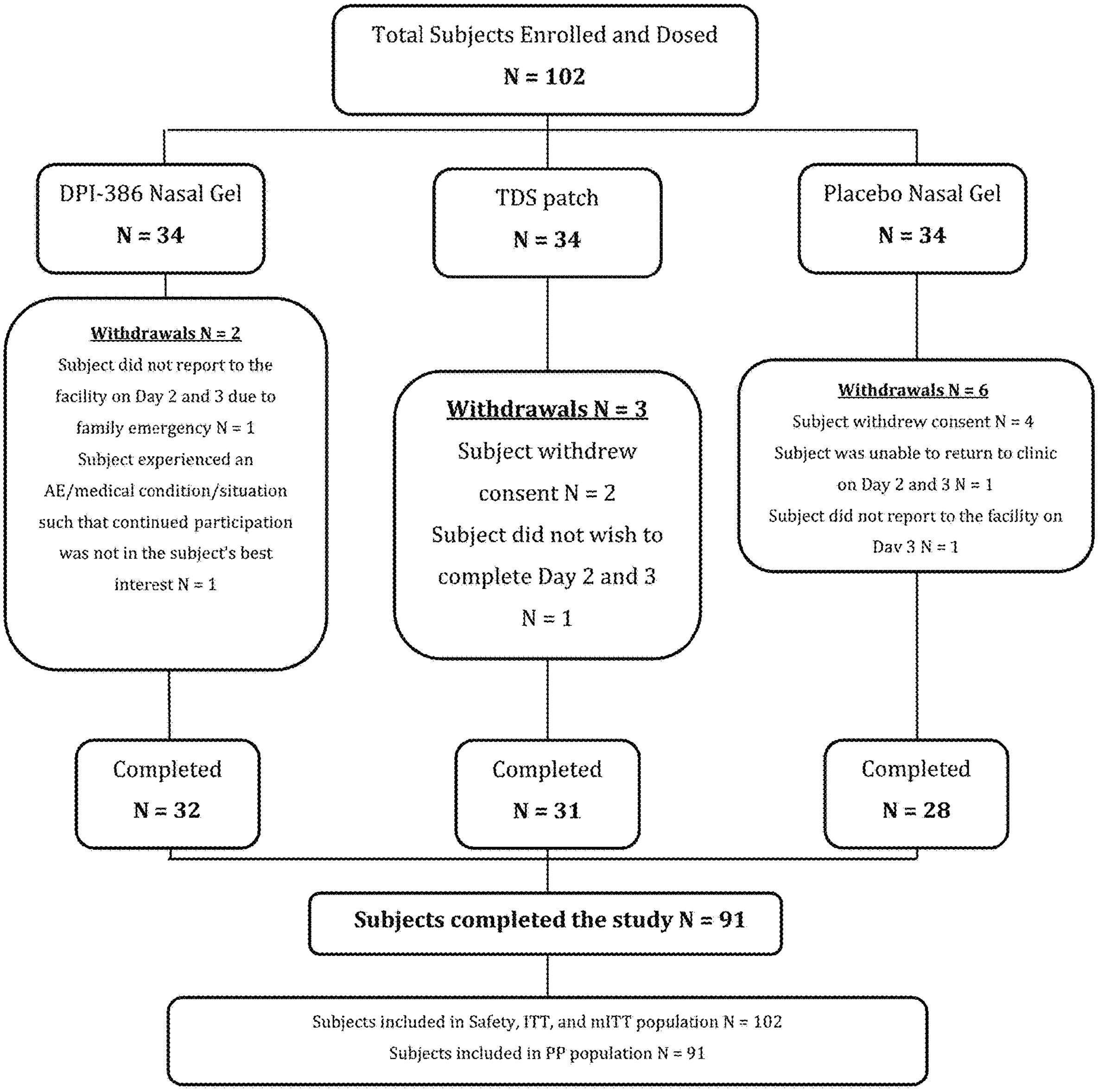
Abbreviations: ITT = Intent-to-Treat; mITT = modified Intent-to-Treat; TDS = transdermal scopolamine.
Source: Table 14.1.5

Median Plasma Scopolamine Concentration-Time Profiles, Days 2 and 3

Source: Figure 14.2.4.1, Table 14.2.3.1.1

Median Plasma Unbound Scopolamine Concentration-Time Profiles

Source: Figure 14.2.5.1, Table 14.2.3.1.2

Median Plasma Unbound Scopolamine Concentration-Time Profiles

COMPOSITIONS AND METHODS FOR THE TREATMENT OF MOTION SICKNESS AND EMESIS

CROSS-REFERENCE TO RELATED APPLICATIONS

This application is a continuation of U.S. patent application Ser. No. 18/230,236, filed on Aug. 4, 2023 which is incorporated by reference in its entirety.

TECHNICAL FIELD OF THE INVENTION

This disclosure is related to the area of treatment of one or more of motion sickness, nausea, and emesis, including prevention and rescue therapy. In particular, the disclosure relates to method and compositions for the efficacious treatment of motion sickness/emesis by administration of a nasal formulation of scopolamine.

BACKGROUND OF THE INVENTION

Scopolamine has been shown to be an effective anti-emetic for the prevention of one or more of nausea and emesis associated with motion sickness. Transdermal scopolamine has been commercially available in the US market since 1979. It was approved for the prevention of emesis due to motion sickness and for prevention of post-operative emesis. Scopolamine delivered as a transdermal patch has a delayed onset of at least 4-6 hours which makes it unsuitable for treatment of emesis once that has begun. This long delay of onset also means that the patch must be applied hours in advance of the stimulus leading to motion sickness, in order to prevent emesis.

The sensation of motion sickness has many manifestations. Motion sickness symptoms can be differentiated along four domains: gastrointestinal, central, peripheral, and sopite-related. The Motion Sickness Assessment Questionnaire (MSAQ) may be used to assess the overall experience of motion sickness using total scores, or may be used to assess the four distinct domains of motion sickness using subscale scores (Gianoros, P. J. et al., A Questionnaire for the Assessment of the Multiple Dimensions, Aviat Space Environ Med. 2001; 72(2): 115-119; also, see Graybiel, A, Knepton J. Sopite Syndrome: a sometimes sole manifestation of motion sickness. Aviat. Space Environ Med. 1976; 47(8): 873-882. Keshavarz, Behrang, Golding John F. Motion Sickness: current concepts and management. Current Opinion in Neurology, 2022; 35 Issue (1):107-112). Herein, the term motion sickness shall encompass any one or more of these symptoms in the four domains. What has been needed, then, is a fast-acting, effective, and safe drug for the prevention and the treatment of the effects of motion sickness.

Most subjects who experience motion sickness do not have emesis. Nevertheless, the sensation of motion sickness in any of its assorted manifestations can impair functioning because of adverse effects of motion sickness on cognition and motor performance. For example, motion sickness degrades attention, memory, reaction time, and concentration. Its adverse effects on motor function include impairment of hand-eye coordination and balance. Military and space personnel need a means of controlling motion sickness and its associated impairment of cognitive and motor function especially in an operational setting with potential life or death situations. Motion sickness can also impair training conducted in a simulator and in virtual environments as well (motion sickness may be induced by actual motion or by the sensation/perception of motion). Reference may be had to Gresty M A, Golding J F. Impact of Vertigo and Spatial disorientation on concurrent cognitive tasks. Ann NY Acad Sci 2009:1164:263-267, and Gresty M A, Golding J F, Le H, Nightingale K. Cognitive Impairment by Spatial Disorientation. Aviat Space Environ Med 2008; 79:105-111, each herein incorporated by reference regarding such background teaching. Accordingly, there is a need for a self-administered remedy, which may be administered repeatedly, if needed, safely and without a risk of substantial anticholinergic side effects.

There is also a need for a formulation and method of delivery that is safe and avoids anti-cholinergic adverse effects and toxicity, especially when dosing in real world situations is required or repeated sooner than advisable.

SUMMARY OF THE INVENTION

Disclosed herein is a formulation of scopolamine delivered transmucosally, by example intranasally, which is unexpectedly effective as a preventative for the sensation of motion sickness and for treatment of motion sickness. One aspect of the present disclosure is a surprising intranasal dosage that achieves bioequivalence when compared to existing transdermal formulations. While the formulation is effective for prevention and treatment of nausea and emesis often associated with motion sickness, it is able to provide the quick onset of prevention and relief from the one or more domains of motion sickness, including but not limited to Sopite related sensations and symptoms even when unaccompanied by nausea and emesis. Impairment of function due to motion sickness can start well before or even in the absence of nausea and vomiting. Indeed, most subjects who experience motion sickness do not progress to emesis, and yet they are dysfunctional due to symptoms such as dizziness, disorientation, sleepiness, fatigue, irritability, profuse sweating, and the like (Graybiel, A, Knepton J. Sopite Syndrome: a sometimes sole manifestation of motion sickness. Aviat. Space Environ Med. 1976; 47(8): 873-882).

A formulation and method of delivery that has satisfied the need for efficacy without unwanted anticholinergic side effects has not been previously identified. Herein, it is disclosed that superior efficacy can surprisingly be achieved at a lower Cmax and AUC than previous attempts. In fact, it was previously believed that intranasal formulations required a significantly higher Cmax and AUC (Wu, L. et al., "Dose Escalation Pharmacokinetics of Intranasal Scopolamine Gel Formulation," J. Clin. Pharmacology, 55(2): 195-203 (2014). Some even suggested dosages of scopolamine in intranasal formulations that contained twice as much scopolamine as the present disclosure (Simmons, R G, et al., The efficacy of low-dose intranasal scopolamine for motion sickness. Aviat Space Environ Med 2010; 81:405-12.). The logical assumption, albeit, incorrect, was that given the short half-life (approx. 90 minutes) of scopolamine, it was necessary to deliver a significantly higher dose to achieve the desired efficacy. A formulation and method of delivery are also disclosed wherein the bioavailability of the intranasal scopolamine achieved the dual goals of efficacy and safety. This results in an unexpectantly advantageous safety profile wherein the adverse events (AEs) associated with an anticholinergic effect were essentially identical to placebo. Also, the present disclosure surprisingly demonstrated significant protection from the degradation of cognitive and motor performance associated with motion sickness. Moreover, in an operational setting such as fishing, cargo carriers, driving, flying, military transport and combat, and the microgravity of space environments, a formulation is disclosed that provides retention in the nasal cavity to allow for delivery of the intended dose of scopolamine. This increased retention in harsh environments under vigorous movement or microgravity is essential to the ability to reliably deliver the correct dose. Moreover, adjusting viscosity to achieve the desired bioavailabilty exceeds what has been previously recommended. For example, Wu, et al. (2014) taught that higher viscosity of intranasal scopolamine should be avoided.

A formulation and method of delivery needs to be safe even if used inappropriately. When experiencing motion sickness, patients can become confused and, in an effort to ensure relief, they may ignore instructions on proper usage and instead administer to themselves multiple doses in rapid succession.

A formulation and method of delivery needs to be effective and yet safe for use in older patients. It is well recognized that older patients are particularly susceptible to anti-cholinergic side effects. In fact, the American Gerontology Society maintains a list of drugs that should be avoided by seniors and that list includes scopolamine (Beer's list). There is an unmet need, then, for a formulation and method of delivery of intranasal scopolamine that is effective for motion sickness yet safe for seniors to use. Scopolamine has been presumed to be more likely to lead to adverse effects for use by people over the age of 60 (American Gerantology Society). The transdermal scopolamine patch, for example, is not approved for use in seniors. The present disclosure, however, unexpectedly demonstrates that intranasal scopolamine with the bioavailability demonstrated herein can be used safely and effectively in seniors with minimal to no increased risk of adverse side effects or changes in pK parameters, and especially when compared to the pK parameters of 18 to 59 year old subjects.

A gel formulation and method of intranasal delivery preferably is used according to instructions. In particular, bioavailability of the gel formulation may be differentiated as between on delivery to nasal cavity and delivery to nasal septal mucosa. In particular, the nasal cavity defines the space inside the nose. The nasal cavity lies above the bone that forms the roof of the mouth and curves down at the back to join the throat. The space is divided into two sections called nasal passages. Air moves through these passages during breathing. The nasal passages filter and warm the air, and make it moist before it goes into the lungs.

In one aspect of the disclosure, an intranasal pharmaceutical composition for the prevention of one or more of nausea and emesis related to motion is disclosed which includes a pharmaceutically acceptable salt of scopolamine, wherein administration of the composition to a human subject results in a Cmax (pg/mL) of free scopolamine that approximates the steady state plasma concentration of a transdermal administration. One embodiment of the present disclosure provides a intranasal pharmaceutical composition for the prevention of, or rescue from, one or more of nausea and emesis related to motion, comprising a pharmaceutically acceptable salt of scopolamine, wherein administration of the composition to a human subject in a unit dosage amount to deliver about 0.2 mg scopoloamine results in a Cmax of free scopolamine that approximates the steady state plasma levels of free scopolamine by a transdermal administration of 1 mg delivered as a 1.5 mg patch over 72 hours.

One example of a transdermal administration includes a product marketed as TRANSDERM SCOP, scopolamine transdermal system patch, approved in 1979. As referenced in Renner et al., Pharmacokietics and pharmacodynamics in clinical use of scopolamine, Ther Drug Monit., 2005 Oct. 27(5) 655-65, peak plasma concentrations (Cmax) of approximately 100 pg/mL (range 11-240 pg/mL) of the alkaloid are reached after about either (8) hours and achieve steady state. As referenced in Nachu, et al., Transdermal scopolamine for prevention of motion sickness: clinical pharmacokinetics and therapeutic applications, Clin. Pharmacokinet. 2005, 45(6), 543-66, the threshold for therapeutic benefit is estimated to begin at about 50 pg/mL. Transdermal therapeutic system of scopolamine (TTS-S) attains that concentration after six (6) hours, a steady state of about 100 pg/mL is achieved 8-12 hours after application. Notably, 20-30% of subjects fail to attain the estimated protective concentration, and plasma concentrations measured in subjects who failed to respond to TTS-S were lower than in responders.

In some embodiments, the Cmax of the intranasal pharmaceutical composition is measured with a 90% confidence interval which is 80% to 125% of a least squares geometric mean of between about 160 pg/mL to 60 pg/mL. In certain embodiments, the Cmax of the intranasal pharmaceutical composition is measured with a 90% confidence interval which is 80% to 125% of a least squares geometric mean of between about 140 pg/mL to 80 pg/mL. In some embodiments, the Cmax of the intranasal pharmaceutical composition is measured with a 90% confidence interval which is 80% to 125% of a least squares geometric mean of between about 120 pg/mL to 80 pg/mL. In certain embodiments, the Cmax of the intranasal pharmaceutical composition is measured with a 90% confidence interval which is 80% to 125% of a least squares geometric mean of between about 100 pg/mL to 80 pg/mL.

In some embodiments, the Cmax of the intranasal pharmaceutical composition is measured with a 90% confidence interval, which is 80% to 125% of a least squares geometric mean of about 87 pg/mL. In some embodiments, the Cmax of the intranasal pharmaceutical composition is measured with a 90% confidence interval, which is 80% to 125% of a least squares geometric mean of about 92 pg/mL. In some embodiments, the Cmax of the intranasal pharmaceutical composition is measured with a 90% confidence interval, which is 80% to 125% of a least squares geometric mean of about 137 pg/mL. As will be appreciated by those skilled in the art, when making comparisons of pharmacokinetic parameters, such as Cmax, it is preferential to conduct a direct head-to-head comparison, wherein the measurements are collected and analyzed by the same lab, using the same techniques, and under the same conditions. Most preferably, a comparison is made using a crossover trial, namely in which all participants receive the same two or more treatments, but the order in which they receive them depends on the group to which they are randomly assigned. Moreover, comparator analyses should be consistent, whether calculated or measured, to ensure a direct comparison without artificial bias.

In another aspect of the disclosure, an intranasal pharmaceutical composition for the treatment of one or more symptoms associated with nausea or emesis related to motion includes a pharmaceutically acceptable salt of scopolamine, wherein administration of the composition to a human subject results in a Cmax (pg/mL) of free scopolamine that approximates a transdermal administration. In some embodiments, the Cmax of the intranasal pharmaceutical composition is measured with a 90% confidence interval which is 80% to 125% of a least squares geometric mean of between about 160 pg/mL to 60 pg/mL. In certain embodiments, the Cmax of the intranasal pharmaceutical composition is measured with a 90% confidence interval which is 80% to 125% of a least squares geometric mean of between about 140 pg/mL to 80 pg/mL. In certain embodiments, the Cmax of the intranasal pharmaceutical composition is measured with a 90% confidence interval which is 80% to 125% of a least squares geometric mean of between about 120 pg/mL to 80 pg/mL. In some embodiments, the Cmax of the intranasal pharmaceutical composition is measured with a 90% confidence interval which is 80% to 125% of a least squares geometric mean of between about 100 pg/mL to 80 pg/mL.

In some embodiments, the Cmax of the intranasal pharmaceutical composition is measured with a 90% confidence interval which is 80% to 125% of a least squares geometric mean of about 87 pg/mL. In certain embodiments, the Cmax of the intranasal pharmaceutical composition is measured with a 90% confidence interval which is 80% to 125% of a least squares geometric mean of about 137 pg/mL.

In one aspect of the disclosure, an intranasal pharmaceutical composition for the prevention of one or more of nausea and emesis related to motion includes a pharmaceutically acceptable salt of scopolamine, wherein administration of the composition to a human subject results in a Cmax (pg/mL) of free scopolamine with a 90% confidence interval which is 80% to 125% of a least squares geometric mean of between about 160 pg/mL to about 60 pg/mL. In some embodiments, the intranasal pharmaceutical composition has a least squares geometric mean of between about 140 pg/mL to 80 pg/mL. In certain embodiments, the intranasal pharmaceutical composition has a least squares geometric mean of between about 137 pg/mL to about 87 pg/mL.

In another aspect of the disclosure, an intranasal pharmaceutical composition for the treatment of one or more of nausea and emesis related to motion includes a pharmaceutically acceptable salt of scopolamine, wherein administration of the composition to a human subject results in a Cmax (pg/mL) of free scopolamine with a 90% confidence interval which is 80% to 125% of a least squares geometric mean of between about 160 pg/mL to about 60 pg/mL. In certain embodiments, the intranasal pharmaceutical composition has a least squares geometric mean of between about 140 pg/mL to 80 pg/mL. In some embodiments, the intranasal pharmaceutical composition has a least squares geometric mean of between about 137 pg/mL to about 87 pg/mL.

In one aspect of the disclosure, an intranasal pharmaceutical composition for the prevention of one or more of nausea and emesis related to motion includes a pharmaceutically acceptable salt of scopolamine, wherein administration of the composition to a human subject results in a Cmax of free scopolamine with a 90% confidence interval which is 80% to 125% of a least squares geometric mean of less than about 160 pg/mL following administration. In some embodiments, the intranasal pharmaceutical composition has a least squares geometric mean of greater than about 60 pg/mL. In certain embodiments, the intranasal pharmaceutical composition has a least squares geometric mean of about 155, 150, 145, 140, 135, 130, 125, 120, 115, 110, 105, 100, 95, 90, 85, 80, 75, 70, 65, or 60 pg/mL.

In another aspect of the disclosure, an intranasal pharmaceutical composition for the treatment of one or more of nausea and emesis related to motion includes a pharmaceutically acceptable salt of scopolamine, wherein administration of the composition to a human subject results in a Cmax of free scopolamine with a 90% confidence interval which is 80% to 125% of a least squares geometric mean of less than about 160 pg/mL following administration. In some embodiments, the intranasal pharmaceutical composition has a least squares geometric mean of greater than about 60 pg/mL. In certain embodiments, the intranasal pharmaceutical composition has a least squares geometric mean of about 155, 150, 145, 140, 135, 130, 125, 120, 115, 110, 105, 100, 95, 90, 85, 80, 75, 70, 65, or 60 pg/mL.

In one aspect of the disclosure, an intranasal pharmaceutical composition for the prevention of nausea and emesis related to motion includes a pharmaceutically acceptable salt of scopolamine, wherein administration of the composition to a human subject results in a least squares geometric mean Cmax of free scopolamine of from about 160 pg/mL to about 60 pg/mL. In certain embodiments, the intranasal pharmaceutical composition has a least squares geometric mean Cmax of free scopolamine of from about 150 pg/mL to about 70 pg/mL. In some embodiments, the intranasal pharmaceutical composition has a least squares geometric mean Cmax of free scopolamine of from about 140 pg/mL to about 80 pg/mL. In some embodiments, the intranasal pharmaceutical composition has a least squares geometric mean Cmax of free scopolamine of from about 137 pg/mL to about 87 pg/mL.

In another aspect of the disclosure, an intranasal pharmaceutical composition for the prevention of one or more of nausea and emesis related to motion includes a pharmaceutically acceptable salt of scopolamine, wherein administration of the composition to a human subject results in a Cmax (pg/mL) of free scopolamine with a 90% confidence interval which is 80% to 125% of a least squares geometric mean of about 160 pg/mL to about 80 pg/mL. In some embodiments, the intranasal pharmaceutical composition has a least squares geometric mean of about 137 pg/mL. In certain embodiments, the least squares geometric mean of the intranasal pharmaceutical composition is about 87 pg/mL.

In one aspect of the present disclosure, an intranasal pharmaceutical composition for the treatment of one or more of nausea and emesis related to motion includes a pharmaceutically acceptable salt of scopolamine, wherein administration of the composition to a human subject results in a Cmax (pg/mL) of free scopolamine with a 90% confidence interval which is 80% to 125% of a least squares geometric mean of about 160 pg/mL to about 90 pg/mL. In certain embodiments, the least squares geometric mean of the intranasal pharmaceutical composition is about 137 pg/mL. In some embodiments, the least squares geometric mean of the intranasal pharmaceutical composition is about 87 pg/mL.

In another aspect of the disclosure, an intranasal pharmaceutical composition for the prevention of one or more of nausea and emesis related to motion includes a pharmaceutically acceptable salt of scopolamine, wherein administration of the composition to a human subject results in a Cmax (pg/mL) of free scopolamine with a 90% confidence interval which is 80% to 125% of a least squares geometric mean of about 137 pg/mL.

In another aspect of the disclosure, an intranasal pharmaceutical composition for the treatment of one or more of nausea and emesis related to motion includes a pharmaceutically acceptable salt of scopolamine, wherein administration of the composition to a human subject results in a Cmax (pg/mL) of free scopolamine with a 90% confidence interval which is 80% to 125% of a least squares geometric mean of about 137 pg/mL.

In one aspect of the disclosure, an intranasal pharmaceutical composition for the treatment of one or more of nausea and emesis related to motion includes a pharmaceutically acceptable salt of scopolamine, wherein administration of the composition to a human subject results in a Cmax (pg/mL) of free scopolamine with a 90% confidence interval which is 80% to 125% of a least squares geometric mean of about 87 pg/mL.

In one aspect of the present disclosure, an intranasal pharmaceutical composition for the treatment of one or more of nausea and emesis related to motion includes a pharmaceutically acceptable salt of scopolamine, wherein administration of the composition to a human subject results in a Cmax (pg/mL) of free scopolamine with a 90% confidence interval which is 80% to 125% of a least squares geometric mean of about 87 pg/mL.

In one aspect of the disclosure, an intranasal pharmaceutical composition for the prevention of nausea and emesis related to motion is disclosed which includes a pharmaceutically acceptable salt of scopolamine, wherein administration of the composition to a human subject results in an AUC selected from one or more of AUC3d, AUCinf, AUCt, and AUCtau with a 90% confidence interval (CI) which is 80% to 125% of a least squares geometric mean that approximates a transdermal administration. In another aspect of the disclosure, an intranasal pharmaceutical composition for the treatment of nausea and emesis related to motion includes a pharmaceutically acceptable salt of scopolamine, wherein administration of the composition to a human subject results in an AUC selected from one or more of AUC3d, AUCinf, AUCt, and AUCtau with a 90% confidence interval (CI) which is 80% to 125% of a least squares geometric mean that approximates a transdermal administration. In some embodiments, the AUC of the intranasal pharmaceutical composition is AUC3d and the least squares geometric mean is about 155,937 min*pg/mL. In certain embodiments, the AUC of the intranasal pharmaceutical composition is AUCinf and the least squares geometric mean is about 26305 min*pg/mL. In some embodiments, the AUC of the intranasal pharmaceutical composition is AUCt and the least squares geometric mean is about 18545 min*pg/mL to about 26532 min*pg/mL. In some embodiments, the AUC of the intranasal pharmaceutical composition is AUCtau and the least squares geometric mean is about 18624 min*pg/mL to about 29120 min*pg/mL.

In one aspect of the present disclosure, an intranasal pharmaceutical composition for the prevention of nausea and emesis related to motion includes a pharmaceutically acceptable salt of scopolamine, wherein administration of the composition to a human subject results in an AUC3d of free scopolamine with a 90% confidence interval (CI) which is 80% to 125% of a least squares geometric mean of about 155,937 min*pg/mL. In another aspect of the disclosure, an intranasal pharmaceutical composition for the prevention of nausea and emesis related to motion includes a pharmaceutically acceptable salt of scopolamine, wherein administration of the composition to a human subject results in an AUC0-inf of free scopolamine with a 90% confidence interval (CI) which is 80% to 125% of a least squares geometric mean of about 26305 min*pg/mL following administration. In another aspect of the disclosure, an intranasal pharmaceutical composition for the prevention of nausea and emesis related to motion includes a pharmaceutically acceptable salt of scopolamine, wherein administration of the composition to a human subject results in an AUCt of free scopolamine with a 90% confidence interval (CI) which is 80% to 125% of a least squares geometric mean of about 18545 min*pg/mL to about 26532 min*pg/mL following administration.

In one aspect of the present disclosure, an intranasal pharmaceutical composition for the prevention of nausea and emesis related to motion includes a pharmaceutically acceptable salt of scopolamine, wherein administration of the composition to a human subject results in an AUCtau of free scopolamine with a 90% confidence interval (CI) which is 80% to 125% of a least squares geometric mean of about 18624 min*pg/mL to about 29120 min*pg/mL following administration. In another aspect of the present disclosure, an intranasal pharmaceutical composition for the treatment of nausea and emesis related to motion includes a pharmaceutically acceptable salt of scopolamine, wherein administration of the composition to a human subject results in an AUC3d of free scopolamine with a 90% confidence interval (CI) which is 80% to 125% of a least squares geometric mean of about 155,937 min*pg/mL.

In one aspect of the present disclosure, an intranasal pharmaceutical composition for the treatment of nausea and emesis related to motion includes a pharmaceutically acceptable salt of scopolamine, wherein administration of the composition to a human subject results in an AUC0-inf of free scopolamine with a 90% confidence interval (CI) which is 80% to 125% of a least squares geometric mean of about 26305 min*pg/mL following administration. In one aspect of the disclosure, an intranasal pharmaceutical composition for the treatment of nausea and emesis related to motion includes a pharmaceutically acceptable salt of scopolamine, wherein administration of the composition to a human subject results in an AUCt of free scopolamine with a 90% confidence interval (CI) which is 80% to 125% of a least squares geometric mean of about 18545 min*pg/mL to about 26532 min*pg/mL following administration. In another aspect of the disclosure, an intranasal pharmaceutical composition for the treatment of nausea and emesis related to motion includes a pharmaceutically acceptable salt of scopolamine, wherein administration of the composition to a human subject results in an AUCtau of free scopolamine with a 90% confidence interval (CI) which is 80% to 125% of a least squares geometric mean of about 18624 min*pg/mL to about 29120 min*pg/mL following administration.

In one aspect of the present disclosure, an intranasal pharmaceutical composition for the prevention of nausea and emesis related to motion includes a pharmaceutically acceptable salt of scopolamine, wherein administration of the composition to a human subject results in an AUC3d of free scopolamine with a 90% confidence interval which is 80% to 125% of a least squares geometric mean of less than about 182,116 min*pg/mL following administration. In one aspect of the present disclosure, an intranasal pharmaceutical composition for the prevention of nausea and emesis related to motion includes a pharmaceutically acceptable salt of scopolamine, wherein administration of the composition to a human subject results in an AUC3d of free scopolamine of from about 91,058 min*pg/mL to about 182,116 min*pg/mL following administration.

In another aspect of the present disclosure, an intranasal pharmaceutical composition for the treatment of nausea and emesis related to motion includes a pharmaceutically acceptable salt of scopolamine, wherein administration of the composition to a human subject results in an AUC3d of free scopolamine with a 90% confidence interval which is 80% to 125% of a least squares geometric mean of less than about 182,116 min*pg/mL following administration. In one aspect of the disclosure, an intranasal pharmaceutical composition for the treatment of nausea and emesis related to motion includes a pharmaceutically acceptable salt of scopolamine, wherein administration of the composition to a human subject results in an AUC3d of free scopolamine of from about 91,058 min*pg/mL to about 182,116 min*pg/mL following administration.

In one aspect of the present disclosure, an intranasal pharmaceutical composition for the prevention of symptoms associated with motion includes a pharmaceutically acceptable salt of scopolamine, wherein administration of the composition to a human subject results in a Cmax (pg/mL) of free scopolamine with a 90% confidence interval which is 80% to 125% of a least squares geometric mean that approximates a transdermal administration. In another aspect of the present disclosure, an intranasal pharmaceutical composition for the treatment of symptoms associated with motion includes a pharmaceutically acceptable salt of scopolamine, wherein administration of the composition to a human subject results in a Cmax (pg/mL) of free scopolamine with a 90% confidence interval which is 80% to 125% of a least squares geometric mean that approximates a transdermal administration. In some embodiments, the least squares geometric mean of the intranasal pharmaceutical composition is less than about 160 pg/mL. In certain embodiments, the least squares geometric mean of the intranasal pharmaceutical composition is from about 160 pg/mL to about 60 pg/mL. In certain embodiments, the least squares geometric mean of the intranasal pharmaceutical composition is about 155, 150, 145, 140, 135, 130, 125, 120, 115, 110, 105, 100, 95, 90, 85, 80, 75, 70, 65, or 60 pg/mL.

In one aspect of the present disclosure, an intranasal pharmaceutical composition for the presentation of symptoms associated with motion includes a pharmaceutically acceptable salt of scopolamine, wherein administration of the composition to human subject results in an AUC selected from one or more of AUC3d, AUCinf, AUCt, and AUCtau with a 90% confidence interval (CI) which is 80% to 125% of a least squares geometric mean that approximates a transdermal administration. In another aspect of the present disclosure, an intranasal pharmaceutical composition for the treatment of symptoms associated with motion includes a pharmaceutically acceptable salt of scopolamine, wherein administration of the composition to a human subject results in an AUC selected from one or more of AUC3d, AUCinf, AUCt, and AUCtau with a 90% confidence interval (CI) which is 80% to 125% of a least squares geometric mean that approximates a transdermal administration. In certain embodiments, the AUC of the intranasal pharmaceutical composition is AUC3d and the least squares geometric mean is about 155,937 min*pg/mL. In some embodiments, the AUC of the intranasal pharmaceutical composition is AUCinf and the least squares geometric mean is about 26305 min*pg/mL. In some embodiments, the AUC of the intranasal pharmaceutical composition is AUCt and the least squares geometric mean is about 18545 min*pg/mL to about 26532 min*pg/mL. In certain embodiments, the AUC of the intranasal pharmaceutical composition is AUCtau and the least squares geometric mean is about 18624 min*pg/mL to about 29120 min*pg/mL.

In another aspect of the present disclosure, an intranasal pharmaceutical composition for the prevention of symptoms associate with motion comprises a pharmaceutically acceptable salt of scopolamine, wherein administration of the composition to a human subject results in an AUC3d of free scopolamine with a 90% confidence interval (CI) which is 80% to 125% of a least squares geometric mean of about 155,937 min*pg/mL. In one aspect of the present disclosure, an intranasal pharmaceutical composition for the prevention of symptoms associated with motion comprises a pharmaceutically acceptable salt of scopolamine, wherein administration of the composition to a human subject results in an AUC0-inf of free scopolamine with a 90% confidence interval (CI) which is 80% to 125% of a least squares geometric mean of about 26305 min*pg/mL following administration.

In one aspect of the present disclosure, an intranasal pharmaceutical composition for the prevention of symptoms associated with motion includes a pharmaceutically acceptable salt of scopolamine, wherein administration of the composition to a human subject results in an AUCt of free scopolamine with a 90% confidence interval (CI) which is 80% to 125% of a least squares geometric mean of about 18545 min*pg/mL to about 26532 min*pg/mL following administration. In another aspect of the present disclosure, an intranasal pharmaceutical composition for the prevention of symptoms associated with motion includes a pharmaceutically acceptable salt of scopolamine, wherein administration of the composition to a human subject results in an AUCtau of free scopolamine with a 90% confidence interval (CI) which is 80% to 125% of a least squares geometric mean of about 18624 min*pg/mL to about 29120 min*pg/mL following administration.

In one aspect of the disclosure, an intranasal pharmaceutical composition for the treatment of symptoms associated with motion includes a pharmaceutically acceptable salt of scopolamine, wherein administration of the composition to a human subject results in an AUC3d of free scopolamine with a 90% confidence interval (CI) which is 80% to 125% of a least squares geometric mean of about 155,937 min*pg/mL. In another aspect of the present disclosure, an intranasal pharmaceutical composition for the treatment of symptoms associated with motion includes a pharmaceutically acceptable salt of scopolamine, wherein administration of the composition to a human subject results in an AUC0-inf of free scopolamine with a 90% confidence interval (CI) which is 80% to 125% of a least squares geometric mean of about 26305 min*pg/mL following administration.

In another aspect of the present disclosure, an intranasal pharmaceutical composition for the treatment of symptoms associated with motion includes a pharmaceutically acceptable salt of scopolamine, wherein administration of the composition to a human subject results in an AUCt of free scopolamine with a 90% confidence interval (CI) which is 80% to 125% of a least squares geometric mean of about 18545 min*pg/mL to about 26532 min*pg/mL following administration. In one aspect of the disclosure, an intranasal pharmaceutical composition for the treatment of symptoms associated with motion includes a pharmaceutically acceptable salt of scopolamine, wherein administration of the composition to a human subject results in an AUCtau of free scopolamine with a 90% confidence interval (CI) which is 80% to 125% of a least squares geometric mean of about 18624 min*pg/mL to about 29120 min*pg/mL following administration.

In one aspect of the present disclosure, an intranasal pharmaceutical composition for the of symptoms associated with motion includes a pharmaceutically acceptable salt of scopolamine, wherein administration of the composition to a human subject results in an AUC3d of free scopolamine with a 90% confidence interval which is 80% to 125% of a least squares geometric mean of less than about 182,116 min*pg/mL following administration. In one aspect of the present disclosure, an intranasal pharmaceutical composition for the prevention of symptoms associated with motion includes a pharmaceutically acceptable salt of scopolamine, wherein administration of the composition to a human subject results in an AUC3d of free scopolamine of from about 91,058 min*pg/mL to about 182,116 min*pg/mL following administration.

In one aspect of the disclosure, an intranasal pharmaceutical composition for the treatment of symptoms associated with motion includes a pharmaceutically acceptable salt of scopolamine, wherein administration of the composition to a human subject results in an AUC3d of free scopolamine with a 90% confidence interval which is 80% to 125% of a least squares geometric mean of less than about 182,116 min*pg/mL following administration. In another aspect of the present disclosure, an intranasal pharmaceutical composition for the treatment of symptoms associated with motion includes a pharmaceutically acceptable salt of scopolamine, wherein administration of the composition to a human subject results in an AUC3d of free scopolamine of from about 91,058 min*pg/mL to about 182,116 min*pg/mL following administration.

In one aspect of the present disclosure, a method is disclosed for one or more of treating, rescue therapy, and preventing one or more symptoms associated with one or more of nausea and emesis related to one or more of actual motion and virtual motion, the method including administering to a human subject in need thereof the intranasal pharmaceutical composition of any of the above embodiments.

In one aspect of the present disclosure, an intranasal pharmaceutical composition is disclosed which includes scopolamine or a pharmaceutically acceptable salt thereof as a gel having a viscosity of about 1750 to 3500 centistokes. In certain embodiments, the intranasal pharmaceutical composition is a gel comprising scopolamine or a pharmaceutically acceptable salt thereof having a viscosity of about 1750 to 3500 centistokes. In some embodiments, the intranasal pharmaceutical composition is a gel comprising scopolamine or a pharmaceutically acceptable salt thereof, having a viscosity of about 2000 to 3000 centistokes. In some embodiments, the intranasal pharmaceutical composition is a gel comprising scopolamine or a pharmaceutically acceptable salt thereof, having a viscosity of about 2300 centistokes.

In certain embodiments, the intranasal pharmaceutical composition or method of using the intranasal pharmaceutical composition has scopolamine present at a concentration of from about 0.15% (w/w) to about 0.18% (w/w). In some embodiments, the intranasal pharmaceutical composition or method of using the intranasal pharmaceutical composition has scopolamine present at a concentration of about 0.167% (w/w). In some embodiments, the intranasal pharmaceutical composition or method of using the intranasal pharmaceutical composition has scopolamine that is scopolamine hydrobromide. In certain embodiments, the intranasal pharmaceutical composition or method of using the intranasal pharmaceutical composition includes polyvinyl alcohol. In certain embodiments, the intranasal pharmaceutical composition or method of using the intranasal pharmaceutical composition includes polyvinyl alcohol that is present at a concentration of from 8% (w/w) to about 12% (w/w). In certain embodiments, the intranasal pharmaceutical composition or method of using the intranasal pharmaceutical composition includes polyvinyl alcohol that is present at a concentration of about 10% (w/w).

In some embodiments, the intranasal pharmaceutical composition or method of using the intranasal pharmaceutical composition includes sodium citrate. In certain embodiments, the intranasal pharmaceutical composition or method of using the intranasal pharmaceutical composition includes sodium citrate at a concentration of from about 0.2% (w/w) to about 0.6% (w/w). In some embodiments, the intranasal pharmaceutical composition or method of using the intranasal pharmaceutical composition includes sodium citrate at a concentration of from about 0.3% (w/w) to about 0.4% (w/w). In some embodiments, the intranasal pharmaceutical composition or method of using the intranasal pharmaceutical composition includes sodium citrate at a concentration of about 0.35% (w/w).

In some embodiments, the intranasal pharmaceutical composition or method of using the intranasal pharmaceutical composition includes citric acid. In certain embodiments, the intranasal pharmaceutical composition or method of using the intranasal pharmaceutical composition includes citric acid at a concentration of from about 0.5% (w/w) to about 1.3% (w/w). In certain embodiments, the intranasal pharmaceutical composition or method of using the intranasal pharmaceutical composition includes citric acid at a concentration of from about 0.6% (w/w) to about 1.0% (w/w). In some embodiments, the intranasal pharmaceutical composition or method of using the intranasal pharmaceutical composition includes citric acid at a concentration of from about 0.7% (w/w) to about 0.8% (w/w). In some embodiments, the intranasal pharmaceutical composition or method of using the intranasal pharmaceutical composition includes citric acid at a concentration of about 0.74% (w/w).

In some embodiments, the intranasal pharmaceutical composition or method of using the intranasal pharmaceutical composition includes sodium metabisulfite. In certain embodiments, the intranasal pharmaceutical composition or method of using the intranasal pharmaceutical composition includes sodium metabisulfite at a concentration of from about 0.05% (w/w) to about 0.15% (w/w). In some embodiments, the intranasal pharmaceutical composition or method of using the intranasal pharmaceutical composition includes sodium metabisulfite at a concentration of about 0.1% (w/w).

In some embodiments, the intranasal pharmaceutical composition or method of using the intranasal pharmaceutical composition includes glycerin. In certain embodiments, the intranasal pharmaceutical composition or method of using the intranasal pharmaceutical composition includes glycerin at a concentration of from about 3% (w/w) to about 7% (w/w). In certain embodiments, the intranasal pharmaceutical composition or method of using the intranasal pharmaceutical composition includes glycerin at a concentration of about 5.00% (w/w).

In some embodiments, the intranasal pharmaceutical composition or method of using the intranasal pharmaceutical composition includes a solution of 50% benzalkonium chloride. In certain embodiments, the intranasal pharmaceutical composition or method of using the intranasal pharmaceutical composition includes the solution of 50% benzalkonium chloride at a concentration of from about 0.03% (w/w) to about 0.05% (w/w). In certain embodiments, the intranasal pharmaceutical composition or method of using the intranasal pharmaceutical composition includes the solution of 50% benzalkonium chloride at a concentration of about 0.04% (w/w).

In some embodiments, the intranasal pharmaceutical composition or method of using the intranasal pharmaceutical composition is administered in an amount from about 0.1 g to about 0.14 g. In certain embodiments, the intranasal pharmaceutical composition or method of using the intranasal pharmaceutical composition is administered in an amount of 0.12 g per dose. In certain embodiments, the intranasal pharmaceutical composition or method of using the intranasal pharmaceutical composition is administered in an amount which provides from about 0.15 mg to about 0.25 mg of scopolamine per dose. In some embodiments, the intranasal pharmaceutical composition or method of using the intranasal pharmaceutical composition is administered in an amount which provides about 0.2 mg per dose.

In some embodiments, the intranasal pharmaceutical composition or method of using the intranasal pharmaceutical composition is administered to the subject twice daily in the amount of about 0.12 g of the composition. In certain embodiments, the intranasal pharmaceutical composition or method of using the intranasal pharmaceutical composition is administered in a dose comprising 0.16 mg of scopolamine in a volume of about 120 mL. In certain embodiments, the intranasal pharmaceutical composition or method of using the intranasal pharmaceutical composition is administered before the subjected is exposed to a stimulus that may induce emesis, nausea, or symptoms associated with motion. In certain embodiments, the intranasal pharmaceutical composition or method of using the intranasal pharmaceutical composition is administered after onset of emesis, nausea, or symptoms associated with motion.

In some embodiments, the intranasal pharmaceutical composition or method of using the intranasal pharmaceutical is administered to a human subject who is from about 60 to about 80 years old. In some embodiments, the intranasal pharmaceutical composition or method of using the intranasal pharmaceutical composition is administered to a geriatric human subject. In certain embodiments, the intranasal pharmaceutical composition or method of using the intranasal pharmaceutical composition is administered to a human subject over the age of about 60 years old. In certain embodiments, the intranasal pharmaceutical composition or method of using the intranasal pharmaceutical composition is administered to a human subject over the age of about 65 years old.

In certain embodiments, administration of the intranasal pharmaceutical composition or method of using the intranasal pharmaceutical composition results in substantially no anticholinergic side effects. Anticholinergic side effects may include, but are not limited to, dry mouth, hot or dry skin, constipation, urinary retention, bowel obstruction, dilated pupils, blurred vision, increased heart rate, drowsiness, decreased sweating, impaired concentration, confusion, attention deficit, memory impairment, delirium, agitation, and seizures. Anticholinergic effects may be monitored and recorded using the Anticholinergic Toxicity Screen (ACTS).

In some embodiments, the gel of the intranasal pharmaceutical composition or method of using the intranasal pharmaceutical composition has a viscosity of about 2300 centistokes and is delivered by means of a pump. In some embodiments, the intranasal pharmaceutical composition or method of using the intranasal pharmaceutical composition is administered to a subject experiencing or expecting to be exposed to one or more of microgravity, boating, air travel, vehicular travel, and combat activity, including but not limited to military naval and coast guard vessels. Experience or exposure to microgravity may include, but is not limited to, outer space environments and simulations. Experience or exposure to boating may include sailboats, speedboats, submarines, cruises, dinghys, kayaks, canoes, or other watercraft. Experience or exposure to air travel may include airplanes, jets, helicopters, blimps, hot air balloons, parachutes or paragliders, or other forms of aircraft. Experience or exposure to vehicular travel may include automobiles, motorcycles, trains, buses, trolleys, subways, street cars, or other forms of vehicles. Experience or exposure to combat activity may include, but is not limited to, combat training, military vehicle travel (i.e., tanks, armored trucks, jets), tactical exercises, airborne operations, parachute duty, and diving duty.

In certain embodiments, the intranasal pharmaceutical composition or method of using the intranasal pharmaceutical composition is administered to a subject experiencing cybersickness or is expecting to be exposed to stimuli known to induce cybersickness. Such stimuli may include, but are not limited to, virtual reality, video games, and internet use, including simulators and artificial intelligence.

In certain embodiments, the intranasal pharmaceutical composition or method of using the intranasal pharmaceutical composition is administered to a subject who is experiencing or expecting to be exposed to microgravity. Such exposure may include outer space environments and simulations. In certain embodiments, the intranasal pharmaceutical composition or method of using the intranasal pharmaceutical composition is administer to a subject experiencing or expecting to be exposed to simulated motion during use of virtual reality equipment. Such exposure may include, but is not limited to, headsets, goggles, or other equipment for use in recreation, employment (i.e., virtual reality practice for employment needs), testing, and military use.

In one aspect of the present disclosure, an intranasal pharmaceutical composition for the prevention or rescue from degradation of one or more of cognition, motor function, and mood due to motion includes a pharmaceutically acceptable salt of scopolamine, where administration of the composition to a human subject results in a Cmax of free scopolamine with a 90% confidence interval which is 80% to 125% of a least squares geometric mean of less than about 160 pg/mL, and where motion sickness degradation of one or more of cognition, motor function, and mood is substantially prevented or eliminated.

In one aspect of the present disclosure, an intranasal pharmaceutical composition for the prevention of one or more of nausea or emesis related to motion includes a pharmaceutically acceptable salt of scopolamine, where administration of the composition to a human subject results in a Cmax of free scopolamine that is from about 20% less to about 20% more than an average steady-state level resulting from application of a transdermal scopolamine, having a total of 1.5 mg scopolamine and formulated for delivery of about 1 mg to a human subject over about three days. In another aspect of the present disclosure, a composition for the prevention of one or more of nausea or emesis related to motion includes a pharmaceutically acceptable salt of scopolamine, where administration of the composition to a human subject results in a Cmax of free scopolamine that is less than about 120% of an average steady-state level resulting from application of a transdermal scopolamine system, having a total of 1.5 mg scopolamine and formulated for delivery of about 1 mg to a human subject over about three days. In some embodiments, the intranasal pharmaceutical composition has a max of free scopolamine that is less than about 115% of an average steady-state level resulting from application of the transdermal scopolamine system. In certain embodiments, the intranasal pharmaceutical composition has a Cmax of free scopolamine that less than about 110% of an average steady-state level resulting from application of the transdermal scopolamine system. In certain embodiments, administration of the intranasal pharmaceutical composition twice daily for three days achieves a total dose of about 0.95 mg of free scopolamine in plasma of the human subject. In certain embodiments, the pharmaceutical composition has transdermal scopolamine as a patch marketed as Transderm Scop®.

In some embodiments, the intranasal pharmaceutical composition or method of using the intranasal pharmaceutical composition is delivered by a pump capable of delivering about 0.12 g of a composition having a viscosity of about 2000 centistokes or greater, where the volume of the composition delivered varies by no more than about 15%. In certain embodiments, the volume of the intranasal pharmaceutical composition or method of using the intranasal pharmaceutical composition varies by no more than about 10%. In certain embodiments, the volume of the intranasal pharmaceutical composition or method of using the intranasal pharmaceutical composition varies by no more than about 8%. In certain embodiments, the volume of the intranasal pharmaceutical composition or method of using the intranasal pharmaceutical composition varies by no more than about 5%.

In one aspect of the present disclosure, an intranasal pharmaceutical composition for the prevention of, or rescue from, one or more of nausea and emesis related to motion includes a pharmaceutically acceptable salt of scopolamine, where administration of the composition to a human subject results in a Cmax of free scopolamine that approximates the steady state plasma levels of free scopolamine delivered by a transdermal administration. In certain embodiments, the intranasal pharmaceutical composition has a Cmax measured with a 90% confidence interval which is 80% to 125% of a least squares geometric mean of between about 160 pg/mL to 60 pg/mL. In some embodiments, the intranasal pharmaceutical composition has a Cmax measured with a 90% confidence interval which is 80% to 125% of a least squares geometric mean of between about 140 pg/mL to 80 pg/mL. In some embodiments, the intranasal pharmaceutical composition has a Cmax measured with a 90% confidence interval which is 80% to 125% of a least squares geometric mean of between about 120 pg/mL to 80 pg/mL. In certain embodiments, the intranasal pharmaceutical composition has a Cmax measured with a 90% confidence interval which is 80% to 125% of a least squares geometric mean of between about 100 pg/mL to 80 pg/mL. In some embodiments, the intranasal pharmaceutical composition has a Cmax measured with a 90% confidence interval which is 80% to 125% of a least squares geometric mean of about 87 pg/mL.

In one aspect of the present disclosure, an intranasal pharmaceutical composition for the prevention of, or rescue from, one or more of nausea and emesis related to motion includes a pharmaceutically acceptable salt of scopolamine, where administration of the composition to a human subject results in a Cmax of free scopolamine measured with a 90% confidence interval which is 80% to 125% of a least squares geometric mean of less than about 160 pg/mL. In certain embodiments, the least squares geometric mean is greater than 60 pg/mL. In some embodiments, the least squares geometric mean is about 155, 150, 145, 140, 135, 130, 125, 120, 115, 110, 105, 100, 95, 90, 85, 80, 75, 70, 65, or 60 pg/mL.

In some embodiments, the intranasal pharmaceutical composition has a Cmax measured with a 90% confidence interval which is 80% to 125% of a least squares geometric mean of between about 160 pg/mL to 60 pg/mL. In certain embodiments, the intranasal pharmaceutical composition has a Cmax measured with a 90% confidence interval which is 80% to 125% of a least squares geometric mean of between about 140 pg/mL to 80 pg/mL. In certain embodiments, the intranasal pharmaceutical composition has a Cmax measured with a 90% confidence interval which is 80% to 125% of a least squares geometric mean of between about 140 pg/mL to 80 pg/mL. In certain embodiments, the intranasal pharmaceutical composition has a Cmax measured with a 90% confidence interval which is 80% to 125% of a least squares geometric mean of between about 120 pg/mL to 80 pg/mL. In some embodiments, the intranasal pharmaceutical composition has a Cmax measured with a 90% confidence interval which is 80% to 125% of a least squares geometric mean of between about 100 pg/mL to 80 pg/mL. In some embodiments, the intranasal pharmaceutical composition has a Cmax measured with a 90% confidence interval which is 80% to 125% of a least squares geometric mean of about 87 pg/mL. In some embodiments, the least squares geometric mean is about 116 pg/mL to about 158 pg/mL. In some embodiments, the least squares geometric mean is about 137 pg/mL. In some embodiments, the least squares geometric mean is above 85 pg/mL. In some embodiments, the least squares geometric mean is about 85 pg/mL to about 115 pg/mL.

In another aspect of the present disclosure, a method is disclosed for the treatment of, prevention of, or rescue from, one or more of nausea and emesis related to motion in a patient in need thereof, the method including administering an intranasal composition of a pharmaceutically acceptable salt of scopolamine, where administration of the composition results in a Cmax (pg/mL) of free scopolamine that approximates the steady state plasma level of free scopolamine delivered by transdermal administration; the composition provides absolute bioavailability of about 10-14%; the composition is a gel that has a viscosity of about 2100 to 2700 centistokes; the patient is over the age of about 60 years old; and administration does not create a significant anticholinergic side effect.

In some embodiments, the administration of the intranasal composition provides scopolamine at a concentration from about 0.15% (w/w) to about 0.18% (w/w) to the subject twice daily, each in a unit dose of 0.12 g. In some embodiments, the patient is of geriatric age. In certain embodiments, the human subject is from about 60 years old to about 90 years old. In some embodiments, administration of the intranasal composition does not create significant dry mouth, constipation, urinary retention, bowel obstruction, dilated pupils, blurred vision, increased heart rate, drowsiness, or decreased sweating. In some embodiments, the intranasal composition is administered in at least two consecutive doses to both nostrils in less than about 5, 4, 3, 2, or 1 minutes, or less than about 60, 55, 50, 45, 40, 35, 30, 25, 20, 15, 10, or 5 seconds.

In one aspect of the present disclosure, an intranasal pharmaceutical composition includes a pharmaceutically acceptable salt of scopolamine at a concentration from about 0.15% (w/w) to about 0.18% (w/w), where administration of the intranasal composition to a human subject for the prevention of, or rescue from, one or more of nausea or vomiting related to motion results in a Cmax of free scopolamine with a 90% confidence interval (CI) which is 80% to 125% of a least squares geometric mean of about 160 pg/mL to about 60 pg/mL. In certain embodiments, the intranasal composition includes polyvinyl alcohol, where the polyvinyl alcohol is present at a concentration of about 8% (w/w) to about 12% (w/w). In certain embodiments, the intranasal composition includes citric acid present at a concentration of from about 0.7% (w/w) to about 0.8% (w/w); a solution of 50% benzalkonium chloride present at a concentration of from about 0.03% (w/w) to about 0.05% (w/w); sodium metabisulfite present at a concentration of from about 0.05% (w/w) to about 0.15% (w/w); and glycerin present at a concentration of from about 3% (w/w) to about 7% (w/w).

In some embodiments, the intranasal composition provides absolute bioavailability of about 10-14%. In some embodiments, the intranasal composition has a pH of from about 3.2 to about 3.6. In certain embodiments, the intranasal composition is directed to be administered before the subject is exposed to a stimulus that may induce emesis associated with motion, or, after the onset of emesis associated with motion.

BRIEF DESCRIPTION OF THE DRAWINGS

FIG. 3C is a graphic presentation from clinical study MS-33 showing Least Squares Mean (SE) Change from Baseline in PSAQ Alertness (ITT Population). For FIGS. 3C-3Q, PSAQ scores were assigned as 1=significantly worse, 2=somewhat worse, 3=no effect, 4=somewhat better, 5=significantly better. Analysis was based on mixed model for repeated measures (MMRM) including fixed effects of treatment, visit, baseline score and interaction terms of treatment by visit.

FIG. 3D is a graphic presentation from clinical study MS-33 showing Least Squares Mean (SE) Change from Baseline in PSAQ Balance (ITT Population).

FIG. 3E is a graphic presentation from clinical study MS-33 showing Least Squares Mean (SE) Change from Baseline in PSAQ Concentration (ITT Population).

FIG. 3F is a graphic presentation from clinical study MS-33 showing Least Squares Mean (SE) Change from Baseline in PSAQ Hand-eye coordination (ITT Population).

FIG. 3G is a graphic presentation from clinical study MS-33 showing Least Squares Mean (SE) Change from Baseline in PSAQ Mood (ITT Population).

FIG. 3H is a graphic presentation from clinical study MS-33 showing Least Squares Mean (SE) Change from Baseline in PSAQ Reaction Time (ITT Population).

FIG. 3I is a graphic presentation from clinical study MS-33 showing Least Squares Mean (SE) Change from Baseline in PSAQ Overall performance (ITT Population).

FIG. 3J is a graphic presentation from clinical study MS-33 showing Least Squares Mean (SE) of Treatment Difference from Placebo Change from Baseline PSAQ Memory (ITT Population).

FIG. 3K is a graphic presentation from clinical study MS-33 showing Least Squares Mean (SE) of Treatment Difference from Placebo Change from Baseline PSAQ Alertness (ITT Population).

FIG. 3L is a graphic presentation from clinical study MS-33 showing Least Squares Mean (SE) of Treatment Difference from Placebo Change from Baseline PSAQ Balance (ITT Population).

FIG. 3M is a graphic presentation from clinical study MS-33 showing Least Squares Mean (SE) of Treatment Difference from Placebo Change from Baseline PSAQ Concentration (ITT Population).

FIG. 3N is a graphic presentation from clinical study MS-33 showing Least Squares Mean (SE) of Treatment Difference from Placebo Change from Baseline PSAQ Hand-eye coordination (ITT Population).

FIG. 3O is a graphic presentation from clinical study MS-33 showing Least Squares Mean (SE) of Treatment Difference from Placebo Change from Baseline PSAQ Mood (ITT Population).

FIG. 3P is a graphic presentation from clinical study MS-33 showing Least Squares Mean (SE) of Treatment Difference from Placebo Change from Baseline PSAQ Reaction Time (ITT Population).

FIG. 4A is a graphic depiction for the disposition of subjects.

FIG. 4B is a Kaplan-Meier Plot of Time to Vomiting or Use of Rescue Medication, ITT Population.

FIG. 4C is a Kaplan-Meier Plot of Time to Vomiting or Use of Rescue Medication, Per Protocol Population.

FIG. 4D is a Forest Plot of Treatment Difference for Key Efficacy Endpoints (ITT Population).

FIG. 4E is a Forest Plot of Relative Risk or Hazard Ratio for Key Efficacy Endpoints (ITT Population).

FIG. 4I is a graphic illustration of LSM change from baseline in PSAQ concentration.

FIG. 4L is a graphic illustration of LSM change from baseline in PSAQ reaction time.

FIG. 4N is a graphic illustration of the Least Squares Mean of Treatment Difference from Placebo in Nausea Assessment Score-MMRM, ITT Population.

FIG. 4O is a graphic illustration of a Forest Plot of Between-group Treatment Differences in the Proportions of Subjects without Nausea and without Use of Rescue Medication, Pooled Analysis and By Study, ITT Population FIG. 4P is a graphic illustration of a Forest Plot of Between-group Treatment Differences in the Proportions of Subjects without Moderate or Severe Nausea and without Use of Rescue Medication, Pooled Analysis and By Study, ITT Population FIG. 4Q is a graphic illustration of a Kaplan-Meier Plot of Time to Vomiting or to Use of Rescue Medication, Pooled Analysis, ITT Population. Subjects who reported vomiting or have taken rescue treatment within 4 hours after receiving study drug are considered as having the event, and time to event is derived as the number of hours from dosing to the earliest time of vomiting or rescue medication use. The within 4 hours after receiving study drug window is from the time of the dose to the time of the end of voyage. Subjects without an event were censored at the time of the end of voyage (approximately 4 hours post dose).

FIG. 4R is a graphic illustration of a Forest Plot of Hazard Ratios for Time to Vomiting or Use of Rescue Medication, Pooled Analysis and By Study, ITT Population

FIG. 6AA is a graphical illustration of mean concentration-time plot of Study 07 Data using Study 31 formatting.

FIG. 6BB is a graphical illustration of median concentration-time plot of Study 07 Data using Study 31 formatting.

FIG. 8A is an illustration of the distribution of subjects.

DETAILED DESCRIPTION OF THE INVENTION

Figure 1:
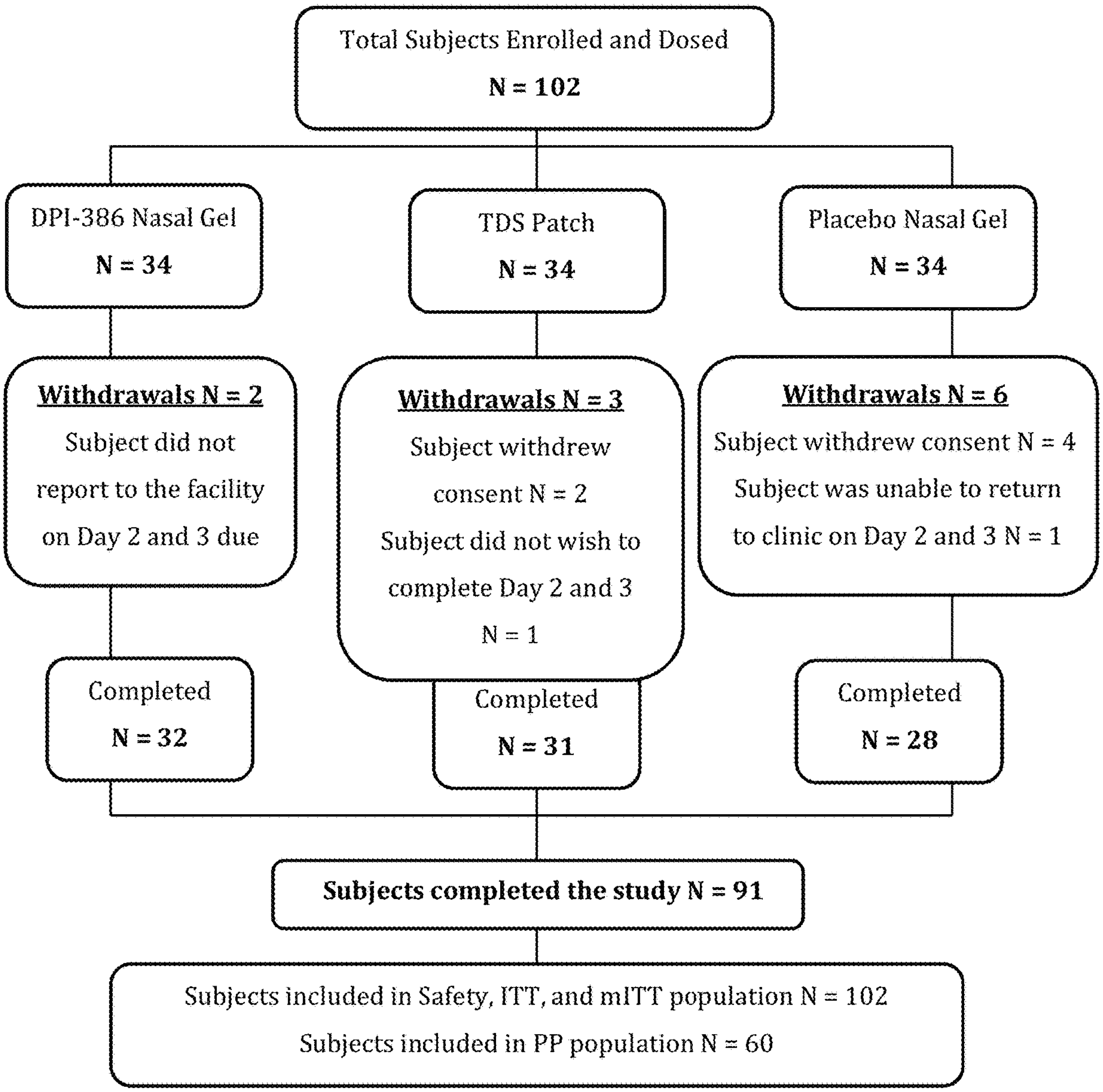
FIG. 1 is a schematic diagram depicting the disposition of subjects for clinical study MS-22.

As presented herein, intranasal scopolamine provides treatment and prevention of motion sickness (including space motion sickness), nausea, and emesis resulting from motion or the sensation of motion. Although it has been known for some time that scopolamine can be effective against nausea and vomiting or emesis, that is associated with or related to motion or the sensation of motion, certain problems with existing formulations and delivery methods have been acknowledged. At particular levels, scopolamine becomes effective in treating and preventing motion sickness, but at higher levels scopolamine leads to side effects due primarily to anticholinergic activity. In order to solve this problem, to the present disclosure outlines novel and unexpected scopolamine levels which are 1) effective and 2) avoid anticholinergic side effects, including but not limited to one or more of drowsiness, dry mouth, and blurred vision.

The present disclosure demonstrates that particular levels of free scopolamine in subject plasma provides effective treatment and prevention of nausea and vomiting/emesis associated with motion, while avoiding anticholinergic side effects. Further, these levels can be achieved by administering scopolamine as a nasal gel according to the disclosure herein.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Definitions

As used herein, the following terms have the meaning indicated, unless otherwise specifically noted in context. Unless otherwise defined herein, all technical terms used herein have the same meaning as commonly understood by one of ordinary skill in the art to which this disclosure belongs.

The terms “a,” “an,” and “the” and similar referents used herein are to be construed to cover both the singular and the plural unless their usage in context indicates otherwise.

“About” is used to provide flexibility to a numerical range endpoint by providing that a given value may be “slightly above” or “slightly below” the endpoint without affecting the desired result.

The term “bioavailability” refers to the peak concentration of the therapeutic molecule, amount of that therapeutic, and the speed of its absorption into the body.

The term “comprise” and variations of the term, such as “comprising” and “comprises,” are not intended to exclude other additives, components, integers or steps.

The term “consisting essentially of” excludes any other additive, component, or action that substantially affects the recited properties of the claimed method or composition.

The term “consisting of” excludes any other additive, component or action other than those recited in the claimed method or composition.

Recitation of ranges of values herein are merely intended to serve as a shorthand method of referring individually to each separate value falling within the range, unless otherwise-indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification, in addition to the indicated values themselves, e.g., “1%” and “50%” in the foregoing illustration. All possible combinations of numerical values between and including the lowest value and the highest value enumerated are to be considered to be expressly stated in this disclosure.

A “pharmaceutical composition” and a “medicament” are compositions having a pharmaceutical effect.

“Pharmaceutically acceptable salt” refers to a compound derived from the chemical reaction of an acid or base with a parent compound, and which is safe and effective for use with humans and other subjects. For example, a scopolamine salt can be produced by reacting scopolamine with various acids such as hydrochloric acid, hydrobromic acid, hydroiodic acid, nitric acid, phosphoric acid, sulfuric acid, and the like. Pharmaceutically acceptable salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, ptoluenesulfonate and pamoate salts.

“Pump” means a pump capable of delivering about 1.2 g of a composition having a viscosity of about 2000 centistokes or greater, where the volume of the composition delivered varies by no more than about 15%. The pump also can be a pump that is capable of no more than about 5% variation in delivered volume of the composition.

“Gel” refers to a composition in which the constituents are present in a viscous liquid or in a true gel, i.e., a cross-linked system in which liquid particles are dispersed in a solid medium.

“Viscosity” means the resistance that a liquid system offers to flow when it is subjected to a shear stress. Viscosity herein is provided in units of centistokes (cSt; 1 cSt=1 $mm^2 \cdot s^{-1} = 10^{-6}\ m^2 \cdot s^{-1}$). The kinematic viscosity of water at 20° C. is about 1 cSt. Viscosity in centistokes is determined by measuring the time in seconds, required for a fixed volume of fluid to flow a known distance by gravity through a capillary within a calibrated viscometer at a closely controlled temperature. Herein, unless otherwise noted, viscosities of compositions of the present disclosure were determined using an Anton Paar AMVn viscometer, following the manufacturer’s instructions. (Anton Paar GmbH, Graz, Austria). “High viscosity” means a viscosity greater than 1800 centistokes, as determined herein.

The terms “motion” and “motion sickness” includes, but is not limited to, all four domain symptoms of the Motion Sickness Assessment Questionnaire (MSAQ)), as well as vomiting, retching, dry heaving, and similar physical manifestations resulting from motion, whether actual or virtual. In other words, the stimulus may be actual motion, including motion in a simulator or microgravity, for example in outer space, or it can be just the perception of motion commonly referred to as cybersickness associated with exposure to virtual reality.

"MSSQ" means "Motion Sickness Susceptibility Questionnaire"

"MSAQ" means "Motion Sickness Assessment Questionnaire"

"Complete responder" is a clinical study subject who does not experience treatment-emergent vomiting and does not receive rescue medication after the first dose of study treatment on Treatment Day 1. Vomiting is derived from AE (adverse event) data collection where the verbatim event term begins with the text string "Vomit".

"Associated with" or "related to" motion means actual motion or a perception of motion.

"Scopolamine" refers to the compound (−)-(S)-3-Hydroxy-2-phenylpropionic acid (1R,2R,4S,7S,9S)-9-methyl-3-oxa-9-azatricyclo[3.3. 1.02,4]non-7-yl ester (represented by the formula $C_{17}H_{21}NO_4$), pharmaceutically acceptable salts thereof, single isomers and racemic mixtures thereof, and analogues thereof, such as scopolamine hydrobromide and scopolamine hydrobromide trihydrate. Scopolamine hydrobromide trihydrate has the following structure:

Formula I

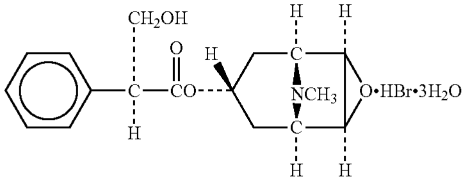

Scopolamine Hydrobromide Trihydrate

"Scopolamine analog(s)" refers to compounds that have the same backbone as scopolamine, but in which one or more moieties have been substituted by, or replaced with, other substituents or moieties. Such substitutions or replacements are in accordance with the permitted valence of the substituted atom and the substituent and result in a stable compound, i.e., a compound that does not spontaneously undergo transformation under conditions of storage and use of the present formulation. It is to be understood that any and all known substituents or moieties of organic compounds can be used. In a broad aspect, the permissible substituents include acyclic and cyclic, branched and unbranched, carbocyclic and heterocyclic, aromatic and nonaromatic substituents of organic compounds.

"Scopolamine suitable pharmaceutical salt" means hydrobromide trihydrate, or any acceptable salt providing equivalent pharmacokinetic results as described herein.

"Suitable for intranasal administration" refers to any mode of administration of a medicament (i.e., a composition comprising scopolamine) intranasally, i.e., into the nose of a subject.

"Therapeutically effective amount" refers to the amount of a composition, or amount of scopolamine or analog thereof, that, when administered to a subject, is sufficient to have an effect in restoring, correcting, or modifying a physiological function of a subject, including in treatment of a medical condition associated with exposure to motion.

"Treatment," with respect to the exposure of a subject to motion and the ensuing symptoms of motion sickness with or without emesis, refers to a medical intervention which prevents, attenuates, and/or counteracts the effects of such exposure. Treatments can refer to the prophylactic administration of the present compounds and compositions to subjects at risk of exposure to a stimulus causing motion sickness prior to an anticipated exposure, and/or can refer to the administration of the present compounds and compositions following such exposure and development of symptoms, e.g., rescue therapy. Although "prevention" may be discussed herein, specifically to refer to administration of a therapeutic substance prior to onset of symptoms, the term "treatment" as used herein includes administration of a therapeutic agent prior to or after the onset of symptoms unless otherwise noted. The terms "rescue" and "rescue therapy" are used herein periodically to refer to specifically to treatment administered after the onset of symptoms, as distinguished from "prevention" or "preventative treatment."

The term "effective amount" or "therapeutically effective amount" refers to an amount sufficient to effect beneficial or desirable biological and/or clinical results.

The term "subject" and "patient" are used interchangeably herein and refer to both human and nonhuman animals. The term "nonhuman animals" includes all vertebrates, e.g., mammals and non-mammals, such as nonhuman primates, sheep, dog, cat, horse, cow, chickens, amphibians, reptiles, and the like. Preferably, the subject is a human patient is suffering from, or at risk of motion sickness and/or emesis.

When used herein the term "motion sickness" refers to one or more of the four domains of motion sickness (Gianaros, 2001). The signs and symptoms of motion sickness may be associated with motion of the subject, motion of the subject's mechanism of transportation, or by the subject's sensory perception of motion despite the subject being stationary, e.g., via virtual reality.

Scopolamine is a muscarinic antagonist structurally similar to the neurotransmitter acetylcholine and can act by blocking the muscarinic acetylcholine receptors. Blocking acetylcholine from binding to its receptors blocks acetylcholine-mediated nerve impulses from travelling through the body. It is thus classified as an anticholinergic agent. Scopolamine is also referred to as hyoscine, hyoscamine, and scopine tropate. The scopolamine used in the present disclosure can be the compound scopolamine itself, a scopolamine salt, an analog of scopolamine, or mixtures thereof. A preferred salt is scopolamine hydrobromide (scopolamine HBr). Other suitable scopolamine compounds that can be used in the compositions and methods of the present disclosure include, but are not limited to scopolamine hydrobromide trihydrate, scopolamine hydrochloride, scopolamine methyl nitrate, methscopolamine nitrate, scopolamine methyl bromide, scopolamine hydrobromide hydrate, scopolamine bromide, and the like.

The scopolamine of the present disclosure is formulated as a pharmaceutical composition for intranasal administration. The pharmaceutical composition can include one or more pharmaceutically acceptable carriers and/or other pharmaceutically acceptable excipients, for example to stabilize and/or deliver the composition to a subject. Excipients for the present pharmaceutical composition can include appropriate additives such as pharmaceutically effective carriers (i.e., sterile water, water, saline, and the like), buffers, neutralizing agents, stabilizers, humectants, viscosity builders, chemical stabilizers, thickeners, diluents, and/or solvents. Examples of excipients for some embodiments include, but are not limited to, alcohols and polyglycols, glycerin, waxes, water, deionized water, fatty acid esters, and the like, mixtures thereof and combinations thereof.

Additives that can be included in the present formulation include components with beneficial properties in connection with the use of the present formulation. For example, components that soothe or protect the nasal mucosa such as aloe or a nasal moisturizer can be included in formulations for nasal administration. A component such as caffeine which enhances absorption of other components of the formulation can also be included. In addition, components which confer other beneficial properties to a subject, such as vitamins, can be included in the formulation. Natural preservatives can also be included.

For intranasal administration, the composition preferably includes one or more gelling agents such as acacia, alginic acid, bentonite, Carbopols (carbomers), carboxymethyl cellulose, ethylcellulose, gelatin, hydroxyethyl cellulose, hydroxypropyl cellulose, magnesium aluminum silicate (Veegum), methylcellulose, poloxamers (Pluronics), polyvinyl alcohol, sodium alginate, tragacanth, and xanthan gum. Such gels can be either a true gel or a viscous liquid. When a viscous liquid is used according to the compositions herein, the viscosity of the liquid is preferably from about 1800 and to about 3,500 centistokes (square millimeters per second), and more preferably from about 1850 to about 3000 centistokes, about 1900 to about 2900 centistokes, about 1950 to about 2800 centistokes, or about 2000 to about 2600 centistokes. The viscosity of the liquid can be about 2300 centistokes. The gel has the capability to adsorb or stick to the inner lining of the nasal cavity of a subject so that at least the active ingredient or ingredients of the formulation can be absorbed.

Compositions for nasal administration can advantageously further include buffering agents and preservatives. Examples of buffering agents include, but are not limited to, sodium citrate, phosphate buff er, sodium salts of various acids, and the like. Compositions with sodium citrate can have a pH of less than about 5, such as a pH of between 3 and 4, for example a pH of between about 3.4 and 3.6. In other embodiments, the buffering agent can be omitted from the composition. Preservatives such as benzalkonium chloride, parabens, quaternary ammonium compounds, aryl acids, aryl alcohols, alkyl acids, thiomersal, and antimicrobial agents can be used, for example. During the formulation of the compositions, the scopolamine hydrobromide trihydrate (the API) is not introduced to the formulation matrix until the pH of the matrix is between 3 and 4. The required pH of 3 to 4 is achieved by the buffer system. Consequently, the API structure is protected from degradation by maintaining the pH of the formulation matrix between 3 and 4.

A scopolamine composition can be administered intranasally in the form of a gel. In order to administer a desired amount of gel, the gel can be administered with a metered dispenser device adapted to dispense the desired amount of gel. In some uses, the device is adjustable in order to administer different, predetermined, metered amounts of the gel as needed. The device can be either a single use or multiple-use device. The gel can also be packaged in single-use ampules or other containers such as containers made with a blow-fill-seal process. In this case, such containers can retain either the desired amount of gel for a single administration, or can retain gel in smaller units of administration so that different doses can be administered through the use of a combination of ampules or other containers.

For high viscosity gels, i.e., those having a viscosity of 2000 centistokes or greater, specialized pumps may be used advantageously to deliver the scopolamine composition nasally. For example, the VP1 Multi-Dose Spray Pump (Aptar®, Crystal Lake, IL) can be used for such applications.

In some embodiments, the intranasal dosage of a nasal gel having 0.2 mg per 0.12 g of gel, in adults 18-59 years of age is 0.2 mg scopolamine HBr, delivered into one nostril twice daily. The dosage may be administered initially at least 15-30 minutes prior to motion to prevent motion sickness. The twice daily does should be separated by a minimum of six hours, with no more than two does given in 24 hours.

Six clinical studies are presented in the Examples below.

Clinical study MS-33, Example 3, was a Phase 3, randomized, double-blind, placebo-controlled study of the efficacy and safety of DPI-386 Nasal Gel for the prevention of nausea and vomiting associated with motion. See FIGS. 3A through 3S.

Figure 4F:
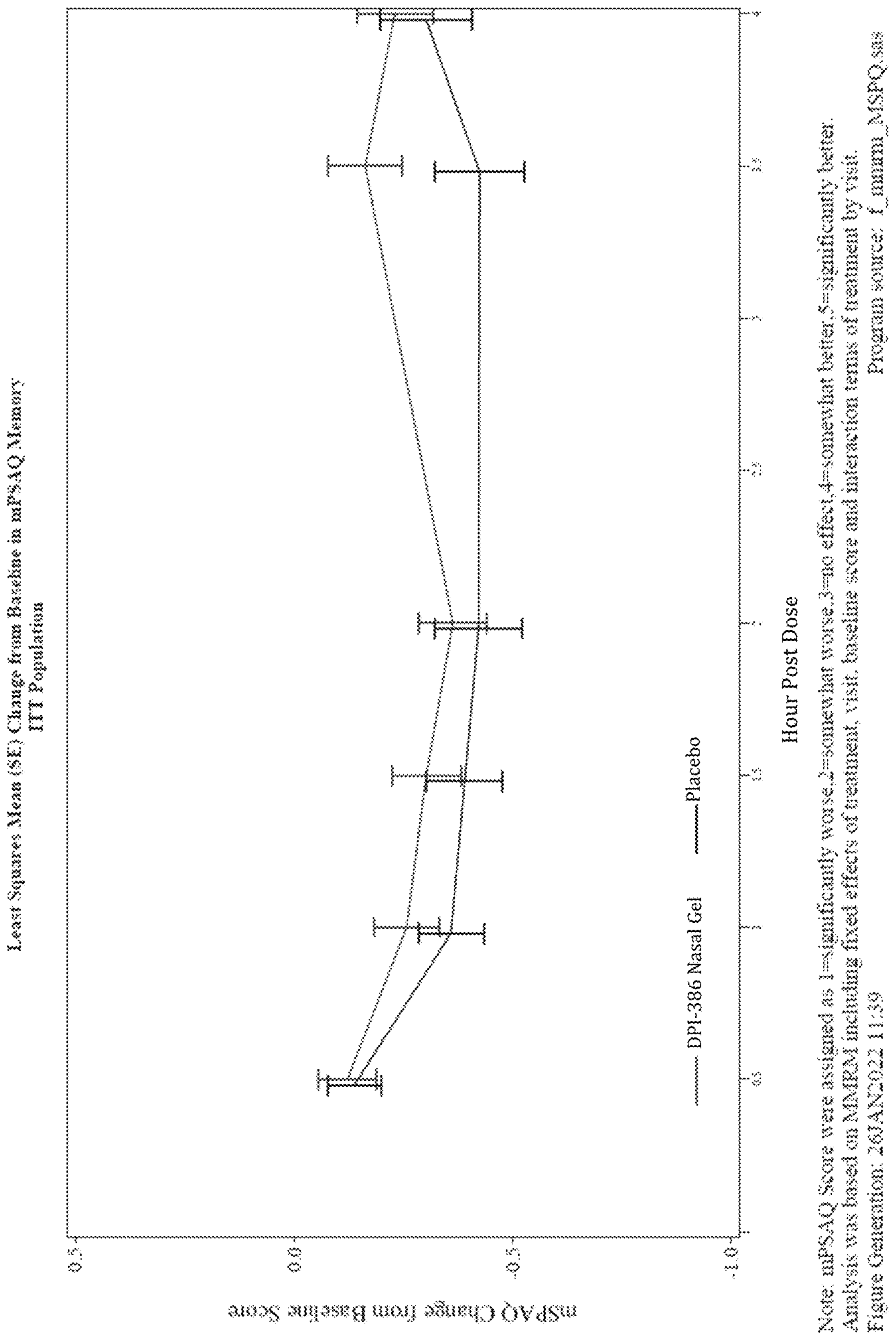
FIG. 4F is a graphic illustration of LSM change from baseline in PSAQ memory.
Figure 4G:
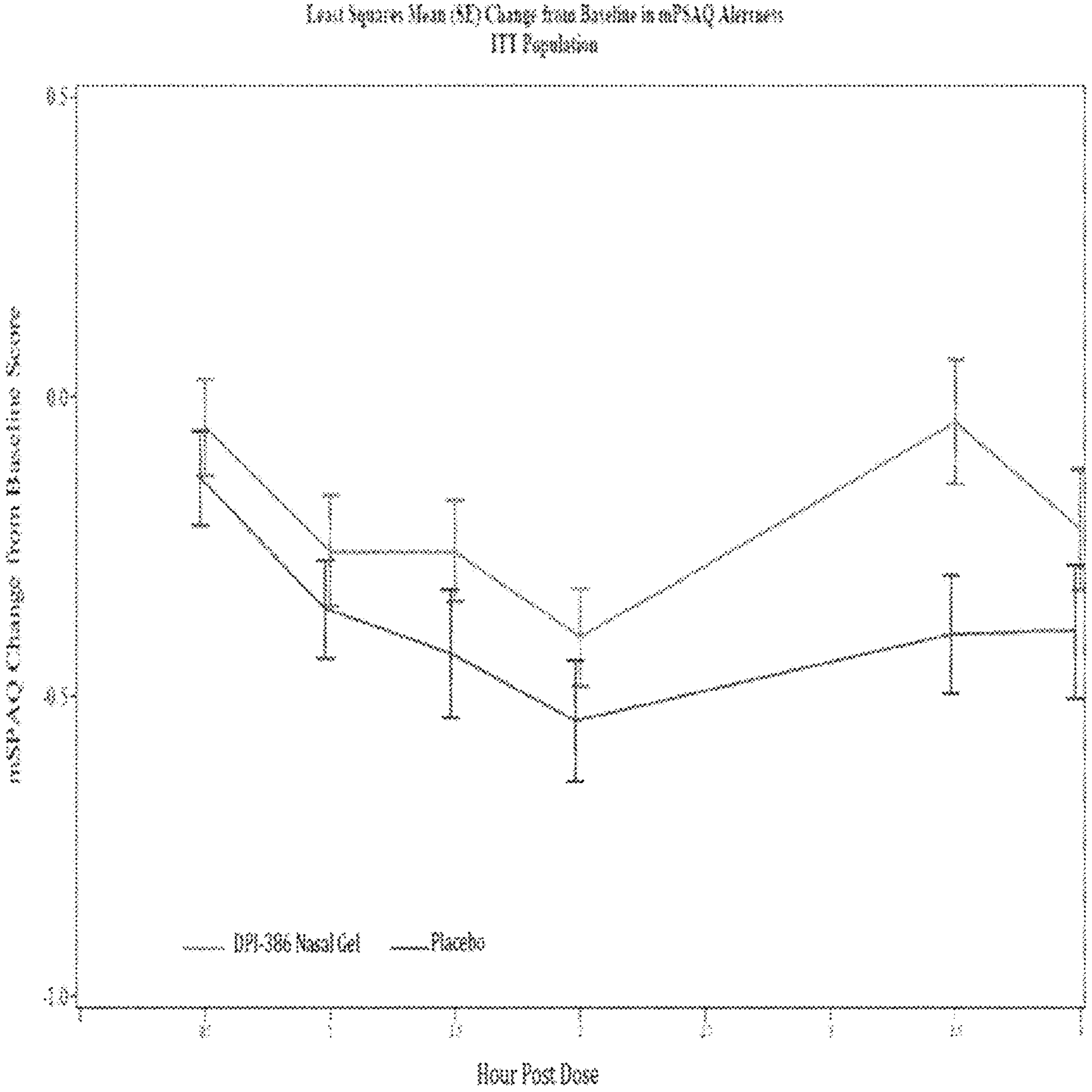
FIG. 4G is a graphic illustration of LSM change from baseline in PSAQ alertness.
Figure 4H:
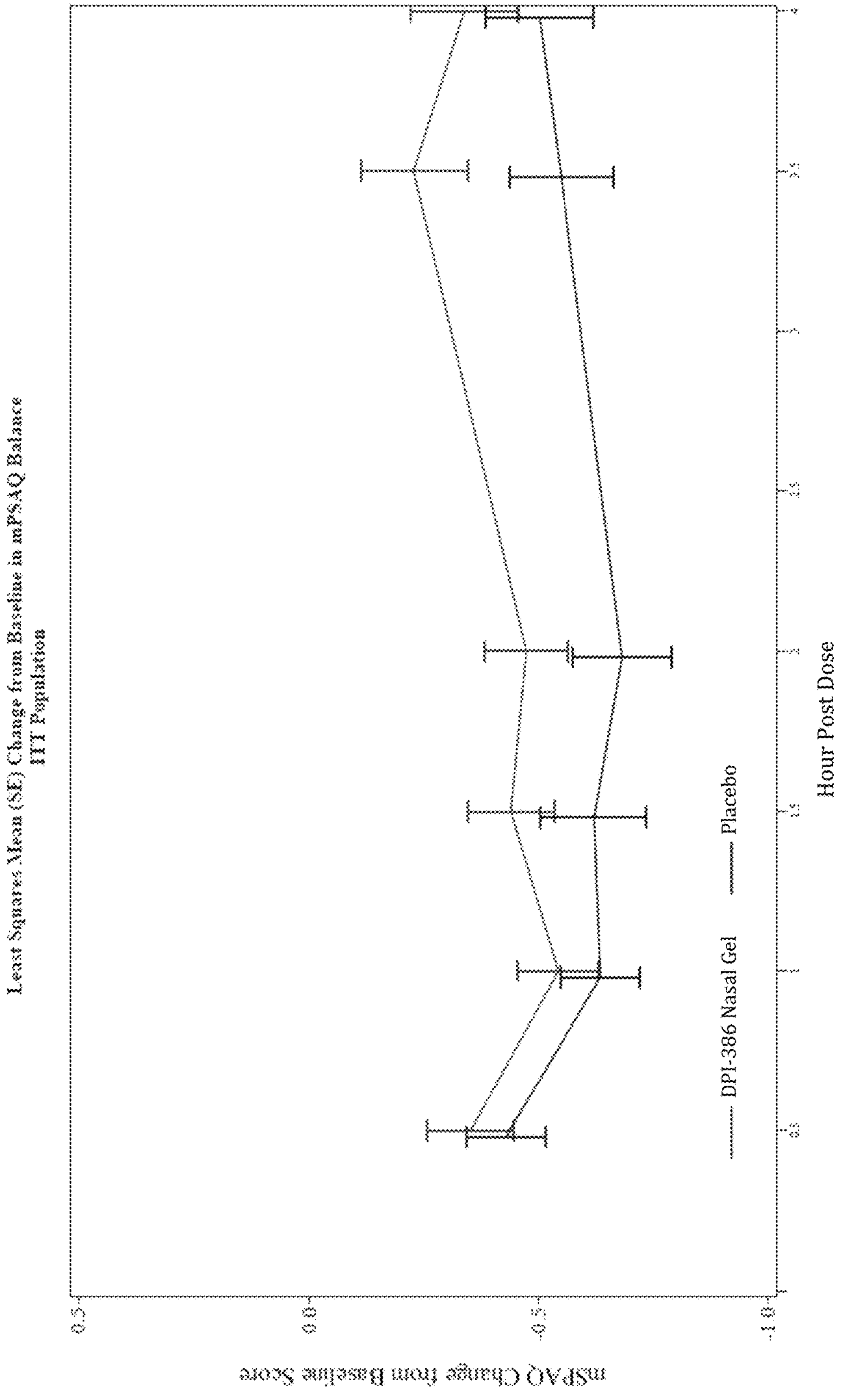
FIG. 4H is a graphic illustration of LSM change from baseline in PSAQ balance.
Figure 41:
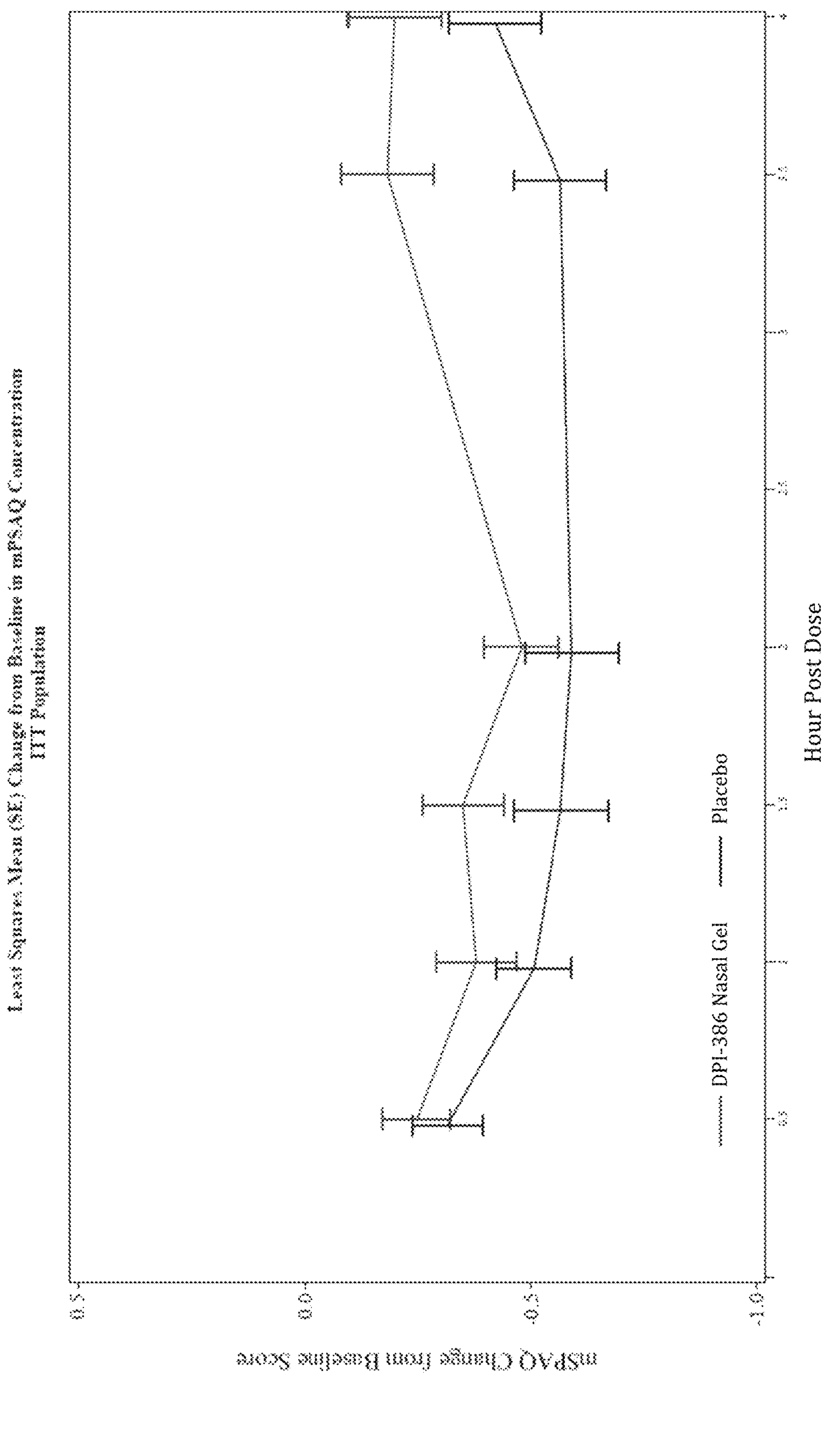
Figure 4J:
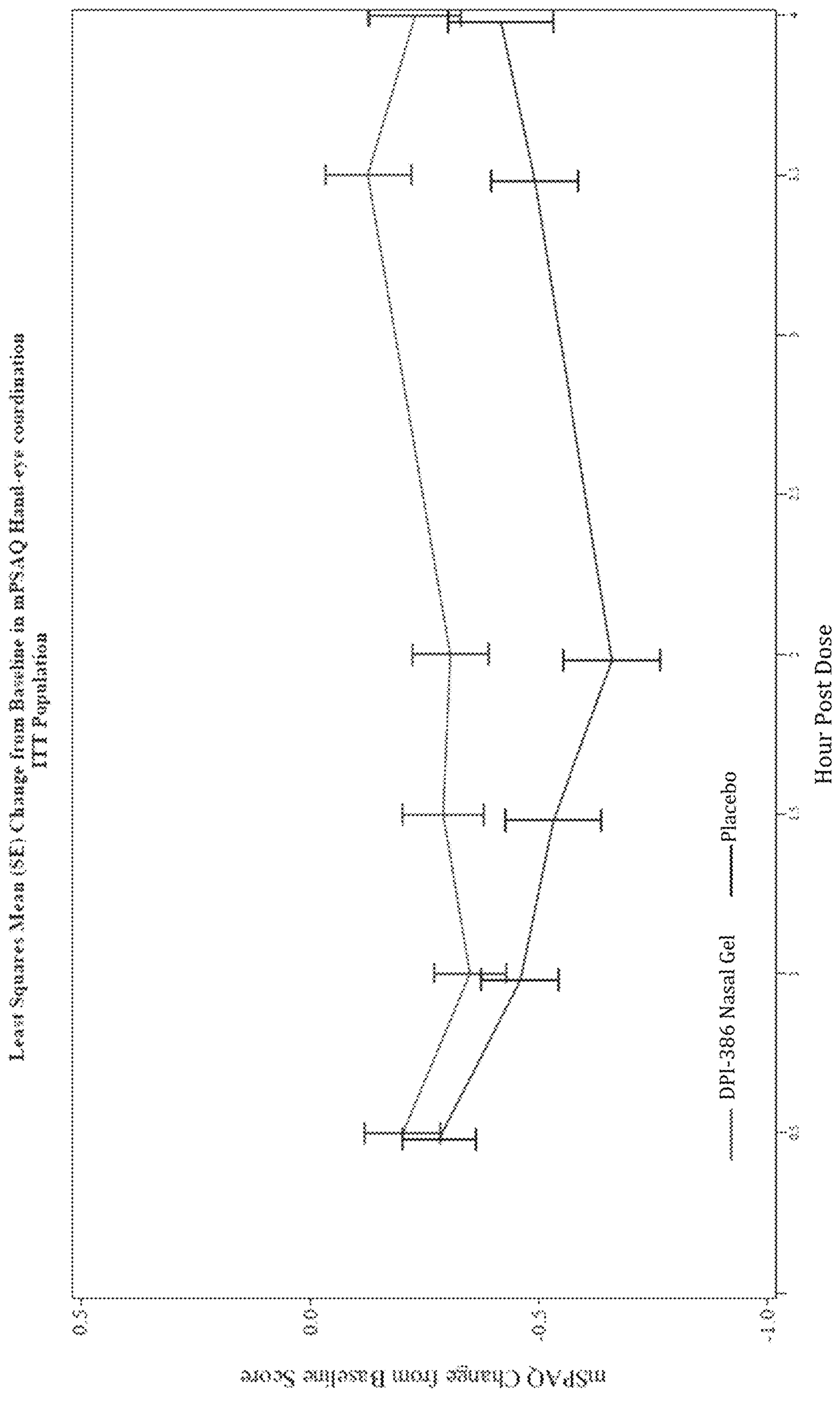
FIG. 4J is a graphic illustration of LSM change from baseline in PSAQ hand-eye coordination.
Figure 4K:
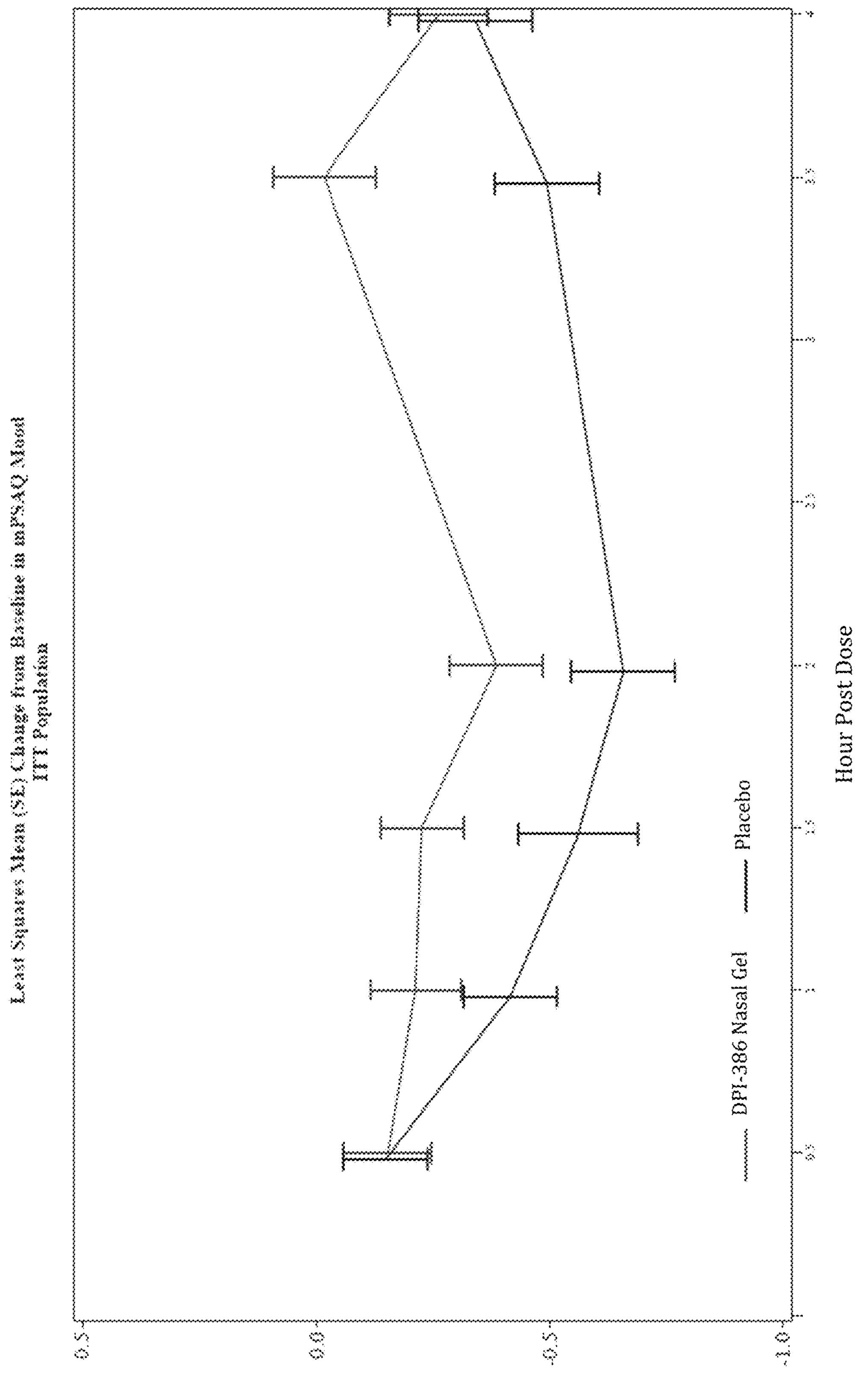
FIG. 4K is a graphic illustration of LSM change from baseline in PSAQ mood.
Figure 4M:
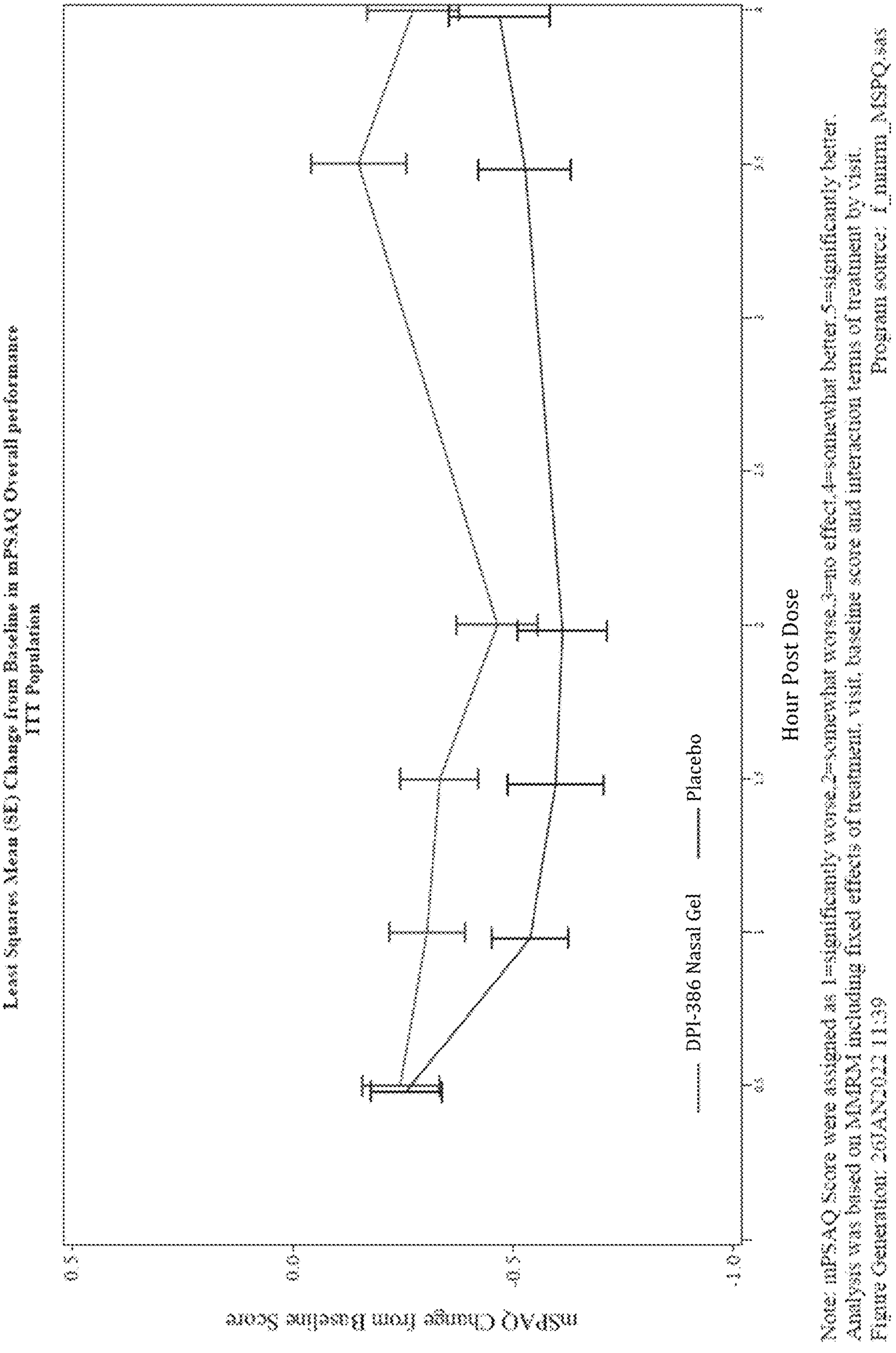
FIG. 4M is a graphic illustration of LSM change from baseline in PSAQ overall performance.

Clinical study MS-29, Example 4, was a randomized, double-blind, placebo-controlled phase 3 study of the efficacy and safety of DPI-386 nasal gel for the prevention of nausea and vomiting associated with motion. See FIGS. 4A through 4R. MS-29 is reported in conjunction with MS-33 as an integration of safety and efficacy endpoints. The data is integrated to demonstrate the studied population and present comprehensive results.

Clinical study MS-24, Example 5, was a randomized, double-blind, placebo-controlled Phase 3 study of the safety and efficacy of DPI-386 nasal gel for the prevention and treatment of nausea associated with motion sickness in senior subjects aged 60-80 years of age with open-label follow-up. See FIGS. 5A through 5H.

Clinical study MS-31, Example 6, was a Phase 1, randomized, open-label, crossover study to assess the relative bioavailability of scopolamine administered as the DPI-386 Nasal Gel and scopolamine transdermal system (Transderm Scop) in healthy participants. See FIGS. 6A through 6GG.

Figure 7A:
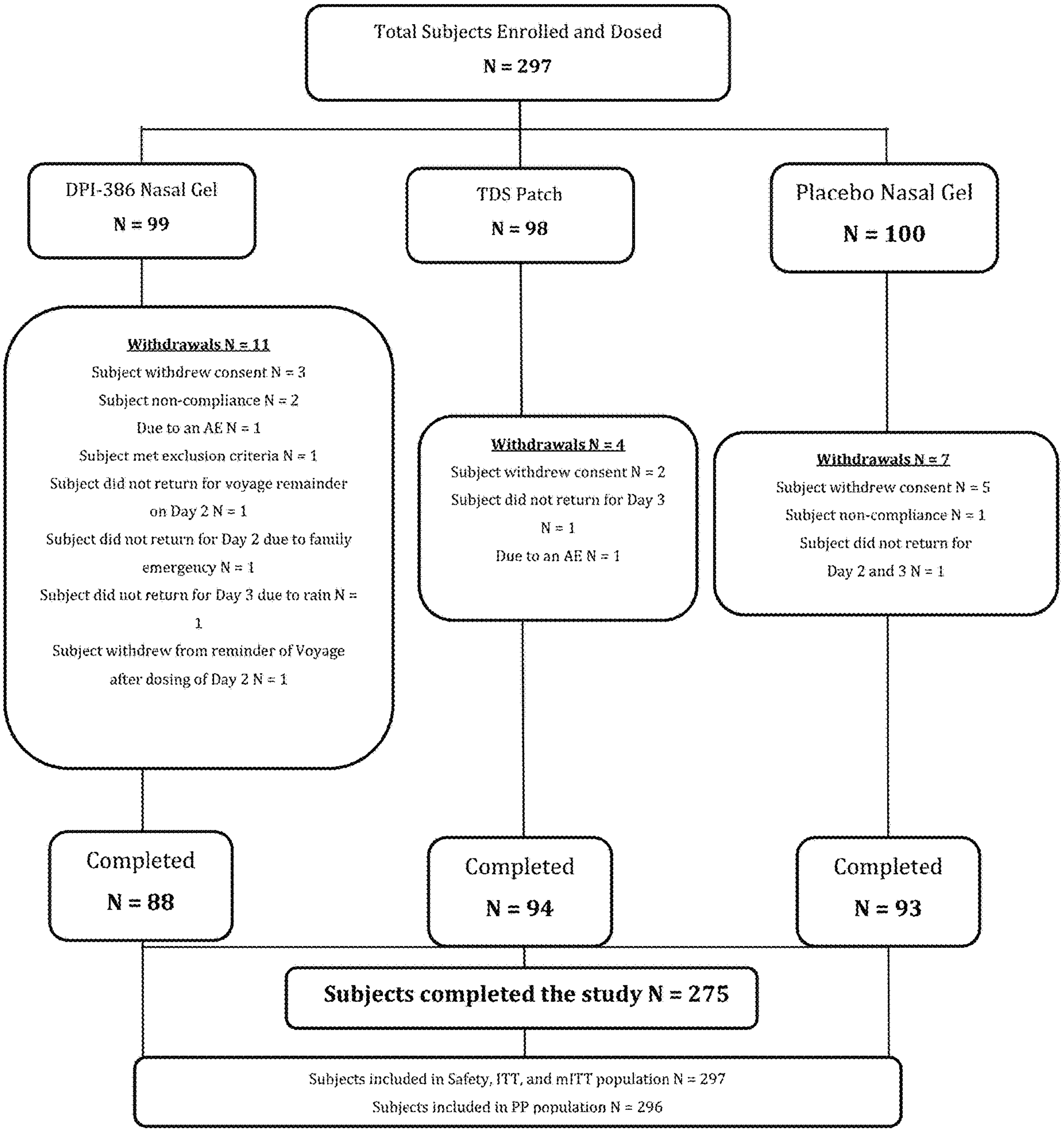
FIG. 7A is an illustration of the disposition of subjects.

Clinical study MS-21, Example 7, was a randomized, double-blind, placebo-controlled Phase 3 study of the safety and efficacy of DPI-386 nasal gel on ocean-going vessels for the prevention and treatment of nausea associated with motion sickness. See FIG. 7A.

Clinical study MS-22, Example 8, was a randomized, double-blind, placebo-controlled Phase 3 study of the safety, efficacy and pharmacokinetics of DPI-386 nasal gel for the prevention and treatment of nausea associated with motion sickness. This study included a comparison of DPI-386 Nasal Gel to Placebo Nasal Gel and a transdermal scopolamine (TDS) patch. Subjects were administered 0.2 mg twice a day for three consecutive days. The subjects were male or females, aged 18 to 59. See FIGS. 8A through 8C.

Clinical study DE-10, Example 9, was an open-label, dose-escalating, non-randomized, single-center study to determine the safety of scopolamine in healthy volunteers. See FIG. 9.

The studies included co-primary endpoints of 1) the incidence of subject-reported motion sickness and/or 2) complete response. All endpoints were analyzed as binary outcome variables (i.e., response vs. non-response). For each endpoint, the estimand is the difference in treatment group proportions between DPI-386 Nasal Gel and each control arm (TDS Patch and/or Placebo Nasal Gel). All primary analyses in each of the three studies are based on the ITT Population, defined as all subjects randomized on Treatment Day 1. All randomized subjects in all three studies reported at least one post-baseline efficacy evaluation.

For each study, endpoint, and time interval, the proportion of subjects were to be compared between DPI-386 Nasal Gel and each control arm using a logistic regression model based on the binomial distribution with an identity link function (Freedman, L. S., An analysis of the controversy over classical one-sided tests, Clin Trials. 2008; 5(6): 635-40 (2008); Freedman, L. S., et al., A comparison of regression calibration, moment reconstruction and imputation for adjusting for covariate measurement error in regression, Stat. Med. 27(25):5195-5216 (2008)). The number and percentage of subjects who meet the condition of interest was presented for each treatment group and time interval, along with the estimate of the difference in proportions and the associated 95% confidence interval (CI) estimated from the logistic regression model. The planned logistic regression model was used to compare treatment groups for the co-primary endpoints for studies MS-21 and MS-22. The planned logistic regression model for study MS-24 did not fit as specified and a contingency logistic regression model was used instead. The contingency model included all of the same factors as planned in the original model, but with a logit link function for the assumed binomial distribution to compare treatment group odds ratios.

The Complete Response rate was numerically higher for DPI-386 Nasal Gel compared with placebo and Transderm Scop; DPI-386 Nasal Gel was noninferior to Transderm Scop, but DPI-386 Nasal Gel was superior to placebo in the MS-24 study, as well as for the MS-33 study (pivotal) and per protocol on the MS-29 study.

Figure 2:
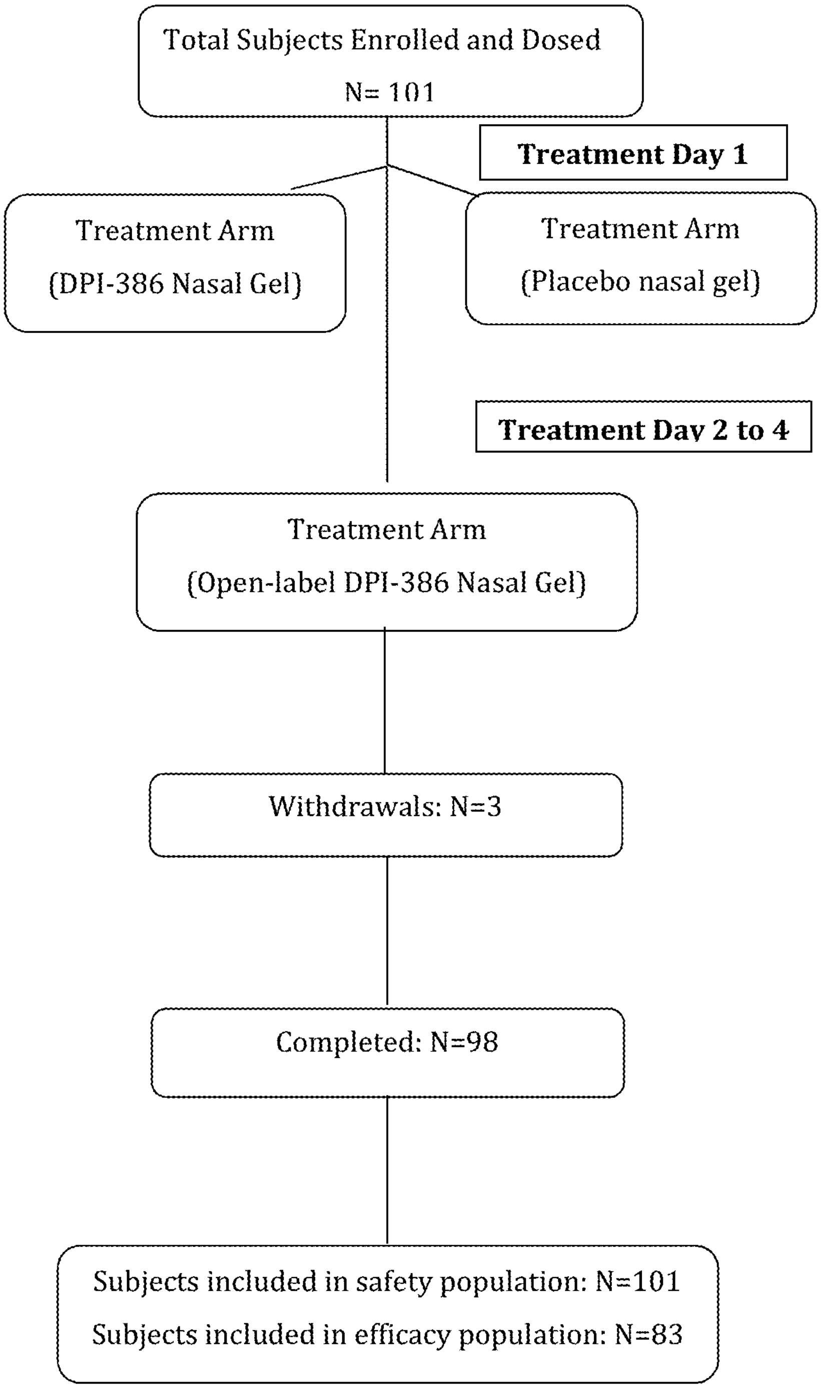
FIG. 2 is a schematic diagram depicting the disposition of subjects for clinical study MS-24.
Figure 3A:
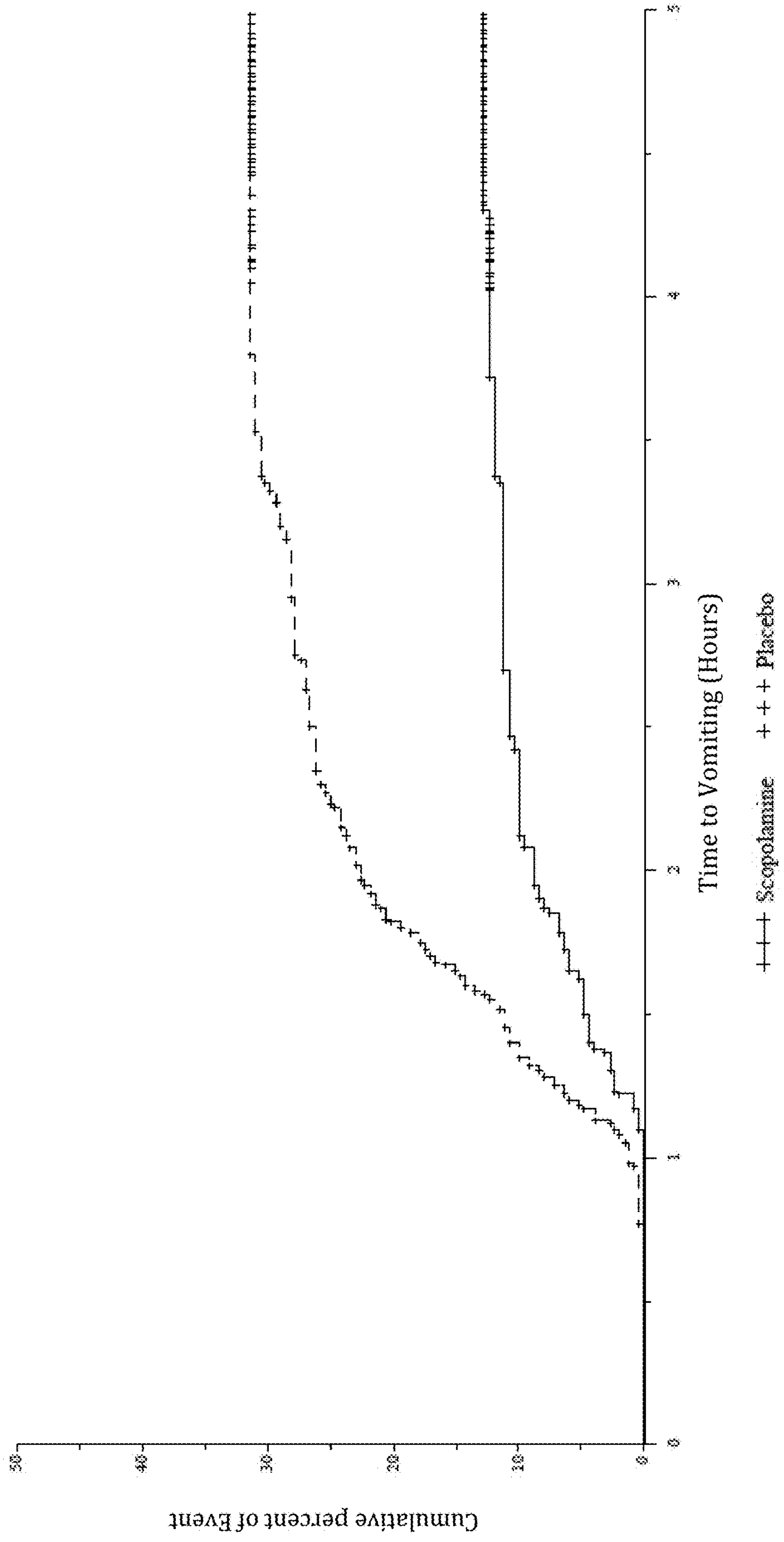
FIG. 3A is a graphic presentation from clinical study MS-33 showing Kaplan-Meier Plot of Time to Vomiting or Use of Rescue Medication (ITT Population). Subjects who reported vomiting or have taken rescue treatment within 4 hours after receiving study drug are considered having the event, and time to event is derived as the number of hours from dosing to the earliest time of vomiting or rescue medication use. Subjects without an event were censored at the time of the end of voyage (approximately 4 hours post dose). Log Rank P-value<0.0001.
Figure 3B:
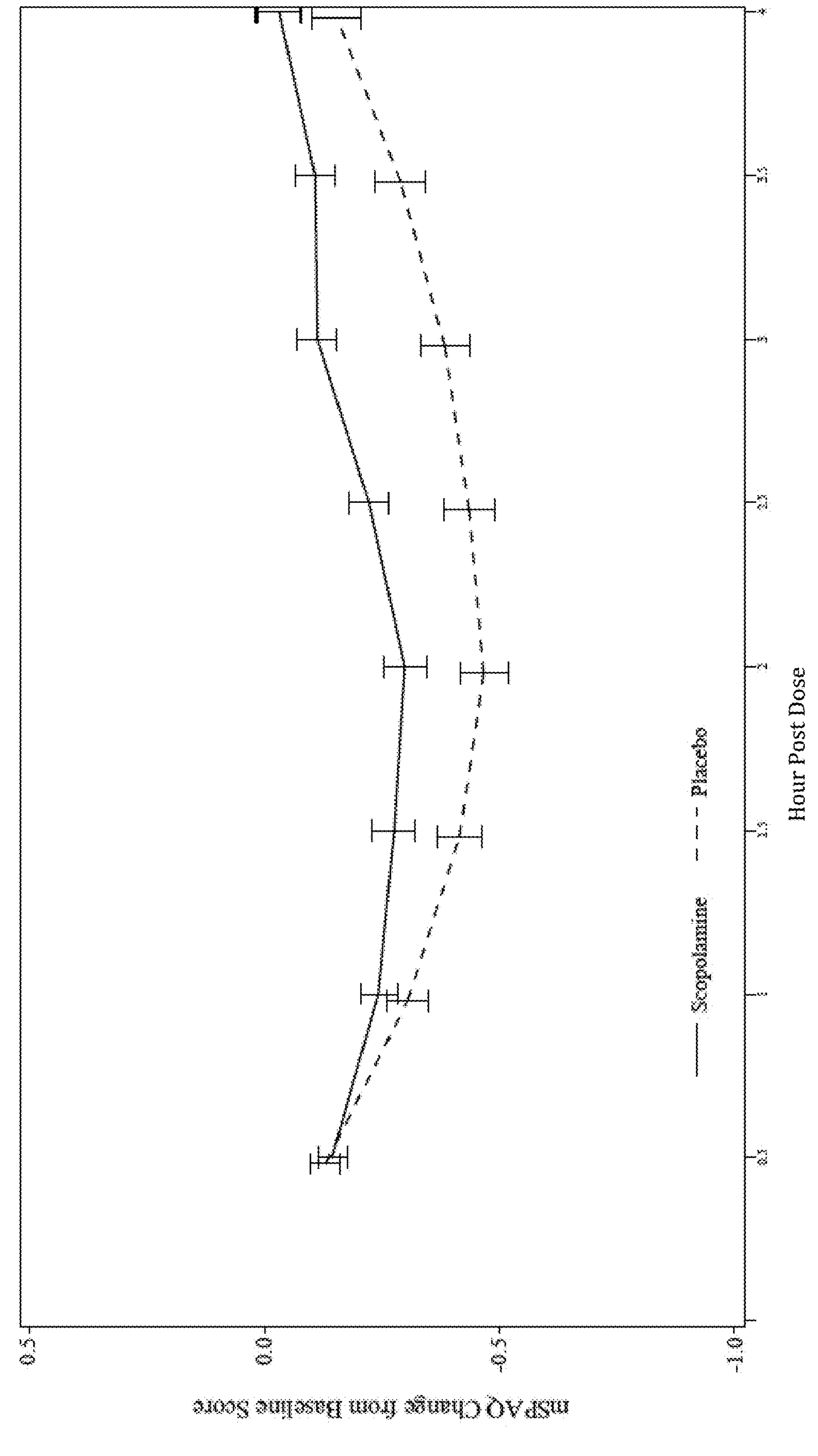
FIG. 3B is a graphic presentation from clinical study MS-33 showing Least Squares Mean (SE) Change from Baseline in PSAQ Memory (ITT Population). PSAQ Score were assigned as 1=significantly worse, 2-somewhat worse, 3-no effect, 4=somewhat better, 5=significantly better. Analysis was based on MMRM including fixed effects of treatment, visit, baseline score and interaction terms of treatment by visit.
Figure 5A:
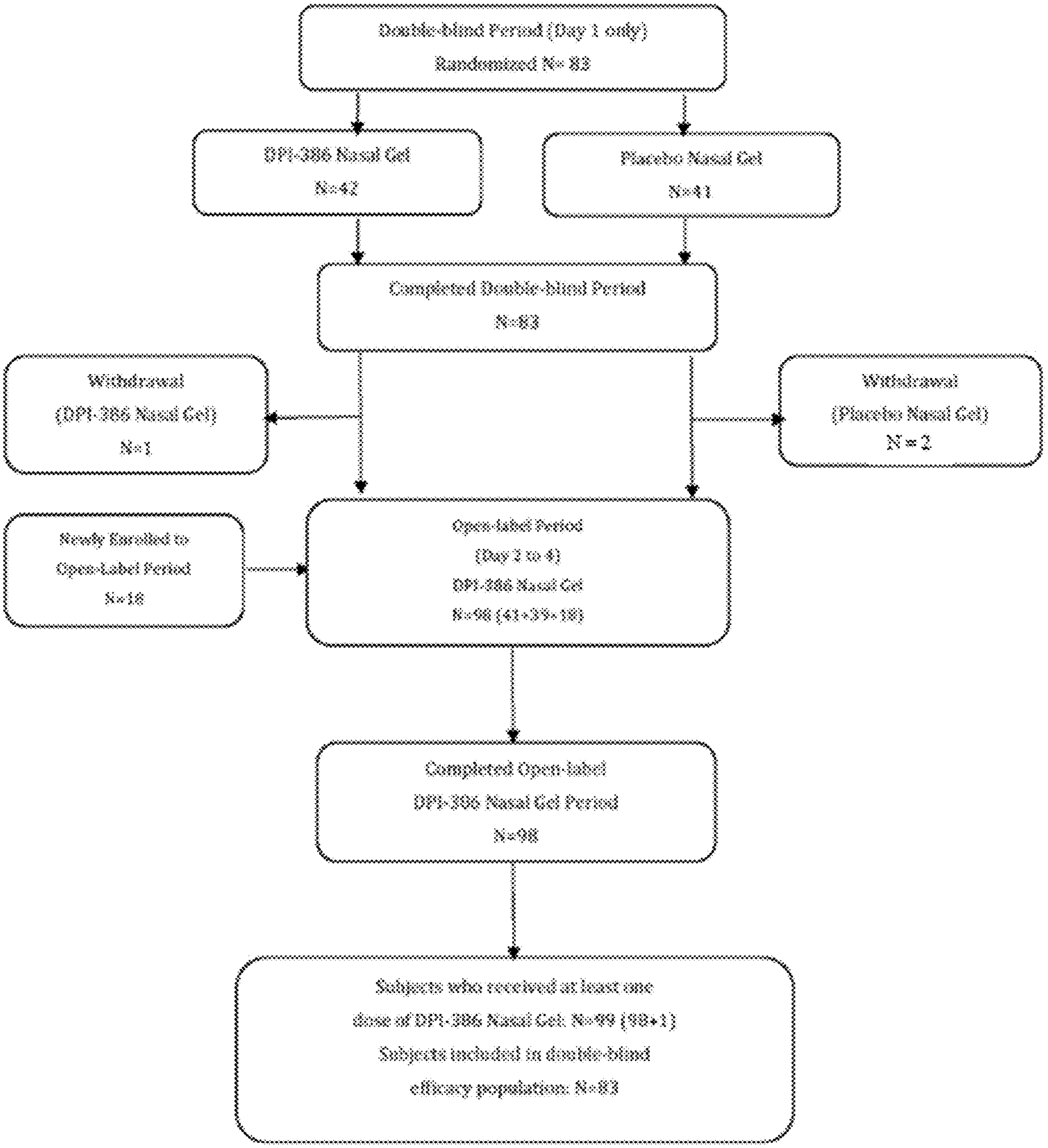
FIG. 5A is an illustration of the workflow associated with the disposition of subjects.

For the Nausea endpoint, DPI-386 Nasal Gel was superior to placebo and noninferior to Transderm Scop for all studies and time points (as applicable) except Day 1 within the first 4 hours of first dose in the MS-22 study (See Tables 3a-3g below, and FIGS. 3A, 2B, and 5C). DPI-386 Nasal Gel was still noninferior to TDS at this timepoint, and as will be demonstrated herein, superior to placebo in MS-33.

The data herein show that DPI-386 provides safe and efficacious treatment of nausea and motion sickness, with a unexpectedly low Cmax achieved which is fully efficacious and which does not generate undesirable side effects, e.g., anticholinergic effects. Additional details of clinical studies are provided in the Examples, below.

EXAMPLES

The following Examples are provided by way of illustration and not by way of limitation.

Example 1: Formulation and Unit Composition of a Scopolamine Nasal Gel

Table 1, below, provides one embodiment of a scopolamine nasal gel in accordance with the present disclosure, referred to herein as DPI-386.

TABLE 1

Formulation and unit composition of DPI-386 nasal gel, 0.2 mg/0.12 g.

| Component | Reference to Quality Standards | Function | Amount % w/w | mg/g | mg/0.12 [b] g | mg/Bottle [c] 6 actuations | 6 actuations + Overfill (2.5 g fill) |
|---|---|---|---|---|---|---|---|
| Scop. HBr [a] | USP | Active ingredient | 0.167 | 1.67 | 0.20 | 1.20 | 4.2 |
| Polyvinyl Alcohol, 40 cps | USP | Gelling agent | 10.00 | 100.0 | 12.0 | 72.0 | 250.0 |
| Sodium Citrate, Dihydrate | USP | Buffer | 0.35 | 3.5 | 0.42 | 2.52 | 8.75 |
| Citric Acid, Anhydrous | USP | Buffer | 0.74 | 7.4 | 0.89 | 5.33 | 18.5 |
| Sodium Metabisulfite | NF | Antioxidant | 0.10 | 1.0 | 0.12 | 0.72 | 2.5 |
| Glycerin | USP | Humectant | 5.00 | 50.0 | 6.00 | 36.0 | 125 |
| Benzalkon. Chloride, 50% [d] | NF | Preservative | 0.04 | 0.40 | 0.05 | 0.29 | 1.0 |
| Purified Water | USP | Solvent | qs ad to weight | | | | |

[a] = Amount adjusted per the assay value and water content found in each drug substance lot.
[b] = Based on a nominal actuation of 0.12 g.
[c] = The stated values are based on 6 actuations = 0.72 g with an overfill to give a nominal fill weight of NLT 2.5 g/bottle.
[d] = The benzalkonium chloride concentrations are expressed in this table as the amount of 50% solution nominally present, which is twice the concentration on a neat basis. The actual amount added is calculated based on the assay value of the lot utilized.
NF = National Formulary; USP = United States Pharmacopeia.

Example 2: Process for Preparing a Scopolamine Nasal Gel

One embodiment of a process for preparing a scopolamine nasal gel according to the disclosure is outlined as follows. Phase 1: Add 10% of the purified water to a suitable vessel and begin stirring; add sodium citrate and stir until dissolved; add citric acid and stir until dissolved; add sodium metabisulfite and stir until dissolved; add scopolamine hydrobromide trihydrate and stir until dissolved; add glycerin and stir until dissolved; add in benzalkonium chloride and stir until dissolved. Phase 2: In a closed mixing vessel, mix (85%) purified water and polyvinyl alcohol, stir and heat to 75° C.±5° C.; cool to 30° C. Phase 3: Once Phase 2 is cooled, add Phase 1 to Phase 2; rinse the Phase 1 container with 500 g of purified water, and add the rinsate to the Phase 2 container; continue mixing; QS the batch and mix for 30±5 minutes; assemble a 100 μm filter (e.g., Sartopure®), and filter product into receiving vessel; remove samples for pre-fill testing; if passing, seal receiving vessel and hold for a minimum of 12 hours.

In some embodiments, the viscosity of the gel should be between 1800 and 3500. Varying viscosities may be achieved by controlling mixing conditions, dwell time, and temperature during processing. Alternatively, viscosity may be affected by the amount of gelling agent, e.g., polyvinyl alcohol, included in the composition.

In this regard, while the present disclosure provides specific delivery for an intranasal route, the present disclosure may be extended to any transmucosal delivery including transbuccal, namely the ability to deliver scopolamine in an amount previously believed to be less than efficacious, but nevertheless herein demonstrated to control one or more symptoms, including nausea and vomiting, associated with motion. In this aspect, the transmucosal delivery of the present disclosure alleviates symptoms without creating significant anticholinergic adverse effects. To those skilled in the art, therefore, it would be apparent that other means of transmucosal delivery, such as transbuccal, may be used to deliver a dosage of scopolamine that achieves the favorable systemic pharmacokinetics of this disclosure.

Clinical Studies

Abbreviations used in the clinical study examples that follow are shown in Table 2, below.

TABLE 2

Clinical Study Abbreviations

| | | | |
|---|---|---|---|
| ACTS | Anticholinergic Toxicity Screen | IRB | Institutional Review Board |
| AE | adverse event | ITT | intent-to-treat |
| Ae | amount excreted | IV | intravenous |
| AESI | adverse event of special interest | KSS | Karolinska Sleepiness Scale |
| ANAM | Automated Neuropsychological Assessment Metrics | LC-MS/MS | liquid chromatography with tandem mass spectrometry |
| ANCOVA | analysis of covariance | LSLV | Last Subject Last Visit |
| AUC | area under the curve | LSM | least-squares mean |
| AUC % ex | the percent of AUCinf obtained by extrapolation | LSMD | least-squares mean estimate of group differences |
| AUC0-t or AUCt | area under the concentration-time curve from time zero to time of the last quantifiable concentration | MedDRA | Medical Dictionary for Regulatory Activities |
| AUCtau | area under the concentration-time curve over a dosing interval | mITT | modified intent-to-treat |
| AUC3d | area under the concentration-time curve over 3 days of dosing | MSAQ | Motion Sickness Assessment Questionnaire |
| BMI | body mass index | MSSQ | Motion Sickness Susceptibility Questionnaire |
| BQL | below the quantifiable limit | NCA | non-compartmental analysis |
| CEBQ | Confidential Exclusionary Behavior Questionnaire | NCS | not clinically significant |
| CI | confidence interval | NG | nasal gel |
| $C_{max}$ | maximum plasma concentration | PD | pharmacodynamic |
| CFR | Code of Federal Regulations | PI | Principal Investigator |
| CL/F | apparent clearance following extravascular administration | PK | pharmacokinetic |
| CLr | renal clearance | PP | per protocol |
| CMQ | Confidential Medical Questionnaire | PSAQ | Performance Self-Assessment Questionnaire |
| CNS | central nervous system | PT | preferred term (MedDRA) |
| CFR | Code of Federal Regulations | PVT | Psychomotor Vigilance Task |
| CPR | cardio-pulmonary resuscitation | QC | quality assurance |
| CS | clinically significant | R(AUCtau) | accumulation ratio for AUCtau |
| C-SSRS | Columbia-Suicide Severity Rating Scale | R(Cmax) | accumulation ratio for Cmax |
| Ctau | concentration at the end of dosing interval | SAE | serious adverse event |
| CV % | coefficient of variation percent | SAP | statistical analysis plan |
| DBP | diastolic blood pressure | SAS | Statistical Analysis System |
| ECG | electrocardiogram | SBP | systolic blood pressure |
| FDA | Food and Drug Administration | SD | standard deviation |
| eCRF | electronic case report form | SE | standard error |
| EOUQ | Ease-of-Use Questionnaire | SOC | System Organ Class |
| FSFV | First Subject First Visit | SOP | standard operating procedure |
| GCP | Good Clinical Practices | $t_{1/2}$ | terminal half-life |
| GI | gastrointestinal | TDS | transdermal scopolamine |
| GLM | geometric least squares mean | TEAE | treatment-emergent adverse event |
| GM | geometric mean | tlag | lag time; time point before the first quantifiable concentration |
| HBr | hydrogen bromide | tlast | time of last quantifiable concentration |
| hCG | human chorionic gonadotropin | $t_{max}$ | time of maximum concentration |
| ICF | informed consent form | US | United States |
| ICH | International Council for Harmonisation | VAS | visual analogue scale |
| IEC | Independent Ethics Committee | Vz/F | Apparent volume of distribution based on the terminal phase following extravascular administration |
| IM | intramuscular | | |
| IMP | Investigational Medicinal Product | | |
| IFU | Instructions for Use | | |

Example 3: Clinical Study MS-33: Efficacy and Safety of DPI-386 Nasal Gel for the Prevention of Nausea and Vomiting Associated with Motion Clinical MS-33 was a randomized, double-blind, placebo-controlled phase 3 study of the efficacy and safety of DPI-386 Nasal Gel for the prevention of nausea and vomiting associated with motion.

Primary Efficacy Objective

To assess the efficacy of DPI-386 Nasal Gel (0.2 mg scopolamine HBr) compared to matching Placebo Nasal Gel in the prevention of vomiting. Complete Response is defined as no vomiting and no rescue treatment (e.g., antihistamine) induced by motion.

Secondary Efficacy Objectives

Assess the efficacy of DPI-386 Nasal Gel (0.2 mg scopolamine HBr) compared to matching Placebo Nasal Gel for: time to vomiting or use of rescue medication; severity of nausea; and presence of nausea.

Safety Objective:

Assess the safety of DPI-386 Nasal Gel (0.2 mg scopolamine HBr) compared to matching Placebo Nasal Gel with an emphasis on adverse events (AEs).

Methodology

This was a Phase 3, two-arm, randomized, double-blind, placebo-controlled, single dose efficacy and safety study evaluating the use of a nasal gel to prevent nausea and vomiting induced by motion.

Study Design

This was a Phase 3, randomized, double-blind, placebo-controlled study evaluating DPI-386 Nasal Gel versus placebo. Approximately 500 subjects were randomized 1:1 (250 DPI-386 Nasal Gel/250 matching Placebo Nasal Gel) and were planned to be enrolled. Unless deemed a prohibited medication, standard of care treatment (e.g., antihistamine) was permitted upon request by the subject after boarding the boat but any such medications were captured as concomitant medications.

Recruitment and Screening Phase

The Recruitment and Screening Phase assessed the potential subjects susceptibility to motion sickness with the Motion Sickness Susceptibility Questionnaire Short-Form (MSSQ-Short). Reference is made to Golding, John F., *Predicting Individual Differences in Motion Sickness Susceptibility by Questionnare, Personality and Individual Differences*, Volume 41, Issue 2, July 2006, Pages 237-246, and Golding, John F., *Motion Sickness Susceptibility Questionnaire Revised and Its Relationship to other Forms of Sickness*, Brain Research Bulletin, 1998, each incorporated by reference with regard to the MSSQ. Subjects provided at least three responses of "Frequently" from the "Over the Last 10 Years" section of the MSSQ-Short indicating susceptibility to motion sickness to enter the study. The subjects were also be asked about their medical history and complete a Mini-Mental Status Exam (MMSE). If the subject met the inclusion/exclusion criteria they proceeded to the Treatment Phase of the study.

Treatment Phase

Eligible subjects were randomized 1:1 to DPI-386 Nasal Gel or Matching Placebo Nasal Gel and assigned a time and date for travel on an ocean-going vessel. Study drug was administered while the ship was in harbor. The Modified Performance Self-Assessment Questionnaire (PSAQ) was completed by each subject prior to the administration of nasal gel, approximately every 30 minutes after dosing, and at the end of travel. The subjects completed the Nausea Assessment Scale (NAS) every 30 minutes after dosing, and at the end of travel. The subjects were also asked to complete a Sopite Assessment Questionnaire (SAQ) and a Patient Global Assessment of Severity (PGI-S) at 4 hours to describe their travel experience. Reference for the PGI-S is made to Yalcin I., et al., *Validation of two global impression questionnaires for incontinence*, Am J Obstet Gynecol 2003; 189:98-101. All questionnaires were submitted for analysis. An exit interview was also conducted.

Post Treatment Follow-Up

Subjects were asked to complete 2 post-treatment follow-ups, at Day 2 (+3 days)/Visit 3 and at Day 15 (±3 days)/Visit 4, to further assess safety. Safety and tolerability was evaluated by monitoring the occurrence of AEs during ocean travel, Day 2 (+3 days)/Visit 3, and Day 15 (±3 days)/Visit 4. The Day 2 and Day 15 follow-up visits were conducted virtually via the sites' telehealth process.

Diagnosis and Main Criteria for Inclusion

Ability to provide written, informed consent prior to initiation of any study-related procedures, and ability in the opinion of the Investigator to understand and comply with all the requirements of the study, which includes abstaining from the use of prohibited medications.

Male and female subjects ≥18 years of age;

Susceptible to provocative motion as evidenced by at least three responses of "Frequently" from the "Over the Last 10 Years" section of the MSSQ-Short;

Acceptable overall medical condition to be safely enrolled in and complete the study in the opinion of the Investigator;

Ability to take intranasal medication;

Males, non-fecund females (i.e., surgically sterilized, if procedure was done 6 months before screening or subject is 2 years postmenopausal), or females of childbearing potential using an acceptable method of birth control (i.e., condoms, diaphragm, spermicidal agents, cervical cap, copper intrauterine device, etc.) for a period of up to 30 days before dosing and for one month after dosing and must have a negative pregnancy test at screening;

Agree to adhere to the following lifestyle compliance considerations:

Refrain from consumption of grapefruit and any substance containing grapefruit for 7 days prior to, during, and 7 days after study drug administration;

Abstain from alcohol for 24 hours prior to the administration of study drug and through the ocean travel;

Abstain from marijuana within the 7-day period prior to the Treatment Day and throughout Day 2.

Severe Acute Respiratory Syndrome Coronavirus-2 (SARS-CoV-2) negative test, confirmed by Food and Drug Administration (FDA) authorized COVID-19 test ≤7 days prior to study drug administration or no COVID-19 symptoms up to 10 days prior to study drug administration.

Main Criteria for Exclusion

Nauseated Prior to Boarding.

Mini-Mental State Examination score of <24;

Women of childbearing potential, or men whose sexual partner(s) is a woman of childbearing potential, who:

Are or intend to become pregnant (including use of fertility drugs) during the study;

Are nursing (female subjects only);

Are not using an acceptable, highly effective method of contraception until all follow-up procedures are complete.

Known allergic reactions to scopolamine or other anticholinergics;

Hospitalization or significant surgery requiring hospital admittance within the past 6 months;
Treatment with another investigational product within the past 30 days;
Donated blood or plasma or suffered significant blood loss within the past 30 days;
Chronic nausea caused by conditions such as irritable bowel syndrome, gastroparesis, cyclic vomiting syndrome or any other cause;
Having any of the following medical conditions within the last 2 years or if any of the following medical conditions were experienced more than 2 years ago and are deemed as clinically significant by the Investigator:
Significant gastrointestinal disorder, asthma, or seizure disorders;
History or current cardiovascular disease;
History or current vestibular disorders;
History or current narrow-angle glaucoma;
History or current urinary retention problems; or
History or current alcohol or drug abuse.
Has had any prior nasal, nasal sinus, or nasal mucosa surgery.
Currently taking any of the following medication types within the specified washout period:
Any form of scopolamine (including Transderm Scop®/washout 5 days;
Belladonna alkaloids/washout 14 days;
Antihistamines (including meclizine/washout 14 days;
Tricyclic antidepressants/washout 14 days;
Muscle relaxants/washout 4 days; or
Nasal decongestants/washout 4 days.

Has used marijuana within the 7-day period prior to the Treatment Day. (Note: this criterion will only be confirmed at Eligibility Confirmation, not at Recruitment and Screening, although heavy users of marijuana can be determined ineligible at Screening. All potential study subjects deemed eligible at Screening must be informed at that time that this requirement must be met at Eligibility Confirmation.)

Unwilling or unable to follow the medication restrictions or unwilling to wash-out the use of restricted medications as noted in Exclusion Criterion #11.

Subject participated in a previous study of DPI-386 Nasal Gel.

Dose and Mode of Administration

Investigational Product and Other Study Drugs

The investigational product was DPI-386 Nasal Gel (0.2 mg scopolamine HBr per dose) and matching placebo gel. Single administration of Nasal Gel (active or placebo) was delivered into one nostril prior to motion. All study drug was administered in a single nostril. The administration was identical for all subjects. On Study Day 1/Visit 2, randomized subjects received a single administration of DPI-386 Nasal Gel (0.2 mg scopolamine HBr) or Matching Placebo Nasal Gel.

Dose Selection

The DPI-386 dose was based on safety and efficacy findings from four completed Phase 3 studies.

Permitted Concomitant Medication

All current stable medications were allowed during the course of the study except those listed as prohibited.

Clinical Trial Duration

Counting the time from initial screening to trial completion, the trial duration was up to 75 days for enrolled subjects, with assessments as follows: Screening/−60 to Day 0, Day 1, Day 2 (+3 days), and Day 15 (+3 day). Follow-up visits on Day 2 and Day 15 were conducted virtually via the institution's telehealth process.

Trial Endpoints

The primary efficacy endpoint in this study was the proportion of subjects who report no vomiting within 4 hours or to end of voyage, whichever came later, after receiving study drug and no use of rescue treatment (e.g., antihistamine) within 4 hours or to end of voyage, whichever came later, after receiving study drug (Complete Responders).

The secondary efficacy endpoints: time to vomiting or use of rescue medication; the proportion of subjects who did not have moderate or severe nausea, which was defined as those subjects who report no moderate and severe nausea within 4 hours after receiving study drug and who did not use rescue treatment (e.g., antihistamine) within 4 hours after receiving study drug; and the proportion of subjects who did not have nausea, which was defined as those subjects who report no nausea within 4 hours after receiving study drug and who did not use rescue treatment (e.g., antihistamine) within 4 hours after receiving study drug.

Exploratory Endpoint

Patient Global Impression of Severity (PGI-S) of Motion Sickness as measured by a verbal rating scale (none, mild, moderate, and severe).

Safety endpoints in the study evaluated the safety of DPI-386 relative to placebo by assessing: incidence of AEs; incidence of serious AEs (SAEs); incidence of Grade 3 and Grade 4 AEs; and performance self-assessment measured before, during, and after the ocean travel using the Modified Performance Self-Assessment Questionnaire (PSAQ).

Sample Size/Power and Statistical Methods

A total of approximately 500 subjects were planned to be enrolled in this study in a 1:1 ratio of DPI-386 Nasal Gel to Matching Placebo Nasal Gel. Assuming that the response on the primary endpoint in the DPI-386 Nasal Gel Arm was 82.5% and the response in the placebo arm was 62.5%, sample sizes of 250 in the placebo arm and 250 in the DPI-386 Nasal Gel arm achieved at least 90% power to detect a difference between the group proportions of 15% using the 2-sided Z test with pool variance at the significance level of 0.05.

Analysis Populations

Intent-to-Treat (ITT) population consisted of all subjects who were randomized and dispensed study drug. Modified Intent to Treat (mITT) population included subjects who had at least one post-dose baseline primary efficacy assessment. Per Protocol (PP) population included subjects who received study drug and had no major protocol deviations as noted in the Statistical Analysis Plan (SAP). Safety Population included all subjects who received study drug.

The between-treatment comparison for the primary endpoint was performed using a 2-sided Z test. The between-treatment difference and 95% confidence intervals (CIs) was provided. The between-treatment comparison of the binary response endpoints was also performed using a 2-sided Z test. The between-treatment difference and 95% CIs was provided.

Time to vomit or use of rescue medication was summarized using the Kaplan-Meier method. Time to vomit was defined as the number of hours from dosing to the first event of vomiting or use of rescue medication; subjects who did not have the event were censored at 4 hours post dose. The median time to vomit along with the 95% CIs was provided by treatment group. The between-treatment comparison was provided using the log-rank test.

Subject reported outcomes were summarized descriptively by treatment group. If data permitted, the between-treatment comparisons were performed.

Results

Results are presented in Tables 3a-3f, below, and in FIGS. 3A-3S, herein.

TABLE 3a

MS-33 Study, Analysis of Complete Response Rate (ITT Population)

| Category Subjects with no vomiting and no rescue medication | DPI-386 Nasal Gel (N = 251 | Placebo Nasal Gel (N = 252) |
|---|---|---|
| n/N (%) | 219/251 (87.3) | 173/252 (68.7) |
| 95% CI | (82.5, 91.1) | (62.5, 74.3) |
| Treatment difference (95% CI) | 18.6 (11.5, 25.7) | |
| p-value [a] | <0.0001 | |

CI = confidence interval; ITT = intent-to-treat.

[a] P-value was based on chi square test.

Note:

Complete response is defined as no vomiting and not using rescue treatment within 4 hours after receiving study drug.

The within 4 hours after receiving study drug window is from the time of the first dose to the time of the end of voyage.

TABLE 3b

MS-33 Study, Analysis Proportion of Subjects without Nausea and without Rescue Medication (ITT Population)

| Category Subjects with no nausea and no rescue medication | DPI-386 Nasal Gel (N = 251 | Placebo Nasal Gel (N = 252) |
|---|---|---|
| n/N (%) | 51/251 (20.3) | 33/252 (13.1) |
| 95% CI | (15.5, 25.8) | (9.2, 17.9) |
| Treatment difference (95% CI) | 7.2 (0.7, 13.7) | |
| p-value [a] | 0.0299 | |

CI = confidence interval; ITT = intent-to-treat.

[a] P-value was based on chi square test.

Note:

Response is defined as NAS score of No symptoms and did not use rescue treatment within 4 hours after receiving study drug.

The within 4 hours after receiving study drug window is from the time of the first dose to the time of the end of voyage.

TABLE 3c

MS-33 Study, Analysis Proportion of Subjects without Moderate or Severe Nausea and without Rescue Medication (ITT Population)

| Category Subjects with no moderate or severe nausea and no rescue medication | DPI-386 Nasal Gel (N = 251 | Placebo Nasal Gel (N = 252) |
|---|---|---|
| n/N (%) | 169/251 (67.3) | 112/252 (44.4) |
| 95% CI | (61.1, 73.1) | (38.2, 50.8) |
| Treatment difference (95% CI) | 22.9 (14.4, 31.3) | |
| p-value [a] | <0.0001 | |

CI = confidence interval; ITT = intent-to-treat.

[a] P-value was based on chi square test.

Note:

Response is no NAS score of moderate or severe and did not use rescue treatment within 4 hours after receiving study drug.

The within 4 hours after receiving study drug window is from the time of the first dose to the time of the end of voyage.

TABLE 3d

MS-33 Study, Analysis of Time to Vomiting (ITT Population)

| Category | DPI-386 Nasal Gel (N = 251 | Placebo Nasal Gel (N = 252) |
|---|---|---|
| Number (%) Subjects with Event | 32 (12.7) | 79 (31.3) |
| Number (%) Subjects Censored | 219 (87.3) | 173 (68.7) |
| Time to Event (hours) | | |
| 25% (95% CI) | NE | 2.3 (1.9, 3.2) |
| Median (95% CI) | NE | NE |
| 75% (95% CI) | NE | NE |
| Log Rank p-value | <0.0001 | |
| Hazard Ratio (95% CI) | 0.361 (0.240, 0.544) | |
| Probability of Event (95% CI) | | |
| Hour 1 | 0.003 (0.001, 0.006) | 0.009 (0.002, 0.016) |
| Hour 2 | 0.088 (0.066, 0.110) | 0.225 (0.190, 0.259) |
| Hour 3 | 0.112 (0.085, 0.138) | 0.281 (0.241, 0.318) |
| Hour 4 | 0.126 (0.096, 0.154) | 0.311 (0.269, 0.350) |

CI = confidence interval; ITT = intent-to-treat; NE = not estimable.

Note:

Subjects who reported vomiting or have taken rescue treatment within 4 hours after receiving study drug are considered as having the event, and time to event is derived as the number of hours from dosing to the earliest time of vomiting or rescue medication use. The within 4 hours after receiving study drug window is from the time of the first dose to the time of the end of voyage.

TABLE 3e

MS-33 Study, Analysis of Proportion of Subjects without Motion Sickness based on PGI-S (ITT Population)

| Category Subjects with no symptoms per PGI-S | DPI-386 Nasal Gel (N = 251 | Placebo Nasal Gel (N = 252) |
|---|---|---|
| n/N (%) | 76/250 (30.4) | 44/250 (17.6) |
| 95% CI | (24.8, 36.5) | (13.1, 22.9) |
| Treatment difference (95% CI) | 12.8 (5.4, 20.0) | |
| p-value [a] | 0.0008 | |

CI = confidence interval; ITT = intent-to-treat; PGI-S = Patient Global Impression of Severity.

[a] P-value was based on chi square test.

Note:

Response is patient global impression of severity (PGIS) score of None at the end of study.

Differences in PSAQ change from baseline scores (DPI-386 Nasal Gel scores minus Placebo Nasal Gel scores) and p-values for all PSAQ parameters and timepoints are summarized in Table 3f, below.

TABLE 3f

MS-33 Study, MMRM Analysis of Change from Baseline in PSAQ Scores

| PSAQ Parameter Timepoint (Minutes) | LS Mean Difference in Change from Baseline (DPI-386 Nasal Gel Score minus Placebo Nasal Gel Score)[a] | p-value[b] |
|---|---|---|
| Alertness | | |
| 30 | 0.007 | 0.8969 |
| 60 | 0.080 | 0.2703 |
| 90 | 0.139 | 0.0700 |
| 120 | 0.231 | **0.0029** |
| 150 | 0.192 | **0.0141** |
| 180 | 0.264 | **0.0008** |
| 210 | 0.153 | **0.0480** |
| 240 | 0.174 | **0.0269** |

TABLE 3f-continued

MS-33 Study, MMRM Analysis of Change from Baseline in PSAQ Scores

| PSAQ Parameter Timepoint (Minutes) | LS Mean Difference in Change from Baseline (DPI-386 Nasal Gel Score minus Placebo Nasal Gel Score)[a] | p-value[b] |
|---|---|---|
| Balance | | |
| 30 | 0.062 | 0.3413 |
| 60 | 0.166 | 0.1012 |
| 90 | 0.179 | **0.0214** |
| 120 | 0.144 | 0.0662 |
| 150 | 0.244 | **0.0028** |
| 180 | 0.257 | **0.0018** |
| 210 | 0.186 | **0.0222** |
| 240 | 0.176 | **0.0387** |
| Concentration | | |
| 30 | 0.026 | 0.6765 |
| 60 | 0.130 | 0.0654 |
| 90 | 0.222 | **0.0031** |
| 120 | 0.266 | **0.0006** |
| 150 | 0.275 | **0.0005** |
| 180 | 0.255 | **0.0014** |
| 210 | 0.204 | **0.0093** |
| 240 | 0.166 | **0.0382** |
| Hand-eye coordination | | |
| 30 | −0.003 | 0.9469 |
| 60 | 0.069 | 0.2877 |
| 90 | 0.176 | **0.0128** |
| 120 | 0.200 | **0.0064** |
| 150 | 0.228 | **0.0022** |
| 180 | 0.273 | **0.0003** |
| 210 | 0.166 | **0.0283** |
| 240 | 0.127 | 0.0942 |
| Memory | | |
| 30 | −0.013 | 0.7615 |
| 60 | 0.062 | 0.2864 |
| 90 | 0.144 | **0.0316** |
| 120 | 0.169 | **0.0136** |
| 150 | 0.214 | **0.0018** |
| 180 | 0.273 | **<0.0001** |
| 210 | 0.182 | **0.0072** |
| 240 | 0.123 | 0.0790 |
| Mood | | |
| 30 | 0.000 | 0.9969 |
| 60 | 0.141 | 0.0615 |
| 90 | 0.268 | **0.0011** |
| 120 | 0.284 | **0.0004** |
| 150 | 0.329 | **<0.0001** |
| 180 | 0.406 | **<0.0001** |
| 210 | 0.271 | **0.0012** |
| 240 | 0.280 | **0.0014** |
| Reaction time (speed) | | |
| 30 | −0.201 | 0.3730 |
| 60 | 0.110 | 0.0860 |
| 90 | 0.173 | **0.0177** |
| 120 | 0.185 | **0.0128** |
| 150 | 0.180 | **0.0173** |
| 180 | 0.238 | **0.0016** |
| 210 | 0.179 | **0.0203** |
| 240 | 0.116 | 0.1349 |
| Overall performance | | |
| 30 | −0.009 | 0.8830 |
| 60 | 0.157 | **0.0298** |
| 90 | 0.236 | **0.0018** |
| 120 | 0.232 | **0.0031** |
| 150 | 0.241 | **0.0021** |
| 180 | 0.206 | **0.0003** |

TABLE 3f-continued

MS-33 Study, MMRM Analysis of Change from Baseline in PSAQ Scores

| PSAQ Parameter Timepoint (Minutes) | LS Mean Difference in Change from Baseline (DPI-386 Nasal Gel Score minus Placebo Nasal Gel Score)[a] | p-value[b] |
|---|---|---|
| 210 | 0.203 | **0.0117** |
| 240 | 0.160 | 0.0525 |

[a]A positive value means that the change from baseline in the DPI-386 Nasal Gel group was less than the change from baseline in the Placebo Nasal Gel group.
[b]Bold p-values are nominally significant in favor of the DPI-386 Nasal Gel group (<0.05).
PSAQ scores were assigned as 1 = significantly worse, 2 = somewhat worse, 3 = no effect, 4 = somewhat better, 5 = significantly better.
Analysis was based on mixed model for repeated measures (MMRM) including fixed effects of treatment, visit, baseline score and interaction terms of treatment by visit.

As noted, this trial included a primary efficacy endpoint for the proportion of subjects who report no vomiting within 4 hours or to end of voyage, whichever came later, after receiving study drug and no use of rescue treatment (e.g., antihistamine) within 4 hours or to end of voyage, whichever came later, after receiving study drug (Complete Responders). Moreover, secondary efficacy endpoints included: (a) time to vomiting or use of rescue medication; (b) the proportion of subjects who did not have moderate or severe nausea, which was defined as those subjects who report no moderate and severe nausea within 4 hours after receiving study drug and who did not use rescue treatment (e.g., antihistamine) within 4 hours after receiving study drug; and (c) the proportion of subjects who did not have nausea, which was defined as those subjects who report no nausea within 4 hours after receiving study drug and who did not use rescue treatment (e.g., antihistamine) within 4 hours after receiving study drug. Lastly, the trial included an exploratory endpoint based on the Patient Global Impression of Severity (PGI-S) of Motion Sickness as measured by a verbal rating scale (none, mild, moderate, and severe). Lastly, the trial included safety endpoints in the study for DPI-386 relative to placebo by assessing: incidence of AEs; incidence of serious AEs (SAEs); incidence of Grade 3 and Grade 4 AEs; and performance self-assessment measured before, during, and after the ocean travel using the Modified Performance Self-Assessment Questionnaire (PSAQ).

As presented herein, intranasal scopolamine provides treatment and prevention of motion sickness (including space motion sickness), nausea, and emesis resulting from motion or the sensation of motion. Although it has been known for some time that scopolamine can be effective against nausea and vomiting or emesis, that is associated with or related to motion or the sensation of motion, certain problems with existing formulations and delivery methods have been acknowledged. At particular levels, scopolamine becomes effective in treating and preventing motion sickness, but at higher levels scopolamine leads to side effects due primarily to anticholinergic activity. In order to solve this problem, to the present disclosure outlines novel and unexpected scopolamine levels which are 1) effective and 2) avoid anticholinergic side effects, including but not limited to one or more of drowsiness, dry mouth, and blurred vision.

As demonstrated herein, and with reference to the tables above as well as FIGS. 3A, 3B, 3R, and 3S, Example 3 demonstrates statistically significant results across the stated endpoints.

Primary Efficacy Endpoint: Complete Response Rate

The primary efficacy endpoint was the proportion of subjects who were Complete Responders, defined as no vomiting and no use of rescue medication within 4 hours after receiving study drug or to end of voyage.

In the ITT population, 219 subjects (87.3%) in the DPI-386 Nasal Gel group and 173 subjects (68.7%) in the Placebo Nasal Gel group were Complete Responders—Table 3a. The difference between treatment groups was statistically significant ($p<0.0001$; Chi-square test).

Secondary Efficacy Endpoints

Time to Vomiting or Use of Rescue Medication

Time to vomiting or use of rescue medication was statistically significantly different between the 2 treatment groups in favor of DPI-386 Nasal Gel ($p<0.0001$, log rank test; FIG. 3A).

In the ITT population, 32 subjects (12.7%) in the DPI-386 Nasal Gel group and 79 subjects (31.3%) in the Placebo Nasal Gel treatment group had an event of vomiting or rescue medication use (Table 3d). The difference between treatment groups in time to vomiting or use of rescue medication was statistically significant in favor of the DPI-386 Nasal Gel group (<0.0001; log rank test).

The hazard ratio (95% CI) of having vomiting or using rescue medication within 4 hours of receiving study medication for subjects in the DPI-386 Nasal Gel group was 0.361 (0.240, 0.544) (the Placebo Nasal Gel group was the reference group).

The probability of having vomiting or using rescue medication in each hour for subjects in the DPI-386 Nasal Gel group was roughly one-third that of subjects in the Placebo Nasal Gel group.

The median time to vomiting or use of rescue medication in the 4-hour period after receiving study drug was not estimable (NE) for subjects in the DPI-386 Nasal Gel group or the Placebo Nasal Gel group, as <50% of subjects in either group had the event of vomiting or rescue medication use.

Proportion of Subjects without Moderate or Severe Nausea or Use of Rescue Medication In the ITT population, 169 subjects (67.3%) in the DPI-386 Nasal Gel group and 112 subjects (44.4%) in the Placebo Nasal Gel group did not have moderate or severe nausea and did not use rescue medication within the 4-hour period after receiving study drug (Table 3c). The difference was statistically significant in favor of the DPI-386 Nasal Gel group ($p<0.0001$; Chi-square test).

Proportion of Subjects without Nausea or Use of Rescue Medication

In the ITT population, 51 subjects (20.3%) in the DPI-386 Nasal Gel group and 33 subjects (13.1%) in the Placebo Nasal Gel group did not have nausea and did not use rescue medication within the 4-hour period after receiving study drug (Table 3b). The difference was statistically significant in favor of the DPI-386 Nasal Gel group ($p=0.0299$; Chi-square test).

The results of this study support a conclusion that DPI-386 Nasal Gel is superior to Placebo Nasal Gel in its ability to prevent nausea and vomiting induced by motion. Efficacy endpoints, represented by the proportion of subjects who had a Complete Response, the time to vomiting or use of rescue medication, the proportion of subjects who did not have moderate or severe vomiting and did not use rescue medication, the proportion of subjects who did not have nausea and did not use rescue medication, and the proportion of subjects who did not have motion sickness (per PGI-S), all showed statistically significant differences in favor of DPI-386 Nasal Gel when compared to Placebo Nasal Gel.

All 503 subjects were included in the ITT, mITT, and PP populations in this randomized, double blind, placebo-controlled Phase 3 study of a single administration of either DPI-386 Nasal Gel or Placebo Nasal Gel to subjects with a susceptibility to motion sickness. The study was conducted aboard an ocean-going vessel.

The results of this study support a conclusion that DPI-386 Nasal Gel is superior to Placebo Nasal Gel in its ability to prevent nausea and vomiting induced by motion. Analyses of the primary efficacy endpoint, three secondary efficacy endpoints, and an exploratory efficacy endpoint all showed statistically significant differences between treatment groups in favor of DPI-386 Nasal Gel.

The difference between treatment groups in the proportion of subjects who had a Complete Response, the primary efficacy endpoint, was statistically significant (87.3% in the DPI-386 Nasal Gel group and 68.7% in the Placebo Nasal Gel group; $p<0.0001$; Chi-square test).

For all three secondary endpoints the differences between treatment groups were statistically significant in favor of DPI-386 Nasal Gel: time to vomiting or use of rescue medication (<0.0001; log rank test), the proportion of subjects who did not have moderate or severe vomiting and did not use rescue medication ($p<0.0001$; Chi-square test), and the proportion of subjects who did not have nausea and did not use rescue medication ($p=0.0299$; Chi-square test).

For the exploratory endpoint of the proportion of subjects who did not have motion sickness (PGI-S), the difference between treatment groups was statistically significant in favor of the DPI-386 Nasal Gel group ($p=0.0008$; Chi-square-test).

The Complete Response rate, the proportion of subjects without moderate or severe nausea and without use of rescue medication, and the proportion of subjects without nausea and without use of rescue medication were evaluated in the following subgroups: gender, race, and age group (≤50 years, >50 years). In every subgroup the proportion of subjects who met each endpoint was higher the DPI-386 Nasal Gel group. Many of the comparisons were nominally significant.

Figure 3Q:
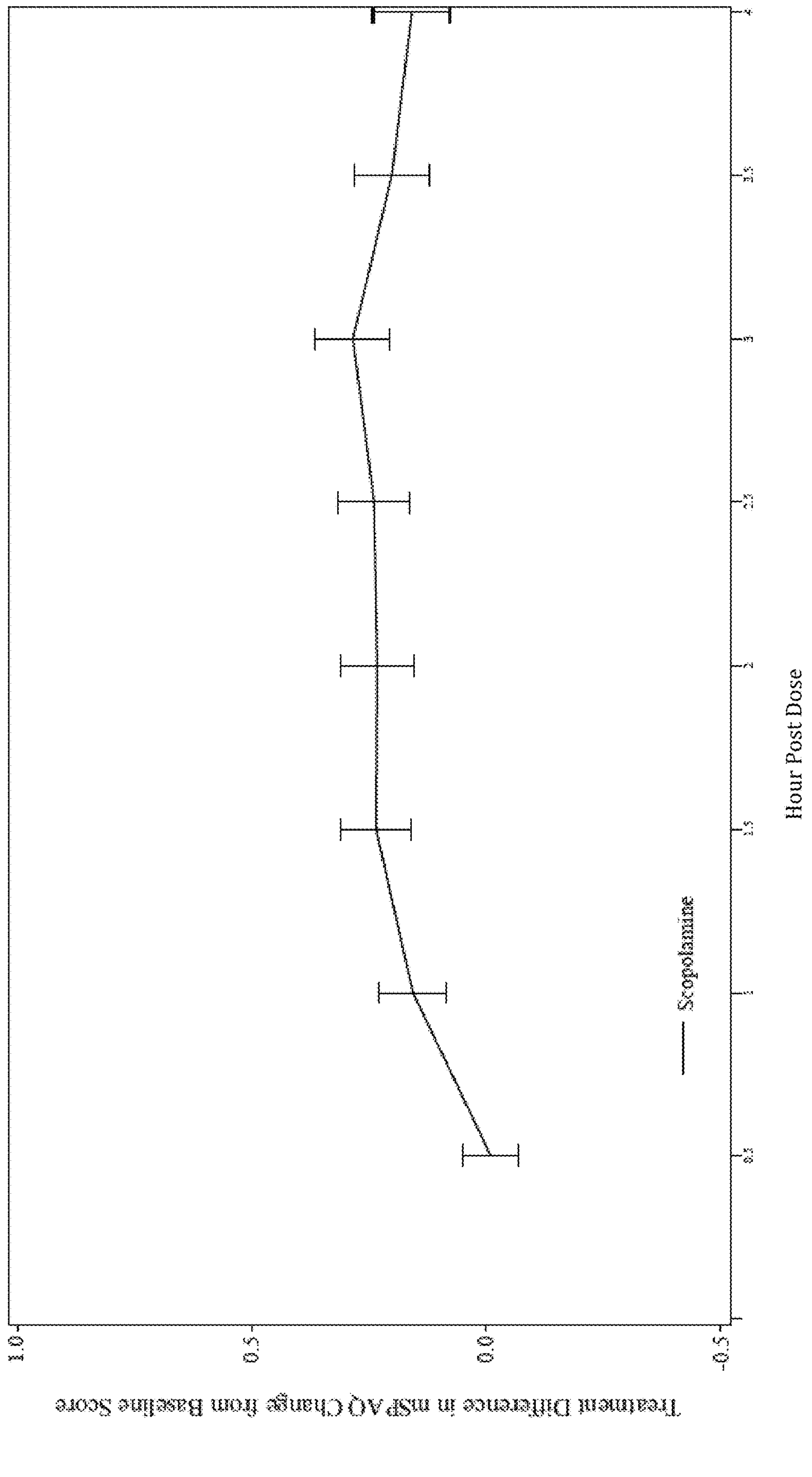
FIG. 3Q is a graphic presentation from clinical study MS-33 showing Least Squares Mean (SE) of Treatment Difference from Placebo Change from Baseline PSAQ Overall performance (ITT Population).
Figure 3R:
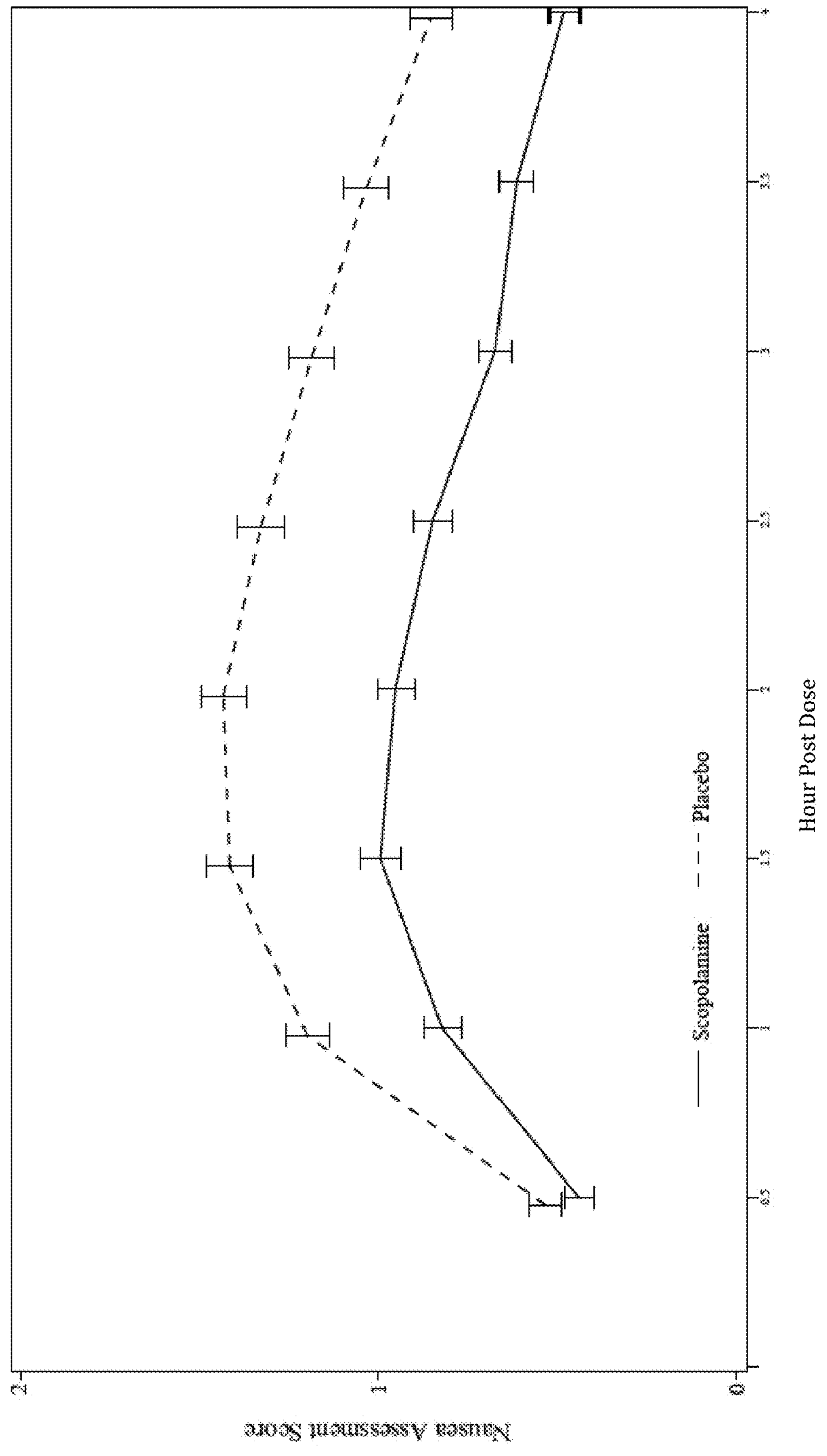
FIG. 3R is a graphic presentation from clinical study MS-33 showing Least Squares Mean (SE) in Nausea Assessment Scale Score-MMRM (ITT Population). For FIG. 3R and FIG. 3S, below, Nausea Assessment Scale Score were assigned as following: 0=No symptoms; 1=mild nausea; 2=moderate nausea; 3=severe nausea.
Figure 3S:
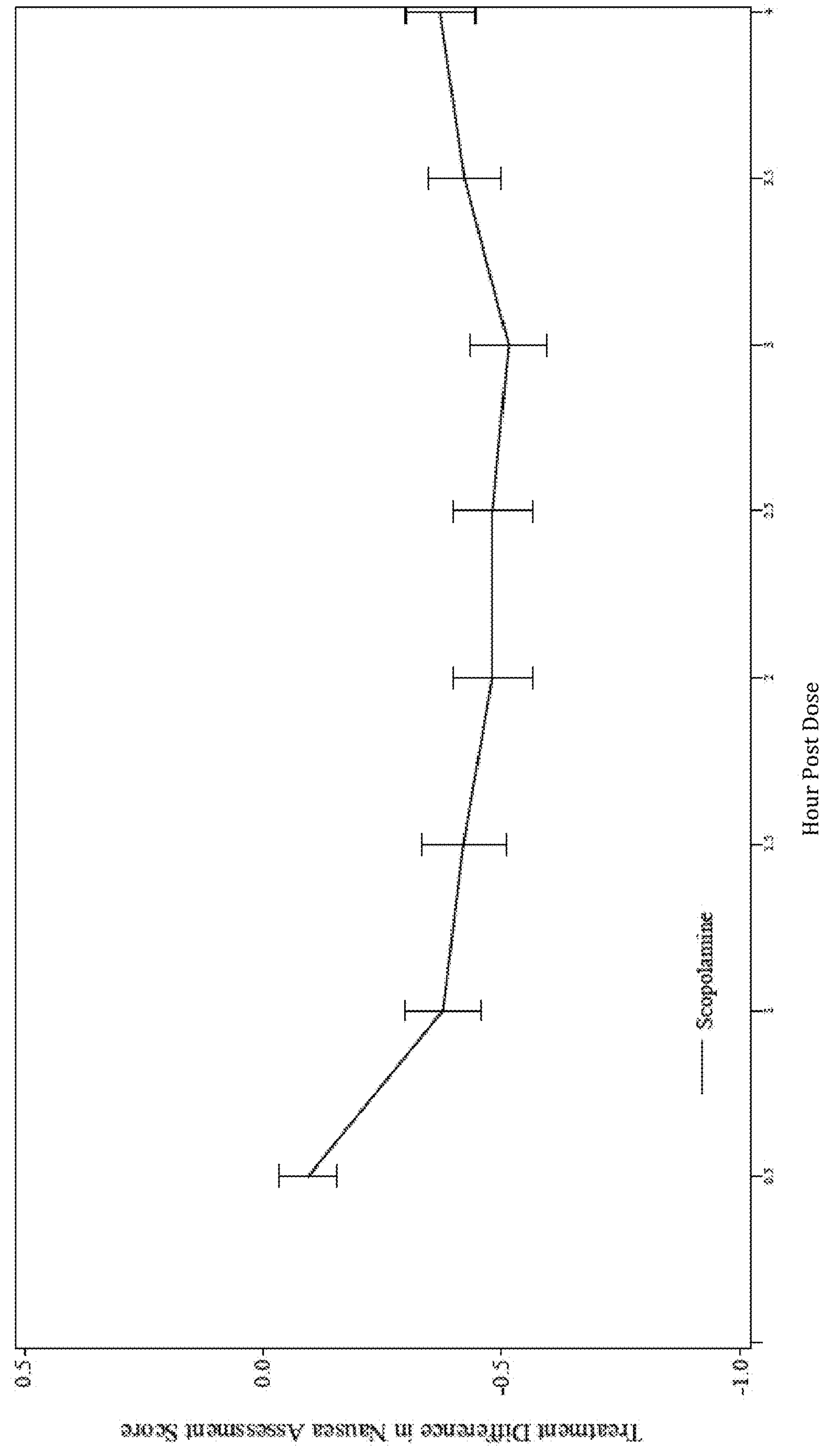
FIG. 3S is a graphic presentation from clinical study MS-33 showing Least Squares Mean (SE) of Treatment Difference from Placebo in Nausea Assessment Scale Score—MMRM (ITT Population).

Moreover, with regard to the safety results, as demonstrated herein and with reference to the tables above as well as FIGS. 3C through 3Q, patients tested were protected against the degradation of cognitive and motor function due to motion sickness.

Brief Summary of Adverse Events

A total of 108 subjects (43.0%) in the DPI-386 Nasal Gel group and 138 subjects (54.8%) in the Placebo Nasal Gel group had at least one TEAE. Eighty-one subjects (32.3%) in the DPI-386 Nasal Gel group and 94 subjects (37.3%) in the Placebo Nasal Gel group had at least one TEAE that was assessed as related to treatment with study drug.

Twenty-two subjects (8.8%) in the DPI-386 Nasal Gel group and 52 subjects (20.6%) in the Placebo Nasal Gel group had a Grade 3 TEAE, and 2 subjects (0.8%) in the DPI-386 Nasal Gel group and 5 subjects (2.0%) in the Placebo Nasal Gel group had a Grade 3 TEAE that was related to treatment with study drug. No Grade 4 TEAEs were reported during the study.

No TEAE in either treatment group led to discontinuation from the study.

No SAEs or deaths occurred in the study.

For FIGS. 3C-3Q, PSAQ scores were assigned as 1=significantly worse, 2=somewhat worse, 3=no effect, 4=somewhat better, 5=significantly better. Analysis was based on mixed model for repeated measures (MMRM) including fixed effects of treatment, visit, baseline score and interaction terms of treatment by visit.

FIG. 3C is a graphic presentation from clinical study MS-33 showing Least Squares Mean (SE) Change from Baseline in PSAQ Alertness (ITT Population). FIG. 3D is a graphic presentation from clinical study MS-33 showing Least Squares Mean (SE) Change from Baseline in PSAQ Balance (ITT Population). FIG. 3E is a graphic presentation from clinical study MS-33 showing Least Squares Mean (SE) Change from Baseline in PSAQ Concentration (ITT Population). FIG. 3F is a graphic presentation from clinical study MS-33 showing Least Squares Mean (SE) Change from Baseline in PSAQ Hand-eye coordination (ITT Population). FIG. 3G is a graphic presentation from clinical study MS-33 showing Least Squares Mean (SE) Change from Baseline in PSAQ Mood (ITT Population). FIG. 3H is a graphic presentation from clinical study MS-33 showing Least Squares Mean (SE) Change from Baseline in PSAQ Reaction Time (ITT Population). FIG. 3I is a graphic presentation from clinical study MS-33 showing Least Squares Mean (SE) Change from Baseline in PSAQ Overall performance (ITT Population). FIG. 3J is a graphic presentation from clinical study MS-33 showing Least Squares Mean (SE) of Treatment Difference from Placebo Change from Baseline PSAQ Memory (ITT Population). FIG. 3K is a graphic presentation from clinical study MS-33 showing Least Squares Mean (SE) of Treatment Difference from Placebo Change from Baseline PSAQ Alertness (ITT. Population). FIG. 3L is a graphic presentation from clinical study MS-33 showing Least Squares Mean (SE) of Treatment Difference from Placebo Change from Baseline PSAQ Balance (ITT Population). FIG. 3M is a graphic presentation from clinical study MS-33 showing Least Squares Mean (SE) of Treatment Difference from Placebo Change from Baseline PSAQ Concentration (ITT Population). FIG. 3N is a graphic presentation from clinical study MS-33 showing Least Squares Mean (SE) of Treatment Difference from Placebo Change from Baseline PSAQ Hand-eye coordination (ITT Population). FIG. 3O is a graphic presentation from clinical study MS-33 showing Least Squares Mean (SE) of Treatment Difference from Placebo Change from Baseline PSAQ Mood (ITT Population). FIG. 3P is a graphic presentation from clinical study MS-33 showing Least Squares Mean (SE) of Treatment Difference from Placebo Change from Baseline PSAQ Reaction Time (ITT Population). FIG. 3Q is a graphic presentation from clinical study MS-33 showing Least Squares Mean (SE) of Treatment Difference from Placebo Change from Baseline PSAQ Overall performance (ITT Population).

Lower proportions of subjects in the DPI-386 Nasal Gel group had TEAEs, treatment-related TEAEs, Grade 3 TEAEs, and related Grade 3 TEAEs compared to the Placebo Nasal Gel group.

Based on self-assessment questionnaires, measurements of performance (PSAQ) favored the DPI-386 Nasal Gel group, and cognitive function (per SAQ) was better preserved in subjects who received DPI-386 Nasal Gel compared to subjects who received Placebo Nasal Gel. DPI-386 Nasal Gel was well tolerated and no new safety signals for DPI-386 Nasal Gel were observed.

Importantly, other treatment options have been demonstrated to actually worsen anticholinergic effects, including cognitive and motor functions. For example, each of Scopolamine-Trasnderm Scop, Promethazine-Phenergan, Cyclizine-Marezine, Dimenhydrinate-Dramamine, and Meclizine-Bonine include side effect profile warnings for one or more of drowsiness, dry mouth, blurred vision, and disorientation.

Surprisingly, the formulation of the present disclosure does not appear to cause such side effects. Individual and combined scoring for one or more of alertness, balance, concentration, hand-eye coordination, mood, reaction time (speed), and memory was surprisingly unaffected for study patients.

Motion sickness is a complex syndrome that includes many features besides nausea and vomiting. Symptoms of motion sickness include a wide range of signs and symptoms including cold sweating, pallor of varying degrees, increases in salivation, drowsiness, headache, and even severe pain, as well as nausea and vomiting. One facet of motion sickness that often is not recognized is referred to as Sopite Syndrome, which refers to profound drowsiness and persistent fatigue that can follow brief exposures to highly provocative stimulation or prolonged exposures to low-intensity motion stimulation. Sopite Syndrome can persist for hours or even days and when exposure is prolonged even longer. It is characterized by boredom, apathy, failure of initiative, increased irritability, and even changes in personality. It may be one of the only syndromes that persist when nausea is not elicited or has abated. Also, many manual performance and cognitive tasks are substantially impaired.

The following table summarizes the results of the SAQ.

TABLE 3g

Analysis of Sopite Assessment Questionnaire Responses at 4 Hours Post Dose, Safety Population

| Parameter | Statistic | DPI-386 Nasal Gel (N = 251) | Placebo Nasal Gel (N = 252) |
|---|---|---|---|
| Felt annoyed/ irritated | N | 250 | 252 |
| | Mean (SE) | 3.628 (0.178) | 4.774 (0.177) |
| | Mean difference | −1.146 | |
| | (95% CI) | (−1.638, −0.653) | |
| | p-value | <0.0001 | |
| Felt drowsy | N | 249 | 251 |
| | Mean (SE) | 4.353 (0.175) | 5.072 (0.175) |
| | Mean difference | −0.718 | |
| | (95% CI) | (−1.205, −0.232) | |
| | p-value | 0.0039 | |
| Felt tired/ fatigued | N | 250 | 251 |
| | Mean (SE) | 4.096 (0.175) | 4.904 (0.175) |
| | Mean difference | −0.808 | |
| | (95% CI) | (−1.294, −0.323) | |
| | p-value | 0.0011 | |
| Felt uneasy | N | 249 | 252 |
| | Mean (SE) | 3.900 (0.185) | 5.095 (0.184) |
| | Mean difference | −1.196 | |
| | (95% CI) | (−1.708, −0.683) | |
| | p-value | <0.0001 | |

CI = confidence interval;
SE = standard error
Note:
Each statement is rated 1-9 with 1 representing the lowest severity and 9 representing the highest severity.

The formulation of the present disclosure demonstrates a therapeutic effects to reduce the presentation or manifestation of one or more symptoms associated with Sopite Syndrome. To the knowledge of the inventors, no other therapy has been able to demonstate therapeutic efficacy as against components of Sopite Syndrome.

While motion sickness degrades cognitive and motor functions, the present disclosure demonstrates that the tested intranasal gel was surprisingly effective in providing a protective effect against the degradation of these functions, each of which is believed to be caused by motion. The impact of this protective effect may be especially important in an operational setting such as driving, combat, or microgravity of space. The present inventors believe that a protective effect has never been demonstrated before, so it is an unexpected outcome for the formulation of the present disclosure.

Example 4: Clinical Study MS-29: Efficacy and Safety of DPI-386 Nasal Gel for the Prevention of Nausea and Vomiting Associated with Motion The purpose of this study (DPI-386-MS-29) was to prospectively evaluate the difference in the rate of complete response, defined as no vomiting and no rescue treatment (e.g., dimenhydrinate) within the 4 hours after study drug administration between 0.2 mg scopolamine administered as the DPI-386 Nasal Gel and Placebo Nasal Gel to subjects 18 to 70 years of age (inclusive) with a history of symptoms consistent with motion sickness. The sample size of 75 subjects per treatment was considered sufficient to demonstrate a statistically significant difference between treatments.

The target population for the study was males and females aged 18 to 70 years of age (inclusive), who were minimally susceptible to motion as evidenced by at least two responses of “Sometimes” or “Frequently” on the Motion Sickness Susceptibility Questionnaire Short Form (MSSQ-S). The duration of the clinical part of the study was 53 days (17 Jun. 2021 [First Subject First Visit-FSFV] to 9 Aug. 2021 [Last Subject Last Visit-LSLV]).

Study Objectives

Primary Objective: The primary objective of the study was to assess the efficacy of DPI-386 Nasal Gel (0.2 mg scopolamine HBr) compared to matching Placebo Nasal Gel in the prevention of vomiting. Complete Response was defined as no vomiting and no rescue treatment (e.g., dimenhydrinate) induced by motion.

Secondary: One secondary objective of this study was to assess the efficacy of DPI-386 Nasal Gel (0.2 mg scopolamine HBr) compared to matching Placebo Nasal Gel for: Presence of nausea; Severity of nausea; and Time to vomiting or use of rescue medication. Another secondary objective of this study was to assess the safety of DPI-386 Nasal Gel (0.2 mg scopolamine HBr) compared to matching Placebo Nasal Gel with an emphasis on AEs.

Overall Study Design and Plan-Description

Study Design

This was a Phase 3, randomized, double-blind, placebo-controlled study evaluating a single dose of DPI-386 Nasal Gel versus matching Placebo Nasal Gel. Approximately 150 subjects were planned to be randomized 1:1 to DPI-386 Nasal Gel or matching Placebo Nasal Gel.

Unless deemed a prohibited medication as outlined, standard of care treatment (e.g., dimenhydrinate) was permitted upon request by the subject after boarding the boat, but any such medications were captured as concomitant medications.

In the Recruitment and Screening Phase subjects were assessed for their susceptibility to motion sickness with the MSSQ-S. If the potential subject met this requirement they were asked to read and if agreeable to study participation, sign an ICF. The subject was also asked about their medical history and they completed a Mini-Mental State Exam (MMSE). If the subject met the inclusion/exclusion criteria they proceeded to the Treatment Phase of the study.

Eligible subjects were randomized 1:1 to DPI-386 Nasal Gel or matching Placebo Nasal Gel and assigned a time and date for travel on an ocean vessel. Subjects were asked to self-administer the study medication while the ship was in harbor. The Modified Performance Self-Assessment Questionnaire (PSAQ) was completed by each subject prior to the administration of nasal gel, approximately every 30 minutes of travel, and at the end of travel. The subjects completed the Nausea Assessment Scale (NAS) every 30 minutes after dosing, and at the end of travel. The subjects were also asked to complete a Sopite Assessment Questionnaire (SAQ) and a Patient Global Assessment of Severity (PGI-S) at 4 hours to describe their travel experience. All questionnaires were submitted for analysis. An exit interview was also conducted.

The treatment phase lasted approximately 4-5 hours.

Subjects were asked to complete 3 Post-Treatment follow-ups at Day 2 (±3 days)/Visit 3, Day 15 (±3 days)/Visit 4, and Day 30 (±3 days)/Visit 5 to further assess safety. At the first follow-up (Day 2/Visit 3) the Nasal Gel Device Ease-of-Use Questionnaire (EOUQ) was completed.

Safety and tolerability were evaluated by monitoring the occurrence of AEs during ocean travel/Day 1, Day 2 (±3 days)/Visit 3; Day 15 (±3 days)/Visit 4; and Day 30 (±3 days)/Visit 5. The Day 15 and Day 30 follow-up visits were conducted virtually via the sites' telehealth process.

Due to the ongoing Coronavirus Disease 2019 (COVID-19) health restrictions, the recruitment activities may not all have occurred at the clinic.

The schedule of events is presented in Table 4a.

TABLE 4a

| | Period: | | | | | |
|---|---|---|---|---|---|---|
| | Recruitment | Confirm Eligibility; Treatment (On Boat) | | Post- | | |
| | and Screening [a] | Eligibility Confirmation | Treatment | Treatment Follow-up | Telehealth | Telehealth |
| | Visit: | | | | | |
| | 1 | 2 | | 3 | 4 | 5 |
| | Study Day: | | | | | |
| | −60 days to Day 0 | 1 | | 2 (±3 days) | 15 (±3 days) | 30 (±3 days) |
| Eligibility | | | | | | |
| Informed consent form | X | | | | | |
| Inclusion/exclusion | X | X | | | | |
| Height, weight, body mass index | X | | | | | |
| Medical history | X | | | | | |

TABLE 4a-continued

| | Period: | | | | | |
|---|---|---|---|---|---|---|
| | Recruitment and Screening [a] | Confirm Eligibility; Treatment (On Boat): Eligibility Confirmation | Confirm Eligibility; Treatment (On Boat): Treatment | Post-Treatment Follow-up | Telehealth | Telehealth |
| Visit: | 1 | 2 | | 3 | 4 | 5 |
| Study Day: | −60 days to Day 0 | 1 | | 2 (±3 days) | 15 (±3 days) | 30 (±3 days) |
| MSSQ-S | X | | | | | |
| Demographics [b] | X | | | | | |
| Verify negative COVID status | | X | | | | |
| **Randomization** | | | | | | |
| Randomization | | X | | | | |
| **Safety Assessments** | | | | | | |
| Vital signs [c] | X | X | | X [c] | | |
| Urine pregnancy test [d] | X | | | | | |
| Adverse events [e] | | | X | X | X | X |
| Concomitant medications/treatments [f] | X | X | X | X | X | X |
| **Activity Assessments** | | | | | | |
| MMSE [g] | X | | | | | |
| NAS [h] | | | X | | | |
| PSAQ [h] | | | X | | | |
| SAQ [i] | | | X | | | |
| PGI-S [i] | | | X | | | |
| Nasal Gel Device Ease-of-Use | | | | X | | |
| Exit interview [j] | | | X | | | |
| **Other** | | | | | | |
| Record weather and sea state conditions [h] | | | X | | | |
| **Study Materials** | | | | | | |
| Study drug administration [k] | | | X | | | |
| IFU training (see Appendix 8 in the study protocol) | X | | X | | | |

Legend for Table 4a:

COVID = Coronavirus disease; IFU = instructions for use; MMSE = Mini-Mental State Exam; PSAQ = Modified Performance Self-Assessment Questionnaire; MSSQ-S = Motion Sickness Susceptibility Questionnaire-Short Form; NAS = Nausea Assessment Scale; PGI-S = Patient Global Impression of Severity of motion sickness; SAQ = Sopite Assessment Questionnaire.

[a] Screening occurred within 60 days prior to ship departure.

[b] Date of birth (DOB), race, ethnicity, and gender.

[c] Vitals were taken at the clinical site at Screening/Day 0, Baseline/Day 1 Visit, and Visit 3/Day 2.

[d] For females of child-bearing potential, a urine pregnancy test was administered and must have been negative within 7 days of the Treatment Day.

[e] Assess AEs after randomization through the Day 30 follow-up.

[f] All concomitant medications/treatments taken within 30 days of randomization through the Treatment Day, in addition to, any medications/treatments taken for reported AEs during follow-up was recorded.

[g] Subjects completed the MMSE at screening.

[h] NAS was completed after dosing every 30 minutes. PSAQ forms were completed immediately prior to dosing, then every 30 minutes. Timing coincided with times the Research staff recorded weather and sea state conditions every 30 minutes.

[i] SAQ and PGI-S forms were completed at 4 hours.

[j] Exit interview was completed at end of voyage.

[k] On the Treatment Day, the investigator notified all study subjects when to administer the study drug. The administration was under the supervision by the research staff.

This study was designed as a randomized, double-blind trial of DPI-386 Nasal Gel and a placebo control (Placebo Nasal Gel). A single dose of study medication was administered. Efficacy and safety results with DPI-386 Nasal Gel were compared with those of Placebo Nasal Gel to establish the effectiveness of DPI-386 for prevention and treatment of nausea and vomiting associated with motion, and the safety of DPI-386 Nasal Gel.

Subjects were screened either by phone or email to determine initial eligibility.

Inclusion Criteria

As per the protocol, inclusion criteria were as follows:

1. Ability to provide written, informed consent prior to initiation of any study-related procedures, and ability in the opinion of the Investigator to understand and comply with all the requirements of the study, which includes abstaining from the use of prohibited medications as outlined;
2. Male and female subjects, aged 18 to 70 years of age (inclusive);
3. Minimally susceptible to provocative motion as evidenced by at least 2 responses on the MSSQ-S of "Sometimes" or "Frequently;"
4. Acceptable overall medical condition to be safely enrolled in and complete the study in the opinion of the Investigator;
5. Ability to take intranasal medication;

6. Males, non-fecund females (i.e., surgically sterilized, if procedure was done 6 months before screening or subject is 2 years postmenopausal), or females of child-bearing potential using an acceptable method of birth control (i.e., oral contraception, systemic [injectable or patch] contraception, double barrier methods, strict abstinence, condoms, diaphragm, spermicidal agents, cervical cap, copper intrauterine device, etc.) for a period of up to 30 days before dosing and for 1 month after dosing and must have a negative pregnancy test at screening;
7. Agreement to adhere to the following lifestyle compliance considerations:
a. Refrain from consumption of grapefruit and any substance containing grapefruit for 7 days prior to, during, and 7 days after study drug administration;
b. Abstain from alcohol for 24 hours prior to the administration of study drug and throughout the ocean travel;
c. Abstain from marijuana within the 7-day period prior to the Treatment Day and throughout Day 3.
8. Severe Acute Respiratory Syndrome Coronavirus-2 (SARS-COV-2) negative test, confirmed by Food and Drug Administration (FDA) authorized Coronavirus Disease 2019 (COVID-19) test≤7 days prior to study drug administration or no COVID-19 symptoms 10 days prior to study drug administration.

Exclusion Criteria

As per the protocol, exclusion criteria were as follows:
1. Nauseated prior to boarding.
2. MMSE score of <24.
3. Women of childbearing potential, or men whose sexual partner(s) is a woman of childbearing potential, who:
a. Are or intend to become pregnant (including use of fertility drugs) during the study;
b. Are nursing (female subjects only);
c. Are not using an acceptable, highly effective method of contraception until all follow-up procedures are complete.
4. Known allergic reactions to scopolamine or other anticholinergics;
5: Hospitalization or significant surgery requiring hospital admittance within the past 6 months;
6. Treatment with another investigational product within the past 30 days;
7. Donated blood or plasma or suffered significant blood loss within the past 30 days;
8.-Chronic nausea caused by conditions such as irritable bowel syndrome, gastroparesis, cyclic vomiting syndrome or any other cause;
9. Having any of the following medical conditions within the last 2 years or if any of the following medical conditions were experienced more than 2 years ago and are deemed as clinically significant by the Investigator:
a. Significant gastrointestinal disorder, asthma, or seizure disorders;
b. History of or current cardiovascular disease;
c. History of or current vestibular disorders;
d. History of or current narrow-angle glaucoma;
e. History of or current urinary retention problems;
f. History of or current alcohol or drug abuse;
g. History of or current nasal, nasal sinus or nasal mucosa surgery.
10. Currently taking any of the following medication types within the specified washout period:
a. Any form of scopolamine (including Transderm Scop®)/washout 5 days;
b. Belladonna alkaloids/washout 14 days;
c. Antihistamines (including meclizine)/washout 14 days;
d. Tricyclic antidepressants/washout 14 days;
e. Muscle relaxants/washout 4 days; and
f. Nasal decongestants/washout 4 days.
11. Has used marijuana within the 7-day period prior to the Treatment Day. (Note: this criterion will only be confirmed at Eligibility Confirmation, not at Recruitment and Screening, although heavy users of marijuana can be determined ineligible at Screening. All potential study subjects deemed eligible at Screening must be informed at that time that this requirement must be met at Eligibility Confirmation.)
12. Unwilling or unable to follow the medication restrictions or unwilling to wash-out the use of restricted medications as noted in Exclusion Criterion #10.

Each subject was informed, prior to the trial's commencement, that he/she had the right to withdraw from the trial at any time (withdraw consent), for any reason, without prejudice to his/her safety or medical care. Subjects who withdrew consent or were lost to follow-up were withdrawn from the study.

Subjects who had received at least 1 dose of study drug and wished to withdraw from the study were asked to complete the follow-up safety visits.

Treatments

Study drug is defined as DPI-386 Nasal Gel (0.2 mg scopolamine HBr) or matching Placebo Nasal Gel. Each 0.12 gram of DPI-386 Nasal Gel contains 0.2 mg of scopolamine HBr as the active ingredient (0.167% w/w) along with the following common pharmaceutical excipients: sodium citrate, citric acid, sodium metabisulfite, glycerin, benzalkonium chloride, polyvinyl alcohol, and purified water.

The Placebo Nasal Gel product was the same in feel and appearance but did not contain scopolamine HBr.

DPI-386 Nasal Gel and the matching Placebo Nasal Gel were administered intranasally via a nasal gel pump. A single dose of DPI-386 Nasal Gel (0.2 mg scopolamine HBr) or matching Placebo Nasal Gel was administered in 1 nostril using a delivery device comprised of: (a) a vial prefilled with DPI-386 Nasal Gel or Placebo Nasal Gel, and (b) a nasal gel pump attached to the vial during the manufacturing process. Subjects self-administered the single dose of DPI 386 Nasal Gel or matching Placebo Nasal Gel into 1 nostril under the supervision of the research team.

Dimenhydrinate (the recue medication) was provided as a 50 mg tablet.

Subjects followed the instructions of the study protocol to administer the study drug.

Identity of Investigational Product. Table 4b provides the descriptions of the investigational products used in this study.

TABLE 4b

| DPI-386 Nasal Gel | |
|---|---|
| Active content | Scopolamine Hydrobromide |
| Strength | Each 0.12 gram of the gel contains 0.2 mg of scopolamine HBr |

TABLE 4b-continued

| | |
|---|---|
| Storage condition | Store at 20° C. to 25° C., inclusive (68° F. to 77° F., inclusive), with brief temperature excursions permitted between 15° C. and 30° C., inclusive (59° F. and 86° F., inclusive). |
| Placebo Nasal Gel (Placebo gel for DPI-386 Nasal Gel) | |
| Storage condition | Store at 20° C. to 25° C., inclusive (68° F. to 77° F., inclusive), with brief temperature excursions permitted between 15° C. and 30° C., inclusive (59° F. and 86° F., inclusive). |

The Method of Assigning Subjects to Treatment Groups

Subjects were randomized 1:1 (75 DPI-386 Nasal Gel: 75 matching Placebo Nasal Gel). See FIG. 4A.

The Sponsor's independent statistician generated the randomization scheme, which was then provided to the Sponsor's designated unblinded clinical trial supply management vendor. Upon site activation, the Sponsor's clinical trial supply management vendor distributed a randomized set of investigational kits to the clinical site. The site randomized the subjects who met all eligibility criteria and sequentially allocated a labeled kit containing the device and vial of study drug to the subject.

Blinding

A double-blind/masking technique was used: DPI-386 Nasal Gel and matching Placebo Nasal Gel were packaged identically so that the treatment blind/masking was maintained. The subject, the Investigator, and Sponsor personnel or delegate(s) who were involved in the treatment or clinical evaluation of the subjects were unaware of the treatment group assignments.

At the end of the study (inclusive the Day 30 follow-up visit) and after medical/scientific review had been performed and data had been declared final and complete, the official, final database was frozen and unblinded. The Sponsor was granted access to the frozen and unblinded database in order to analyze the data.

Prior and Concomitant Therapy

All concomitant medications/treatments taken within 30 days of randomization through the treatment period were recorded.

Per Exclusion Criterion #10 if the subject was taking any of the following medications the washout period was to be strictly adhered to: (a) Any form of scopolamine (including TDS)/washout 5 days; (b) Belladonna alkaloids/washout 14 days; (c) Antihistamines (including meclizine)/washout 14 days; (d) Tricyclic antidepressants/washout 14 days; (e) Muscle relaxants/washout 4 days; and (f) Nasal decongestants/washout 4 days.

During the treatment period the following restrictions were required: (a) Blood-donation; (b) Administration of another investigational drug; (c) No product containing grapefruit or grapefruit juice should be consumed; (d) No alcohol should be consumed; (e) No use of any motion sickness remedies (e.g., medications, wrist bands, pressure bands, herbals, etc. which state on the label for use in motion sickness) outside of the study protocol; and (f) Permitted medications were determined by the medical PI or qualified designee.

Treatment Compliance

Subjects self-administered the single dose of nasal gel under research staff supervision as per the procedure discussed, therefore compliance to treatment was assured.

Efficacy and Safety Variables

Efficacy Endpoints

Primary Efficacy Endpoint

The primary efficacy endpoint in this study was the proportion of subjects who reported no vomiting within 4 hours after receiving study drug and no use of rescue treatment (e.g., dimenhydrinate) within 4 hours after receiving study drug (Complete Responders).

Secondary Efficacy Endpoints

Proportion of Subjects Who Did not have Nausea

This endpoint was the proportion of subjects who did not have nausea, which was defined as those subjects who reported no nausea within 4 hours after receiving study drug and who did not use rescue treatment (e.g., dimenhydrinate) within 4 hours after receiving study drug.

The severity of nausea was assessed on a 4-point scale using the NAS every 30 minutes after dosing. In response to the question 'In the last 30 minutes how severe is your nausea?', the possible responses were: no symptoms (score=0), mild nausea (score=1), moderate nausea (score=2), or severe nausea (score=3).

Proportion of Subjects Who Did not have Moderate or Severe Nausea

This endpoint was the proportion of subjects who did not have moderate or severe nausea, which was defined as those subjects who reported no moderate or severe nausea within 4 hours after receiving study drug and who did not use rescue treatment (e.g., dimenhydrinate) within 4 hours after receiving study drug.

Time to Vomiting or Use of Rescue Medication

Subjects who reported vomiting or who had taken rescue medication within 4 hours after receiving study drug were considered as having the event of vomiting, and the time to event was derived as the number of hours from dosing to the earliest time of vomiting or rescue medication use.

Exploratory Efficacy Endpoints

Modified Performance Self-Assessment Questionnaire

Performance was self-assessed and measured before, every 30 minutes during, and after the ocean travel using the PSAQ. Eight parameters of performance were assessed on a 5-point Likert scale: significantly worse (score=1), somewhat worse (score=2), no effect (score=3), somewhat better (sore=4), and significantly better (score=5). The 8 parameters were concentration, mood, alertness, memory, hand-eye coordination, balance, reaction time (speed), and overall performance.

Lower scores indicated poorer performance, and "minus" numbers in change from baseline indicated a lower score at that timepoint than the score at baseline.

Patient Global Impression of Severity

The severity of motion sickness was assessed using the PGI-S, which was a 4-point verbal rating scale with choices of none (score=1), mild (score=2), moderate (score=3), or severe (score=4). The PGI-S was completed at Hour 4 and subjects were asked to record the severity of their motion sickness over the past 4 hours.

Nausea Assessment Scale

In addition to the exploratory efficacy endpoints that were set forth in the study protocol, NAS scores were identified in the SAP as an additional exploratory efficacy endpoint.

Safety Endpoints

Safety endpoints evaluated the safety of DPI-386 Nasal Gel relative to Placebo Nasal Gel by assessing: (a) The incidence of AEs; (b) The incidence of serious AEs (SAEs); and (c) The incidence of Grade 3 and Grade 4 AEs.

Safety Assessments

Adverse Events

Adverse events were collected after randomization and continued thru Visit 5/Day 30. Only SAEs or AEs deemed related to study drug were followed after Visit 5/Day 30.

It was the responsibility of the Investigator to document all AEs that occurred during the course of the trial. AEs were documented as a single medical diagnosis. When this was not possible, the AE was documented in terms of signs and/or symptoms observed by the Investigator or reported by the subject at each trial visit.

In addition to reporting all AEs on the electronic case report form (eCRF), the Investigator indicated via a checked box and a text field on a separate eCRF if a subject experienced nausea and when it was first noticed.

Vital Signs

Vital signs (pulse rate, resting blood pressure, and temperature) were recorded at Screening/Day 0, Baseline/Day 1 Visit, and Visit 3/Day 2.

Sopite Assessment Questionnaire

The SAQ is a 4-statement questionnaire to assess sopite-related events. Each statement was rated 1 to 9 with 1 representing the ‘Not at all’ and 9 representing ‘Severely.’ It was administered at Hour 4 on the Treatment Day. The statements in the SAQ are: (a) I felt annoyed/irritated; (b) I felt drowsy; (c) I felt fatigued; and d) I felt uneasy.

Exit Interview

An exit interview consisting of 13 questions was conducted at the end of the voyage for the purpose of learning about the subject’s experiences on the boat trip.

Nasal Gel Device Ease-of-Use Questionnaire

The Nasal Gel Device EOUQ was administered at Visit 3 in the post-treatment follow-up for the purpose of learning if the subjects had any difficulties in using the device.

Urine Pregnancy Test

Women who had undergone hysterectomy, bilateral oophorectomy, bilateral tubal ligation or had been without menses for 12 months were considered to be of non-childbearing potential. All other women were required to have a urine pregnancy test at the Screening/Day 0 Visit and at Visit 2/Day 1 (pre-dose).

Adverse Event Assessment and Reporting

Assessment of Severity

AEs were graded for severity in accordance with the US Department of Health and Human Services Common Terminology Criteria for Adverse Events (CTCAE) Grading Scale v5.0, November 2017. For terms not specified by the CTCAE Grading Scale, the criteria in Table 4c were used to determine the grade severity.

TABLE 4c

Classification of Adverse Events by Intensity

| Grade | Criteria |
| --- | --- |
| 1/Mild | Asymptomatic or mild symptoms, clinical or diagnostic observations only; intervention not indicated |
| 2/Moderate | Minimal, local, or noninvasive intervention indicated; limiting age-appropriate instrumental activities of daily living |
| 3/Severe or medically significant | Not immediately life-threatening; hospitalization or prolongation of hospitalization indicated; disabling; limiting self-care activities of daily living |
| 4/Life-threatening | Life threatening consequences; urgent intervention indicated |
| 5/Death | Death related to AE |

AE = adverse event

Assessment of Causality

The causality of all AEs/SAEs (i.e., their relationship to the study drug) was assessed by a medically qualified Investigator at the study site. Assessing causality required considering whether there was a reasonable possibility that the event may have been caused by the study drug.

Factors that were to be considered in assessing the possible causal relationship between the study drug and an AE included the temporal relationship between treatment and the event, the subject’s clinical state, coexisting therapies, and any known response patterns to the study drug. Table 4d provides the categories that were used when assessing causality of the study drug.

TABLE 4d

Guidelines for Determining the Relationship Between Any Adverse Event and Study Drug

| Causality | Description |
| --- | --- |
| Related | There is a reasonable causal relationship between study drug administration and the (AE). |
| Probable | There is a reasonable temporal sequence from study drug administration. The event abates upon discontinuation of study drug and cannot be reasonably explained by the known characteristics of the subject’s clinical state. |
| Possible | The event may or may not follow a reasonable temporal sequence from study drug administration. The event could have been produced or mimicked by the subject’s clinical state or by other modes of therapy concomitantly administered to the subject. |
| Unlikely | There is no reasonable temporal association between study drug administration and the event. The event could have been produced by the subject’s clinical state or by other modes of therapy administered to the subject. |

TABLE 4d-continued

| Guidelines for Determining the Relationship Between Any Adverse Event and Study Drug | |
|---|---|
| Causality | Description |
| Unrelated | There is not a temporal relationship to study drug administration or there is a reasonable causal relationship between another therapy, concurrent disease, or circumstance and the event. |

Assessment of Outcome

For each recorded AE or SAE, the Investigator assessed the outcome at the time of last observation. The outcome of AEs or SAEs was documented as described in Table 4e.

TABLE 4e

| Classifications for Adverse Event Outcomes | |
|---|---|
| Classification | Definition |
| Recovered/resolved | The AE or SAE has ended. |
| Resolved with sequelae | The AE or SAE has ended but changes are noted from baseline. |
| Ongoing | The AE or SAE is unresolved at the time of study completion or early termination from the study. |
| Fatal | The subject died. |

AE = adverse event;
SAE = serious adverse event

Reporting of Serious Adverse Events

Investigators and other site personnel were required to report SAEs to Safety within 24 hours of becoming aware of the SAE, regardless of causality, by completing the information within the electronic data capture (EDC) system or emailing the SAE form.

The Sponsor requested that the Medical Monitor be consulted on all SAEs.

Follow-up information on SAEs was also reported by the investigational site within the same time frame. The Investigator was not to wait to receive additional information to document fully the event before notification of an SAE, though additional information could be requested.

Where applicable, information from relevant laboratory results, hospital case records, and autopsy reports were to be obtained.

The SAE report was to contain, at a minimum, the following information: Subject's identification number; Site number; Drug name; Event; and The Investigator's opinion of the seriousness and causality.

Any SAE was reported by the Investigator if it occurred during the clinical study, i.e., up to and including the follow-up telephone contact on Day 30 (+3 days), whether or not the SAE was considered to be related to study drug.

Back-up SAE Forms together with reporting details were provided should the EDC not be available. The Investigator was required to notify the IRB of any SAE in accordance with local requirements.

Reporting of Suspected Unexpected Serious Adverse Reactions

Suspected unexpected serious adverse reactions (SUSARs) were subject to expedited reporting to applicable regulatory authorities.

It was the responsibility of the Sponsor to determine whether a reported SAE fit the classification of a SUSAR and to notify the Investigator of their decision as soon as possible. The Sponsor or designee was responsible for reporting to applicable regulatory authorities and the sites.

The Investigator was required to notify the IRB of any SUSAR in accordance with local requirements.

Reporting of Pregnancy

Any known or suspected pregnancy occurring during the study (including those occurring during the study but confirmed after completion of the study), in subjects or female partners of male subjects, was to be reported to the Sponsor (or designee) within 24 hours of becoming aware of the event. The Investigator was to perform a pregnancy test to confirm the subject's pregnancy.

Reported pregnancies were to be followed to term, and the status of mother and child reported to the Sponsor after delivery.

Full details were to be recorded on a Pregnancy Notification Form. Details of the outcome were to be reported on a Pregnancy Outcome Form as soon as possible once the outcome was known.

Appropriateness of Measurements

Efficacy assessments were based on subject reports of vomiting or no vomiting, the use of rescue medication, NAS scores, and PSAQ and PGI-S scores.

Safety assessments were based on AEs and vital signs.

Drug Concentration Measurements: Not applicable.

Data Quality Assurance

Monitoring

Sponsor representatives were allowed to visit all study site locations to assess the data, quality, and study integrity in a manner consistent with applicable health authority regulations and the procedures adopted by sponsor. Prior to the start of the study, members of sponsor reviewed the protocol, eCRF, regulatory obligations and other material or equipment relevant to the conduct of the study with the Investigator and relevant study site personnel.

Monitoring visits and telephone consultations occurred as necessary and per the monitoring plan, during the course of the investigation to verify the following: (a) The rights and well-being of subjects were protected, (b) The conduct of the investigation was in compliance with the currently approved protocol/amendment, 21 Code of Federal Regulations Parts 50, 54, 56, and 812; 42 United States Code 282 (j); ICH Good Clinical Practices (GCP); and applicable local regulations, (c) The integrity of the data, including adequate study documentation, (d) The facilities remained acceptable, (e) The Investigator and site personnel remained qualified and able to conduct the study, and (f) Test article accountability.

Training

The investigator and team were trained in ICH-GCP guideline. Before the start of the study, the study team was trained on the protocol, informed consent procedures, eCRF completion and correction, source documentation, monitoring procedures, management of documents and timelines of subject recruitment and completion.

Quality Assurance

Compliance to the study requirements were observed as per GCP, Internal Standard Operating Procedures, Protocol, and applicable regulatory requirements.

Report summaries were generated using validated SAS® software, version 9.3 or higher. Additional validated software was used to generate analyses, as needed. All SAS programs that create outputs or supporting analysis datasets were validated by a second statistical programmer or biostatistician. At a minimum, validation of programs consisted of a review of the program log, review of output or dataset format and structure, and independent confirmatory programming to verify output results or dataset content. Additionally, all outputs underwent a review by a senior level team member before finalization.

The content of the source data was reviewed on an ongoing basis by project statistical programmers and statisticians. Data was checked for missing values, invalid records, and extreme outliers through defensive programming applications, analysis-based edit checks, and other programmatic testing procedures. All findings were forwarded to the project data manager for appropriate action and resolution.

Clinical Data Management

The eCRF data were stored in a fully validated, 21 CFR Part 11-compliant database and were processed electronically. The data were reviewed for legibility, completeness, and logical consistency.

Automated data validation programs for front-end and back-end edit checks identified missing data, out-of-range data, and other data inconsistencies. Requests for data clarification were notified to the investigative site within the system for resolution. All plausibility checks were defined in the Data Validation section of the Data Management Plan approved by the Sponsor.

Statistical Methods Planned in the Protocol and Determination of Sample Size

Statistical and Analytical Plans

Analysis Populations: The analysis populations were defined as follows: (a) Intent-to-Treat (ITT): The ITT population included all subjects who had been randomized and dispensed study drug; (b) Modified Intent-to-Treat (mITT): The mITT population included subjects who had at least one post-baseline primary efficacy assessment; (c) Per-Protocol (PP): The PP population included subjects who received study drug and had no major protocol deviations; (d) Safety: The Safety population included all subjects who received study drug. All analyses were performed using SAS® Version 9.3 or higher (SAS Institute Inc., USA).

As the number of subjects in the ITT, mITT, PP, and Safety populations were the same, no separate tables for the mITT or PP populations were generated. Tables that were generated for the safety analysis included the same subjects that were in the ITT population but were labeled "Safety population."

Study Subjects

Disposition of Subjects

Subject disposition was summarized for the ITT population by treatment group and over all subjects combined. Summaries included the number (%) of subjects completing the study and discontinuing the study early by the primary reason for discontinuation.

Protocol Deviations

Protocol deviations were recorded on a Site Deviation Log. These data were not entered into the clinical database. The protocol deviations were categorized as significant, major, or minor.

Significant protocol deviations were defined as those that were deemed by the Sponsor to potentially impact the efficacy or safety conclusions of the study.

Measurements of Treatment Compliance

Only a single dose of study drug was administered, and it was given under the observation of members of the study staff. The administration of the single dose was recorded.

Extent of Exposure

Extent of exposure to study treatment was summarized for the Safety Population by treatment group. The number (%) of subjects who received full dose was summarized. The total nasal gel dose administered in grams was summarized with descriptive statistics.

Efficacy Evaluation

Demographic and Other Baseline Characteristics

Demographic variables including age, sex, ethnicity, and race were summarized by treatment group and over all subjects combined for the ITT population. Age was summarized using descriptive statistics. Sex, ethnicity, and race were summarized with the number and percentage of subjects. In addition to demographics, the raw score of the MSSQ-S administered at screening was summarized by treatment group using descriptive statistics.

Primary Efficacy Endpoint Analysis Methods

The primary endpoint was the difference between treatment groups in the rate of response defined as the proportion of subjects in the ITT Population who reported no vomiting and no use of rescue treatment within 4 hours after receiving study drug. A subject who did not have any post-baseline efficacy evaluations reported was considered as having reported vomiting.

The primary statistical framework was to demonstrate superiority of DPI-386 Nasal Gel over Placebo Nasal Gel based on the rate of complete response (defined as no vomiting and no use of rescue medication within 4 hours of study drug dosing). The null hypothesis for the comparison was: (a) Hypothesis H1: The null hypothesis was that there is no difference between DPI-386 Nasal Gel and Placebo Nasal Gel in the rate of complete response. The alternative hypothesis was that there was a difference between DPI-386 Nasal Gel and Placebo Nasal Gel in the rate of complete response. Treatment groups were compared using the 2-sided Z test at the 5% level of significance. The number and percentage of subjects who met the condition of interest were presented for each treatment group, along with the difference in proportions and the associated 95% confidence interval (CI).

Sensitivity Analyses of the Primary Endpoints

Analyses of the mITT population were not necessary as the ITT and mITT populations were the same. The following sensitivity analyses were performed to confirm the robustness of the primary efficacy analysis results: 1. A "Completed-Case" analysis of the primary endpoints was performed using the subgroup of Completers based on the ITT population. Completers were defined as those subjects who completed the study and underwent the post-dose assessment for the primary endpoint. 2. If more than 5% of data were missing for determining the primary efficacy endpoint in any treatment group, a tipping point analysis was performed when the statistical significance of a treatment difference between two groups had been claimed for each of the primary endpoint. If needed, the tipping point analysis of the primary endpoint was to be performed using the ITT population to determine the number of subjects with imputed data in the Placebo Nasal Gel group whose response status would have to be changed from Non- Responder to Responder in order to make the treatment difference between the two treatment groups no longer statistically significant.

Secondary Endpoint Analysis Methods

Proportion of Subjects without Nausea or without Moderate or Severe Nausea

Nausea was reported using a numerical rating scale to evaluate the symptoms of nausea (NAS). Responses were measured on a 4-point scale in which 0 equals no symptoms, 1 equals mild nausea, 2 equals moderate nausea, and 3 equals severe nausea. Subjects were instructed to select the number that best represented the severity of their nausea symptoms in the past 30 minutes. The proportion of subjects who did not have nausea was defined as those subjects who reported no nausea (reported no symptoms on NAS between the 30-minute and the 4-hour post-dose timepoints, inclusive) and who did not use rescue treatment (e.g., dimenhydrinate) within 4 hours after receiving study drug. The estimate for the endpoint was the difference between treatment groups in the proportion of subjects in the ITT population who reported no nausea and no use of rescue treatment within 4 hours after receiving study drug. A subject who did not have any post-baseline evaluations reported was considered as having reported nausea. The null hypothesis for the comparison was: Hypothesis H2: The null hypothesis was that there was no difference between DPI-386 Nasal Gel and Placebo Nasal Gel in the proportion of subjects in the ITT Population who reported no nausea and no use of rescue treatment within 4 hours after receiving study drug.

The proportion of subjects who did not have moderate and severe nausea was defined as those subjects who reported no moderate or severe nausea (reported no moderate or severe nausea on NAS between the 30-minute and the 4-hour post-dose timepoints, inclusive) and who did not use rescue treatment (e.g., dimenhydrinate) within 4 hours after receiving study drug. The null hypothesis for the comparison was: Hypothesis H3: The null hypothesis was that there was no difference between DPI-386 Nasal Gel and Placebo Nasal Gel in the proportion of subjects in the ITT Population who reported no moderate or severe nausea and no use of rescue treatment within 4 hours after receiving study drug. Treatment groups were compared using the 2-sided Z test at the 5% level of significance for the above secondary endpoints. The number and percentage of subjects who met the condition of interest are presented for each treatment group, along with the difference in proportions and the associated 95% CI.

Time to Vomiting

Subjects who reported vomiting or had taken rescue treatment within 4 hours after receiving study drug were considered as having an event, and time to event was defined as the number of hours from the time of first dose to the earliest time of vomiting or rescue medication use.

Subjects who reported no vomiting and who did not taking recue medication were censored at 4 hours or at the end of the voyage, whichever was earlier. Subjects who reported no vomiting and who did not take recue medication and dropped out of study before their 4-hour visit were considered as having the event of vomiting at time of dropout. The null hypothesis for the comparison was: Hypothesis H4: The null hypothesis was that there is no difference between DPI-386 Nasal Gel and Placebo Nasal Gel in the time to vomit or use of rescue medication.

The between-treatment group comparison was performed using a two-sided log rank test. The treatment effect was estimated using a Cox's Proportional Hazard model to calculate the hazard ratio with 95% CI. With reference to FIG. 4B, Kaplan-Meier estimates (product-limit estimates) were presented by treatment group together with a summary of associated statistics of Kaplan-Meier estimates of the 25th, 50th (median), and 75th percentiles with associated CIs (where estimable). In particular, as shown in FIG. 4C, the Kaplan-Meier estimates at 1, 2, 3, and 4 hours were estimated with corresponding two-sided 95% CIs. Kaplan-Meier estimates of the survival distribution function over time were plotted by treatment group.

Analyses of the Overall Trends Observed in the Primary and Secondary Efficacy Endpoints Two Forest plots were produced (FIG. 4D and FIG. 4E) to show the overall trends observed in the primary and secondary efficacy endpoints. The first plot shows the difference in the proportion of subjects who were Complete Responders, the difference in the proportion of subjects who had no nausea, and the difference in the proportion of subjects who had no moderate or severe nausea. The second plot shows the relative risk of having an event of vomiting, the relative risk of having an event of nausea, the relative risk of having an event of moderate or severe nausea, and the hazard ratio for time to vomiting. 95% CIs are shown for all values.

Analyses of Exploratory Efficacy Endpoints

Exploratory efficacy endpoints were analyzed using the ITT population as indicated below.

Modified Performance Self-Assessment Questionnaire

The frequency of subject responses to the individual items of the PSAQ administered were summarized by Treatment Group. The number and percentage of subjects who reported each of the possible responses for each item were summarized by treatment group and visit.

The mean PSAQ score (1=significantly worse, 2-somewhat worse, 3=no effect, 4=somewhat better, 5=significantly better) for each item was also summarized descriptively by treatment and visit. A plot of the mean and mean change from baseline (+standard error [SE]) over time was presented by treatment group. Treatment comparisons for the PSAQ change from baseline between groups were analyzed using a mixed model for repeated measures (MMRM). The statistical model was fitted with terms for treatment group, visit, and treatment by visit interaction. Baseline scores were included as a covariate in the model. The estimated treatment difference for "DPI-386—Placebo" at each visit was displayed in the summary of statistical analysis together with the 95% CI and the associated p-value. Least Squares Means (LSM) for each visit were also presented with the SE.

Patient Global Impression of Severity

PGI-S of motion sickness was measured by a verbal rating scale (none, mild, moderate, and severe). The PGI-S was summarized by severity and treatment group. In addition, the proportion of subjects who did not have motion sickness (reported no symptom on PGI-S) was analyzed similar to the primary efficacy endpoint. Reference is made to: Food and Drug Administration Center for Drug Evaluation and Research. FDA COA Full Qualification Package Outline. See, https://www.fda.gov/media/147025/download.

Nausea Assessment Scale (NAS)

The mean NAS score was summarized descriptively by treatment and visit. A plot of the mean (±SE) over time was presented by treatment group.

Treatment comparisons between groups were analyzed using a MMRM. The statistical model was fitted with terms for treatment group, visit, and treatment by visit interaction. The estimated treatment difference for "DPI-386—Placebo" at each visit was displayed in the summary of statistical analysis together with the 95% CI and the associated p-value. LSM (+SE) for each visit were also presented.

Safety Evaluation

The safety analysis was carried out using the Safety Population, which included all subjects who received study drug. Subjects who do not complete the study, for whatever reason, had all available data up until the time of termination included in the analysis.

Adverse Events

Treatment-emergent adverse events (TEAEs) were defined as those AEs with onset after the administration of study drug or existing events that worsened after the administration of study drug. TEAEs were summarized by treatment group.

Summaries that are displayed by Medical Dictionary for Regulatory Activities (MedDRA) System Organ Class (SOC) and preferred terms were ordered by descending incidence of SOC and preferred term within each SOC. Summaries displayed by preferred term only were ordered by descending incidence of preferred term.

At each level of summarization (e.g., any AE, SOC, and preferred term), subjects experiencing more than one TEAE were counted only once. In the summary of TEAEs by severity grade, subjects were counted once at the highest severity reported at each level of summarization; in the summary of TEAEs by relationship, subjects were counted once at the closest relationship to study drug. Related events include those reported as "Possibly related," "Probably related," or "Definitely related" relationship to study drug; events considered not related are those reported as "Remotely related" or "Unable to determine" with respect to relationship to study drug. AE data were presented in data listings by subject, treatment group, and event.

Vital Signs

Vital sign parameter measurements were summarized by treatment group. Descriptive statistics were presented for observed measurements and changes from baseline.

Other Observations Related to Safety

Sopite Assessment Questionnaire

Scores for each SAQ statement were summarized by treatment group with descriptive statistics.

Exit Interview

The number and percentage of subjects who reported each of the possible responses for the following items were summarized by treatment group: (a) At any time during boat trip, did you experience motion sickness?; (b) At any time during the boat trip, did you experience nausea?; (c) Were your expectations about the study treatment met?; and (d) Did you experience any unwanted or unexpected effects from the study treatment? If you experienced motion sickness during the boat trip, how would you compare it to motion sickness that you have experienced in the past 5 years? If you experienced nausea during the boat trip, how would you compare it to nausea that you have experienced in the past 5 years?

Nasal Gel Device Ease-of-Use Questionnaire

Responses to the questions on the questionnaire were listed.

Determination of Sample Size

The planned sample size was 150 subjects: 75 subjects per treatment arm for each of 2 treatment arms. Assuming that the response in the DPI-386 Nasal Gel arm was 90% and the response in the Placebo Nasal Gel arm was 65%, sample sizes of 75 in the Placebo Nasal Gel arm and 75 in the DPI 386 Nasal Gel arm would achieve at least 90% power to detect a difference between the group proportions of 25%, using the 2-sided Z test with pooled variance at the significance level of 0.05.

Changes in the Conduct of the Study or Planned Analyses: There were no changes in the conduct of the study.

Study Subjects

Disposition of Subjects

Subjects were assigned to 1 of 3 groups. Each group participated in a single boat trip. Boat travel occurred under variable sea conditions in the Pacific Ocean near Los Angeles. Within each boat trip the number of subjects receiving DPI-386 Nasal Gel and Placebo Nasal Gel were approximately equal. The disposition of all study subjects is shown in FIG. 4A.

A total of 140 subjects (68 male and 72 female) were enrolled and dosed in the study. No subject was discontinued from the study.

Protocol Deviations

A total of 59 protocol deviations were recorded in the Site Deviation Log. Two protocol deviations were considered significant, 6 were considered major, and 51 were considered minor.

The 2 significant protocol deviations occurred in Subject 091 and Subject 118, both of whom did not meet the study entry criteria for randomization based on Protocol Exclusion Criterion 9g (history or current nasal, nasal sinus or nasal mucosa surgery). These 2 subjects were excluded from the PP population (1 subject in each treatment group).

Five of the 6 major protocol deviations involved the ICF signing process and 1 major protocol deviation involved the California Bill of Rights signing process. None of the major or minor protocol deviations required that the subject be removed from the study nor did they affect the results of the study.

Efficacy Evaluation

Data Sets Analyzed

One hundred-forty subjects were enrolled in the study, 70 in each treatment group. All 140 subjects were included in the ITT population, the mITT population, and the Safety population. As the ITT and mITT populations are the same, summary tables for results in the mITT population were not produced.

One hundred-thirty-eight subjects were included in the PP population. Subject 1101-091 (DPI-386 Nasal Gel group) and Subject 1101-118 (Placebo Nasal Gel group) were not eligible for the study based on protocol Exclusion Criterion 9g (history of, or current nasal, nasal sinus or nasal mucosa surgery).

Demographic and Other Baseline Characteristics

Demographic Characteristics

The study population was comprised of 68 (48.6%) males and 72 (51.4%) females-Table 4f.

The mean age of the two treatment groups was the same (41.6 years) and the median ages (range) were similar at 42.7 years (18, 67) and 41.6 years (20, 70) in the DPI-386 Nasal Gel and Placebo Nasal Gel treatment groups, respectively. Overall, 61 (43.6%) of the subjects were White, 46 (32.9%) were Asian, 18 (12.9%) were Black or African American, 1 (0.7%) subject reported their race as 'Other,' and for 14 subjects (10.0%) information about race was missing. Mean (standard deviation [SD]) MSSQ-S scores were similar in the two groups: 33.69 (10.384) and 34.06 (11.636) in the DPI-386 Nasal Gel and Placebo Nasal Gel treatment groups, respectively. Median (range) MSSQ-S scores were 35.04 (12.0, 54.0) and 33.88 (7.0, 54.0) in the DPI-386 Nasal Gel and Placebo Nasal Gel treatment groups, respectively. Mean (SD) MMSE total scores were similar in the two groups:

28.79 (1.178) and 28.91 (1.316) in the DPI-386 Nasal Gel and Placebo Nasal Gel treatment groups, respectively. Median (range) MNSE total scores were 29 (25, 30) and 29 (24, 30) in the DPI-386 Nasal Gel and Placebo Nasal Gel treatment groups, respectively.

TABLE 4f

Demographic Data, ITT Population

| Parameter | DPI-386 Nasal Gel (N = 70) | Placebo Nasal Gel (N = 70) | Total (N = 140) |
|---|---|---|---|
| Age (years) | | | |
| N | 70 | 70 | 140 |
| Mean (SD) | 41.6 (15.49) | 41.6 (14.59) | 41.6 (14.99) |
| Median | 42.7 | 41.6 | 42.3 |
| Min, Max | 18, 67 | 20, 70 | 18, 70 |
| Sex, n (%) | | | |
| Male | 36 (51.4) | 32 (45.7) | 68 (48.6) |
| Female | 34 (48.6) | 38 (54.3) | 72 (51.4) |
| Race, n (%) | | | |
| American Indian or Alaska Native | 0 | 0 | 0 |
| Asian | 23 (32.9) | 23 (32.9) | 46 (32.9) |
| Black or African American | 8 (11.4) | 10 (14.3) | 18 (12.9) |
| White | 30 (42.9) | 31 (44.3) | 61 (43.6) |
| Other | 0 | 1 (1.4) | 1 (0.7) |
| Multiple | 0 | 0 | 0 |
| Missing | 9 (12.9) | 5 (7.1) | 14 (10.0) |
| Ethnicity, n (%) | | | |
| Hispanic or Latino | 21 (30.0) | 20 (28.6) | 41 (29.3) |
| Not Hispanic or Latino | 49 (70.0) | 50 (71.4) | 99 (70.7) |
| Raw MSSQ Score | | | |
| N | 70 | 70 | 140 |
| Mean (SD) | 33.69 (10.384) | 34.06 (11.636) | 33.88 (10.990) |
| Median | 35.04 | 33.88 | 34.35 |
| Min, Max | 12.0, 54.0 | 7.0, 54.0 | 7.0, 54.0 |
| MMSE Total Score | | | |
| N | 70 | 70 | 140 |
| Mean (SD) | 28.79 (1.178) | 28.91 (1.316) | 28.85 (1.246) |
| Median | 29.00 | 29.00 | 29.00 |
| Min, Max | 25.0, 30.0 | 24.0, 30.0 | 24.0, 30.0 |

ITT = Intent-to-Treat; max = maximum; min = minimum; MMSE = Mini-Mental State Examination; MSSQ = Motion Sickness Susceptibility Questionnaire; SD = standard deviation.

Medical History

All 140 subjects had a medical history of motion sickness. The SOC that was associated with the next most common medical history was 'Surgical and medical procedures' (in 27.1% and 28.6% of subjects in the DPI-386 Nasal Gel and Placebo Nasal Gel groups, respectively), followed by 'Social circumstances' (in 21.4% of subjects in each group). All other SOCs had ≤10% of subjects reporting a positive medical history in the SOC category.

Specific medical history preferred terms in the 'Surgical and medical procedures' SOC were comprised of a variety of procedures, none occurring in more than 4 subjects (appendectomy, 5.7%). All of the medical history preferred terms in the 'Social circumstances' SOC were post-menopause.

Prior and Concomitant Medications

Thirty-six subjects (51.4%) in each treatment group reported taking at least one medication prior to the study. The most common medication taken before the study was an 'Other viral vaccine,' taken by 36 subjects (51.4%) in the DPI-386 Nasal Gel group and 34 subjects (48.6%) in the Placebo Nasal Gel group. All other medications taken before the study were taken by only 1 subject (1.4%).

Twenty-two subjects (31.4%) in the DPI-386 Nasal Gel group and 25 subjects (35.7%) took at least 1 non-study medication during the study. Overall, the most common class of medication taken during the study was 'Antiemetics and antinauseants,' which were taken by 6 subjects (8.6%) in the DPI-386 Nasal Gel group and 10 subjects (14.3%) in the Placebo Nasal Gel group. The next most common class of medications was 'Sex hormones and modulators of the genital system,' taken by 8 subjects (11.4%) in the DPI-386 Nasal Gel group and 5 subjects (7.1%) in the Placebo Nasal Gel group.

Measurements of Treatment Compliance

Compliance to treatment with study drug was 100% in both treatment groups, as only a single dose of study drug was administered under the supervision of the study staff.

Efficacy Results and Tabulations of Individual Subject Data

Analyses of Efficacy

All 140 enrolled subjects were included in the ITT, mITT, and Safety populations. The PP population was comprised of 138 subjects, 69 subjects (98.6%) in each treatment group. Subject 1101-091 in the DPI-386 Nasal Gel group and Subject 1101-118 in the Placebo Nasal Gel group were not eligible for randomization because they met Exclusion Criterion 9g (history or current nasal, nasal sinus or nasal mucosa surgery). Both subjects were excluded from the PP population.

Primary Efficacy Endpoint: Complete Response Rate

The primary efficacy endpoint was the proportion of subjects who were Complete Responders, defined as no vomiting and no use of rescue medication within 4 hours after receiving study drug.

In the ITT population, 61 subjects (87.1%) in the DPI-386 Nasal Gel group and 53 subjects (75.7%) in the Placebo Nasal Gel group were Complete Responders (Table 4g). The difference between treatment groups was not statistically significant (p=0.0821; Chi-square test).

TABLE 4g

Complete Response Rate, ITT Population

| Parameter | DPI-386 Nasal Gel (N = 70) | Placebo Nasal Gel (N = 70) |
|---|---|---|
| Number of subjects with no vomiting and no rescue medication, n/N (%) | 61/70 (87.1) | 53/70 (75.7) |
| 95% CI | (77.0, 93.9) | (64.0, 85.2) |
| Treatment difference (95% CI) | 11.4 (−1.3, 24.2) | |
| p-value[1] | 0.0821 | |

CI = confidence interval;
ITT = intent-to-treat.
Note:
Complete response is defined as no vomiting and not using rescue treatment within 4 hours after receiving study drug. The within 4 hours after receiving study drug window is from the time of the first dose to the time of the end of voyage.
[1]P-value was based on Chi-square test.

In the PP population, 61 subjects (88.4%) in the DPI-386 Nasal Gel group and 52 subjects (75.4%) in the Placebo Nasal Gel group were Complete Responders (Table 4h). The difference between treatment groups was statistically significant in favor of the DPI-386 Nasal Gel group (p=0.0467; Chi-square test).

Two enrolled subjects were not eligible due to violations of entry criteria for the study (i.e., Exclusion Criterion: history of, or current nasal, nasal sinus or nasal mucosa surgery within the last 2 years) and were therefore excluded from the PP population. The subject in the DPI-386 Nasal Gel group was not a Complete Responder and the subject in the Placebo Nasal Gel group was a Complete Responder. The differences between the ITT population and the PP population in the proportions of Complete Responders in each treatment group are the reason that a statistically non-significant result (p=0.0821) was observed in the ITT population and a statistically significant result (p=0.0467) was observed in the PP population.

TABLE 4h

Complete Response Rate, Per Protocol Population

| Parameter | DPI-386 Nasal Gel (N = 69) | Placebo Nasal Gel (N = 69) |
|---|---|---|
| Number of subjects with no vomiting and no rescue medication, n/N (%) | 61/69 (88.4) | 52/69 (75.4) |
| 95% CI | (78.4, 94.9) | (63.5, 84.9) |
| Treatment difference (95% CI) | 13.0 (0.4, 25.7) | |
| p-value[1] | 0.0467 | |

CI = confidence interval.
Note:
Complete response is defined as no vomiting and not using rescue treatment within 4 hours after receiving study drug. The within 4 hours after receiving study drug window is from the time of the first dose to the time of the end of voyage.
[1] P-value was based on Chi-square test.

Secondary Efficacy Endpoints

Nausea Assessment: Proportion of Subjects without Nausea or Use of Rescue Medication This endpoint was the proportion of subjects without nausea and no reported use of rescue medication within 4 hours after receiving study drug.

In the ITT population when the subject in the Placebo Nasal Gel group with missing data was treated as failure (i.e., having nausea within the 4-hour period), 16 subjects (22.9%) in the DPI-386 Nasal Gel group and 9 subjects (12.9%) in the Placebo Nasal Gel group did not have nausea and did not use rescue medication within the 4-hour period after receiving study drug. No difference between treatment groups was observed (p=0.1224; Chi-square test) (Table 4i). The result was similar when the subject in the Placebo Nasal Gel group with missing data was excluded from the analysis (p=0.1320; Chi-square test).

TABLE 4i

Proportion of Subjects without Nausea or Use of Rescue Medication within 4 Hours of Receiving Study Medication, ITT Population

| Parameter | DPI-386 Nasal Gel (N = 70) | Placebo Nasal Gel (N = 70) |
|---|---|---|
| Worst Case, Missing = Failure | | |
| Number of subjects with no nausea, n/N (%) | 16/70 (22.9) | 9/70 (12.9) |
| 95% CI | (13.7, 34.4) | (6.1, 23.0) |
| Treatment difference (95% CI) | 10.0 (−2.6, 22.6) | |
| p-value[1] | 0.1224 | |
| Missing = Excluded | | |
| Number of subjects with no nausea, n/N (%) | 16/70 (22.9) | 9/69 (13.0) |
| 95% CI | (13.7, 34.4) | (6.1, 23.3) |
| Treatment difference (95% CI) | 9.8 (−2.8, 22.5) | |
| p-value[1] | 0.1320 | |

CI = confidence interval;
ITT = intent-to-treat.
Note:
Response is defined as NAS score of No symptoms and did not use rescue treatment within 4 hours after receiving study drug.

The within 4 hours after receiving study drug window is from the time of the first dose to the time of the end of voyage.

[1] P-value was based on Chi-square test.

In the PP population when the subject in the Placebo Nasal Gel group with missing data was treated as failure (i.e., having nausea within the 4-hour period), 16 subjects (23.2%) in the DPI-386 Nasal Gel group and 9 subjects (13.0%) in the Placebo Nasal Gel group did not have nausea and did not use rescue medication within the 4-hour period after receiving study drug. No difference between treatment groups was observed (p=0.1218; Chi-square test) (Table 4j). The result was similar when the subject in the Placebo Nasal Gel group with missing data was excluded from the analysis (p=0.1315; Chi-square test).

TABLE 4j

Proportion of Subjects without Nausea or Use of Rescue Medication within 4 Hours of Receiving Study Medication, Per Protocol Population

| Parameter | DPI-386 Nasal Gel (N = 69) | Placebo Nasal Gel (N = 69) |
|---|---|---|
| Worst Case, Missing = Failure | | |
| Number of subjects with no nausea, n/N (%) | 16/69 (23.2) | 9/69 (13.0) |
| 95% CI | (13.9, 34.9) | (6.1, 23.3) |
| Treatment difference (95% CI) | 10.1 (−2.6, 22.9) | |
| p-value[1] | 0.1218 | |
| Missing = Excluded | | |
| Number of subjects with no nausea, n/N (%) | 16/69 (23.2) | 9/68 (13.2) |
| 95% CI | (13.9, 34.9) | (6.2, 23.6) |
| Treatment difference (95% CI) | 10.0 (−2.9, 22.8) | |
| p-value[1] | 0.1315 | |

CI = confidence interval;
NAS = Nausea Assessment Scale.
Note:
Response is defined as NAS score of No symptoms and did not use rescue treatment within 4 hours after receiving study drug. The within 4 hours after receiving study drug window is from the time of the first dose to the time of the end of voyage.
[1] P-value was based on Chi-square test.

Nausea Assessment: Proportion of Subjects without Moderate or Severe Nausea or Use of Rescue Medication This endpoint was the proportion of subjects without moderate or severe nausea and no use of rescue medication within 4 hours after receiving study drug.

In the ITT population when the subject in the Placebo Nasal Gel group with missing data was treated as failure (i.e., having moderate or severe nausea within the 4-hour period), 46 subjects (65.7%) in the DPI-386 Nasal Gel group and 36 subjects (51.4%) in the Placebo Nasal Gel group did not have moderate or severe nausea and did not use rescue medication within the 4-hour period after receiving study drug. No difference between treatment groups was observed (p=0.0862; Chi-square test) (Table 4k). The result was similar when the subject in the Placebo Nasal Gel group with missing data was excluded from the analysis (p=0.1046; Chi-square test).

TABLE 4k

Proportion of Subjects without Moderate or Severe Nausea or Use of Rescue Medication within 4 Hours of Receiving Study Medication, ITT Population

| Parameter | DPI-386 Nasal Gel (N = 70) | Placebo Nasal Gel (N = 70) |
|---|---|---|
| Worst Case, Missing = Failure | | |
| Number of subjects with no moderate or severe nausea, n/N (%) | 46/70 (65.7) | 36/70 (51.4) |
| 95% CI | (53.4, 76.7) | (39.2, 63.6) |
| Treatment difference (95% CI) | 14.3 (−1.9, 30.4) | |
| p-value[1] | 0.0862 | |
| Missing = Excluded | | |
| Number of subjects with no moderate or severe nausea, n/N (%) | 46/70 (65.7) | 36/69 (52.2) |
| 95% CI | (53.4, 76.7) | (39.8, 64.4) |
| Treatment difference (95% CI) | 13.5 (−2.7, 29.7) | |
| p-value[1] | 0.1046 | |

TABLE 4k-continued

Proportion of Subjects without Moderate or Severe Nausea or Use of Rescue Medication within 4 Hours of Receiving Study Medication, ITT Population

| Parameter | DPI-386 Nasal Gel (N = 70) | Placebo Nasal Gel (N = 70) |
|---|---|---|

CI = confidence interval;
ITT = Intent-to-Treat;
NAS = Nausea Assessment Scale.
Note:
Response is no NAS score of Moderate or Severe and did not use rescue treatment within 4 hours after receiving study drug. The within 4 hours after receiving study drug window is from the time of the first dose to the time of the end of voyage.
[1] P-value was based on Chi-square test.

In the PP population when the subject in the Placebo Nasal Gel group with missing data was treated as failure (i.e., having moderate or severe nausea within the 4-hour period), 46 subjects (66.7%) in the DPI-386 Nasal Gel group and 35 subjects (50.7%) in the Placebo Nasal Gel group did not have moderate or severe nausea and did not use rescue medication within the 4-hour period after receiving study drug. No difference between treatment groups was observed (p=0.0572; Chi-square test) (Table 41). The result was similar when the subject in the Placebo Nasal Gel group with missing data was excluded from the analysis (p=0.0705; Chi-square test).

TABLE 4l

Proportion of Subjects without Moderate or Severe Nausea or Use of Rescue Medication within 4 Hours of Receiving Study Medication, Per Protocol Population

| Parameter | DPI-386 Nasal Gel (N = 69) | Placebo Nasal Gel (N = 69) |
|---|---|---|
| Worst Case, Missing = Failure | | |
| Number of subjects with no moderate or severe nausea, n/N (%) | 46/69 (66.7) | 35/69 (50.7) |
| 95% CI | (54.3, 77.6) | (38.4, 63.0) |
| Treatment difference (95% CI) | 15.9 (−0.3, 32.2) | |
| p-value[1] | 0.0572 | |
| Missing = Excluded | | |
| Number of subjects with no moderate or severe nausea, n/N (%) | 46/69 (66.7) | 35/68 (51.5) |
| 95% CI | (54.3, 77.6) | (39.0, 63.8) |
| Treatment difference (95% CI) | 15.2 (−1.1, 31.5) | |
| p-value[1] | 0.0705 | |

CI = confidence interval;
NAS = Nausea Assessment Scale.
Note:
Response is no NAS score of Moderate or Severe and did not use rescue treatment within 4 hours after receiving study drug. The within 4 hours after receiving study drug window is from the time of the first dose to the time of the end of voyage.
[1] P-value was based on Chi-square test.

Time to Vomiting or Use of Rescue Medication

In the ITT population, the median time to vomiting or use of rescue medication in the 4-hour period after receiving study drug was not estimable (NE) for subjects in the DPI-386 Nasal Gel group and was 4.1 hours (range NE) for subjects in the Placebo Nasal Gel group (Table 4m). The difference between the treatment groups in median time to vomiting or use of rescue medication favored the DPI-386 Nasal Gel group (0.0105; log-rank test).

The hazard ratio (95% CI) of having vomiting or using rescue medication within 4 hours of receiving study medication for subjects in the DPI-386 Nasal Gel group was 0.483 (0.217, 1.078) (the Placebo Nasal Gel group was the reference group).

The probabilities (95% CI) of having vomiting or using rescue medication for Hour 1, Hour 2, Hour 3, and Hour 4, for each treatment group, are presented in Table 4m. The probability in each hour for subjects in the DPI-386 Nasal Gel group is roughly one-half that of subjects in the Placebo Nasal Gel group.

A Kaplan-Meier plot (ITT population) of time to vomiting or use of rescue medication is presented in FIG. 4B.

TABLE 4m

Time to Vomiting or Use of Rescue Medication, ITT Population

| Parameter | DPI-386 Nasal Gel (N = 70) | Placebo Nasal Gel (N = 70) |
|---|---|---|
| Number (%) subjects with event | 9 (12.9) | 17 (24.3) |
| Number (%) subjects censored | 61 (87.1) | 53 (75.7) |
| Time to event (hours) | | |
| 25% (95% CI) | NE | 4.1 (2.7, 4.1) |
| Median (95% CI) | NE | 4.1 (NE, NE) |
| 75% (95% CI) | NE | 4.1 (NE, NE) |
| Log Rank p-value | 0.0105 | |
| Hazard ratio (95% CI) | 0.483 (0.217, 1.078) | |
| Probability of event (95% CI) | | |
| Hour 1 | 0.005 (0.000, 0.011) | 0.010 (0.000, 0.023) |
| Hour 2 | 0.052 (0.023, 0.080) | 0.104 (0.058, 0.149) |
| Hour 3 | 0.096 (0.050, 0.140) | 0.189 (0.124, 0.248) |
| Hour 4 | 0.121 (0.066, 0.173) | 0.235 (0.162, 0.301) |

CI = confidence interval;
ITT = intent-to-treat.
Note:
Subjects who reported vomiting or have taken rescue treatment within 4 hours after receiving study drug are considered having the event and time to event is derived as number of hours from the dosing to the earliest time of vomiting or rescue medication use.

In the PP population, the median time to vomiting or use of rescue medication in the 4-hour period after receiving study drug was NE for subjects in the DPI-386 Nasal Gel group and was 4.1 hours (range NE) for subjects in the Placebo Nasal Gel group (Table 4n). The difference between the treatment groups in median time to vomiting or use of rescue medication favored the DPI-386 Nasal Gel group (0.0039; log-rank test).

The hazard ratio (95% CI) of having vomiting or using rescue medication within 4 hours of receiving study medication for subjects in the DPI-386 Nasal Gel group was 0.429 (0.186, 0.990) (the Placebo Nasal Gel group was the reference group).

The probabilities (95% CI) of having vomiting or using rescue medication for Hour 1, Hour 2, Hour 3, and Hour 4, for each treatment group, are presented in Table 4n. The probability in each hour for subjects in the DPI-386 Nasal Gel group is 40% to 45% that of subjects in the Placebo Nasal Gel group.

A Kaplan-Meier plot (PP population) of time to vomiting or use of rescue medication is presented in FIG. 4C.

TABLE 4n

Time to Vomiting or Use of Rescue Medication, Per Protocol Population

| Parameter | DPI-386 Nasal Gel (N = 69) | Placebo Nasal Gel (N = 69) |
|---|---|---|
| Number (%) subjects with event | 8 (11.6) | 17 (24.6) |
| Number (%) subjects censored | 61 (88.4) | 52 (75.4) |
| Time to event (hours) | | |
| 25% (95% CI) | NE | 4.1 (2.7, 4.1) |
| Median (95% CI) | NE | 4.1 (NE, NE) |
| 75% (95% CI) | NE | 4.1 (NE, NE) |
| Log Rank p-value | 0.0039 | |
| Hazard ratio (95% CI) | 0.429 (0.186, 0.990) | |
| Probability of event (95% CI) | | |
| Hour 1 | 0.004 (0.000, 0.011) | 0.010 (0.000, 0.024) |
| Hour 2 | 0.049 (0.020, 0.076) | 0.110 (0.061, 0.156) |
| Hour 3 | 0.090 (0.045, 0.133) | 0.198 (0.131, 0.260) |
| Hour 4 | 0.109 (0.057, 0.159) | 0.237 (0.163, 0.304) |

CI = confidence interval.
Note:
Subjects who reported vomiting or have taken rescue treatment within 4 hours after receiving study drug are considered having the event and time to event is derived as number of hours from the dosing to the earliest time of vomiting or rescue medication use.

Primary and Secondary Efficacy Endpoints-Overall Trend

Although the primary efficacy outcome measure failed to demonstrate a statistically significant difference between DPI-386 Nasal Gel and Placebo Nasal Gel, a consistent treatment benefit in favor of DPI-386 Nasal Gel is demonstrated when the primary endpoint and the 3 secondary endpoints are examined overall. An approach in which the efficacy results are taken as a whole is supported in certain situations (See, e.g., Pocock, 2016).

The difference in the proportion of subjects who were Complete Responders was +11.4% (95% CI −1.3, 24.4) in favor of the DPI-386 Nasal Gel group. The difference in the proportion of subjects who had no nausea was +10.0% (95% CI −2.6, 22.6) in favor of the DPI-386 Nasal Gel group, and the difference in the proportion of subjects who had no moderate or severe nausea was +14.3% (95% CI −1.9, 30.4) in favor of the DPI-386 Nasal Gel group (FIG. 4D).

Compared to the subjects treated with Placebo Nasal Gel, DPI-386 Nasal Gel treatment reduced the risk of having an event of vomiting by 47%; it reduced the risk of having an event of moderate or severe nausea by 29%. Compared to the subjects treated with Placebo Nasal Gel, DPI-386 Nasal Gel treatment reduced the hazard for time to vomiting by 52% (FIG. 4E).

Exploratory Efficacy Endpoints

Performance Self-Assessment

Performance was self-assessed and measured before, every 30 minutes during, and after the ocean travel using the PSAQ. Eight parameters of performance were assessed on a 5-point Likert scale: significantly worse (score=1), somewhat worse (score=2), no effect (score=3), somewhat better (sore=4), and significantly better (score=5). The 8 parameters were concentration, mood, alertness, memory, hand-eye coordination, balance, reaction time (speed), and overall performance. Lower scores indicated poorer performance, and "minus" numbers in change from baseline indicated a lower score at that timepoint than the score at baseline.

In general, in the ITT population performance (as measured by the PSAQ) favored the DPI-386 Nasal Gel group compared with the Placebo Nasal Gel group, with large differences observed at the 2.5-hour timepoint.

Plots of the LSM (SE) change from baseline in PSAQ in the ITT population for the parameters of memory, alertness, balance, concentration, hand-eye coordination, mood, reaction time, and overall performance are provided in FIGS. 4F to 4M.

Patient Global Impression of Severity of Motion Sickness

PGI-S of motion sickness was measured by a verbal rating scale (none, mild, moderate, and severe). This endpoint was the proportion of subjects without motion sickness (score=none) at the end of the study.

In the ITT population when the subjects with missing data were treated as failure (i.e., having motion sickness at the end of the study), 24 subjects (34.3%) in the DPI-386 Nasal Gel group and 15 subjects (21.4%) in the Placebo Nasal Gel group did not have motion sickness at the end of the study. No difference between treatment groups was observed (p=0.0897; Chi-square test) (Table 40). The result was similar when subjects with missing data were excluded from the analysis (p=0.0972; Chi-square test).

In the DPI-386 Nasal Gel group (ITT population), 24 subjects (34.3%) reported no motion sickness at the end of the study, 32 subjects (45.7%) reported mild motion sickness, 9 subjects (12.9%) reported moderate motion sickness, and 2 subjects (2.9%) reported severe motion sickness. In the Placebo Nasal Gel group, 15 subjects (21.4%) reported no motion sickness at the end of the study, 26 subjects (37.1%) reported mild motion sickness, 15 subjects (21.4%) reported moderate motion sickness, and 10 subjects (14.3%) reported severe motion sickness.

TABLE 4o

Proportion of Subjects without Motion Sickness, based on the PGI-S, ITT Population

| Parameter | Nasal Gel (N = 70) | Placebo Nasal Gel (N = 70) |
|---|---|---|
| Worst Case, Missing = Failure | | |
| Number of subjects with no symptoms per PGI-S, n/N (%) | 24/70 (34.3) | 15/70 (21.4) |
| 95% CI | (23.3, 46.6) | (12.5, 32.9) |
| Treatment difference (95% CI) | 12.9 (−1.8, 27.6) | |
| p-value[1] | 0.0897 | |
| Missing = Excluded | | |
| Number of subjects with no symptoms per PGI-S, n/N (%) | 24/67 (35.8) | 15/66 (22.7) |
| 95% CI | (24.5, 48.5) | (13.3, 34.7) |
| Treatment difference (95% CI) | 13.1 (−2.2, 28.4) | |
| p-value[1] | 0.0972 | |

CI = confidence interval;
ITT = Intent-to-Treat;
PGI-S = Patient Global Impression of Severity.
Note:
A response is a PGI-S score of None at the end of study.
[1] P-value was based on Chi-square test.

In the PP population when the subjects with missing data were treated as failure (i.e., having motion sickness at the end of the study), 24 subjects (34.8%) in the DPI-386 Nasal Gel group and 15 subjects (21.7%) in the Placebo Nasal Gel group did not have motion sickness at the end of the study. No difference between treatment groups was observed (p=0.0888; Chi-square test) (Table 4p). The result was similar when subjects with missing data were excluded from the analysis (p=0.0963; Chi-square test)

TABLE 4p

Proportion of Subjects without Motion Sickness, based on the PGI-S, Per Protocol Population

| Parameter | DPI-386 Nasal Gel (N = 69) | Placebo Nasal Gel (N = 69) |
|---|---|---|
| Worst Case, Missing = Failure | | |
| Number of subjects with no symptoms per PGI-S, n/N (%) | 24/69 (34.8) | 15/69 (21.7) |
| 95% CI | (23.7, 47.2) | (12.7, 33.3) |
| Treatment difference (95% CI) | 13.0 (−1.8, 27.9) | |
| p-value[1] | 0.0888 | |
| Missing = Excluded | | |
| Number of subjects with no symptoms per PGI-S, n/N (%) | 24/66 (36.4) | 15/65 (23.1) |
| 95% CI | (24.9, 49.1) | (13.5, 35.2) |
| Treatment difference (95% CI) | 13.3 (−2.2, 28.8) | |
| p-value[1] | 0.0963 | |

CI = confidence interval;
PGI-S = Patient Global Impression of Severity.
Note:
A response is a PGI-S score of None at the end of study.
[1] P-value was based on Chi-square test.

Nausea Assessment Scale: LSM (±SE) NAS scores and the estimated treatment difference for 'DPI-386—Placebo (95% CI) and associated p-values at each timepoint are presented for the ITT population in Table 4q. There were no differences between treatment groups in LSM scores at 30, 60, 90, or 120 minutes post-dose. The differences between the treatment groups favored the DPI-386 Nasal Gel group at 150, 180, 210, and 240 minutes post-dose. The results were similar in the PP population A plot of the differences between treatment groups over time for the ITT population is presented in FIG. 4N.

TABLE 4q

Summary of MMRM Analysis of Nausea Assessment Scores, ITT Population

| Visit Statistic | DPI-386 Nasal Gel (N = 70) | Placebo Nasal Gel (N = 70) |
|---|---|---|
| 30 min post-dose | 70 | 68 |
| LSM (SE) | 0.429 (0.078) | 0.478 (0.077) |
| LSM difference | −0.050 | |
| (95% CI) | (−0.266, 0.167) | |
| p-value | 0.6498 | |
| 60 min post-dose | 70 | 68 |
| LSM (SE) | 0.671 (0.095) | 0.791 (0.093) |
| LSM difference | −0.119 | |
| (95% CI) | (−0.382, 0.143) | |
| p-value | 0.3702 | |
| 90 min post-dose | 70 | 68 |
| LSM (SE) | 0.771 (0.096) | 0.973 (0.106) |
| LSM difference | −0.202 | |
| (95% CI) | (−0.484, 0.080) | |
| p-value | 0.1594 | |
| 120 min post-dose | 69 | 68 |
| LSM (SE) | 0.827 (0.100) | 1.105 (0.116) |
| LSM difference | −0.278 | |
| (95% CI) | (−0.581, 0.025) | |
| p-value | 0.0714 | |
| 150 min post-dose | 69 | 68 |
| LSM (SE) | 0.711 (0.102) | 1.030 (0.112) |
| LSM difference | −0.320 | |
| (95% CI) | (−0.620, −0.019) | |
| p-value | 0.0372 | |
| 180 min post-dose | 68 | 67 |
| LSM (SE) | 0.683 (0.096) | 1.077 (0.112) |
| LSM difference | −0.394 | |

TABLE 4q-continued

| Summary of MMRM Analysis of Nausea Assessment Scores, ITT Population | | |
|---|---|---|
| Visit Statistic | DPI-386 Nasal Gel (N = 70) | Placebo Nasal Gel (N = 70) |
| (95% CI) | (−0.685, −0.102) | |
| p-value | 0.0085 | |
| 210 min post-dose | 67 | 63 |
| LSM (SE) | 0.550 (0.092) | 0.652 (0.106) |
| LSM difference | −0.443 | |
| (95% CI) | (−0.722, −0.163) | |
| p-value | 0.0021 | |
| 240 min post-dose | 68 | 63 |
| LSM (SE) | 0.353 (0.066) | 0.652 (0.106) |
| LSM difference | −0.299 | |
| (95% CI) | (−0.546, −0.051) | |
| p-value | 0.0187 | |

CI = confidence interval;

ITT = Intent-to-Treat

LSM = least squares mean;

min = minutes;

MMRM = mixed model for repeated measures;

SE = standard error.

Note:

Nausea Assesment Score were assigned as following: 0 = No symptoms; 1 = mild nausea; 2 = moderate nausea; 3 = severe nausea.

Analysis was based on MMRM including fixed effects of treatment, visit, and interaction terms of treatment by visit.

Subgroup Analyses

Gender

Complete Response Rate

A marked difference between treatment groups (ITT population) in the Complete Response rate in favor of DPI-386 Nasal Gel was observed in the male population but not in the female population.

In males, all 36 subjects (100%) in the DPI-386 Nasal Gel group and 25 subjects (78.1%) in the Placebo Nasal Gel group were Complete Responders (p=0.0035; Fisher's Exact test; Table 4r).

In females, 25 subjects (73.5%) in the DPI-386 Nasal Gel group and 28 subjects (73.7%) in the Placebo Nasal Gel group were Complete Responders. No difference between treatment groups was observed (p>0.9999; Fisher's Exact test).

TABLE 4r

| Complete Response Rate, by Gender, ITT Population | | |
|---|---|---|
| Parameter | DPI-386 Nasal Gel | Placebo Nasal Gel |
| Male | | |
| Number of subjects with no vomiting, n/N (%) | 36/36 (100.0) | 25/32 (78.1) |
| 95% CI | (90.3, 100.0) | (60.0, 90.7) |
| Treatment difference (95% CI) | 21.9 (7.6, 36.2) | |
| p-value[1] | 0.0035 | |
| p-value[2] | 0.0030 | |
| Female | | |
| Number of subjects with no vomiting, n/N (%) | 25/34 (73.5) | 28/38 (73.7) |
| 95% CI | (55.6, 87.1) | (56.9, 86.6) |
| Treatment difference (95% CI) | −0.2 (−20.5, 20.2) | |
| p-value[1] | >.9999 | |
| p-value[2] | 0.9881 | |

CI = confidence interval;

ITT = Intent-to-Treat

Note:

Complete response was defined as no vomiting and not using rescue treatment within 4 hours after receiving study drug. The within 4 hours after receiving study drug window was from the time of the first dose to the time of the end of voyage.

P-values were based on Fishers exact test.

P-values were based on Chi-square test.

Proportion of Subjects without Nausea

In the male and female subgroups, no differences were observed in the proportions of subjects who did not have nausea and who did not use rescue medication between the DPI-386 Nasal Gel arm and the Placebo Nasal Gel arm.

Proportion of Subjects without Moderate or Severe Nausea

In the male and female subgroups, no differences were observed in the proportions of subjects who did not have moderate or severe nausea and who did not use rescue medication between the DPI-386 Nasal Gel arm and the Placebo Nasal Gel arm.

Race

Complete Response Rate

In the 3 subgroups of Asian subjects, Black or African American subjects, and White subjects, no differences were observed in Complete Response rates between the DPI-386 Nasal Gel arm and the Placebo Nasal Gel arm.

Proportion of Subjects without Nausea

In the 3 subgroups of Asian subjects, Black or African American subjects, and White subjects, no differences were observed in the proportions of subjects who did not have nausea and who did not use rescue medication between the DPI-386 Nasal Gel arm and the Placebo Nasal Gel arm.

Proportion of Subjects without Moderate or Severe Nausea

In the 3 subgroups of Asian subjects, Black or African American subjects, and White subjects, no differences were observed in the proportions of subjects who did not have moderate or severe nausea and who did not use rescue medication between the DPI-386 Nasal Gel arm and the Placebo Nasal Gel arm.

Age

Complete Response Rate

In the 2 subgroups of subjects aged ≤50 years and >50 years, no differences were observed in Complete Response rates between the DPI-386 Nasal Gel arm and the Placebo Nasal Gel arm.

Proportion of Subjects without Nausea

A difference between treatment groups (ITT population) in the proportion of subjects without nausea and who did not use rescue medication, in favor of DPI-386 Nasal Gel, was observed in the subgroup of subjects >50 years of age but not in the subgroup of subjects ≤50 years of age (Table 4s).

TABLE 4s

Proportion of Subjects without Nausea or Use of Rescue Medication within 4 Hours of Receiving Study Medication, by Age Group, ITT Population

| Parameter | DPI-386 Nasal Gel | Placebo Nasal Gel |
|---|---|---|
| Age ≤50 years | | |
| Worst Case, Missing = Failure | | |
| Number of subjects without nausea or use of rescue medication, n/N (%) | 5/42 (11.9) | 7/46 (15.2) |
| 95% CI | (4.0, 25.6) | (6.3, 28.9) |
| Treatment difference (95% CI) | −3.3 (−17.6, 11.0) | |
| p-value[1] | 0.7607 | |
| p-value[2] | 0.6511 | |
| Missing = Excluded | | |
| Number of subjects without nausea or use of rescue medication, n/N (%) | 5/42 (11.9) | 7/46 (15.2) |
| 95% CI | (4.0, 25.6) | (6.3, 28.9) |
| Treatment difference (95% CI) | −3.3 (−17.6, 11.0) | |
| p-value[1] | 0.7607 | |
| p-value[2] | 0.6511 | |
| Age > 50 years | | |
| Worst Case, Missing = Failure | | |
| Number of subjects without nausea or use of rescue medication, n/N (%) | 11/28 (39.3) | 2/24 (8.3) |
| 95% CI | (21.5, 59.4) | (1.0, 27.0) |
| Treatment difference (95% CI) | 31.0 (9.8, 52.2) | |
| p-value[1] | 0.0122 | |
| p-value[2] | 0.0102 | |
| Missing = Excluded | | |
| Number of subjects without nausea or use of rescue medication, n/N (%) | 11/28 (39.3) | 2/24 (8.7) |
| 95% CI | (21.5, 59.4) | |
| Treatment difference (95% CI) | 31.0 (9.8, 52.2) | |
| p-value[1] | 0.0122 | |
| p-value[2] | 0.0102 | |

CI = confidence interval;
ITT = Intent-to-Treat
Note:
Complete response was defined as no vomiting or no symptoms and did not use rescue treatment within 4 hours after receiving study drug. The within 4 hours after receiving study drug window was from the time of the first dose to the time of the end of voyage.
P-values were based on Fishers exact test.
P-values were based on Chi-square test.

Age

Proportion of Subjects without Moderate or Severe Nausea

In the 2 subgroups of subjects aged ≤50 years and >50 years, no differences in the proportions of subjects who did not have moderate or severe nausea and who did not use rescue medication between the DPI-386 Nasal Gel arm and the Placebo Nasal Gel arm were observed.

Statistical/Analytical Issues

Adjustments for Covariates: Covariate analyses were not planned or performed.

Handling of Dropouts or Missing Data: In the analysis of the primary and secondary efficacy endpoints, subjects in the ITT Population who did not have any post-baseline data reported in the efficacy evaluations during first 4 hours post-dose or who discontinued the study prior to the 4-hour visit were treated as follows: In the analysis of the response endpoints (i.e., subjects who did not experience vomiting, nausea, moderate or severe nausea), subjects were considered to be non-responders; and In the analysis of the time to vomit, subjects were considered as having vomited at time of last efficacy assessment. Subjects without a post-baseline assessment were considered as having vomited at time 0.

Subject 072 did not have post-baseline NAS assessments. This subject was considered to have experienced nausea in the missing=failure analyses. The subject completed the study without vomiting or use of rescue medication.

Interim Analysis and Data Monitoring: No interim analyses were planned or performed, nor was there a plan to establish a data monitoring committee for this study.

Multicenter Studies: This study was conducted at a single site.

Multiple Comparisons/Multiplicity: The 4 null hypotheses of no treatment effect for the primary and key secondary endpoints were defined as follows: (a) Hypothesis H1: The null hypothesis was that there was no difference between DPI-386 Nasal Gel and Placebo Nasal Gel in the rate of complete response; (b) Hypothesis H2: The null hypothesis was that there was no difference between DPI-386 Nasal Gel and Placebo Nasal Gel in the proportion of subjects in the ITT population who reported no nausea and no use of rescue treatment within 4 hours after receiving study drug; (c) Hypothesis H3: The null hypothesis was that there was no difference between DPI-386 Nasal Gel and Placebo Nasal Gel in the proportion of subjects in the ITT population who reported no moderate and severe nausea and no use of rescue treatment within 4 hours after receiving study drug; and (d) Hypothesis H4: The null hypothesis was that there was no difference between DPI-386 Nasal Gel and Placebo Nasal Gel in the time to vomit or use of rescue medication.

To address the multiplicity induced by the analysis of the primary and key secondary endpoints, a multiplicity adjustment based on the fixed-sequence testing procedure was applied. This procedure controlled the overall Type I error rate at a two-sided a=0.05.

The multiplicity adjustment was applied to the 4 hypotheses as follows, where a=0.05 for all tests: (a) Hypothesis H1 was tested at the 0.05 level, i.e., it was rejected if p1≤30.05. Proceed to H2 if H1 is rejected. If H1 is not rejected, the remaining hypotheses were accepted without testing; (b) Hypothesis H2 was tested at the 0.05 level, i.e., it was rejected if p2≤0.05. Proceed to H3 if H2 is rejected. If H2 is not rejected, the remaining hypotheses were accepted without testing; (c) Hypothesis H3 will be tested at the 0.05 level, i.e., it will be rejected if p3≤0.05. Proceed to H4 if H3 is rejected. If H3 is not rejected, the remaining hypothesis was accepted without testing; and (d) Hypothesis H4 will be tested at the 0.05 level, i.e., it will be rejected if p4≤0.05.

The primary analysis failed to demonstrate the superiority of DPI-386 Nasal Gel over Placebo Nasal Gel. No formal hypothesis testing for the secondary endpoints was performed. The comparisons of secondary endpoints were performed, and nominal p-values are presented as supportive analyses.

Use of an “Efficacy Subset” of Subjects

The primary efficacy analysis was based on the ITT population, and the mITT and PP populations were the same as the ITT population. No efficacy subsets of subjects were analyzed.

Active-control Studies Intended to Show Equivalence: Not applicable. This study did not have an active control.

Examination of Subgroups

Analyses of efficacy results across important subject subgroups such as age categories, gender, and race were performed; subject demographics and screening raw MSSQ-S score were examined as covariates in the efficacy analyses, as necessary.

Drug Dose, Drug Concentration and Relationships to Response: the pharmacokinetics of scopolamine were not investigated in this study.

Drug-drug and Drug-disease Interactions: Not applicable.

By-Subject Displays: By-subject displays of efficacy results were not produced.

Efficacy Conclusions

All 140 enrolled subjects were included in the ITT population and 138 subjects were included in the PP population in this randomized, double-blind study in subjects with a susceptibility to motion sickness of a single administration of either DPI-386 Nasal Gel or Placebo Nasal Gel while aboard an ocean-going vessel.

The study population was divided fairly equally between males (48.6%) and females (51.4%) and the mean age of both treatment groups was 41.6 years.

The primary efficacy endpoint in the study was the proportion of subjects who were Complete Responders, defined as no vomiting and no use of rescue medication within 4 hours after receiving study drug. In the ITT population, the difference between treatment groups in the proportion of subjects who had a Complete Response was not statistically significant (87.1% in the DPI-386 Nasal Gel group and 75.7% in the Placebo Nasal Gel group; p=0.0821; Chi-square test). The difference in the Per Protocol population was statistically significant (88.4% in the DPI-386 Nasal Gel group and 75.4% in the Placebo Nasal Gel group; p=0.0467; Chi-square test).

Two enrolled subjects were not eligible for the study and were therefore excluded from the PP population. The subject in the DPI-386 Nasal Gel group was not a Complete Responder and the subject in the Placebo Nasal Gel group was a Complete Responder. The differences between the ITT population and the PP population in the proportions of Complete Responders in each treatment group are the reason that a statistically non-significant result (p=0.0821) was observed in the ITT population and a statistically significant result (p=0.0467) was observed in the PP population.

In the ITT and PP populations, no differences between treatment groups in the proportions of subjects without nausea and no reported use of rescue medication within 4 hours after receiving study drug, and in the proportions of subjects without moderate or severe nausea and no use of rescue medication within 4 hours after receiving study drug (both were secondary efficacy endpoints), were observed.

In the ITT and PP populations, differences between the treatment groups in time to vomiting or use of rescue medication (a secondary efficacy endpoint) were observed in favor of the DPI-386 Nasal Gel group (ITT population: p=0.0105; Per Protocol population: p=0.0039; log-rank test), with the probability of vomiting in each hour for subjects in the DPI-386 Nasal Gel group being between 40% to 50% of that for subjects in the Placebo Nasal Gel group.

In general, in the ITT population performance (as measured by the PSAQ) was favored in the DPI-386 Nasal Gel group compared with the Placebo Nasal Gel group, with large observed differences observed at the 2.5-hour timepoint.

No difference between treatment groups in PGI-S was observed.

Although the primary efficacy outcome measure failed to demonstrate a statistically significant difference between DPI-386 Nasal Gel and Placebo Nasal Gel, a consistent treatment benefit in favor of DPI-386 Nasal Gel is demonstrated when the primary endpoint and the 3 secondary endpoints are examined overall.

The difference in the proportion of subjects who were Complete Responders was +11.4% (95% CI −1.3, 24.4) in favor of the DPI-386 Nasal Gel group. The difference in the proportion of subjects who had no nausea was +10.0% (95% CI −2.6, 22.6) in favor of the DPI-386 Nasal Gel group, and the difference in the proportion of subjects who had no moderate or severe nausea was +14.3% (95% CI −1.9, 30.4) in favor of the DPI-386 Nasal Gel group.

Compared to the subjects treated with Placebo Nasal Gel, DPI-386 Nasal Gel treatment reduced the risk of having an event of vomiting by 47%; it reduced the risk of having an event of moderate or severe nausea by 29%. Compared to the subjects treated with Placebo Nasal Gel, DPI-386 Nasal Gel treatment reduced the hazard for time to vomiting by 52%.

Subgroups

Complete Response rate, the proportion of subjects with nausea, and the proportion of subjects with moderate or severe nausea were evaluated in the following subgroups: gender, race, and age group (≤50 years, >50 years). Marked differences were observed in 2 subgroup/endpoint combinations: (a) In males, the Complete Response rate was markedly higher in the DPI-386 Nasal Gel group (100% vs. 78.1%). No difference was observed in females; and (b) In subjects >50 years of age, the proportion of subjects without nausea was markedly higher in the DPI-386 Nasal Gel group. It was not different in subjects ≤50 years of age.

Safety Evaluation

Extent of Exposure

All 140 subjects (70 subjects in each arm) received a single dose of study drug per protocol, thus the extent of exposure in both treatment groups was 100%.

Adverse Events

Brief Summary of Adverse Events

Forty-three subjects (61.4%) in the DPI-386 Nasal Gel group and 46 subjects (65.7%) in the Placebo Nasal Gel group had at least one TEAE (Table 4t). Thirty-seven subjects (52.9%) in each treatment group had at least one TEAE that was related to treatment with study drug.

Five subjects (7.1%) in the DPI-386 Nasal Gel group and 7 subjects (10.0%) in the Placebo Nasal Gel group had a Grade 3 TEAE, and 1 subject (1.4%) in each treatment group had a Grade 3 TEAE that was related to treatment with study drug. No Grade 4 TEAEs were reported during the study.

No TEAE in either treatment group led to discontinuation from the study. No SAEs or deaths occurred in the study:

TABLE 4t

Overall Summary of Treatment-Emergent Adverse Events, Safety Population

| Parameter | DPI-386 Nasal Gel (N = 70) n (%) | Placebo Nasal Gel (N = 70) n (%) |
|---|---|---|
| Any adverse event | 43 (61.4) | 46 (65.7) |
| Any adverse event related to study drug | 37 (52.9) | 37 (52.9) |
| Any adverse event Grade 2 or higher | 17 (24.3) | 26 (37.1) |
| Any adverse event Grade 3 or higher | 5 (7.1) | 7 (10.0) |
| Any adverse event Grade 3 or higher related to study drug | 1 (1.4) | 1 (1.4) |
| Any adverse event leading to discontinuation from study drug | 0 | 0 |
| Any related adverse event leading to discontinuation from study drug | 0 | 0 |
| Any serious adverse event | 0 | 0 |
| Any serious adverse event related to study drug | 0 | 0 |
| Any adverse event leading to death | 0 | 0 |

Extent of Exposure

Display of Adverse Events

Adverse Events by System Organ Class and Preferred Term

Forty-three subjects (61.4%) in the DPI-386 Nasal Gel group and 46 subjects (65.7%) in the Placebo Nasal Gel group had at least one TEAE (Table 4u).

For both treatment groups the SOC that was associated with the most TEAEs was ‘Nervous system disorders.’ Thirty-four subjects (48.6%) in the DPI-386 Nasal Gel group and 36 subjects (51.4%) in the Placebo Nasal Gel group had a TEAE in that SOC. The second most common SOC for both treatment groups was ‘Gastrointestinal disorders,’ with 14 subjects (20.0%) in the DPI-386 Nasal Gel group and 20 subjects (28.6%) in the Placebo Nasal Gel group.

In the DPI-386 Nasal Gel group, the most common TEAE was somnolence (17 subjects, 24.3%), followed by dizziness (11 subjects, 15.7%), headache (9 subjects, 12.9%), and vomiting (8 subjects, 11.4%). In the Placebo Nasal Gel group, the most common TEAE was headache (17 subjects, 24.3%), followed by dizziness (15 subjects, 21.4%), and somnolence and vomiting (13 subjects each, 18.6%). All other TEAEs in both treatment groups were reported in ≤10% of subjects.

TABLE 4u

Summary of Treatment-Emergent Adverse Events (Safety Population)

| System Organ Class<br>Preferred Term | DPI-386 Nasal Gel (N = 70) n (%) | Placebo Nasal Gel (N = 70) n (%) |
|---|---|---|
| Subjects with at least one adverse event | 43 (61.4) | 46 (65.7) |
| Nervous system disorders | 34 (48.6) | 36 (51.4) |
| Somnolence | 17 (24.3) | 13 (18.6) |
| Dizziness | 11 (15.7) | 15 (21.4) |
| Headache | 9 (12.9) | 17 (24.3) |
| Dysgeusia | 0 | 2 (2.9) |
| Memory impairment | 1 (1.4) | 0 |
| Tunnel vision | 1 (1.4) | 0 |
| Gastrointestinal disorders | 14 (20.0) | 20 (28.6) |
| Vomiting | 8 (11.4) | 13 (18.6) |
| Nausea | 4 (5.7) | 6 (8.6) |
| Dry mouth | 2 (2.9) | 2 (2.9) |
| Abdominal pain | 1 (1.4) | 0 |
| Diarrhoea | 1 (1.4) | 0 |
| Gastrooesophageal reflux disease | 1 (1.4) | 0 |
| General disorders and administration site conditions | 5 (7.1) | 3 (4.3) |
| Fatigue | 4 (5.7) | 2 (2.9) |
| Feeling hot | 1 (1.4) | 0 |
| Thirst | 0 | 1 (1.4) |
| Infections and infestations | 1 (1.4) | 3 (4.3) |
| COVID-19 | 0 | 2 (2.9) |
| Hordeolum | 1 (1.4) | 0 |
| Nasopharyngitis | 0 | 1 (1.4) |
| Respiratory, thoracic and mediastinal disorders | 1 (1.4) | 2 (2.9) |
| Nasal discomfort | 1 (1.4) | 1 (1.4) |
| Rhinalgia | 0 | 1 (1.4) |
| Rhinorrhoea | 0 | 1 (1.4) |
| Psychiatric disorders | 2 (2.9) | 0 |
| Disorientation | 1 (1.4) | 0 |
| Irritability | 1 (1.4) | 0 |
| Injury, poisoning and procedural complications | 1 (1.4) | 0 |
| Hand fracture | 1 (1.4) | 0 |
| Reproductive system and breast disorders | 0 | 1 (1.4) |
| Dysmenorrhoea | 0 | 1 (1.4) |
| Menstruation delayed | 0 | 1 (1.4) |

Abbrevation: MedDRA = Medical Dictionary for Regulatory Activities

Note:

Adverse Events were coded using MedDRA Version 24.0.

Adverse Events by Maximum Severity

Overall, most of the TEAEs in the 43 subjects in the DPI-386 Nasal Gel group who had a TEAE had a maximum severity of either mild (26 subjects, 37.1%) or moderate (12 subjects, 17.1%) (Table 4v). Five subjects (7.1%) in the DPI-386 Nasal Gel group had a severe TEAE. There were no Grade 4 AEs in the DPI-386 Nasal Gel group.

Overall, most of the TEAEs in the 43 subjects in the Placebo Nasal Gel group who had a TEAE had a maximum severity of either mild (20 subjects, 28.6%) or moderate (19 subjects, 27.1%). Seven subjects (10.0%) in the Placebo Nasal Gel group had a severe TEAE. There were no Grade 4 TEAEs in the Placebo Nasal Gel group.

Of the TEAEs that occurred in ≥10% of subjects (somnolence, dizziness, headache, and vomiting), the majority were mild (Table 4v). One subject (1.4%) in the DPI-386 Nasal Gel group had a severe TEAE of dizziness, 1 subject (1.4%) in the Placebo Nasal Gel group had a severe TEAE of headache, and 4 subjects in each group (5.7%) had severe TEAEs of vomiting.

TABLE 4v

Summary of Treatment-Emergent Adverse Events, by Maximum Severity, System Organ Class, and Preferred Term, Safety Population

| | DPI-386 Nasal Gel (N = 70) n (%) | Placebo Nasal Gel (N = 70) n (%) |
|---|---|---|
| All TEAEs<br>Subjects with at least one adverse event | | |
| Mild | 26 (37.1) | 20 (28.6) |
| Moderate | 12 (17.1) | 19 (27.1) |
| Severe | 5 (7.1) | 7 (10.0) |
| TEAEs Occurring in ≥10% of Subjects<br>Somnolence | | |
| Mild | 13 (18.6) | 9 (12.9) |
| Moderate | 4 (5.7) | 4 (5.7) |
| Dizziness | | |
| Mild | 10 (14.3) | 10 (14.3) |
| Moderate | 0 | 5 (7.1) |
| Severe | 1 (1.4) | 0 |
| Headache | | |
| Mild | 8 (11.4) | 9 (12.9) |
| Moderate | 1 (1.4) | 7 (10.0) |
| Severe | 0 | 1 (1.4) |
| Vomiting | | |
| Moderate | 4 (5.7) | 9 (12.9) |
| Severe | 4 (5.7) | 4 (5.7) |

Abbreviations: MedDRA = Medical Dictionary for Regulatory Activities; TEAE = treatment-emergent adverse event.

Note:

Adverse Events were coded using MedDRA Version 24.0.

Adverse Events by Relationship to Study Treatment

Thirty-seven subjects (52.9%) in each treatment group had at least one TEAE that was considered to be related to the administration of study drug (Table 4w).

For both treatment groups the SOC that was associated with the most treatment-related TEAEs was ‘Nervous system disorders.’ Thirty-four subjects (48.6%) in the DPI-386 Nasal Gel group and 36 subjects (51.4%) in the Placebo Nasal Gel group had a TEAE in that SOC. The second most common SOC with treatment-related TEAEs was ‘General disorders and administration site conditions,’ with 5 subjects (7.1% %) in the DPI-386 Nasal Gel group and 3 subjects (4.3%) in the Placebo Nasal Gel group.

In the DPI-386 Nasal Gel group, the most common treatment-related TEAE was somnolence (17 subjects, 24.3%), followed by dizziness (11 subjects, 15.7%), and headache (9 subjects, 12.9%). In the Placebo Nasal Gel group, the most common treatment-related TEAE was headache (17 subjects, 24.3%), followed by dizziness (15 subjects, 21.4%), and somnolence (13 subjects, 18.6%). All other treatment-related AEs in both treatment groups were reported in ≤6% of subjects. One subject (1.4%) in the DPI-386 Nasal Gel group had 2 treatment-related TEAEs that were Grade 3 in severity (dizziness and vomiting), and 1 subject (1.4%) in the Placebo Nasal Gel group had 1 treatment-related TEAE that was Grade 3 (headache).

TABLE 4x

Summary of Treatment-Emergent Adverse Events Related to Study Drug by System Organ Class and Preferred Term, Safety Population

| System Organ Class Preferred Term | DPI-386 Nasal Gel (N = 70) n (%) | Placebo Nasal Gel (N = 70) n (%) |
|---|---|---|
| Subjects with at least one treatment related adverse event | 37 (52.9) | 37 (52.9) |
| Nervous system disorders | 34 (48.6) | 36 (51.4) |
| Somnolence | 17 (24.3) | 13 (18.6) |
| Dizziness | 11 (15.7) | 15 (21.4) |
| Headache | 9 (12.9) | 17 (24.3) |
| Dysgeusia | 0 | 2 (2.9) |
| Memory impairment | 1 (1.4) | 0 |
| Tunnel vision | 1 (1.4) | 0 |
| General disorders and administration site conditions | 5 (7.1) | 3 (4.3) |
| Fatigue | 4 (5.7) | 2 (2.9) |
| Feeling hot | 1 (1.4) | 0 |
| Thirst | 0 | 1 (1.4) |
| Gastrointestinal disorders | 4 (5.7) | 3 |
| Dry mouth | 2 (2.9) | 2 (2.9) |
| Abdominal pain | 1 (1.4) | 0 |
| Nausea | 0 | 1 (1.4) |
| Vomiting | 1 (1.4) | 0 |
| Respiratory, thoracic and mediastinal disorders | 1 (1.4) | 2 (2.9) |
| Nasal discomfort | 1 (1.4) | 1 (1.4) |
| Rhinalgia | 0 | 1 (1.4) |
| Rhinorrhoea | 0 | 1 (1.4) |
| Psychiatric disorders | 2 (2.9) | 0 |
| Disorientation | 1 (1.4) | 0 |
| Irritability | 1 (1.4) | 0 |
| Reproductive system and breast disorders | 0 | 1 (1.4) |
| Dysmenorrhoea | 0 | 1 (1.4) |
| Menstruation delayed | 0 | 1 (1.4) |

Abbreviation: MedDRA = Medical Dictionary for Regulatory Activities

Note:

Adverse Events were coded using MedDRA Version 24.0.

Analysis of Adverse Events

The proportion of subjects that had a TEAE was similar in the two treatment groups (61.4% and 65.7% in the DPI-386 Nasal Gel and Placebo Nasal Gel groups, respectively). The 4 most common TEAEs in each treatment group were the same but had slightly different frequencies (the proportion in the DPI-386 Nasal Gel group is shown first: somnolence (24.3% vs. 18.6%), dizziness (15.7% vs. 21.4%), headache (12.9% vs. 24.3%), and vomiting (11.4% vs. 18.6%).

Treatment with DPI-386 Nasal Gel may have mitigated some symptoms that can occur in subjects who experience motion sickness-dizziness, vomiting, and headache.

There was no difference in the proportion of subjects who had a treatment-related TEAE (52.9% in each group); and a lower proportion of subjects in the DPI-386 Nasal Gel group had TEAEs that were Grade 2 or higher (24.3% vs. 37.1%), and that were Grade 3 (7.1% vs. 10.0%).

No Grade 4 TEAEs, SAEs, or deaths occurred during the study.

Deaths, Other Serious Adverse Events and Other Significant Adverse Events: No deaths occurred in the study. Other Serious Adverse Events: No SAEs occurred in the study. Other Significant Adverse Events: No subject discontinued the study due to a TEAE. Narratives of Deaths, Other Serious Adverse Events and Certain Other Significant Adverse Events: Not applicable. Analysis and Discussion of Deaths, Other Serious Adverse Events and Other Significant Adverse Events: Not applicable.

Clinical Laboratory Evaluation: Clinical laboratory testing was not performed during the study.

Listing of Individual Laboratory Measurements by Subject and Each Abnormal Laboratory Value: Not applicable. Evaluation of Each Laboratory Parameter: Not applicable. Laboratory Values Over Time: Not applicable. Individual Subject Changes: Not applicable. Individual Clinically Significant Abnormalities: Not applicable.

Vital Signs, Physical Findings and Other Observations Related to Safety

No appreciable changes in mean vital sign values were observed from baseline to Day 2, nor were any appreciable differences in mean vital sign values observed between treatment groups.

Sopite Assessment Questionnaire

Descriptive statistics of the responses to each of the 4 questions were collected. There was no clinically meaningful difference between the treatment groups for any of the 4 statements.

Exit Interview

The exit interview was conducted at the end of the voyage for the purpose of learning about the subject's experiences on the boat trip.

A slightly lower proportion of subjects in the DPI-386 Nasal Gel group experienced motion sickness (67.1% vs. 72.9%) and nausea (68.6% vs. 77.1%). A slightly higher proportion of subjects in the DPI-386 Nasal Gel group said that their expectations had been met (78.6% vs. 67.1%). A majority of subjects in both groups had no unwanted effects from participating in the study (72.9% of subjects in the DPI-386 Nasal Gel group and 74.3% of subjects in the Placebo Nasal Gel group).

When asked if the motion sickness they experienced on the voyage was worse than they had experienced previously, a lower proportion of subjects in the DPI-386 Nasal Gel group said it was worse (10.0% vs. 20.0%).

When asked if the nausea they experienced on the voyage was worse than they had experienced previously, a lower proportion of subjects in the DPI-386 Nasal Gel group said it was worse (5.7% vs. 20.0%).

Safety Conclusions

DPI-386 Nasal Gel was well tolerated and no new safety signals for DPI-386 Nasal Gel were observed.

Discussion and Overall Conclusions

Efficacy

All 140 enrolled subjects were included in the ITT population and 138 subjects were included in the PP population in this randomized, double-blind study in subjects with a susceptibility to motion sickness of a single administration of either DPI-386 Nasal Gel or Placebo Nasal Gel while aboard an ocean-going vessel.

The study population was divided fairly equally between males (48.6%) and females (51.4%) and the mean age of both treatment groups was 41.6 years.

The primary efficacy endpoint in the study was the proportion of subjects who were Complete Responders, defined as no vomiting and no use of rescue medication within 4 hours after receiving study drug. In the ITT population, the difference between treatment groups in the proportion of subjects who had a Complete Response was not statistically significant (87.1% in the DPI-386 Nasal Gel group and 75.7% in the Placebo Nasal Gel group; p=0.0821; Chi-square test). The difference in the Per Protocol population was statistically significant (88.4% in the DPI-386 Nasal Gel group and 75.4% in the Placebo Nasal Gel group; p=0.0467; Chi-square test).

Two enrolled subjects were not eligible for the study and were therefore excluded from the PP population. The subject in the DPI-386 Nasal Gel group was not a Complete Responder and the subject in the Placebo Nasal Gel group was a Complete Responder. The differences between the ITT population and the PP population in the proportions of Complete Responders in each treatment group are the reason that a statistically non-significant result (p=0.0821) was observed in the ITT population and a statistically significant result (p=0.0467) was observed in the PP population.

In the ITT population, no difference between treatment groups in the proportion of subjects without nausea and no reported use of rescue medication within 4 hours after receiving study drug (a secondary efficacy endpoint) was observed. When missing data was treated as failure, 16 subjects (22.9%; 95% CI: 13.7, 34.4) in the DPI-386 Nasal Gel group and 9 subjects (12.9%; 95% CI: 6.1, 23.0) in the Placebo Nasal Gel group did not have nausea and did not use rescue medication within the 4-hour period after receiving study drug (p=0.1224; Chi-square test). No differences were observed in the PP population as well.

In the ITT population, no difference between treatment groups in the proportion of subjects without moderate or severe nausea and no use of rescue medication within 4 hours after receiving study drug (a secondary efficacy endpoint) was observed. When missing data was treated as failure, 46 subjects (65.7%; 95% CI: 53.4, 76.7) in the DPI-386 Nasal Gel group and 36 subjects (51.4%; 95% CI: 39.2, 63.6) in the Placebo Nasal Gel group did not have moderate or severe and did not use rescue medication within the 4-hour period after receiving study drug (p=0.0862; Chi-square test). No differences were observed in the PP population as well.

In the ITT and PP populations, marked differences between the treatment groups in time to vomiting or use of rescue medication (a secondary efficacy endpoint) were observed in favor of the DPI-386 Nasal Gel group (ITT population: p=0.0105; Per Protocol population: p=0.0039; log-rank test), with the probability of vomiting in each hour for subjects in the DPI-386 Nasal Gel group being roughly 40% to 50% of that for subjects in the Placebo Nasal Gel group.

In general, performance (as measured by the PSAQ) was favored in the DPI-386 Nasal Gel group compared with the Placebo Nasal Gel group, with large observed differences observed at the 2.5-hour timepoint.

No difference between treatment groups in PGI-S was observed. When missing data was treated as failure, 24 subjects (34.3%; 95% CI: 23.3, 46.6) in the DPI-386 Nasal Gel group and 15 subjects (21.4%; 95% CI: 12.5, 32.9) in the Placebo Nasal Gel group did not have motion sickness at the end of the study (p=0.0897; Chi-square test).

Although the primary efficacy outcome measure failed to demonstrate a statistically significant difference between DPI-386 Nasal Gel and Placebo Nasal Gel, a consistent treatment benefit in favor of DPI-386 Nasal Gel is demonstrated when the primary endpoint and the 3 secondary endpoints are examined overall.

Integration: Examples 3 (MS-33) and 4 (MS-29)

The integration of data between and amongst Examples 3 and 4 offers therapeutically relevant information.

Subgroups—MS-29

Complete Response rate, the proportion of subjects with nausea, and the proportion of subjects with moderate or severe nausea were evaluated in the following subgroups: gender, race, and age group (≤50 years, >50 years). Marked differences were observed in 2 subgroup/endpoint combinations: (a) In males, the Complete Response rate was markedly higher in the DPI-386 Nasal Gel group (100% vs. 78.1%). It was not different in females; (b) In subjects >50 years of age, the proportion of subjects without nausea was markedly higher in the DPI-386 Nasal Gel group. It was not different in subjects ≤50 years of age.

Safety-MS-29

The proportion of subjects that had a TEAE was similar in the two treatment groups (61.4% and 65.7% in the DPI-386 Nasal Gel and Placebo Nasal Gel groups, respectively). The 4 most common TEAEs in each treatment group were the same but had slightly different frequencies (the proportion in the DPI-386 Nasal Gel group is shown first: somnolence (24.3% vs. 18.6%), dizziness (15.7% vs. 21.4%), headache (12.9% vs. 24.3%), and vomiting (11.4% vs. 18.6%).

Treatment with DPI-386 Nasal Gel may have mitigated some symptoms that can occur in subjects who experience motion sickness-dizziness, vomiting, and headache.

There was no difference in the proportion of subjects who had a treatment-related TEAE (52.9% in each group), and a lower proportion of subjects in the DPI-386 Nasal Gel group had TEAEs that were Grade 2 or higher (24.3% vs. 37.1%), and that were Grade 3 (7.1% vs. 10.0%). No Grade 4 TEAEs, SAEs, or deaths occurred during the study. No appreciable changes in mean vital sign values were observed from baseline to Day 2, nor were any appreciable differences in mean vital sign values observed between treatment groups.

There was no clinically meaningful difference between the treatment groups for any of the 4 statements in the SAQ.

In the exit interview, more subjects in the Placebo Nasal Gel group said that the motion sickness they experienced and the nausea they experienced was worse than what they had experienced previously.

Conclusions

Efficacy-MS-29

The efficacy results in this study were mixed. The study failed to show statistically significant superiority of DPI-386 Nasal Gel over Placebo Nasal Gel in the primary efficacy endpoint of Complete Response rate in the ITT population but did show superiority of DPI-386 Nasal Gel in the Per Protocol population analysis of that endpoint.

No differences in the proportion of subjects without nausea and the proportion of subjects without moderate or severe nausea were observed between treatment groups, although a difference in time to vomiting was observed in favor of the DPI-386 Nasal Gel group, and the probability of vomiting in each hour for subjects in the DPI-386 Nasal Gel group was between 40% to 50% of that for subjects in the Placebo Nasal Gel group.

Although the primary efficacy outcome measure failed to demonstrate a statistically significant difference between DPI-386 Nasal Gel and Placebo Nasal Gel, a consistent treatment benefit in favor of DPI-386 Nasal Gel is demonstrated when the primary endpoint and the 3 secondary endpoints are examined overall.

Subgroup analysis in males who received DPI-386 Nasal Gel showed a higher Complete Response rate than in males who received Placebo Nasal Gel, and in subjects >50 years of age the proportion of subjects without nausea was markedly higher in the DPI-386 Nasal Gel group than in the Placebo Nasal Gel group.

Safety

DPI-386 Nasal Gel was well tolerated and no new safety signals for DPI-386 Nasal Gel were observed.

Sopite Assessment Questionnaire-Pooled

Subjects scored four statements on the SAQ at the completion of the voyage (4 hours). The statements were "I felt: Annoyed/irritated; Drowsy; Tired/fatigued; Uneasy," and each statement was scored 1 to 9, with 1 representing the lowest severity and 9 representing the highest severity. Mean scores on all four statements were lower in the DPI-386 Nasal Gel group compared with the Placebo Nasal Gel group.

Mean (95% CI) differences between treatment groups in the scores for each statement, all in favor of DPI-386 Nasal Gel, were as follows (p-values by pooled 2-sample t-test:

Felt annoyed/irritated: −0.970 (−1.402, −0.538); p<0.0001

Felt drowsy: −0.754 (−1.187, −0.321); p=0.0007

Felt tired/fatigued: −0.719 (−1.147, −0.290); p=0.0010

Felt uneasy: −1.085 (−1.535, −0.635); p<0.0001

These findings suggest that treatment differences observed on the primary outcome measures were associated with self-reported benefits by subjects regarding symptoms often associated with motion assessed by the SAQ.

Summary of Sopite Assessment Questionnaire Scores at 4 Hours Post Dose, Pooled Analysis, ITT Population

| Category<br>Statistic | DPI-386<br>Nasal Gel<br>(N = 321) | Placebo<br>Nasal Gel<br>(N = 322) |
|---|---|---|
| Felt annoyed/irritated | | |
| N | 316 | 318 |
| Mean (SD) | 3.6 (2.67) | 4.5 (2.89) |
| Median | 3.0 | 5.0 |
| Min, max | 1, 9 | 1, 9 |
| Felt drowsy | | |
| N | 314 | 317 |
| Mean (SD) | 4.3 (2.79) | 5.1 (2.75) |
| Median | 4.0 | 5.0 |
| Min, max | 1, 9 | 1, 9 |
| Felt tired/fatigued | | |
| N | 316 | 317 |
| Mean (SD) | 4.1 (2.68) | 4.8 (2.81) |
| Median | 4.0 | 5.0 |
| Min, max | 1, 9 | 1, 9 |
| Felt uneasy | | |
| N | 314 | 318 |
| Mean (SD) | 3.8 (2.81) | 4.9 (2.98) |

-continued

| Category<br>Statistic | DPI-386<br>Nasal Gel<br>(N = 321) | Placebo<br>Nasal Gel<br>(N = 322) |
|---|---|---|
| Median | 3.0 | 5.0 |
| Min, max | 1, 9 | 1, 9 |

ITT = intent-to-treat; max = maximum; min = minimum; SD = standard deviation

Note:

Each statement is rated 1-9 with 1 representing the lowest severity and 9 representing the highest severity.

Analysis of Sopite Assessment Questionnaire Scores at 4 Hours Post Dose, Pooled Analysis, ITT Population

| Parameter<br>Statistic | DPI-386<br>Nasal Gel<br>(N = 321) | Placebo<br>Nasal Gel<br>(N = 322) |
|---|---|---|
| Felt annoyed/irritated | | |
| N | 316 | 318 |
| Mean (SE) | 3.381 (0.175) | 4.351 (0.174) |
| Mean difference | −0.970 | |
| (95% CI) | (−1.402, −0.538) | |
| p-value | <0.0001 | |
| Felt drowsy | | |
| N | 314 | 317 |
| Mean (SE) | 4.333 (0.175) | 5.087 (0.175) |
| Mean difference | −0.754 | |
| (95% CI) | (−1.187, −0.321) | |
| p-value | 0.0007 | |
| Felt tired/fatigued | | |
| N | 316 | 317 |
| Mean (SE) | 3.948 (0.173) | 4.666 (0.173) |
| Mean difference | −0.719 | |
| (95% CI) | (−1.147, −0.290) | |
| p-value | 0.0010 | |
| Felt uneasy | | |
| N | 314 | 318 |
| Mean (SE) | 3.579 (0.182) | 4.663 (0.182) |
| Mean difference | −1.085 | |
| (95% CI) | (−1.535, −0.635) | |
| p-value | <0.0001 | |

CI = confidence interval; ITT = intent-to-treat; SE = standard error

Note:

Each statement is rated 1-9 with 1 representing the lowest severity and 9 representing the highest severity.

Note:

The between-treatment comparisons were performed using a pooled 2-sample t-test.

Correlation of Assessment Tools Used in the Pooled Studies to Patient Global Impression of Severity of Motion Sickness Scores Modified Performance Self-Assessment Questionnaire and Patient Global Impression of Severity of Motion Sickness PGI-S was assessed once by each subject at the end of the voyage. PSAQ was assessed every 30 minutes during the 4-hour voyage. A lower score on the PSAQ indicated a poorer self-assessment of performance in the parameter being evaluated.

Subjects who rated their motion sickness symptoms on the PGI-S at the end of the voyage (Hour 4) as more severe had lower mean PSAQ scores (i.e., poorer performance) at the end of the voyage.

Subjects who rated their motion sickness symptoms on the PGI-S at the end of the voyage (Hour 4) as more severe had lower average change from baseline PSAQ scores (i.e., greater worsening of performance from baseline) at the end of the voyage.

Subjects who rated their motion sickness symptoms on the PGI-S at the end of the voyage (Hour 4) as more severe had lower means of all post-dose PSAQ scores (i.e., poorer average performance throughout the voyage).

Subjects who rated their motion sickness symptoms on the PGI-S at the end of the voyage (Hour 4) as more severe had lower post-dose average changes from baseline PSAQ scores (i.e., greater worsening of performance from baseline) throughout the voyage.

These findings demonstrate the association between subject self-reported performance on specific parameters assessed by the PSAQ and their subjective global report of severity of motion sickness on the PGI-S. These results support the clinical meaningfulness of treatment differences observed regarding the primary and other secondary outcome measures.

Summary of Modified Performance Self-Assessment Questionnaire Scores at 4 Hours, by Patient Global Impression of Severity Category, Pooled Analysis, ITT Population

| | PGI-S Category [1] | | | |
|---|---|---|---|---|
| PSAQ Parameter | No Symptoms (N = 159) | Mild Motion Sickness (N = 252) | Moderate Motion Sickness (N = 124) | Severe Motion Sickness (N = 98) |
| Alertness | | | | |
| N | 159 | 252 | 124 | 97 |
| Mean (SD) | 3.2 (0.67) | 3.0 (0.69) | 2.9 (0.91) | 2.5 (1.30) |
| Median | 3.0 | 3.0 | 3.0 | 2.0 |
| Q1, Q3 | 3, 3 | 3, 3 | 2, 3 | 1, 3 |
| Min, max | 2, 5 | 1, 5 | 1, 5 | 1, 5 |
| Balance | | | | |
| N | 159 | 252 | 124 | 97 |
| Mean (SD) | 3.2 (0.70) | 2.9 (0.85) | 2.7 (0.94) | 2.6 (1.29) |
| Median | 3.0 | 3.0 | 3.0 | 2.0 |
| Q1, Q3 | 3, 3 | 2, 3 | 2, 3 | 2, 3 |
| Min, max | 1, 5 | 1, 5 | 1, 5 | 1, 5 |

Summary of Modified Performance Self-Assessment Questionnaire Scores at 4 Hours, by Patient Global Impression of Severity Category, Pooled Analysis, ITT Population (Continued)

| | PGI-S Category [1] | | | |
|---|---|---|---|---|
| PSAQ Parameter | No Symptoms (N = 159) | Mild Motion Sickness (N = 252) | Moderate Motion Sickness (N = 124) | Severe Motion Sickness (N = 98) |
| Concentration | | | | |
| N | 159 | 252 | 124 | 97 |
| Mean (SD) | 3.2 (0.69) | 3.0 (0.71) | 2.7 (0.91) | 2.5 (1.23) |
| Median | 3.0 | 3.0 | 3.0 | 2.0 |
| Q1, Q3 | 3, 3 | 3, 3 | 2, 3 | 2, 3 |
| Min, max | 2, 5 | 1, 5 | 1, 5 | 1, 5 |
| Hand-eye coordination | | | | |
| N | 159 | 252 | 123 | 97 |
| Mean (SD) | 3.2 (0.68) | 3.0 (0.66) | 2.9 (0.84) | 2.6 (1.26) |
| Median | 3.0 | 3.0 | 3.0 | 2.0 |
| Q1, Q3 | 3, 3 | 3, 3 | 2, 3 | 2, 3 |
| Min, max | 2, 5 | 1, 5 | 1, 5 | 1, 5 |

Summary of Modified Performance Self-Assessment Questionnaire Scores at 4 Hours, by Patient Global Impression of Severity Category, Pooled Analysis, ITT Population (Continued)

| | PGI-S Category [1] | | | |
|---|---|---|---|---|
| PSAQ Parameter | No Symptoms (N = 159) | Mild Motion Sickness (N = 252) | Moderate Motion Sickness (N = 124) | Severe Motion Sickness (N = 98) |
| Memory | | | | |
| N | 159 | 250 | 124 | 97 |
| Mean (SD) | 3.2 (0.63) | 3.0 (0.55) | 3.0 (0.79) | 2.7 (1.24) |
| Median | 3.0 | 3.0 | 3.0 | 3.0 |
| Q1, Q3 | 3, 3 | 3, 3 | 3, 3 | 2, 3 |
| Min, max | 2, 5 | 1, 5 | 1, 5 | 1, 5 |
| Mood | | | | |
| N | 159 | 252 | 124 | 97 |
| Mean (SD) | 3.2 (0.72) | 2.9 (0.84) | 2.8 (1.03) | 2.5 (1.35) |
| Median | 3.0 | 3.0 | 3.0 | 2.0 |
| Q1, Q3 | 3, 3 | 2, 3 | 2, 3 | 1, 3 |
| Min, max | 1, 5 | 1, 5 | 1, 5 | 1, 5 |

Summary of Modified Performance Self-Assessment Questionnaire Scores at 4 Hours, by Patient Global Impression of Severity Category, Pooled Analysis, ITT Population (Continued)

| | PGI-S Category [1] | | | |
|---|---|---|---|---|
| PSAQ Parameter | No Symptoms (N = 159) | Mild Motion Sickness (N = 252) | Moderate Motion Sickness (N = 124) | Severe Motion Sickness (N = 98) |
| Overall performance | | | | |
| N | 159 | 252 | 124 | 97 |
| Mean (SD) | 3.2 (0.67) | 3.0 (0.78) | 2.8 (0.92) | 2.5 (1.32) |
| Median | 3.0 | 3.0 | 3.0 | 2.0 |
| Q1, Q3 | 3, 3 | 3, 3 | 2, 3 | 1, 3 |
| Min, max | 2, 5 | 1, 5 | 1, 5 | 1, 5 |
| Reaction time (speed) | | | | |
| N | 159 | 252 | 124 | 97 |
| Mean (SD) | 3.2 (0.65) | 3.0 (0.69) | 2.8 (0.88) | 2.6 (1.26) |
| Median | 3.0 | 3.0 | 3.0 | 2.0 |
| Q1, Q3 | 3, 3 | 3, 3 | 2, 3 | 2, 3 |
| Min, max | 2, 5 | 1, 5 | 1, 5 | 1, 5 |

ITT = intent-to-treat; max = maximum; min = minimum; PSAQ = modified Performance Self-Assessment Questionnaire; PGI-S = Patient Global Impression of Severity; Q1 = first quartile; Q3 = third quartile; SD = standard deviation

[1] PGI-S and PSAQ data from the DPI-386 Nasal Gel and Placebo Nasal Gel groups were combined in this summary.

Note:

PSAQ Scores were assigned as 1 = significantly worse, 2 = somewhat worse, 3 = no effect, 4 = somewhat better, and 5 = significantly better.

Summary of Modified Performance Self-Assessment Questionnaire Scores Change from Baseline at 4 Hours, by Patient Global Impression of Severity Category, Pooled Analysis, ITT Population

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Alertness | | | | |
| N | 158 | 250 | 124 | 97 |
| Mean (SD) | −0.0 (0.77) | −0.1 (0.83) | −0.2 (1.10) | -0.5 (1.37) |
| Median | 0.0 | 0.0 | 0.0 | −1.0 |
| Q1, Q3 | 0, 0 | 0, 0 | −1, 0 | −2, 0 |
| Min, max | −3, 3 | −3, 4 | −4, 2 | −3, 2 |
| Balance | | | | |
| N | 158 | 250 | 124 | 97 |
| Mean (SD) | 0.1 (0.87) | −0.0 (1.00) | −0.1 (1.23) | −0.3 (1.36) |
| Median | 0.0 | 0.0 | 0.0 | 0.0 |
| Q1, Q3 | 0, 0 | −1, 0 | −1, 1 | −1, 0 |
| Min, max | −3, 3 | −3, 3 | −4, 3 | −3, 3 |

Summary of Modified Performance Self-Assessment Questionnaire Scores Change from Baseline at 4 Hours, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Concentration | | | | |
| N | 158 | 250 | 124 | 97 |
| Mean (SD) | 0.1 (0.74) | −0.0 (0.81) | −0.3 (1.08) | −0.4 (1.35) |
| Median | 0.0 | 0.0 | 0.0 | −1.0 |
| Q1, Q3 | 0, 0 | 0, 0 | −1, 0 | −1, 0 |
| Min, max | −3, 2 | −3, 2 | −4, 2 | −3, 2 |
| Hand-eye coordination | | | | |
| N | 158 | 250 | 123 | 97 |
| Mean (SD) | 0.1 (0.78) | −0.0 (0.78) | −0.2 (1.07) | −0.4 (1.29) |
| Median | 0.0 | 0.0 | 0.0 | −1.0 |
| Q1, Q3 | 0, 0 | 0, 0 | −1, 0 | −1, 0 |
| Min, max | −3, 3 | −3, 3 | −4, 2 | −3, 2 |

Summary of Modified Performance Self-Assessment Questionnaire Scores Change from Baseline at 4 Hours, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Memory | | | | |
| N | 158 | 248 | 124 | 97 |
| Mean (SD) | 0.0 (0.70) | −0.1 (0.67) | −0.1 (0.95) | −0.4 (1.25) |
| Median | 0.0 | 0.0 | 0.0 | 0.0 |
| Q1, Q3 | 0, 0 | 0, 0 | 0, 0 | −1, 0 |
| Min, max | −3, 2 | −3, 2 | −4, 3 | −3, 2 |
| Mood | | | | |
| N | 158 | 250 | 124 | 97 |
| Mean (SD) | 0.2 (0.82) | 0.0 (0.99) | −0.3 (1.20) | −0.4 (1.41) |
| Median | 0.0 | 0.0 | 0.0 | −1.0 |
| Q1, Q3 | 0, 0 | 0, 0 | −1, 1 | −1, 0 |
| Min, max | −2, 3 | −3, 3 | −4, 3 | −3, 2 |

Summary of Modified Performance Self-Assessment Questionnaire Scores Change from Baseline at 4 Hours, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Overall performance | | | | |
| N | 158 | 250 | 124 | 97 |
| Mean (SD) | 0.1 (0.78) | −0.0 (0.92) | −0.2 (1.08) | −0.4 (1.36) |
| Median | 0.0 | 0.0 | 0.0 | −1.0 |
| Q1, Q3 | 0, 0 | 0, 0 | −1, 0 | −1, 0 |
| Min, max | −3, 3 | −3, 3 | −4, 3 | −3, 2 |
| Reaction time (speed) | | | | |
| N | 158 | 250 | 124 | 97 |
| Mean (SD) | 0.1 (0.74) | −0.1 (0.82) | −0.2 (1.06) | −0.4 (1.36) |
| Median | 0.0 | 0.0 | 0.0 | −1.0 |
| Q1, Q3 | 0, 0 | 0,0 | −1, 0 | −1, 0 |
| Min, max | −3, 3 | −3, 2 | −4, 2 | −3, 3 |

ITT = intent-to-treat;
max = maximum;
min = minimum;
PSAQ = modified Performance Self-Assessment Questionnaire;
PGI-S = Patient Global Impression of Severity;
Q1 = first quartile;
Q3 = third quartile;
SD = standard deviation
[1] PGI-S and PSAQ data from the DPI-386 Nasal Gel and Placebo Nasal Gel groups were combined in this summary.
Note:
PSAQ Scores were assigned as 1 = significantly worse, 2 = somewhat worse, 3 = no effect, 4 = somewhat better, and 5 = significantly better.

Summary of Modified Performance Self-Assessment Questionnaire Post Dose Average Scores, by Patient Global Impression of Severity Category, Pooled Analysis, ITT Population

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Alertness | | | | |
| N | 159 | 252 | 124 | 98 |
| Mean (SD) | 3.2 (0.57) | 2.8 (0.47) | 2.5 (0.55) | 2.1 (0.68) |
| Median | 3.0 | 3.0 | 2.5 | 2.0 |
| Q1, Q3 | 3, 3 | 3, 3 | 2, 3 | 2, 3 |
| Min, max | 2, 5 | 2, 5 | 1, 4 | 1, 4 |
| Balance | | | | |
| N | 159 | 252 | 124 | 98 |
| Mean (SD) | 3.0 (0.62) | 2.6 (0.51) | 2.3 (0.55) | 2.0 (0.64) |
| Median | 3.0 | 2.6 | 2.3 | 1.9 |
| Q1, Q3 | 3, 3 | 2, 3 | 2, 3 | 1, 3 |
| Min, max | 1, 5 | 1, 5 | 1, 4 | 1, 4 |

Summary of Modified Performance Self-Assessment Questionnaire Post Dose Average Scores, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Concentration | | | | |
| N | 159 | 252 | 124 | 98 |
| Mean (SD) | 3.1 (0.56) | 2.8 (0.46) | 2.4 (0.55) | 2.0 (0.59) |
| Median | 3.0 | 2.9 | 2.4 | 2.0 |
| Q1, Q3 | 3, 3 | 2, 3 | 2, 3 | 2, 3 |
| Min, max | 2, 5 | 2, 5 | 1, 4 | 1, 3 |
| Hand-eye coordination | | | | |
| N | 159 | 252 | 124 | 98 |
| Mean (SD) | 3.1 (0.55) | 2.8 (0.43) | 2.6 (0.56) | 2.1 (0.63) |
| Median | 3.0 | 3.0 | 2.6 | 2.1 |
| Q1, Q3 | 3, 3 | 3, 3 | 2, 3 | 2, 3 |
| Min, max | 2, 5 | 2, 5 | 1, 4 | 1, 3 |

Summary of Modified Performance Self-Assessment Questionnaire Post Dose Average Scores, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Memory | | | | |
| N | 159 | 252 | 124 | 98 |
| Mean (SD) | 3.2 (0.52) | 2.9 (0.36) | 2.7 (0.53) | 2.3 (0.68) |
| Median | 3.0 | 3.0 | 2.9 | 2.4 |
| Q1, Q3 | 3, 3 | 3, 3 | 2, 3 | 2, 3 |
| Min, max | 2, 5 | 2, 5 | 1, 4 | 1, 4 |
| Mood | | | | |
| N | 159 | 252 | 124 | 98 |
| Mean (SD) | 3.1 (0.59) | 2.7 (0.53) | 2.3 (0.59) | 1.9 (0.62) |
| Median | 3.0 | 2.8 | 2.4 | 1.9 |
| Q1, Q3 | 3, 3 | 2, 3 | 2, 3 | 1, 2 |
| Min, max | 2, 5 | 1, 5 | 1, 4 | 1, 4 |

Summary of Modified Performance Self-Assessment Questionnaire Post Dose Average Scores, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Overall performance | | | | |
| N | 159 | 252 | 124 | 98 |
| Mean (SD) | 3.1 (0.56) | 2.8 (0.50) | 2.4 (0.55) | 2.0 (0.65) |
| Median | 3.0 | 2.9 | 2.3 | 1.9 |
| Q1, Q3 | 3, 3 | 2, 3 | 2, 3 | 1, 3 |
| Min, max | 2, 5 | 2, 5 | 1, 4 | 1, 4 |
| Reaction time (speed) | | | | |
| N | 159 | 252 | 124 | 98 |
| Mean (SD) | 3.1 (0.57) | 2.8 (0.45) | 2.5 (0.52) | 2.1 (0.64) |
| Median | 3.0 | 2.9 | 2.5 | 2.0 |
| Q1, Q3 | 3, 3 | 3, 3 | 2, 3 | 2, 3 |
| Min, max | 2, 5 | 2, 5 | 1, 4 | 1, 4 |

ITT = intent-to-treat;
max = maximum;
min = minimum;
PSAQ = modified Performance Self-Assessment Questionnaire;
PGI-S = Patient Global Impression of Severity;
Q1 = first quartile;
Q3 = third quartile;
SD = standard deviation
[1] PGI-S and PSAQ data from the DPI-386 Nasal Gel and Placebo Nasal Gel groups were combined in this summary.
Note:
PSAQ Scores were assigned as 1 = significantly worse, 2 = somewhat worse, 3 = no effect, 4 = somewhat better, and 5 = significantly better.

Summary of Modified Performance Self-Assessment Questionnaire Score Post Dose Average Changes from Baseline, by Patient Global Impression of Severity Category, Pooled Analysis, ITT Population

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Alertness | | | | |
| N | 158 | 250 | 124 | 97 |
| Mean (SD) | −0.0 (0.63) | −0.2 (0.68) | −0.5 (0.71) | −0.9 (0.80) |
| Median | 0.0 | 0.0 | −0.5 | −0.9 |
| Q1, Q3 | −0, 0 | −1, 0 | −1, −0 | −2, −0 |
| Min, max | −2, 2 | −3, 2 | −4, 1 | −3, 1 |
| Balance | | | | |
| N | 158 | 250 | 124 | 97 |
| Mean (SD) | −0.0 (0.68) | −0.3 (0.67) | −0.6 (0.83) | −0.9 (0.80) |
| Median | 0.0 | −0.3 | −0.6 | −0.9 |
| Q1, Q3 | −0, 0 | −1, 0 | −1, −0 | −1, −0 |
| Min, max | −2, 2 | −3, 2 | −4, 1 | −3, 2 |

Summary of Modified Performance Self-Assessment Questionnaire Score Post Dose Average Changes from Baseline, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Concentration | | | | |
| N | 158 | 250 | 124 | 97 |
| Mean (SD) | −0.0 (0.57) | −0.3 (0.60) | −0.6 (0.73) | −0.9 (0.81) |
| Median | 0.0 | −0.1 | −0.5 | −0.9 |
| Q1, Q3 | −0, 0 | −1, 0 | −1, −0 | −1, −0 |
| Min, max | −2, 2 | −3, 2 | −4, 1 | −3, 1 |
| Hand-eye coordination | | | | |
| N | 158 | 250 | 124 | 97 |
| Mean (SD) | −0.0 (0.59) | −0.2 (0.57) | −0.5 (0.76) | −0.9 (0.69) |
| Median | 0.0 | 0.0 | −0.4 | −0.9 |
| Q1, Q3 | 0, 0 | −1, 0 | −1, 0 | −1, −0 |
| Min, max | −2, 2 | −3, 2 | −4, 1 | −3, 0 |

Summary of Modified Performance Self-Assessment Questionnaire Score Post Dose Average Changes from Baseline, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Memory | | | | |
| N | 158 | 250 | 124 | 97 |
| Mean (SD) | −0.0 (0.54) | −0.1 (0.52) | −0.3 (0.68) | −0.8 (0.74) |
| Median | 0.0 | 0.0 | −0.1 | −0.8 |
| Q1, Q3 | 0, 0 | −0, 0 | −1, 0 | −1, −0 |
| Min, max | −2, 2 | −3, 2 | −4, 1 | −3, 1 |
| Mood | | | | |
| N | 158 | 250 | 124 | 97 |
| Mean (SD) | 0.1 (0.68) | −0.2 (0.73) | −0.7 (0.83) | −1.0 (0.76) |
| Median | 0.0 | −0.1 | −0.6 | −1.0 |
| Q1, Q3 | 0, 0 | −1, 0 | −1, −0 | −2, −0 |
| Min, max | −2, 2 | −3, 2 | −4, 2 | −3, 1 |

Summary of Modified Performance Self-Assessment Questionnaire Score Post Dose Average Changes from Baseline, by Patient Global Impression of Severity Category, Pooled Analysis, ITT Population (Continued)

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Overall performance | | | | |
| N | 158 | 250 | 124 | 97 |
| Mean (SD) | 0.0 (0.64) | −0.2 (0.65) | −0.6 (0.72) | −1.0 (0.78) |
| Median | 0.0 | 0.0 | −0.6 | −1.0 |
| Q1, Q3 | −0, 0 | −1, 0 | −1, −0 | −2, −0 |
| Min, max | −2, 3 | −3, 2 | −4, 1 | −3, 2 |
| Reaction time (speed) | | | | |
| N | 158 | 250 | 124 | 97 |
| Mean (SD) | −0.0 (0.60) | −0.2 (0.58) | −0.5 (0.69) | −0.9 (0.76) |

-continued

| PSAQ Parameter | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Median | 0.0 | −0.1 | −0.4 | −1.0 |
| Q1, Q3 | 0, 0 | −1, 0 | −1, 0 | −2, −0 |
| Min, max | −2, 2 | −3, 2 | −4, 1 | −3, 1 |

ITT = intent-to-treat;
max = maximum;
min = minimum;
PSAQ = modified Performance Self-Assessment Questionnaire;
PGI-S = Patient Global Impression of Severity;
Q1 = first quartile;
Q3 = third quartile;
SD = standard deviation
[1] PGI-S and PSAQ data from the DPI-386 Nasal Gel and Placebo Nasal Gel groups were combined in this summary.
Note:
PSAQ Scores were assigned as 1 = significantly worse, 2 = somewhat worse, 3 = no effect, 4 = somewhat better, and 5 = significantly better.

Nausea Assessment Scale and Patient Global Impression of Severity of Motion Sickness Subjects who rated their motion sickness symptoms on the PGI-S at the end of the voyage (Hour 4) as more severe had higher mean NAS scores (i.e., more severe nausea) at the end of the voyage.

Subjects who rated their motion sickness symptoms on the PGI-S at the end of the voyage (Hour 4) as more severe had higher mean NAS scores (i.e., more severe nausea) throughout the voyage.

Summary of Nausea Assessment Scale Scores at Hour 4, by Patient Global Impression of Severity Category, Pooled Analysis, ITT Population

| NAS Parameter Severity of nausea, Hour 4 | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| N | 158 | 251 | 124 | 97 |
| Mean (SD) | 0.0 (0.16) | 0.4 (0.50) | 1.0 (0.75) | 1.6 (1.06) |
| Median | 0.0 | 0.0 | 1.0 | 1.0 |
| Q1, Q3 | 0, 0 | 0, 1 | 1, 2 | 1, 3 |
| Min, max | 0, 1 | 0, 2 | 0, 3 | 0, 3 |

ITT = intent-to-treat;
max = maximum;
min = minimum;
NAS = Nausea Assessment Scale;
PGI-S = Patient Global Impression of Severity;
Q1 = first quartile;
Q3 = third quartile;
SD = standard deviation
[1] PGI-S and NAS data from the DPI-386 Nasal Gel and Placebo Nasal Gel groups were combined in this summary.
Note:
Nausea Assessment Scale Scores were based on the subject's severity of nausea in the past 30 minutes and were assigned as follows: 0 = No symptoms; 1 = mild nausea; 2 = moderate nausea; 3 = severe nausea.

Summary of all Post Dose Average Nausea Assessment Scale Scores, by Patient Global Impression of Severity Category, Pooled Analysis, ITT Population

| NAS Parameter Severity of nausea, all timepoints | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| N | 158 | 252 | 124 | 98 |
| Mean (SD) | 0.1 (0.27) | 0.7 (0.34) | 1.4 (0.42) | 2.0 (0.52) |
| Median | 0.0 | 0.7 | 1.4 | 2.0 |
| Q1, Q3 | 0, 0 | 1, 1 | 1, 2 | 2, 2 |
| Min, max | 0, 1 | 0, 2 | 0, 2 | 1, 3 |

ITT = intent-to-treat;
max = maximum;
min = minimum;
NAS = Nausea Assessment Scale;
PGI-S = Patient Global Impression of Severity;
Q1 = first quartile;
Q3 = third quartile;
SD = standard deviation
[1] PGI-S and NAS data from the DPI-386 Nasal Gel and Placebo Nasal Gel groups were combined in this summary.
Note:
Nausea Assessment Scale Scores were based on the subject's severity of nausea in the past 30 minutes and were assigned as follows: 0 = No symptoms; 1 = mild nausea; 2 = moderate nausea; 3 = severe nausea.

Sopite Assessment Questionnaire and Patient Global Impression of Severity of Motion Sickness Subjects who rated their motion sickness symptoms on the PGI-S at the end of the voyage (Hour 4) as more severe had higher mean scores on each statement of the SAQ questionnaire (i.e., more severe sopite symptoms) at the end of the voyage.

Summary of Sopite Assessment Questionnaire Scores, by Patient Global Impression of Severity Category, Pooled Analysis, ITT Population

| SAQ Statement | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Felt annoyed/irritated | | | | |
| N | 158 | 250 | 124 | 98 |
| Mean (SD) | 2.3 (2.17) | 3.8 (2.44) | 5.1 (2.73) | 6.3 (2.62) |
| Median | 1.0 | 3.0 | 6.0 | 7.0 |
| Q1, Q3 | 1, 2 | 1, 6 | 3, 7 | 5, 9 |
| Min, max | 1, 9 | 1, 9 | 1, 9 | 1, 9 |
| Felt drowsy | | | | |
| N | 157 | 248 | 124 | 98 |
| Mean (SD) | 3.0 (2.54) | 4.5 (2.51) | 5.3 (2.59) | 7.2 (2.07) |
| Median | 2.0 | 5.0 | 6.0 | 8.0 |
| Q1, Q3 | 1, 5 | 2, 7 | 3, 7 | 6, 9 |
| Min, max | 1, 9 | 1, 9 | 1, 9 | 1, 9 |

Summary of Sopite Assessment Questionnaire Scores, by Patient Global Impression of Severity Category, Pooled Analysis, ITT Population (Continued)

| SAQ Statement | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Felt tired/fatigued | | | | |
| N | 158 | 249 | 124 | 98 |
| Mean (SD) | 2.4 (2.14) | 4.3 (2.44) | 5.3 (2.54) | 7.0 (2.18) |

-continued

| SAQ Statement | PGI-S Category [1] No Symptoms (N = 159) | Mild Motion Sickness (N = 252) | Moderate Motion Sickness (N = 124) | Severe Motion Sickness (N = 98) |
|---|---|---|---|---|
| Median | 1.0 | 4.0 | 6.0 | 8.0 |
| Q1, Q3 | 1, 3 | 2, 6 | 3, 7 | 6, 9 |
| Min, max | 1, 9 | 1, 9 | 1, 9 | 1, 9 |
| Felt uneasy | | | | |
| N | 157 | 249 | 124 | 98 |
| Mean (SD) | 1.9 (1.75) | 3.9 (2.37) | 5.7 (2.60) | 7.8 (1.92) |
| Median | 1.0 | 4.0 | 6.0 | 9.0 |
| Q1, Q3 | 1, 2 | 2, 5 | 4, 8 | 7, 9 |
| Min, max | 1, 9 | 1, 9 | 1, 9 | 1, 9 |

ITT = intent-to-treat;
max = maximum;
min = minimum;
PGI-S = Patient Global Impression of Severity;
Q1 = first quartile;
Q3 = third quartile;
SAQ = Sopite Assessment Questionnaire;
SD = standard deviation
[1] PGI-S and SAQ data from the DPI-386 Nasal Gel and Placebo Nasal Gel groups were combined in this summary.
Note:
Each statement is rated 1-9 with 1 representing the lowest severity and 9 representing the highest severity.

As previously notes, one facet of motion sickness that often is not recognized is referred to as Sopite Syndrome, which refers to profound drowsiness and persistent fatigue that can follow brief exposures to highly provocative stimulation or prolonged exposures to low-intensity motion stimulation. Sopite Syndrome can persist for hours or even days and when exposure is prolonged even longer. It is characterized by boredom, apathy, failure of initiative, increased irritability, and even changes in personality. It may be one of the only syndromes that persist when nausea is not elicited or has abated. Also, many manual performance and cognitive tasks are substantially impaired.

The formulation of the present disclosure demonstrates a therapeutic effects to reduce the presentation or manifestation of one or more symptoms associated with Sopite Syndrome. To the knowledge of the inventors, no other therapy has been able to demonstate therapeutic efficacy as against components of Sopite Syndrome.

PSAQ: The Modified Performance Self-Assessment Questionnaire

Performance was self-assessed and measured before dosing and every 30 minutes after dosing during ocean travel using the PSAQ. Eight parameters of performance were assessed on a 5-point Likert scale: significantly worse (score=1), somewhat worse (score=2), no effect (score=3), somewhat better (sore=4), and significantly better (score=5). The 8 parameters were concentration, mood, alertness, memory, hand-eye coordination, balance, reaction time (speed), and overall performance. Lower scores indicated poorer performance, and "minus" numbers in change from baseline indicated a lower score at that timepoint than the score at baseline.

A summary of the distribution of PSAQ score categories for each question and each timepoint is provided. Descriptive statistics of PSAQ scores for each question and each timepoint are provided. Descriptive statistics of the change from baseline in PSAQ scores for each question and each timepoint are provided.

In general, performance (as measured by change from pre-dosing baseline on the PSAQ) favored the DPI-386 Nasal Gel group compared with the Placebo Nasal Gel group, with nominally significant differences in favor of DPI-386 Nasal Gel observed at many post-dosing timepoints in the individual PSAQ domains.

Summary of MMRM Analysis of Change from Baseline in Modified Performance Self-Assessment Questionnaire Score, all Domains, ITT Population

| Domain Time (Post-Dose) | DPI-386 Nasal Gel/Placebo Nasal Gel N/N | LSM Difference [1] | p-value |
|---|---|---|---|
| Alertness | | | |
| 30 min | 288/289 | 0.026 | 0.6169 |
| 60 min | 316/319 | 0.083 | 0.1854 |
| 90 min | 317/320 | 0.146 | 0.0300 |
| 120 min | 317/319 | 0.210 | 0.0017 |
| 150 min | 316/319 | 0.224 | 0.0012 |
| 180 min | 316/318 | 0.243 | 0.0005 |
| 210 min | 316/315 | 0.163 | 0.0194 |
| 240 min | 316/316 | 0.140 | 0.0429 |

Summary of MMRM Analysis of Change from Baseline in Modified Performance Self-Assessment Questionnaire Score, All Domains, ITT Population (Continued)

| Domain Time (Post-Dose) | DPI-386 Nasal Gel/Placebo Nasal Gel N/N | LSM Difference [1] | p-value |
|---|---|---|---|
| Balance | | | |
| 30 min | 288/289 | 0.066 | 0.2568 |
| 60 min | 318/320 | 0.111 | 0.0711 |
| 90 min | 318/320 | 0.180 | 0.0091 |
| 120 min | 317/318 | 0.157 | 0.0219 |
| 150 min | 316/319 | 0.261 | 0.0003 |
| 180 min | 316/318 | 0.243 | 0.0009 |
| 210 min | 316/316 | 0.206 | 0.0044 |
| 240 min | 316/316 | 0.159 | 0.0357 |
| Concentration | | | |
| 30 min | 288/289 | 0.035 | 0.5204 |
| 60 min | 318/320 | 0.130 | 0.0338 |
| 90 min | 318/320 | 0.221 | 0.0008 |
| 120 min | 317/319 | 0.233 | 0.0005 |
| 150 min | 316/319 | 0.295 | <0.0001 |
| 180 min | 316/318 | 0.251 | 0.0003 |
| 210 min | 316/316 | 0.232 | 0.0010 |
| 240 min | 316/316 | 0.150 | 0.0304 |
| Hand-eye coordination | | | |
| 30 min | 288/289 | 0.015 | 0.7518 |
| 60 min | 318/320 | 0.077 | 0.1731 |
| 90 min | 318/319 | 0.189 | 0.0026 |
| 120 min | 317/318 | 0.230 | 0.0003 |
| 150 min | 316/319 | 0.254 | 0.0001 |
| 180 min | 315/318 | 0.258 | 0.0001 |
| 210 min | 316/316 | 0.168 | 0.0120 |
| 240 min | 315/316 | 0.109 | 0.1031 |

Summary of MMRM Analysis of Change from Baseline in Modified Performance Self-Assessment Questionnaire Score, All Domains, ITT Population (Continued)

| Domain Time (Post-Dose) | DPI-386 Nasal Gel/Placebo Nasal Gel N/N | LSM Difference [1] | p-value |
|---|---|---|---|
| Memory | | | |
| 30 min | 287/289 | −0.001 | 0.9717 |
| 60 min | 318/320 | 0.075 | 0.1400 |
| 90 min | 318/320 | 0.134 | 0.0194 |
| 120 min | 317/319 | 0.149 | 0.0126 |
| 150 min | 315/319 | 0.227 | 0.0002 |
| 180 min | 316/318 | 0.238 | <0.0001 |
| 210 min | 316/316 | 0.162 | 0.0070 |
| 240 min | 315/315 | 0.113 | 0.0654 |
| Mood | | | |
| 30 min | 288/289 | −0.001 | 0.9895 |
| 60 min | 318/320 | 0.155 | 0.0203 |
| 90 min | 318/320 | 0.283 | 0.0001 |
| 120 min | 317/319 | 0.280 | <0.0001 |
| 150 min | 316/319 | 0.359 | <0.0001 |
| 180 min | 316/318 | 0.339 | <0.0001 |
| 210 min | 316/316 | 0.292 | <0.0001 |
| 240 min | 316/316 | 0.260 | 0.0007 |
| Overall performance | | | |
| 30 min | 287/287 | −0.006 | 0.9086 |
| 60 min | 318/320 | 0.172 | 0.0057 |
| 90 min | 318/320 | 0.241 | 0.0003 |
| 120 min | 317/319 | 0.214 | 0.0018 |
| 150 min | 316/319 | 0.268 | 0.0001 |
| 180 min | 316/317 | 0.267 | 0.0002 |
| 210 min | 316/316 | 0.226 | 0.0015 |
| 240 min | 316/316 | 0.178 | 0.0136 |

Summary of MMRM Analysis of Change from Baseline in Modified Performance Self-Assessment Questionnaire Score, All Domains, ITT Population (Continued)

| Domain Time (Post-Dose) | DPI-386 Nasal Gel/Placebo Nasal Gel N/N | LSM Difference [1] | p-value |
|---|---|---|---|
| Reaction time (speed) | | | |
| 30 min | 287/289 | 0.027 | 0.5593 |
| 60 min | 318/320 | 0.099 | 0.0815 |
| 90 min | 318/319 | 0.174 | 0.0074 |
| 120 min | 317/319 | 0.184 | 0.0049 |
| 150 min | 316/318 | 0.224 | 0.0008 |
| 180 min | 316/318 | 0.225 | 0.0008 |
| 210 min | 316/316 | 0.180 | 0.0088 |
| 240 min | 316/316 | 0.136 | 0.0477 |

ITT = intent-to-treat;
LSM = least squares mean;
min = minute;
MMRM = mixed model for repeated measures;
PSAQ = modified Performance Self-Assessment Questionnaire
[1] The LSM difference is calculated as the LSM change from baseline value in the DPI-386 Nasal Gel group minus the LSM change from baseline value in the Placebo Nasal Gel group. A positive LSM difference value indicates that the change from baseline in the DPI-386 Nasal Gel group was smaller than the change from baseline in the Placebo Nasal Gel group, therefore more favorable to the DPI-386 Nasal Gel group.
Note:
PSAQ Scores were assigned as 1 = significantly worse, 2 = somewhat worse, 3 = no effect, 4 = somewhat better, and 5 = significantly better.
Analysis was based on MMRM including fixed effects of treatment, study, visit, baseline score and interaction terms of treatment by visit.

An analysis of the post-dose average change from baseline in PSAQ scores from all timepoints showed statistically significant differences between treatment groups in favor of DPI-386 Nasal Gel for each of the 8 domains in the questionnaire (from $p<0.0001$ to $p=0.0016$; ANCOVA). These findings suggest that treatment differences observed on the primary outcome measures were associated with self-reported benefits by subjects regarding performance on clinically relevant parameters. In addition, because the PSAQ was administered pre-dose as well as post-dose, it provides pre-to-post-dose change data to supplement other measures that were taken post-dosing. Correlations among PSAQ and other outcome measures (Section 7.2) support the clinical meaningfulness of treatment differences observed on the other outcome measures.

As noted, measurements of performance (PSAQ) favored the DPI-386 Nasal Gel group, and cognitive function (per the SAQ) was better preserved in subjects who received DPI-386 Nasal Gel compared to subjects who received Placebo Nasal Gel. DPI-386 Nasal Gel was well-tolerated and no new safety signals for DPI-386 Nasal Gel were observed.

Efficacy Results, Secondary Endpoints of Both/Pooled for MS-33 (Example 3) and MS-29 Studies (Example 4)

Proportion of Subjects without Nausea and without Use of Rescue Medication: a secondary efficacy endpoint in both the MS-29 and MS-33 studies was the proportion of subjects with no nausea and no use of rescue medication within 4 hours or by end of voyage (if later) after receiving study drug.

In the pooled analysis, 67 subjects (20.9%) in the DPI-386 Nasal Gel group and 42 subjects (13.0%) in the Placebo Nasal Gel group met this endpoint, for a statistically significant treatment difference (95% CI) of 7.8% (2.1, 13.6) in favor of the DPI-386 Nasal Gel group (p=0.0083; CMH test; Table 4y).

A Forest plot of the between-group treatment differences in the proportions of subjects without nausea and without the use of rescue medication for the pooled analysis and for each study alone is presented in FIG. 4O.

TABLE 4y

Analysis of Proportion of Subjects without Nausea and without Use of Rescue Medication, Pooled Analysis, ITT Population

| Parameter | DPI-386 Nasal Gel | Placebo Nasal Gel |
|---|---|---|
| Subjects with no nausea and no rescue medication, n/N (%) | 67/321 (20.9) | 42/322 (13.0) |
| 95% CI | (16.6, 25.7) | (9.6, 17.2) |
| Treatment difference, % (95% CI) | 7.8 (2.1, 13.6) | |
| p-value [1] | 0.0083 | |

CI = confidence interval;
ITT = Intent-to-Treat;
NAS = Nausea Assessment Scale
Note:
Response is defined as NAS score of No symptoms and did not use rescue treatment within 4 hours after receiving study drug.
The within 4 hours after receiving study drug window is from the time of dose to the time of the end of voyage.
[1] Analyzed using a Cochran-Mantel-Haenszel (CMH) test statistic for stratified proportions.

Proportion of Subjects without Moderate or Severe Nausea and without Use of Rescue Medication A secondary efficacy endpoint in both the MS-29 and MS-33 studies was the proportion of subjects without moderate or severe nausea and without use of rescue medication within 4 hours or by end of voyage (if later) after receiving study drug.

In the pooled analysis, 215 subjects (67.0%) in the DPI-386 Nasal Gel group and 148 subjects (46.0%) in the Placebo Nasal Gel group met this endpoint, for a statistically significant treatment difference (95% CI) of 21.0% (13.5, 28.5) in favor of the DPI-386 Nasal Gel group (p<0.0001; CMH; Table 4z).

A Forest plot of the between-group treatment differences in the proportions of subjects without moderate or severe nausea and without the use of rescue medication for the pooled analysis and for each study alone is presented in FIG. 4O.

TABLE 4z

Analysis of Proportion of Subjects without Moderate or Severe Nausea and without Use of Rescue Medication, ITT Population

| Parameter | DPI-386 Nasal Gel | Placebo Nasal Gel |
|---|---|---|
| Subjects with no moderate or severe nausea and no rescue medication, n/N (%) | 215/321 (67.0) | 148/322 (46.0) |
| 95% CI | (61.5, 72.1) | (40.4, 51.6) |
| Treatment difference, % (95% CI) | 21.0 (13.5, 28.5) | |
| p-value [1] | <0.0001 | |

CI = confidence interval;
ITT = Intent-to-Treat;
NAS = Nausea Assessment Scale
Note:
Response is no NAS score of Moderate or Severe and did not use rescue treatment within 4 hours after receiving study drug.
The within 4 hours after receiving study drug window is from the time of dose to the time of the end of voyage.
[1] Analyzed using a Cochran-Mantel-Haenszel (CMH) test statistic for stratified proportions.

Time to Vomiting or Use of Rescue Medication

A secondary efficacy endpoint in both the MS-29 and MS-33 studies was time to vomiting or use of rescue medication within 4 hours or by end of voyage (if later) after receiving study drug.

In the pooled analysis, time to vomiting or use of rescue medication was statistically significantly different between the 2 treatment groups in favor of DPI-386 Nasal Gel (p<0.0001, stratified log rank test; FIG. 4Q).

In the pooled analysis, 41 subjects (12.8%) in the DPI-386 Nasal Gel group and 96 subjects (29.8%) in the Placebo Nasal Gel treatment group had an event of vomiting or rescue medication use (Table 4aa). The difference between treatment groups in median time to vomiting or use of rescue medication was statistically significant in favor of the DPI-386 Nasal Gel group (p<0.0001; log rank test).

In the pooled analysis, the hazard ratio (95% CI) of having vomiting or using rescue medication within 4 hours of receiving study medication for subjects in the DPI-386 Nasal Gel group was 0.384 (0.266, 0.553) (the Placebo Nasal Gel group was the reference group). The probability of having vomiting or using rescue medication in Hour 1, Hour 2, Hour 3, and Hour 4 for subjects in the DPI-386 Nasal Gel group ranged from 33% to 42% of the probability for subjects in the Placebo Nasal Gel group (Table 4aa). The median time to vomiting or use of rescue medication in the 4-hour period after receiving study drug was not estimable (NE) for subjects in the DPI-386 Nasal Gel group or the Placebo Nasal Gel group, as <50% of subjects in either group had the event of vomiting or rescue medication use.

A Forest plot of the hazard ratios for time to vomiting or use of rescue medication in the pooled analysis one is presented in FIG. 4R.

TABLE 4aa

Analysis of Time to Vomiting or Use of Rescue Medication, Pooled Analysis, ITT Population

| Parameter | DPI-386 Nasal Gel (N = 321) | Placebo Nasal Gel (N = 322) |
|---|---|---|
| Number (%) subjects with event | 41 (12.8) | 96 (29.8) |
| Number (%) subjects censored | 280 (87.2) | 226 (70.2) |
| Log rank p-value | <0.0001 | |
| Hazard ratio (95% CI) | 0.384 (0.266, 0.553) | |
| Probability of event (95% CI) | | |
| Hour 1 | 0.003 (0.001, 0.006) | 0.009 (0.003, 0.015) |
| Hour 2 | 0.081 (0.063, 0.100) | 0.198 (0.169, 0.227) |
| Hour 3 | 0.109 (0.086, 0.132) | 0.261 (0.227, 0.293) |
| Hour 4 | 0.125 (0.100, 0.150) | 0.295 (0.259, 0.329) |

CI = confidence interval;
ITT = Intent-to-Treat;
NE = not estimable
Note:
Subjects who reported vomiting or have taken rescue treatment within 4 hours after receiving study drug are considered having the event and time to event is derived as number of hours from the dosing to the earliest time of vomiting or rescue medication use. The within 4 hours after receiving study drug window is from the time of the dose to the time of the end of voyage.
Subjects without an event were censored at the time of the end of voyage (approximately 4 hours post dose).

Example 5: Clinical Study MS-24: Safety and Efficacy in Senior Subjects

This Phase 3 clinical trial was a randomized, double-blind, placebo-controlled study with open-label follow-up to identify the safety and efficacy of a repeated-dose regimen of DPI-386 Nasal Gel (intranasal scopolamine gel) for the prevention and treatment of nausea associated with motion sickness and requested further treatment (i.e., subjects who received rescue medication).

Study Sites:

This study was a combination field and clinical site trial that was carried out on both an ocean-going vessel (Treatment Day 1) and at two clinical sites (Treatment Days 2-4). Collaborative Neuroscience Network enrolled subjects to the double-blind period (ocean-going vessel; Day 1) and those subjects continued into the open-label period (Days 2 to 4). M3 Wake Research enrolled subjects ≥70 years of age only into the open-label period.

Objectives:

Primary Objectives

1. Determine the efficacy of DPI-386 Nasal Gel (0.2 mg scopolamine hydrobromide (HBr) per dose twice a day for one day) compared to Placebo Nasal Gel in the prevention and treatment of nausea associated with motion sickness.

2. Determine the safety of DPI-386 Nasal Gel compared to Placebo Nasal Gel with an emphasis on cognitive adverse events (AEs).

Secondary Objectives

1. Determine the efficacy of DPI-386 Nasal Gel compared to Placebo Nasal Gel in severity of nausea.

2. Determine the safety of DPI-386 Nasal Gel compared to Placebo Nasal Gel in terms of cognition.

3. Describe the pharmacokinetics (PK) of a multi-dose schedule of DPI-386 Nasal Gel.

Pharmacokinetic Objectives

1. Describe the PK profile of scopolamine following administration of DPI-386 Nasal Gel 0.2 mg twice a day for 3 consecutive days.

2. Compare scopolamine PK between male and female subjects receiving DPI-386 Nasal Gel.

Pharmacokinetic/Pharmacodynamic Objective

1. Explore the relationships between scopolamine PK and pharmacodynamics (PD) (safety) endpoints collected on PK days for DPI-386 Nasal Gel.

Methodology:

This Phase 3 clinical trial was a randomized, double-blind, placebo-controlled study to evaluate the safety and efficacy of DPI-386 nasal gel for the prevention and treatment of nausea associated with motion sickness (double-blind period [Session 1], Treatment Day 1), followed by an open-label period to evaluate safety and PK and explore relationships between PK exposure and pharmacodynamics (PD; safety) response (Session 2, Treatment Days 2 to 4) in senior subjects (≥55 years of age; N=83). In addition, a separate group of subjects ≥70 years of age (N=18) was enrolled into the open-label period (Session 2); these 18 subjects did not participate in the double-blind period of the study and did not contribute to the efficacy analysis. Eighty-three subjects were randomized 1:1 to one of two treatment arms (DPI-386 Nasal Gel or Placebo Nasal Gel), and was stratified by age group (55-59 years, 60-64 years, 65-69 years, 70-74 years, and ≥75 years). Each enrolled subject was assigned a subject number per one of the 5 age groups (starting with 101, 201, 301, 401, and 501), in consecutive order. The subject number was linked to a multi-digit random number (study drug kit number) which randomized the subject to one of the two arms for the double-blind period (Session 1, Treatment Day 1), which was conducted aboard an ocean-going vessel to obtain data in an operationally relevant real-world environment.

Ninety-eight subjects participated in the open-label period (Session 2; Treatment Days 2 to 4), including 83 subjects who participated in the double-blind period (Session 1) and the 18 subjects enrolled only to the open-label period (Session 2). All subjects received open-label DPI-386 Nasal Gel in Session 2, which was conducted at a clinical site on land within 30 days following Treatment Day 1.

A third group of subjects was defined as all subjects who received at least one dose of DPI-386 Nasal Gel at any time during the study. There were 99 subjects in this group-83 subjects from the double-blind period who were also in the open-label period, 18 subjects enrolled only into the open-label period, and 1 subject in the DPI-386 Nasal Gel arm of the double-blind period who was discontinued from the study and did not enter the open-label period.

There were 6 study phases: Recruitment and Screening; Treatment; Post-Voyage treatment Assessment; 2 Short-term Follow-up phases; and 1 Long-term Follow-up phase.

The Recruitment and Screening Phase consisted of 1 visit prior to ship departure to determine eligibility.

The Treatment Phase (Session 1, Treatment Day 1 and Session 2, consecutive Treatment Days 2 to 4) consisted of 4 Treatment Days: Treatment Day 1, approximately 12 hours in duration, followed by consecutive Treatment Days 2 to 4, each approximately 10-12 hours in duration with overnight stays, conducted within 30 days of Treatment Day 1. Treatment Day 1 was carried out on an ocean-going vessel. Treatment Days 2 to 4 were carried out in a clinical study site.

The Post-Treatment Phase consisted of 2 visits, at the end of Treatment Day 1 and at the end of Treatment Day 4 (clinic visit).

The first Short-term Follow-up Phase (following Treatment Day 1) consisted of 1 telephone or email contact on Day 6+3 days after Treatment Day 1.

The second Short-term Follow-up Phase (following Treatment Days 2 to 4) consisted of 1 telephone or email contact 5 days following Treatment Day 4.

The Long-Term Follow-up Phase (following Treatment Days 2 to 4) consisted of telephone or email contacts over 2 to 6 weeks following Treatment Day 4.

Number of Subjects (Planned and Analyzed)

Double-blind period (Session 1): 83 subjects were planned, randomized, enrolled, and analyzed.

Open-label period (Session 2): 100 subjects were planned; 98 subjects (80 subjects from the double-blind period and 18 subjects enrolled only into the open-label period) were admitted/enrolled into this period and analyzed.

Diagnosis and Main Criteria for Inclusion

To be eligible to participate in this study, subjects met all the following criteria:

1. Provision of a signed and dated informed consent form (ICF).

2. Stated willingness to comply with all study procedures and availability for the duration of the study.

3. Male or female aged 55 and over.

4. In good general health as evidenced by medical history with no recent history or current diagnosis of uncontrolled clinical problems as assessed by the Principal Investigator (PI) or qualified designee.

5. Ability to take intranasal medication and willingness to adhere to the study schedule and time constraints.

6. Agreement to adhere to the following lifestyle compliance considerations:

a. Refrain from consumption of grapefruit and any substance containing grapefruit for 7 days prior to, during, and for 7 days after the 4 treatment days.

b. Abstain from alcohol for 24 hours prior to first dose of study medication and during the 4 treatment days.

Note: there was no restriction on caffeine or nicotine use during the study; however, the actual use of these substances was recorded as part of the CEBQ.

Investigational Medicinal Product

DPI-386 Nasal Gel

- Active content: Scopolamine HBr
- Strength: Each 0.12 gram of the gel contains 0.2 mg of scopolamine HBr
- Dosage Regimen: 0.2 mg scopolamine HBr administered twice daily. The 2 daily doses were separated by a minimum of 6 hours with no more than 2 doses administered within 24 hours.
- Route of administration: Intranasal
- Storage: Store at 20° C. to 25° C., inclusive (68° F. to 77° F., inclusive), with brief temperature excursions permitted between 15° C. and 30° C., inclusive (59° F. and 86° F., inclusive).

Placebo Nasal Gel

Placebo Nasal Gel administered twice daily. The 2 daily doses were separated by a minimum of 6 hours with no more than 2 doses administered within 24 hours.

- Route of administration: Intranasal
- Storage: Store at 20° C. to 25° C., inclusive (68° F. to 77° F., inclusive), with brief temperature excursions permitted between 15° C. and 30° C., inclusive (59° F. and 86° F., inclusive).

All DPI-386 Nasal Gel and Placebo Nasal Gel vials were opaque and indistinguishable. DPI-386 Nasal Gel and Placebo Nasal Gel were identical in color and viscosity, and without identifiable smell.

Duration of Treatment

The duration of treatment was 1 day in the double-blind period (Session 1) and 3 days in the open-label period (Session 2). Subjects who completed both the double-blind period and the open-label period had a total duration of treatment of 4 days.

Criteria for Evaluation

Safety and Tolerability Evaluations

Safety and tolerability assessments included assessment of cognitive performances, assessment of alertness, assessment of anticholinergic toxicity symptoms, vital signs and electrocardiogram (ECG) recording, and recording of AEs and concomitant medications.

Study Endpoints

Primary Efficacy Endpoint:

The primary efficacy endpoint was the incidence of subjects who developed motion sickness and requested further treatment (i.e., subjects who received rescue medication). This efficacy endpoint was assessed only in the double-blind period (Session 1), as it was only in this period that subjects were travelling on an ocean-going vessel.

Secondary Efficacy Endpoint:

The secondary efficacy endpoint was the severity of nausea over the treatment period as measured by a Visual Analogue Scale (VAS). This efficacy endpoint was assessed only in the double-blind period (Session 1), as it was only in this period that subjects were travelling on an ocean-going vessel.

Other Efficacy Endpoint:

Another efficacy endpoint was time to use of rescue medication. This efficacy endpoint was assessed only in the double-blind period (Session 1), as it was only in this period that subjects were travelling on an ocean-going vessel.

Post-Hoc Efficacy Endpoint:

A post-hoc efficacy endpoint was the Complete Response rate at Day 1 Hour 4 (Intent-to-Treat [ITT] population). A Complete Responder was a subject who did not experience vomiting or require rescue medication within the first 4 hours of the first dose of study treatment on Treatment Day 1.

Primary Safety Endpoint:

The primary safety endpoint was the incidence of AEs.

Secondary Safety Endpoints:

Secondary safety endpoints were cognition as assessed by the Psychomotor Vigilance Task (PVT) and as assessed by the Automated Neuropsychological Assessment Metrics (ANAM).

Other Safety Endpoints:

- Change from −60 minutes on Treatment Day 2 in vital sign and ECG measurements.
- Assessment of sleepiness using the Karolinska Sleepiness Scale (KSS).
- Symptoms of anticholinergic toxicity as recorded using the Anticholinergic Toxicity Screen (ACTS).
- Assessment of performance of activities using the Performance Self-Assessment Questionnaire (PSAQ).

Pharmacokinetic Endpoints (Secondary Endpoints):

PK endpoints were maximum plasma concentration ($C_{max}$), lag time ($t_{lag}$), time of maximum concentration ($t_{max}$), terminal half-life ($t_{1/2}$), and area under the curve (AUC) from time 0 to the last time point ($_{0\text{-}t}$) and from time 0 to 6 hours ($_{0\text{-}6}$). PK endpoints were assessed at the following timepoints in the open-label period (Session 2):

- $C_{max}$, $AUC_{(0\text{-}t)}$, $AUC_{(0\text{-}6)}$, $t_{lag}$, $t_{max}$, and $t_{1/2}$ for morning doses
- $C_{max}$, $AUC_{(0\text{-}t)}$, $t_{lag}$, and $t_{max}$ for afternoon doses
- $C_{max}$, $AUC_{(0\text{-}t)}$, and $AUC_{(0\text{-}6)}$ for comparisons between gender (for Dose 1 on the last treatment day of the open-label period [Session 2; Day 4]).

For exploration of relationships between the following PK exposure endpoints and the following PD (safety) endpoints:

PK exposure metrics $C_{max}$, $AUC_{(0-4)}$, and $AUC_{(0-6)}$ (for Dose 1 on the first day of the open-label period [Session 2])

Cognition (ANAM) maximum change from baseline

ACTS symptoms of maximum severity post-baseline

Statistical Analysis

Primary Efficacy Endpoint

Incidence of Subjects Who Developed Motion Sickness and Requested Further Treatment To assess prevention and treatment of nausea associated with motion sickness, the primary efficacy endpoint was the incidence of subjects receiving rescue medication by treatment arm.

Secondary Efficacy Endpoint

Nausea Assessment (Visual Analogue Scale)

The severity of nausea was assessed on a VAS. Subjects specified their degree of nausea by indicating a point along a continuous 100-mm line. The scale ranged from 0 (no nausea) to 100 (very severe nausea). Scoring was based on the length from the left edge of the scale to the point reported, and a higher score indicated a more severe degree of nausea.

Other Efficacy Endpoint

Time to First Use of Rescue Medication

Time to first use of rescue medication during Treatment Day 1 was calculated in hours as the start time of administration of the first rescue medication dose minus the start time of the first dose of study drug. Subjects who did not receive any rescue medication were censored at the time of their last assessment on Treatment Day 1.

Post-Hoc Efficacy Endpoint

Complete Response Rate at Day 1 Hour 4

The difference in proportions between the DPI-386 Nasal Gel arm and the Placebo Nasal Gel arm was determined along with the associated two-sided 95% confidence interval (CI) for the difference in treatment group proportions (DPI-386 Nasal Gel—Placebo Nasal Gel).

A p-value was obtained from a logistic regression model based on the binomial distribution with a logit link function comparing DPI-386 Nasal Gel to Placebo Nasal Gel and it included subject Complete Responder status as the response variable, a main effect for the treatment group, age category at randomization, and the raw Motion Sickness Susceptibility Questionnaire (MSSQ) total score at Screening as a covariate.

Safety Endpoints

Throughout the course of the study all AEs were monitored and recorded on the source document and the appropriate case report form (CRF). The following information was reported: AE description, onset date and time, stop date and time, outcome, frequency, severity, relationship to study drug, action taken regarding study drug, associated concomitant medications or treatments, and seriousness.

Primary Safety Endpoint

The primary safety endpoint was the subject incidence of treatment-emergent adverse events (TEAEs) while on study treatment. TEAEs are those with onset after the first dose of study treatment or existing events that worsened after the first dose of study treatment.

Other Safety Endpoints

Other safety endpoints included:

Mean change from baseline to all post-baseline measurements in cognition as measured by PVT median response time and number of performance lapses.

Mean change from baseline to all post-baseline measurements in cognition as measured by throughput scores for each ANAM subtest.

Mean observed values and change from pre-dose on Treatment Day 2 in vital sign and ECG measurements for each parameter, as collected by time point at the in-clinic visits on Treatment Days 2 to 4.

Mean change from baseline to Hour 4 and Hour 8 on Treatment Day 1 in the assessments of sleepiness using the KSS.

Subject incidence in reporting symptoms of anticholinergic toxicity using the ACTS, at each visit and time point when collected.

Frequency of subject responses to the individual items of the PSAQ administered at the Post-Treatment visit, as an assessment of whether the subject perceived nasal gel application to be detrimental to the performance of activities at any time during the study period:

Frequency of subject responses to the individual items of the Nasal Gel Device Ease-of-Use Questionnaire (EOUQ) at the Post-Treatment visit.

Statistical Analysis:

As the subjects in the ITT and modified ITT (mITT) populations were the same, separate tables for the mITT population were not generated.

Disposition of Subjects

Subject disposition was summarized for the study population by treatment group and overall subjects combined. Summaries included the number (%) of subjects completing the study and discontinuing the study early by the primary reason for discontinuation.

Protocol Deviations

There were no major protocol violations during the double-blind period of the study, therefore the mITT, ITT, and Per Protocol (PP) populations consisted of the same subjects.

Demographic and Other Baseline Characteristics

Demographic variables including age, sex, ethnicity, and race were summarized for the Safety population by treatment group in the double-blind period, for all subjects in the open-label period (Session 2), and for all subjects who received at least one dose of DPI-386 Nasal Gel at any time during the study.

Age was summarized using descriptive statistics. Sex, ethnicity, and race were summarized with the number (%) of subjects.

Primary Efficacy Endpoint Analysis Methods

The primary efficacy endpoint was the incidence of subjects who developed motion sickness and requested further treatment in the double-blind period of the study (i.e., subjects who received rescue medication).

The difference between treatment groups in proportions and the p-value were obtained using a Fishers Exact test.

The analysis was performed on the ITT population.

Secondary Endpoint Analysis Methods

The secondary efficacy endpoint was the severity of nausea in the double-blind period of the study as recorded by subjects on a VAS.

The mean VAS score was analyzed at Treatment Day 1 Hour 4 and Hour 8. Analysis was based on mixed model of repeated measure (MMRM) including fixed effects of treatment, visit, and interaction term of treatment by visit. Baseline value was included as a covariate in the model.

Summaries were based on observed data in the ITT population.

Other Efficacy Endpoint Analysis Methods

Time to first use of rescue medication in the double-blind period of the study was another efficacy endpoint.

Time to first use of rescue medication during Treatment Day 1 was calculated in hours as the start time of administration of the first rescue medication dose minus the start time of the first dose of study drug. Subjects who took no rescue medication during the study were censored at the time of the last VAS MSAQ assessment. The comparison of the DPI-386 Nasal Gel group versus the Placebo Nasal Gel group was performed using a log-rank test.

Post-Hoc Efficacy Endpoint Analysis Methods

A post-hoc efficacy endpoint was the Complete Response rate in the double-blind period of the study at Day 1 Hour 4 (ITT population).

A Complete Responder was a subject who did not experience vomiting or require rescue medication within the first 4 hours of the first dose of study treatment on Treatment Day 1. Vomiting was derived from the AE data collection where the verbatim event term began with the text string "Vomit."

The difference in proportions between the DPI-386 Nasal Gel arm and Placebo Nasal Gel arm along with the associated two-sided 95% CI for the difference in treatment group proportions (DPI-386 Nasal Gel—Placebo Nasal Gel), along with a p-value, was determined using a Fishers Exact test.

Safety Analysis

Safety analyses were performed on the Safety population, which included all subjects who received at least one dose of study drug. Subjects who did not complete the study, for whatever reason, had all available data up until the time of termination included in the analysis.

Extent of Exposure

Extent of exposure to study treatment was summarized for the Safety population by treatment group. The total number of doses received was summarized by counts and percentages of subjects and total nasal gel dose administered in grams was summarized with descriptive statistics. The total dose administered for each subject was derived as the number of full nasal gel doses given as reported on the Study Drug Dosing Log form×1.2 grams.

Primary Safety Endpoint Analysis Methods

The primary safety endpoint was the subject incidence of TEAEs while on study treatment. TEAEs were those with onset after the first dose of study treatment or existing events that worsened after the first dose of study treatment.

TEAEs were summarized for the following groups of subjects:

- Subjects randomized to DPI-386 Nasal Gel, double-blind period (Day 1 only) (N=42)
- Subjects randomized to Placebo Nasal Gel, double-blind period (Day 1 only) (N=41)
- Subjects in the DPI-386 Nasal Gel open-label period (Day 2 to 4) (N=98)
- Subjects who received at least one dose of DPI-386 Nasal Gel at any time during the study (Day 1 to 4) (N=99)

Secondary Safety Endpoint Analysis Methods

Secondary safety endpoints were cognition as assessed by the PVT and as assessed by the ANAM.

The PVT is a neurocognitive assessment that measures alertness and tests sustained attention and reaction time. The mean change from baseline to all post-baseline measurements in cognition as measured by median response time and number of performance lapses was to be evaluated.

Two ANAM batteries were customized for this study: ANAM CORE battery plus the Running Memory Continuous Performance Test (CPT) and ANAM CORE Battery with CPT added but Code Substitution—Delayed (CDD) removed.

The ANAM subtest responses were to be summarized by treatment group. Descriptive statistics were to be presented for the observed values and changes from baseline to all post-baseline evaluations of cognition as measured by the throughput scores for each subtest.

ANAM data were to be analyzed and results reported by Vista LifeSciences.

Other Safety Endpoint Analysis Methods

Vital Sign and ECG Measurements

Mean observed values and change from pre-dose on Treatment Day 2 were calculated in vital sign and ECG measurements for each parameter, as collected by timepoint at the in-clinic visits on Treatment Days 2 to 4.

The number (%) of subjects having corrected (Fridericia) QT values (QTcF) >450 msec and QTcF change from baseline values >30 msec and >60 msec were tabulated.

Sleepiness

The KSS scores were summarized by treatment group. Descriptive statistics were presented for the observed values and changes from baseline to Treatment Day 1 Hour 4 and Hour 8.

Anticholinergic Toxicity Screen

Subject incidence in reporting symptoms of anticholinergic toxicity using ACTS was presented by treatment group. The number (%) of subjects who report symptoms were summarized at each visit and time point were collected by symptom.

Performance of Activities

The frequency of subject responses to the individual items of the PSAQ administered at Post-Treatment Day 4 were summarized by Treatment Group. The number (%) of subjects who report each of the possible responses for each item were summarized.

Other Evaluations

Nasal Gel Device Ease-of-Use Questionnaire

The frequency of subject responses to the individual items of the EOUQ administered at the Post-Treatment Day visit was summarized by Treatment Group. The number (%) of subjects who reported each of the possible responses for each item were summarized.

Prior and Concomitant Medications

Prior and concomitant medications were summarized for each treatment arm.

Efficacy Results

Primary Efficacy Endpoint

The primary efficacy endpoint was the proportion of subjects in the ITT population who developed motion sickness and requested further treatment (rescue medication) on Treatment Day 1 (i.e., subjects who received rescue medication). The difference between the DPI-386 Nasal Gel arm and the Placebo Nasal Gel arm (9.5% vs. 36.6%) was statistically significant in favor of the DPI-386 Nasal Gel arm (p=0.0041, Fishers Exact test; Table 5a).

The results for subjects who used rescue medication within 4 hours after receiving the first dose of study drug are presented in Table 5b. The difference between the DPI-386 Nasal Gel arm and the Placebo Nasal Gel arm (7.1% vs. 26.8%) was statistically significant in favor of the DPI-386 Nasal Gel arm (p=0.0204, Fishers Exact test).

TABLE 5a

| Proportion of Subjects Using Rescue Medication (ITT Population) | | |
|---|---|---|
| Parameter Treatment Day 1 | DPI-386 Nasal Gel (N = 42) | Placebo Nasal Gel (N = 41) |
| Subjects who took rescue medication, n (%) | 4 (9.5) | 15 (36.6) |
| 95% CI | (2.7, 22.6) | (22.1, 53.1) |
| Treatment difference (%) (95% CI) | −27.1 (−44.3, −9.9) | |
| P-value[1] | 0.0041 | |

CI = confidence interval; ITT = Intent-to-Treat.
[1]Fishers Exact test.
Source: Table 14.2.1.1

TABLE 5b

| Proportion of Subjects Using Rescue Medication within 4 Hours After the First Dose of Study Medication (ITT Population) | | |
|---|---|---|
| Parameter Treatment Day 1 | DPI-386 Nasal Gel (N = 42) | Placebo Nasal Gel (N = 41) |
| Subjects who took rescue medication, n (%) | 3 (7.1) | 11 (26.8) |
| 95% CI | (1.5, 19.5) | (14.2, 42.9) |
| Treatment difference (%) (95% CI) | −19.7 (−35.3, −4.0) | |
| P-value[1] | 0.0204 | |

CI = confidence interval; ITT = Intent-to-Treat.
[1]Fishers Exact test.
Source: Table 14.2.1.2

Secondary Efficacy Endpoint

The secondary efficacy endpoint was the severity of nausea over the treatment period as measured by the subject on a VAS that measured 0 to 100 mm.

In the ITT population, the median measurement for nausea severity at baseline was 0.0 in both treatment groups (Table 5c). VAS score change from baseline at Treatment Day 1 Hour 4 was statistically significantly different in favor of the DPI-386 Nasal Gel arm (p=0.0221, MMRM). At Treatment Day 1 Hour 8, VAS score change from baseline was not statistically significantly different between treatment groups (p=0.0850, MMRM).

TABLE 5c

| Summary of Nausea Assessment (Visual Analogue Scale, mm) (ITT Population) | | |
|---|---|---|
| Time Point Statistic | DPI-386 Nasal Gel (N = 42) | Placebo Nasal Gel (N = 41) |
| Baseline | | |
| N | 41 | 41 |
| Mean (SD) | 1.0 (3.31) | 0.9 (1.79) |
| Median | 0.0 | 0.0 |
| Min, Max | 0, 15 | 0, 8 |
| Day 1 4-hour Post dose | | |
| N | 42 | 41 |
| Mean (SD) | 9.0 (18.60) | 22.1 (30.26) |
| Median | 1.0 | 4.0 |
| Min, Max | 0, 94 | 0, 100 |
| Day 1 4-hour Post dose change from baseline | | |
| N | 41 | 41 |
| Mean (SD) | 8.0 (19.10) | 21.2 (29.87) |
| Median | 1.0 | 2.0 |
| Min, Max | −15, 94 | −2, 100 |
| LSM (SE) | 8.081 (2.943) | 21.138 (4.733) |
| Treatment difference (95% CI) | −13.06 (−24.18, −1.93) | |
| P-value[1] | 0.0221 | |
| Day 1 8-hour Post dose | | |
| N | 42 | 41 |
| Mean (SD) | 2.5 (5.02) | 8.5 (20.89) |
| Median | 1.0 | 1.0 |
| Min, Max | 0, 22 | 0, 100 |
| Day 1 8-hour Post dose change from baseline | | |
| N | 41 | 41 |
| Mean (SD) | 1.5 (6.33) | 7.6 (20.37) |
| Median | 0.0 | 0.0 |
| Min, Max | −15, 22 | −4, 100 |
| LSM (SE) | 1.593 (0.799) | 7.529 (3.274) |
| Treatment difference (95% CI) | −5.935 (−12.72, 0.854) | |
| P-value[1] | 0.0850 | |

ITT = intent-to-treat; max = maximum; min = minimum; SD = standard deviation; VAS = visual analogue scale.
Note:
Analysis was based on Mixed Model of Repeated Measure (MMRM) including fixed effects of treatment, visit, and interaction term of treatment by visit. Baseline value was included as a covariate in the model.
[1]Between-group p-value.
Source: Table 14.2.4.1, Table 14.2.4.2, Table 14.2.4.3

Applicants note, however, that certain patients from the placebo group did receive rescue medication. As such, the calculation may be more properly made by excluding those patients who received rescue medication from the placebo group.

Other Efficacy Endpoint

Another efficacy endpoint was time to use of rescue medication.

In the ITT population, 4 subjects (9.5%) in the DPI-386 Nasal Gel arm and 15 subjects (36.6%) in the Placebo Nasal Gel arm received rescue medication.

The difference between DPI-386 Nasal Gel and Placebo Nasal Gel in time to use of rescue medication was statistically significant in favor of DPI-386 Nasal Gel ($p<0.0001$, log rank test; Table 5d).

TABLE 5d

| Summary of Time to Rescue Medication (Hours) (ITT Population) | | |
|---|---|---|
| Description | DPI-386 Nasal Gel (N = 42) | Placebo Nasal Gel (N = 41) |
| Number (%) of subjects who received rescue medication | 4 (9.5) | 15 (36.6) |
| Number (%) of subjects censored | 38 (90.5) | 26 (63.4) |
| Time to event (hours) | | |
| 25th percentile (95% CI) | NE | 4.0 (2.3, 4.8) |
| Median (95% CI) | NE | NE |

TABLE 5d-continued

Summary of Time to Rescue Medication (Hours) (ITT Population)

| Description | DPI-386 Nasal Gel (N = 42) | Placebo Nasal Gel (N = 41) |
|---|---|---|
| 75th percentile (95% CI) | NE | NE |
| Log-rank test p-value[1] | <0.0001 | |

CI = confidence interval; ITT = Intent-to-Treat; NE = not estimable; MSAQ = Motion Sickness Assessment Questionnaire; VAS = visual analogue scale.

Note:

Subjects without taking rescue medication during the study were censored at the time of the last VAS MSAQ assessment.

[1]Comparison vs Placebo group was performed using Log-rank test.

Source: Table 14.2.1.3

Post-Hoc Efficacy Endpoint

In the post-hoc analysis of Complete Response rate at Treatment Day 1 Hour 4 in the ITT population, 38 subjects (90.5%) in the DPI-386 Nasal Gel arm and 26 subjects (63.4%) in the Placebo Nasal Gel arm had a Complete Response. The difference was statistically significant in favor of the DPI-386 Nasal Gel arm (nominal p=0.0041, Fishers Exact test; Table 5e).

TABLE 5e

Complete Response Rate within Four Hours of First Study Drug Dose (ITT Population)

| Parameter | DPI-386 Nasal Gel (N = 42) | Placebo Nasal Gel (N = 41) |
|---|---|---|
| Complete response (subjects with no vomiting and no rescue medication), n (%) | 38 (90.5) | 26 (63.4) |
| 95% CI | (77.4, 97.3) | (46.9, 77.9) |
| Difference in proportions, (%) (95% CI) | 27.1 (9.9, 44.3) | |
| P-value[1] | 0.0041 | |

TABLE 5e-continued

CI = confidence interval; ITT = Intent-to-Treat.

Note:

A Complete Responder is a subject who does not experience vomiting or require rescue medication within the first four hours of the first dose of study treatment on Treatment Day 1. The within 4 hours after receiving study drug window is from the time of the first dose to the time of the end of voyage.

[1]Fishers Exact test.

Source: Table 14.2.2.1

Safety Results

Primary Safety Endpoint: Incidence of Adverse Events

TEAEs are summarized by system organ class (SOC) and preferred term in Table 5f.

In the double-blind period the most common TEAE in both treatment groups was motion sickness, which was reported by 13 subjects (31.0%) in the DPI-386 Nasal Gel arm and by 25 subjects (61.0%) in the Placebo Nasal Gel arm. The second most common TEAE in the DPI-386 Nasal Gel arm was dry mouth (6 subjects, 14.3%) and the second most common TEAEs in the Placebo Nasal Gel arm were dry mouth and vomiting (3 subjects each, 7.3%). No subject in the DPI-386 Nasal Gel arm reported nausea or vomiting. Two subjects (4.9%) in the Placebo Nasal Gel arm reported nausea.

In the open-label period the most common TEAE was dry mouth (9 subjects, 9.2%). Three subjects (3.1%) reported headache and 3 subjects (3.1%) reported dizziness. Two subjects (2.0%) reported TEAEs of blurred vision. One subject (1.0%) reported one episode of nausea and 1 subject (1.0%) reported 2 episodes of vomiting. All other TEAEs in the open-label period were reported by only 1 subject (1.0%).

Of the subjects who received at least one dose of DPI-386 Nasal Gel at any time during the study (N=99), the most common TEAE reported while receiving DPI-386 Nasal Gel was dry mouth (14 subjects, 14.1%), followed by motion sickness (13 subjects, 13.1%), headache (4 subjects, 4.0%), dizziness (3 subjects, 3.0%), and blurred vision (2 subjects, 2.0%). All other TEAEs in subjects who received at least one dose of DPI-386 Nasal Gel were reported in only 1 subject (1.0%).

TABLE 5f

Summary of Adverse Events by System Organ Class and Preferred Term (Safety Population)

| System Organ Class Preferred Term | Statistic | DPI 386 Nasal Gel (N = 42) | Placebo Nasal Gel (N = 41) | Open-label DPI-386 Nasal Gel (N = 98) | At Least One DPI-386 Nasal Gel (N = 99) |
|---|---|---|---|---|---|
| Cardiac disorders | n (%) E | 0 (0.0) 0 | 1 (2.4) 1 | 0 (0.0) 0 | 0 (0.0) 0 |
| Atrial fibrillation | n (%) E | 0 (0.0) 0 | 1 (2.4) 1 | 0 (0.0) 0 | 0 (0.0) 0 |
| Ear and labyrinth disorders | n (%) E | 13 (31.0) 15 | 25 (61.0) 26 | 0 (0.0) 0 | 13 (13.1) 15 |
| Motion sickness | n (%) E | 13 (31.0) 15 | 25 (61.0) 26 | 0 (0.0) 0 | 13 (13.1) 15 |
| Eye disorders | n (%) E | 1 (2.4) 1 | 0 (0.0) 0 | 0 (0.0) 0 | 1 (1.0) 1 |
| Photophobia | n (%) E | 1 (2.4) 1 | 0 (0.0) 0 | 0 (0.0) 0 | 1 (1.0) 1 |
| Gastrointestinal disorders | n (%) E | 6 (14.3) 6 | 7 (17.1) 8 | 11 (11.2) 13 | 16 (16.2) 19 |
| Constipation | n (%) E | 0 (0.0) 0 | 0 (0.0) 0 | 1 (1.0) 1 | 1 (1.0) 1 |
| Dry mouth | n (%) E | 6 (14.3) 6 | 3 (7.3) 3 | 9 (9.2) 9 | 14 (14.1) 15 |
| Nausea | n (%) E | 0 (0.0) 0 | 2 (4.9) 2 | 1 (1.0) 1 | 1 (1.0) 1 |
| Vomiting | n (%) E | 0 (0.0) 0 | 3 (7.3) 3 | 1 (1.0) 2 | 1 (1.0) 2 |
| General disorders and administration site conditions | n (%) E | 1 (2.4) 1 | 0 (0.0) 0 | 0 (0.0) 0 | 1 (1.0) 1 |

TABLE 5f-continued

Summary of Adverse Events by System Organ Class and Preferred Term (Safety Population)

| System Organ Class Preferred Term | Statistic | DPI 386 Nasal Gel (N = 42) | Placebo Nasal Gel (N = 41) | Open-label DPI-386 Nasal Gel (N = 98) | At Least One DPI-386 Nasal Gel (N = 99) |
|---|---|---|---|---|---|
| Fatigue | n (%) E | 1 (2.4) 1 | 0 (0.0) 0 | 0 (0.0) 0 | 1 (1.0) 1 |
| Nervous system disorders | n (%) E | 2 (4.8) 2 | 1 (2.4) 1 | 5 (5.1) 5 | 6 (6.1) 7 |
| Headache | n (%) E | 1 (2.4) 1 | 1 (2.4) 1 | 3 (3.1) 3 | 4 (4.0) 4 |
| Somnolence | n (%) E | 1 (2.4) 1 | 0 (0.0) 0 | 0 (0.0) 0 | 1 (1.0) 1 |
| Vision blurred | n (%) E | 0 (0.0) 0 | 0 (0.0) 0 | 2 (2.0) 2 | 2 (2.0) 2 |
| Respiratory, thoracic and mediastinal disorders | n (%) E | 2 (4.8) 2 | 2 (4.9) 2 | 0 (0.0) 0 | 2 (2.0) 2 |
| Nasal discomfort | n (%) E | 1 (2.4) 1 | 2 (4.9) 2 | 0 (0.0) 0 | 1 (1.0) 1 |
| Rhinalgia | n (%) E | 1 (2.4) 1 | 0 (0.0) 0 | 0 (0.0) 0 | 1 (1.0) 1 |
| Skin and subcutaneous tissue disorders | n (%) E | 0 (0.0) 0 | 1 (2.4) 1 | 1 (1.0) 1 | 1 (1.0) 1 |
| Erythema | n (%) E | 0 (0.0) 0 | 1 (2.4) 1 | 0 (0.0) 0 | 0 (0.0) 0 |
| Pruritus | n (%) E | 0 (0.0) 0 | 0 (0.0) 0 | 1 (1.0) 1 | 1 (1.0) 1 |
| Vascular disorders | n (%) E | 0 (0.0) 0 | 1 (2.4) 2 | 3 (3.1) 3 | 3 (3.0) 3 |
| Dizziness | n (%) E | 0 (0.0) 0 | 1 (2.4) 2 | 3 (3.1) 3 | 3 (3.0) 3 |

Medical Dictionary for Regulatory Activities (MedDRA) version 23.1

E: Number of events; N: Number of subjects dosed with each treatment; n: Number of subjects with adverse event with particular category; %: Calculated using the number of subjects treated with each treatment as the denominator (n/N)*100.

Source: Table 14.3.1.2

Secondary Efficacy Endpoints

Psychomotor Vigilance Test

PVT data were collected but not analyzed.

Automated Neuropsychological Assessment Metrics

ANAM data were collected but not analyzed.

Other Safety Endpoints

Vital Signs and 12-Lead ECG

Per protocol, ECGs were not obtained on Day 1 so there was no comparison of ECG results between treatment groups. Mean changes from baseline at all timepoints in vital sign measurements were not clinically meaningful.

In the open-label period of the study, cardiac safety was assessed by the administration of a resting 12-lead ECG on 9 different occasions across Treatment Days 2 to 4. No clinically meaningful changes in mean values of ECG parameters were observed over the 3-day open-label period.

On Day 2, 3 subjects (3.1%) at 120 minutes post-dosing and 1 subject (1.0%) at 480 minutes post-dosing had an increase in QTcF value of >30 msec. On Day 3, 1 subject (1.0%) at the pre-dosing timepoint, 1 subject (1.0%) at 120 minutes post-dosing, and 1 subject (1.0%) at 480 minutes post-dosing had an increase in QTcF value of >30 msec. On Day 4, 1 subject (1.0%) at 120 minutes post-dosing and 1 subject (1.0%) at 480 minutes post-dosing had an increase in QTcF value of >30 msec. No subject had a QTcF value >500 msec at any timepoint, and no subject had an increase from the Day 2 baseline in QTcF >60 msec at any timepoint.

Karolinska Sleepiness Scale

Mean (standard deviation [SD]) KSS scores at baseline were 2.3 (1.56) and 2.0 (1.45) for subjects in the DPI-386 Nasal Gel and Placebo Nasal Gel treatment arms, respectively. Median (range) KSS scores at baseline were 1 (1 to 7) and 1 (1 to 7) for subjects in the DPI-386 Nasal Gel and Placebo Nasal Gel treatment arms, respectively. Descriptive statistics of the scores at all timepoints (n, mean, SD, median, minimum, maximum) are presented by treatment arm.

Mean (SD) changes from baseline in the KSS showed a slight increase in sleepiness in both treatment arms at the Hour 4 timepoint (+0.8 in the DPI-386 Nasal Gel arm and +0.9 in the Placebo Nasal Gel arm). At the Hour 8 timepoint the increase in sleepiness from baseline was slightly larger in the DPI-386 Nasal Gel arm compared to the Placebo Nasal Gel arm (+0.8 vs +0.2). Changes from baseline in the median scores were 0 at both timepoints in both treatment arms.

Anticholinergic Toxicity Screen

In the double-blind period of the study, the most common ACTS AE reported by subjects at Treatment Day 1 Hour 4 was dry mouth (5 subjects, 11.9%) in the DPI-386 Nasal Gel arm and dizziness (6 subjects, 14.6%) in the Placebo Nasal Gel arm. Four subjects (9.5%) in the DPI-386 Nasal Gel arm reported dizziness at Treatment Day 1 Hour 4. In both treatment groups, all other ACTS AEs reported at Treatment Day 1 Hour 4 occurred in only 1 subject each.

At Treatment Day 1 Hour 8, 3 subjects (7.1%) in the DPI-386 Nasal Gel arm reported dry mouth and 3 subjects (7.3%) in the Placebo Nasal Gel arm reported dizziness. One subject (2.4%) in the Placebo Nasal Gel arm reported increased skin redness/flushing.

Dry mouth was the most reported ACTS AE (in up to 6.1% of subjects) across the 3-day open-label period of the study. All other ACTS AEs at any timepoint in the open-label period were reported by ≤2 subjects (2.0%).

Performance Self-Assessment Questionnaire

The responses to the PSAQ, taken as a whole, were favorable in terms of the effect of study medication on work performance.

Other Endpoint

Nasal Gel Device Ease-of-Use Questionnaire

The responses reported on the Nasal Gel EOUQ indicated that the nasal gel preparation was easy to use and administer.

Efficacy Conclusions:

DPI-386 Nasal Gel was demonstrated to be superior to Placebo Nasal Gel in the prevention of nausea associated with motion sickness in older subjects when assessed using several efficacy endpoints, including the proportion of subjects who developed motion sickness and requested rescue medication (the primary endpoint), the severity of nausea at Treatment Day 1 Hour 4 as assessed using a VAS, the time to use of rescue medication, and in a post-hoc analysis of Complete Response rate.

Pharmacokinetic Conclusions:

Scopolamine was rapidly absorbed following intranasal administration. Scopolamine concentrations did not accumulate with twice daily dosing as demonstrated by the similar concentration time profiles and PK parameter values across the 8 doses for the 83 patients and 6 doses for the 18 additional patients.

Following administration of DPI-386 Nasal Gel, scopolamine PK exposure was similar in male and female subjects.

Following intranasal administration, scopolamine geometric mean $C_{max}$, $AUC_{0-t}$, and $AUC_{0-6}$ values, and median $t_{1/2}$ estimates were similar among the age groups of <65, 65 to 74, and ≥75 years.

Higher plasma levels of scopolamine were associated with the occurrence of dry mouth, one of the AEs listed on the ACTS and a known side effect of scopolamine.

Safety Conclusions:

Overall, the TEAEs that were reported in this study were consistent with the AE profile of scopolamine. DPI-386 Nasal Gel was well tolerated, and no new safety signals were observed.

In addition, based on the lower intranasal dosage to achieve bioequivalence, the present formulation offers an improved side effect profile as compared to the available transdermal product.

The nasal gel application device was easy to use and administer.

2. Introduction 2.1. Background

Motion sickness is a problem for the general population and the modern military across the Services, regardless of the mode of transportation. Unlike civilian populations, military personnel do not have the option of refusing transport aboard vehicles with known propensity to cause motion sickness (ships in rough seas, fighter jets, amphibious landing vehicles, etc.) Pharmacological studies have shown that the anticholinergic scopolamine is the most effective medication for the prevention of motion sickness (Wood and Graybiel, 1968); (Spinks and Wasiak, 2011); however, the 2 most common methods of administration, oral and transdermal, have drawbacks that often compromise its utility, whereas intravenous (IV), intramuscular (IM), and subcutaneous (SQ) administrative routes are impractical in most military and civilian operational settings. For oral administration, first-pass metabolism decreases bioavailability to between 11 and 48%, and the reduced gastric motility seen in motion sickness can prevent timely absorption (Putcha et al, 1989); (Renner et al, 2005). The oral dosage's shortcomings are significant enough that it is no longer commercially available in the U.S. The transdermal scopolamine (TDS) patch bypasses first-pass metabolism and is designed to provide prophylaxis for 72 hours, yet can require up to 12 hours after placement to reach therapeutic plasma levels (Nachum et al, 2001); (Parrott, 1989); (Repurposed Therapeutics, Inc., 2016). About 10% of individuals using TDS on a long-term basis will experience allergic contact dermatitis which precludes further use of the drug. Both methods can produce significant side effects, primarily sedation. Also, TDS's extended duration (up to 96 hours) and application-site deposition produces an increase in the half-life of elimination. This in turn can result in additional detrimental physiological and cognitive side effects (Parrott, 1989); (Renner et al, 2005); (Repurposed Therapeutics, Inc., 2016).

Scopolamine is absorbed from all mucous membranes as well as from subcutaneous and muscle tissue. At therapeutic doses, scopolamine can inhibit the secretion of saliva and sweat, decrease gastrointestinal secretions and motility, cause drowsiness, dilate the pupils, increase heart rate, and depress motor function. An overdose of scopolamine can cause disorientation, memory disturbances, dizziness, restlessness, hallucinations, confusion, or in cases of severe overdose, coma.

Scopolamine hydrobromide (HBr) was initially available commercially as an oral or parenteral (IM and IV) drug. Given limitations with these routes of administration, a TDS patch was developed and is currently the only available dosage form in the United States of America (USA). The TDS patch is marketed for the prevention of nausea and vomiting associated with motion sickness, though it is also used in clinical management of post-operative nausea and vomiting.

DPI-386 Nasal Gel is an intranasal formulation of the approved drug scopolamine HBr. This study (DPI-386-MS-24) evaluated safety, efficacy, and pharmacokinetics (PK) of 0.2 mg of scopolamine HBr (equivalent to 0.16 mg scopolamine free base) administered as a nasal gel.

2.2. Target Population and Duration of the Study

It was planned to enroll 100 subjects into the study and 101 subjects were enrolled.

Eighty-three subjects with motion sickness susceptibility were randomized 1:1 into the double-blind period of the study (Session 1) to receive either DPI-386 Nasal Gel or Placebo Nasal Gel. Randomization was stratified by age group (55-59 years, 60-64 years, 65-69 years, 70-74 years, and ≥75 years).

In addition, 18 subjects ≥70 years of age with or without motion sickness susceptibility were enrolled into the open-label period of the study (Session 2), which took place on land in a clinic setting. These subjects did not participate in the double-blind treatment period on the ocean-going vessel and did not contribute to the efficacy analysis.

Eighty of the 83 randomized subjects continued into the open-label treatment period along with the 18 subjects who were enrolled only into the open-label period, for a total of 98 subjects who received open-label DPI-386 Nasal Gel on Days 2 to 4.

The duration of the clinical part of the study was 539 days (3 Jun. 2019 [First Subject First Visit-FSFV] to 23 Nov. 2020 [Last Subject Last Visit-LSLV]).

3. Study Objectives 3.1. Primary Objectives

1. Determine the efficacy of DPI-386 Nasal Gel (0.2 mg scopolamine HBr per dose twice a day for one day) compared to Placebo Nasal Gel in the prevention and treatment of nausea associated with motion sickness.

2. Determine the safety of DPI-386 Nasal Gel compared to Placebo Nasal Gel with an emphasis on cognitive AEs.

3.2. Secondary Objectives

1. Determine the efficacy of DPI-386 Nasal Gel compared to the Placebo Nasal Gel in severity of nausea.

2. Determine the safety of DPI-386 Nasal Gel compared to Placebo Nasal Gel in terms of cognition.

3. Describe the PK of a multi-dose schedule of DPI-386 Nasal Gel.

3.3. Pharmacokinetic Objectives

1. Describe the PK profile of scopolamine following administration of DPI-386 Nasal Gel 0.2 mg twice a day for 3 consecutive days.

2. Compare scopolamine PK between male and female subjects receiving DPI-386 Nasal Gel.

3.4. Pharmacokinetic/Pharmacodynamic Objective

1. To explore the relationships between scopolamine PK and pharmacodynamics (PD) (safety) endpoints collected on PK days for DPI-386 Nasal Gel.

4. Investigational Plan 4.1. Overall Study Design and Plan-Description

This Phase 3 clinical trial was a randomized, double-blind, placebo-controlled study to evaluate the safety and efficacy of DPI-386 Nasal Gel in subjects aged ≥55 years for the prevention and treatment of nausea associated with motion sickness (double-blind period [Session 1]). Treatment Day 1 was followed by an open-label period to evaluate safety and PK and explore relationships between PK exposure and pharmacodynamics (PD; safety) response (Session 2, Treatment Days 2 to 4) (N=80). In addition, a separate group of subjects ≥70 years of age (N=18) was enrolled into the open-label period (Session 2); these 18 subjects did not participate in the double-blind period of the study and did not contribute to the efficacy analysis. Eighty-three subjects were randomized 1:1 to one of two treatment arms (DPI-386 Nasal Gel or Placebo Nasal Gel), and were stratified by age group (55-59 years, 60-64 years, 65-69 years, 70-74 years, and ≥75 years). Each enrolled subject was assigned a subject number per one of the 5 age groups (starting with 101, 201, 301, 401, and 501), in consecutive order. The subject number was linked to a multi-digit random number (study drug kit number) which randomized the subject to one of the two arms for the double-blind period (Session 1, Treatment Day 1), which was conducted aboard an ocean-going vessel to obtain data in an operationally relevant real-world environment.

Ninety-eight subjects participated in the open-label period (Session 2; Treatment Days 2 to 4), including 80 subjects who participated in the double-blind period (Session 1) and the 18 subjects enrolled only to the open-label period (Session 2). All subjects received open-label DPI-386 Nasal Gel in Session 2, which was conducted at a clinical site on land within 30 days following Treatment Day 1.

A third group of subjects was defined as all subjects who received at least one dose of DPI-386 Nasal Gel at any time during the study. There were 99 subjects in this group-80 subjects from the double-blind period who were also in the open-label period, 18 subjects enrolled only into the open-label period, and 1 subject in the DPI-386 Nasal Gel arm of the double-blind period who was discontinued from the study and did not enter the open-label period.

There were 6 study phases: Recruitment and Screening; Treatment; Post-Voyage treatment Assessment; 2 Short-term Follow-up phases; and 1 Long-term Follow-up phase.

The Recruitment and Screening Phase consisted of 1 visit prior to ship departure to determine eligibility.

The Treatment Phase (Session 1, Treatment Day 1 and Session 2, consecutive Treatment Days 2 to 4) consisted of 4 Treatment Days. Treatment Day 1, approximately 12 hours in duration, followed by consecutive Treatment Days 2 to 4, each approximately 10-12 hours in duration with overnight stays, conducted within 30 days of Treatment Day 1. Treatment Day 1 was carried out on an ocean-going vessel. Treatment Days 2 to 4 were carried out in a clinical study site.

The Post-Treatment Phase consisted of 2 visits, at the end of Treatment Day 1 and at the end of Treatment Day 4 (clinic visit).

The first Short-term Follow-up Phase (following Treatment Day 1) consisted of 1 telephone or email contact on Day 6+3 days after Treatment Day 1.

The second Short-term Follow-up Phase (following Treatment Days 2 to 4) consisted of 1 telephone or email contact 5 days following Treatment Day 4.

The Long-Term Follow-up Phase (following Treatment Days 2 to 4) consisted of telephone or email contacts over 2 to 6 weeks following Treatment Day 4.

4.2. Discussion of Study Design, Including the Choice of Control Groups

The randomized, double-blind study design and the efficacy endpoints selected for the study allowed for a comparison of the effectiveness in subjects aged ≥55 years of DPI-386 Nasal Gel vs. Placebo Nasal Gel in the prevention and treatment of nausea associated with motion sickness in an operationally relevant real-world environment, as that portion of the study was conducted aboard an ocean-going vessel. Likewise, the safety endpoints allowed for a comparison of the safety of DPI-386 Nasal Gel vs. Placebo Nasal Gel in the same environment.

The open-label period of the study, which occurred on Days 2 to 4 in a clinic setting on land, allowed for the additional evaluation of safety in subjects who received DPI-386 Nasal Gel twice daily for 3 days. Scopolamine PK were also investigated in the open-label period.

4.3. Selection of Study Population

Male and female, healthy subjects, aged 55 years and over were enrolled in the study. Once initially screened, subjects were directed to meet the research staff for their Screening Visit. At the Screening Visit, the protocol was fully explained, including all potential risks known to DPI-386 Nasal Gel. Any questions were answered by the Principal Investigator or qualified designee. After a person expressed interest in participation, the potential subject read and then signed the ICF, with the help of the researcher who consented the subject.

4.3.1. Inclusion Criteria

As per the protocol, inclusion criteria were as follows:

1. Provision of a signed and dated ICF.
2. Stated willingness to comply with all study procedures and availability for the duration of the study.
3. Male or female, aged 55 and over.
4. In good general health as evidenced by medical history with no recent history or current diagnosis of uncontrolled clinical problems as assessed by the PI or qualified designee.
5. Ability to take intranasal medication and willingness to adhere to the study schedule and time constraints.
6. Agreement to adhere to the following lifestyle compliance considerations:
   a. Refrain from consumption of grapefruit and any substance containing grapefruit for 7 days prior to, during, and for 7 days after the 4 treatment days.
   b. Abstain from alcohol for 24 hours prior to first dose of study medication and during the 4 treatment days.

Note: there was no restriction on caffeine or nicotine use during the study; however, the actual use of these substances was recorded as part of the CEBQ.

4.3.2. Exclusion Criteria

As per the protocol, exclusion criteria were as follows:

1. Fever (temperature of 100.4° F. (38° C.) or greater.
2. Tested positive for COVID-19.
3. Known allergic reactions to scopolamine or other anticholinergics.
4. Currently prescribed any of the following medication types and used within the specified washout periods below:
   - any form of scopolamine (including Transderm Scop®) (washout 5 days),
   - belladonna alkaloids (washout 2 weeks),
   - antihistamines (including meclizine) (washout 2 weeks),
   - tricyclic antidepressants (washout 2 weeks),
   - muscle relaxants (washout 4 days), and
   - nasal decongestants (washout 4 days).

1. Hospitalization or significant surgery requiring hospital admittance within the past 6 months.

2. Treatment with another investigational drug or other intervention within the past 30 days.

3. Having donated blood or plasma or suffered significant blood loss within the past 30 days.

4. Having any of the following medical conditions within the last 2 years or if any of the following medical conditions were experienced more than 2 years ago and are deemed clinically significant by the PI or qualified designee:

Significant gastrointestinal disorder, asthma, or seizure disorders.

History of cardiovascular disease.

History of vestibular disorders.

History of narrow-angle glaucoma.

History of urinary retention problems.

History of alcohol or drug abuse.

Nasal, nasal sinus, or nasal mucosa surgery.

1. Prohibited medications include any form of scopolamine (including Transderm Scop®) belladonna alkaloids, antihistamines (including meclizine), tricyclic antidepressants, muscle relaxants, and nasal decongestants.

2. No use of any motion sickness remedies (e.g., medications, wrist bands, pressure bands, herbals, etc. which state on the label for use in motion sickness) outside of the study protocol was allowed.

4.3.3. Removal of Subjects from Therapy or Assessment

As per the protocol, withdrawal criteria were as follows:

1. Subjects are free to withdraw from the study at any time upon request.

2. The PI or qualified designee must discontinue or withdraw any subject from the study for the following reasons:

Significant non-compliance to study requirements as listed in Inclusion and Exclusion Criteria.

If any serious adverse event (SAE) or other medical condition or situation occurs such that continued participation in the study would not be in the best interest of the subject.

Significant non-compliance with lifestyle study requirements as listed in Inclusion Criteria No. 6.

If any AE or other medical condition or situation occurs such that continued participation in the study would not be in the best interest of the subject.

If the subject meets an exclusion criterion (not previously recognized) that precludes further study participation.

If the subject fails to follow timeline requirements.

If the subject is disruptive, combative, or otherwise uncooperative with research staff.

4.4. Treatments 4.4.1. Treatments Administered

The initial study drug dosing on Treatment Day 1 for all subjects in both treatment arms occurred at approximately the same time upon notification by the investigator and after study drug dosing training completed on the ship. On Treatment Days 2 to 4 at the clinic, subject treatment occurred according to the dosing schedule.

Nasal Gel Treatment Schedule

Subjects self-administered the first dose of DPI-386 Nasal Gel (0.2 mg/0.12 g) or Placebo Nasal Gel (0.12 g) into one nostril under research staff supervision upon notification by the investigator, and then self-administered a total of 7 additional doses over 4 treatment days always under research staff supervision, unless a rescue dose was administered on Treatment Day 1. There was a minimum of 6 hours #15 minutes separating any 2 doses. No more than 2 doses were administered, unless a third dose was deemed necessary by the investigator during Treatment Day 1 on the ship. After the initial dose on Treatment Day 1, all subsequent nasal gel doses occurred only during the subject's controlled 8-hour-period.

Nasal gel vials were primed by the research staff prior to dosing using the instructions and methods described in the DPI-386 Nasal Gel INSTRUCTIONS FOR USE (provided to each subject prior to initial dosing).

Procedure of Self-Administration of Nasal Gel

1. Before self-administration of the study drug, the subjects were required to clean their hands to prevent contamination.

2. Subjects were instructed to blow their nose into a clean tissue to clear both nostrils.

3. Subjects were handed the vial by research staff and told to remove the clip and cap and to insert the gel unit tip approximately 1 cm into their nostril, pointing the tip toward the back of their nose.

4. Subjects closed their other nostril with their forefinger and tilted head slightly forward.

5. Subjects pumped the gel vial firmly and quickly by pushing down on the finger grips of the pump unit and against the thumb at the bottom of the vial delivering 1 dose of gel into the nostril.

6. Subjects removed vial from nose and placed the clip and cap back on vial. Subjects sniffed gently with their mouth closed.

7. The subjects returned the vial to the researcher after each dose administration for storage in the assigned kit at the secure storage location.

8. Subjects were instructed to avoid sniffing or sneezing and remained in an upright position for at least 30 minutes. Subjects did not need to stay with research staff during that time and only self-report if sniffing and sneezing happened when they visited the research staff next.

9. Subjects were instructed to refrain from blowing their nose for at least 1 hour after dosing.

10. After self-administration of the study drug administration, subjects were required to clean their hands to prevent contamination.

4.4.2. Identity of Investigational Products

See Table 5g for descriptions of the investigational products used in this study.

TABLE 5g

| Investigational Products | |
|---|---|
| DPI-386 Nasal Gel | |
| Active content | Scopolamine Hydrobromide |
| Strength | Each 0.12 gram of the gel contains 0.2 mg of scopolamine HBr |
| Storage condition | Store at 20° C. to 25° C., inclusive (68° F. to 77° F., inclusive), with brief temperature excursions permitted between 15° C. and 30° C., inclusive (59° F. and 86° F., inclusive). |
| Lot No. | RDD1004 |
| Expiry Date | Date of fill - 25 Oct. 2017 |
| Placebo Nasal Gel (Placebo Gel for DPI-386 Nasal Gel) | |
| Storage condition | Store at 20° C. to 25° C., inclusive (68° F. to 77° F., inclusive), with brief temperature excursions permitted between 15° C. and 30° C., inclusive (59° F. and 86° F., inclusive). |
| Lot No. | PLD1202 |
| Expiry Date | Date of fill - 19 Dec. 2017 |

C = Centigrade;
F = Fahrenheit;
HBr—hydrobromide 4.4.3. Method of Assigning Subjects to Treatment Groups Each subject randomized on Treatment Day 1 to one of the two treatment arms: DPI-386 Nasal Gel or Placebo Nasal Gel and was assigned a subject number (starting with 101, 201, 301, 401, or 501) in consecutive order. The subject number was linked to a multi-digit random number (study drug kit number) different from the subject number. The nasal gel vial was labelled with the same study drug kit random number for Treatment Day 1. Open-label DPI-386 Nasal Gel was assigned for Treatment Days 2 to 4. The randomization scheme was secured with limited access to research staff delegated by the PI. For all subjects, the link between each subject's number and that subject's study drug kit number with the actual treatment assignment was stored in individual secured envelopes. In a medical emergency, it was allowed for unblinding of just one double-blind subject at a time.

4.4.4. Timing of Dose for Each Subject

For DPI-386 Nasal Gel (0.2 mg scopolamine HBr per dose) or Placebo Nasal Gel, 1 dose was delivered into 1 nostril twice daily over 4 treatment days (alternating nostrils). On the first day study drug was administered at sea and on the second, third, and fourth days study drug was administered at the clinic. The 2 daily doses were separated by a minimum of 6 hours with no more than 2 doses given per day, unless a third dose (rescue) was deemed necessary by the investigator (applicable for Treatment Day 1 only).

4.4.5. Blinding

This study was double-blinded placebo-controlled for both treatment arms on Treatment Day 1. All DPI-386 Nasal Gel and Placebo Nasal Gel vials were opaque and indistinguishable. The DPI-386 Nasal Gel and Placebo Nasal Gel were identical in color and viscosity, and without identifiable smell.

To prevent bias, all research staff were trained to not make any leading or suggestive statements to subjects. All staff and subjects were instructed on proper administration of study drug and were instructed to clean their hands thoroughly immediately after handling any study drug.

The sealed randomization scheme and individual unblinding envelopes were delivered to the vessel by the research staff with the accompanying study drugs on the morning of Treatment Day 1. The randomization scheme and individual unblinding envelopes were not kept in the same room as the clinical trial material aboard the vessel. Instead, the randomization scheme and individual unblinding envelopes were kept in a locked container in a separate room accessible by a designated research staff member.

The randomization scheme was opened only if the study had officially concluded all aspects of subject recruitment and data collection and the study Sponsor had been informed and agreed. Emergency un-blinding was not done during the study.

4.4.6. Prior and Concomitant Therapy

All concomitant medications/treatments taken within 30 days of randomization through Treatment Day 4 and any medications/treatments taken for reported AEs during follow-up were recorded.

Prohibited medications included any form of scopolamine, belladonna alkaloids, antihistamines (including meclizine), tricyclic antidepressants, muscle relaxants and nasal decongestants. The required washout periods for these medications are listed below:

- Any form of scopolamine (including Transderm Scop®)—washout 5 days prior to Treatment Day 1
- Belladonna alkaloids—washout 2 weeks prior to Treatment Day 1
- Antihistamines (including meclizine)—washout 2 weeks prior to Treatment Day 1
- Tricyclic antidepressants—washout 2 weeks prior to Treatment Day 1
- Muscle relaxants—washout 4 days prior to Treatment Day 1
- Nasal decongestants—washouts 4 days prior to Treatment Day 1

For 30 days prior to, during Treatment Days 1 to 4 and 7 days after Treatment Day 4 the following restrictions are required:

- Blood donation
- Administration of another investigational drug

For 7 days prior to, during Treatment Days 1 to 4 and 7 days after Treatment Day 4:

- No product containing grapefruit or grapefruit juice should be consumed.
- For 24 hours prior to Treatment Day 1 and during Treatment Days 1 to 4:
- No alcohol should be consumed.
- No use of any motion sickness remedies (e.g., medications, wrist bands, pressure bands, herbals, etc., which state on the label for use in motion sickness) outside of the study protocol.
- Permitted medications will be determined by the medical PI or qualified designee.

4.4.7. Treatment Compliance

The subjects self-administered each dose under research staff supervision as per the procedure mentioned in Section 4.4.1 and as per the training given prior to start of the dosing activity.

4.5. Efficacy and Safety Variables 4.5.1. Schedule of Assessments

The timing of the study assessments is described in Table 5h.

TABLE 5h

Schedule of Assessments

| | Study Phase: | | | | | | | |
|---|---|---|---|---|---|---|---|---|
| | Recruitment and Screening[1] | Treatment (3-day Duration) | | | | Post-treatment | Short-term Follow-up[2] | Long-term Follow-up[3] |
| | VISIT: | | | | | | | |
| | 1 | 2* boat | 3 clinic | 4 clinic | 5 clinic | 6 | | |
| | STUDY DAY: | | | | | | | |
| | | 1 | 2 | 3 | 4 | X[4] | X[2] | X[3] |
| ICF | X | | | | | | | |
| Demographics[5] | X | | | | | | | |
| MSSQ | X | | | | | | | |
| CMQ | X | | | | | | | |
| CEBQ[6] | X | X | X | X | X | | | |
| Inclusion/Exclusion | X | | X | | | | | |
| COVID-19 Swab(s) for testing and Temperature | X | | | | | | | |

TABLE 5h-continued

Schedule of Assessments

| | Study Phase: | | | | | | | |
|---|---|---|---|---|---|---|---|---|
| | Recruitment and Screening[1] | Treatment (3-day Duration) | | | | Post-treatment | Short-term Follow-up[2] | Long-term Follow-up[3] |
| | VISIT: | | | | | | | |
| | 1 | 2* boat | 3 clinic | 4 clinic | 5 clinic | 6 | | |
| | STUDY DAY: | | | | | | | |
| | | 1 | 2 | 3 | 4 | X[4] | X[2] | X[3] |
| Timed Up and Go (TUG) | X | | | | | | | |
| Subject Handout | X | X[7] | X[6] | X[5] | X[6] | | | |
| Randomization | | X | | | | | | |
| Study Drug Dosing: DPI-386 Nasal Gel or Placebo Nasal Gel | | X[8] | | | | | | |
| DPI-386 Nasal Gel Rescue | | X[9] | | | | | | |
| Vitals[10] | X | | X | X | X | | | |
| ECG[11] | | | X | X | X | | | |
| Open Label DPI-386 Nasal Gel[12] | | | X | X | X | | | |
| PVT[13] | X | X | | | | | | |
| ANAM CORE + CPT[14] | | | X | X | X | | | |
| ANAM CORE + CPT-CDD[15] | | | X | X | X | | | |
| KSS[16] | X | X | | | | | | |
| ACTS[16] | X | X | X | X | X | | X[2] | |
| MSAQ[16] | X | X | | | | | | |
| VAS[16] | X | X | | | | | | |
| PK Blood Draw[17] | | | X | X | X | | | |
| Adverse Events[18] | | X | X | X | X | X | X | X |
| IFU Training | X | X | X | X | X | | | |
| Concomitant Medications/ Treatments[19] | X | X | X | X | X | X | X | X |
| PSAQ[20] | | X | | | X | | | |
| Nasal Gel Device Ease-of-Use Questionnaire | | | | | | X | | |
| Debriefing[21] | | | | | | X | | |
| Record weather and sea state conditions[22] | | X | | | | | | |

*18 subjects enrolled for safety only and did not participate in the Boat trip and associated assessments.

ACTS = Anticholinergic Toxicity Screen; ANAM = Automated Neuropsychological Assessment Metrics; CDD = Code Substitution - Delayed; CEBQ = Confidential Exclusionary Behavior Questionnaire; CMQ = Confidential Medical Questionnaire; CPT = Continuous Performance Test; ECG = electrocardiogram; ICF = Informed Consent Form; IFU = Instructions for Use; KSS = Karolinska Sleepiness; MSAQ = Motion Sickness Assessment Questionnaire; MSSQ = Motion Sickness Susceptibility Questionnaire; PK = pharmacokinetic; PSQAQ = Performance Self-Assessment Questionnaire; PVT = Psychomotor Vigilance Test; TUG = Timed Up and Go; VAS = Visual Analogue Scale

[1]Screening occurred within 30 days prior to ship departure.

[2]The Session 1 Short-term Follow-up Period consisted of research staff contacting the subject via phone or email on Day 6 to ask if subjects have experienced any new signs or symptoms (includes ACTS). The acceptable window was +3 days. Session 2 Short-Term Follow-up Period (following Treatment Days 2-4) consisted of one telephone or email contact 5 days following Treatment Day 4.

[3]Long-term Follow-up (two to six weeks following Treatment Day 4) consisted of subjects having a standing obligation to contact research staff via phone or email at any time during this period to report any new signs or symptoms. There is no acceptable window requirement. Long-term Follow-up ends at the close of 42 days following Treatment Day 4. However, all adverse events (AEs) were followed until resolution.

[4]Post-Treatment Period assessments were performed at the end of the Treatment Day 1 (voyage) and at the end of Treatment Day 4 (clinic visit).

[5]Date of birth (DOB), age, race, and gender.

[6]Subjects must complete the Confidential Exclusionary Behavior Questionnaire (CEBQ) to confirm compliance with life-style compliance points listed under the inclusion criterion (i.e., no use of grapefruit and no use of alcohol) prior to dosing at the beginning of each visit.

[7]Re-explain the lifestyle adherence requirements (i.e., grapefruit, alcohol, etc.) of the treatment days listed in the IFU and Subject Handout.

[8]On Treatment Day 1, the investigator notified all study subjects and independent (unblinded) applicators when to administer the first study drug doses (nasal gel). This was the start of the controlled 8-hour period. A second treatment of nasal gel was self-administered 6 hours (±15 minutes) after the 1st dose administration time. The administration was only under the supervision by the research staff.

[9]A rescue dose was only administered to subjects who request further treatment for motion sickness.

[10]Refer to Table 9.3 vital signs assessment schedule

[11]Refer to Table 9.4 ECG assessment schedule.

[12]For Treatment Days 2-4, Dose #1 of DPI-386 Nasal Gel was administered at 0 minutes and Dose #2 was administered at 360 minutes.

[13]PVT was performed during screening as a baseline and at 4 and 8 hours after first dose administration on Treatment Day 1.

[14]ANAM CORE + CPT was performed at −60 minutes on Treatment Day 2 as a baseline and at 420 minutes on Treatment Days 2-4.

[15]ANAM CORE + CPT-CDD was performed at 60 minutes on Treatment Days 2-4.

[16]Safety Questionnaires and Tests including KSS, ACTS, MSAQ, and VAS were completed by the subject at the following time points: Screening, twice on Treatment Days 1 at 4 and 8 hours post Dose #1 and in the event a rescue dose is administered (ACTS, MSAQ, and VAS only). For Treatment Days 2-4, the ACTS was administered per the schedule.

[17]Refer to Section 4.5.6 for PK sampling time points.

[18]Assess AEs throughout Screening and Treatment Days 1-4, including ACTS at specified time points for Treatment Day 1 and for Treatment Days 2-4. Assess AEs by asking the subjects the following questions and recording the answers in the source document each time you see the subject: How do you feel? Is this normal for you at this time of day?

[19]All concomitant medications/treatments taken within 30 days of randomization through Treatment Day 4, in addition to any medications/treatments taken for reported AEs during follow up were recorded.

[20]Subjects must complete the questionnaire at the end of Treatment Day 1 voyage and at the end of Treatment Day 4 clinic visit.

[21]Research staff informed subjects of the follow-up periods (short and long term) procedures (timing, responsibilities, contact information) and remind subjects to contact research staff if any new signs or symptoms arise.

[22]Research staff transcribed weather and sea state conditions from the ship's log into the source data for all entries made during the one day of treatment.

Note:

this was done one time at the end of each voyage, on one log, not per subject. The ship captain used the provided log template.

4.5.2. Efficacy Endpoints 4.5.2.1. Primary Efficacy Endpoint

To assess prevention and treatment of nausea associated with motion sickness, the primary efficacy endpoint was the proportion of subjects who developed motion sickness and requested further treatment (i.e., subjects who received rescue medication).

This efficacy endpoint was assessed only in the double-blind period (Session 1), as it was only in this period that subjects were travelling on an ocean-going vessel.

4.5.2.2. Secondary Efficacy Endpoint

The secondary efficacy endpoint was the severity of nausea over the treatment period. Severity of nausea was assessed on a VAS. Subjects specified their degree of nausea by indicating a point along a continuous 100-mm line between two endpoints. The scale ranged from 0 (no nausea) to 100 (very severe nausea). Scoring was based on the length from the left edge of the scale to point reported and a higher score indicated a more severe degree of nausea.

This efficacy endpoint was assessed only in the double-blind period (Session 1), as it was only in this period that subjects were travelling on an ocean-going vessel.

4.5.2.3. Other Efficacy Endpoint

Another efficacy endpoint was time to first use of rescue medication during Treatment Day 1. It was calculated in hours as the start time of administration of the first rescue medication dose minus the start time of the first dose of study drug. Subjects who did not receive any rescue medication were censored at the time of their last assessment on Treatment Day 1.

This efficacy endpoint was assessed only in the double-blind period (Session 1), as it was only in this period that subjects were travelling on an ocean-going vessel.

4.5.2.4. Post-hoc Efficacy Endpoint

A post-hoc efficacy endpoint was the Complete Response rate at Day 1 Hour 4 (ITT population).

A Complete Responder was a subject who did not experience vomiting or require rescue medication within the first 4 hours of the first dose of study treatment on Treatment Day 1. Vomiting was derived from the AE data collection where the verbatim event term began with the text string "Vomit."

4.5.3. Safety Endpoints

Safety endpoints included AEs, vital signs, 12-lead electrocardiogram (ECG), PVT, ANAM, ACTS, KSS, PSAQ, EOUQ, and prior concomitant medications.

4.5.3.1. Primary Safety Endpoint

The primary safety endpoint was the incidence of AEs.

4.5.3.2. Secondary Safety Endpoints

Secondary safety endpoints were cognition as assessed by the PVT and by the ANAM. The selected tests and questionnaires were chosen for their ability to measure broad functional domains that have been designated as important for the operation of motor vehicles and other operational tasks, including alertness, attention and processing speed, reaction time and psychomotor functions, sensory-perceptual functioning, and executive functions. The PVT and ANAM tests are self-administered by the subject using a tablet computer with PVT and ANAM software. The PVT takes about 3 minutes to complete and the ANAM takes about 30-35 minutes to complete.

4.5.3.2.1. Cognition as Assessed by the Psychomotor Vigilance Task

The PVT is a neurocognitive assessment that measures alertness and tests sustained attention and reaction time. It was originally developed for sleep studies and involves simple reaction time testing by requiring the participant to push a button as soon as the stimulus (a light) appears. After a response, the reaction time (in ms) is displayed. The inter-stimulus interval varies from two to 10 seconds, so it is not predictable, and the entire task takes 10 minutes (Dorrian, Rogers, and Dinges, 2005).

The mean change from baseline to all post-baseline measurements in cognition as measured by median response time and number of performance lapses was to be evaluated.

4.5.3.2.2. Cognition as Assessed by Automated Neuropsychological Assessment Metrics Two ANAM batteries were customized for this study. ANAM CORE+CPT was collected at the clinical site on Treatment Days 2 to 4 prior to dosing (only on Day 2) and at multiple time points post-dose (Table 5i). The acceptable window for ANAM CORE+CPT time points was ±1 hour.

TABLE 5i

| ANAM CORE + CPT Assessment Schedule | | |
|---|---|---|
| Assessment Type | Assessment | Time Relative to Start of First Dose (Minutes) on Day 2, 3, and 4 |
| Safety | ANAM CORE + CPT | −60, 60, and 420 minutes |

ANAM = Automate Neuropsychological Assessment Metrics;
CPT = Continuous Performance Test ANAM CORE+CPT−CDD was collected at the clinical site on Treatment Days 2 to 4 at 60 minutes from Start of first dose. The acceptable window for ANAM CORE+CPT−CDD time points was ±1 hour.

ANAM CORE battery plus the Running Memory Continuous Performance Test (CPT). This battery has the following tests:

- Sleepiness Scale
- Symptoms Checklist
- Mood Scale
- Simple Reaction Time
- Code Substitution-Learning (CPS)
- Procedural Reaction Time
- Mathematical Processing
- Matching to Sample (M2S)
- Code Substitution-Delayed (CDD)
- Simple Reaction time (repeated)
- Go/No-Go
- Running Memory Continuous Performance Test (CPT)

ANAM CORE Battery with CPT added but CDD removed. This battery has the following tests:

- Sleepiness Scale
- Symptoms Checklist
- Mood Scale
- Simple Reaction Time
- Code Substitution-Learning (CPS)
- Procedural Reaction Time
- Mathematical Processing
- Matching to Sample (M2S)
- Simple Reaction time (repeated)
- Go/No-Go
- Running Memory Continuous Performance Test (CPT)

During Treatment Days 2 to 4 at the study site, ANAM was performed multiple times as outlined in the study protocol.

4.5.3.3. Other Safety Endpoints 4.5.3.3.1. Vital Sign and ECG Measurements

Vital signs were collected at Screening and at the clinical site on Treatment Days 2 to 4 prior to dosing and at multiple time points post-dose (Table 5j). The acceptable window for vital signs time points was −15 minutes to +5 minutes.

TABLE 5j

| Vital Signs Assessment Schedule | | |
|---|---|---|
| Assessment Type | Assessment | Time Relative to Start of First Dose (Minutes) on Day 2, 3, and 4[a] |
| Safety | Vital signs | −60, 30, 60, 120, 180, 330, 390, 420, 480, and 600 minutes |

[a]Vital signs were also collected at Screening.

12-lead ECGs were collected at Screening and at the clinical site on Treatment Days 2 to 4 prior to dosing and at multiple time points post-dose (Table 5k). The acceptable window for ECG time points was −15 minutes to +5 minutes.

TABLE 5k

| Electrocardiogram Assessment Schedule | | |
|---|---|---|
| Assessment Type | Assessment | Time Relative to Start of First Dose (Minutes) on Day 2, 3, and 4[a] |
| Safety | 12-lead ECG | −60, 120, and 480 minutes |

ECG = electrocardiogram
[a]ECG was also done at Screening.

The change from −60 minutes on Treatment Day 2 in vital sign and ECG measurements was calculated.

4.5.3.3.2. Sleepiness

Sleepiness was assessed using the KSS.

The KSS measures sleepiness using a 9-point scale based on 5 states ranging from "extremely alert" to "extremely sleepy, fighting sleep." There are 4 intermediary states that are not designated with words. Higher scores indicated a greater degree of sleepiness. Previous research has found that the KSS is closely linked to the objective measures of encephalographic and oculographic signs of sleep onset (Akerstedt and Gillberg, 1990). Scores on the KSS were evaluated to determine the potential impact of the study medication on alertness. The KSS was completed by subjects after each block of cognitive test times throughout the 4 treatment days.

4.5.3.3.3. Symptoms of Anticholinergic Toxicity

Symptoms of anticholinergic toxicity were monitored and recorded using the ACTS, which was collected at Screening and at the clinical site on Treatment Days 2 to 4 prior to dosing and at multiple time points post-dose (Table 51). The acceptable window for ACTS time points was −15 minutes to +5 minutes.

TABLE 5l

| Anticholinergic Toxicity Screen Assessment Schedule | | |
|---|---|---|
| Assessment Type | Assessment | Time Relative to Start of First Dose (Minutes) on Day 2, 3, and 4[a] |
| Safety | ACTS | −60, 180, 330, and 600 minutes |

ACTS = Anticholinergic Toxicity Screen
[a]ACTS was also done at Screening.

Subjects were asked the following questions:

Have you experienced any of the following symptoms in the past 24 hours?

Dry mouth
Increased skin redness/flushing
Blurry vision
Light sensitivity
Difficulty urinating
Dizziness
Confusion
Hallucinations
Palpitations The questions were asked in ascending order of symptom severity. Subjects who responded "yes" to confusion, hallucinations, or palpitations were to be immediately disqualified, and emergency medical services was to be contacted immediately. If any subject responded "yes" to dizziness, increased skin redness/flushing, blurry vision, light sensitivity, or difficulty urinating, the PI or qualified designee and medical consultant was to be contacted immediately, and they were to determine whether these subjects should be disqualified or if they required medical care. If any subject responded "yes" to dry mouth, it was recorded as a non-significant non-serious AE, and the subject was allowed to continue in the study as long as he or she responded "no" to queries about all other symptoms.

4.5.3.3.4. Performance of Activities

The PSAQ is a brief questionnaire that was completed by subjects at the end Treatment Day 4. Each statement in the questionnaire had 5 possible Likert-style responses, i.e., Strongly disagree, Disagree, Neither agree nor disagree, Agree, and Strongly agree.

The questionnaire allowed subjects to subjectively identify any perceived performance decrements or enhancements due to medication use over the Treatment period. The 6 statements in the PSAQ to which subjects were asked to respond are:

Over the past four days the medication had no effect on my work performance.
Over the past four days the medication had a positive on my work performance.
Over the past four days the medication had a negative effect on my work performance.
I experienced motion sickness.
Motion sickness had no effect on my work performance.
Motion sickness had a negative effect on my performance.

4.5.3.3.5. Nasal Gel Device Ease-of-Use Questionnaire

Subjects evaluated the ease of use of the Nasal Gel device using the EOUQ. The EOUQ is a brief questionnaire and was completed by subjects at the end of Treatment Day 4. Each statement had 5 possible Likert-style responses, i.e., Strongly disagree, Disagree, Neither agree nor disagree, Agree, and Strongly agree.

The 7 statements in the EOUQ to which subjects were asked to respond are:

Over the past four days the medication was easy to use.
Over the past four days the instructions for using the medication were easy to understand.
Over the past four days I easily remembered how to use the medication.
Over the past four days I was able to use the medication successfully every time.
Over the past four days I didn't have any problems using the medication.
Over the past four days the medication device worked the way I wanted it to work.
Over the past four days the medication was effective in preventing motion sickness.

4.5.4. Assessment of Adverse Events

AEs that occurred during the study (whether treatment related or not) were recorded in eCRF and followed as appropriate.

Criteria for Assessing the Adverse Events

The severity of the AEs was rated by the PI as mentioned below:

Mild—Events require minimal or no treatment and do not interfere with the subject's daily activities. Mild events require no action other than documentation.

Moderate—Events result in a low level of inconvenience or concern with the therapeutic measures. Moderate events may cause some interference with functioning.

Severe—Events interrupt a participant's usual daily activity and may require medical treatment. Severe events are usually potentially life-threatening or incapacitating.

AEs were additionally identified by temporal qualities in the following categories:

Continuous—The AE has a marked starting point and ending point, without recurrence.

Intermittent—The AE is sporadic in its effect, and recurring.

Causality Assessment of the Adverse Event to the IMP was done based on the following criteria:

Not related—The AE is completely independent of study drug administration, and/or evidence exists that the event is definitely related to another etiology. There must be an alternative definitive etiology documented by the medical monitor.

Related—This category includes (a) definitely related, (b) probably related, (c) possibly related, and (d) remotely related to study drug administration.

AEs of special interest (AESIs) included all symptoms listed for the Anticholinergic Toxicity Screen deemed "related" to study drug by the PI. For monitoring and reporting purposes, these events of special interest were further divided into two categories:

1. Significant Non-Serious Adverse Events

Significant Non-Serious AEs included all symptoms on the ACTS symptoms list deemed "related" to the study drug by the PI except for dry mouth, in addition to lightheadedness, asymptomatic hypotension and symptomatic hypotension deemed "related" to the study drug by the PI. These AEs were reported using the same procedure for SAEs. All significant non-serious adverse events occurring within 30 days of the subject's last exposure to study medication were reported.

The Significant Non-Serious AEs include:

Increased skin redness/flushing
Blurry vision
Light sensitivity
Difficulty urinating
Dizziness
Lightheadedness
Asymptomatic hypotension
Symptomatic hypotension
Confusion
Hallucinations
Palpitations 2. Non-significant Non-Serious Adverse Events Dry mouth was the only event of special interest to be considered a Non-significant Non-Serious AE and was reported using the standard (non-expedited) AE reporting procedure.

4.5.5. Appropriateness of Measurements

Plasma concentrations of scopolamine were measured directly from blood samples collected during the study and using a validated bioanalytical method.

Safety assessments included AEs, vital signs, 12-lead ECG, PVT, ANAM, ACTS, KSS, PSAQ, EOUQ, and prior concomitant medications. All are considered appropriate to evaluate the safety profile of the study drug.

4.5.6. Drug Concentration Measurements

Blood samples for PK analysis of scopolamine concentrations in plasma were collected relative to each of the 6 doses administered in Session 2 at the time points indicated in Table 5m.

TABLE 5m

Pharmacokinetic Sampling Schedule

| Session 2, Treatment Days 2-4 | |
|---|---|
| AM Doses | Pre-dose, 30, 60, 90, 120, 180, 330 minutes |
| PM Doses | Pre-dose, 30, 60, 90, 120, 240 minutes |

Notes:
Session 1 (Day 1): Subjects were randomized (1:1) to receive DPI-386 or placebo nasal gel on Day 1; PK samples were not collected on Day 1.
Session 2 (Days 2, 3, 4): Subjects received open-label DPI-386 Nasal Gel 0.2 mg twice daily for 3 days; PK samples were collected relative to each dose. Doses of nasal gel were administered 6 hours apart within each day and 18 hours apart between days. Session 2 was to take place within 30 days of Session 1.

Blood samples for quantification of scopolamine concentrations were collected in K2EDTA vacutainer tubes. The samples were centrifuged at refrigerated temperature (4° C.) at approximately 3000 rpm for 10 minutes. The plasma obtained was divided equally into two cryovials (approximately 2 mL of plasma/cryovial) via non-sterile pipettes to create two separate sets of plasma samples for each subject. The plasma samples were stored at a temperature of −80° C. until shipped on dry ice to the bioanalytical facility for analysis. Plasma samples were shipped frozen from the clinical site to the bioanalytical facility Pyxant Labs, Inc. Upon receipt, individual samples were assigned unique Pyxant ID numbers and labeled accordingly, then stored frozen at approximately −80° C.

Samples were assayed for scopolamine in plasma at the bioanalytical facility Pyxant Labs, Inc. using a validated high-performance liquid chromatography with tandem mass spectrometry (LC-MS/MS). All plasma samples were analyzed within established long-term frozen, freeze/thaw, and processed extract stability. The bioanalytical method details for each analyte are presented in Table 5n.

TABLE 5n

Summary of Bioanalytical Performance

| Analyte | Matrix | Validated Assay Range (LLQ to ULQ) | Between-Run Precision (CV %) | Accuracy (% difference) |
|---|---|---|---|---|
| Scopolamine | Plasma | 2.0 to 2000 pg/mL | 6.17% to 9.65% | −2.4% to −0.2% |

CV = coefficient of variation'
LLQ = lower limit of quantitation;
ULQ = upper limit of quantitation
Source: Pyxant Labs, Inc. Report for Project Number: 3902

Plasma drug concentration-time data were analyzed by non-compartmental analysis (NCA) using Phoenix® WinNonlin® Version 8.1 (Certara, Inc., Princeton, NJ, USA) to estimate PK parameters. Actual PK sampling times were used for PK analysis.

The PK endpoints were:

$C_{max}$, $AUC_{(0-t)}$, $AUC_{(0-6)}$, $t_{lag}$, $t_{max}$, and $t_{1/2}$ for morning doses $C_{max}$, $AUC_{(0-1)}$, $t_{lag}$, and $t_{max}$ for afternoon doses.

$C_{max}$, $AUC_{(0-t)}$, $AUC_{(0-6)}$ for comparisons between gender

For exploration of relationships between PK exposure and PD (safety) endpoints:

PK exposure metrics $C_{max}$, $AUC_{(0-t)}$, $AUC_{(0-6)}$

ACTS-symptom of maximum severity post-baseline

Cognition (Automated Neuropsychological Assessment Metrics [ANAM])-maximum change from baseline 4.6. Data Quality Assurance 4.6.1. Monitoring Sponsor representatives were allowed to visit all study site locations to assess the data, quality and study integrity in a manner consistent with applicable health authority regulations and the procedures adopted by sponsor. Prior to the start of the study, members of sponsor reviewed the protocol, eCRF, regulatory obligations and other material or equipment relevant to the conduct of the study with the Investigator and relevant study site personnel.

Monitoring visits and telephone consultations occurred as necessary and per the monitoring plan, during the course of the investigation to verify the following:

the rights and well-being of subjects are protected, the conduct of the investigation is in compliance with the currently approved protocol/amendment, 21 Code of Federal Regulations (CFR) Parts 50, 54, 56 and 812; 42 United States Code 282 (j); ICH GCPs; and applicable local regulations, the integrity of the data, including adequate study documentation, the facilities remain acceptable, the Investigator and site personnel remain qualified and able to conduct the study, and test article accountability.

4.6.2 Training

The investigator and team are trained in ICH-GCP guideline. Before the start of the study, the study team was trained on various aspects of the study during the protocol training session. They were trained on the protocol, informed consent procedures, eCRF completion and correction, source documentation, monitoring procedures, management of documents and timelines of subject recruitment and completion.

4.6.3. Quality Assurance

Compliance to the study requirements were observed as per Good Clinical Practices, Internal Standard Operating Procedures, Protocol, and applicable regulatory requirements.

4.6.4. Clinical Data Management

TAB Clinical was provided paper copies of the CRFs and then entered the data into an electronic data capture (EDC) database with double-data entry per FDA guidance. TAB queried all incorrect, out-of-range, and missing data.

4.7 Statistical Methods Planned in the Protocol and Determination of Sample Size 4.7.1. Statistical and Analytical Plans Continuous data were summarized by reporting the number of subjects (n), mean, SD, median, minimum value, and maximum value.

Categorical data were summarized by reporting the frequency (count and percent) of subjects falling within each category of a given assessment. Unless specified otherwise for a particular assessment, the denominator for calculating a percentage was the total number of subjects in the analysis population for the subgroup being analyzed; for example, within study arm, the number of subjects within the study arm in the analysis population was the denominator. For overall summaries, the total number of subjects in the analysis population was used as the denominator.

Statistical tests and confidence intervals are provided. Among-group tests were performed. Tests comparing DPI-386 Nasal Gel to Placebo Nasal Gel were performed with two-sided tests at the 5% significance level.

4.7.1.1. Analysis Populations

The analysis populations were defined as follows:

Intent-to-Treat (ITT): The ITT Population included all randomized subjects.

Modified Intent-to-Treat (mITT): The mITT Population included subjects randomized to treatment who received at least one dose of study treatment and who have at least one post-baseline assessment of at least one efficacy assessment (MSAQ or VAS).

Per-Protocol (PP): The PP Population included all subjects randomized to treatment who received at least one dose of study treatment, who have at least one post-baseline assessment of at least one efficacy assessment (MSAQ or VAS), and who did not have any major protocol violations.

Safety: The Safety Population included all subjects who received at least one dose of study treatment.

All the safety analysis was done on the safety population and efficacy analysis was done on ITT, mITT, and PP population using SAS® Version 9.4 (SAS Institute Inc., USA).

As the subjects in the ITT and mITT populations were the same, separate tables for the mITT population were not generated.

4.7.1.2. Study Subjects 4.7.1.2.1. Disposition of Subjects

Subject disposition was summarized for the study population by treatment group and overall subjects combined. Summaries included the number (%) of subjects completing the study and discontinuing the study early by the primary reason for discontinuation.

4.7.1.2.2. Protocol Deviations

There were no major protocol violations during the double-blind period of the study, therefore the mITT, ITT, and PP populations consisted of the same subjects.

4.7.1.2.3. Measurements of Treatment Compliance

The number of nasal gel doses received were summarized with the number and percentage of subjects receiving 0, 1, 2, 3, 4, 5, 6, 7, or 8 complete doses without dosing errors by treatment group. Compliance with study treatment was summarized for the ITT population.

4.7.1.2.4. Extent of Exposure

Extent of exposure to study treatment was summarized for the Safety population by treatment arm. The number of days that nasal gel was administered was summarized by counts and percentages of subjects in each category (i.e., 1, 2, 3, or 4 days). The total nasal gel dose administered in grams were summarized with descriptive statistics. The total dose administered for each subject was derived as the number of full nasal gel doses given as reported on the Study Drug Dosing Log form×1.2 grams.

4.7.1.3. Efficacy Evaluation 4.7.1.3.1 Demographic and Other Baseline Characteristics Demographic variables including age, sex, ethnicity, and race were summarized for the Safety population by treatment group in the double-blind period, for all subjects in the open-label period, and for all subjects who received at least one dose of DPI-386 Nasal Gel at any time during the study.

Age was summarized using descriptive statistics. Sex, ethnicity, and race were summarized with the number (%) of subjects.

4.7.1.3.2. Primary Efficacy Endpoint Analysis Methods

The primary efficacy endpoint was the proportion of subjects who developed motion sickness and requested further treatment in the double-blind period of the study (i.e., subjects who received rescue medication).

The difference between treatment groups in proportions and the p-value were obtained using a Fishers Exact test.

The analysis was performed on the ITT population.

4.7.1.3.3. Secondary Efficacy Endpoint Analysis Methods

The secondary efficacy endpoint was the severity of nausea in the double-blind period of the study as recorded by the subjects on a VAS.

The mean VAS score was analyzed at Treatment Day 1 Hour 4 and Hour 8. DPI-386 Nasal Gel was compared to Placebo Nasal Gel. The analysis was performed using a MMRM including fixed effects of treatment, visit, and interaction term of treatment by visit. Baseline value was included as a covariate in the model.

Summaries were based on observed data in the ITT population.

4.7.1.3.4. Other Efficacy Endpoint, Analysis Methods

Time to first use of rescue medication in the double-blind period of the study was another efficacy endpoint.

Time to first use of rescue medication during Treatment Day 1 was calculated in hours as the start time of administration of the first rescue medication dose minus the start time of the first dose of study drug. Subjects who took no rescue medication during the study were censored at the time of the last VAS MSAQ assessment. The comparison of the DPI-386 Nasal Gel group versus the Placebo Nasal Gel group was performed using a log-rank test.

4.7.1.3.5. Post-hoc Efficacy Analysis: Complete Response Rate at Day 1 Hour 4

A post-hoc efficacy endpoint was the Complete Response rate in the double-blind period of the study at Day 1 Hour 4 (ITT population).

A Complete Response was defined as no vomiting and not using rescue treatment within 4 hours after receiving study drug. The within 4 hours after receiving study drug window was from the time of first dose to the time of the end of voyage. Vomiting was derived from the AE data collection where the verbatim event term began with the text string "Vomit."

The difference in proportions between the DPI-386 Nasal Gel arm and Placebo Nasal Gel arm along with the associated two-sided 95% CI for the difference in treatment group proportions (DPI-386 Nasal Gel—Placebo Nasal Gel), along with a p-value, was determined using a Fishers Exact test.

4.7.1.4. Safety Evaluation

The safety analysis was performed on the Safety population and included all subjects who received at least one dose of study drug.

4.7.1.4.1 Primary Safety Endpoint: Adverse Events

The primary safety endpoint was the subject incidence of TEAEs while on study treatment. TEAEs were those with onset after the first dose of study treatment or existing events that worsened after the first dose of study treatment.

TEAEs were summarized for the following groups of subjects:

- Subjects randomized to DPI-386 Nasal Gel, double-blind period (Day 1 only) (N=42)
- Subjects randomized to Placebo Nasal Gel, double-blind period (Day 1 only) (N=41)
- Subjects in the DPI-386 Nasal Gel open-label period (Day 2 to 4) (N=98)
- Subjects who received at least one dose of DPI-386 Nasal Gel at any time during the study (Day 1 to 4) (N=99)

Throughout the course of the study, all AEs were monitored and recorded on the source document and the appropriate CRF. The following information was reported: AE description, onset date and time, stope date and time, outcome, frequency, severity, relationship to study drug, action taken regarding study drug, associated concomitant medications or treatments, and seriousness.

Summaries that are displayed by Medical Dictionary for Regulatory Activities (MedDRA) system organ class (SOC) and preferred terms were ordered by descending incidence of SOC and preferred term within each SOC. Summaries displayed by preferred term only were ordered by descending incidence of preferred term.

At each level of summarization (e.g., any AE, SOC, and preferred term), subjects experiencing more than one TEAE were counted only once. In the summary of TEAEs by severity grade, subjects were counted once at the highest severity reported at each level of summarization; in the summary of TEAEs by relationship, subjects were counted once at the closest relationship to study drug. Related events include those reported as "Possibly related," "Probably related," or "Definitely related" relationship to study drug; events considered not related are those reported as "Remotely related" or "Unable to determine" with respect to relationship to study drug. AE data were presented in data listings by subject, treatment group, and event.

4.7.1.4.2. Secondary Safety Endpoints: Cognition (by PVT and ANAM)

Secondary safety endpoints were cognition as assessed by the PVT and as assessed by the ANAM.

The PVT is a neurocognitive assessment that measures alertness and tests sustained attention and reaction time. The mean change from baseline to all post-baseline measurements in cognition as measured by median response time and number of performance lapses was evaluated.

Two ANAM batteries were customized for this study: ANAM CORE battery plus the Running Memory CPT and ANAM CORE Battery with CPT added but CDD removed.

The ANAM subtest responses were to be summarized by treatment group. Descriptive statistics were to be presented for the observed values and changes from baseline to all post-baseline evaluations of cognition as measured by the throughput scores for each subtest.

ANAM data were to be analyzed and results reported by Vista LifeSciences.

4.7.1.4.3. Other Safety Endpoints

Vital Sign and ECG Measurements

Mean observed values and change from pre-dose on Treatment Day 2 were calculated in vital sign and electrocardiogram (ECG) measurements for each parameter, as collected by time point at the in-clinic visits on Treatment Days 2-4.

The number (%) of subjects having corrected (Fridericia) QT values (QTcF) >450 msec and QTcF change from baseline values >30 msec and >60 msec were tabulated.

Sleepiness

The KSS scores were summarized by treatment group. Descriptive statistics were presented for the observed values and changes from baseline to Treatment Day 1 Hour 4 and Hour 8.

Anticholinergic Toxicity Screen

Subject incidence in reporting symptoms of anticholinergic toxicity using ACTS was presented by treatment group. The number and percentage of subjects who report symptoms were summarized at each visit and time point were collected by symptom.

Performance of Activities

The frequency of subject responses to the individual items of the PSAQ administered at Post-Treatment Day 4 were summarized by Treatment Group. The number and percentage of subjects who report each of the possible responses for each item were summarized.

4.7.1.5. Other Evaluations 4.7.1.5.1. Nasal Gel Device Ease of Use

Frequency of subject responses to the individual items of the Nasal Gel Device Ease-of-Use Questionnaire (EOUQ) at the Post-Treatment visit were tabulated. The number (%) of subjects who reported each of the possible responses for each item were summarized.

4.7.1.5.2. Prior and Concomitant Medications

Prior and concomitant medications were summarized for each treatment arm.

4.7.1.6. Statistical Analysis of PK and PK/PD Data

Plasma scopolamine concentrations and PK parameters were listed and summarized dose within day for the overall population and by gender and age group (<65, 65 to 74, and ≥75 years of age). Plasma scopolamine concentrations and PK parameters were plotted by gender; PK parameters were also plotted by age group.

Analysis of variance (ANOVA) was used for the between gender comparisons. PK parameters will be log-transformed prior to statistical analysis. The 90% CI for the difference in the means of the log-transformed data will be calculated. The antilogs of the confidence limits obtained constitute the 90% CI for the ratio of the geometric means between females and males.

4.7.2. Determination of Sample Size

It was planned to enroll 100 subjects ≥55 years of age into the study and 101 subjects were enrolled. The study sample size was not based on a power requirement for a specific parameter.

Eighty-three subjects with motion sickness susceptibility were randomized 1:1 into the double-blind period of the study (Session 1) to receive either DPI-386 Nasal Gel or Placebo Nasal Gel.

In addition, 18 subjects ≥70 years of age with or without motion sickness susceptibility were enrolled into the open-label period of the study (Session 2). These subjects did not participate in the double-blind treatment period on the ocean-going vessel and did not contribute to the efficacy analysis.

Ninety-eight subjects continued in (N=80) or were enrolled into (N=18) the open-label period of the study in the clinic setting for safety observation and PK data collection.

The primary efficacy analysis was conducted as a comparison between DPI-386 Nasal Gel and Placebo Nasal Gel from data collected in the double-blind period (Day 1 only).

4.8. Changes in the Conduct of the Study or Planned Analysis

It was deemed necessary to enroll 18 subjects of age ≥70 to open-label treatment in the clinic only to obtain safety and PK data in this age group.

A post-hoc analysis of the Complete Response rate at Day 1 Hour 4 in the ITT population was performed, and the results are reported in the efficacy section. A Complete Responder was a subject who did not experience vomiting or require rescue medication within the first 4 hours of the first dose of study treatment on Treatment Day 1. Vomiting was derived from the AE data collection where the verbatim event term began with the text string "Vomit."

PVT data were collected but not analyzed.

ANAM data were collected but not analyzed.

5. Study Subjects 5.1. Disposition of Subjects

A total of 101 subjects (41 males and 60 females) were enrolled in the study.

Three subjects were discontinued during the conduct of the study. Subject 216 in the DPI-386 Nasal Gel arm discontinued the study because an exclusion criterion was met that precluded further participation in the study. Subject 226 in the Placebo Nasal Gel arm withdrew consent to participate in the study. Subject 206 in the Placebo Nasal Gel arm was discontinued from the study due to an AE of atrial fibrillation, which was observed on a pre-dose ECG on Treatment Day 2. These 3 subjects did not participate in the open-label period of the study.

5.2. Protocol Deviations

A total of 331 protocol deviations were reported in the trial. All reported deviations were considered as minor. Protocol deviations, all minor in nature, were judged not to have any impact on the conduct, data collection, analysis or reporting in this study.

6. Efficacy Evaluation 6.1. Data Sets Analyzed

A total of 102 subjects were enrolled in the study. Of those 102 subjects, 1 subject was a screen failure. A total of 101 subjects were enrolled and dosed, and included 83 subjects enrolled into the randomized, double-blind period of the study and 18 additional subjects enrolled into the open-label period of the study.

Because of the crossover nature of this study, 3 separate datasets representing 3 separate periods of the study were created to analyze the results:

1. The randomized, double-blind period: This period consists of data only from Treatment Day 1, when subjects were randomized to one treatment arm or another and treatment was double-blinded. This is the only period of the study in which comparisons between DPI-386 Nasal Gel and Placebo Nasal Gel can be made.

2. The open-label period: This period consists of data from Day 2, 3, and 4, when all subjects were receiving open-label DPI-386. Subjects who received DPI-386 on Day 1 continued to receive DPI-386 on Days 2 to 4, and subjects who were receiving Placebo Nasal Gel on Day 1 were crossed over and given open-label DPI-386 on Days 2 to 4. In addition, 18 more subjects were enrolled into this period (they were not treated in the Day-1 double-blind period). All treatments were unblinded, i.e., both the subjects and study staff knew that only DPI-386 was being administered.

3. All subjects who received at least one dose of DPI-386 at any time from Day 1 to Day 4.

Each of the 3 datasets had an ITT, mITT, PP, and Safety Population. All subjects in each period were included in the ITT, mITT, and Safety populations of those periods. No subjects were excluded from the PP population in the double-blind period. Three subjects (1 subject in the DPI-386 Nasal Gel arm and 2 subjects in the Placebo Nasal Gel arm) did not enter the open-label period (Table 50).

TABLE 5o

Summary of Analysis Populations

| Parameter | Statistic | Treatment: DPI 386 Nasal Gel | Placebo Nasal Gel | Open-label DPI-386 Nasal Gel | At Least One DPI-386 Nasal Gel |
|---|---|---|---|---|---|
| Subjects included in the Intent-to-Treat population | n (%) | 42 (100) | 41 (100) | 98 (100) | 99 (100) |
| Subjects included in the modified Intent-to-Treat population | n (%) | 42 (100) | 41 (100) | 98 (100) | 99 (100) |
| Subjects included in the Per Protocol population | n (%) | 42 (100) | 41 (100) | 80 (81.6) | 81 (81.8) |
| Subjects included in the Safety population | n (%) | 42 (100) | 41 (100) | 98 (100) | 99 (100) |
| Was the blind broken? | | | | | |
| Yes | n (%) | 0 (00.0) | 0 (00.0) | 0 (00.0) | 0 (00.0) |
| No | n (%) | 42 (100) | 41 (100) | 80 (81.6) | 81 (81.8) |
| NA | n (%) | 0 (00.0) | 0 (00.0) | 18 (18.4) | 18 (18.2) |
| Subjects completed | n (%) | 41 (97.6) | 39 (95.1) | 98 (100) | 98 (99.0) |
| Subjects discontinued | n (%) | 1 (2.4) | 2 (4.9) | 0 (00.0) | 1 (1.0) |
| Reason for discontinuation | | | | | |
| Failure to meet continuation criteria | n (%) | 1 (2.4) | 1 (2.4) [1] | 0 (00.0) | 1 (1.0) |
| Withdrawal by subject | n (%) | 0 (00.0) | 1 (2.4) | 0 (00.0) | 0 (00.0) |

NA = not applicable.
[1]See Table of Errata, Table 5o.
Source: Table 14.1.1

6.2. Demographic and Other Baseline Characteristics

The study enrolled 101 subjects (41 males and 60 females). Eighty-three subjects were enrolled into the randomized, double-blind period (42 subjects in the DPI-386 Nasal Gel arm and 41 subjects in the Placebo Nasal Gel arm). Demographic characteristics for age, age category, and MSSQ score at baseline were similar between the two treatment groups. Demographic characteristics are presented for subjects in the double-blind period, for subjects who received DPI-386 Nasal Gel in the open-label period, and for all subjects who received at least one dose of DPI-386 Nasal Gel, in Table 5p. Subjects who received at least one dose of DPI-386 Nasal Gel had a mean (SD) age of 63.74±6.27 years.

In the double-blind period, 23 subjects (54.8%) in the DPI-386 Nasal Gel arm were female and 19 (45.2%) were male. In the Placebo Nasal Gel arm, 29 subjects (70.7%) were female and 12 (29.3%) were male (Table 5p). Race and ethnicity were similar between the two treatment groups. In the DPI-386 Nasal Gel arm, 22 subjects (52.4%) were White, 14 (33.3%) were Black or African American, 5 (11.9%) were Asian, and 1 subject (2.4%) was American Indian or Alaska Native. In the Placebo Nasal Gel arm, 21 subjects (51.2%) were White, 15 (36.6%) were Black or African American, 4 (9.6%) were Asian, and 1 subject (2.4%) reported their race as 'Other.' The majority of subjects in both groups were not of Hispanic or Latino ethnicity.

In the double-blind period of the study the ITT and PP populations were the same as the Safety populations, so summaries of the demographics of those populations were not produced.

TABLE 5p

Demographic Data (Safety Population)

| Characteristic | Statistic | DPI-386 Nasal Gel (N = 42) | Placebo Nasal Gel (N = 41) | Open-label DPI-386 Nasal Gel (N = 98) | At Least One DPI-386 Nasal Gel (N = 99) |
|---|---|---|---|---|---|
| Age (years) | n | 42 | 41 | 98 | 99 |
| | Mean | 61.98 | 61.39 | 63.76 | 63.74 |
| | SD | 5.02 | 4.60 | 6.30 | 6.27 |
| | Median | 61.00 | 60.00 | 62.50 | 62.00 |
| | Minimum | 55.00 | 55.00 | 55.00 | 55.00 |
| | Maximum | 76.00 | 73.00 | 81.00 | 81.00 |
| Age category (years) | | | | | |
| 55-59 years | n (%) | 15 (35.7) | 16 (39.0) | 31 (31.6) | 31 (31.3) |
| 60-64 years | n (%) | 14 (33.3) | 15 (36.6) | 26 (26.5) | 27 (27.3) |
| 65-69 years | n (%) | 10 (23.8) | 8 (19.5) | 18 (18.4) | 18 (18.2) |
| 70-74 years | n (%) | 2 (4.8) | 2 (4.9) | 19 (19.4) | 19 (19.2) |
| 75+ years | n (%) | 1 (2.4) | 0 (0.0) | 4 (4.1) | 4 (4.0) |
| Motion Sickness | n | 42 | 41 | — | — |
| Susceptibility | Mean | 9.12 | 9.85 | — | — |
| Questionnaire (MSSQ) [a] | SD | 5.62 | 4.37 | — | — |
| | Median | 9.00 | 10.80 | — | — |

TABLE 5p-continued

| Demographic Data (Safety Population) | | | | | |
|---|---|---|---|---|---|
| Characteristic | Statistic | DPI-386 Nasal Gel (N = 42) | Placebo Nasal Gel (N = 41) | Open-label DPI-386 Nasal Gel (N = 98) | At Least One DPI-386 Nasal Gel (N = 99) |
| | Minimum | 0.00 | 0.00 | — | — |
| | Maximum | 18.00 | 16.00 | — | — |
| Sex | | | | | |
| Female | n (%) | 23 (54.8) | 29 (70.7) | 58 (59.2) | 59 (59.6) |
| Male | n (%) | 19 (45.2) | 12 (29.3) | 40 (40.8) | 40 (40.4) |
| Race | | | | | |
| American Indian or Alaska Native | n (%) | 1 (2.4) | 0 (00.0) | 1 (1.0) | 1 (1.0) |
| Asian | n (%) | 5 (11.9) | 4 (9.8) | 9 (9.2) | 9 (9.1) |
| Black or African American | n (%) | 14 (33.3) | 15 (36.6) | 30 (30.6) | 31 (31.3) |
| Other | n (%) | 0 (00.0) | 1 (2.4) | 2 (2.0) | 2 (2.0) |
| White | n (%) | 22 (52.4) | 21 (51.2) | 56 (57.1) | 56 (56.6) |
| Ethnicity | | | | | |
| Hispanic or Latino | n (%) | 8 (19.0) | 5 (12.2) | 13 (13.3) | 13 (13.1) |
| Not Hispanic or Latino | n (%) | 30 (71.4) | 35 (85.4) | 81 (82.7) | 81 (81.8) |
| Not reported | n (%) | 4 (9.5) | 1 (2.4) | 4 (4.1) | 5 (5.1) |

N = the number of subjects in the Safety population for each treatment;
n = the number of subjects in the specific category.
[a] MSSQ data were not collected in the additional 18 subjects enrolled directly into the Open-label phase of the study.
Source: Table 14.1.2, 14.1.3

6.3. Measurements of Treatment Compliance

All the subjects received study treatment as per protocol. Compliance to treatment was 100% or nearly 100% on all 4 treatment days.

6.4. Efficacy Results and Tabulations of Individual Subject Data

6.4.1. Analyses of Efficacy

6.4.1.1. Primary Efficacy Endpoint: Proportion of Subjects Who Received Rescue Medication The primary efficacy endpoint was the proportion of subjects in the ITT population who developed motion sickness, with or without vomiting and requested further treatment (rescue medication) on Treatment Day 1 (i.e., subjects who received rescue medication). The difference between the DPI-386 Nasal Gel arm and the Placebo Nasal Gel arm (9.5% vs. 36.6%) was statistically significant in favor of the DPI-386 Nasal Gel arm (p=0.0041, Fishers Exact test; Table 5r).

The results for subjects who used rescue medication within 4 hours after receiving the first dose of study drug are presented in Table 5s. The difference between the DPI-386 Nasal Gel arm and the Placebo Nasal Gel arm (7.1% vs. 26.8%) was statistically significant in favor of the DPI-386 Nasal Gel arm (p=0.0204, Fishers Exact test).

TABLE 5r

| Proportion of Subjects Using Rescue Medication (ITT Population) | | |
|---|---|---|
| Parameter | DPI-386 Nasal Gel (N = 42) | Placebo Nasal Gel (N = 41) |
| Treatment Day 1 | | |
| Subjects who took rescue medication, n (%) | 4 (9.5) | 15 (36.6) |
| 95% CI | (2.7, 22.6) | (22.1, 53.1) |

TABLE 5r-continued

| Proportion of Subjects Using Rescue Medication (ITT Population) | | |
|---|---|---|
| Parameter | DPI-386 Nasal Gel (N = 42) | Placebo Nasal Gel (N = 41) |
| Treatment difference (%) (95% CI) | −27.1 (−44.3, −9.9) | |
| P-value[1] | 0.0041 | |

CI = confidence interval;
ITT = Intent-to-Treat.
[1]Fishers Exact test.
Source: Table 14.2.1.1

TABLE 5s

| Proportion of Subjects Using Rescue Medication within 4 Hours After the First Dose of Study Medication (ITT Population) | | |
|---|---|---|
| Parameter | DPI-386 Nasal Gel (N = 42) | Placebo Nasal Gel (N = 41) |
| Treatment Day 1 | | |
| Subjects who took rescue medication, n (%) | 3 (7.1) | 11 (26.8) |
| 95% CI | (1.5, 19.5) | (14.2, 42.9) |
| Treatment difference (%) (95% CI) | −19.7 (−35.3, −4.0) | |
| P-value[1] | 0.0204 | |

CI = confidence interval;
ITT = Intent-to-Treat.
[1]Fishers Exact test.
Source: Table 14.2.1.2

6.4.1.2. Secondary Efficacy Endpoint: Nausea Assessment (Visual Analogue Scale)

The secondary efficacy endpoint was the severity of nausea over the double-blind treatment period as assessed by the subject on a VAS that measured 0 to 100 mm.

In the ITT population, the median measurement for nausea severity at baseline was 0.0 in both treatment groups (Table 5t). VAS score change from baseline at Treatment Day 1 Hour 4 was statistically significantly different in favor of the DPI-386 Nasal Gel arm (p=0.0221, MMRM). At Treatment Day 1 Hour 8, VAS score change from baseline was not statistically significantly different between treatment groups (p=0.0850, MMRM).

TABLE 5t

Summary of Nausea Assessment (Visual Analogue Scale, mm) (ITT Population)

| Time Point Statistic | DPI-386 Nasal Gel (N = 42) | Placebo Nasal Gel (N = 41) |
|---|---|---|
| Baseline | | |
| N | 41 | 41 |
| Mean (SD) | 1.0 (3.31) | 0.9 (1.79) |
| Median | 0.0 | 0.0 |
| Min, Max | 0, 15 | 0, 8 |
| Day 1 4-hour Post dose | | |
| N | 42 | 41 |
| Mean (SD) | 9.0 (18.60) | 22.1 (30.26) |
| Median | 1.0 | 4.0 |
| Min, Max | 0, 94 | 0, 100 |
| Day 1 4-hour Post dose change from baseline | | |
| N | 41 | 41 |
| Mean (SD) | 8.0 (19.10) | 21.2 (29.87) |
| Median | 1.0 | 2.0 |
| Min, Max | −15, 94 | −2, 100 |
| LSM (SE) | 8.081 (2.943) | 21.138 (4.733) |
| Treatment difference (95% CI) | −13.06 (−24.18, −1.93) | |
| P-value[1] | 0.0221 | |
| Day 1 8-hour Post dose | | |
| N | 42 | 41 |
| Mean (SD) | 2.5 (5.02) | 8.5 (20.89) |
| Median | 1.0 | 1.0 |
| Min, Max | 0, 22 | 0, 100 |
| Day 1 8-hour Post dose change from baseline | | |
| N | 41 | 41 |
| Mean (SD) | 1.5 (6.33) | 7.6 (20.37) |
| Median | 0.0 | 0.0 |
| Min, Max | −15, 22 | −4, 100 |
| LSM (SE) | 1.593 (0.799) | 7.529 (3.274) |
| Treatment difference (95% CI) | −5.935 (−12.72, 0.854) | |
| P-value[1] | 0.0850 | |

ITT = intent-to-treat;
max = maximum;
min = minimum;
SD = standard deviation;
VAS = visual analogue scale.
Note:
Analysis was based on Mixed Model of Repeated Measure (MMRM) including fixed effects of treatment, visit, and interaction term of treatment by visit.
Baseline value was included as a covariate in the model.
[1]Between-group p-value.
Source: Table 14.2.4.1, Table 14.2.4.2, Table 14.2.4.3

Other Efficacy Endpoint: Time to First Use of Rescue Medication

In the ITT population, 4 subjects (9.5%) in the DPI-386 Nasal Gel arm and 15 subjects (36.6%) in the Placebo Nasal Gel arm received rescue medication.

The difference between DPI-386 Nasal Gel and Placebo Nasal Gel in time to use of rescue medication was statistically significant in favor of DPI-386 Nasal Gel (p<0.0001, log rank test; Table 5u).

Figure 5B:
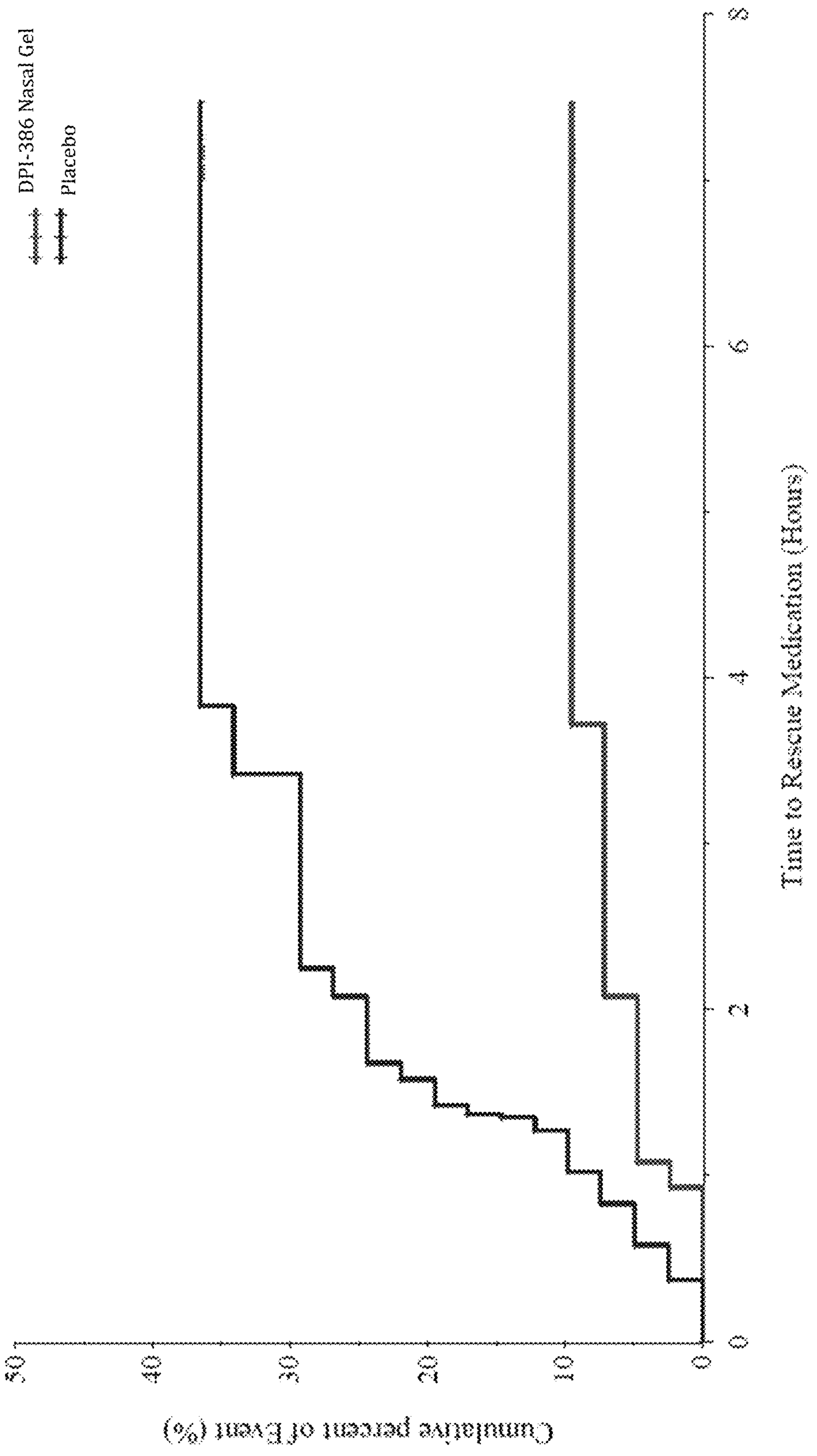
FIG. 5B is an illustration of a Kaplan-Meier plot of time to the first use of rescue medication, ITT population.
Figure 5C:
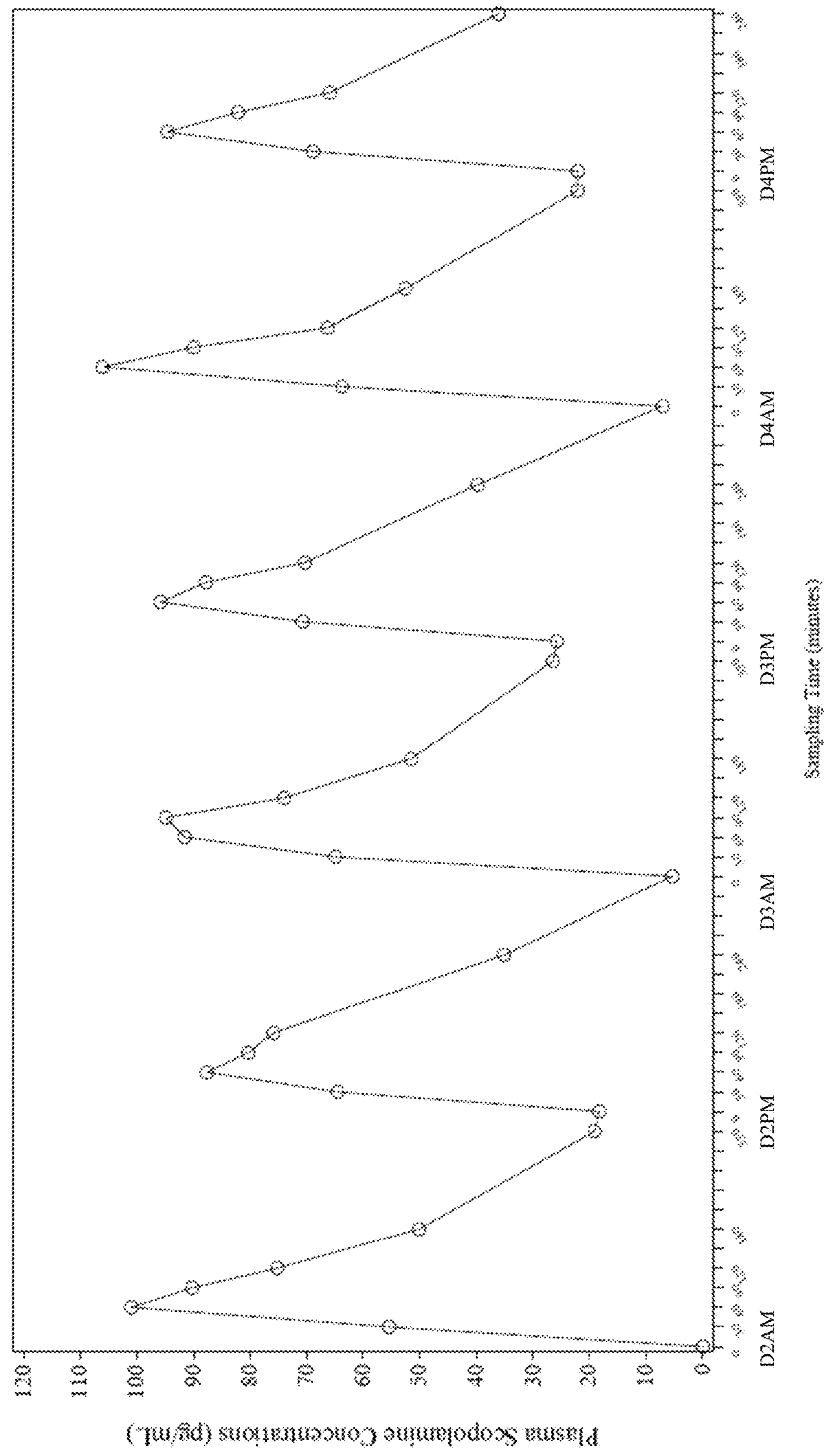
FIG. 5C is an illustration of the median plasma scopolamine concentration-time profiles following intranasal administration of 0.2 mg twice daily for 3 days. Session 1 (Day 1): Subjects were randomized (1:1) to receive DPI-386 or placebo nasal gel on Day 1; PK samples were not collected on Day 1. Session 2 (Days 2, 3, 4): Subjects received open-label DPI-386 Nasal Gel 0.2 mg twice daily for 3 days; PK samples were collected relative to each dose. Doses of nasal gel were administered 6 hours apart within each day and 18 hours apart between days. Session 2 was to take place within 30 days of Session 1.

A Kaplan-Meier plot of time to first use of rescue medication is presented in FIG. 5B.

TABLE 5u

Summary of Time to Rescue Medication (Hours) (ITT Population)

| Description | DPI-386 Nasal Gel (N = 42) | Placebo Nasal Gel (N = 41) |
|---|---|---|
| Number (%) of subjects with event (subjects who received rescue medication) | 4 (9.5) | 15 (36.6) |
| Number (%) of subjects censored | 38 (90.5) | 26 (63.4) |
| Time to event (hours) | | |
| 25th percentile (95% CI) | NE | 4.0 (2.3, 4.8) |
| Median (95% CI) | NE | NE |
| 75th percentile (95% CI) | NE | NE |
| Log-rank test p-value[1] | <0.0001 | |

CI = confidence interval;
ITT = Intent-to-Treat;
NE = not estimable;
MSAQ = Motion Sickness Assessment Questionnaire;
VAS = visual analogue scale.
Note:
Subjects without taking rescue medication during the study were censored at the time of the last VAS MSAQ assessment.
[1]Comparison vs Placebo group was performed using Log-rank test.
Source: Table 14.2.1.3

6.4.1.4. Post-hoc Efficacy Endpoint: Complete Response Rate at Day 1 Hour 4

In the post-hoc analysis of Complete Response rate at Treatment Day 1 Hour 4 in the ITT population, 38 subjects (90.5%) in the DPI-386 Nasal Gel arm and 26 subjects (63.4%) in the Placebo Nasal Gel arm were Complete Responders. The difference was statistically significant in favor of the DPI-386 Nasal Gel arm (nominal p=0.0041, Fishers Exact test; Table 5v).

TABLE 5v

Complete Response Rate Within Four Hours of First Study Drug Dose (ITT Population)

| Parameter | DPI-386 Nasal Gel (N = 42) | Placebo Nasal Gel (N = 41) |
|---|---|---|
| Complete response (subjects with no vomiting and no rescue medication), n (%) | 38 (90.5) | 26 (63.4) |
| 95% CI | (77.4, 97.3) | (46.9, 77.9) |
| Treatment difference, (%) (95% CI) | 27.1 (9.9, 44.3) | |
| P-value[1] | 0.0041 | |

CI = confidence interval;
ITT = intent-to-treat.
Note:
A Complete Responder is a subject who does not experience vomiting or require rescue medication within the first four hours of the first dose of study treatment on Treatment Day 1. The within 4 hours after receiving study drug window is from the time of the first dose to the time of the end of voyage.
[1]Fishers Exact test.
Source: Table 14.2.2.1

6.4.2. Statistical/Analytical Issues 6.4.2.1. Adjustments for Covariates

Not applicable.

6.4.2.2. Handling of Dropouts or Missing Data

There were 3 post-dose discontinuations/withdrawals during the study.

Subject No. 206 (Placebo Nasal Gel) was discontinued from the study due to a TEAE of atrial fibrillation (see Table of Errata, Table 50). Subject No. 216 (DPI-386 Nasal Gel) was discontinued from the study after dosing because the subject met an exclusion criterion that precluded further study participation.

Subject Nos. 226 (Placebo Nasal Gel) withdrew their consent after dosing on Day 1.

6.4.2.3. Interim Analysis and Data Monitoring

No interim analyses were planned or conducted for this study.

6.4.2.4. Multicenter Studies

This study was conducted at 2 centers.

6.4.2.5. Multiple Comparisons/Multiplicity

Not applicable.

6.4.2.6. Use of an "Efficacy Subset" of Subjects

The primary efficacy analysis is based on the ITT population. In the double-blind period the mITT population and PP population were the same as the ITT population.

6.4.2.7. Active-control Studies Intended to Show Equivalence

Not applicable.

6.4.2.8. Examination of Subgroups

Not applicable.

6.4.4. Drug Dose, Drug Concentration and Relationships to Response 6.4.4.1. PK Subject Accountability and Data Handling Overall, 98 subjects received DPI-386 Nasal Gel and underwent PK sampling and all subjects (100%) provided evaluable PK data for at least 1 of 6 doses. The reasons for excluding data from the concentration and/or PK summaries are provided in Table 5w.

TABLE 5w

Summary of Pharmacokinetic Data Handling

| Subject | Doses | PK Data Handling and Accountability Details |
|---|---|---|
| Subject 109 | Day 2 AM, Day 2 PM, Day 3 PM, Day 4 AM, Day 4 PM | Data were excluded from concentration and PK parameter summaries because all concentrations were BLOQ. |
| Subject CNS-110 | Day 3 AM | The actual time of the 30 min sample was prior to dosing; therefore, this sample was excluded from the concentration summary and from PK analysis. |
| Subject WRI-409 | Day 4 PM | The actual time of the 30 min sample was prior to dosing; therefore, this sample was excluded from the concentration summary and from PK analysis. |
| Subject 408 | Day 2 AM | Data were excluded from concentration and PK parameter summaries due to limited quantifiable concentrations (only two quantifiable concentrations). |
| Subject 306 | Day 4 AM, Day 4 PM | Data were excluded from concentration and PK parameter summaries due to limited quantifiable concentrations (only two quantifiable concentrations). |
| Subject 111 | Day 4 PM | Data were excluded from concentration and PK parameter summaries due to limited quantifiable concentrations (only two quantifiable concentrations). |

PK = pharmacokinetic

Nominal PK sampling times were used when the actual collection time was missing in the following 6 instances: Subject 403, Day 3 PM, 120 minutes; Subject 413, Day 3 AM, 330 minutes, Day 3 PM pre-dose (assigned 0) and 120 minutes; Subject 416, Day 2 PM, 120 minutes; and Subject 417, Day 3 PM, 90 minutes.

The following subjects sneezed after intranasal administration of scopolamine on a day with PK sampling: Subject 111 Day 2 PM dose, Subject 203 Day 2 PM dose, Subject 204 Day 4 PM dose, and Subject 205 Day 4 PM dose. Subject 418 also noted sneezing after intranasal administration of scopolamine, but the dose(s) after which sneezing occurred was not recorded. The 4 subjects with recorded data who sneezed all had measurable concentrations of scopolamine and so were included in the statistical analyses.

6.4.4.2. Scopolamine PK Profile after Intranasal Administration of 0.2 mg Twice Daily Scopolamine was rapidly absorbed following intranasal administration; median $t_{lag}$ was 0 hours (i.e., concentrations were quantifiable at the first [30-minute] sampling time point) and median $t_{max}$ ranged from 56 to 60 minutes across doses. Scopolamine concentrations did not accumulate with twice daily dosing as demonstrated by the similar concentration time profiles and PK parameter values across the 6 doses (FIG. 5C, Table 5x).

Arithmetic mean and CV % results for each of the 6 doses for $AUC_{0-6}$, $AUC_{0-t}$, and $C_{max}$ are summarized in Table 5y. This information is included to enable comparisons between arithmetic mean and geometric mean scopolamine concentration-time data.

TABLE 5x

Summary of Scopolamine Pharmacokinetic Parameters Following Intranasal Administration of 0.2 mg Twice Daily

| | Geometric Mean (GM CV %) | | | Median (Min, Max) | | | |
|---|---|---|---|---|---|---|---|
| Timepoint | $AUC_{(0-t)}$[a] (min*pg/mL) | $AUC_{(0-6\ h)}$[b] (min*pg/mL) | $C_{max}$ (pg/mL) | $C_{330\ min}$ (pg/mL) | $t_{1/2}$[b] (min) | $t_{max}$[c] (min) | $t_{lag}$ (min) |
| Day 2 AM | 14,501 (150) [N = 96] | 17,358 (106) [N = 78] | 94.7 (154) [N = 97] | 18.9 (2.1, 325) [N = 92] | 91.7 (44.5, 274) [N = 78] | 58 (0, 321) [N = 97] | 0 (0, 32) |
| Day 2 PM | 14,009 (117) [N = 96] | — | 102 (133) [N = 96] | — | — | 60 (0, 242) [N = 96] | 0 (0, 0) |
| Day 3 AM | 15,041 (145) [N = 98] | 17,642 (109) [N = 71] | 91.3 (152) [N = 98] | 26.5 (2.4, 148) [N = 95] | 110 (62.8, 399) [N = 71] | 56 (0, 330) [N = 98] | 0 (0, 18) |
| Day 3 PM | 12,932 (128) [N = 97] | — | 89.7 (134) [N = 97] | — | — | 59 (0, 230) [N = 97] | 0 (0, 31) |
| Day 4 AM | 15,608 (110) [N = 95] | 17,375 (90) [N = 77] | 94.5 (126) [N = 96] | 22.1 (2.2, 128) [N = 96] | 112 (52.0, 318) [N = 77] | 60 (0, 180) [N = 96] | 0 (0, 0) |
| Day 4 PM | 13,267 (130) [N = 95] | — | 83.6 (168) [N = 97] | — | — | 60 (0, 240) [N = 97] | 0 (0, 60) |

AUC = area under the curve; $C_{330}$ = concentration at 330 minutes; $C_{max}$ = maximum plasma concentration; CV % = percent coefficient of variance; GM = geometric mean; max = maximum; min = minimum; PK = pharmacokinetic; $t_{1/2}$ = terminal half-life; $t_{lag}$ = time to drug appearance in plasma; $t_{max}$ = time of maximum plasma concentration

[a]$AUC_{(0-t)}$: PK sampling for AM doses: pre-dose, 30, 60, 90, 120, 180, 330 minutes; PK sampling for PM doses: pre-dose, 30, 60, 90, 120, 240 minutes.

[b]$AUC_{(0-6\ h)}$ and $t_{1/2}$ were not estimated for PM doses due to the limited PK sampling schedule.

cThere were 15/581 (2.6%) instances where $t_{max}$ = 0. Five instances were for AM doses and 10 instances were for PM doses. For PM doses, the 330-minute PK sample collected after the AM dose was used as the pre-dose sample.

Notes:

Session 1 (Day 1): Subjects were randomized (1:1) to receive DPI-386 Nasal Gel or Placebo Nasal Gel on Day 1; PK samples were not collected on Day 1.

Session 2 (Days 2, 3, 4): Subjects received open-label DPI-386 Nasal Gel 0.2 mg twice daily for 3 days; PK samples were collected relative to each dose. Doses of nasal gel were administered 6 hours apart within each day and 18 hours apart between days. Session 2 was to take place within 30 days of Session 1.

Source: Table 14.2.1, Table 14.2.2

TABLE 5y

Summary of Arithmetic Mean (CV %) Scopolamine Pharmacokinetic Parameters Following Intranasal Administration of 0.2 mg Twice Daily

| | Arithmetic Mean CV %) | | |
|---|---|---|---|
| Timepoint | $AUC_{(0-t)}$[a] (min*pg/mL) | $AUC_{(0-6\ h)}$[b] (min*pg/mL) | $C_{max}$ (pg/mL) |
| Day 2 AM | 21.6 (80) [N = 96] | 23.171 (71) [N = 78] | 145 (80) [N = 97] |
| Day 2 PM | 20.013 (84) [N = 96] | — | 154 (87) [N = 96] |
| Day 3 AM | 22.012 (69) [N = 98] | 23.632 (63) [N = 71] | 139 (78) [N = 98] |
| Day 3 PM | 18.834 (78) [N = 97] | — | 133 (79) [N = 97] |
| Day 4 AM | 21.010 (67) [N = 95] | 22.091 (62) [N = 77] | 132 (68) [N = 96] |
| Day 4 PM | 19.549 (79) [N = 95] | — | 135 (83) [N = 97] |

AUC = area under the curve;

$C_{max}$ = maximum plasma concentration;

CV % = percent coefficient of variance.

[a]$AUC_{(0-t)}$: PK sampling for AM doses: pre-dose, 30, 60, 90, 120, 180, 330 minutes; PK sampling for PM doses: pre-dose, 30, 60, 90, 120, 240 minutes.

[b]$AUC_{(0-6\ h)}$ was not estimated for PM doses due to the limited PK sampling schedule.

Notes:

Session 1 (Day 1): Subjects were randomized (1:1) to receive DPI-386 Nasal Gel or Placebo Nasal Gel on Day 1; PK samples were not collected on Day 1.

Session 2 (Days 2, 3, 4): Subjects received open-label DPI-386 Nasal Gel 0.2 mg twice daily for 3 days; PK samples were collected relative to each dose. Doses of nasal gel were administered 6 hours apart within each day and 18 hours apart between days. Session 2 was to take place within 30 days of Session 1.

Source: Table 14.2.1, Table 14.2.2

6.4.4.3. Comparison of Scopolamine Pharmacokinetics Between Males and Females

Figure 5D:
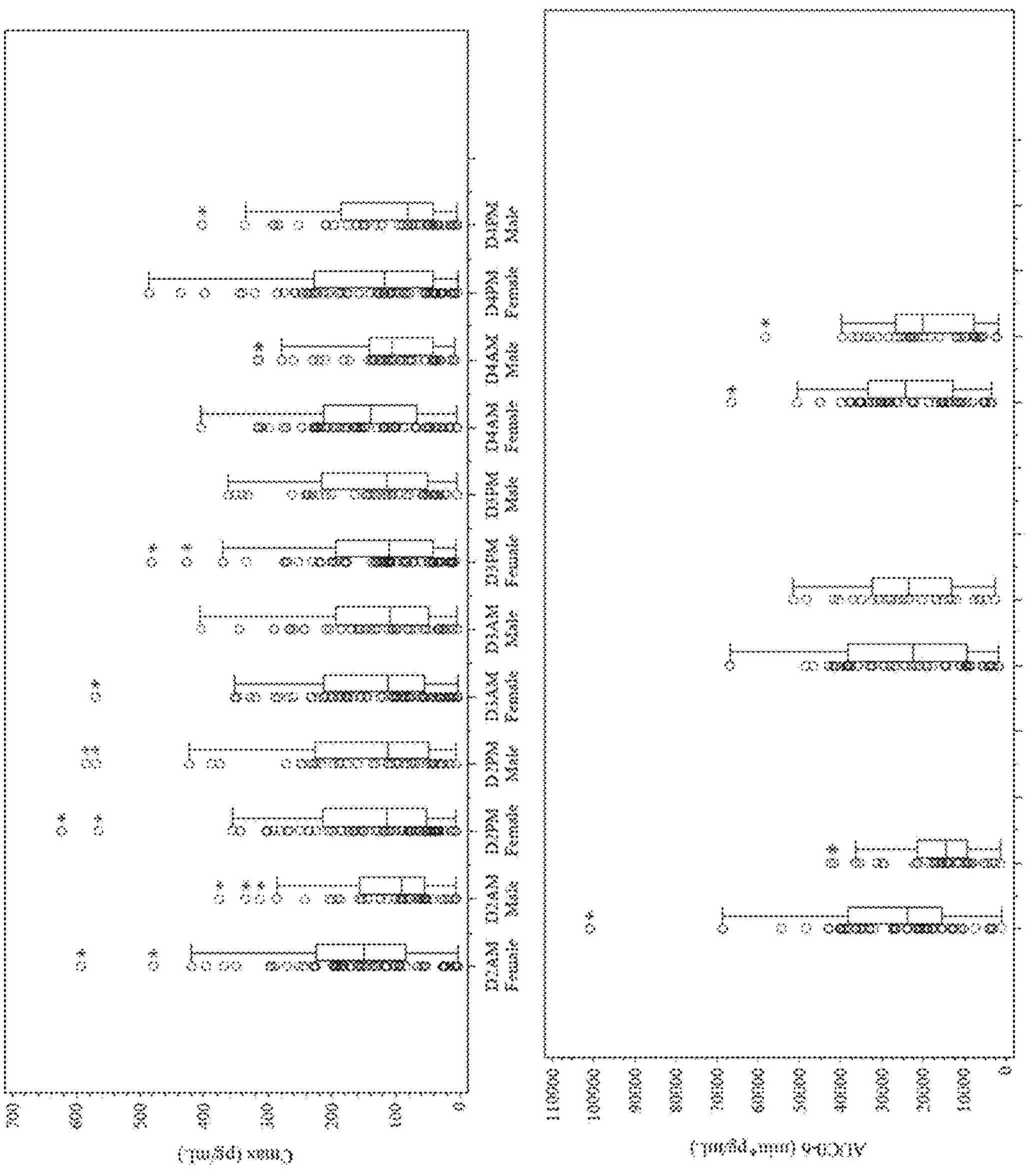
FIG. 5D is an illustration of a comparison of scopolamine pharmacokinetic exposure by gender following intranasal administration of 0.2 mg twice daily. The center horizontal line is drawn at the 50th percentiles (median). By default, the vertical lines, or whiskers, extend from the box as far as the data extend, to a distance of at most 1.5 interquartile ranges (an interquartile range is the distance between the 25th and the 75th sample percentiles). Any individual value (circle) more extreme than this is marked with the star symbol.
Figure 5E:
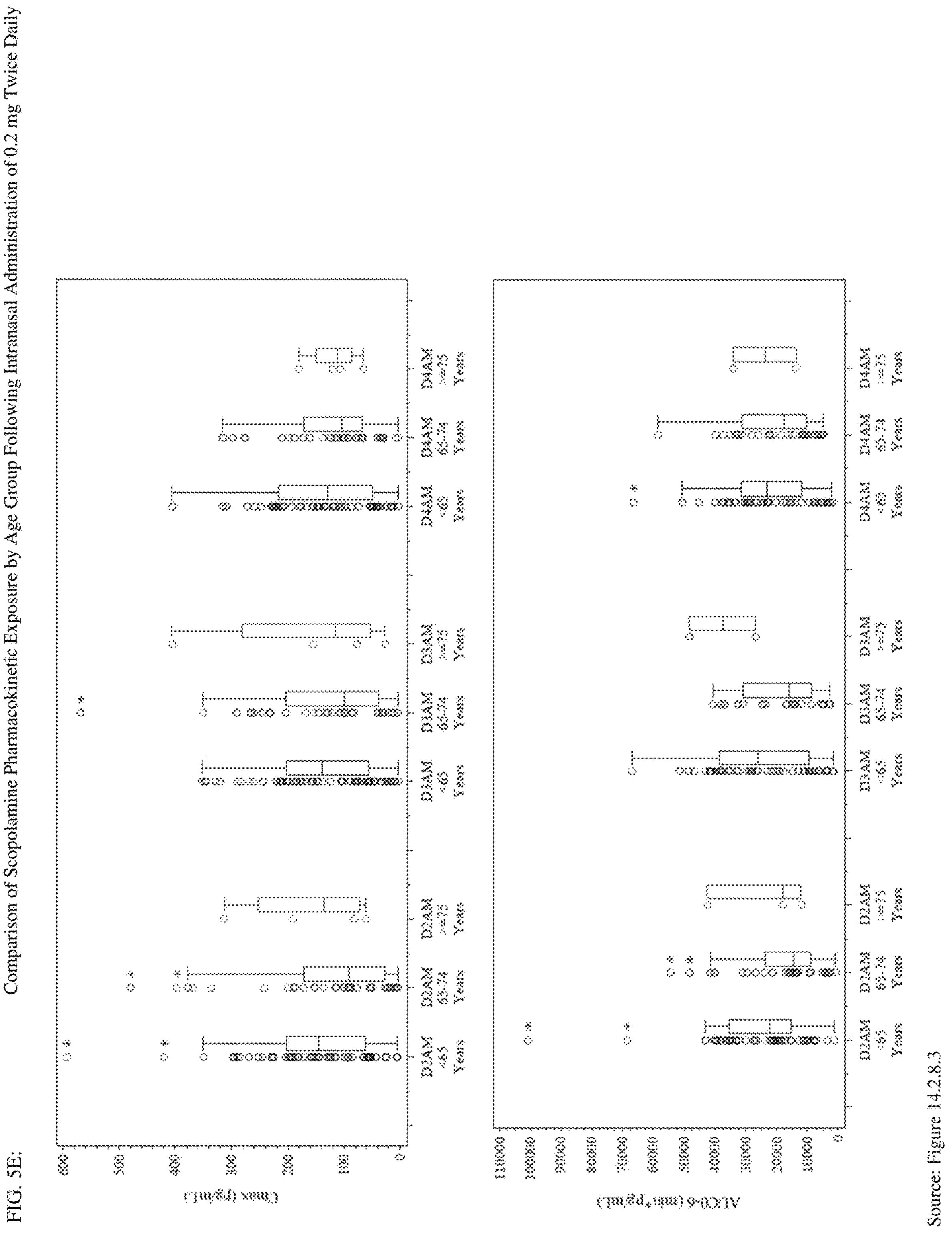
FIG. 5E is an illustration of a comparison of scopolamine pharmacokinetic exposure by age group following intranasal administration of 0.2 mg twice daily. The center horizontal line is drawn at the 50th percentiles (median). By default, the vertical lines, or whiskers, extend from the box as far as the data extend, to a distance of at most 1.5 interquartile ranges (an interquartile range is the distance between the 25th and the 75th sample percentiles). Any individual value (circle) more extreme than this is marked with the star symbol.
Figure 5F:
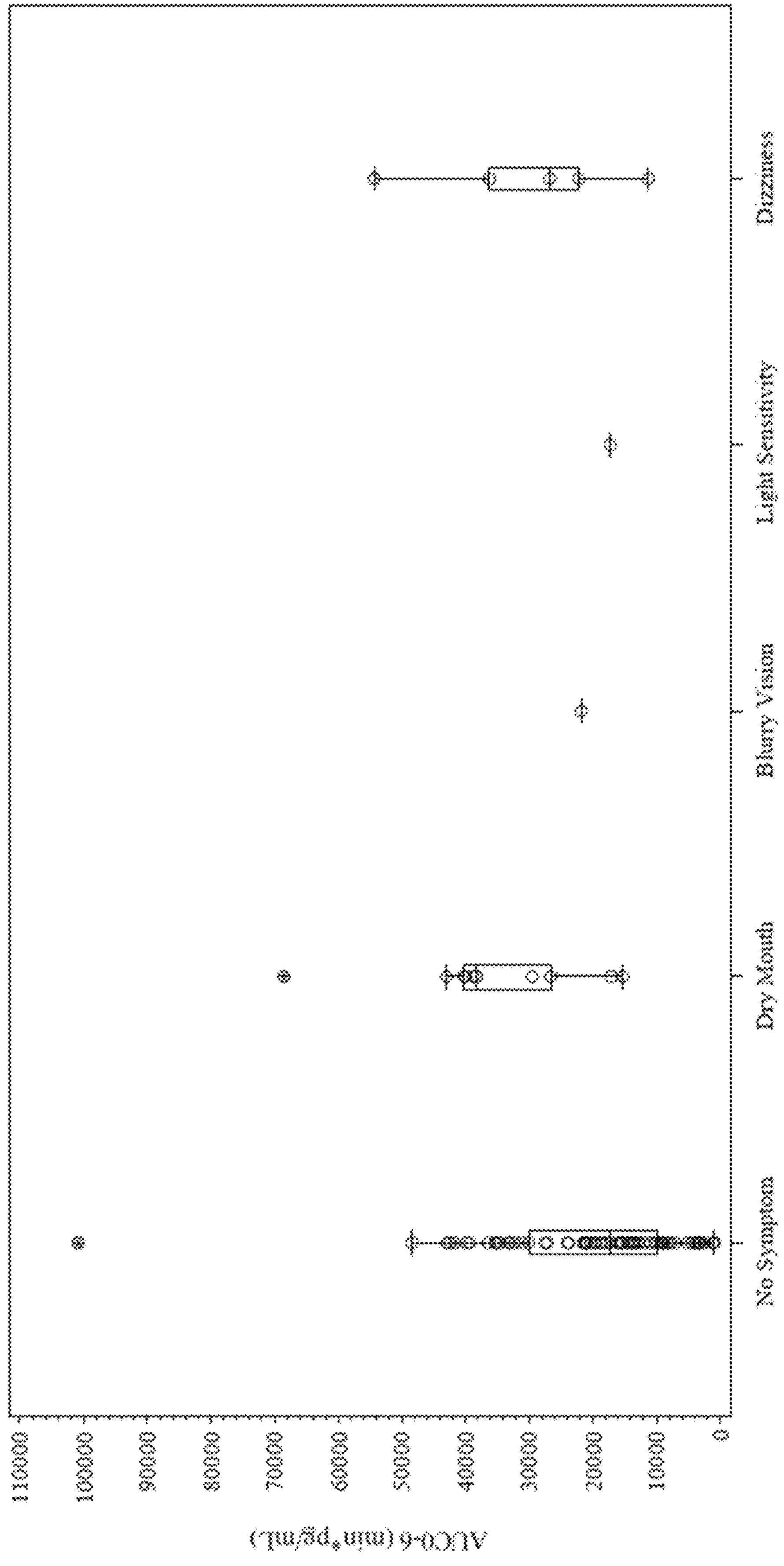
FIG. 5F is an illustration of a box plot of subjects with and without acts symptoms and the Day 2 (am) scopolamine pK parameter $AUC_{0-6}$ (min*pg/ml). Scopolamine PK Parameters on Day 2 AM from all subjects were used in the analysis.
Figure 5G:
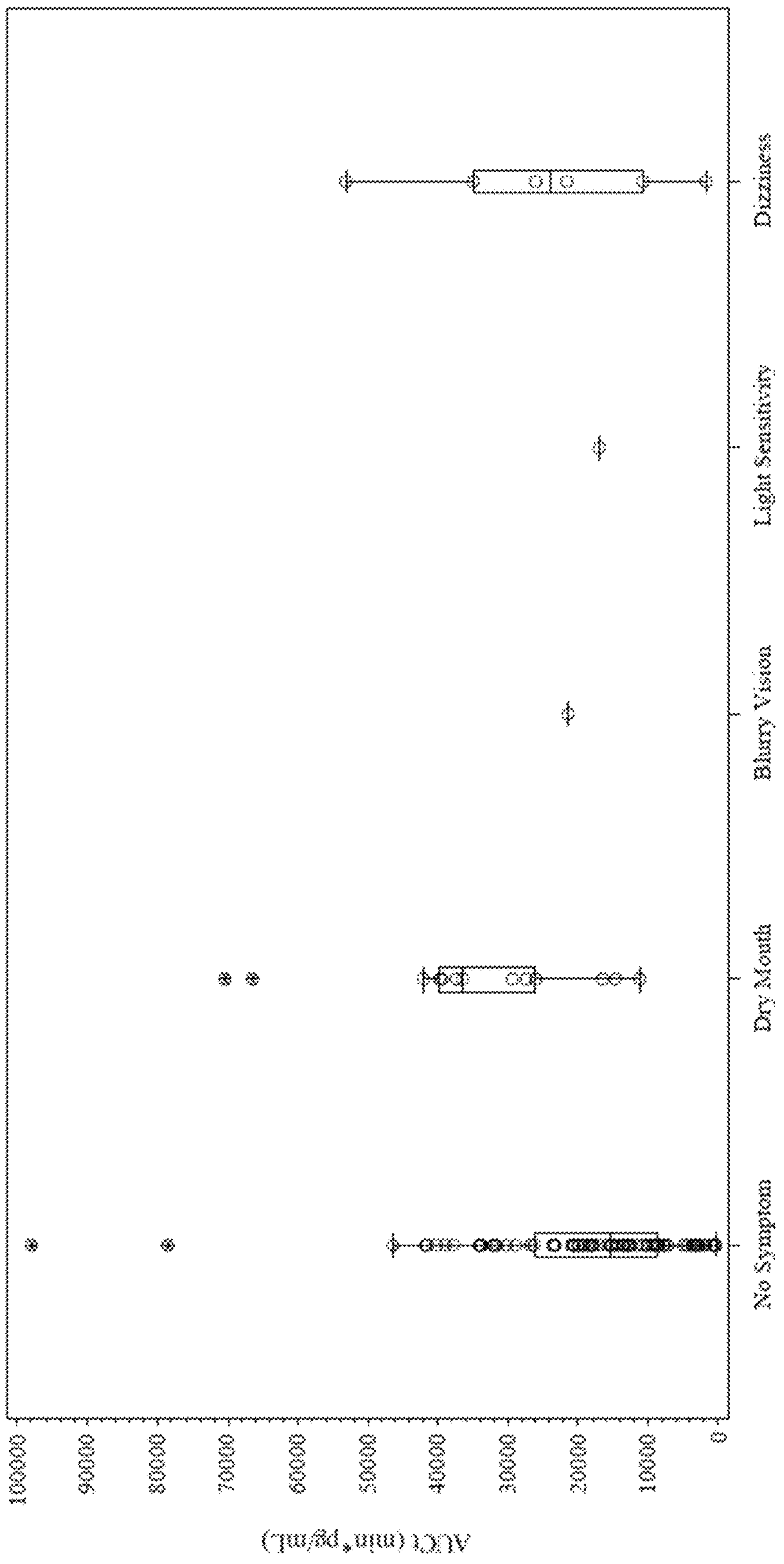
FIG. 5G is an illustration of a box plot of subjects with and without acts symptoms and the Day 2 (am) scopolamine pK parameter $AUC_t$ (min*pg/ml). Scopolamine PK Parameters on Day 2 AM from all subjects were used in the analysis.
Figure 5H:
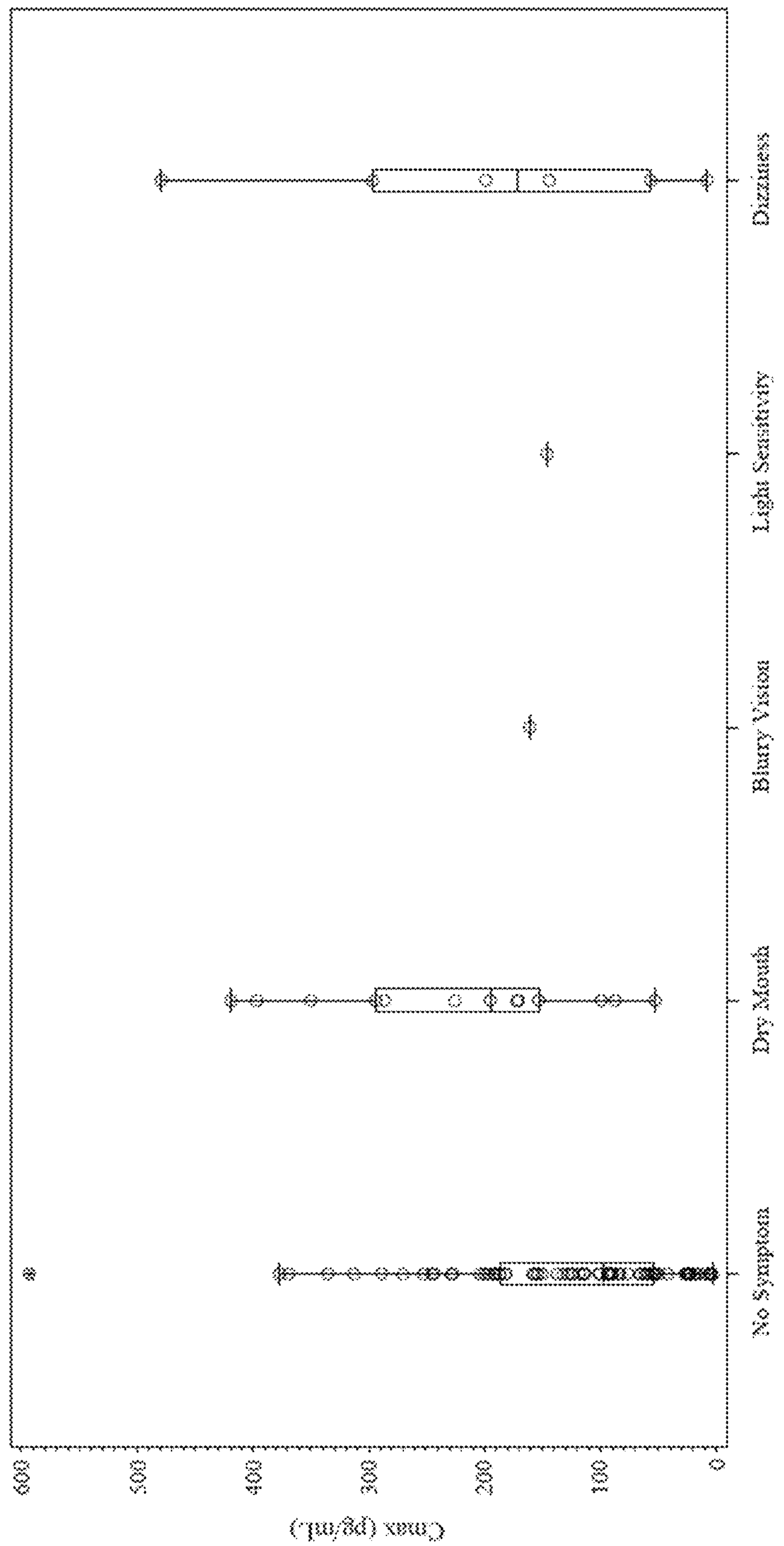
FIG. 5H is an illustration of a box plot of subjects with and without acts symptoms and the day 2 (am) scopolamine pK parameter $C_{max}$ (pg/ml). Scopolamine PK Parameters on Day 2 AM from all subjects were used in the analysis.

Following intranasal administration, scopolamine geometric mean $C_{max}$, $AUC_{0-t}$, and $AUC_{0-6}$ values, and median $t_{1/2}$ estimates were similar between male and female subjects (FIG. 5D.

6.4.4.4. Evaluation of the Impact of Age on Scopolamine Pharmacokinetics

Following intranasal administration, scopolamine geometric mean $C_{max}$, $AUC_{0-t}$, and $AUC_{0-6}$ values, and median $t_{1/2}$ estimates were similar among the age groups of <65, 65 to 74, and ≥75 years (FIG. 5E) and across the studied age range of 54 to 80 years.

6.4.4.5. Evaluation of the Relationship Between Anticholinergic Toxicity Screen Symptoms and Scopolamine Pharmacokinetic Parameters Box plots exploring the relationship between the occurrence of ACTS AEs and the 3 PK scopolamine parameters of $AUC_{0-6}$, $AUC_t$, and $C_{max}$ are presented in FIG. 5F, FIG. 5G, and FIG. 5H, respectively. Descriptive statistics of all 3 PK parameter values from the Day 2 morning dose are provided.

Seventy-six subjects reported no ACTS symptoms, and 13 and 6 subjects, respectively, reported ACTS AEs of dry mouth and dizziness. Single instances of blurry vision and light sensitivity were reported.

For the 13 subjects who had dry mouth, the upper and lower 95% CI values for $C_{max}$ were higher than and did not overlap with the upper and lower 95% CI values of the 76 subjects who had no ACTS events, so it can be concluded that higher plasma levels of scopolamine are associated with the occurrence of dry mouth, a known side effect of scopolamine.

For the 6 subjects with dizziness, the upper and lower 95% CI values for $C_{max}$ overlapped with that of the 76 subjects who reported no ACT symptoms, so in this small sample size there was no association between scopolamine plasma levels and the occurrence of dizziness.

6.4.5. Drug-Drug and Drug-Disease Interactions

Not applicable.

6.4.6. By-Subject Displays

Not applicable.

6.4.7. Efficacy Conclusions

DPI-386 Nasal Gel was demonstrated to be superior to Placebo Nasal Gel in the prevention of nausea associated with motion sickness in older subjects when assessed using several efficacy endpoints, including the proportion of subjects who developed motion sickness and requested rescue medication (the primary endpoint), the severity of nausea at Treatment Day 1 Hour 4 as assessed using a VAS, the time to use of rescue medication, and in a post-hoc analysis of Complete Response rate.

7. Safety Evaluation 7.1. Extent of Exposure

A total of 101 subjects (83 randomized across 2 treatment arms in the double-blind period and an additional 18 subjects with or without motion sickness susceptibility who received DPI-386 Nasal Gel in the open-label period in a clinic setting (for an evaluation of safety) were enrolled in the study.

All the subjects received study treatment as per protocol.

7.2. Adverse Events 7.2.1. Brief Summary of Adverse Events

The primary safety endpoint was the subject incidence of TEAEs while on study treatment.

An overall summary of TEAEs is provided in Table 5z. No SAEs or deaths occurred during the study. One subject in the Placebo Nasal Gel group was discontinued from the study due to an AE of atrial fibrillation.

7.2.1.1. Double-blind Period

In the double-blind period of the study, 15 subjects (35.7%) in the DPI-386 Nasal Gel treatment group reported 27 TEAEs and 29 subjects (70.7%) in the Placebo Nasal Gel treatment group reported 41 TEAEs. The majority of TEAEs in both treatment groups were not related to administration of study drug (19 of 27 TEAEs in the DPI-386 Nasal Gel arm and 36 of 41 TEAEs in the Placebo Nasal Gel arm). The majority of TEAEs in both treatment groups were mild in intensity (23 of 27 TEAEs in the DPI-386 Nasal Gel arm and 24 of 41 TEAEs in the Placebo Nasal Gel arm). There were no TEAEs of severe intensity nor were there any SAEs in either treatment group.

Four subjects (9.5%) in the DPI-386 Nasal Gel treatment group and 15 subjects (36.6%) in the Placebo Nasal Gel treatment group had TEAEs that led to a request for rescue administration of DPI-386 Nasal Gel.

Seven AESIs were reported by 6 subjects (14.3%) while receiving DPI-386 Nasal Gel and 5 AESIs were reported by 4 subjects (9.8%) while receiving Placebo Nasal Gel.

7.2.1.2. Open-Label Period

Seventeen subjects (17.3%) reported 22 TEAEs during the open-label period of the study, when all subjects received DPI-386 Nasal Gel (N=98). The majority of TEAEs were related to administration of DPI-386 Nasal Gel (14 of 22 TEAEs). All reported TEAEs (n=22) were mild in intensity. No SAEs were reported.

No subject had a TEAE that led to a request for rescue administration of DPI-386 Nasal Gel.

Fourteen AESIs were reported by 12 subjects (12.2%).

7.2.1.3. Subjects Who Received at Least One Dose of DPI-386 Nasal Gel

A total of 49 TEAEs were reported by 28 of the 99 subjects (28.3%) who received at least one dose of DPI-386 Nasal Gel at any time during the study. Eighteen subjects (18.2%) had 27 TEAEs that were considered by the investigator to be unrelated to treatment with DPI-386 Nasal Gel and 16 subjects (16.2%) had 22 TEAEs that were related to treatment.

Forty-five of the 49 TEAEs (91.8%) reported by subjects were mild in intensity and 4 TEAEs (8.2%) were moderate in intensity.

Four subjects (4.0%) had a TEAE that led to a request for rescue administration of DPI-386 Nasal Gel. All of the TEAEs occurred during the double-blind period of the study.

Twenty-one AESIs were reported by 17 subjects (17.2%).

TABLE 5z

Summary of Treatment-Emergent Adverse Events (Safety Population)

| Parameter | Statistic | DPI-386 Nasal Gel (N = 42) | Placebo Nasal Gel (N = 41) | Open-label DPI-386 Nasal Gel (N = 98) | At Least One DPI-386 Nasal Gel (N = 99) |
|---|---|---|---|---|---|
| All TEAEs (subjects with at least one TEAE) | n (%) E | 15 (35.7) 27 | 29 (70.7) 41 | 17 (17.3) 22 | 28 (28.3) 49 |
| Relationship of TEAEs to IMP | | | | | |
| Not related | n (%) E | 14 (33.3) 19 | 29 (70.7) 36 | 6 (6.1) 8 | 18 (18.2) 27 |
| Related | n (%) E | 6 (14.3) 8 | 3 (7.3) 5 | 11 (11.2) 14 | 16 (16.2) 22 |
| Severity of TEAEs | | | | | |
| Mild | n (%) E | 14 (33.3) 23 | 18 (43.9) 24 | 17 (17.3) 22 | 27 (27.3) 45 |
| Moderate | n (%) E | 4 (9.5) 4 | 13 (31.7) 17 | 0 (0.0) 0 | 4 (4.0) 4 |
| Severe | n (%) E | 0 (0.0) 0 | 0 (0.0) 0 | 0 (0.0) 0 | 0 (0.0) 0 |
| TEAEs leading to Rescue DPI-386 Nasal Gel | n (%) E | 4 (9.5) 4 | 15 (36.6) 19 | 0 (0.0) 0 | 4 (4.0) 4 |
| Subjects with at least one AESI in TEAE | n (%) E | 6 (14.3) 7 | 4 (9.8) 5 | 12 (12.2) 14 | 17 (17.2) 21 |
| Subjects with at least one SAE | n (%) E | 0 (0.0) 0 | 0 (0.0) 0 | 0 (0.0) 0 | 0 (0.0) 0 |

AESI = adverse event of special interest;
IMP = investigational medicinal treatment;
SAE = serious adverse event;
TEAE = treatment-emergent adverse event.
See also Table of Errata, Table 5o.
E: Number of events;
N: Number of subjects dosed with each treatment;
n: Number of subjects with adverse event with particular category;
%: Calculated using the number of subjects treated with each treatment as the denominator (n/N) * 100.
Source: Table 14.3.1.1

7.2.2. Display of Adverse Events

TEAEs are summarized by SOC and preferred term in Table 5aa.

In the double-blind period the most common TEAE in both treatment groups was motion sickness, which was reported by 13 subjects (31.0%) in the DPI-386 Nasal Gel arm and by 25 subjects (61.0%) in the Placebo Nasal Gel arm. The second most common TEAE in the DPI-386 Nasal Gel arm was dry mouth (6 subjects, 14.3%) and the second most common TEAEs in the Placebo Nasal Gel arm were dry mouth and vomiting (3 subjects each, 7.3%). No subject in the DPI-386 Nasal Gel arm reported nausea or vomiting. Two subjects (4.9%) in the Placebo Nasal Gel arm reported nausea.

In the open-label period the most common TEAE was dry mouth (9 subjects, 9.2%). Three subjects (3.1%) reported headache and 3 subjects (3.1%) reported dizziness. Two subjects (2.0%) reported TEAEs of blurred vision. One subject (1.0%) reported one episode of nausea and 1 subject (1.0%) reported 2 episodes of vomiting. All other TEAEs in the open-label period were reported by only 1 subject (1.0%).

Of the subjects who received at least one dose of DPI-386 Nasal Gel at any time during the study (N=99), the most common TEAE reported while receiving DPI-386 Nasal Gel was dry mouth (14 subjects, 14.1%), followed by motion sickness (13 subjects, 13.1%), headache (4 subjects, 4.0%), dizziness (3 subjects, 3.0%), and blurred vision (2 subjects, 2.0%). All other TEAEs in subjects who received at least one dose of DPI-386 Nasal Gel were reported in only 1 subject (1.0%).

TABLE 5aa

Summary of Adverse Events by System Organ Class and Preferred Term (Safety Population)

| System Organ Class Preferred Term | Statistic | DPI-386 Nasal Gel (N = 42) | Placebo Nasal Gel (N = 41) | Open-label DPI-386 Nasal Gel (N = 98) | At Least One DPI-386 Nasal Gel (N = 99) |
|---|---|---|---|---|---|
| Cardiac disorders | n (%) E | 0 (0.0) 0 | 1 (2.4) 1 | 0 (0.0) 0 | 0 (0.0) 0 |
| Atrial fibrillation | n (%) E | 0 (0.0) 0 | 1 (2.4) 1 | 0 (0.0) 0 | 0 (0.0) 0 |
| Ear and labyrinth disorders | n (%) E | 13 (31.0) 15 | 25 (61.0) 26 | 0 (0.0) 0 | 13 (13.1) 15 |
| Motion sickness | n (%) E | 13 (31.0) 15 | 25 (61.0) 26 | 0 (0.0) 0 | 13 (13.1) 15 |
| Eye disorders | n (%) E | 1 (2.4) 1 | 0 (0.0) 0 | 0 (0.0) 0 | 1 (1.0) 1 |
| Photophobia | n (%) E | 1 (2.4) 1 | 0 (0.0) 0 | 0 (0.0) 0 | 1 (1.0) 1 |
| Gastrointestinal disorders | n (%) E | 6 (14.3) 6 | 7 (17.1) 8 | 11 (11.2) 13 | 16 (16.2) 19 |
| Constipation | n (%) E | 0 (0.0) 0 | 0 (0.0) 0 | 1 (1.0) 1 | 1 (1.0) 1 |
| Dry mouth | n (%) E | 6 (14.3) 6 | 3 (7.3) 3 | 9 (9.2) 9 | 14 (14.1) 15 |
| Nausea | n (%) E | 0 (0.0) 0 | 2 (4.9) 2 | 1 (1.0) 1 | 1 (1.0) 1 |
| Vomiting | n (%) E | 0 (0.0) 0 | 3 (7.3) 3 | 1 (1.0) 2 | 1 (1.0) 2 |
| General disorders and administration site conditions | n (%) E | 1 (2.4) 1 | 0 (0.0) 0 | 0 (0.0) 0 | 1 (1.0) 1 |
| Fatigue | n (%) E | 1 (2.4) 1 | 0 (0.0) 0 | 0 (0.0) 0 | 1 (1.0) 1 |
| Nervous system disorders | n (%) E | 2 (4.8) 2 | 1 (2.4) 1 | 5 (5.1) 5 | 6 (6.1) 7 |
| Headache | n (%) E | 1 (2.4) 1 | 1 (2.4) 1 | 3 (3.1) 3 | 4 (4.0) 4 |
| Somnolence | n (%) E | 1 (2.4) 1 | 0 (0.0) 0 | 0 (0.0) 0 | 1 (1.0) 1 |
| Vision blurred | n (%) E | 0 (0.0) 0 | 0 (0.0) 0 | 2 (2.0) 2 | 2 (2.0) 2 |
| Respiratory, thoracic and mediastinal disorders | n (%) E | 2 (4.8) 2 | 2 (4.9) 2 | 0 (0.0) 0 | 2 (2.0) 2 |
| Nasal discomfort | n (%) E | 1 (2.4) 1 | 2 (4.9) 2 | 0 (0.0) 0 | 1 (1.0) 1 |
| Rhinalgia | n (%) E | 1 (2.4) 1 | 0 (0.0) 0 | 0 (0.0) 0 | 1 (1.0) 1 |
| Skin and subcutaneous tissue disorders | n (%) E | 0 (0.0) 0 | 1 (2.4) 1 | 1 (1.0) 1 | 1 (1.0) 1 |
| Erythema | n (%) E | 0 (0.0) 0 | 1 (2.4) 1 | 0 (0.0) 0 | 0 (0.0) 0 |
| Pruritus | n (%) E | 0 (0.0) 0 | 0 (0.0) 0 | 1 (1.0) 1 | 1 (1.0) 1 |
| Vascular disorders | n (%) E | 0 (0.0) 0 | 1 (2.4) 2 | 3 (3.1) 3 | 3 (3.0) 3 |
| Dizziness | n (%) E | 0 (0.0) 0 | 1 (2.4) 2 | 3 (3.1) 3 | 3 (3.0) 3 |

Medical Dictionary for Regulatory Activities (MedDRA) version 23.1

E: Number of events; N: Number of subjects dosed with each treatment; n: Number of subjects with adverse event with particular category; %: Calculated using the number of subjects treated with each treatment as the denominator (n/N)*100.

Source: Table 14.3.1.2

7.2.3. Analysis of Adverse Events 7.2.3.1. Double-Blind Period

In the double-blind period, a smaller proportion of subjects in the DPI-386 Nasal Gel arm reported at least one TEAE (35.7% vs. 70.7% of subjects in the Placebo Nasal Gel arm). In that period a larger proportion of subjects in the DPI-386 Nasal Gel arm had a treatment-related TEAE (14.3% vs 7.3% of subjects in the Placebo Nasal Gel arm) (Table 5z).

TEAEs reported in the double-blind period were generally of lower intensity in subjects in the DPI-386 Nasal Gel arm: 33.3% of subjects receiving DPI-386 Nasal Gel and 43.9% of subjects receiving Placebo Nasal Gel had a mild TEAE; 9.5% of subjects receiving DPI-386 Nasal Gel and 31.7% of subjects receiving Placebo Nasal Gel had a moderate TEAE. No severe TEAEs were reported by subjects in any treatment group.

A smaller proportion of subjects in the DPI-386 Nasal Gel arm had a TEAE that led to a request for rescue treatment with DPI-386 Nasal Gel (9.5% vs. 36.6% of subjects in the Placebo Nasal Gel arm).

AESIs occurred slightly more frequently in subjects in the DPI-386 Nasal Gel arm (14.3% vs. in 9.8% of subjects in the Placebo Nasal Gel arm). See Section 7.3.1.3 for a discussion of AESIs.

The TEAEs that occurred during the double-blind period of the study fit well with the treatment received in that period (DPI-386 Nasal Gel or Placebo Nasal Gel). The most common TEAE in both treatment groups was motion sickness, but this event occurred less frequently in the DPI-386 Nasal Gel arm than in the Placebo Nasal Gel arm (31.0% vs.

61.0%; Table 5aa). The second most common TEAE was dry mouth, but this event occurred more frequently in the DPI-386 Nasal Gel arm than in the Placebo Nasal Gel arm (14.3% vs. 7.3%). Nausea and vomiting did not occur in DPI-386 Nasal Gel-treated subjects, but were reported in 4.9% and 7.3%, of subjects, respectively, who received Placebo Nasal Gel.

In the double-blind period the causality assessment was judged as not related to IMP for 55 TEAEs and related to IMP for 13 TEAEs (Table 5z). Although motion sickness was the most common TEAE in both treatment groups, none of those events were considered by the investigator to be related to treatment with study drug. Dry mouth was the second most common TEAE reported in the double-blind period of the study, and in 5 of the 6 subjects in the DPI-386 Nasal Gel arm the event was determined to be related to treatment with study drug. In 1 of the 3 subjects in the Placebo Nasal Gel arm who had dry mouth, the event was related to treatment with study drug. The events of nausea and vomiting reported by subjects in the Placebo Nasal Gel arm were not related to treatment with study drug. TEAEs in the double-blind period are summarized by causality.

Fourteen subjects (33.3%) in the DPI-386 Nasal Gel arm had 23 TEAEs that were mild in intensity and 4 subjects (9.5%) had 4 TEAEs that were moderate in intensity (Table 5z). Eighteen subjects (43.9%) in the Placebo Nasal Gel arm had 24 TEAEs that were mild in intensity and 13 subjects (31.7%) had 17 TEAEs that were moderate in intensity. No TEAE in either treatment group was severe. TEAEs are summarized by intensity.

The TEAEs occurring in >10% of subjects are summarized by preferred term. In the double-blind period of the study, the incidence of motion sickness was 31.0% in the DPI-386 Nasal Gel arm and 61.0% in the Placebo Nasal Gel arm. The incidence of dry mouth was 14.3% in the DPI-386 Nasal Gel arm and 7.3% in the Placebo Nasal Gel arm.

Related TEAEs occurring in >10% of subjects are summarized by preferred term. In the double-blind period of the study, the incidence of dry mouth that was considered to be related to treatment with study drug was 11.9% in the DPI-386 Nasal Gel arm and 2.4% in the Placebo Nasal Gel arm.

Overall, the TEAEs that were reported in the double-blind period of the study were consistent with the AE profile of scopolamine and no new AE safety signals were observed.

7.2.3.2. Open-Label Period

Seventeen subjects (17.3%) reported 22 TEAEs in the open-label period of the study. Eleven of those subjects (11.2%) had a TEAE that the investigator considered to be related to administration of DPI-386 Nasal Gel (Table 5z).

All TEAEs reported in the open-label period were mild in intensity.

No subject in the open-label period had a TEAE that led to a request for rescue treatment with DPI-386 Nasal Gel.

Twelve subjects (12.2%) reported 14 AESIs in the open-label period of the study. See Section 7.3.1.3 for a discussion of AESIs.

The TEAEs that occurred during the open-label period of the study fit well with the treatment received in that period (DPI-386 Nasal Gel). The most common TEAE during this period was dry mouth (9 subjects, 9.2%; Table 5aa). The next most common TEAE was headache (3 subjects, 3.1%), followed by blurred vision and dizziness (2 subjects each, 2.0%).

In the open-label period, the causality assessment was judged as not related to treatment with DPI-386 Nasal Gel for 8 TEAEs reported by 6 subjects (6.1%) and related to treatment for 14 TEAEs reported by 11 subjects (11.2%; Table 5z). Dry mouth was the most common TEAE reported in the open-label period of the study, and in 8 of the 9 subjects who had dry mouth the event was determined to be related to treatment with DPI-386 Nasal Gel (Table 14.3.1.3). The events of nausea and vomiting reported by 1 subject each were not related to treatment with DPI-386 Nasal Gel. TEAEs in the open-label period are summarized by causality in Table 14.3.1.3.

In the open-label period, 17 subjects (17.3%) had 22 TEAEs that were mild in intensity (Table 5z). No TEAEs of moderate or severe intensity were reported during the open-label period of the study. TEAEs are summarized by intensity.

Overall, the TEAEs that were reported in the open-label period of the study were consistent with the AE profile of scopolamine and no new AE safety signals were observed.

7.2.3.3. Subjects Who Received at Least One Dose of DPI-386 Nasal Gel

Of all subjects who received at least one dose of DPI-386 Nasal Gel at any time during the study (N=99), 28 subjects (28.3%) reported 49 TEAEs. Sixteen of those subjects (16.2%) had a TEAE that the investigator considered to be related to administration of DPI-386 Nasal Gel (Table 5z).

Twenty-seven subjects (27.3%) had 45 TEAEs that were mild in intensity and 4 subjects (4.0%) had 4 TEAEs that were moderate in intensity. No subject had a severe TEAE.

Four subjects (4.0%) had a TEAE that led to a request for rescue treatment with DPI-386 Nasal Gel. All 4 of these TEAEs occurred in the double-blind period of the study.

Seventeen subjects (17.2%) reported 21 AESIs. Seven of those AESIs occurred in the double-blind period of the study and 14 of the AESIs occurred in the open-label period of the study. See Example 5, Section 7.3.1.3 for a discussion of AESIs.

The TEAEs that were reported fit well with the treatment received (DPI-386 Nasal Gel). The most common TEAE was dry mouth (14 subjects, 14.1%; Table 5aa). The next most common TEAE was motion sickness, all of which occurred in the double-blind period of the study. Headache was reported in 4 subjects (4.0%), dizziness in 3 subjects (3.0%), and blurred vision in 2 subjects (2.0%).

The causality assessment was judged as not related to treatment with DPI-386 Nasal Gel for 27 TEAEs reported by 18 subjects (18.2%) and related to treatment for 22 TEAEs reported by 16 subjects (16.2%; Table 5z). Dry mouth was the most common TEAE, and in 12 (12.1%) of the 14 subjects who had dry mouth the event was determined to be related to treatment with DPI-386 Nasal Gel (Table 14.3.1.3). None of the 15 events of motion sickness in 13 subjects (13.1%) were related to treatment with DPI-386 Nasal Gel. Two TEAEs of headache in 2 subjects (2.0%) were related to treatment with DPI-386 Nasal Gel and 2 TEAEs of headache in 2 subjects (2.0%) were not related to treatment. The 3 TEAEs of dizziness in 3 subjects (3.0%) were all related to treatment with DPI-386 Nasal Gel. The events of nausea and vomiting reported by 1 subject each were not related to treatment with DPI-386 Nasal Gel. TEAEs are summarized by causality.

Overall, the TEAEs that were reported in subjects who received at least one dose of DPI-386 Nasal Gel at any time during the study were consistent with the AE profile of scopolamine, and no new AE safety signals were observed.

7.3. Deaths, Other Serious Adverse Events and Other Significant Adverse Events 7.3.1. Listing of Deaths, Other Serious Adverse Events and Other Significant Adverse Events 7.3.1.1. Deaths There were no deaths in the study.

7.3.1.2. Other Serious Adverse Events

There were no SAEs in the study.

7.3.1.3. Other Significant Adverse Events

One subject was discontinued from the study due to an AE. Subject 206 was screened and met all requirements for enrollment. The subject was randomized to the Placebo Nasal Gel arm, received two doses of study drug on Treatment Day 1 (7 Jun. 2019), and reported no AEs or ACTS events. The subject reported to the clinic 4 days later for Day 2 activities/assessments on 11 Jun. 2019 and per protocol an ECG was performed 60 minutes prior to the scheduled first dose of study drug for that day. That ECG revealed the following: "atrial fibrillation, indeterminate axis right bundle branch block, abnormal ECG." The ECG was assessed as "clinically significant." The subject was discontinued from the study on the basis of that ECG finding, however the reason for discontinuation was reported on the CRF incorrectly as "Subject meets an exclusion criterion that precludes further study participation." In fact, the subject was immediately discontinued from the study for the AE of atrial fibrillation. No further study evaluations or procedures were performed after the ECG was completed.

An AESI was defined as an AE that was reported on the ACTS and was deemed by the investigator to be related to the administration of study drug. Twenty-six AEs from those reported on the ACTS were determined to be AESIs, and they are summarized in Table 5bb.

In the double-blind period of the study, 7 AESIs occurred in the DPI-386 Nasal Gel arm and 5 AESIs occurred in the Placebo Nasal Gel arm. The AESIs in the DPI-386 Nasal Gel arm were dry mouth (6 subjects, 14.3%) and photophobia (1 subject, 2.4%). The AESIs in the Placebo Nasal Gel arm were dry mouth (3 subjects, 7.3%) and dizziness (2 events in 1 subject, 2.4%).

Fourteen AESIs occurred in the open-label period of the study: dry mouth (9 subjects, 9.2%), dizziness (3 subjects, 3.1%), and blurred vision (2 subjects, 2.0%).

Twenty-one AESIs occurred in subjects who received at least one dose of DPI-386 Nasal Gel: dry mouth (15 events in 14 subjects, 14.1%), dizziness (3 subjects, 3.1%), blurred vision (2 subjects, 2.0%), and photophobia (1 subject, 1.0%).

TABLE 5bb

Adverse Events of Special Interest (Safety Population)

| System Organ Class Preferred Term | Statistic | DPI-386 Nasal Gel (N = 42) | Placebo Nasal Gel (N = 41) | Open-label DPI-386 Nasal Gel (N = 98) | At Least One DPI-386 Nasal Gel (N = 99) |
|---|---|---|---|---|---|
| Eye disorders | n (%) E | 1 (2.4) 1 | 0 (0.0) 0 | 0 (0.0) 0 | 1 (1.0) 1 |
| Photophobia | n (%) E | 1 (2.4) 1 | 0 (0.0) 0 | 0 (0.0) 0 | 1 (1.0) 1 |
| Gastrointestinal disorders | n (%) E | 6 (14.3) 6 | 3 (7.3) 3 | 9 (9.2) 9 | 14 (14.1) 15 |
| Dry mouth | n (%) E | 6 (14.3) 6 | 3 (7.3) 3 | 9 (9.2) 9 | 14 (14.1) 15 |
| Nervous system disorders | n (%) E | 0 (0.0) 0 | 0 (0.0) 0 | 2 (2.0) 2 | 2 (2.0) 2 |
| Vision blurred | n (%) E | 0 (0.0) 0 | 0 (0.0) 0 | 2 (2.0) 2 | 2 (2.0) 2 |
| Vascular disorders | n (%) E | 0 (0.0) 0 | 1 (2.4) 2 | 3 (3.1) 3 | 3 (3.0) 3 |
| Dizziness | n (%) E | 0 (0.0) 0 | 1 (2.4) 2 | 3 (3.1) 3 | 3 (3.0) 3 |

Source: Table 14.3.2.3

7.3.2. Narratives of Deaths, Other Serious Adverse Events and Certain Other Significant Adverse Events There were no SAEs or deaths during the study. Narratives were not written for the subjects who had an AESI or for the subject who was discontinued from the study due to an AE.

7.3.3. Analysis and Discussion of Deaths, Other Serious Adverse Events and Other Significant Adverse Events There were no SAEs or deaths during the study.

Except for dry mouth, which occurred in 14.3% of subjects receiving DPI-386 Nasal Gel, AESIs occurred infrequently. All AESIs were mild in intensity except for one moderate event of dizziness reported in a subject who received Placebo Nasal Gel.

One subject in the Placebo Nasal Gel group was discontinued from the study due to an AE of atrial fibrillation, which was discovered during a pre-dose ECG on Treatment Day 2. The subject was discontinued immediately, and no further study assessments or procedures were performed. Treatment Day 2 study drug was not administered to the subject.

7.4. Secondary Safety Endpoints 7.4.1. Psychomotor Vigilance Task

PVT data were collected but not analyzed.

7.4.2. Automated Neuropsychological Assessment Metrics

ANAM data were collected but not analyzed.)

7.5. Other Safety Endpoints 7.5.1. Vital Signs and 12-lead ECG 7.5.1.1. Vital Signs Vital signs (blood pressure, heart rate, respiratory rate, and temperature) were taken at the clinical site on Treatment Days 2 to 4 as per the schedule: at pre-dose (within 60 minutes before dosing) and at 30, 60, 120, 180, 330, 390, 420, 480, and 600 minutes after first dosing. Descriptive statistics of vital sign measurements at each timepoint on Treatment Days 2, 3, and 4 are provided.

Mean changes from baseline at all timepoints in vital sign measurements were not clinically meaningful. Descriptive statistics of the changes from baseline at each timepoint on Treatment Days 2, 3, and 4 are also provided.

7.5.1.2. 12-Lead Electrocardiogra

ECGs were not taken on Day 1 and therefore there are no ECG data from the double-blind period of the study.

In the open-label period of the study, cardiac safety was assessed by the administration of a resting 12-lead ECG on 9 different occasions across Treatment Days 2 to 4. The first ECG was taken on Treatment Day 2 prior to the first medication dose and served as a baseline to compare to subsequent ECGs. On Treatment Days 2 to 4, a resting ECG was recorded at the clinical site as per the schedule: at pre-dose (within 60 minutes before dosing) and at 120 and 480 minutes after first dosing. Descriptive statistics of ECG parameters at each timepoint on Treatment Days 2, 3, and 4 are provided in Table 14.3.4.7. No clinically meaningful changes in mean values of ECG parameters were observed over the 3-day open-label period.

A summary of QTcF results are presented in Table 5cc for subjects who participated in the open-label period of the study (N=98). On Day 2, 3 subjects (3.1%) at 120 minutes post-dosing and 1 subject (1.0%) at 480 minutes post-dosing had an increase in QTcF value of >30 msec. On Day 3, 1 subject (1.0%) at the pre-dosing timepoint, 1 subject (1.0%) at 120 minutes post-dosing, and 1 subject (1.0%) at 480 minutes post-dosing had an increase in QTcF value of >30 msec. On Day 4, 1 subject (1.0%) at 120 minutes post-dosing and 1 subject (1.0%) at 480 minutes post-dosing had an increase in QTcF value of >30 msec. No subject had a QTcF value >500 msec at any timepoint, and no subject had an increase from the Day 2 baseline in QTcF >60 msec at any timepoint.

TABLE 5cc

Subjects with QTcF Greater than 500 msec or an Increase of Greater than 30 msec (Safety Population)

| Treatment Day<br>Time Point | Open-label<br>DPI-386 Nasal Gel<br>(N = 98) |
|---|---|
| Increase from Day 2 baseline in QTcF value >30 msec | |
| Day 2 | |
| 120 min post-dosing, n (%) | 3 (3.1) |
| 480 min post-dosing, n (%) | 1 (1.0) |
| Day 3 | |
| 60 min prior to dosing, n (%) | 1 (1.0) |
| 120 min post-dosing, n (%) | 1 (1.0) |
| 480 min post-dosing, n (%) | 1 (1.0) |
| Day 4 | |
| 60 min prior to dosing, n (%) | 1 (1.0) |
| 480 min post-dosing, n (%) | 1 (1.0) |

Min = minutes; msec = milliseconds; QTcF = QT interval corrected using Fridericia's formula.
Note:
ECGs were not obtained at study baseline or on Day 1.
Source: Adapted from Table 14.3.4.9

7.5.2. Sleepiness

Sleepiness was assessed using the KSS, which was completed by the subjects at Screening, Treatment Day 1 Hour 4, and Treatment Day 1 Hour 8. The KSS measures sleepiness using a 9-point scale based on 5 states ranging from "extremely alert" to "extremely sleepy, fighting sleep." Higher scores indicated a greater degree of sleepiness.

Mean (SD) KSS scores at baseline were 2.3 (1.56) and 2.0 (1.45) for subjects in the DPI-386 Nasal Gel and Placebo Nasal Gel treatment arms, respectively. Median (range) KSS scores at baseline were 1 (1 to 7) and 1 (1 to 7) for subjects in the DPI-386 Nasal Gel and Placebo Nasal Gel treatment arms, respectively. Descriptive statistics of the scores at all timepoints (n, mean, SD, median, minimum, maximum) are presented by treatment arm in Table 14.3.4.2.

Mean (SD) changes from baseline in the KSS showed a slight increase in sleepiness in both treatment arms at the Hour 4 timepoint (+0.8 in the DPI-386 Nasal Gel arm and +0.9 in the Placebo Nasal Gel arm) (Table 14.3.4.2). At the Hour 8 timepoint the increase in sleepiness from baseline was slightly larger in the DPI-386 Nasal Gel arm compared to the Placebo Nasal Gel arm (+0.8 vs+0.2). Changes from baseline in the median scores were 0 at both timepoints in both treatment arms.

7.5.3. Symptoms of Anticholinergic Toxicity

Symptoms of anticholinergic toxicity were recorded using the ACTS. See Example 5, Section 4.5.3.3.3 for a list of symptoms about which the subjects were queried.

In the double-blind period of the study, the most common ACTS AE reported by subjects at Treatment Day 1 Hour 4 was dry mouth (5 subjects, 11.9%) in the DPI-386 Nasal Gel arm and dizziness (6 subjects, 14.6%) in the Placebo Nasal Gel arm. Four subjects (9.5%) in the DPI-386 Nasal Gel arm reported dizziness at Treatment Day 1 Hour 4. In both treatment groups, all other ACTS AEs reported at Treatment Day 1 Hour 4 occurred in only 1 subject each. A complete summary of reported ACTS AEs is provided. At Treatment Day 1 Hour 8, 3 subjects (7.1%) in the DPI-386 Nasal Gel arm reported dry mouth and 3 subjects (7.3%) in the Placebo Nasal Gel arm reported dizziness. One subject (2.4%) in the Placebo Nasal Gel arm reported increased skin redness/flushing.

Dry mouth was the most reported ACTS AE across the 3-day open-label period of the study. The timepoints at which subjects had the highest incidence of dry mouth were Day 3 180 minutes and Day 3 330 minutes, with 6 subjects (6.1%) reporting that ACTS AE. All reports of dry mouth at other timepoints were reported by fewer than 6 subjects, and all other ACTS AEs at any timepoint were reported by ≤2 subjects (2.0%).

AEs that were reported on the ACTS and that were deemed related to treatment were considered to be AESIs. AESIs are summarized in Table 5bb.

See Example 5, Section 6.4.4.5 for results of the assessment of the relationship between scopolamine PK exposure and ACTS symptoms.

7.5.4. Performance of Activities

Performance of activities was assessed using the PSAQ. See, Example 5, Section 4.5.3.3.4 for a list of the statements to which the subjects were asked to respond.

Subjects completed the PSAQ at the post-treatment visit and their answers were to be based on their experience over the past 4 days. Each of the 6 statements had 5 possible Likert-style responses, i.e., Strongly disagree, Disagree, Neither agree nor disagree, Agree, and Strongly agree. The number (%) of subjects who responded to each possible answer is provided.

The responses to the PSAQ, taken as a whole, were favorable in terms of the effect of study medication on work performance.

7.6. Nasal Gel Device Ease of Use

Nasal Gel device ease of use data were collected using the EOUQ at Post-Treatment Day 4. See Example 5, Section 4.5.3.3.5 for a list of the statements to which the subjects were asked to respond.

In general, the responses indicated that the nasal gel device was easy to use and administer.

7.8. Vital Signs, Physical Findings and Other Observations Related to Safety

The results of the evaluation of vital signs and 12-lead ECG data are presented in Section 7.5.1.1 and Section 7.5.1.2, respectively.

7.9. Clinical Laboratory Evaluation

Clinical laboratory testing was not conducted in this study.

7.9.1. Listing of Individual Laboratory Measurements by Subject and Each Abnormal Laboratory Value Not applicable.

7.9.2. Evaluation of Each Laboratory Parameter

Not applicable.

7.9.3. Laboratory Values Over Time

Not applicable.

7.9.4. Individual Subject Changes

Not applicable.

7.9.5. Individual Clinically Significant Abnormalities

Not applicable.

7.10. Safety Conclusions

Overall, the TEAEs that were reported in this study were consistent with the AE profile of scopolamine.

No deaths or SAEs were reported during the study. No subjects were discontinued from the study due to an AE.

DPI-386 Nasal Gel was well tolerated, and no new safety signals were observed.

8. Discussion and Overall Conclusions 8.1. Discussion 8.1.1. Efficacy

A total of 101 subjects (83 randomized across 2 treatment arms and an additional 18 subjects with or without motion sickness susceptibility who received DPI-386 Nasal Gel in the open-label period in a clinic setting (for an evaluation of safety) were enrolled in the study.

In the analysis of the primary efficacy endpoint (double-blind period only; Day 1), a statistically significantly lower proportion of subjects in the DPI-386 Nasal Gel arm developed motion sickness and requested rescue medication compared to subjects in the Placebo Nasal Gel arm (9.5% vs. 36.6%; p=0.0041).

The difference between treatment groups in the change from baseline in nausea severity as measured on a 100-mm VAS (higher numbers indicated more severe nausea) was statistically significant in favor of the DPI-386 Nasal Gel group at Treatment Day 1 Hour 4 (treatment difference [95% CI] was −13.06 [−24.18, −1.93]; p=0.0221). The difference between treatment groups in the change from baseline in nausea severity was not statistically significant at Treatment Day 1 Hour 8 (p=0.0850).

The time to use of rescue medication was statistically significantly longer in the DPI-386 Nasal Gel arm compared to the Placebo Nasal Gel arm (p<0.0001).

A post-hoc analysis compared the Complete Response rates between the two treatment groups. Subjects were Complete Responders if they did not experience vomiting or require rescue medication within the first 4 hours of the first dose of study treatment on Treatment Day 1. The Complete Response rate was 90.5% (95% CI 77.4, 97.3) in the DPI-386 Nasal Gel arm and 63.4% (46.9, 77.9) in the Placebo Nasal Gel arm (nominal p=0.0041).

8.1.2. Safety

Double-Blind Period

In the double-blind period, a smaller proportion of subjects in the DPI-386 Nasal Gel arm reported at least one TEAE (35.7% vs. 70.7% of subjects in the Placebo Nasal Gel arm). In that period a larger proportion of subjects in the DPI-386 Nasal Gel arm had a treatment-related TEAE (14.3% vs 7.3% of subjects in the Placebo Nasal Gel arm).

TEAEs reported in the double-blind period were generally of lower intensity in subjects in the DPI-386 Nasal Gel arm: 33.3% of subjects receiving DPI-386 Nasal Gel and 43.9% of subjects receiving Placebo Nasal Gel had a mild TEAE; 9.5% of subjects receiving DPI-386 Nasal Gel and 31.7% of subjects receiving Placebo Nasal Gel had a moderate TEAE. No severe TEAEs were reported by subjects in any treatment group.

A smaller proportion of subjects in the DPI-386 Nasal Gel arm had a TEAE that led to a request for rescue treatment with DPI-386 Nasal Gel (9.5% vs. 36.6% of subjects in the Placebo Nasal Gel arm).

AESIs occurred slightly more frequently in subjects in the DPI-386 Nasal Gel arm (14.3% vs. in 9.8% of subjects in the Placebo Nasal Gel arm).

The most common TEAE in both treatment groups was motion sickness, but this event occurred less frequently in the DPI-386 Nasal Gel arm than in the Placebo Nasal Gel arm (31.0% vs. 61.0%). The second most common TEAE was dry mouth, but this event occurred more frequently in the DPI-386 Nasal Gel arm than in the Placebo Nasal Gel arm (14.3% vs. 7.3%). Nausea and vomiting did not occur in DPI-386 Nasal Gel-treated subjects, but were reported in 4.9% and 7.3%, of subjects, respectively, who received Placebo Nasal Gel. All other TEAEs in the double-blind period were reported by ≤2 subjects.

In the double-blind period of the study, the most common ACTS AE reported by subjects at Treatment Day 1 Hour 4 was dry mouth (5 subjects, 11.9%) in the DPI-386 Nasal Gel arm and dizziness (6 subjects, 14.6%) in the Placebo Nasal Gel arm. Four subjects (9.5%) in the DPI-386 Nasal Gel arm reported dizziness at Treatment Day 1 Hour 4. In both treatment groups, all other ACTS AEs reported at Treatment Day 1 Hour 4 occurred in only 1 subject each.

Seven AESIs occurred in the DPI-386 Nasal Gel arm and 5 AESIs occurred in the Placebo Nasal Gel arm. The AESIs in the DPI-386 Nasal Gel arm were dry mouth (6 subjects, 14.3%) and photophobia (1 subject, 2.4%). The AESIs in the Placebo Nasal Gel arm were dry mouth (3 subjects, 7.3%) and dizziness (2 events in 1 subject, 2.4%).

Open-Label Period

Seventeen subjects (17.3%) reported 22 TEAEs in the open-label period of the study. Eleven of those subjects (11.2%) had a TEAE that the investigator considered to be related to administration of DPI-386 Nasal Gel.

All TEAEs reported in the open-label period were mild in intensity.

No subject in the open-label period had a TEAE that led to a request for rescue treatment with DPI-386 Nasal Gel.

Twelve subjects (12.2%) reported 14 AESIs in the open-label period of the study.

The most common TEAE during this period was dry mouth (9 subjects, 9.2%). The next most common TEAE was headache (3 subjects, 3.1%), followed by blurred vision and dizziness (2 subjects each, 2.0%). All other TEAEs in the open-label period were reported by only 1 subject (1.0%).

Dry mouth was the most reported ACTS AE across the 3-day open-label period of the study.

Fourteen AESIs occurred in the open-label period of the study: dry mouth (9 subjects, 9.2%), dizziness (3 subjects, 3.1%), and blurred vision (2 subjects, 2.0%).

Subjects Who Received at Least One Dose of DPI-386 Nasal Gel

Of all subjects who received at least one dose of DPI-386 Nasal Gel at any time during the study (N=99), 28 subjects (28.3%) reported 49 TEAEs. Sixteen of those subjects (16.2%) had a TEAE that the investigator considered to be related to administration of DPI-386 Nasal Gel.

Twenty-seven subjects (27.3%) had 45 TEAEs that were mild in intensity and 4 subjects (4.0%) had 4 TEAEs that were moderate in intensity. No subject had a severe TEAE.

Four subjects (4.0%) had a TEAE that led to a request for rescue treatment with DPI-386 Nasal Gel. All 4 of these TEAEs occurred in the double-blind period of the study.

Seventeen subjects (17.2%) reported 21 AESIs. Seven of those AESIs occurred in the double-blind period of the study and 14 of the AESIs occurred in the open-label period of the study.

The most common TEAE was dry mouth (14 subjects, 14.1%). The next most common TEAE was motion sickness, all of which occurred in the double-blind period of the study. Headache was reported in 4 subjects (4.0%), dizziness in 3 subjects (3.0%), and blurred vision in 2 subjects (2.0%). All other TEAEs in subjects who received at least one dose of DPI-386 Nasal Gel were reported in only 1 subject (1.0%).

Twenty-one AESIs occurred in subjects who received at least one dose of DPI-386 Nasal Gel: dry mouth (15 events in 14 subjects, 14.1%), dizziness (3 subjects, 3.1%), blurred vision (2 subjects, 2.0%), and photophobia (1 subject, 1.0%).

Overall Safety Findings

Overall, the TEAEs that were reported in this study were consistent with the AE profile of scopolamine and no new AE safety signals were observed.

No deaths or SAEs were reported during the study. No subjects were discontinued from the study due to an AE.

Mean changes from baseline at all timepoints in vital sign measurements were not clinically meaningful.

ECGs were not taken on Day 1 and therefore there are no ECG data from the double-blind period of the study. In the open-label period, QTcF interval changes were generally clinically insignificant. No subject had a QTcF value >500 msec at any timepoint, and no subject had an increase from the Day 2 baseline in QTcF >60 msec at any timepoint.

Mean (SD) changes from baseline in the KSS showed a slight increase in sleepiness in both treatment arms at the Hour 4 timepoint (+0.8 in the DPI-386 Nasal Gel arm and +0.9 in the Placebo Nasal Gel arm). At the Hour 8 timepoint the increase in sleepiness from baseline was slightly larger in the DPI-386 Nasal Gel arm compared to the Placebo Nasal Gel arm (+0.8 vs. +0.2).

The responses to the PSAQ, taken as a whole, were favorable in terms of the effect of study medication on work performance.

The responses reported on the Nasal Gel EOUQ indicated that the nasal gel device was easy to use and administer.

8.2 Conclusions 8.2.1. Efficacy

DPI-386 Nasal Gel was demonstrated to be superior to Placebo Nasal Gel in the prevention of nausea associated with motion sickness in older subjects when assessed using several efficacy endpoints, including the proportion of subjects who developed motion sickness and requested rescue medication (the primary endpoint), the severity of nausea at Treatment Day 1 Hour 4 as assessed using a VAS, the time to use of rescue medication, and in a post hoc analysis of Complete Response rate.

8.2.2. Pharmacokinetics

Scopolamine was rapidly absorbed following intranasal administration. Scopolamine concentrations did not accumulate with twice daily dosing as demonstrated by the similar concentration time profiles and PK parameter values across the 6 doses.

Following administration of DPI-386 Nasal Gel, scopolamine PK exposure was similar in male and female subjects.

Following intranasal administration, scopolamine geometric mean $C_{max}$, $AUC_{0-t}$, and $AUC_{0-6}$ values, and median $t_{1/2}$ estimates were similar among the age groups of <65, 65 to 74, and ≥75 years.

Higher plasma levels of scopolamine were associated with the occurrence of dry mouth, one of the AEs listed on the ACTS and a known side effect of scopolamine.

8.2.3. Safety

Overall, the TEAEs that were reported in this study were consistent with the AE profile of scopolamine. DPI-386 Nasal Gel was well tolerated, and no new safety signals were observed.

The nasal gel application device was easy to use and administer.

Example 6: Clinical Study MS-31: Relative Bioavailability of Scopolamine Administered as the DPI-386 Nasal Gel and Scopolamine Transdermal System (Transderm Scop) in Healthy Participants Clinical study MS-31 was a Phase 1, randomized, open-label, crossover study to assess the relative bioavailability of scopolamine administered as the DPI-386 Nasal Gel and scopolamine transdermal system (Transderm Scop) in healthy participants. For pharmacokinetic values recited in claims herein, such values should be determined according to the details of clinical study MS-31.

DPI-386 Nasal Gel is an intranasal formulation of the approved drug scopolamine HBr. Previous studies have demonstrated that scopolamine is rapidly absorbed following application of DPI-386 Nasal Gel; scopolamine concentrations were quantifiable within 5 minutes and median tmax was 50 minutes (cf., Study DPI-386-DE-10). After reaching Cmax, plasma scopolamine concentrations decreased in a monophasic manner and the median t½ was 105 minutes (1.75 hours). Following a single dose of scopolamine HBr 0.2 mg administered as the DPI-386 nasal gel in Study DPI-386-DE-10, the geometric mean scopolamine Cmax was 92.3 pg/mL, which is similar to the average plasma scopolamine concentration of 87 pg/mL achieved with transdermal scopolamine (Transderm Scop, US Prescribing Information, November 2021).

Study and Dose Rationale

DPI-386 Nasal Gel (0.2 mg scopolamine HBr/0.12 g gel) is being evaluated for safety and efficacy for the prevention of nausea and vomiting induced by motion. The purpose of this study (DPI-386-MS-31) was to evaluate the bioavailability of scopolamine administered as the DPI-386 Nasal Gel (0.2 mg scopolamine HBr/0.12 g gel) twice daily for 3 days (total dose of 1.2 mg scopolamine HBr [equivalent to 0.95 mg scopolamine]) compared with the marketed scopolamine transdermal system (Transderm Scop). Transderm Scop is designed for continuous release of scopolamine 1 mg over 3 days y a 1.5 mg patch.

Study Objectives and Endpoints

Objectives and Endpoints

To evaluate the bioavailability of scopolamine administered as the DPI-386 Nasal Gel compared with the scopolamine transdermal system (Transderm Scop).

Primary Pharmacokinetic (PK) Endpoints:

DPI-386 Nasal Gel: Cmax following Dose 5, AUC3d (sum of AUCtau for Doses 1-6)

Scopolamine Transdermal System: Cmax, AUC3d

Secondary PK Endpoints:

DPI-386 Nasal Gel: Dose 1 and Dose 5: Cmax, AUC0-t, AUCtau, AUCinf (Dose 1 only), Ctau, tmax, tlag, t½, CL/F, Vz/F, percent of dose recovered as parent in urine (Dose 6 only). Doses 2, 3, 4, 6: Cmax, AUC0-t, AUCtau, Ctau (Doses 2, 3, 4), tmax. Scopolamine accumulation ratios, R(Cmax) and R(AUCtau), which are defined as the Dose 5/Dose 1 values. In addition, if AUCinf can be accurately estimated following the first dose on Day 1, time variance will be assessed as R(AUCtau/AUCinf), where AUCtau is estimated on Dose 5 and AUCinf is estimated on Dose 1.

Scopolamine Transdermal System: AUC(0-t), AUCinf, tmax, tlag, t½, CL/F, Vz/F.

To evaluate the safety of scopolamine administered as the DPI-386 Nasal Gel compared with the scopolamine transdermal system (Transderm Scop).

Endpoints: Anticholinergic Toxicity Scale (ACTS), Adverse Events (AEs), Vital Signs, 12-lead electrocardiogram (ECG), Clinical laboratory tests.

To explore the relationship between PK exposure metrics and ACTS.

Endpoints: PK exposure metrics: Cmax, AUC(0-t), AUCtau (DPI-386 nasal gel), and AUC3d; ACTS symptom of maximum severity post-baseline.

Investigational Plan

Overall Study Design and Plan

This was a Phase 1, randomized, open label, crossover study to evaluate the bioavailability and safety of scopolamine administered as the DPI-386 Nasal Gel (0.2 mg scopolamine HBr/0.12 g gel) compared with the scopolamine transdermal system (Transderm Scop) in healthy adult participants. Approximately 20 participants were to be randomized 1:1 to sequence (see Table 6a, below).

TABLE 6a

Study Design

| Sequence | N | Period 1 | Washout | Period 2 |
|---|---|---|---|---|
| 1 | 10 | DPI-386 Nasal Gel twice daily[a] | 7-10 days | Transderm Scōp[b] |
| 2 | 10 | Transderm Scōp[b] | | DPI-386 Nasal Gel twice daily[a] |

[a]DPI-386 Nasal Gel 0.2 mg scopolamine HBr is administered into one nostril twice daily, 6 hours apart within day, for 3 consecutive days. The total dose of 1.2 mg scopolamine HBr is equivalent to 0.95 mg scopolamine.

[b]The scopolamine transdermal system (Transderm Scōp) will be applied once and is designed for continuous release of scopolamine 1 mg over 3 days.

Written informed consent was obtained prior to performance of any study related procedures. Screening was completed within 28 days prior to dosing to determine eligibility for participation in the study. Prior to dosing on Day 1 of Period 1, participants were randomized to sequence (the order in which the participant received each treatment). For the DPI-386 Nasal Gel treatment, participants received study drug twice daily on Days 1 to 3. For the scopolamine transdermal system, the patch was applied on Day 1 and removed 72 hours later. Participants completed a post-treatment follow-up visit 7 days (±3 days) after the second treatment period.

The trial duration was approximately 51 days for all enrolled participants with assessments as follows: Screening: Days-28 to-1, Period 1: Days 1 to 4, Wash-out: Days 5 to 11, Period 2: Days 12 to 15, Follow-up: Day 22 (+3 days). Participants remained in-patient from Day-1 to Day 4 of each period.

Discussion of Study Design, Including the Choice of Control Groups

The cross-over design of this study allowed for a within-subject comparison of pharmacokinetics (PK) between the two treatments, which minimized the impact of factors other than treatment on the comparison and minimized variability.

Selection of Study Population

All inclusion and exclusion criteria were reviewed by the Investigator or qualified designee at the Screening Visit and at the Day-1 visits (where relevant) to ensure that the participants qualified for the study. To be eligible for participation in this study, all inclusion criteria must have been met and none of the exclusion criteria applied.

Inclusion Criteria

Provision of signed and dated ICF at screening (prior to performance of any study-related procedures).

Stated willingness to comply with all study procedures and availability for the duration of the study at screening.

Ability to take intranasal medication at screening and Day-1 of each period.

Male or female aged 18 to 55 years (inclusive) at screening.

Have a body mass index within a range of 18 to 30 $kg/m^2$ inclusive, at screening.

Males and females of childbearing potential (and their partners) must agree to use highly effective contraception from screening and until 4 weeks after receiving the last dose of treatment.

For women of childbearing potential: A negative pregnancy test at screening and on Day-1 of each period. Note: Women of non-childbearing potential are defined as those who are non-surgically sterile (i.e., without menses for at least 12 consecutive months) or surgically sterile (i.e., those who underwent a hysterectomy with or without oophorectomy, bilateral fallopian tube ligation, or bilateral oophorectomy).

In good general health as evidenced by medical history with no recent history or current diagnosis of significant cardiovascular, respiratory, gastrointestinal, neurological, renal, or other health problems as assessed by the principal investigator (PI) or qualified designee at screening and on Day-1 of each period.

Hematology, chemistry, urinalysis, and drug and alcohol laboratory test results that are determined by the PI or qualified designee to be not clinically significant at screening and on Day-1 of each period.

Results from a screening ECG that are determined by the PI or qualified designee to be not clinically significant.

Agreement to adhere to the following lifestyle and dietary restrictions at screening:

Abstain from consumption of grapefruit and any substance containing grapefruit for 7 days prior to, during, and for 7 days after the final Treatment Day.

Abstain from caffeine for 24 hours prior to study drug administration and until discharged from the study center.

Abstain from alcohol for 24 hours prior to the first dose of study drug and through the follow-up visit.

Abstain from any type of nicotine (tobacco/vaping/e-cigarette/etc.) within 30 days prior to the Screening Visit and through the follow-up visit.

Abstain from strenuous exercise for 72 hours prior to each blood collection for clinical laboratory tests.

Negative test for the Severe Acute Respiratory Syndrome Coronavirus-2 (SARS-CoV-2) virus on Day-1 of each period.

Negative serology test for Hepatitis B surface Antigen, Hepatitis C Antibody, or HIV-1/HIV-2 Antibodies at screening.

Negative drug and alcohol screen at screening and on Day-1 of each period.

Exclusion Criteria

Poses a suicide risk as assessed by a "yes" response regarding the prior year to item 4 (Active Suicidal Ideation with some intent to act) or higher on the Lifetime version of the Columbia-Suicide Severity Rating Scale (C-SSRS) at screening, or by responding "yes" to item 4 or higher on the Since-Last-Visit version of the C SSRS on Day-1. NOTE: If at any time the subject responds "yes" to item 4 or higher they should be referred for medical evaluation/assistance.

Lactating at Screening or on Day −1 of each period.

Elevated temperature (>100.4° F.) at screening or on Day-1 of each period.

Known allergic reactions to scopolamine or other anticholinergics or any component of the formulation or delivery system (assessed at screening).

Use of any prescriptions or over-the-counter drugs within 2 weeks, or 5 half-lives of the drug, whichever is longer, before the first dose of study and during the conduct of the trial, to avoid any potential drug-drug interactions. [Note: In Administrative Memo #1 to the protocol, this exclusion criteria was clarified to permit acetaminophen, hormonal contraceptives, and hormonal replacement therapy for consistency with Inclusion Criteria 6 and the permitted medication section of the protocol.]

Hospitalization or significant surgery requiring hospital admittance within the past 6 months.

Treatment with another investigational drug or other intervention within the past 30 days.

Having donated blood or plasma or suffered significant blood loss within the past 60 days.

Having any of the following medical conditions within the last 2 years or if any of the following medical conditions were experienced more than two years ago and are deemed clinically significant by the PI or qualified designee: Significant gastrointestinal disorder, asthma, or seizure disorders; Narrow-angle glaucoma; Urinary retention or clinically significant symptomatic benign prostatic hypertrophy; Moderate or severe substance use disorder; or Nasal, nasal sinus, deviated septum, or nasal mucosa surgery Removal of Participants from Therapy or Assessment The Investigator was to discontinue/withdraw a study participant's participation in the study if any of the following criteria applied: Any clinical AE, laboratory abnormality, or other medical condition or situation occurs such that continued participation in the study would not be in the best interest of the participant; Participant pregnancy; Significant protocol violation; Behavioral or administrative reason; Participant request to discontinue/withdraw consent for any reason; Discontinuation of the study at the request of the Sponsor, regulatory agency, or an IRB/IEC.

Treatments

Treatments Administered

Participants received two treatments separated by 7 to 10 days 0.2 mg scopolamine HBr administered as the DPI-386 Nasal Gel (0.2 mg scopolamine HBr/0.12 g gel) was administered into one nostril twice daily, 6 hours apart within day, for 3 consecutive days. The total dose of 1.2 mg scopolamine HBr is equivalent to 0.95 mg scopolamine.

The scopolamine transdermal system (Transderm Scop) was applied to a hairless area of skin behind the ear and removed 72 hours later. Transderm Scop is designed for continuous release of scopolamine 1 mg over 3 days.

TABLE 6b

Identity of Investigational Products

| | DPI-386 Nasal Gel | Transderm Scōp |
|---|---|---|
| Formulation | The DPI-386 Delivery Device is comprised of four components (1) safety clip, (2) removable cap, (3) actuator with finger grips, and (4) prefilled bottle of DPI-386 Nasal Gel. Each pumping action is designed to deliver 0.12 g of nasal gel. Each bottle of DPI-386 is sufficient for 6 individual doses. | Each system contains 1.5 mg of scopolamine base. The Transderm Scōp transdermal system is a circular, 0.2 mm thick, 2.5 cm2 film with four layers. Proceeding from the visible surface towards the surface attached to the skin, these layers are: (1) a backing membrane of tan-colored, aluminized, polyester film; (2) a drug layer of scopolamine, light mineral oil, and polyisobutylene; (3) a microporous polypropylene membrane that controls the rate of delivery of scopolamine from the system to the skin surface; and (4) a contact layer formulation of mineral oil, polyisobutylene, and scopolamine. A release liner of siliconized polyester, which covers the adhesive layer, is removed before the system is used. |
| Strength | 0.2 mg scopolamine HBr per 0.12 gram gel | Transderm Scōp is designed for continuous release of scopolamine 1 mg over 3 days following application to an area of intact skin behind the ear. |
| Manufacturer | Excite Pharma Services<br>324 NW Capital Drive<br>Lees Summit, MO 64086, USA | Manufactured by:<br>ALZA Corporation<br>700 Eubanks Drive<br>Vacaville, CA 95688, USA<br>Marketed by:<br>Baxter Healthcare Corporation<br>1 Baxter Parkway<br>Deerfield, IL 60015, USA |
| Lot No. | BR2021-025.1 | 1904021 |
| Expiry Date | 30 Jun. 2023<br>DPI-386 Nasal Gel | May 2022<br>Transderm Scop |
| Storage condition | Store DPI-386 Nasal Gel upright with the safety clip and cap attached. Store DPI-386 Nasal Gel at controlled room temperature between 20° C. to 25° C., inclusive (68° F. to 77° F., inclusive), with brief temperature excursions permitted between | Store the scopolamine transdermal system (Transderm Scōp) at controlled room temperature between 20° C. to 25° C., inclusive (68° F. to 77° F., inclusive). Store pouch(es) in an upright position. Do not bend or roll pouch(es). |

TABLE 6b-continued

| Identity of Investigational Products | | |
|---|---|---|
| | DPI-386 Nasal Gel | Transderm Scōp |
| | 5° C. and 30° C., inclusive (41° F. and 86° F., inclusive).[a] | |
| Device Manufacturer | Aptar Pharma<br>Öschlestraβe 54-56<br>78315 Radolfzell am Bodensee<br>Baden-Württemberg<br>Germany | Not applicable |

Method of Assigning Participants to Treatment Groups

Participants were randomized 1:1 to sequence according to the randomization scheme produced by the Sponsor's independent statistician.

Selection and Timing of Dose for Each Participant

Participants were randomized to sequence and received each of two treatments as described herein.

Blinding

This was an open-label study.

Prior and Concomitant Therapy

Permitted Concomitant Medications/Therapies

Acetaminophen, at doses of ≤2 grams/day, hormone-based contraceptives, and hormonal replacement therapy were permitted for use any time during the study. Other concomitant medications were considered on a case by case basis by the Investigator for treatment of a medical need in consultation with the Medical Monitor. Concomitant medications were recorded in the study records, including the doses administered, the route of administration, the dates and times of administration, and the reason for administration.

Contraception

Males and females of childbearing potential (and their partners) were required to use acceptable methods of contraception from the screening visit through the follow-up visit. Acceptable methods of contraception were 2 of the following: intrauterine device, systemic hormonal contraceptives (such as oral, transdermal patch, implant/insertable), diaphragm, spermicides, cervical cap, contraceptive sponge, and/or condoms. Note: If hormonal-based birth control was being used, the participant or participant's sexual partner(s) must have been on a stable-dose for ≥3 months prior to Day 1 and maintained at the same dose level throughout the study.

Participants who practiced sexual abstinence, when this was in line with the preferred and usual lifestyle of the participant, were eligible for the study. Periodic abstinence (e.g., calendar, ovulation, symptothermal, post-ovulation methods) and withdrawal were not acceptable methods of contraception.

Vasectomized male participants and female participants of childbearing potential whose male partner was vasectomized were eligible. The vasectomy must have occurred at least 6 months prior to the first administration of the study drug.

Prohibited Concomitant Medications/Therapies

Participants were to abstain from taking prescriptions or over-the-counter drugs, including dietary and herbal supplements (note: vitamin and mineral supplements were permitted) within 2 weeks, or 5 half-lives of the drug, whichever was longer, before the study drug administration and during the conduct of the trial, unless in the opinion of the Investigator and Sponsor Medical Monitor the medication would not interfere with the study or the medication was needed for proper medical management of the participant.

Treatment Compliance

Site staff administered study drugs directly to the participants. The assigned treatment and study participant identification was confirmed at the time of dosing by a member of the study site staff. The date and time of each dose administered in the clinic was recorded.

Pharmacokinetic and Safety Variables

Schedule of Assessments (see Table 6c, below).

TABLE 6c

Schedule of Assessments for DPI-386 Nasal Gel

| | Screening | Inpatient (Period 1 or Period 2) Study Day | | | | | | | | | | | | | | Follow-up[a] |
|---|---|---|---|---|---|---|---|---|---|---|---|---|---|---|---|---|
| | Within 28 days | −1 | 1 | | | | 2 | | | | 3 | | | | 4 | 22 (±3) |
| | | | Time Relative to Morning Dose (hours) | | | | | | | | | | | | | |
| | — | | 0 | 1 | 6 | 7 | 0 | 1 | 6 | 7 | 0 | 1 | 6 | 7 | 24 | — |
| | | | Time Relative to First Dose (hours) | | | | | | | | | | | | | |
| | — | | 0 | 1 | 6 | 7 | 24 | 25 | 30 | 31 | 48 | 49 | 54 | 55 | 72 | |
| Informed consent | X | | | | | | | | | | | | | | | |
| Inclusion/exclusion criteria | X | X[b] | | | | | | | | | | | | | | |
| C-SSRS | X | X | | | | | | | | | | | | | X | X |
| Medical history | X | X | | | | | | | | | | | | | | |
| Physical examination | X | X | | | | | | | | | | | | | X | |
| Demographics | X | | | | | | | | | | | | | | | |
| Height, Weight | X | | | | | | | | | | | | | | | |

TABLE 6c-continued

Schedule of Assessments for DPI-386 Nasal Gel

| | Screening | | Inpatient (Period 1 or Period 2) Study Day | | | | | | | | | | | | | Follow-up[a] |
|---|---|---|---|---|---|---|---|---|---|---|---|---|---|---|---|---|
| | Within 28 days | −1 | 1 | | | | 2 | | | | 3 | | | | 4 | 22 (±3) |
| Time Relative to Morning Dose (hours) | — | | 0 | 1 | 6 | 7 | 0 | 1 | 6 | 7 | 0 | 1 | 6 | 7 | 24 | — |
| Time Relative to First Dose (hours) | — | | 0 | 1 | 6 | 7 | 24 | 25 | 30 | 31 | 48 | 49 | 54 | 55 | 72 | |
| Vital signs[c] | X | X | | X | | X | | X | | X | | X | | X | X | |
| 12-lead Electrocardiogram | X | | | | | | | | | | | | | | X | |
| SARS-CoV-2 | | X | | | | | | | | | | | | | | |
| Viral serology | X | | | | | | | | | | | | | | | |
| Drug and alcohol screen | X | X | | | | | | | | | | | | | | |
| Pregnancy test (women of childbearing potential) | X | X | | | | | | | | | | | | | | |
| Urinalysis | X | X | | | | | | | | | | | | | X | |
| Blood chemistry | X | X | | | | | | | | | | | | | X | |
| Hematology and coagulation | X | X | | | | | | | | | | | | | X | |
| DPI-386 Nasal Gel dosing | | | X | | X | | X | | X | | X | | X | | | |
| ACTS[c] | | X | | X | | X | | X | | X | | X | | X | X | |
| Adverse events[c] | | | | X | X | X | X | X | X | X | X | X | X | X | X | X |
| Concomitant medications | X | X | | X | | | | X | | | | X | | | X | X |
| Blood PK sampling[d] | | | | X | | | | X | | | | X | | | | |
| Urine PK sampling[e] | | | | | | | | | | | | pre-dose, 0-4 h, 4-8 h, 8-18 h[e] | | | | |

[a]Follow-up is after Period 2.

[b]Review the Inclusion/Exclusion criteria relevant to Day −1.

[c]Vital signs, ACTs, and AEs should be done within ±15 minutes of the schedule time. For assessments scheduled at the same time, the order of the assessments is: PK sample, vital signs, ACTs, and AEs. [Note: Administrative Memo #1 to the protocol: The intent was to have the clinical staff record AEs that were spontaneously reported by a subject in response to an open question from the study personnel or revealed through observation and not to imply that assessment of AEs should occur at a specific hour.]

[d]Blood PK Sampling for DPI-386 Nasal Gel

[e]Urine PK sampling is relative to the last (6th; Day 3 PM) dose of DPI-386 Nasal Gel.

TABLE 6d

Schedule of Assessments for Transderm Sco̅p

| | Screening | | Inpatient (Period 1 or Period 2) Study Day | | | | | | | | | | | Follow-up[a] |
|---|---|---|---|---|---|---|---|---|---|---|---|---|---|---|
| | Within 28 days | −1 | 1 | | | | | | 2 | | 3 | | 4 | 22 (±3) |
| Time Relative to Dose (hours) | — | | 0 | 1 | 2 | 4 | 7 | 12 | 25 | 31 | 49 | 55 | 72 | — |
| Informed consent | X | | | | | | | | | | | | | |
| Inclusion/exclusion criteria | X | X[b] | | | | | | | | | | | | |
| C-SSRS | X | X | | | | | | | | | | | X | X |
| Medical history | X | X | | | | | | | | | | | | |
| Physical examination | X | X | | | | | | | | | | | X | |
| Demographics | X | | | | | | | | | | | | | |
| Height, Weight | X | | | | | | | | | | | | | |
| Vital signs[c] | X | X | | | | | | X | X | X | X | X | X | |
| 12-lead Electrocardiogram | X | | | | | | | | | | | | X | |
| SARS-CoV-2 | | X | | | | | | | | | | | | |
| Viral serology | X | | | | | | | | | | | | | |
| Drug and alcohol screen | X | X | | | | | | | | | | | | |
| Pregnancy test (women of childbearing potential) | X | X | | | | | | | | | | | | |
| Urinalysis | X | X | | | | | | | | | | | X | |
| Blood chemistry | X | X | | | | | | | | | | | X | |
| Hematology and coagulation | X | X | | | | | | | | | | | X | |
| Transderm Sco̅p application | | | X | | | | | | | | | | | |
| Transderm Sco̅p removal | | | | | | | | | | | | | X | |
| ACTS[c] | | X | | X | | | X | | X | | X | | X | |

TABLE 6d-continued

Schedule of Assessments for Transderm Scōp

| | Screening | Inpatient (Period 1 or Period 2) Study Day | | | | | | | | | | | | Follow-up[a] |
|---|---|---|---|---|---|---|---|---|---|---|---|---|---|---|
| | Within 28 days | −1 | 1 | | | | | | 2 | | 3 | | 4 | 22 (±3) |
| | Time Relative to Dose (hours) | | | | | | | | | | | | | |
| | — | | 0 | 1 | 2 | 4 | 7 | 12 | 25 | 31 | 49 | 55 | 72 | — |
| Adverse events[c] | | | | X | X | X | X | X | X | X | X | X | X | X |
| Concomitant medications | X | X | | | X | | | | X | | X | | X | X |
| Blood PK samplingc | | X | X[d] | X | X | X | X | X | X | X | X | X | X | |

[a]Follow-up is after Period 2.
[b]Review the Inclusion/Exclusion criteria relevant to Day −1.
[c]Vital signs, ACTs, AEs, and blood PK sampling for Transderm Scōp should be done within ±15 minutes of the schedule time. For assessments scheduled at the same time, the order of the assessments is: PK sample, vital signs, ACTs, and AEs. [Note: Administrative Memo #1 to the protocol: The intent was to have the clinical staff record AEs that were spontaneously reported by a subject in response to an open question from the study personnel or revealed through observation and not to imply that assessment of AEs should occur at a specific hour.]
[d]Collect the pre-dose blood PK sample within 0.5 h before application of the TDS patch.

Appropriateness of Measurements

The PK and safety assessments in the study were typical for Phase 1 studies and considered appropriate to meet the study objectives.

Pharmacokinetic Variables

The PK objectives and endpoint variables are described herein.

Drug Concentration Measurement

Blood PK Sampling

Blood samples for quantification of scopolamine concentrations were collected in 4 mL K2EDTA vacutainer tubes at the time points specified in Table 5d (transdermal scopolamine) and Table 5f (DPI-386 Nasal Gel). If PK samples were collected via an indwelling catheter, the catheter was kept patent with saline and 1 mL of blood was wasted before collection of each PK sample to avoid sample dilution. If PK samples were collected via direct stick, no blood needed to be wasted.

Immediately following blood collection, the collection tubes were inverted eight to ten times, then the samples were maintained in an upright position in an ice-water bath or in a refrigerator for no more than 60 minutes prior to centrifugation. The samples were centrifuged at refrigerated temperature (4° C.) at approximately 3000 rpm for 10 minutes. The plasma was divided equally into two cryovials (approximately 1 mL per cryovial) via non-sterile pipettes to create two separate sets of plasma samples for each participant. The plasma samples were stored at −80° C. until shipped on dry ice to the bioanalytical facility for analysis.

Samples were assayed for scopolamine in plasma at the bioanalytical facility Pyxant Labs, Inc. (Colorado Springs, CO, USA) using a validated high-performance liquid chromatography with tandem mass spectrometry (LC-MS/MS) method. All plasma samples were analyzed within established long-term frozen, freeze/thaw, and processed extract stability. A summary of bioanalytical method performance is presented in Table 6e, below.

TABLE 6e

Summary of Bioanalytical Performance (Plasma QC Samples)

| Analyte | Matrix | Validated Assay Range (LLQ to ULQ) | Accuracy (% difference from nominal) | Between-Run Precision (CV %) |
|---|---|---|---|---|
| Scopolamine | Plasma | 2.00 to 2000 pg/mL | −4.7% to 7.8% | 3.80% to 10.84% |

TABLE 6f

Blood PK Sampling Schedule for DPI-386 Nasal Gel

| | | Time Relative to Dose | | | | | | | | | | | | | | |
|---|---|---|---|---|---|---|---|---|---|---|---|---|---|---|---|---|
| | | Pre-dose | Minutes | | | | | | | Hours (±minutes) | | | | | | |
| Day | Dose | (within 0.5 h) | 5 (±1) | 10 (±1) | 15 (±1) | 20 (±1) | 30 (±2) | 40 (±2) | 50 (±2) | 1 (±2) | 1.25 (±2) | 1.5 (±2) | 2 (±2) | 4 (±5) | 5 (±5) | 6 (±5) |
| 1 | 1 | X | X | X | X | X | X | X | X | X | X | X | X | X | X | X[a] |
| | 2 | X | | | X | | X | | | X | | X | X | X | X | X |
| 2 | 3 | X | | | X | | X | | | X | | X | X | X | X | X[a] |
| | 4 | X[a] | | | X | | X | | | X | | X | X | X | X | X |
| 3 | 5 | X | X | X | X | X | X | X | X | X | X | X | X | X | X | X[a] |
| | 6 | X[a] | | | X | | X | | | X | | X | X | X | X | X |

[a]The 6-hour post-dose samples following Doses 1, 3, and 5 (AM doses) are the same as the pre-dose samples for Doses 2, 4, and 6 (PM doses).

Urine PK Sampling

Urine samples were collected during the following time intervals relative to administration of the last ($6^{th}$, Day 3 PM) dose of DPI-386 Nasal Gel dose for measurement of scopolamine concentrations: Pre-dose (within 30 minutes), 0-4 hours, 4-8 hours, 8-18 hours.

All urine was collected within each collection interval. During each collection interval, subjects may have voided as needed, but each participant was asked to void at the scheduled end of each collection interval. The start and stop date and time of each urine collection interval (start being the first void and stop being the last void during the interval), the total volume of urine collected during each interval, and whether each collection was complete was recorded in the electronic case report form (eCRF).

The urine collected during each interval was pooled in a collection container (of sufficient capacity). The container was kept on ice or refrigerated during the collection interval. At the end of the collection interval, the container was gently shaken to ensure complete mixing, without spilling the contents, then 5 mL aliquots were transferred to each of 2 storage tubes and immediately frozen upright at −80° C. until shipped on dry ice to the bioanalytical facility for analysis.

Urine samples were assayed for scopolamine using a fully validated bioanalytical method.

Samples were assayed for scopolamine in urine at the bioanalytical facility Pyxant Labs, Inc. (Colorado Springs, CO, USA) using a validated LC-MS/MS method. A summary of bioanalytical method performance is presented in Table 6g, below.

TABLE 6g

Summary of Bioanalytical Performance (Urine QC Samples)

| Analyte | Matrix | Validated Assay Range (LLQ to ULQ) | Accuracy (% difference from nominal) | Between-Run Precision (CV %) |
|---|---|---|---|---|
| Scopolamine | Urine | 5.00 to 2000 pg/mL | 2.0% to 7.6% | 1.00% to 6.60% |

Safety Variables

Adverse Events: information on AEs were collected throughout the study.

Anticholinergic Toxicity Scale

The anticholinergic effects of scopolamine were assessed using the ACTS, as defined in Table 6h, below.

TABLE 6h

Anticholinergic Toxicity Scale Details

| Instrument | Instrument Description | Assessment Details |
|---|---|---|
| Anticholinergic Toxicity Scale (ACTS) | Have you experienced any of the following symptoms in the past 24 hours?<br>Dry mouth; Increased skin redness/flushing; Blurry vision; Light sensitivity; Difficulty urinating; Dizziness; Confusion; Hallucinations; Palpitations | The questions are asked in ascending order of symptom severity. |

Clinical Laboratory Assessments

Clinical chemistry, coagulation, hematology, and urinalysis assessments were performed.

Vital Signs

Vital signs were measured in the supine position after at least 5 minutes rest and included pulse, respiratory rate, blood pressure, and temperature.

Electrocardiogram 12-lead ECGs were performed in the supine position after at least 5 minutes rest.

Physical Examinations

A complete physical examination included, at a minimum, assessment of the cardiovascular, respiratory, gastrointestinal, and neurological systems, and skin.

Columbia-Suicide Severity Rating Scale

The C-SSRS is comprised of 10 categories with binary responses. Reference is made to Posner, K. et al. The Columbia-Suicide Severity Rating Scale: initial validity and internal consistency findings from three multisite studies with adolescents and adults. Am J. Psychiatry. 2011:168: 1266-1277. The 10 categories include:

Suicidal Ideation

Question 1—Wish to be Dead

Question 2—Non-specific Active Suicidal Thoughts

Questions 3 to 5 are only collected if the answer to Question 2 is "Yes"

Question 3—Active Suicidal Ideation with Any Methods (Not Plan) without Intent to Act Question 4—Active Suicidal Ideation with Some Intent to Act, without Specific Plan Question 5—Active Suicidal Ideation with Specific Plan and Intent Suicidal Behavior Question 6—Preparatory Acts or Behavior Question 7—Aborted Attempt Category 8—Interrupted Attempt Question 9—Actual Attempt (non-fatal)

Question 9a—Non-Suicidal Self-Injurious Behavior

Category 10—Completed Suicide

Categories 1-5 represent suicidal ideation and categories 6-10 represent suicidal behavior. C-SSRS was used to identify whether an individual was at risk for suicide and to assess the severity and immediacy of that risk.

Two versions of the C-SSRS were used in this study: the 'Lifetime' version gathers lifetime or recent history of suicidal ideation and/or behavior; and the 'Since Last Visit' version assesses suicidal thoughts or behaviors since the C-SSRS was last administered. C-SSRS 'Lifetime' version was used at Screening and 'Since Last Visit' version was used in each treatment period.

Data Quality Assurance

Monitoring

Sponsor representatives were allowed to visit all study site locations to assess the data, quality, and study integrity in a manner consistent with applicable health authority regulations and the procedures adopted by sponsor. Prior to the start of the study, members of sponsor reviewed the protocol, eCRF, regulatory obligations, and other material or equipment relevant to the conduct of the study with the Investigator and relevant study site personnel.

Monitoring visits and telephone consultations occurred as necessary and per the monitoring plan during the course of the investigation to verify the following: the rights and well-being of subjects were protected; the conduct of the investigation was in compliance with the currently approved protocol/amendment, 21 Code of Federal Regulations Parts 50, 54, 56, and 812; 42 United States Code 282 (j); ICH Good Clinical Practices; and applicable local regulations; the integrity of the data, including adequate study documentation; the facilities remained acceptable; the Investigator and site personnel remained qualified and able to conduct the study; test article accountability.

Training

The investigator and team were trained in ICH-Good Clinical Practices guideline. Before the start of the study, the study team was trained on the protocol, informed consent procedures, eCRF completion and correction, source documentation, monitoring procedures, management of documents, and timelines of subject recruitment and completion.

Quality Assurance

Compliance to the study requirements were observed as per Good Clinical Practices, Internal Standard Operating Procedures, Protocol, and applicable regulatory requirements.

Report summaries were generated using validated SAS® software, version 9.3. All SAS programs that created outputs or supporting analysis datasets were validated by a second statistical programmer or biostatistician. At a minimum, validation of programs consisted of a review of the program log, review of output or dataset format and structure, and independent confirmatory programming to verify output results or dataset content. Additionally, all outputs underwent a review by a senior level team member before finalization.

The content of the source data was reviewed on an ongoing basis by project statistical programmers and statisticians. Data was checked for missing values, invalid records, and extreme outliers through defensive programming applications, analysis-based edit checks, and other programmatic testing procedures. All findings were forwarded to the project data manager for appropriate action and resolution.

Statistical Methods Planned in the Protocol and Determination of Sample Size

Statistical and Analytical Plans

SAS® Version 9.3 (SAS Institute Inc., Cary, NC, USA) was used for data displays (tables, figures, listings) and statistical analysis of PK data. Details of the statistical methods are in the statistical analysis plan (SAP) (Appendix 16.1.9).

Disposition, Demographics, Baseline Characteristics, Prior and Concomitant Medications, Medical History, and Screening Tests Disposition, demographic and baseline characteristics, protocol deviations, prior and concomitant medications, medical history, and results of screening tests were listed. Disposition and demographic and baseline characteristics were summarized overall.

Pharmacokinetic Analysis

Plasma drug concentration-time data were analyzed by non-compartmental analysis (NCA) using Phoenix® WinNonlin® version 8.1 (Certara, Inc., Princeton, NJ, USA) to estimate PK parameters (See Table 6i and Table 6j, below). Actual PK sampling times were used for PK analysis.

TABLE 6i

Scopolamine Plasma PK Parameters

| Plasma PK Parameters | Treatments and Doses for Which PK Parameter is Derived | Derivation |
|---|---|---|
| Cmax, Ctau (pg/mL)<br>tmax, tlag, tlast (minutes) | Cmax, tmax, tlast<br>DPI-386 nasal gel Doses 1-6<br>Scopolamine transdermal system<br>tlag<br>DPI-386 nasal gel Doses 1 & 5<br>Scopolamine transdermal system<br>Ctau<br>DPI-386 nasal gel Doses 1-5 | Obtained directly from the concentration-time data<br>Note: if Ctau = BLOQ, a concentration of 0 pg/mL was assigned. |
| t½ (minutes) | DPI-386 nasal gel Doses 1 & 5<br>Scopolamine transdermal system | t½ = 1n2/λz<br>Where λz is estimated by linear regression of at least 3 log-transformed concentration-time data points in the terminal phase.<br>R2 values >0.85 are preferred and the duration of time over which λz is estimated should be ≥2 times the estimated t½. |
| AUC(0-t) (pg · min/mL)<br>AUCinf (pg · min/mL)<br>AUCtau (pg · min/mL)<br>AUC3d (pg · min/mL) | AUC(0-t)<br>DPI-386 nasal gel: Doses 1-6<br>Scopolamine transdermal system<br>AUCinf<br>DPI-386 nasal gel Dose 1<br>Scopolamine transdermal system<br>AUCtau<br>DPI-386 nasal gel: Doses 1-6<br>AUC3d<br>DPI-386 nasal gel<br>Scopolamine transdermal system | AUCs were calculated using the Linear Up/Log Down Method.<br>The linear trapezoidal rule was used when concentrations were increasing, and the logarithmic trapezoidal rule was used when concentrations were decreasing.<br>AUC(0-t) is the sum of areas up to the last quantifiable time.<br>AUCinf = AUC(0-t) + Ct/λz<br>AUCtau = AUC(0-6) for AM doses and AUC(0-18) for PM doses<br>For AUCtau, λz will be used to estimate the concentration at the end of the dosing interval. If λz cannot be estimated and the 360-minute (6-hour) PK sample is collected within ±15 minutes of the scheduled time, then AUCtau may be calculated directly for AM doses of DPI-386 nasal gel. Similarly, if λz cannot be estimated and the pre-dose PK sample is collected within ±30 minutes of the scheduled time, then AUCtau may be calculated directly for PM doses of DPI-386 nasal gel.<br>***Note: BLOQ values at the end of the concentration-time profile were assigned*** |

TABLE 6i-continued

| Scopolamine Plasma PK Parameters | | |
|---|---|---|
| Plasma PK Parameters | Treatments and Doses for Which PK Parameter is Derived | Derivation |
| | | ***values of 0 pg/mL for purposes of estimating AUCtau.*** Note: The Dose 5 pre-dose concentration may be carried forward to estimate AUCtau for Dose 6. For DPI-386 nasal gel, AUC3d is the sum of AUCtau over the 3 days (6 doses) |
| AUC % ex (%) | DPI-386 nasal gel Dose 1 Scopolamine transdermal system | AUC % ex = AUCinf − AUC(0-t))/AUCinf * 100 |
| CL/F (mL/min) | DPI-386 nasal gel Doses 1 & 5 Scopolamine transdermal system | ***DPI-386 nasal gel Dose 1: AUCinf/Dose * (303.35/384.3)*** [a] ***DPI-386 nasal gel Dose 5: Dose/AUCtau * (303.35/384.3)*** [a] Transdermal system: Dose/AUCinf |
| Vz/F (mL) | DPI-386 nasal gel Doses 1 & 5 Scopolamine transdermal system | DPI-386 nasal gel Dose 1: ***Dose/λz * AUCinf * (303.35/384.3)*** [a] DPI-386 nasal gel Dose 5: ***Dose/λz * AUCtau * (303.35/384.3)*** [a] Transdermal system: Dose/λz * AUCinf |

[a] 303.35 = molecular weight of scopolamine; 384.3 = molecular weight of scopolamine HBr
Ctau, AUCtau, CL/F, and Vz/F: Bold Italicized text indicates clarification of and/or change from the SAP.

TABLE 6j

| Scopolamine Urine PK Parameters | | |
|---|---|---|
| Urine PK Parameters | Treatments and Doses for Which PK Parameter is Derived | Derivation |
| Ae (pg) | DPI-386 nasal gel Dose 6 | Concentration*Volume |
| Cumulative amount excreted (pg) | DPI-386 nasal gel Dose 6 | Σ(Concentration*Volume) Where Σ is the sum of the urine collection intervals |
| Percent of dose recovered as parent in urine | DPI-386 nasal gel Dose 6 | Σ(Concentration*Volume)/administered dose (200,000,000 pg) |
| CLr (mL/min) | DPI-386 nasal gel Dose 6 | Σ(Concentration*Volume)/AUCtau |

Statistical Analysis of Drug Concentrations, PK Parameters, and PK/PD Relationships Plasma scopolamine concentrations were summarized by treatment, dosing occasion, and PK sampling time. Scopolamine PK parameters were summarized by treatment and dosing occasion. Plasma scopolamine concentration-time profiles and PK parameters were plotted as described in the SAP.

Accumulation and Time Invariance

Accumulation of scopolamine following administration of the DPI-386 nasal gel was assessed by estimating R(Cmax) and R(AUCtau), defined as the Dose 5/Dose 1 values. In addition, time variance was assessed as R(AUCtau/AUCinf), where AUCtau was estimated on Dose 5 and AUCinf was estimated on Dose 1.

Relative Bioavailability

A mixed model analysis with treatment, period, and sequence as fixed effects and participant within sequence as a random effect was used to evaluate the relative bioavailability of scopolamine administered as the DPI-386 Nasal Gel and the scopolamine transdermal system (Transderm Scop). Scopolamine AUC3d and Cmax (Dose 5) for the DPI-386 Nasal Gel were compared to AUC3d and Cmax for scopolamine transdermal system; PK parameters were log-transformed prior to statistical analysis. The 90% confidence interval (CI) for the difference in the means of the log-transformed data were calculated. The antilogs of the confidence limits obtained constituted the 90% CI for the ratio of the geometric means between DPI-386 Nasal Gel and scopolamine transdermal system.

PK/PD Analysis

Relationships between plasma scopolamine PK and pharmacodynamic (PD; ACTS) endpoint were explored graphically. PK exposure metrics Cmax, AUC(0-t), and AUC3d were plotted vs. the ACTS symptom of maximum severity post-baseline using box-plots.

Safety Analysis

All safety data were listed. Exposure, AEs, and ACTS were summarized by treatment. Clinical laboratory data, vital signs, and ECGs were summarized by treatment and time point.

Determination of Sample Size

A total of 20 participants were to be enrolled in the study to achieve 18 evaluable participants. The between-subject coefficient of variation in geometric mean (GM CV %) for scopolamine Cmax was 136% and for scopolamine AUClast was 103% (Study DPI-386-MS-22 Day 3 AM dose). Assuming a with-in subject CV of 100% for Cmax and 75% for AUC3d, a sample size of 18 participants was selected to provide precision of at least 62% for Cmax and 48% for AUC3d for the comparison of PK between the two products; for example, for a point estimate of 1.00, the estimated 90% CIs for the Cmax and AUC3d comparisons were 0.62-1.62 and 0.68-1.48, respectively.

Study Participants

Disposition of Participants

Twenty-eight participants were screened, 21 participants received study drug, and 18 participants completed the study (Table 6k, below). Three participants prematurely withdrew from the study; Subject 013 withdrew after completing Period 1 and Subject 005 and Subject 006 both withdrew after receiving the second dose of DPI-386 Nasal Gel in Period 2; the reasons for withdrawal were landlord requiring participants to return home (Subject 005 and Subject 006) and work issues (Subject 013). One participant, Subject 020, prematurely discontinued the Transderm Scop treatment due to rash; the transdermal scopolamine system was removed on the evening of Period 2 Day 2, rather than on the morning of Period 2 Day 3.

TABLE 6k

Disposition of Participants

| Category | All Participants N = 28 n (%) |
|---|---|
| Enrolled (Screened) Population | 28 |
| Safety (Dosed) Population | 21 |
| PK Concentration Population | 21 (100%) |
| PK Parameter Population | 21 (100%) |
| PK/PD Population | 21 (100%) |
| Participants in the Safety Population Who Completed the Study | 18 (85.7%) |
| Participants in the Safety Population Who Discontinued the Study | 3 (14%) |
| Primary reason for discontinuation | |
| Adverse event | 0 |
| Lost to follow-up | 0 |
| Protocol violation | 0 |
| Withdrawal by participant | 0 |
| Other[a] | 3 (14%) |

[a]Other: Landlord required participant to return home; did not withdraw consent (n = 2); Withdrew due to work issues (n = 1).

Protocol Deviations

All participants in the safety population met the Inclusion/Exclusion criteria. Overall, 18/21 (85.7%) participants reported minor protocol deviations related to assessments outside of the protocol-specified window: ACTS (10 events), vital signs (10 events), or PK sample (5 events), 1 instance where rest time was documented during vital signs collection, and 1 instance of missed reticulocyte count at screening. In addition, one participant had the Transderm Scop patch removed early due to development of a maculopapular rash.

Demographic and Baseline Characteristics

A summary of demographics and baseline characteristics for the safety population is presented in Table 61, below.

TABLE 6l

Summary of Demographic and Baseline Characteristics

| Variable; statistics | Safety Population N = 21 |
|---|---|
| Age (years); mean (SD) [min, max] | 31.9 (7.03) [23, 51] |
| Weight (kg); mean (SD) [min, max] | 76.38 (10.989) [55.3, 100.1] |
| BMI (kg/m2); mean (SD) [min, max] | 25.46 (2.908) [20.4, 29.9] |
| Sex; n (%) | |
| Male | 17 (81%) |
| Female | 4 (19%) |
| Race; n (%) | |
| Asian | 1 (4.8%) |
| Black or African American | 13 (61.9%) |
| White | 5 (23.8%) |
| Other | 1 (4.8%) |
| Not Reported | 1 (4.8%) |
| Ethnicity; n (%) | |
| Hispanic or Latino | 4 (19.0%) |
| Not Hispanic or Latino | 19 81%) |

Measurements of Treatment Compliance

Study drugs were administered as planned, except for Subject 020 who had the transdermal scopolamine patch removed on the evening of Period 2 Day 2, rather than on the morning of Period 2 Day 3.

Pharmacokinetic Evaluation

Pharmacokinetic Subject Accountability and Data Handling

Overall, 21 and 20 participants underwent plasma PK sampling after receiving transdermal scopolamine and DPI-386 Nasal Gel, respectively. All 21 participants provided evaluable plasma PK data for at least one treatment. The reasons for excluding data from the plasma concentration and/or PK parameter summaries are provided in Table 6m, below.

TABLE 6m

Summary of Plasma Pharmacokinetic Data Handling

Data excluded from plasma concentration and PK parameter summaries

| Treatment | Participants | PK Data Handling & Accountability Details |
|---|---|---|
| Transderm Scōp | 020 | The transdermal scopolamine patch was removed early. |

Data excluded from plasma PK parameter summaries where R2 <0.85 for estimation of λz

| Treatment | Participants | PK parameters excluded from summary |
|---|---|---|
| DPI-386 Nasal Gel | 020 (Dose 5) | t½, Vz/F |
| Transderm Scōp | 002, 003, 004, 005, 006, 014, 015, 019, 024, 026 | AUCinf, AUC % ex, t½, CL/F, Vz/F |

Data excluded from plasma PK parameter summaries where AUC % ex >30%.

| Treatment | Participants | PK parameters excluded from summary |
|---|---|---|
| Transderm Scōp | 002, 003, 004, 005, 006, 010, 014, 015, 019, 024, 026, 027 | AUCinf, CL/F, Vz/F |

Plasma PK parameters not estimated because λz was not estimable

| Treatment | Participants | PK parameters not estimated |
|---|---|---|
| DPI-386 Nasal Gel | 019 (Dose 1), 020 (Dose 1) | AUCinf, AUC % ex, t½, CL/F, Vz/F |

Overall, 18 participants underwent urine PK sampling after receiving the last (64) dose of DPI-386 Nasal Gel. All 18 participants provided evaluable urine PK data and were included in the urine concentration and PK parameter summaries.

Pharmacokinetic Results

Plasma Pharmacokinetic Profile

DPI-386 Nasal Gel Pharmacokinetic Profile

Figure 6A:
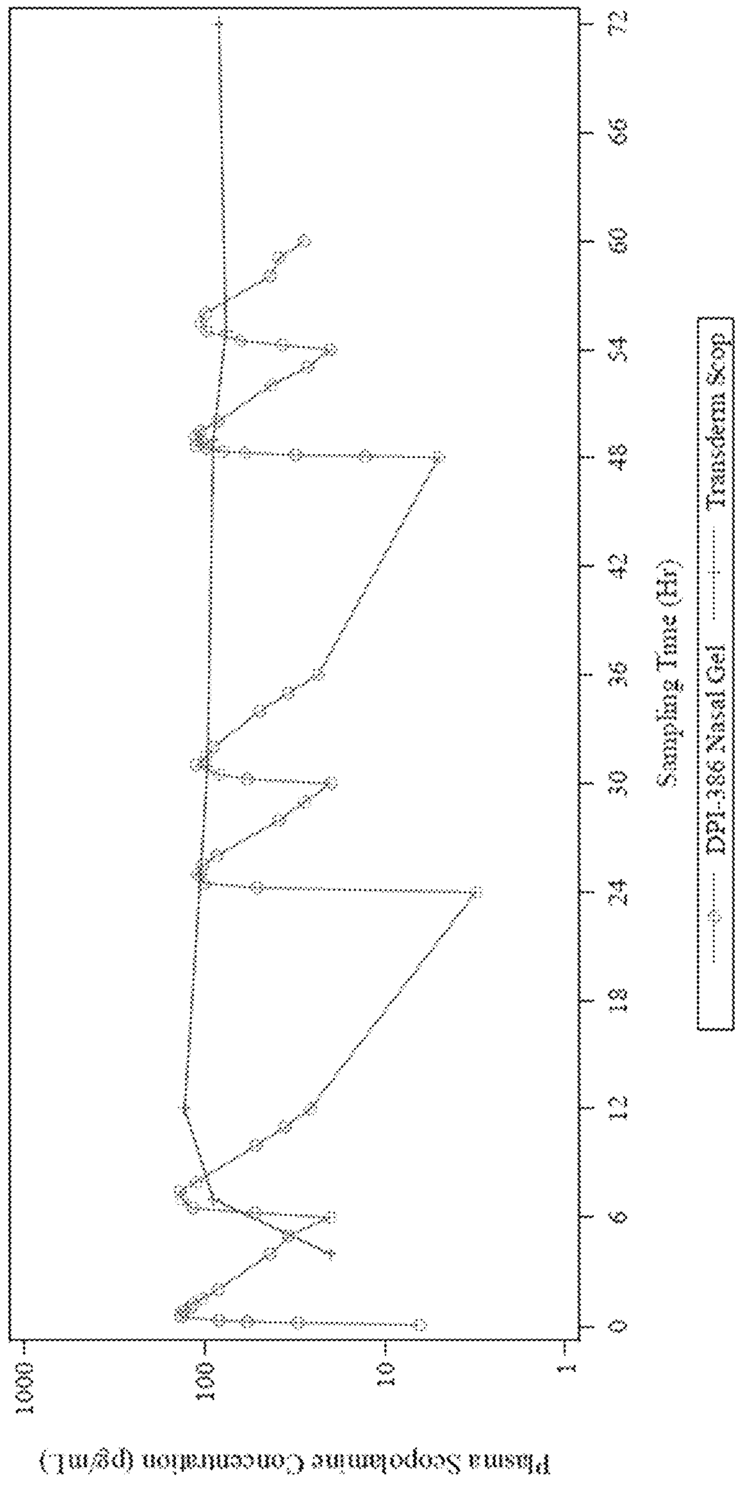
FIG. 6A is a graphic presentation from clinical study MS-31 showing Median Plasma Scopolamine Concentration-Time Profiles-Semi-log (PK Parameter Population) Note: DPI-386 Nasal Gel 0.2 mg scopolamine HBr was administered into one nostril twice daily, 6 hours apart within a day, for 3 consecutive days. The total dose of 1.2 mg scopolamine HBr is equivalent to 0.95 mg scopolamine. Note: The scopolamine transdermal system (Transderm Scop) was applied once and is designed for continuous release of scopolamine 1 mg over 3 days, in a 1.5 mg patch.
Figure 6T:
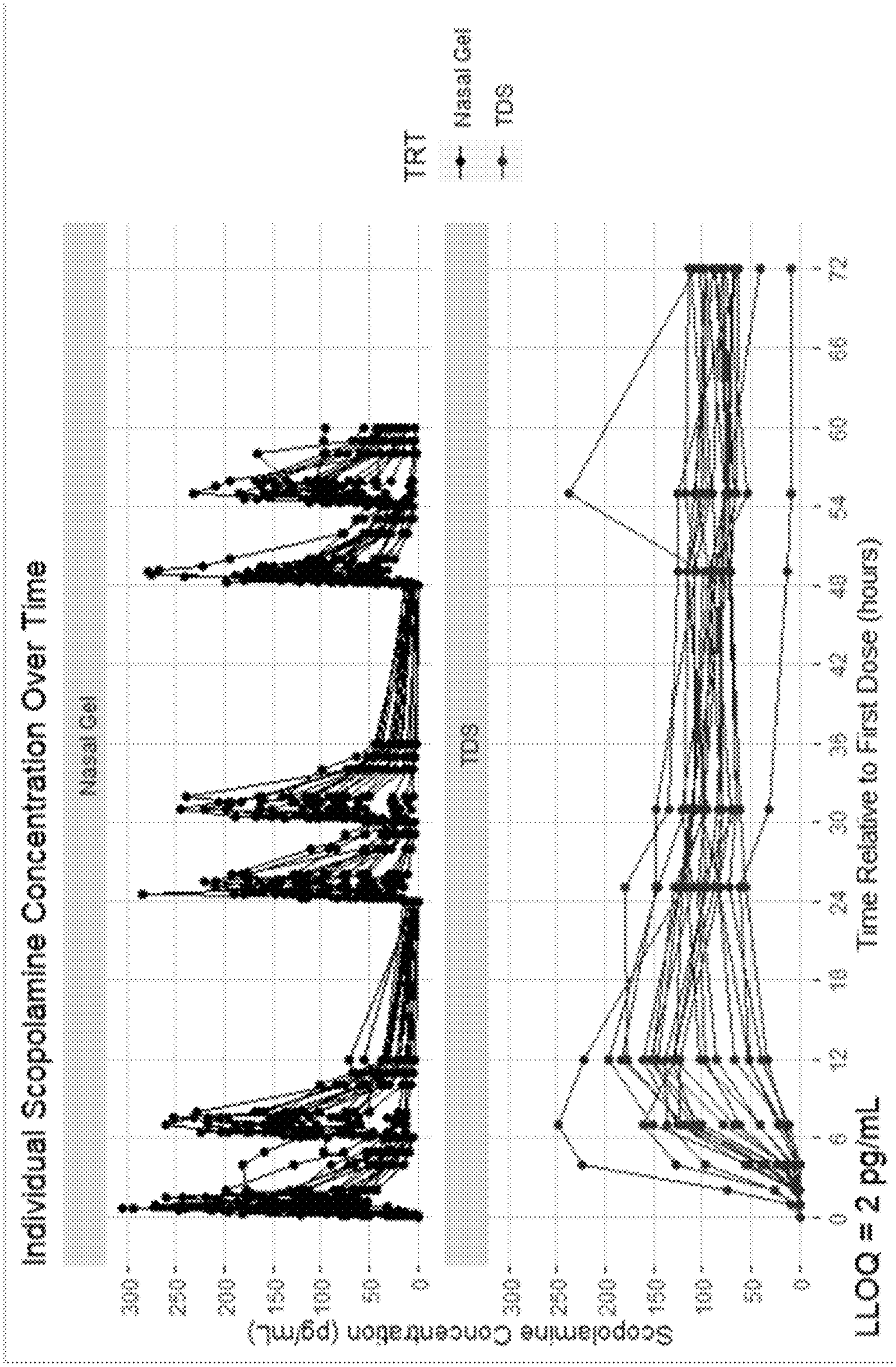
FIGS. 6T, 6U, and 6V, each provide a graphic illustration of a pharmaceutical composition of the present disclosure shown as a profile of scopolamine concentration over time.
Figure 6U:
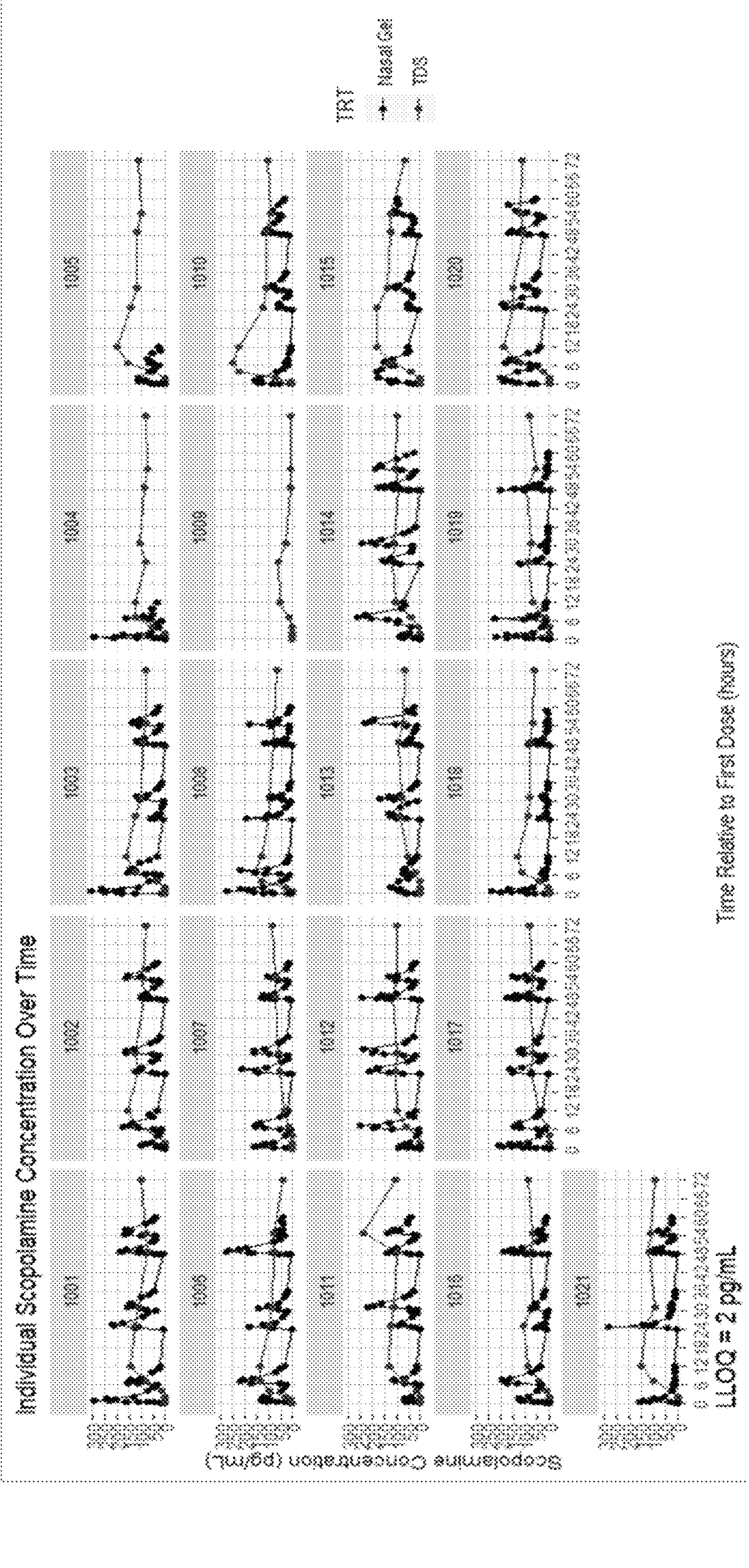
Figure 6V:
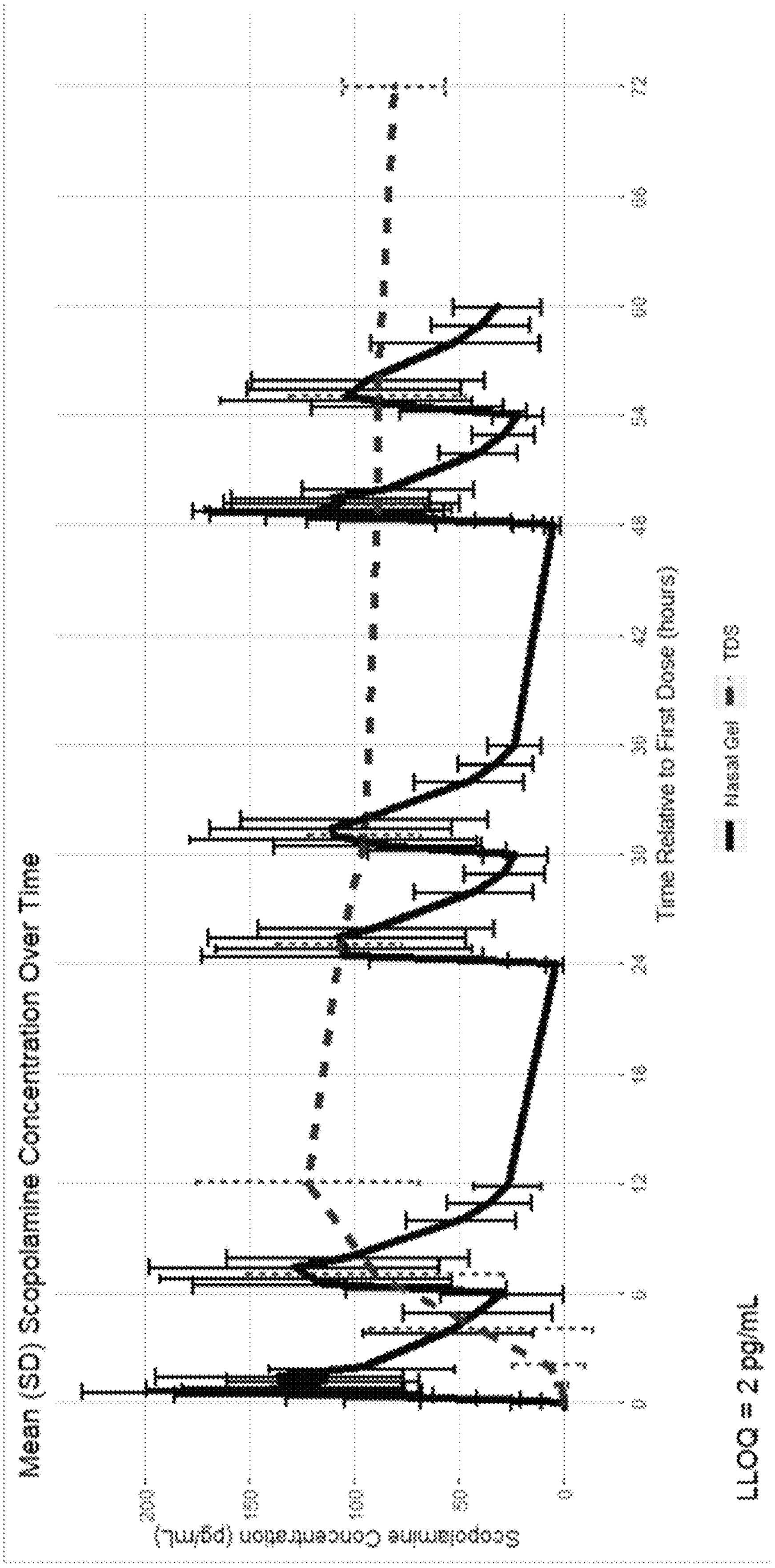
Figure 6W:
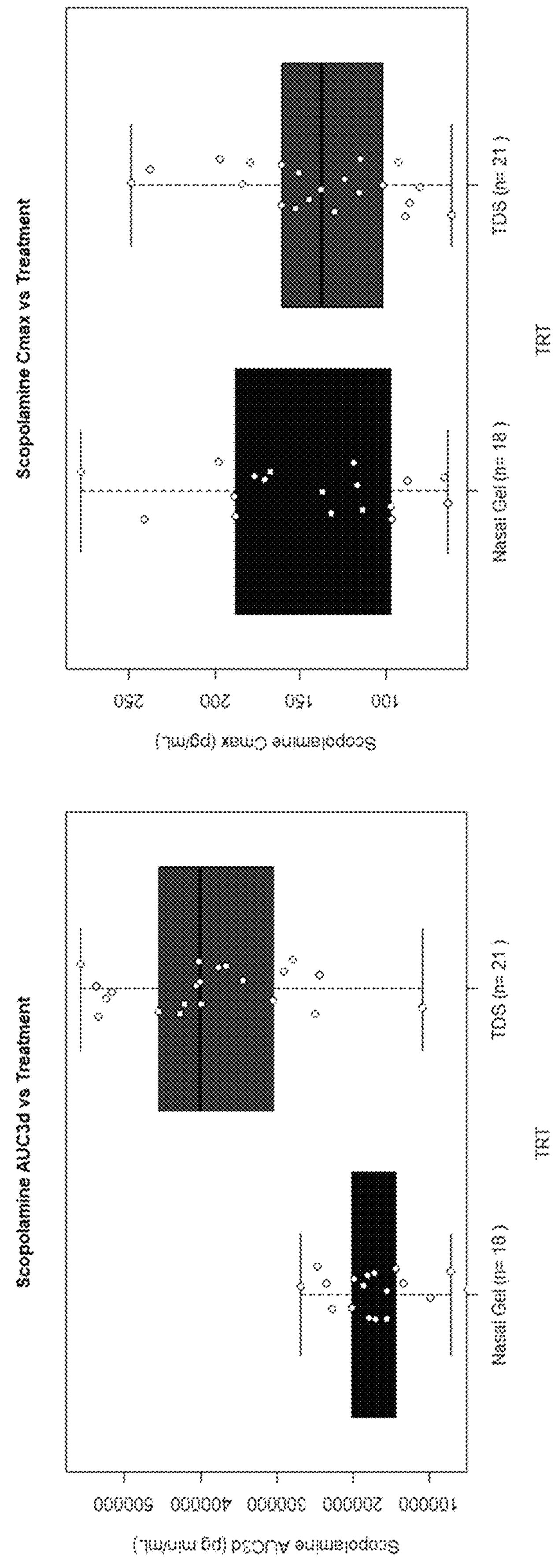
FIG. 6W illustrates comparator of an embodiment of the present disclosure compared to a transdermal administration of scopolamine for each of AUC3d and Cmax
Figure 6Z:
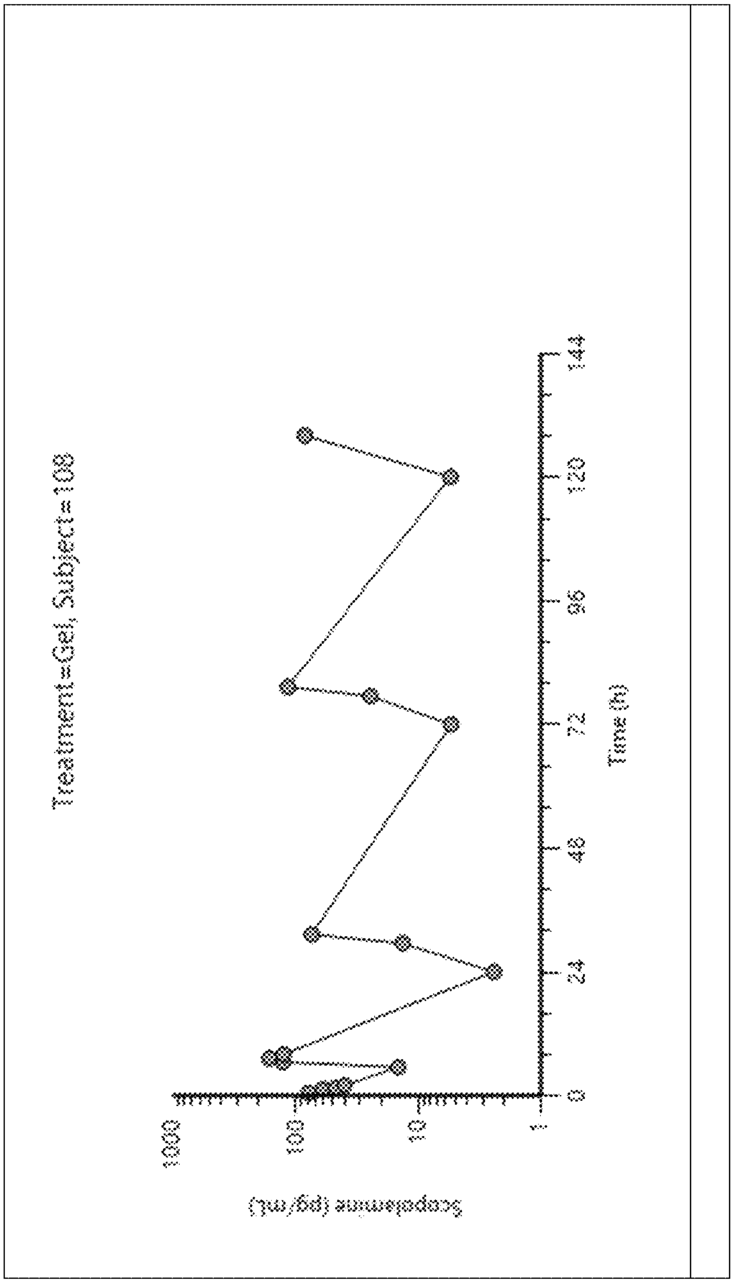
FIGS. 6B through 6S, respectively, provide summary tables of pK parameters forming embodiments and aspects of the present disclosure.
FIG. 6X is a tabulated summary of pharmacokinetic data for an embodiment of the present disclosure.
FIG. 6Y is a statistical comparison of pharmacokinetic data for an embodiment of the present disclosure FIGS. 6Zi through 6Zix each illustrate individual subject concentration-time profiles (log-linear plots).
FIG. 6CC is a graphical illustration of mean concentration-time plot of Study 07 Data using Study 31 formatting-linear plot.
FIG. 6DD is a graphical illustration of mean concentration-time plot of Study 31 Data-linear plot.
FIG. 6EE is a graphical illustration of mean concentration-time plot of Study 31 Data-log-linear plot.
FIG. 6FF is a graphical illustration of a linear plot of mean concentration-time plot of Study 31 data with period(s) of time with gel concentrations greater than patch.
FIG. 6GG is a table providing calculation of time that gel concentration is greater than the patch concentration over the 72-hour sampling time.
Figure 6Z:
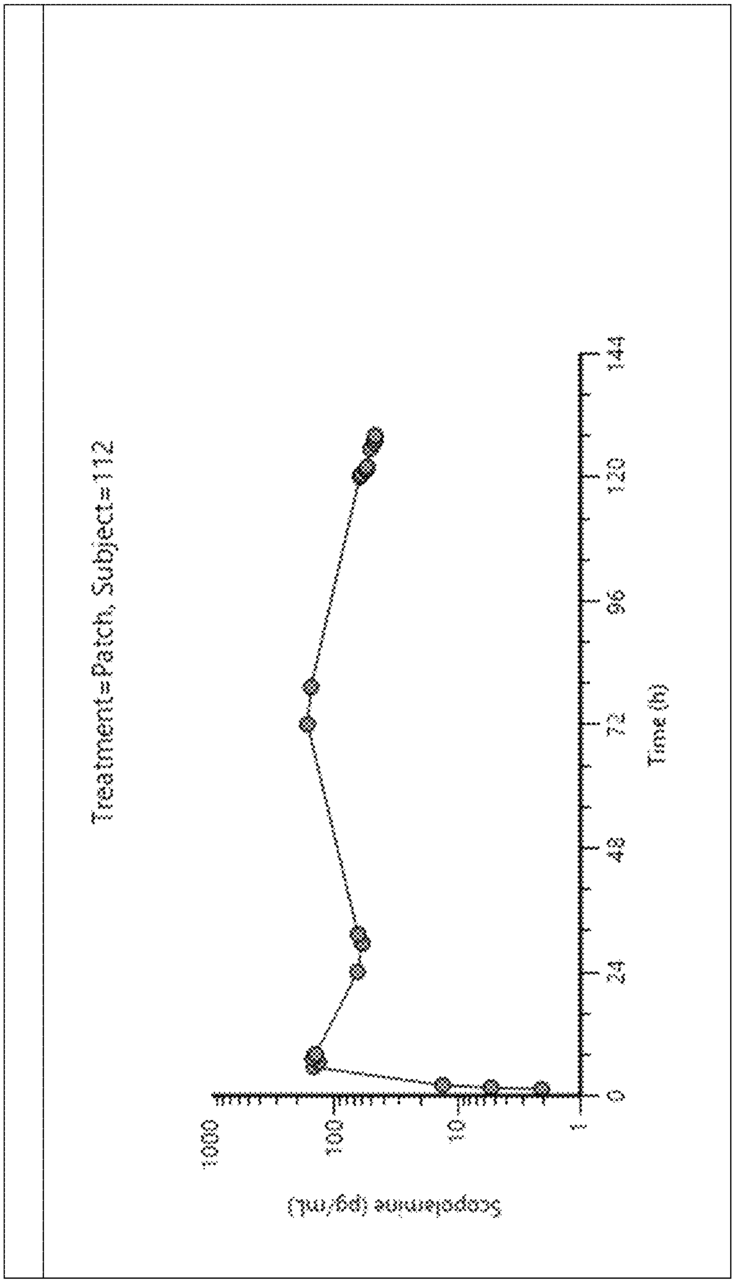
Figure 6A:
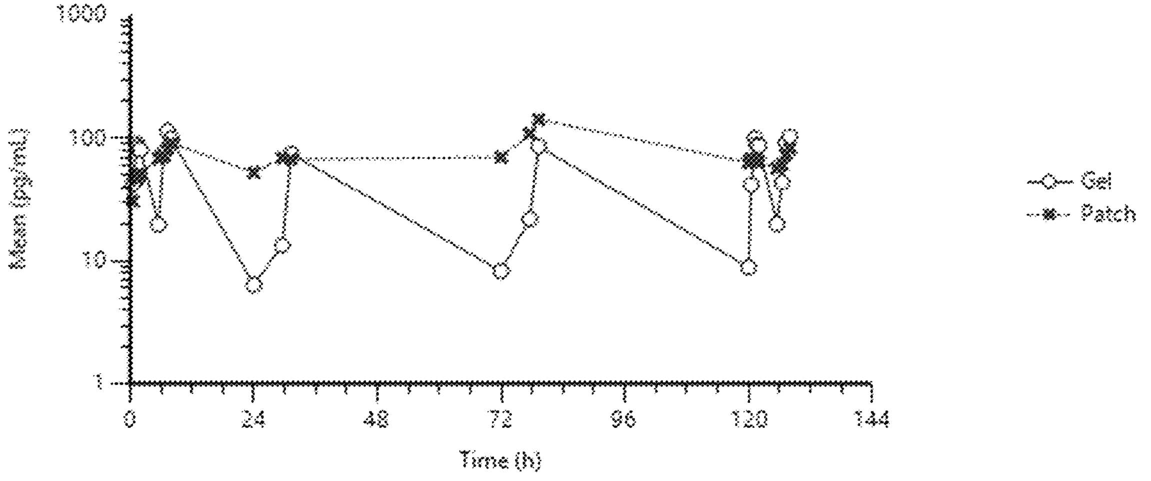

Scopolamine was rapidly absorbed following intranasal administration; concentrations were quantifiable at the first (10-minute) sampling time point and median tmax ranged from 40 to 60 minutes (Table 6n, below). After reaching Cmax, plasma scopolamine concentrations decreased in a monophasic manner (FIG. 6A). Median t½ values ranged from 91.4 to 110 minutes (1.5 to 1.8 hours) (Table 6n). Inter-subject variability (CV %) in scopolamine Cmax and AUCtau ranged from 40 to 53% and 41 to 52%, respectively, following intranasal administration.

Transdermal Scopolamine Pharmacokinetic Profile

Following application of Transderm Scop patch, scopolamine concentrations were quantifiable within approximately 4 hours (median tlag was 2 hours [120 minutes; Table 50, below]) and median tmax was 12 hours (721 minutes). After reaching Cmax, plasma scopolamine concentrations were sustained near Cmax until the patch was removed on Day 4 (72 hours after application) (FIG. 6A). Inter-subject variability (CV %) in scopolamine Cmax and AUC3d were 33% and 28%, respectively.

TABLE 6n

Summary of Scopolamine PK Parameters for DPI-386 Nasal Gel

| | | Mean ± SD (CV %) | | | | | Median (min, max) | |
|---|---|---|---|---|---|---|---|---|
| Treatment | Day/Dose | AUCinf (min * pg/mL) | AUC(0-t) (min * pg/mL) | AUCtau[a] (min * pg/mL) | Cmax (pg/mL) | Ctau (pg/mL) | t½ (min) | tmax (min) |
| DPI-386 Nasal Gel 0.2 mg scopolamine HBr/0.12 g gel | Day 1/ Dose 1 N = 20 | 28,348 ± 10,726 (38) [N = 18] | 26,484 ± 10,796 (41) | 26,576 ± 10,821 (41) | 176 ± 74.3 (42) | 29.6 ± 29.2 (99) | 91.4 (67.7, 139) | 50 (20, 300) |
| | Day 1/ Dose 2 N = 20 | — | 32,478 ± 17,297 (53) | 34,278 ± 16,436 (48) | 148 ± 72.7 (49) | 4.14 ± 3.92 (95) [N = 18] | — | 60 (30, 120) |
| | Day 2/ Dose 3 N = 18 | — | 21,957 ± 11,363 (52) | 22,051 ± 11,417 (52) | 141 ± 71.0 (50) | 23.1 ± 15.4 (67) | — | 60 (15, 122) |
| | Day 2/ Dose 4 N = 18 | — | 31,181 ± 15,431 (49) | 31,607 ± 14,976 (47) | 127 ± 66.6 (53) | 5.42 ± 4.01 (74) | — | 60 (15, 120) |
| | Day 3/ Dose 5 N = 18 | — | 21,783 ± 9001 (41) | 21,885 ± 9035 (41) | 147 ± 58.9 (40) | 21.7 ± 11.7 (54) | 110 (72.5, 201) | 40 (10, 75) |
| | Day 3/ Dose 6 N = 18 | — | 32,959 ± 16,812 (51) | 32,264 ± 16,498 (50) | 119 ± 61.0 (51) | — | — | 60 (15, 240) |

[a]tau = 6 hours for Doses 1, 3, 5 and 18 hours for Doses 2, 4, 6

TABLE 6o

Summary of Scopolamine PK Parameters for DPI-386 Nasal Gel and Transdermal Scopolamine

| | | | Mean ± SD (CV %) | | Median (min, max) | |
|---|---|---|---|---|---|---|
| Treatment | Dosing Frequency | N | AUC3 d[a] (min*pg/mL) | Cmax[a] (pg/mL) | tlag[a] (min) | tmax[a] (min) |
| DPI-386 Nasal Gel 0.2 mg scopolamine HBr/0.12 g gel | Twice Daily for 3 days (total dose = 1.2 mg[b]) | 18 | 170,741 ± 57,978 (34) | 147 ± 58.9 (40) | 0 (0, 0) | 40 (10, 75) |
| Transderm Scop | Continuous release of scopolamine 1 mg over 3 days | 20 | 378,186 ± 106,417 (28) | 134 ± 44.3 (33) | 120 (0, 240) | 721 (420, 4320) |

[a]For DPI-386 Nasal Gel, AUC3 d is the sum of AUCtau over 3 days/6 doses and Cmax, tlag, and tmax are for Day 3/Dose 5.
[b]The total dose of 1.2 mg scopolamine HBr is equivalent to 0.95 mg scopolamine.

Accumulation and Time Invariance

There was no accumulation with twice daily dosing of the DPI-386 Nasal Gel and scopolamine PK were time invariant (see Table 6p, below).

TABLE 6p

| Statistical Assessment of Accumulation and Time Invariance | | | | |
|---|---|---|---|---|
| | | GLM | | GLM Ratio (90% CI) |
| Assessment | Parameter | Day 1/Dose 1 | Day 3/Dose 5 | Dose 5 vs Dose 1 |
| Accumulation | R(AUCtau) | 24,510.57 | 20,069.33 | 0.82 (0.65, 1.04) |
| | R(Cmax) | 161.47 | 135.56 | 0.84 (0.66, 1.06) |
| Time Invariance | R(AUCtau/AUCinf) | 26,281.28 | 20,080.7 | 0.76 (0.60, 0.97) |

Units for GLM AUCtau and AUCinf are min*pg/mL and for Cmax are pg/mL

Relative Bioavailability

Figure 6B:
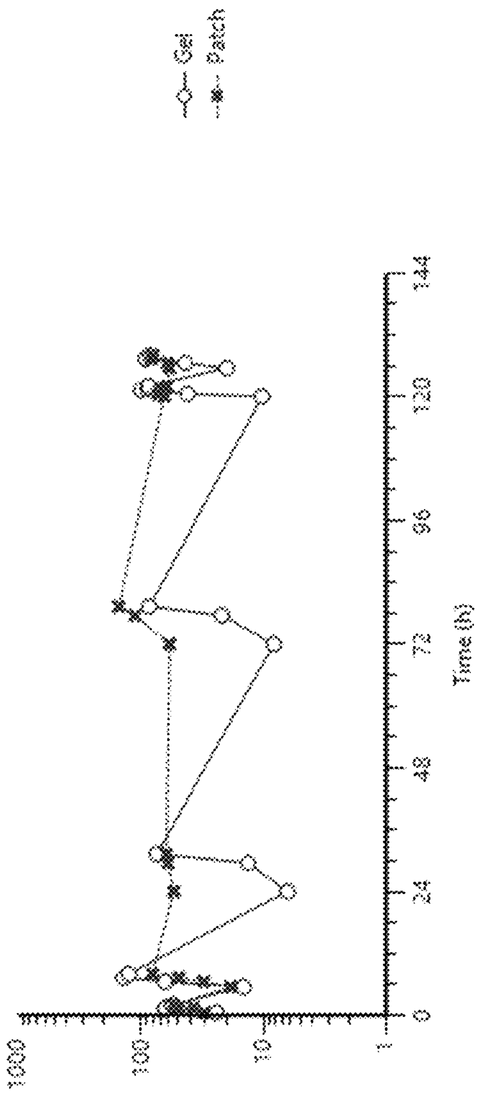
Figure 6C:
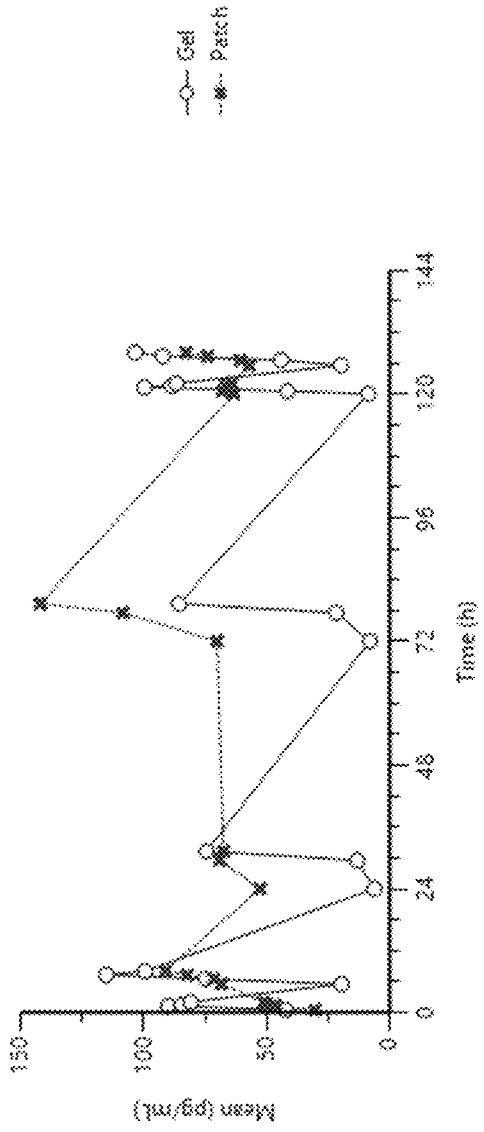
Figure 6D:
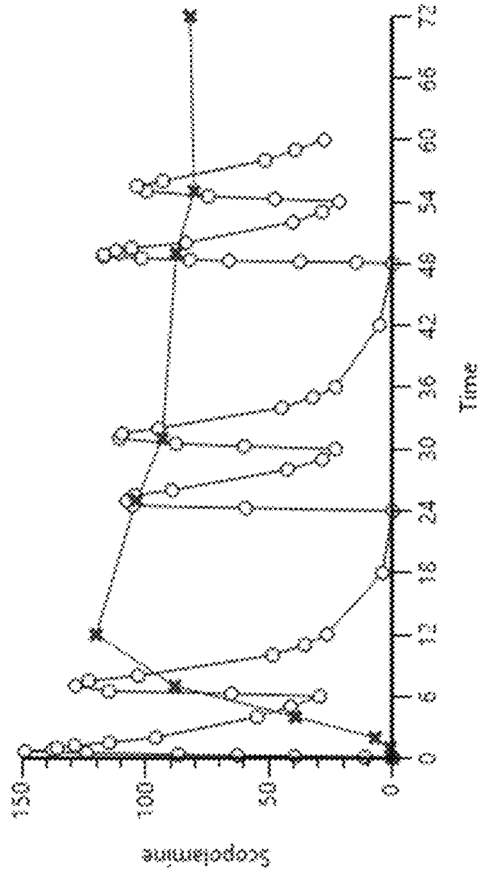
Figure 6E:
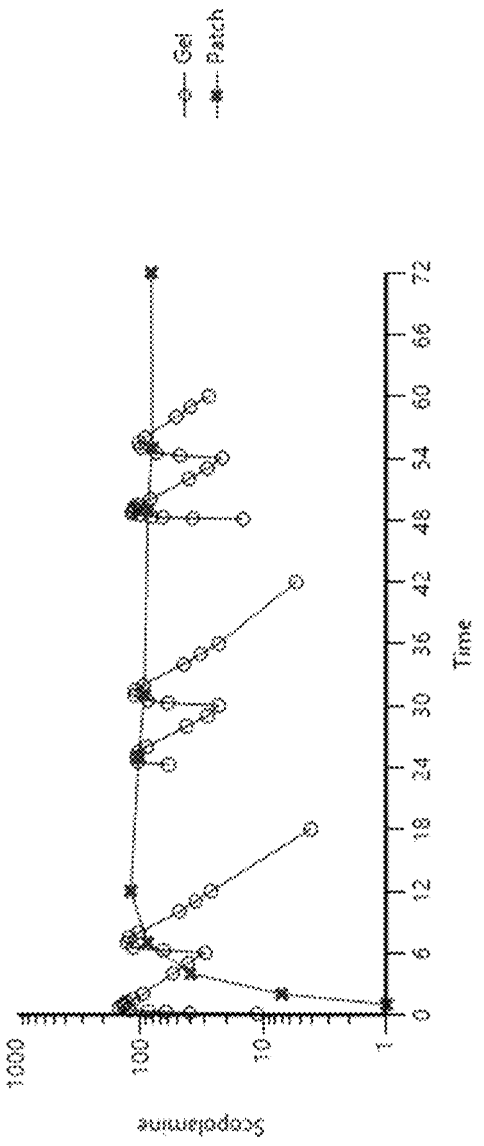
Figure 6F:
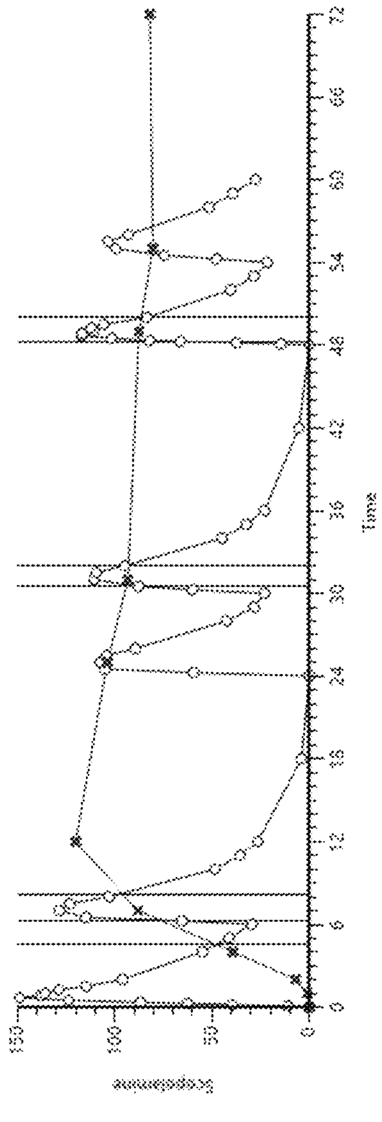

Intranasal administration of scopolamine HBr 0.2 mg twice daily for 3 days delivered similar scopolamine Cmax values and 57% lower AUC3d values, on average, compared with transdermal scopolamine (see Table 6q and FIG. 6B).

TABLE 6q

| Statistical Assessment of Relative Bioavailability | | | |
|---|---|---|---|
| | GLM | | GLM Ratio (90% CI) DPI-386 Nasal Gel |
| Parameter | DPI-386 Nasal Gel | Transderm Scop | vs. Transderm Scop |
| AUC3 d (min*pg/mL) | 155,937 | 363,343 | 0.43 (0.35, 0.53) |
| Cmax (pg/mL) | 137 | 128 | 1.07 (0.87, 1.32) |

Urine Pharmacokinetic Profile

Only a small proportion (median 1.10%) of the administered dose of DPI-386 Nasal Gel was excreted as unchanged scopolamine in urine (see Table 6r, below).

Plasma scopolamine concentrations decreased between each dose of DPI-386 Nasal Gel (median t½ of 1.5 to 1.8 hours); whereas concentrations were sustained near Cmax until the Transderm Scop patch was removed on Day 4 (72 hours after application). There was no accumulation with twice daily dosing of the DPI-386 Nasal Gel and scopolamine PK were time invariant. A small proportion (median 1.10%) of the administered dose of DPI-386 Nasal Gel was excreted as unchanged scopolamine in urine.

Across the range of scopolamine exposures observed in this study there was no apparent relationship between scopolamine exposure and ACTS severity.

Safety Evaluation

Extent of Exposure

The extent of exposure to study drug is summarized in Table 6s, below. One participant had the transdermal scopolamine patch removed one day early.

TABLE 6r

| Summary of Scopolamine Urine Excretion Data for DPI-386 Nasal Gel | | | | | |
|---|---|---|---|---|---|
| Treatment | Day/Dose | Statistic | Cumulative Amount Excreted (μg) | Cumulative Percent of Dose Excreted as Unchanged Scopolamine (%) | CLr (L/h) |
| DPI-386 Nasal Gel | Day 3/Dose 6 | Median | 1.75 | 1.10 | 3.47 |
| 0.2 mg scopolamine | N = 18 | (min, max) | (0.18, 4.35) | (0.11, 2.76) | (1.18, 6.08) |
| HBr/0.12 g gel | | Mean (±SD) | 1.91 (1.104) | 1.21 (0.700) | 3.691.223) |

Pharmacokinetic/Pharmacodynamic Results

Across the range of scopolamine exposures observed in this study there was no apparent relationship between scopolamine exposure and ACTS severity.

Pharmacokinetic and Pharmacokinetic/Pharmacodynamic Conclusions

Intranasal administration of scopolamine HBr 0.2 mg twice daily for 3 days delivered similar scopolamine Cmax values and 57% lower AUC3d values, on average, compared with Transderm Scop (continuous release of scopolamine 1 mg over 3 days).

Absorption of scopolamine was more rapid following administration of DPI-386 Nasal Gel compared with Transderm Scop. For DPI-386 Nasal Gel, scopolamine concentrations were quantifiable within approximately 10 minutes and median tmax was 40 to 60 minutes. For Transderm Scop, scopolamine concentrations were quantifiable within approximately 4 hours and median tmax was 12 hours.

TABLE 6s

| Study Drug Exposure | | |
|---|---|---|
| | DPI-386 Nasal Gel (N = 20)[a] | Transdermal Scopolamine (N = 21)[b] |
| Number of Doses | 6 doses: 18 | 1 dose: 21 |
| | 2 doses: 2 | |
| Duration of Exposure | 3 days: 18 | 3 days: 20 |
| | 1 day: 2 | 2 days: 1 |
| Cumulative Exposure | 1.2 mg: 18 | 1.0 mg: 20 |
| | 0.4 mg: 2 | 0.86 mg: 1 |

[a]DPI-386 Nasal Gel 0.2 mg scopolamine HBr was administered into one nostril twice daily, 6 hours apart within day, for 3 consecutive days. The total dose of 1.2 mg scopolamine HBr is equivalent to 0.95 mg scopolamine.

[b]The scopolamine transdermal system (Transderm Scop) was applied once and is designed for continuous release of scopolamine 1 mg over 3 days.

Adverse Events

Brief Summary of Adverse Events

No participants reported AEs during DPI-386 Nasal Gel treatment, whereas 10/21 (47.6%) participants reported AEs during transdermal scopolamine treatment (see Table 6t, below). One participant discontinued transdermal scopolamine treatment due to a maculopapular rash on the face and neck considered possibly drug related. There were no deaths, no serious AEs, and no AEs >Grade 1.

TABLE 6t

Overall Summary of TEAEs

| | DPI-386 Nasal Gel | Transdermal Scopolamine |
|---|---|---|
| Subjects with Any TEAE, n (%) | 0 | 10 (47.6) |
| Subjects with Any Serious TEAE, n (%) | 0 | 0 |
| Subjects with Any DPI-386 Nasal Gel-Related TEAE, n (%) | 0 | 0 |
| Subjects with Any Transderm Scop-Related TEAE, n (%) | 0 | 10 (47.6%) |
| Subjects with Any TEAE Leading to Permanent Discontinuation from Study Drug, n (%) | 0 | 0[a] |
| Subjects with Any TEAE of Grade 3 or Grade 4, n (%) | 0 | 0 |
| Subjects with Any Fatal TEAE, n (%) | 0 | 0 |

[a]Per the AE listing and protocol deviations log, one participant discontinued transdermal scopolamine treatment due to a maculopapular rash on the face and neck considered possibly drug related. However, on the AE eCRF page, the response to Action taken with Transderm Scōp was recorded as dose not changed.

Display of Adverse Events

TEAEs are summarized by system organ class (SOC) and preferred term (PT) in Table 6u, below. All TEAEs were Grade 1. All TEAEs reported for transdermal scopolamine were considered drug-related (adverse drug reactions).

TABLE 6u

Summary of TEAEs by SoC and PT

| SoC/PT | DPI-386 Nasal Gel | Transdermal Scopolamine |
|---|---|---|
| Subjects with at Least One TEAE, n (%) | 0 | 10 (47.6) |
| Eye Disorders | 0 | 1 (4.8%) |
| Vision Blurred | 0 | 1 (4.8%) |
| Gastrointestinal Disorders | 0 | 7 (33.3%) |
| Dry Mouth | 0 | 7 (33.3%) |
| General disorders and administration site conditions | 0 | 4 (19.0%) |
| Application site erythema | 0 | 2 (9.5%) |
| Application site pruritus | 0 | 3 (14.3%) |
| Skin and subcutaneous tissue disorders | 0 | 1 (4.8%) |
| Rash maculo-papular | 0 | 1 (4.8%) |

Anticholinergic Toxicity Scale (ACTS)

No participants reported ACTS symptoms during the DPI-386 Nasal Gel treatment, whereas 7/21 (33.3%) participants reported ACTS symptoms of blurry vision (1/21 [4.8%]) and/or dry mouth (7/21 [33.3%]) during the transdermal scopolamine treatment.

Deaths, Other Serious Adverse Events, and Other Significant Adverse Events

There were no deaths, SAEs, or other significant AEs.

Clinical Laboratory Evaluation

Evaluation of Each Laboratory Parameter

Laboratory Values Over Time: There were no trends in clinical laboratory values over time.

Individual Participant Changes: There were no clinically meaningful changes in clinical laboratory values over time within an individual participant.

Individual Clinically Significant Abnormalities: There were no clinically significant abnormalities in clinical laboratory parameters.

Vital Signs

There were not trends in vital signs over time, and there were no clinically significant vital sign abnormalities.

ECG

There were no trends for changes in ECG parameters during the study, and there were no clinically significant abnormal ECG results.

Columbia-Suicide Severity Rating Scale

All responses to the C-SSRS questions were negative for suicidal ideation and suicidal behavior.

Physical Findings, and Other Observations Related to Safety

Five participants had abnormal physical examination findings of head, eyes, ears, nose, and throat and dermatological systems; these physical examination finding were captured as AEs (dry mouth, erythema, maculopapular rash).

Safety Conclusions

No participants reported TEAEs during the DPI-386 Nasal Gel treatment, whereas 10/21 (47.6%) participants reported TEAEs during the transdermal scopolamine treatment. All TEAS reported for transdermal scopolamine were considered drug related (adverse drug reactions). Drug-related TEAEs associated with transdermal scopolamine were blurred vision, dry mouth, maculopapular rash, and application site erythema and pain. One participant discontinued transdermal scopolamine treatment due to maculopapular rash on the face and neck considered possibly drug related. There were no deaths, no serious AEs, and no AEs >Grade 1. There were no trends, clinically meaningful changes, or clinically significant abnormalities in clinical laboratory, vital signs, or ECG parameters. All responses to the C-SSRS questions were negative for suicidal ideation and suicidal behavior.

Discussion and Overall Conclusions

DPI-386 Nasal Gel was designed to achieve therapeutic scopolamine concentrations more quickly than the transdermal system (Transderm Scop). Reference is made to FIGS. 5A through 5GG.

Following application of the transdermal system (Transderm Scop), scopolamine concentrations were quantifiable within approximately 4 hours and the median tmax was 12 hours. Following intranasal administration (DPI-386 Nasal Gel), scopolamine was rapidly absorbed; concentrations were quantifiable at the first (10-minute) sampling time point and median tmax ranged from 40 to 60 minutes.

The Transderm Scop prescribing information recommends that the transdermal system be applied at least 4 hours before the antiemetic effect is required (Transderm Scop US Prescribing Information, 2020). The median scopolamine concentrations at the end of the 6-hour dosing interval (Ctau) following morning doses of DPI-386 Nasal Gel ranged from 19.70 to 20.05 pg/mL for Doses 1, 3, and 5, and these values were the same as the median concentration observed 4 hours after application of the transdermal system (C4 hr) (19.95 pg/mL) (FIG. 5A). In addition, scopolamine Cmax values were similar for DPI-386 Nasal Gel and Transderm Scop (GLM Ratio [90% CI]=1.07 [0.87, 1.32]), supporting that DPI-386 Nasal Gel achieves therapeutic concentrations.

A small proportion (median 1.10%) of the administered dose of DPI-386 Nasal Gel was excreted as unchanged scopolamine in urine. This is consistent with published information, see Wu L, et al., Dose escalation pharmacokinetics of intranasal scopolamine gel formulation. J Clin Pharmacol. 2015 February; 55(2):195-203, which reported that following administration of scopolamine nasal gel formulations, <1.5% of the dose was excreted as unchanged scopolamine in urine & <5.2% of the dose was excreted as glucuronide metabolite(s) in urine.

No participants reported AEs during DPI-386 Nasal Gel treatment, whereas 10/21 (47.6%) participants reported TEAEs during transdermal scopolamine treatment. The approximately 57% lower AUC3d for DPI-386 Nasal Gel compared with Transderm Scop may have contributed to the apparent difference in the TEAE profile.

Conclusions

Intranasal administration of scopolamine HBr 0.2 mg twice daily for 3 days delivered similar scopolamine Cmax values and 57% lower AUC3d values, on average, compared with Transderm Scop (continuous release of scopolamine 1 mg over 3 days).

Absorption of scopolamine was more rapid following administration of DPI-386 Nasal Gel compared with Transderm Scop. Plasma scopolamine concentrations decreased between each dose of DPI-386 Nasal Gel (median t½ of 1.5 to 1.8 hours); whereas concentrations were sustained near Cmax until the Transderm Scop patch was removed on Day 4 (72 hours after application). There was no accumulation with twice daily dosing of the DPI-386 Nasal Gel and scopolamine PK were time invariant. A small proportion (median 1.10%) of the administered dose of DPI-386 Nasal Gel was excreted as unchanged scopolamine in urine.

No participants reported TEAEs during the DPI-386 Nasal Gel treatment, whereas 10/21 (47.6%) participants reported TEAEs during the transdermal scopolamine treatment. All TEAS reported for transdermal scopolamine were considered drug related (adverse drug reactions). Drug-related TEAEs associated with transdermal scopolamine were blurred vision, dry mouth, maculopapular rash, and application site erythema and pain. One participant discontinued transdermal scopolamine treatment due to maculopapular rash on the face and neck considered possibly drug related. There were no deaths, no serious AEs, and no AEs >Grade 1. There were no trends, clinically meaningful changes, or clinically significant abnormalities in clinical laboratory, vital signs, or ECG parameters.

While the steady state plasma level of the TDS is a recorded value, the Cmax of the nasal gel is "calculated" from the sampling intervals. In other words, the Cmax of the nasal gel is not a continuous sampling. Nonetheless, it is supportive for a demonstration that the Cmax of a pharmaceutical composition of the present disclosure does NOT need to be significantly greater than the steady state plasma levels of the TDS. The Cmax mean may be expressed as a GLSM.

TABLE 6v

Sampling Interal Tables - calculate Transdermal Patch Interval AUCs

| SUBJID | D2AM | D2PM | D3AM | D3PM |
|---|---|---|---|---|
| | TPT AUCt (h*pg/mL) | | | |
| 1003 | 11453 | 7332 | 13482 | 10002 |
| 1006 | | 14583 | 19391 | 13017 |
| 1009 | 31250 | 8076 | 25862 | 18600 |
| 1012 | 30438 | 22524 | 31392 | 25695 |
| 1015 | 17711 | 6077 | 16703 | 12009 |
| 1017 | 20718 | 14078 | 22115 | 16016 |
| 1020 | 21243 | 21230 | 27068 | 20292 |
| 1022 | 25467 | 17678 | 27584 | 20181 |
| 1026 | 45891 | 33360 | 41700 | 29310 |
| 1029 | 25176 | 17229 | 24519 | 19715 |
| 1033 | 18050 | 12288 | 18009 | 15150 |
| 1034 | 13034 | 10202 | 19901 | 16268 |
| 1038 | 19932 | 14469 | 20397 | 15237 |
| 1039 | 16481 | 12557 | 15522 | 10853 |
| 1046 | 25326 | 16941 | 17370 | 13806 |
| 1047 | 29132 | 23978 | 43440 | 50955 |

TABLE 6v-continued

Sampling Interal Tables - calculate Transdermal Patch Interval AUCs

| SUBJID | D2AM | D2PM | D3AM | D3PM |
|---|---|---|---|---|
| | TPT AUCt (h*pg/mL) | | | |
| 1050 | 19535 | 13587 | 17046 | 12867 |
| 1056 | 16115 | 8880 | 5502 | 5744 |
| 1058 | 36675 | 27156 | 32370 | 25677 |
| 1064 | 25053 | 17883 | 23747 | 18072 |
| 1066 | 44145 | 29985 | 32396 | 25772 |
| 1068 | 45465 | 34410 | 36675 | 31305 |
| 1075 | 30182 | 17390 | 29280 | 19235 |
| 1078 | 21333 | 14030 | 19397 | 12737 |
| 1081 | 35082 | 23900 | 95289 | 46170 |
| 1082 | 28367 | 19682 | 24096 | 18933 |
| 1086 | 25836 | 19227 | 24048 | 17633 |
| 1092 | 23489 | 16394 | 27708 | 16478 |
| 1094 | 33975 | 26265 | 36405 | 27150 |
| 1098 | 37605 | 28542 | 13397 | 20054 |
| 1102 | 31269 | 22646 | 25487 | 20772 |
| N | 30 | 31 | 31 | 31 |
| Mean | 26800 | 18500 | 26700 | 20200 |
| SD | 9180 | 7470 | 15300 | 9570 |
| CV % | 34.2 | 40.4 | 57.3 | 47.4 |
| Min | 11500 | 6080 | 5500 | 5740 |
| Median | 25400 | 17400 | 24100 | 18600 |
| Max | 45900 | 34400 | 95300 | 51000 |
| Geometric Mean | 25300 | 16900 | 23800 | 18400 |
| Geometric CV % | 36.41 | 46.23 | 50.82 | 45.72 |

Transdermal Patch Interval Cmax Values

| SUBJID | D2AM | D2PM | D3AM | D3PM |
|---|---|---|---|---|
| | TPT Cmax (pg/mL) | | | |
| 1003 | 37.7 | 33.6 | 45.4 | 43.0 |
| 1006 | | 67.7 | 73.6 | 55.8 |
| 1009 | 76.6 | 73.4 | 84.1 | 85.6 |
| 1012 | 97.7 | 95.7 | 108 | 115 |
| 1015 | 60.2 | 55.7 | 59.4 | 63.5 |
| 1017 | 71.2 | 73.2 | 85.2 | 70.3 |
| 1020 | 90.2 | 97.2 | 91.9 | 91.5 |
| 1022 | 82.7 | 77.1 | 92.4 | 88.8 |
| 1026 | 170 | 143 | 129 | 129 |
| 1029 | 86.7 | 90.5 | 80.1 | 89.4 |
| 1033 | 61.5 | 55.7 | 64.4 | 77.6 |
| 1034 | 41.9 | 45.2 | 66.9 | 83.6 |
| 1038 | 64.3 | 62.9 | 102 | 102 |
| 1039 | 77.0 | 77.0 | 51.6 | 49.5 |
| 1046 | 80.2 | 75.6 | 69.7 | 60.4 |
| 1047 | 114 | 105 | 147 | 137 |
| 1050 | 65.0 | 59.0 | 57.9 | 57.0 |
| 1056 | 53.9 | 39.8 | 21.3 | 25.2 |
| 1058 | 122 | 125 | 123 | 115 |
| 1064 | 81.2 | 81.2 | 73.6 | 79.7 |
| 1066 | 144 | 138 | 108 | 112 |
| 1068 | 150 | 147 | 123 | 140 |
| 1075 | 99.0 | 105 | 92.0 | 90.9 |
| 1078 | 70.5 | 64.6 | 64.3 | 60.2 |
| 1081 | 120 | 105 | 283 | 268 |
| 1082 | 102 | 86.1 | 80.5 | 80.2 |
| 1086 | 85.3 | 84.4 | 76.4 | 79.5 |
| 1092 | 89.2 | 76.9 | 92.0 | 80.1 |
| 1094 | 148 | 119 | 115 | 120 |
| 1098 | 140 | 136 | 44.8 | 121 |
| 1102 | 106 | 103 | 88.9 | 89.3 |
| N | 30 | 31 | 31 | 31 |
| Mean | 92.9 | 87.0 | 90.1 | 92.3 |
| SD | 33.3 | 30.3 | 45.1 | 42.9 |
| CV % | 35.9 | 34.8 | 50.0 | 46.5 |

-continued

| Transdermal Patch Interval Cmax Values | | | | |
|---|---|---|---|---|
| | TPT | | | |
| | D2AM | D2PM | D3AM | D3PM |
| SUBJID | Cmax (pg/mL) | | | |
| Min | 37.7 | 33.6 | 21.3 | 25.2 |
| Median | 86.0 | 81.2 | 84.1 | 85.6 |
| Max | 170 | 147 | 283 | 268 |
| Geometric Mean | 87.2 | 81.8 | 81.9 | 84.5 |
| Geometric CV % | 38.04 | 38.18 | 46.93 | 44.74 |

| Nasal Gel Interval AUCs | | | | |
|---|---|---|---|---|
| | TPT | | | |
| | D2AM | D2PM | D3AM | D3PM |
| SUBJID | AUClast (min*pg/mL) | | | |
| 1010 | 7830 | 11389 | 8648 | 1782 |
| 1011 | 2363 | 5440 | 6880 | 12173 |
| 1013 | 11708 | | 48 | 7972 |
| 1016 | 10052 | 13380 | 12556 | 1818 |
| 1019 | 16377 | 8669 | 26134 | 24244 |
| 1023 | 4053 | 1456 | 3241 | 981 |
| 1025 | 11314 | 16862 | 5207 | 11345 |
| 1030 | 26169 | 30387 | 13725 | 22000 |
| 1031 | 6037 | 11094 | 17901 | 39456 |
| 1035 | 21493 | 41792 | 40722 | 44695 |
| 1037 | 9126 | 8639 | 21332 | |
| 1042 | 16186 | 57810 | 32816 | 12035 |
| 1045 | 16898 | 7199 | 13912 | 11444 |
| 1052 | 39315 | 30884 | 52565 | 39296 |
| 1055 | 18248 | 30006 | 29265 | 35956 |
| 1057 | 8864 | 18531 | 9715 | 7360 |
| 1061 | 19224 | 9781 | 6639 | 2994 |
| 1063 | 4212 | 13387 | 4686 | 4831 |
| 1067 | | 17059 | 3559 | 3802 |
| 1072 | 16690 | 7267 | 1376 | 925 |
| 1073 | 1600 | 5541 | 502 | |
| 1076 | 44673 | 22302 | 23708 | 14558 |
| 1079 | 15141 | 20571 | 12840 | 11533 |
| 1080 | 35344 | 33683 | 8244 | 18604 |
| 1085 | 11644 | 33857 | 24205 | 13680 |
| 1088 | 33573 | 10950 | 6276 | 7045 |
| 1091 | 3256 | 12174 | | |
| 1096 | 10231 | 6745 | 10386 | 13847 |
| 1100 | 38106 | 20003 | 7870 | 1612 |
| 1101 | 13258 | 16003 | 18941 | 8125 |
| N | 29 | 29 | 29 | 27 |
| Mean | 16300 | 18000 | 14600 | 13900 |
| SD | 11800 | 12800 | 12600 | 12700 |
| CV % | 72.6 | 70.7 | 86.2 | 91.7 |
| Min | 1600 | 1460 | 48.2 | 925 |
| Median | 13300 | 13400 | 10400 | 11400 |
| Max | 44700 | 57800 | 52600 | 44700 |

-continued

| Nasal Gel Interval AUCs | | | | |
|---|---|---|---|---|
| | TPT | | | |
| | D2AM | D2PM | D3AM | D3PM |
| SUBJID | AUClast (min*pg/mL) | | | |
| Geometric Mean | 12200 | 14100 | 8540 | 8520 |
| Geometric CV % | 102.36 | 88.80 | 252.70 | 158.68 |

| Nasal Gel Interval Cmax Values | | | | |
|---|---|---|---|---|
| | TPT | | | |
| | D2AM | D2PM | D3AM | D3PM |
| SUBJID | Cmax (pg/mL) | | | |
| 1010 | 176 | 106 | 32.1 | 29.3 |
| 1011 | 32.2 | 27.0 | 44.7 | 77.3 |
| 1013 | 71.4 | 15.4 | 6.43 | 91.1 |
| 1016 | 47.5 | 93.7 | 102 | 11.0 |
| 1019 | 93.3 | 63.1 | 199 | 177 |
| 1023 | 16.8 | 7.90 | 18.0 | 4.87 |
| 1025 | 60.6 | 144 | 33.5 | 77.4 |
| 1030 | 215 | 301 | 137 | 180 |
| 1031 | 31.4 | 83.9 | 80.2 | 226 |
| 1035 | 219 | 190 | 188 | 286 |
| 1037 | 58.7 | 39.4 | 146 | |
| 1042 | 285 | 262 | 330 | 102 |
| 1045 | 97.8 | 41.9 | 70.2 | 63.9 |
| 1052 | 200 | 166 | 299 | 230 |
| 1055 | 118 | 195 | 189 | 347 |
| 1057 | 52.3 | 174 | 44.3 | 45.5 |
| 1061 | 98.2 | 66.3 | 49.5 | 25.6 |
| 1063 | 15.7 | 81.4 | 33.7 | 27.8 |
| 1067 | | 103 | 15.3 | 21.6 |
| 1072 | 68.1 | 41.5 | 7.68 | 4.10 |
| 1073 | 6.07 | 33.9 | 3.29 | |
| 1076 | 288 | 106 | 152 | 81.6 |
| 1079 | 93.1 | 114 | 80.5 | 67.3 |
| 1080 | 325 | 238 | 60.1 | 215 |
| 1085 | 141 | 218 | 169 | 139 |
| 1088 | 260 | 97.7 | 35.3 | 60.2 |
| 1091 | 23.8 | 139 | | |
| 1096 | 78.5 | 44.9 | 42.3 | 86.2 |
| 1100 | 379 | 160 | 64.4 | 9.31 |
| 1101 | 79.9 | 107 | 165 | 64.6 |
| N | 29 | 30 | 29 | 27 |
| Mean | 125 | 115 | 96.5 | 102 |
| SD | 103 | 76.3 | 86.1 | 92.3 |
| CV % | 82.6 | 66.1 | 89.2 | 90.6 |
| Min | 6.07 | 7.90 | 3.29 | 4.10 |
| Median | 93.1 | 105 | 64.4 | 77.3 |
| Max | 379 | 301 | 330 | 347 |
| Geometric Mean | 84.0 | 87.4 | 59.2 | 60.6 |
| Geometric CV % | 133.27 | 103.78 | 166.19 | 179.43 |

TABLE 6w

| Summary of Individual Subject Concentration-Time Tables for Individual Subjects (excluding Subject 110) | | | | | | | | | | | |
|---|---|---|---|---|---|---|---|---|---|---|---|
| | | | Time (h) | | | | | | | | |
| | | | 0.00 | 0.50 | 1.25 | 1.50 | 2.00 | 5.50 | 6.50 | 7.25 | 8.00 |
| Treatment | Day | Subject | Scopolamine (pg/mL) | | | | | | | | |
| Gel | 1 | 108 | BLOQ | 78.5 | 60.2 | 47.6 | 40.0 | 14.6 | 127 | 164 | 126 |
| | | 205 | BLOQ | 24.2 | 63.7 | 63.4 | 55.7 | 12.0 | 64.0 | 140 | 142 |
| | | 504 | BLOQ | 24.4 | 146 | 143 | 147 | 32.7 | 33.6 | 41.5 | 29.9 |
| | | Mean | | 42.4 | 90.0 | 84.7 | 80.9 | 19.8 | 74.9 | 115 | 99.3 |
| | | Median | | 24.4 | 63.7 | 63.4 | 55.7 | 14.6 | 64.0 | 140 | 126 |

TABLE 6w-continued

Summary of Individual Subject Concentration-Time Tables for Individual Subjects (excluding Subject 110)

| | | | Time (h) | | |
|---|---|---|---|---|---|
| | | | 24.00 | 29.50 | 31.25 |
| Treatment | Day | Subject | Scopolamine (pg/mL) | | |
| Gel | 2 | 108 | 2.44 | 13.4 | 74.5 |
| | | 504 | 10.4 | 13.4 | |
| | | Mean | 6.42 | 13.4 | 74.5 |
| | | Median | 6.42 | 13.4 | 74.5 |

| | | | Time (h) | | |
|---|---|---|---|---|---|
| | | | 72.00 | 77.50 | 79.25 |
| Treatment | Day | Subject | Scopolamine (pg/mL) | | |
| Gel | 4 | 108 | 5.44 | 24.6 | 116 |
| | | 504 | 11.1 | 19.2 | 55.3 |
| | | Mean | 8.27 | 21.9 | 85.7 |
| | | Median | 8.27 | 21.9 | 85.7 |

| | | | Time (h) | | | | | | | | |
|---|---|---|---|---|---|---|---|---|---|---|---|
| | | | 120.00 | 120.50 | 121.25 | 121.50 | 122.00 | 125.50 | 126.50 | 127.25 | 128.00 |
| Treatment | Day | Subject | Scopolamine (pg/mL) | | | | | | | | |
| Gel | 6 | 108 | 5.49 | | | | | | | | 84.5 |
| | | 205 | 11.0 | 53.2 | 97.4 | 91.1 | 78.4 | 21.5 | 60.0 | 143 | 196 |
| | | 504 | 10.3 | 30.1 | 102 | 86.5 | 94.9 | 18.7 | 28.4 | 41.5 | 29.4 |
| | | Mean | 8.93 | 41.7 | 99.7 | 88.8 | 86.7 | 20.1 | 44.2 | 92.3 | 103 |
| | | Median | 10.3 | 41.7 | 99.7 | 88.8 | 86.7 | 20.1 | 44.2 | 92.3 | 84.5 |

| | | | Time (h) | | | | | | | | |
|---|---|---|---|---|---|---|---|---|---|---|---|
| | | | 0.00 | 0.50 | 1.25 | 1.50 | 2.00 | 5.50 | 6.50 | 7.25 | 8.00 |
| Treatment | Day | Subject | Scopolamine (pg/mL) | | | | | | | | |
| Patch | 1 | 106 | BLOQ | BLOQ | BLOQ | BLOQ | BLOQ | 9.54 | 17.4 | 20.7 | 81.1 |
| | | 112 | BLOQ | BLOQ | 2.09 | 5.39 | 13.3 | 148 | 135 | 151 | 143 |
| | | 209 | BLOQ | 30.6 | 99.1 | 97.2 | 86.0 | 17.3 | 21.5 | 57.2 | 19.8 |
| | | 210 | BLOQ | BLOQ | BLOQ | BLOQ | BLOQ | 18.0 | 29.1 | 34.8 | |
| | | 502 | BLOQ | BLOQ | BLOQ | 37.3 | 54.5 | 199 | 194 | 188 | 164 |
| | | 606 | BLOQ | BLOQ | BLOQ | BLOQ | BLOQ | 19.1 | 32.3 | 42.2 | 48.3 |
| | | Mean | | 30.6 | 50.6 | 46.6 | 51.3 | 68.5 | 71.6 | 82.3 | 91.2 |
| | | Median | | 30.6 | 50.6 | 37.3 | 54.5 | 18.6 | 30.7 | 49.7 | 81.1 |

| | | | Time (h) | | |
|---|---|---|---|---|---|
| | | | 24.00 | 29.50 | 31.25 |
| Treatment | Day | Subject | Scopolamine (pg/mL) | | |
| Patch | 2 | 106 | 54.3 | 61.4 | 60.0 |
| | | 112 | 65.3 | 60.0 | 64.6 |
| | | 209 | 4.15 | | |
| | | 210 | | 95.9 | 89.4 |
| | | 502 | 94.2 | | |
| | | 606 | 45.9 | 59.5 | 56.5 |
| | | Mean | 52.8 | 69.2 | 67.6 |
| | | Median | 54.3 | 60.7 | 62.3 |

| | | | Time (h) | | |
|---|---|---|---|---|---|
| | | | 72.00 | 77.50 | 79.25 |
| Treatment | Day | Subject | Scopolamine (pg/mL) | | |
| Patch | 4 | 106 | 55.5 | 146 | 152 |
| | | 112 | 166 | | 156 |
| | | 209 | 5.03 | 24.9 | |
| | | 502 | 65.6 | 185 | |
| | | 606 | 58.8 | 78.2 | 118 |
| | | Mean | 70.2 | 109 | 142 |
| | | Median | 58.8 | 112 | 152 |

TABLE 6w-continued

| Summary of Individual Subject Concentration-Time Tables for Individual Subjects (excluding Subject 110) | | | | | | | | | | | |
|---|---|---|---|---|---|---|---|---|---|---|---|
| | | | Time (h) | | | | | | | | |
| | | | 120.00 | 120.50 | 121.25 | 121.50 | 122.00 | 125.50 | 126.50 | 127.25 | 128.00 |
| Treatment | Day | Subject | Scopolamine (pg/mL) | | | | | | | | |
| Patch | 6 | 106 | 64.9 | 72.8 | 66.5 | 69.0 | 61.5 | 58.9 | 61.1 | 57.8 | 62.3 |
| | | 112 | 62.6 | 60.9 | 55.6 | 55.6 | 54.8 | 51.4 | 47.9 | 47.1 | 46.9 |
| | | 209 | 7.11 | 14.6 | 24.2 | 21.8 | 19.6 | 13.8 | 28.2 | 95.3 | 133 |
| | | 502 | 99.0 | 104 | 100 | 97.3 | 98.3 | 85.7 | 85.4 | 82.1 | 80.4 |
| | | 606 | 83.5 | 88.3 | 86.0 | 90.1 | 86.8 | 75.6 | 81.4 | 88.0 | 91.6 |
| | | Mean | 63.4 | 68.1 | 66.5 | 66.8 | 64.2 | 57.1 | 60.8 | 74.1 | 82.8 |
| | | Median | 64.9 | 72.8 | 66.5 | 69.0 | 61.5 | 58.9 | 61.1 | 82.1 | 80.4 |

Example 7: Clinical Study MS-21-Safety and Efficacy

Clinical study MS-21 was a randomized, double-blind, placebo-controlled Phase 3 study of the safety and efficacy of DPI-386 Nasal Gel on ocean going vessels for the prevention and treatment of nausea associated with motion sickness. The study was a single site field trial and took place on three ocean voyages of a single ocean-going vessel chartered for this study.

Title of Study: A randomized, double-blind, placebo-controlled Phase 3 study of the safety and efficacy of DPI-386 Nasal Gel on ocean going vessels for the prevention and treatment of nausea associated with motion sickness Study Site: This study was a single site field trial and took place on three ocean voyages of a single ocean-going vessel chartered for this study.

Objectives:

Primary Objectives:

1. Determine the efficacy of DPI-386 nasal gel (0.2 mg scopolamine hydrobromide [HBr] per dose twice a day for 3 consecutive days) compared to the Transdermal Scopolamine (Transderm Scop®; TDS) patch and Placebo Nasal Gel in the prevention and treatment of nausea associated with motion sickness.

2. Determine the safety of DPI-386 Nasal Gel compared to the TDS patch and Placebo Nasal Gel with an emphasis on cognitive adverse events (AEs).

Secondary Objectives:

1. Determine the efficacy of DPI-386 Nasal Gel compared to the TDS patch and the Placebo Nasal Gel in the severity of nausea.

2. Determine the safety of DPI-386 Nasal Gel as compared to TDS patch and Placebo Nasal Gel in terms of cognition.

Methodology:

This single-site Phase 3 clinical trial was a randomized, double-blind, placebo-controlled study to identify the safety and efficacy of a repeated dose regimen of DPI-386 nasal gel (intranasal scopolamine gel) for the prevention and treatment of nausea associated with motion sickness.

The study was conducted aboard an ocean-going vessel to obtain data in a real-world environment.

The study had 3 arms: DPI-386 nasal gel, Placebo Nasal Gel, and TDS patch (1.5 mg/72 hours), the current standard of care for the treatment of motion sickness. The study included 297 subjects (99 subjects in DPI-386 Nasal Gel, 98 subjects in TDS patch, 100 subjects in Placebo Nasal Gel). Multiple voyages with the same vessel were used until the required enrollment was completed. A double-dummy design was used to mask the treatment assignment. Each subject received both a patch and nasal gel as per randomization to one of the following 3 arms: DPI-386 Nasal Gel+placebo patch, Placebo Nasal Gel+placebo patch, or Placebo Nasal Gel+TDS patch.

Statistical analysis was carried out using SAS® Version 9.4 (SAS Institute Inc., USA) to assess the efficacy and safety endpoints.

Number of Subjects (Planned and Analyzed):

Planned Enrollment:

As per the protocol, 300 subjects (100 in each of 3 treatment arms), between the ages of 18 and 59 (inclusive) were to be enrolled in the study. They were to be at least minimally susceptible to provocative motion as evident by a minimum score of 3.0 on the Motion Sickness Susceptibility Questionnaire (MSSQ).

Actual Enrollment:

A total of 297 subjects (99 subjects in the DPI-386 Nasal Gel arm, 98 subjects in the TDS patch arm, and 100 subjects in the Placebo Nasal Gel arm) were enrolled in the study.

Diagnosis and Main Criteria for Inclusion:

In order to be eligible to participate in this study, an individual met all of the following criteria:

1. Provision of a signed and dated informed consent form (ICF).

2. Stated willingness to comply with all study procedures and availability for the duration of the study.

3. Male or female, aged 18 to 59 (inclusive).

4. At least minimally susceptible to provocative motion as evidenced by a minimum score of 3.0 on the MSSQ.

5. In good general health as evidenced by medical history with no recent history or current diagnosis of uncontrolled clinical problems as assessed by the Principal Investigator (PI) or qualified designee.

6. Ability to take intranasal medication and willingness to adhere to the study schedule and time constraints.

7. For females of child-bearing potential: willingness to provide a urine sample for the human chorionic gonadotropin (hCG) pregnancy test. The test must be negative within seven days of Treatment Day 1.

8. Note: Women of non-childbearing potential are defined as those who are non-surgically sterile (i.e., without menses for at least 12 consecutive months) or surgically sterile (i.e., those who underwent a hysterectomy with or without oophorectomy, fallopian tube ligation, and endometrial ablation).

9. Agreement to adhere to the following lifestyle compliance considerations:

a. Refrain from consumption of grapefruit and any substance containing grapefruit for 7 days prior to, during, and for 7 days after the 3 treatment days.

b. Abstain from alcohol for 24 hours prior to first dose of study medication and during the 3 treatment days.

Note: there was no restriction on caffeine or nicotine use during the study; however, the actual use of these substances was recorded as part of the Confidential Exclusionary Behavior Questionnaire (CEBQ).

Investigational Medicinal Product

DPI-386 Nasal Gel

- Active content: Scopolamine HBr
- Strength: Each 0.12 gram of the gel contains 0.2 mg of scopolamine HBr
- Dosage Regimen: 0.2 mg scopolamine HBr per dose (each 0.12 gram of the gel contains 0.2 mg of scopolamine HBr)—twice daily for 3 consecutive days
- Route of administration: Intranasal
- Storage: Store at 20° C. to 25° C., inclusive (68° F. to 77° F., inclusive), with brief temperature excursions permitted between 15° C. and 30° C., inclusive (59° F. and 86° F., inclusive).

TDS Patch [Transderm Scop®, a commercial TDS patch]

- Strength: one patch of 1.5 mg reservoir of scopolamine, designed to deliver 1.0 mg of scopolamine, can be delivered over a period of 72 hours
- Dosage Regimen: 1.5 mg reservoir of scopolamine-1 patch on Treatment Day 1 only
- Route of administration: transdermal, applied behind the ear Placebo Nasal Gel Placebo Gel for DPI-386 Nasal Gel

- Storage: Store at 20° C. to 25° C., inclusive (68° F. to 77° F., inclusive), with brief temperature excursions permitted between 15° C. and 30° C., inclusive (59° F. and 86° F., inclusive).
- Route of administration: Intranasal Duration of Treatment:

For DPI-386 Nasal Gel (0.2 mg scopolamine HBr per dose) and Placebo Nasal Gel, 1 dose was delivered into 1 nostril twice daily over 3 consecutive treatment days (alternating nostrils) during the subject's controlled 8 hours period. The 2 daily doses were separated by a minimum of 6 hours with no more than 2 doses in 24 hours, unless a third dose (rescue) was deemed necessary by the investigator.

For the TDS patch and placebo patch, 1 patch was applied behind the ear on Treatment Day 1 only.

Criteria for Evaluation

Safety and Tolerability Evaluations:

Safety and tolerability assessments included demography, assessment of cognitive performances, assessment of alertness, assessment of anticholinergic toxicity symptoms, urine pregnancy test (for females of child-bearing potential) and recording of AEs and concomitant medications.

Study Endpoints:

Primary Efficacy Endpoint

The primary efficacy endpoint was the incidence of subjects who developed motion sickness and requested further treatment with rescue medication (for more detailed rational for the selection of the primary endpoint see section 9.7.1. Methodological Planning for the Design of the Study).

The primary endpoint was evaluated for the following treatment comparisons and treatment intervals:

- A comparison of DPI-386 Nasal Gel to TDS patch within the first 4 hours on or after the first dose of study treatment on Treatment Day 1
- A comparison of DPI-386 Nasal Gel to TDS patch on or after the first dose of study treatment on Treatment Day 1

Secondary Efficacy Endpoints

Time to First Use of Rescue Medication

A secondary efficacy endpoint was the time to first use of rescue medication during the treatment period, and was calculated in hours as the start time of administration of the first rescue medication dose minus the start time of the first dose of study drug. Subjects who did not receive any rescue medication were censored at the time of their last VAS MSAQ assessment during the treatment period.

Motion Sickness Assessment Questionnaire

A secondary efficacy endpoint was the Motion Sickness Assessment Questionnaire (MSAQ) total score, which was evaluated for the following treatment comparisons and treatment intervals:

- A comparison of the differences in change from baseline in MSAQ total score,

DPI-386 Nasal Gel vs. Placebo Nasal Gel at all timepoints.

- A comparison of the differences in change from baseline in MSAQ total score,

DPI-386 Nasal Gel vs. TDS patch at all timepoints.

Nausea Assessment (Visual Analogue Scale)

A secondary efficacy endpoint was the severity of nausea as assessed on a visual analogue scale (VAS). Subjects specified their degree of nausea by indicating a point along a continuous 100-mm line between 2 endpoints. The scale ranged from 0 (no nausea) to 100 (very severe nausea) and was completed at screening and twice on Treatment Days 1-3 at 4 and 8 hours following the first dose for each treatment day. Scoring was based on the length from the left edge of the scale to point reported, and a higher score indicated a more severe degree of nausea.

Treatment comparisons were performed at time point intervals in the same manner as described for the secondary efficacy endpoint MSAQ scores.

Primary Safety Endpoint

The primary safety endpoint was the incidence of treatment-emergent adverse events (TEAEs) while on study treatment. TEAEs were those with onset after the first dose of study treatment or existing events that worsened after the first dose of study treatment.

Secondary Safety Endpoint

The secondary safety endpoint was cognition as measured by the Psychomotor Vigilance Task (PVT).

Other Safety Endpoints

Other safety endpoints were as follows:

- Mean change from baseline to all post-baseline measurements during the treatment period in the assessments of sleepiness using the Karolinska Sleepiness Scale (KSS).
- Subject incidence in reporting symptoms of anticholinergic toxicity using the Anticholinergic Toxicity Screen (ACTS) at each visit and time point were collected.
- Frequency of subject responses to the individual items of the Performance Self-Assessment Questionnaire (PSAQ) administered at Post-Treatment Day 3, as an assessment of whether the subject perceived DPI-386 Nasal Gel or TDS patch application to be detrimental to the performance of activities at any time during the study period.

Other Evaluations

The frequency of subject responses to the individual items of the Nasal Gel Device Ease-of-Use Questionnaire (EOUQ) at Post-Treatment Day 3 was evaluated.

Statistical Analysis:

Disposition of Subjects

Subject disposition was summarized for the safety, intent-to-treat (ITT), and per protocol (PP) populations by treatment group and over all subjects combined. Summaries included the number and percentage of subjects in each analysis population, completing the study, and discontinuing the study early by the primary reason for discontinuation.

Protocol Deviations

Major protocol violations were summarized by treatment group and over all subjects combined. Major protocol violations are protocol deviations captured on-study that are deemed by the Sponsor to potentially impact the efficacy or safety conclusions of the study.

Demographic and Other Baseline Characteristics

Demographic variables including age, sex, ethnicity, and race were summarized by treatment group and over all subjects combined for the ITT, PP, and Safety populations.

Age was summarized using descriptive statistics. Sex, ethnicity, and race were summarized with the number and percentage of subjects.

Primary Efficacy Endpoint Analysis Methods

To assess prevention and treatment of nausea associated with motion sickness, the primary efficacy endpoint was the incidence of subjects who developed motion sickness and requested further treatment with rescue medication. Treatment groups were compared using a Fisher-Exact test. 95% CIs were constructed to describe differences between treatment groups (DPI-386—TDS patch; DPI-386—Placebo Nasal Gel; TDS patch—Placebo Nasal Gel). The analysis was performed on the ITT population.

Secondary Efficacy Endpoint Analysis Methods

Time to First Use of Rescue Medication

Time to administration of rescue medication was analyzed using the log rank test. Subjects who took no rescue medication during the study were censored at the time of the last VAS MSAQ assessment.

Motion Sickness Assessment Questionnaire: Total Score

Differences in the change from baseline in LSM MSAQ total score were compared between treatment groups.

The data were analyzed using a mixed model of repeated measure (MMRM) including fixed effects of treatment, visit, and interaction term of treatment by visit. Baseline value was included as a covariate in the model.

The total MSAQ score was derived from the sum of points from all items/144×100.

The analysis was performed on the ITT population.

Nausea Assessment (Visual Analogue Scale)

Differences in the change from baseline in VAS scores were compared between treatment groups.

The data were analyzed using a MMRM including fixed effects of treatment, visit, and interaction term of treatment by visit. Baseline value was included as a covariate in the model.

The analysis was performed on the ITT population.

Safety Analysis

Safety analysis was carried out for the Safety population and included all subjects who received at least 1 dose of study drug.

Primary Safety Endpoint Analysis Methods

Adverse Events

TEAEs were defined as those AEs with onset after the first dose of study drug or existing events that worsened after the first dose during the study. TEAEs were summarized by treatment group.

Secondary Safety Endpoint Analysis Methods

Psychomotor Vigilance Task

The mean change from baseline to all post-baseline measurements in cognition as measured by median response time and number of performance lapses was evaluated.

Other Safety Endpoint Analysis Methods

Karolinska Sleepiness Scale

The KSS score was summarized by treatment group. Descriptive statistics were presented for the observed values and changes from baseline to each visit and time point were collected.

Anticholinergic Toxicity Screen

Subject incidence in reporting symptoms of anticholinergic toxicity using ACTS was presented by treatment group. The number and percentage of subjects who reported symptoms was summarized at each visit and time point was tabulated by symptom.

Performance Self-Assessment Questionnaire

The frequency of subject responses to the individual items of the PSAQ administered at Post-Treatment Day 3 was summarized by Treatment Group. The number and percentage of subjects who reported each of the possible responses for each item was summarized.

Other Evaluation Analysis Methods

Nasal Gel Device Ease-of-Use Questionnaire

The frequency of subject responses to the individual items of the EOUQ administered at Post-Treatment Day 3 were summarized by Treatment Group. The number and percentage of subjects who report each of the possible responses for each item were summarized.

Prior and Concomitant Medications

Prior and concomitant medications were summarized for each treatment.

Efficacy Results

Primary Efficacy Endpoint

The primary efficacy endpoint was the proportion of subjects in the ITT population who developed motion sickness and requested further treatment with rescue medication. The differences between the DPI-386 Nasal Gel arm and the TDS patch arm and the differences between the DPI-386 Nasal Gel arm and the Placebo Nasal Gel arm were not statistically significant at Treatment Day 1 Hour 4 or at any time on Treatment Day 1 (Table 7a). The differences between the TDS patch arm and the Placebo Nasal Gel arm were not statistically significant at Treatment Day 1 Hour 4 or at any time on Treatment Day 1.

TABLE 7a

Proportion of Subjects Using Rescue Medication (ITT Population)

| Parameter Statistic | DPI-386 Nasal Gel (N = 99) | TDS Patch (N = 98) | Placebo Nasal Gel (N = 100) |
|---|---|---|---|
| Subjects who took rescue medication within 4 hours after the first dose on Treatment Day 1 | | | |
| n (%) | 9 (9.1) | 12 (12.2) | 9 (9.0) |
| 95% CI | (4.2, 16.6) | (6.5, 20.4) | (4.2, 16.4) |
| Treatment difference (95% CI) | 0.1 (−7.9, 8.1) | 3.2 (−5.3, 11.8) | |
| p-value[1] | >0.9999 | 0.4964 | |
| Treatment difference (95% CI) | −3.2 (−11.8, 5.5) | | |
| p-value[2] | 0.4983 | | |
| Subjects who took rescue medication at any time on Treatment Day 1 | | | |
| n (%) | 15 (15.2) | 15 (15.3) | 12 (12.0) |
| 95% CI | (8.7, 23.8) | (8.8, 24.0) | (6.4, 20.0) |

TABLE 7a-continued

| Proportion of Subjects Using Rescue Medication (ITT Population) | | | |
|---|---|---|---|
| Parameter Statistic | DPI-386 Nasal Gel (N = 99) | TDS Patch (N = 98) | Placebo Nasal Gel (N = 100) |
| Treatment difference (95% CI) | 3.2 (−6.4, 12.7) | 3.3 (−6.3, 12.9) | |
| p-value[1] | 0.5416 | 0.5395 | |
| Treatment difference (95% CI) | −0.2 (−10.2, 9.9) | | |
| p-value[2] | >0.9999 | | |

CI = confidence interval; ITT = Intent-to-Treat.

Note:

Use of rescue medication included subjects who took the rescue medication or reported an adverse event with an assigned action as rescue DPI 386 Nasal Gel.

[1]Comparison vs Placebo group were performed using Fishers Exact test.

[2]Comparison vs TDS Patch was performed using Fishers Exact test. Source: Table 14.2.1.1, Table 14.2.1.2

Secondary Efficacy Endpoints

Time to First Use of Rescue Medication

The difference in time to first use of rescue mediation between the DPI-386 Nasal Gel arm and the Placebo Nasal Gel arm (ITT population) was not statistically significant (p=0.3458, log-rank test). The difference in time to first use of rescue mediation between the DPI-386 Nasal Gel arm and the TDS patch arm (ITT population) was not statistically significant (p=0.9367, log-rank test).

A Kaplan-Meier plot of time to first use of rescue medication in the ITT population is provided.

Motion Sickness Assessment Questionnaire

In the ITT population, the differences between DPI-386 Nasal Gel and TDS patch in least-squares mean (LSM) MSAQ total score changes from baseline at all time points were not statistically significant, and the differences between DPI-386 Nasal Gel and Placebo Nasal Gel in changes from baseline at all time points were also not statistically significant.

Nausea Assessment Via the Visual Analogue Scale

In the ITT population, the differences between DPI-386 Nasal Gel and TDS patch in LSM nausea assessment VAS score changes from baseline at all time points were not statistically significant, and the differences between DPI-386 Nasal Gel and Placebo Nasal Gel in changes from baseline at all time points were also not statistically significant.

Safety Results

Primary Safety Endpoint: Incidence of Adverse Events

An overall summary of TEAEs is provided in Table 7b.

A total of 558 TEAEs were reported by 212 (71.4%) subjects during the study (163 TEAEs in 57 subjects [57.6%] after administration of DPI-386 Nasal Gel, 191 TEAEs in 78 subjects [79.6%] after administration of TDS Patch, and 204 TEAEs in 77 subjects [77.0%] after administration of Placebo Nasal Gel).

The majority of TEAEs were mild (N=483) or moderate (N=71); 1 TEAE was severe. Mild TEAEs were reported in 54.5%, 77.6%, and 74.0% of subjects in the DPI-386 Nasal Gel arm, TDS patch arm, and the Placebo Nasal Gel arm, respectively. Moderate TEAEs were reported in 15.2%, 12.2%, and 17.0% of subjects in the DPI-386 Nasal Gel arm, TDS patch arm, and the Placebo Nasal Gel arm, respectively. The severe TEAE (diarrhea) occurred in a subject in the DPI-386 Nasal Gel arm.

The causality assessment was judged by the investigator as not related for 426 TEAEs and related for 132 TEAEs. Of the 426 unrelated TEAEs, 107 occurred in the DPI-386 Nasal Gel arm, 158 occurred in the TDS patch arm, and 161 occurred in the Placebo Nasal Gel arm. Of the 132 related TEAEs, 56 occurred in the DPI-386 Nasal Gel arm, 33 occurred in the TDS patch arm, and 43 occurred in the Placebo Nasal Gel arm.

TEAEs that were not related to treatment with study drug were reported in 50.5%, 74.5%, and 74.0% of subjects in the DPI-386 Nasal Gel arm, TDS patch arm, and the Placebo Nasal Gel arm, respectively. TEAEs that were related to treatment with study drug were reported in 28.3%, 23.5%, and 27.0% of subjects in the DPI-386 Nasal Gel arm, TDS patch arm, and the Placebo Nasal Gel arm, respectively.

No deaths occurred during the study. No subject discontinued treatment due to a TEAE.

Six SAEs were reported by 3 subjects during the study (dizziness×2 in the same subject, palpitations in 1 subject, and spinal fracture and amnesia×2 in 1 subject). Of the 6 SAEs, 4 were reported after administration of DPI-386 Nasal Gel and 2 (in the same subject) were reported after administration of TDS patch. Three SAEs were mild and the severity of 3 SAEs was not recorded. The causality assessment was judged as probably related for 1 SAE (dizziness), possibly related for 1 SAE (dizziness), possibly related for 1 SAE (palpitations), not related for 1 SAE (spinal fracture), and unable to determine for 2 SAEs (amnesia). Two subjects were followed until resolution of their SAEs; however, for Subject No. 373, his SAE of spinal fracture was ongoing and the outcome of other 2 SAEs of amnesia was not recorded.

Out of 558 TEAEs, 113 TEAEs were AESIs; 42 AESIs occurred in the DPI-386 Nasal Gel arm, 36 AESIs occurred in the TDS patch arm, and 35 AESIs occurred in the Placebo Nasal Gel arm. AESIs occurred in 31.3%, 29.6%, and 24.0% of subjects in the DPI-386 Nasal Gel arm, TDS patch arm, and the Placebo Nasal Gel arm, respectively.

Six SAEs were reported by 3 subjects during the study.

Of the 113 AESIs, 62 (blurred vision, dizziness, increased skin redness/flushing, photophobia, motion sickness, and palpitations) were "Significant, Non-serious" and 51 (dry mouth) were "Non-significant, Non-serious."

TEAEs occurring in >2 subjects in a treatment arm are summarized by System Organ Class (SOC) and preferred term in Table 7c.

TABLE 7b

| Summary of Treatment-Emergent Adverse Events (Safety Population) | | | |
|---|---|---|---|
| Parameter | DPI-386 Nasal Gel (N = 99) n (%) e | TDS Patch (N = 98) n (%) e | Placebo Nasal Gel (N = 100) n (%) e |
| All TEAEs (subjects with at least one TEAE) | 57 (57.6) 163 | 78 (79.6) 191 | 77 (77.0) 204 |
| Any Non-TEAEs (subjects with at least one non-TEAE) | 2 (2.0) 2 | 5 (5.1) 5 | 2 (2.0) 2 |
| Subjects with at least one TEAE leading to discontinuation from study drug | 0 | 0 | 0 |
| Relationship of TEAEs to IMP | | | |

TABLE 7b-continued

Summary of Treatment-Emergent Adverse Events (Safety Population)

| Parameter | DPI-386 Nasal Gel (N = 99) n (%) e | TDS Patch (N = 98) n (%) e | Placebo Nasal Gel (N = 100) n (%) e |
|---|---|---|---|
| Not related | 50 (50.5) 107 | 73 (74.5) 158 | 74 (74.0) 161 |
| Related | 28 (28.3) 56 | 23 (23.5) 33 | 27 (27.0) 43 |
| Severity of TEAEs | | | |
| Mild | 54 (54.5) 137 | 76 (77.6) 172 | 74 (74.0) 174 |
| Moderate | 15 (15.2) 22 | 12 (12.2) 19 | 17 (17.0) 30 |
| Severe | 1 (1.0) 1 | 0 (0.0) 0 | 0 (0.0) 0 |
| Subjects with at least one SAE | 2 (2.0) 4 | 1 (1.0) 2 | 0 (0.0) 0 |
| Subjects with at least one AESI in TEAE | 31 (31.3) 42 | 29 (29.6) 36 | 24 (24.0) 35 |

AESI = adverse event of special interest;
e = number of events;
IMP = investigational medicinal product;
SAE = serious adverse event'
TEAE = treatment-emergent adverse event
Souce: Table 14.3.1.1

TABLE 7c

Safety Analysis: Treatment-Emergent Adverse Events Occurring in >2 Subject in a Treatment Arm, by System Organ Class and Preferred Term, Safety Population

| System Organ Class Preferred Term | DPI-386 Nasal Gel (N = 99) n (%) e | TDS Patch (N = 98) n (%) e | Placebo Nasal Gel (N = 100) n (%) e |
|---|---|---|---|
| Ear and labyrinth disorder | | | |
| Motion sickness | 45 (45.5) 84 | 63 (64.3) 111 | 62 (62.0) 127 |
| Eye disorders | | | |
| Photophobia | 2 (2.0) 2 | 3 (3.1) 3 | 3 (3.0) 3 |
| Gastrointestinal disorder | | | |
| Dry mouth | 12 (12.1) 18 | 18 (18.4) 21 | 13 (13.0) 16 |
| Nausea | 3 (3.0) 3 | 2 (2.0) 3 | 6 (6.0) 6 |
| General disorders and administration site conditions | | | |
| Fatigue | 1 (1.0) 2 | 5 (5.1) 10 | 7 (7.0) 10 |
| Nervous system disorders | | | |
| Headache | 4 (4.0) 4 | 4 (4.1) 5 | 5 (5.0) 5 |
| Somnolence | 10 (10.1) 15 | 10 (10.2) 14 | 5 (5.0) 7 |
| Vision blurred | 3 (3.0) 3 | 1 (1.0) 1 | 0 (0.0) 0 |
| Respiratory, thoracic and mediastinal disorders | | | |
| Nasal discomfort | 5 (5.1) 6 | 3 (3.1) 3 | 5 (5.0) 5 |
| Vascular disorders | | | |
| Dizziness | 7 (7.1) 7 | 3 (3.1) 5 | 4 (4.0) 4 |

N = Number of subjects in respective treatment population; n = Number of subjects in respective categories; e = Number of events.
Source: Adapted from Table 14.3.1.2

Secondary Safety Endpoint: Psychomotor Vigilance Test

There was no effect of either the treatment (DPI-386 Nasal Gel, TDS patch, Placebo Nasal Gel) on reaction time. Also, response times did not vary based on age, sex, race, or motion sickness susceptibility.

Other Safety Endpoints

Karolinska Sleepiness Scale

At no time point either for raw scores or change from baseline scores were the differences between the DPI-386 Nasal Gel arm and either control arm statistically significant.

Anticholinergic Toxicity Screen

The most common ACTS AE reported by subjects in all treatment arms at screening and on Day 1, Day 2, and Day 3 was dry mouth. Dizziness was the next most common ACTS AE at all time points in the DPI-386 Nasal Gel and TDS patch arms, and lightheadedness was the next most common ACTS AE in the Placebo Nasal Gel arm on Day 1 and Day 2.

Performance Self-Assessment Questionnaire

The responses to the PSAQ, taken as a whole, were favorable in terms of the effect of study medication on work performance. Except for the statement "I experienced motion sickness," the percentages of subjects responding favorably were similar among the treatment arms. Fewer subjects in the DPI-386 Nasal Gel arm reported experiencing motion sickness than did subjects in the TDS patch and Placebo Nasal Gel arms.

Nasal Gel Device Ease-of-Use Questionnaire

The responses reported on the Nasal Gel EOUQ indicated that the nasal gel preparation was easy to use and administer.

Efficacy Conclusion:

The analyses of the primary and secondary efficacy endpoints showed no statistically significant differences between the DPI-386 Nasal Gel arm and either of the control arms (TDS patch and Placebo Nasal Gel). The endpoints were the number (%) of subjects who developed motion sickness and requested further treatment (primary endpoint), time to use of rescue medication (secondary), MSAQ total score (secondary), and severity of nausea (VAS score; secondary).

Safety Conclusion:

All study medications were well tolerated and no new safety signals for DPI-386 Nasal Gel were observed.

2. Introduction

DPI-386 Nasal Gel is an intranasal formulation of the approved drug scopolamine hydrobromide (HBr), a naturally occurring belladonna alkaloid anticholinergic/antimuscarinic agent with antiemetic, antiparkinsonian and mydriatic effects. Scopolamine acts as a competitive inhibitor at postganglionic muscarinic receptor sites of the parasympathetic nervous system and smooth muscles that respond to acetylcholine, but lack cholinergic innervation. Scopolamine generally exhibits the pharmacological actions associated with other antimuscarinics: it is more potent than atropine in its antimuscarinic action on the iris, ciliary body, and certain secretory (salivary, bronchial, sweat) glands, and less potent than atropine in its antimuscarinic action on the heart and on bronchial and intestinal smooth muscle.

Although the exact mechanism of action of scopolamine in the treatment of motion sickness is not fully understood, it has been suggested that scopolamine acts in the central nervous system (CNS) by correcting a central imbalance between acetylcholine and norepinephrine by blocking cholinergic transmission from the vestibular nuclei to higher centers in the CNS and from the reticular formation to the vomiting center.

Scopolamine is absorbed from all mucous membranes as well as from subcutaneous and muscle tissue. At therapeutic dose levels, scopolamine can inhibit the secretion of saliva and sweat, decrease gastrointestinal secretions and motility, cause drowsiness, dilate the pupils, increase heart rate, and depress motor function. An overdose of scopolamine can cause disorientation, memory disturbances, dizziness, restlessness, hallucinations, confusion, or in cases of severe overdose, coma.

Scopolamine was initially available commercially in its HBr form as an oral or parenteral (intramuscular [IM] and intravenous [IV]) drug. It is currently only available in the TDS patch form in the United States (US). The TDS patch is marketed for the prevention of nausea and vomiting associated with motion sickness, though it is also used in clinical management of post-operative nausea and vomiting.

2.1. Rationale and Aims

By comparison, a low-dose, rapidly acting nasal gel formulation of scopolamine could provide for the prevention and treatment of nausea associated with motion sickness, with a clinically meaningful reduced adverse events profile. Research into an intranasal formulation of scopolamine first occurred in a series of 1950s military studies, when a scopolamine nasal spray proved effective in reducing motion sickness but was abandoned due to the limitations of medication delivery devices at the time and an inability to deliver a properly metered dose (Chinn, Hyde, & Milch, 1955); (Simmons, et al., 2010). However, modern intranasal drug formulations and medication delivery devices are vastly improved, making reliable, metered dosing possible.

Hence, this study was conducted. This single-site Phase 3 clinical trial was a randomized, double-blind, placebo-controlled study to identify the safety and efficacy of a repeated dose regimen of DPI-386 nasal gel (intranasal scopolamine gel) for the prevention and treatment of nausea associated with motion sickness.

2.2. Target Population and Duration of the Study

As per the protocol, 300 subjects (100 in each of 3 treatment arms), between the ages of 18 and 59 (inclusive) were to be enrolled in the study. They were to be at least minimally susceptible to provocative motion as evident by a minimum score of 3.0 on the Motion Sickness Susceptibility Questionnaire (MSSQ).

For this study, a total of 297 subjects (99 subjects in DPI-386 Nasal Gel, 98 subjects in TDS patch, 100 subjects in Placebo Nasal Gel) were enrolled in the study.

The actual duration of the clinical part of the study was 26 days (24 Apr. 2019 [First Subject First Visit-FSFV] to 19 May 2019 [Last Subject Last Visit-LSLV, i.e., Visit 4 of the last subject]).

3. Study Objectives 3.1 Primary Objectives

1. Determine the efficacy of DPI-386 Nasal Gel (0.2 mg scopolamine HBr per dose administered twice a day for 3 consecutive days) compared to the TDS patch and Placebo Nasal Gel in the prevention and treatment of nausea associated with motion sickness.

2. Determine the safety of DPI-386 Nasal Gel compared to the TDS patch and Placebo Nasal Gel with an emphasis on cognitive AEs.

3.2. Secondary Objectives

1. Determine the efficacy of DPI-386 Nasal Gel compared to the TDS patch and the Placebo Nasal Gel in the severity of nausea.

2. Determine the safety of DPI-386 Nasal Gel as compared to TDS patch and Placebo Nasal Gel in terms of cognition.

4. Investigational Plan 4.1 Overall Study Design and Plan-Description

This single-site Phase 3 clinical trial was a randomized, double-blind, placebo-controlled study to identify the safety and efficacy of a repeated dose regimen of DPI-386 Nasal Gel (intranasal scopolamine gel) for the prevention and treatment of nausea associated with motion sickness.

The study was conducted aboard an ocean-going vessel to obtain data in a real-world environment.

The study had 3 arms: DPI-386 Nasal Gel, Placebo Nasal Gel, and TDS patch (1.5 mg/72 hours), the current standard of care for the treatment of motion sickness. The study included 297 subjects (99 subjects in DPI-386 Nasal Gel, 98 subjects in TDS patch, 100 subjects in Placebo Nasal Gel). Multiple voyages with the same vessel were used until the required enrollment was completed. A double-dummy design was used to mask the treatment assignment. Each subject received both a patch and nasal gel as per randomization to one of the following 3 arms: DPI-386 Nasal Gel+placebo patch, Placebo Nasal Gel+placebo patch, or Placebo Nasal Gel+TDS patch.

There were 5 study periods during the study with acceptable windows: Recruitment and Screening; Treatment; Post-treatment Assessment; Short-term Follow-up; and Long-term Follow-up.

The Recruitment and Screening Period consisted of one visit during which research staff obtained informed consent, obtained self-reported medical history and determined subject eligibility. If eligible, a baseline for cognitive tests and efficacy (nausea) was established and the subjects were provided training on study drug dosing and visit procedures.

The Treatment Period (Treatment Days 1 to 3) consisted of 3 visits in consecutive days of approximately 10-12 hours duration each day. Each Treatment Day visit included twice daily study drug dosing of nasal gel, patch application (Treatment Days 1 only), and cognitive testing and questionnaires (at specified time points described in the below table of schedule of activities). The acceptable window for each measure was ±1 hour.

The Post-Treatment Period (Treatment Day 3) consisted of 1 visit, at the end of the 8 hours control period on Treatment Day 3 to include safety questionnaires, performance self-assessment, ease-of-use questionnaire and debriefing and explanation of follow-up procedures.

The Short-term Follow-up Period (Day 10) consisted of research staff contacting the subject via phone or email at one-week Post-Treatment Period to ask if they had experienced any new signs or symptoms, including the Anticholinergic Toxicity Screen (ACTS). The acceptable window was +3 days.

The Long-term Follow-up Period (Days 11 to 45, 2 weeks to 6 weeks post-Treatment Period) consisted of subjects having a standing obligation to contact research staff via telephone or e-mail at any time during this period and to inform them if they experienced any new signs or symptoms. There was no acceptable window requirement. Long-term Follow-up ended at the close of Day 45 (6 weeks).

The schedule of events is depicted in Table 7d.

TABLE 7d

Schedule of Activities

| | Period: Recruitment and Screening[1] | Treatment (Three Days Duration) | | | Post-treatment | Short-term Follow-up[2] | Long-term Follow-up[3] |
|---|---|---|---|---|---|---|---|
| Visit | 1 | 2 | 3 | 4 | 4 | — | — |
| Study day | Within 30 Days Prior to Day 1 | 1 | 2 | 3 | 3 | 10 + 3 | 11-45 |
| ICF | X | | | | | | |
| MSSQ | X | | | | | | |
| CMQ | X | | | | | | |
| CEBQ[4] | X | X | X | X | | | |
| Inclusion/exclusion | X | | | | | | |
| Subject handout | X | X[5] | | X[5] | | | |
| Randomization | | X | | | | | |
| Pregnancy test[6] | X | | | | | | |
| Study drug dosing: TDS patch or Placebo patch[7] | | X[8] | X | X | | | |
| Study drug dosing: DPI-386 nasal gel or Placebo Nasal Gel[7] | | X[8] | X | X | | | |
| PVT[9] | X[9] | X[9] | X[9] | X[9] | | | |
| KSS[10] | X | X[10] | X[10] | X[10] | | | |
| ACTS[10] | X | X[10] | X[10] | X[10] | | X[2] | |
| MSAQ[10] | X | X[10] | X[10] | X[10] | | | |
| VAS[10] | X | X[10] | X[10] | X[10] | | | |
| Adverse events[11] | | X | X | X | X | X | X |
| IFU training | X | X | X | X | | | |
| Return of study materials[12] | | | | | X | | |
| Concomitant medication/ treatments[13] | | X | X | X | X | X | X |
| PSAQ[14] | | | | | X | | |
| Nasal gel device Ease-of-Use Questionnaire | | | | | X | | |
| Debriefing[15] | | | | | X | | |
| Record weather and sea state conditions[16] | | X | X | X | | | |

Abbreviations:
ACTS = Anticholinergic Toxicity Screen;
CEBQ = Confidential Exclusionary Behavior Questionnaire;
CMQ = Confidential Medical Questionnaire;
ICF = informed consent form;
IFU = instructions for use;
KSS = Karolinska Sleepiness Scale;
MSAQ = Motion Sickness Assessment Questionnaire;
MSSQ = Motion Sickness Susceptibility Questionnaire;
PSAQ = Performance Self-Assessment Questionnaire;
PVT = Psychomotor Vigilance Task;
TDS = Transdermal Scopolamine;
VAS = visual analogue scale.

TABLE 7d-continued

Schedule of Activities

| | Period | | | | | | |
|---|---|---|---|---|---|---|---|
| | Recruitment and Screening[1] | Treatment (Three Days Duration) | | | Post-treatment | Short-term Follow-up[2] | Long-term Follow-up[3] |
| | Visit | | | | | | |
| | 1 | 2 | 3 | 4 | 4 | — | — |
| | Study day | | | | | | |
| | Within 30 Days Prior to Day 1 | 1 | 2 | 3 | 3 | 10 + 3 | 11-45 |

[1]Screening occurred within 30 days prior to ship departure.
[2]The Short-term Follow-up Period (Day 10) consisted of research staff contacting the subject via phone or email at one week post-treatment period to ask if subjects had experienced any new signs or symptoms (includes ACTS). The acceptable window was +3 days.
[3]Long-term Follow-up (Days 11 to 45, two weeks to six weeks post-treatment period) consisted of subjects having a standing obligation to contact research staff via phone or email at any time during this period to report any new signs or symptoms. There was no acceptable window requirement. Long-term Follow-up ended at the close of Day 45 (six weeks). However, all adverse events (AEs) were followed until resolution.
[4]Subjects completed the Confidential Exclusionary Behavior Questionnaire (CEBQ) to confirm compliance with lifestyle compliance points listed under the inclusion criterion (i.e., no use of grapefruit and no use of alcohol) prior to dosing at the beginning of each visit.
[5]Re-explained the lifestyle adherence requirements (i.e., grapefruit, alcohol, etc.) of the treatment days listed in the IFU and Subject Handout.
[6]For females of child-bearing potential, a urine pregnancy test was performed and it was negative within seven days of Treatment Day 1.
[7]For every administration of study drug, details were recorded in the Study Drug Accountability (SDA) Log. With sufficient time prior to the investigator's notification of initial study drug dosing, the research staff trained all subjects on the proper administration and technique for priming the delivery device (using "DPI-386 Nasal Gel/Placebo Nasal Gel - INSTRUCTIONS FOR USE") and monitored the priming of the devices prior to the first dose. For all nasal gel administration, subjects self-administered two doses under supervision by research staff. No more than two doses of nasal gel were administered every 24 hours, with a minimum of six hours ± 15 minutes between doses, unless deemed necessary by the investigator. Each nasal gel administration occurred in the presence of and recorded by research staff. For all patch administration, an independent (unblinded) applicator applied the patches and bandage covers and confirmed that the patch administered on Treatment Day 1 remained appropriately applied on all Treatment Days.
[8]On Treatment Day 1, the investigator notified all the study subjects and independent (unblinded) applicators when to administer the first study drug doses (nasal gel and patch). This was the start of the controlled 8-hour period. A second treatment of nasal gel was self-administered 6 hours (+/−15 minutes) after the 1st dose administration time. The administration was only under the supervision by the research staff.
[9]PVT was performed during screening as a baseline, at 4 and 8 hours after first dose administration, on each of the 3 Treatment days.
[10]Safety Questionnaires and Tests including KSS, ACTS, MSAQ and VAS were completed by the subject at the following time points: Screening, twice on Treatment Day 1-3 at 4 and 8 hours post 1st dose for each treatment day, and in the event a rescue dose was administered (ACTS, MSAQ and VAS only).
[11]Assess AEs (including ACTS) each time the PVT was performed on Treatment days, by asking the subjects the following questions and recorded the answers on the data collection worksheet: How do you feel? Is this normal for you at this time of day?
[12]Subjects returned all study drug to research staff and the removal of the patch was confirmed.
[13]All concomitant medications/treatments taken within 30 days of randomization through Treatment Day 3, in addition to, any medications/treatments taken for reported AEs during follow-up were recorded.
[14]Subjects completed the questionnaire.
[15]Research staff informed subjects of the follow-up periods (short and long term) procedures (timing, responsibilities, contact information) and reminded subjects to contact research staff if any new signs or symptoms arise.
[16]Research staff transcribed weather and sea state conditions from the ship's log into the source data for all entries made during the 3 days of treatment.
Note:
this was done at the end of each voyage, on one log, not per subject. The ship captain used his standard reporting procedure.
Source: Section 3, Schedule of Events.

4.2. Discussion of Study Design, Including the Choice of Control Groups

This study was designed as a randomized, double-blind trial of DPI-386 Nasal Gel that had both an active control (TDS patch) and a placebo control (Placebo Nasal Gel). Study medication was administered for 3 days. Efficacy and safety results with DPI-386 Nasal Gel were compared with those of TDS patch and Placebo Nasal Gel to establish the effectiveness of DPI-386 for prevention and treatment of nausea associated with motion sickness and the safety of DPI-386 when used in the study population.

TDS patch is the current standard of care for the treatment of motion sickness.

4.3. Selection of Study Population

Subjects were screened either by phone or email to determine initial eligibility: "Do you suffer from motion sickness on boats? Are you between the ages of 18 and 59." Once initially screened, subjects were directed to meet the research staff for their Screening Visit. At the Screening Visit, the protocol was fully explained, including all potential risks known to both DPI-386 Nasal Gel and TDS patch. Any questions were answered by the PI or qualified designee. Once a person expressed interest in participation, the potential subject read and then signed the ICF, with the help of the researcher who consented the subject.

4.3. Inclusion Criteria

As per the protocol, inclusion criteria were as follows:

1. Provision of a signed and dated ICF.

2. Stated willingness to comply with all study procedures and availability for the duration of the study.

3. Male or female, aged 18 to 59 (inclusive).

4. At least minimally susceptible to provocative motion as evidenced by a minimum score of 3.0 on the MSSQ.

5. In good general health as evidenced by medical history with no recent history or current diagnosis of uncontrolled clinical problems as assessed by the PI or qualified designee.

6. Ability to take intranasal medication and willingness to adhere to the study schedule and time constraints.

7. For females of child-bearing potential: willingness to provide a urine sample for the human chorionic gonadotropin (hCG) pregnancy test. The test must be negative within 7 days of Treatment Day 1.

Note: Women of non-childbearing potential are defined as those who are non-surgically sterile (i.e., without menses for at least 12 consecutive months) or surgically sterile (i.e., those who underwent a hysterectomy with or without oophorectomy, fallopian tube ligation, and endometrial ablation).

8. Agreement to adhere to the following lifestyle compliance considerations:

a. Refrain from consumption of grapefruit and any substance containing grapefruit for 7 days prior to, during, and for 7 days after the 3 treatment days.

b. Abstain from alcohol for 24 hours prior to first dose of study medication and during the 3 treatment days.

Note: there was no restriction on caffeine or nicotine use during the study; however, the actual use of these substances was recorded as part of the Confidential Exclusionary Behavior Questionnaire (CEBQ).

4.3.2. Exclusion Criteria

As per the protocol, exclusion criteria were as follows:

1. Pregnancy, lactation, or positive urine pregnancy test within 7 days of Treatment Day 1.

2. Known allergic reactions to scopolamine or other anticholinergics.

3. Currently prescribed any of the following medication types and used within the specified washout periods below:

any form of scopolamine (including Transderm Scop®) (washout 5 days), belladonna alkaloids (washout 2 weeks), antihistamines (including meclizine) (washout 2 weeks), tricyclic antidepressants (washout 2 weeks), muscle relaxants (washout 4 days) and nasal decongestants (washout 4 days).

4. Hospitalization or significant surgery requiring hospital admittance within the past 6 months.

5. Treatment with another investigational drug or other intervention within the past 30 days.

6. Having donated blood or plasma or suffered significant blood loss within the past 30 days.

7. Having any of the following medical conditions within the last 2 years or if any of the following medical conditions were experienced more than 2 years ago and are deemed clinically significant by the PI or qualified designee:

Significant gastrointestinal disorder, asthma, or seizure disorders.

History of cardiovascular disease.

History of vestibular disorders.

History of narrow-angle glaucoma.

History of urinary retention problems.

History of alcohol or drug abuse.

Nasal, nasal sinus, or nasal mucosa surgery.

All the enrolled subjects fulfilled all the above inclusion and no exclusion criteria.

4.3.3. Removal of Subject from Therapy or Assessment

As per the protocol, withdrawal criteria were as follows:

1. Subjects were free to withdraw from the study at any time upon request.

2. The PI or qualified designee must have discontinued or withdrawn any subject from the study for the following reasons:

Pregnancy

Significant non-compliance to study requirements as listed in Inclusion and Exclusion Criteria If any serious adverse event (SAE) or other medical condition or situation occurred such that continued participation in the study would not be in the best interest of the subject Significant non-compliance with lifestyle study requirements as listed in Inclusion Criterion No. 8

If any AE or other medical condition or situation occurred such that continued participation in the study would not be in the best interest of the subject If the subject met an exclusion criterion (not previously recognized) that precludes further study participation If a subject deliberately removed the patch prior to the scheduled time If the subject failed to follow timeline requirements If the subject was disruptive, combative, or otherwise uncooperative with research staff 4.4. Treatments 4.4.1. Treatments Administered The initial study drug dosing for all the subjects in all treatment arms occurred at approximately the same time upon notification of the investigator and after study drug dosing training completed.

Each subject received both, a patch and nasal gel as per randomization to one of the following 3 arms: DPI-386 Nasal Gel+placebo patch, Placebo Nasal Gel+placebo patch, or Placebo Nasal Gel+TDS patch.

Nasal Gel Treatment Schedule

Subjects self-administered the first dose of DPI-386 Nasal Gel (0.2 mg/0.12 g) or Placebo Nasal Gel (0.12 g) into 1 nostril under research staff supervision upon notification by the investigator, and then self-administered a total of 5 additional doses over 3 treatment days always under research staff supervision. There was a minimum of 6 hours #15 minutes separating any 2 doses. No more than 2 doses were applied in a 24-hour period, unless a third dose (rescue) was deemed necessary by the investigator. After the initial dose, all subsequent nasal gel doses occurred only during the subject's controlled 8-hour period. Self-administration was supervised by research staff on all occasions.

Patch Treatment Schedule

Subjects were administered, by an independent (unblinded) applicator, a TDS patch or placebo patch placed behind either ear (subject's preference) upon notification by the investigator. The patch was removed and disposed of according to the manufacturer's instructions at the end of Treatment Day 3. The independent (unblinded) applicator applied a waterproof opaque bandage over the patch to ensure that the patch was not visible.

Procedure of Self-administration of Nasal Gel

1. Before self-administration of the study drug, the subjects were required to clean their hands to prevent contamination.

2. Subjects were instructed to blow their nose into a clean tissue to clear both nostrils.

3. Subjects were handed the vial by research staff, and told to remove the clip and cap and insert the gel unit tip approximately one cm into their nostril, pointing the tip toward the back of their nose.

4. Subjects closed their other nostril with their forefinger and tilted head slightly forward.

5. Subjects pumped the gel vial firmly by pushing down on the finger grips of the pump unit and against the thumb at the bottom of the vial delivering one dose of gel into the nostril.

6. Subjects sniffed gently with their mouth closed.

7 Subjects removed vial from nose and placed the clip and cap back on vial. The subjects returned the vial to the researcher after each dose administration for storage in the assigned kit at the secure storage location.

8. Subjects were instructed to avoid sniffing or sneezing and remain in an upright position for at least 30 minutes. Subjects did not need to stay with research staff during that time and only self-report if sniffing and sneezing happened when they visited the research staff next.

9. Subjects were instructed to refrain from blowing their nose for at least 1 hour after dosing.

10. After self-administration of the study drug administration, subjects were required to clean their hands to prevent contamination.

4.4.2. Identity of Investigational Products

| DPI-386 Nasal Gel | |
|---|---|
| Active content | Scopolamine Hydrobromide |
| Strength | Each 0.12 gram of the gel contains 0.2 mg of scopolamine HBr |
| Storage condition | Store at 20° C. to 25° C., inclusive (68° F. to 77° F., inclusive), with brief temperature excursions permitted between 15° C. and 30° C., inclusive (59° F. and 86° F., inclusive). |
| Lot No. | RDF0104 |
| TDS Patch [Transderm Scop ®, a commercial transdermal scopolamine (TDS) patch] | |
| Strength | One patch of 1.5 mg reservoir of scopolamine, designed to deliver 1.0 mg of scopolamine, can be delivered over a period of 72 hours |
| Lot No. | RDF0108 |
| Expiry Date | September 2021 |
| Placebo Nasal Gel (Placebo gel for DPI-386 Nasal Gel) | |
| Storage condition | Store at 20° C. to 25° C., inclusive (68° F. to 77° F., inclusive), with brief temperature excursions permitted between 15° C. and 30° C., inclusive (59° F. and 86° F., inclusive). |

4.4.3. Method of Assigning Subjects to Treatment Groups

Each subject randomized on Treatment Day 1 of the voyage was assigned a subject number (starting with 101) in consecutive order which was randomized the subject to one of the 3 treatment arms: DPI-386 Nasal Gel, Placebo Nasal Gel, and TDS patch. The subject number was linked to a multi-digit random number (study drug kit number) different from the subject number. The nasal gel vial was labelled with the same study drug kit random number. The randomization scheme was secured with limited access to research staff delegated by the PI and was used to be assigned the patch treatment from a bulk supply. For all the subjects, the link between each subject's number and that subject's study drug kit number with the actual treatment assignment was stored in individual secured envelopes. In a medical emergency, unblinding was allowed for one double-blind subject at a time.

| | Patch | | Nasal Gel | |
|---|---|---|---|---|
| Treatment Arm | Active | Placebo | Active | Placebo |
| DPI-386 Nasal Gel | | X | X | |
| Placebo Nasal Gel | | X | | X |
| TDS Patch | X | | | X |

4.4.4. Timing of Dose for Each Subject

For DPI-386 Nasal Gel (0.2 mg scopolamine HBr per dose) and Placebo Nasal Gel, 1 dose was delivered into 1 nostril twice daily over 3 consecutive treatment days (alternating nostrils) during the subject's controlled 8 hours period. The 2 daily doses were separated by a minimum of 6 hours with no more than 2 doses in 24 hours, unless a third dose (rescue) was deemed necessary by the investigator.

For the TDS patch and placebo patch, 1 patch was applied behind the ear on Treatment Day 1 only.

4.4.5. Blinding

This study was double-blinded placebo controlled for all treatment arms. All DPI-386 Nasal Gel and Placebo Nasal Gel vials were opaque and indistinguishable. The DPI-386 Nasal Gel and Placebo Nasal Gels were identical in color and viscosity, and without identifiable smell. Each placebo patch was similar in color and size as the TDS patch but did not deliver any medication or contain any excipients. A designated independent (unblinded) applicator administered all patch application and removal, including an opaque waterproof bandage cover over the patch, to further prevent unblinding.

To prevent bias, all research staff were trained to not make any leading or suggestive statements to subjects. All staff and subjects were instructed on proper administration of study drug, and instructed to clean their hands thoroughly immediately after handling any study drug.

The sealed randomization scheme and individual unblinding envelopes were delivered to the vessel by the research staff with the accompanying study drugs. The randomization scheme and individual unblinding envelopes were not kept in the same room as the clinical trial material aboard the vessel. Instead, the randomization scheme and individual unblinding envelopes were kept in a locked container in a separate room accessible by a designated research staff member.

The randomization scheme was opened only if the study had officially concluded all aspects of subject recruitment and data collection and the study sponsor had been informed and agreed. A subject's unblinding envelope was opened only if a subject suffered an AE after self-administering the blinded material, and medical providers needed to know whether administered study drug was active medication or placebo in order to treat the subject. If a subject suffered an AE, the PI or qualified designee first tried to contact the medical monitor and/or Sponsor by email to obtain approval to unblind the subject. If email was not available and neither could be reached and/or the PI or qualified designee deemed it urgent to unblind without approval, then(s) he could proceed with unblinding the specific subject by opening the unblinding envelope. All actions related to unblinding were documented in writing by the PI or qualified designee to the medial monitor and Sponsor as soon as possible. The medical monitor and Sponsor determined the case's reportability and proceed with additional reporting as per Food and Drug Administration (FDA) regulations.

4.4.6. Prior and Concomitant Therapy

All concomitant medications/treatments taken within 30 days of randomization through Treatment Day 3, in addition to, any medications/treatments taken for reported AEs during follow-up were recorded.

Prohibited medications included any form of scopolamine, belladonna alkaloids, antihistamines (including meclizine), tricyclic antidepressants, muscle relaxants and nasal decongestants. The required washouts for these medications are listed below:

- Any form of scopolamine (including Transderm Scop®)—washout 5 days prior to Treatment Day 1
- Belladonna alkaloids—washout 2 weeks prior to Treatment Day 1
- Antihistamines (including meclizine)—washout 2 weeks prior to Treatment Day 1.

- Tricyclic antidepressants—washout 2 weeks prior to Treatment Day 1
- Muscle relaxants—washout 4 days prior to Treatment Day 1
- Nasal decongestants—washouts 4 days prior to Treatment Day 1

For 30 days prior to, during Treatment Days 1 to 3 and 7 days after Treatment Day 3 the following restrictions are required:

- Blood donation
- Administration of another investigational drug
- For 7 days prior to, during Treatment Days 1 to 3 and 7 days after Treatment Day 3:
- No product containing grapefruit or grapefruit juice should be consumed.
- 24 hours prior to Treatment Day 1 and during Treatment Days 1 to 3:
- No alcohol should be consumed.
- No use of any motion sickness remedies (e.g., medications, wrist bands, pressure bands, herbals, etc. which state on the label for use in motion sickness) outside of the study protocol.
- Permitted medications were determined by the medical PI or qualified designee.

4.4.7. Treatment Compliance

For Nasal Gel, the subjects self-administered each dose under research staff supervision as per the procedure mentioned in Section 4.4.1 and as per the training given prior to start of the dosing activity.

For patch, an independent (unblinded) applicator (research staff who applied the patch) performed the whole activity from placing the patch behind either ear (subject's preference) to removal of the same.

4.5. Efficacy and Safety Variables 4.5.1. Efficacy and Safety Measurements Assessed and Flow Chart 4.5.1.1. Efficacy Evaluations 4.5.1.1.1. Primary Efficacy Endpoint The primary efficacy endpoint was the incidence of subjects who developed motion sickness and requested further treatment with rescue medication.

The primary endpoint was evaluated for the following treatment comparisons and treatment intervals:

- A comparison of DPI-386 Nasal Gel to TDS patch within the first 4 hours on or after the first dose of study treatment on Treatment Day 1.
- A comparison of DPI-386 Nasal Gel to TDS patch on or after the first dose of study treatment on Treatment Day 1.

4.5.1.1.2. Secondary Efficacy Endpoints

Time to First Use of Rescue Medication

A secondary efficacy endpoint was the time to first use of rescue medication during the treatment period, and was calculated in hours as the start time of administration of the first rescue medication dose minus the start time of the first dose of study drug. Subjects who did not receive any rescue medication were censored at the time of their last VAS MSAQ assessment during the treatment period.

Motion Sickness Assessment Questionnaire

A secondary efficacy endpoint was the Motion Sickness Assessment Questionnaire (MSAQ) total score, which was evaluated for the following treatment comparisons and treatment intervals:

A comparison of the differences in change from baseline in MSAQ total score,

DPI-386 Nasal Gel vs. placebo Nasal Gel at all timepoints.

A comparison of the differences in change from baseline in MSAQ total score,

DPI-386 Nasal Gel vs. TDS patch at all timepoints.

Nausea Assessment (Visual Analogue Scale)

A secondary efficacy endpoint was the severity of nausea as assessed on a visual analogue scale (VAS). Subjects specified their degree of nausea by indicating a point along a continuous 100-mm line between 2 endpoints. The scale ranged from 0 (no nausea) to 100 (very severe nausea) and was completed at screening and twice on Treatment Days 1-3 at 4 and 8 hours following the first dose for each treatment day. Scoring was based on the length from the left edge of the scale to point reported, and a higher score indicated a more severe degree of nausea.

Treatment comparisons were performed at time point intervals in the same manner as described for the secondary efficacy endpoint MSAQ scores.

4.5.1.2. Safety Endpoints 4.5.1.2.1. Primary Safety Endpoint

The primary safety endpoint was the subject incidence of treatment-emergent adverse events (TEAEs) while on study treatment. TEAEs were those with onset after the first dose of study treatment or existing events that worsened after the first dose of study treatment.

4.5.1.2.2. Secondary Safety Endpoint

The secondary safety endpoint was cognition as measured by the Psychomotor Vigilance Task (PVT).

The PVT is a neurocognitive assessment that measures alertness and tests sustained attention and reaction time. It was originally developed for sleep studies, and involves simple reaction time testing by requiring the participant to push a button as soon as the stimulus (a light) appears. After a response, the reaction time (in ms) is displayed. The inter-stimulus interval varies from two to 10 seconds, so it is not predictable, and the entire task takes 10 minutes (Dorrian, Rogers, and Dinges, 2005).

The mean change from baseline to all post-baseline measurements in cognition as measured by median response time and number of performance lapses was evaluated.

4.5.1.2.3. Other Safety Endpoints

Other safety endpoints were as follows:

- Mean change from baseline to all post-baseline measurements during the treatment period in the assessments of sleepiness using the Karolinska Sleepiness Scale (KSS).
- Subject incidence in reporting symptoms of anticholinergic toxicity using the ACTS, at each visit and time point where collected.
- . Frequency of subject responses to the individual items of the Performance Self-Assessment Questionnaire (PSAQ) administered at Post-Treatment Day 3, as an assessment of whether the subject perceived DPI-386 Nasal Gel or TDS patch application to be detrimental to the performance of activities at any time during the study period.

4.5.1.3. Other Evaluations

The frequency of subject responses to the individual items of the Nasal Gel Device Ease-of-Use Questionnaire (EOUQ) at Post-Treatment Day 3.

4.5.1.4. Assessment of Safety

It was the responsibility of the investigator to ensure that adequate medical supervision and care was available for the study subjects during each visit to ensure the utmost safety and well-being of the study subjects.

The following measures were taken to monitor and assess the safety of the subjects during the study:

All standard ocean-going vessel safety practices and emergency procedures were followed to ensure maximum safety. All research staff engaged in collecting subject data had cardiopulmonary resuscitation (CPR) training to ensure the safety of all participants.

All the subjects were observed for symptoms related to study drug administration. Moreover, during each collection of vital signs, subjects were evaluated for AEs. All abnormal responses were recorded as AEs.

All research personnel were trained in CPR and in the application of the ACTS based on known signs and symptoms of anticholinergic overdose. The ACTS was assessed each time the subject was seen during the 3 treatment days. The ACTS was performed during screening, at 4 and 8 hours post-dose of $1^{st}$ dosing in all 3 treatment days and at the time of rescue dose (if rescue dose was given).

At screening and prior to randomization, a pregnancy test was administered by research staff under the standing orders of the PI.

Safety Questionnaires and tests including KSS, ACTS, MSAQ, PVT, and VAS were completed by the subject at the following time points: Screening, twice on all 3 treatment days at 4 and 8 hours and in the event a rescue dose was administered (ACTS, MSAQ, and VAS only).

Research staff transcribed weather and sea state conditions from the ship's log into the source data for all entries made during the 3 days of treatment. Note: this was done one time at the end of each voyage, on one log, not per subject. The ship captain used his standard reporting procedure.

4.5.1.4.1. Adverse Events

All AEs that occurred during the study (whether treatment related or not) were recorded in the electronic case report form (eCRF) and followed as appropriate.

Criteria for Assessing Adverse Events:

The severity of the AEs was rated by the PI as mentioned below:

Mild—Events require minimal or no treatment and do not interfere with the subject's daily activities. Mild events require no action other than documentation.

Moderate—Events result in a low level of inconvenience or concern with the therapeutic measures. Moderate events may cause some interference with functioning.

Severe—Events interrupt a participant's usual daily activity and may require medical treatment. Severe events are usually potentially life-threatening or incapacitating. AEs were additionally identified by temporal qualities in the following categories:

Continuous—The AE has a marked starting point and ending point, without recurrence.

Intermittent—The AE is sporadic in its effect, and recurring.

Causality Assessment of the Adverse Event to the Investigational Medicinal Product (IMP) was done based on the following criteria:

Not related—The AE is completely independent of study drug administration, and/or evidence exists that the event is definitely related to another etiology. There must be an alternative definitive etiology documented by the medical monitor.

Related—This category includes (a) definitely related, (b) probably related, (c) possibly related, and (d) remotely related to study drug administration.

4.5.1.4.2. Adverse Events of Special Interest

AEs of special interest (AESIs) included all symptoms listed for the ACTS deemed "related" to study drug by the PI. For monitoring and reporting purposes, these events of special interest were further divided into 2 categories:

1. Significant Non-Serious Adverse Events

Significant Non-Serious AEs included all symptoms on the ACTS symptoms list deemed "related" to the study drug by the PI, in addition to light-headedness, asymptomatic hypotension and symptomatic hypotension deemed "related" to the study drug by the PI. These AEs were reported using the same procedure for SAEs. All significant non-serious AEs occurring within 30 days of the subject's last exposure to study medication were reported.

The Significant Non-Serious AEs include:

Increased skin redness/flushing
Blurry vision
Light sensitivity
Difficulty urinating
Dizziness
Light-headedness
Asymptomatic hypotension
Symptomatic hypotension
Confusion
Hallucinations
Palpitations 2. Non-significant Non-Serious Adverse Events Dry mouth was the only event of special interest to be considered a Non-significant Non-Serious AE and was reported using the standard (non-expedited) AE reporting procedure.

4.5.2. Appropriateness of Measurements

Efficacy assessments were based on the use of rescue medication, MSAQ scores, and nausea assessment via VAS. Subject-initiated AE reports of nausea or motion sickness were assessed in a post-hoc analysis.

Safety assessments were based on AEs, PVT, KSS, ACTS, PSAQ, and EOUQ.

4.5.3. Drug Concentration Measurements

Not applicable.

4.6. Data Quality Assurance 4.6.1. Monitoring

Sponsor representatives were allowed to visit all study site locations to assess the data, quality and study integrity in a manner consistent with applicable health authority regulations and the procedures adopted by sponsor. Prior to the start of the study, members of sponsor reviewed the protocol, eCRF, regulatory obligations and other material or equipment relevant to the conduct of the study with the PI/Sub-Investigator and relevant study site personnel.

Monitoring visits and telephone consultations occurred as necessary and per the monitoring plan, during the course of the investigation to verify the following:

the rights and well-being of subjects were protected, the conduct of the investigation was in compliance with the currently approved protocol/amendment, 21 Code of Federal Regulations Parts 50, 54, 56 and 812; 42 United States Code 282(j); ICH GCPs; and applicable local regulations, the integrity of the data, including adequate study documentation, the facilities remained acceptable, the PI and site personnel remained qualified and able to conduct the study, test article accountability.

4.6.2. Training

The investigator and team were trained in ICH-Good Clinical Practices guideline. Before the start of the study, the study team was trained on the protocol, informed consent procedures, eCRF completion and correction, source documentation, monitoring procedures, management of documents and timelines of subject recruitment and completion.

4.6.3. Quality Assurance

Compliance to the study requirements were observed as per Good Clinical Practices, Internal Standard Operating Procedures, Protocol, and applicable regulatory requirements.

4.6.4. Clinical Data Management

TAB Clinical was provided paper copies of the CRFs and then entered the data into an electronic data capture database with double-data entry per FDA guidance. TAB queried all incorrect, out-of-range, and missing data.

4.7. Statistical Methods Planned in the Protocol and Determination of Sample Size 4.7.1. Methodological Planning for the Design of the Study The FDA advised Defender to focus on safety rather than efficacy in their clinical development plan for DPI-386 Nasal Gel. Thus, the primary reason for inclusion of a rescue dose of active DPI-386 Nasal Gel in the DPI-386-MS-21 study was to be able to retain subjects who might experience motion sickness on Day 1 of the ship's voyage. The use or potential use of active rescue medication would act as an incentive to, and means of retaining, subjects who may have been unwilling to complete the second and third days of the study if DPI-386 Nasal Gel rescue medication was not made available. The subjects' completion of Days 2 and 3 aboard the ship ensured that important data would be collected during the last two study days of the voyage.

For these reasons, the study was not powered to ensure that a sufficient number of subjects received DPI-386 Nasal Gel rescue medication and that a statistically meaningful result could be demonstrated for DPI-386 Nasal Gel rescue medication use alone. The initial planned primary endpoint was prevention of motion sickness, which was revised following discussions with the FDA to "the incidence of subjects who developed motion sickness and request further treatment (rescue medication-DPI-386)." Per a request from the FDA, the sample size was set at 100 subjects per treatment arm and was not based on a power analysis for a specific endpoint.

4.7.2. Statistical and Analytical Plans

Quantitative assessments (continuous data) were summarized by reporting the number of subjects (n), mean, standard deviation (SD), median, minimum value, and maximum value.

Qualitative assessments (categorical data) were summarized by reporting the frequency (count and percent) of subjects falling within each category of a given assessment. Unless specified otherwise for a particular assessment, the denominator for calculating a percentage was the total number of subjects in the analysis population for the subgroup being analyzed; for example, within study arm, the number of subjects within the study arm in the analysis population was the denominator. For overall summaries, the total number of subjects in the analysis population was used as the denominator.

Statistical tests and confidence intervals were provided. Among-group tests were performed. Tests comparing DPI-386 Nasal Gel to Placebo Nasal Gel, and DPI-386 Nasal Gel to TDS patch were performed with two-sided tests at the 5% significance level. Confidence intervals (CIs) were constructed to describe differences (DPI-386—TDS patch and DPI-386—Placebo Nasal Gel) between groups using two one-sided 90% limits.

4.7.2.1. Analysis Populations

The analysis populations were defined as follows:

- Intent-to-treat (ITT): The ITT population included all randomized subjects.
- Modified Intent-to-Treat (mITT): The mITT population included subjects randomized to treatment who received at least 1 dose of study treatment and who have at least 1 post-baseline assessment of the MSAQ.
- Per Protocol (PP): The PP population included all subjects randomized to treatment who received at least 1 dose of study treatment, who have at least 1 post-baseline assessment of the MSAQ, and who did not have any major protocol violations.
- Safety: The Safety population included all subjects who received at least 1 dose of study treatment.

As the subjects in the ITT and mITT populations were the same, no tables for the mITT population were generated.

The safety analyses were performed using the safety population and the efficacy analyses were performed using the ITT and PP populations; all analyses were conducted with SAS® Version 9.4 (SAS Institute Inc., USA).

4.7.2.2. Study Subjects 4.7.2.2.1. Disposition of Subjects

Subject disposition was summarized for the safety, ITT, and PP populations by treatment group and over all subjects combined. Summaries included the number and percentage of subjects in each analysis population, completing the study, discontinuing the study early by the primary reason for discontinuation.

4.7.2.2.2. Protocol Deviations

Major protocol violations were summarized by treatment group and over all subjects combined. Major protocol violations were protocol deviations captured on-study that were deemed by the Sponsor to potentially impact the efficacy or safety conclusions of the study.

4.7.2.2.3. Measurements of Treatment Compliance

Compliance to the study treatment regimen was summarized separately for the nasal gel application and patch application:

- Nasal Gel: The total number of doses administered as the full dose without dosing errors
- Patch: The number of days the patch remained on the subject The number of nasal gel doses received was summarized with the number and percentage of subjects receiving 0, 1, 2, 3, 4, 5, or 6 complete doses without dosing errors by treatment group. The number of days with an administered patch was summarized with the number and percentage of subjects wearing the patch for 0, 1, 2, or 3 days during the treatment period by treatment group. Compliance with study treatment was summarized for the Safety Population.

4.7.2.3. Efficacy Evaluation

All efficacy summaries were based on the ITT population.

4.7.2.3.1. Demographic and Other Baseline Characteristics

Demographic variables including age, sex, ethnicity, and race were summarized by treatment group and over all subjects combined for the ITT, PP, and Safety populations.

Age was summarized using descriptive statistics. Sex, ethnicity, and race were summarized with the number and percentage of subjects.

4.7.2.3.2. Primary Efficacy Endpoint Analysis Methods

The primary efficacy endpoint was the incidence of subjects who developed motion sickness and requested further treatment with rescue medication.

Treatment groups were compared using a Fisher-Exact test. 95% CIs were constructed to describe differences between treatment groups (DPI-386—TDS patch; DPI-386—Placebo Nasal Gel; TDS patch—Placebo Nasal Gel).

The analysis was performed on the ITT population.

4.7.2.3.3. Secondary Efficacy Endpoint Analysis Methods

Secondary efficacy endpoints were time to administration of rescue medication, the MSAQ Total score, and the severity of nausea (as assessed by the subject on a VAS).

Time to administration of rescue medication was analyzed using the log rank test. Subjects who took no rescue medication during the study were censored at the time of the last. VAS MSAQ assessment.

MSAQ and VAS results were analyzed using a MMRM including fixed effects of treatment, visit, and interaction term of treatment by visit. Baseline value was included as a covariate in the model.

The analyses were performed on the ITT population.

4.7.2.4. Safety Evaluation

Safety analysis was carried out for the Safety population, which included all subjects who received at least 1 dose of study drug.

4.7.2.4.1. Primary Safety Endpoint: Adverse Events

TEAEs were defined as those AEs with onset after the first dose of study drug or existing events that worsened after the first dose during the study. TEAEs were summarized by treatment group.

Summaries displayed by system organ class (SOC) and Medical Dictionary for Regulatory Activities (MedDRA) preferred terms were ordered by descending incidence of SOC and preferred term within each SOC. Summaries displayed by preferred term only were ordered by descending incidence of preferred term.

At each level of summarization (e.g., any AE, SOC, and preferred term), subjects experiencing more than one TEAE were counted only once. In the summary of TEAEs by severity grade, subjects were counted once at the highest severity reported at each level of summarization; in the summary of TEAEs by relationship, subjects were counted once at the closest relationship to study drug. Related events include those reported as "Possibly related," "Probably related," or "Definitely related" relationship to study drug; events considered not related are those reported as "Remotely related" or "Unable to determine" with respect to relationship to study drug. AE data were presented in data listings by subject, treatment group, and event.

4.7.2.4.2. Secondary Safety Endpoint: Cognition

The secondary safety endpoint was cognition as measured by the PVT.

The mean change from baseline to all post-baseline measurements in cognition as measured by median response time and number of performance lapses was evaluated.

4.7.2.4.3. Other Safety Endpoints

Karolinska Sleepiness Scale

A higher score on the 10-point scale indicates a greater degree of sleepiness. For example, a score of 1 means 'extremely alert' and a score of 10 means 'extremely sleepy, can't keep awake.'

The KSS score was summarized by treatment group. Descriptive statistics were presented for the observed values at each visit and for changes from baseline to each visit and time point. Between-group comparisons were performed at each time point and for the change from baseline using a logistic regression model that compares DPI-386 Nasal Gel to each control group and includes KSS as the response variable, a main effect for the treatment group, and the KSS score at screening as a covariate.

Anticholinergic Toxicity Screen

Subject incidence in reporting symptoms of anticholinergic toxicity using the ACTS was presented by treatment group. The number and percentage of subjects who reported symptoms were summarized at each visit and time point by symptom.

Performance Self-Assessment Questionnaire

The frequency of subject responses to the individual items of the PSAQ administered at Post-Treatment Day 3 were summarized by Treatment Group. The number and percentage of subjects who reported each of the possible responses for each item were summarized.

4.7.2.5. Other Evaluations

The frequency of subject responses to the individual items of the Nasal Gel Device EOUQ administered at Post-Treatment Day 3 were summarized by Treatment Group. The number and percentage of subjects who reported each of the possible responses for each item were summarized.

4.7.2.6. Prior and Concomitant Medications

Prior and concomitant medications were summarized for each treatment.

4.7.2.7. Determination of Sample Size

Per the request of the FDA, the sample size was 100 subjects per treatment arm (300 subjects total) and was not based on any power calculations for a specific parameter or endpoint.

4.7.2.8. Changes in the Conduct of the Study or Planned Analyses

Vital sign measurements and 12-lead electrocardiogram (ECG) data were not collected in the study.

5. Study Subjects 5.1. Disposition of Subjects

A total of 297 subjects (187 male and 110 female) were enrolled and dosed in the study; 297 subjects on Treatment Day 1, 282 subjects on Treatment Day 2, and 275 subjects on Treatment Day 3 (Table 4.1.3). Across all treatment groups, 22 subjects (7.4%) withdrew from the study prior to completion. Two subjects discontinued the study due to AEs after dosing on Day 1: Subject 205 (TDS patch) discontinued the study due to motion sickness and Subject 246 (DPI-386 Nasal Gel) discontinued the study due to palpitations (both events resolved). A summary of subject disposition is presented in FIG. 7A.

A summary of the number (%) of subjects in each treatment arm who were present on each study day is provided (ITT population) (PP population).

5.2. Protocol Deviations

A total of 360 protocol deviations were reported in the trial. Out of 360 deviations, 2 deviations were considered as major and 358 deviations were considered as minor. The 2 major protocol deviations occurred in the same subject, Subject 324, and the deviations were that on Treatment Day 2 and on Treatment Day 3, Dose #2 of study drug was not administered.

6. Efficacy Evaluation 6.1. Data Sets Analyzed

A total of 297 subjects (187 male and 110 female) were enrolled and dosed in the study and included in the Safety and ITT populations. A total of 296 subjects were included in PP population.

Subject No. 324 was excluded from the PP population because of the major protocol deviations noted in Section 5.2.

6.2 Demographic and Other Baseline Characteristics

A sufficient number of subjects were enrolled in the study. All subjects fulfilled all the inclusion and met none of the exclusion criteria.

Mean (SD) and median age, gender, race, ethnicity, and mean (SD) and median MSSQ scores are presented in Table 7e for the Safety and ITT populations and in Table If for the PP population.

TABLE 7e

Demographic Data (Safety and ITT Population)

| Parameter | DPI-386 Nasal Gel (N = 99) | TDS Patch (N = 98) | Placebo Nasal Gel (N = 100) | Total (N = 297) |
|---|---|---|---|---|
| Age (years), mean (SD) | 34.9 (11.22) | 36.8 (11.57) | 34.8 (11.49) | 35.5 (11.42) |
| Age (years), median | 33.0 | 36.0 | 33.0 | 34.0 |
| Gender | | | | |
| Male, n (%) | 70 (70.7) | 66 (67.3) | 51 (51.0) | 187 (63.0) |
| Female, n (%) | 29 (29.3) | 32 (32.7) | 49 (49.0) | 110 (37.0) |
| Race | | | | |
| American Indian or Alaska Native, n (%) | 1 (1.0) | 1 (1.0) | 2 (2.0) | 4 (1.3) |
| Asian, n (%) | 14 (14.1) | 13 (13.3) | 18 (18.0) | 45 (15.2) |
| Black or African American, n (%) | 35 (35.4) | 36 (36.7) | 35 (35.0) | 106 (35.7) |
| Native Hawaiian or Other Pacific Islander, n (%) | 1 (1.0) | 5 (5.1) | 1 (1.0) | 7 (2.4) |
| Other, n (%) | 3 (3.0) | 1 (1.0) | 3 (3.0) | 7 (2.4) |
| White, n (%) | 45 (45.5) | 42 (42.9) | 41 (41.0) | 128 (43.1) |
| Ethnicity | | | | |
| Hispanic or Latino, n (%) | 27 (27.3) | 21 (21.4) | 25 (25.0) | 73 (24.6) |
| Not Hispanic or not Latino, n (%) | 70 (70.7) | 73 (74.5) | 72 (72.0) | 215 (72.4) |
| Not reported, n (%) | 1 (1.0) | 2 (2.0) | 3 (3.0) | 6 (2.0) |
| Unknown, n (%) | 1 (1.0) | 2 (2.0) | 0 (0.0) | 3 (1.0) |
| MSSQ, mean (SD) | 14.6 (6.35) | 15.4 (6.57) | 15.5 (6.24) | 15.2 (6.38) |
| MSSQ, median | 14.1 | 15.9 | 17.0 | 16.0 |

Abbreviations: ITT = Intent-to-Treat;
MSSQ = Motion Sickness Susceptibility Questionnaire;
SD = standard deviation
Source: Table 14.1.1

TABLE 1f

Demographic Data (PP Population)

| Parameter | DPI-386 Nasal Gel (N = 99) | TDS Patch (N = 98) | Placebo Nasal Gel (N = 99) | Total (N = 296) |
|---|---|---|---|---|
| Age (years), mean (SD) | 34.9 (11.22) | 36.8 (11.57) | 34.6 (11.30) | 35.4 (11.37) |
| Age (years), median | 33.0 | 36.0 | 33.0 | 33.5 |
| Gender | | | | |
| Male, n (%) | 70 (70.7) | 66 (67.3) | 51 (51.5) | 187 (63.2) |
| Female, n (%) | 29 (29.3) | 32 (32.7) | 48 (48.5) | 109 (36.8) |
| Race | | | | |
| American Indian or Alaska Native, n (%) | 1 (1.0) | 1 (1.0) | 2 (2.0) | 4 (1.3) |
| Asian, n (%) | 14 (14.1) | 13 (13.3) | 18 (18.0) | 45 (15.2) |
| Black or African American, n (%) | 35 (35.4) | 36 (36.7) | 35 (35.0) | 106 (35.7) |
| Native Hawaiian or Other Pacific Islander, n (%) | 1 (1.0) | 5 (5.1) | 1 (1.0) | 7 (2.4) |
| Other, n (%) | 3 (3.0) | 1 (1.0) | 3 (3.0) | 7 (2.4) |
| White, n (%) | 45 (45.5) | 42 (42.9) | 40 (40.0) | 127 (42.8) |
| Ethnicity | | | | |
| Hispanic or Latino, n (%) | 27 (27.3) | 21 (21.4) | 25 (25.0) | 73 (24.6) |
| Not Hispanic or not Latino, n (%) | 70 (70.7) | 73 (74.5) | 71 (71.0) | 214 (72.1) |
| Not reported, n (%) | 1 (1.0) | 2 (2.0) | 3 (3.0) | 6 (2.0) |
| Unknown, n (%) | 1 (1.0) | 2 (2.0) | 0 (0.0) | 3 (1.0) |
| MSSQ, mean (SD) | 14.6 (6.35) | 15.4 (6.57) | 15.5 (6.24) | 15.2 (6.38) |
| MSSQ, median | 14.1 | 15.9 | 17.0 | 16.0 |

Abbreviations: MSSQ = Motion Sickness Susceptibility Questionnaire;
PP = Per Protocol:
SD = standard deviation
Source: Table 14.1.2

6.3. Measurements of Treatment Compliance

A summary of treatment compliance by number of doses of Nasal Gel received and number of days that the patch was applied is presented in Table 2. In all treatment arms the number of subjects who received Nasal Gel and who used the patch decreased over time, but by the final dosing time point treatment compliance was still good. The percentages of subjects in the DPI-386 Nasal Gel, TDS patch, and Placebo Nasal Gel arms who administered the Nasal Gel at Dose 6 were 88.9%, 95.9%, and 93.0%, respectively. The percentages of subjects in the DPI-386 Nasal Gel, TDS patch, and Placebo Nasal Gel arms who applied a patch on Day 3 were 88.9%, 95.9%, and 93.0%, respectively.

TABLE 7g

Treatment Compliance (Safety Population)

| Parameter | Dose/Patch | Statistic | DPI-386 Nasal Gel (N = 99) | TDS Patch (N = 98) | Placebo Nasal Gel (N = 100) |
|---|---|---|---|---|---|
| Nasal gel application | | | | | |
| Day 1 | 1 | n (%) | 99 (100.0) | 98 (100.0) | 100 (100.0) |
| | 2 | n (%) | 99 (100.0) | 98 (100.0) | 100 (100.0) |
| Day 2 | 1 | n (%) | 92 (92.9) | 95 (96.9) | 95 (95.0) |
| | 2 | n (%) | 92 (92.9) | 95 (96.9) | 95 (95.0) |
| Day 3 | 1 | n (%) | 88 (88.9) | 94 (95.9) | 93 (93.0) |
| | 2 | n (%) | 88 (88.9) | 94 (95.9) | 93 (93.0) |
| Patch application | | | | | |
| Subject wearing patch on | Day 1 | n (%) | 99 (100.0) | 98 (100.0) | 100 (100.0) |
| | Day 2 | n (%) | 92 (92.9) | 95 (96.9) | 95 (95.0) |
| | Day 3 | n (%) | 88 (88.9) | 94 (95.9) | 93 (93.0) |

Source: Table 14.3.12

6.4. Efficacy Results and Tabulations of Individual Subject Data 6.4.1. Analyses of Efficacy 6.4.1.1. Primary Efficacy Endpoint: Proportion of Subjects Who Received Rescue Medication The primary efficacy endpoint was the proportion of subjects in the ITT population who developed motion sickness and requested further treatment with rescue medication. The differences between the DPI-386 Nasal Gel arm and the TDS patch arm and the differences between the DPI-386 Nasal Gel arm and the Placebo Nasal Gel arm were not statistically significant at Treatment Day 1 Hour 4 or at any time on Treatment Day 1 (Table 7h). The differences between the TDS patch arm and the Placebo Nasal Gel arm were not statistically significant at Treatment Day 1 Hour 4 or at any time on Treatment Day 1.

TABLE 7h

Proportion of Subjects Using Rescue Medication (ITT Population)

| Parameter Statistic | DPI-386 Nasal Gel (N = 99) | TDS Patch (N = 98) | Placebo Nasal Gel (N = 100) |
|---|---|---|---|
| Subjects who took rescue medication within 4 hours after the first dose on Treatment Day 1 | | | |
| n (%) | 9 (9.1) | 12 (12.2) | 9 (9.0) |
| 95% CI | (4.2, 16.6) | (6.5, 20.4) | (4.2, 16.4) |
| Treatment difference (95% CI) | 0.1 (−7.9, 8.1) | 3.2 (−5.3, 11.8) | |
| p-value[1] | >0.9999 | 0.4964 | |
| Treatment difference (95% CI) | −3.2 (−11.8, 5.5) | | |
| p-value[2] | 0.4983 | | |
| Subjects who took rescue medication at any time | | | |

TABLE 7h-continued

Proportion of Subjects Using Rescue Medication (ITT Population)

| Parameter Statistic | DPI-386 Nasal Gel (N = 99) | TDS Patch (N = 98) | Placebo Nasal Gel (N = 100) |
|---|---|---|---|
| on Treatment Day 1 | | | |
| n (%) | 15 (15.2) | 15 (15.3) | 12 (12.0) |
| 95% CI | (8.7, 23.8) | (8.8, 24.0) | (6.4, 20.0) |
| Treatment difference (95% CI) | 3.2 (−6.4, 12.7) | 3.3 (−6.3, 12.9) | |
| p-value[1] | 0.5416 | 0.5395 | |
| Treatment difference (95% CI) | −0.2 (−10.2, 9.9) | | |
| p-value[2] | >0.9999 | | |

CI = confidence interval; ITT = Intent-to-Treat.

Note:

Use of rescue medication included subjects who took the rescue medication or reported an adverse event with an assigned action as rescue DPI 386 Nasal Gel.

[1]Comparison vs Placebo group were performed using Fishers Exact test.

[2]Comparison vs TDS Patch was performed using Fishers Exact test.

Source: Table 14.2.1.1, Table 14.2.1.2

6.4.1.2. Secondary Efficacy Endpoints 6.4.1.2.1. Time to First Use of Rescue Medication A secondary efficacy endpoint was the time to first use of rescue medication during the treatment period. The difference in time to first use of rescue mediation between the DPI-386 Nasal Gel arm and the Placebo Nasal Gel arm (ITT population) was not statistically significant (p=0.3458, log-rank test; Table 14.2.2.1). The difference in time to first use of rescue mediation between the DPI-386 Nasal Gel arm and the TDS patch arm (ITT population) was not statistically significant (p=0.9367, log-rank test).

A Kaplan-Meier plot of time to first use of rescue medication in the ITT population is provided.

6.4.1.2.2. Motion Sickness Assessment Questionnaire

A secondary efficacy endpoint was the MSAQ Total score. In the ITT population, the differences between DPI-386 Nasal Gel and TDS patch in least-squares mean (LSM) MSAQ total score changes from baseline at all time points were not statistically significant, and the differences between DPI-386 Nasal Gel and Placebo Nasal Gel in changes from baseline at all time points were also not statistically significant (Table 8j).

TABLE 7i

Analysis of the Motion Sickness Assessment Questionnaire Total Score (ITT Population)

| Timepoint Statistic | DPI-386 Nasal Gel (N = 99) | TDS Patch (N = 98) | Placebo Nasal Gel (N = 100) |
|---|---|---|---|
| Baseline | | | |
| N | 99 | 98 | 100 |
| Mean (SD) | 1.592 (0.5170) | 1.569 (0.3375) | 1.571 (0.3985) |
| Median | 1.440 | 1.440 | 1.440 |
| Min, max | 1.44, 6.12 | 1.44, 3.33 | 1.44, 4.32 |
| Day 1 4-hour Post dose | | | |
| N | 99 | 98 | 100 |
| Mean (SD) | 2.400 (1.8969) | 2.609 (1.8738) | 2.796 (2.0239) |
| Median | 1.530 | 1.800 | 1.890 |
| Min, max | 1.44, 10.71 | 1.44, 10.62 | 1.44, 9.72 |
| Day 1 4-hour Post dose change from baseline | | | |
| N | 99 | 98 | 100 |
| Mean (SD) | 0.808 (1.9833) | 1.040 (1.8804) | 1.225 (2.0236) |
| Median | 0.090 | 0.360 | 0.360 |
| Min, max | −4.68, 9.00 | −0.90, 9.00 | −2.52, 7.83 |
| LSM (SE) | 0.821 (0.191) | 1.030 (0.189) | 1.217 (0.202) |
| Treatment difference (95% CI) | −0.396 (−0.944, 0.153) | −0.209 (−0.739, 0.321) | |
| P-value | 0.1561 | 0.4383 | |
| Day 1 8-hour Post dose | | | |
| N | 99 | 98 | 100 |
| Mean (SD) | 2.026 (1.4887) | 1.957 (1.1765) | 1.921 (1.1497) |
| Median | 1.440 | 1.530 | 1.440 |
| Min, max | 1.44, 9.54 | 1.44, 8.55 | 1.44, 9.00 |

TABLE 7i-continued

Analysis of the Motion Sickness Assessment Questionnaire Total Score (ITT Population)

| Timepoint Statistic | DPI-386 Nasal Gel (N = 99) | TDS Patch (N = 98) | Placebo Nasal Gel (N = 100) |
|---|---|---|---|
| Day 1 8-hour Post dose change from baseline | | | |
| N | 99 | 98 | 100 |
| Mean (SD) | 0.435 (1.5861) | 0.388 (1.2188) | 0.349 (1.1428) |
| Median | 0.000 | 0.000 | 0.000 |
| Min, max | −4.68, 8.01 | −1.62, 7.11 | −2.88, 6.57 |
| LSM (SE) | 0.448 (0.150) | 0.378 (0.119) | 0.342 (0.115) |
| Treatment difference (95% CI) | 0.106 (−0.266, 0.479) | 0.070 (−0.307, 0.447) | |
| P-value | 0.5746 | 0.7155 | |
| Day 2 4-hour Post dose | | | |
| N | 90 | 95 | 95 |
| Mean (SD) | 1.759 (0.9924) | 1.665 (0.5792) | 1.907 (1.1743) |
| Median | 1.440 | 1.440 | 1.440 |
| Min, max | 1.44, 8.46 | 1.44, 5.31 | 1.44, 8.19 |
| Day 2 4-hour Post dose change from baseline | | | |
| N | 90 | 95 | 95 |
| Mean (SD) | 0.154 (1.1306) | 0.099 (0.6648) | 0.333 (1.2633) |
| Median | 0.000 | 0.000 | 0.000 |
| Min, max | −4.68, 7.02 | −1.89, 3.87 | −2.88, 6.66 |
| LSM (SE) | 0.236 (0.111) | 0.082 (0.059) | 0.333 (0.121) |
| Treatment difference (95% CI) | −0.097 (−0.421, 0.227) | 0.154 (−0.095, 0.403) | |
| P-value | 0.5549 | 0.2226 | |
| Day 2 8-hour Post dose | | | |
| N | 92 | 94 | 95 |
| Mean (SD) | 1.579 (0.4590) | 1.583 (0.4082) | 1.688 (0.6715) |
| Median | 1.440 | 1.440 | 1.440 |
| Min, max | 1.44, 4.95 | 1.44, 3.87 | 1.44, 5.22 |
| Day 2 8-hour Post dose change from baseline | | | |
| N | 92 | 94 | 95 |
| Mean (SD) | −0.023 (0.7042) | 0.016 (0.5403) | 0.115 (0.7625) |
| Median | 0.000 | 0.000 | 0.000 |
| Min, max | −4.68, 3.51 | −1.80, 2.43 | −1.98, 3.78 |
| LSM (SE) | 0.021 (0.050) | −0.002 (0.041) | 0.112 (0.069) |
| Treatment difference (95% CI) | −0.091 (−0.260, 0.078) | 0.022 (−0.107, 0.151) | |
| P-value | 0.2877 | 0.7344 | |
| Day 3 4-hour Post dose | | | |
| N | 88 | 94 | 92 |
| Mean (SD) | 1.552 (0.3018) | 1.579 (0.4146) | 1.609 (0.5208) |
| Median | 1.440 | 1.440 | 1.440 |
| Min, max | 1.44, 3.69 | 1.44, 4.23 | 1.44, 5.04 |
| Day 3 4-hour Post dose change from baseline | | | |
| N | 88 | 94 | 92 |
| Mean (SD) | −0.052 (0.6381) | 0.012 (0.5549) | 0.043 (0.6558) |
| Median | 0.000 | 0.000 | 0.000 |
| Min, max | −4.68, 2.25 | −1.89, 2.79 | −2.52, 3.60 |
| LSM (SE) | 0.004 (0.037) | 0.000 (0.042) | 0.028 (0.053) |
| Treatment difference (95% CI) | −0.023 (−0.152, 0.106) | 0.004 (−0.108, 0.116) | |
| P-value | 0.7208 | 0.9438 | |
| Day 3 8-hour Post dose | | | |
| N | 88 | 94 | 93 |
| Mean (SD) | 1.492 (0.2839) | 1.475 (0.1367) | 1.541 (0.4137) |
| Median | 1.440 | 1.440 | 1.440 |
| Min, max | 1.44, 3.96 | 1.44, 2.34 | 1.44, 4.59 |
| Day 3 8-hour Post dose change from baseline | | | |
| N | 88 | 94 | 93 |
| Mean (SD) | −0.113 (0.6231) | −0.091 (0.3743) | −0.024 (0.5787) |
| Median | 0.000 | 0.000 | 0.000 |

TABLE 7i-continued

Analysis of the Motion Sickness Assessment Questionnaire Total Score (ITT Population)

| Timepoint Statistic | DPI-386 Nasal Gel (N = 99) | TDS Patch (N = 98) | Placebo Nasal Gel (N = 100) |
|---|---|---|---|
| Min, max | −4.68, 2.52 | −1.89, 0.90 | −2.61, 3.15 |
| LSM (SE) | −0.058 (0.035) | −0.103 (0.014) | −0.039 (0.043) |
| Treatment difference (95% CI) | −0.019 (−0.128, 0.091) | 0.046 (−0.030, 0.121) | |
| P-value | 0.7357 | 0.2329 | |

CI = confidence interval; ITT = Intent-to-Treat; LSM = least squares mean; max = maximum; min = minimum; MSAQ = Motion Sickness Assessment Questionnaire; SD = standard deviation; SE = standard error.
Note:
Analysis was based on mixed model of repeated measure (MMRM) including fixed effects of treatment, visit, and interaction term of treatment by visit.
Baseline value was included as a covariate in the model.
The total MSAQ score was derived from the sum of points from all items/144 × 100.
Source: Table 14.2.3.1, Table 14.2.3.2, Table 14.2.3.3

6.4.1.2.3. Nausea Assessment Scores (Visual Analogue Scale)

A secondary efficacy endpoint was the severity of nausea as assessed on a 0 to 100 mm VAS. In the ITT population, the differences between DPI-386 Nasal Gel and TDS patch in LSM nausea assessment VAS score changes from baseline at all time points were not statistically significant, and the differences between DPI-386 Nasal Gel and Placebo Nasal Gel in changes from baseline at all time points were also not statistically significant (Table 7j).

TABLE 7j

Analysis of Nausea Assessment Scores (Visual Analogue Scale [mm]) (ITT Population)

| Timepoint Statistic | DPI-386 Nasal Gel (N = 99) | TDS Patch (N = 98) | Placebo Nasal Gel (N = 100) |
|---|---|---|---|
| Baseline | | | |
| N | 99 | 98 | 100 |
| Mean (SD) | 1.97 (5.329) | 2.47 (7.369) | 1.73 (3.827) |
| Median | 0.00 | 0.00 | 0.00 |
| Min, max | 0.0, 43.0 | 0.0, 57.0 | 0.0, 24.0 |
| Day 1 4-hour Post dose | | | |
| N | 99 | 98 | 100 |
| Mean (SD) | 12.48 (22.443) | 16.97 (23.862) | 17.39 (25.255) |
| Median | 1.00 | 5.00 | 4.75 |
| Min, max | 0.0, 96.0 | 0.0, 100.0 | 0.0, 100.0 |
| Day 1 4-hour Post dose change from baseline | | | |
| N | 99 | 98 | 100 |
| Mean (SD) | 10.51 (23.125) | 14.50 (23.480) | 15.66 (25.305) |
| Median | 1.00 | 4.00 | 2.50 |
| Min, max | −38.0, 94.0 | −15.0, 100.0 | −10.0, 100.0 |
| LSM (SE) | 10.384 (2.255) | 14.869 (2.408) | 15.298 (2.525) |
| Treatment difference (95% CI) | −4.915 (−11.59, 1.763) | −4.485 (−10.99, 2.021) | |
| P-value | 0.1482 | 0.1755 | |
| Day 1 8-hour Post dose | | | |
| N | 99 | 98 | 100 |
| Mean (SD) | 8.06 (20.024) | 9.21 (17.532) | 7.10 (16.066) |
| Median | 0.00 | 1.00 | 0.00 |
| Min, max | 0.0, 95.0 | 0.0, 93.0 | 0.0, 83.0 |
| Day 1 8-hour Post dose change from baseline | | | |
| N | 99 | 98 | 100 |
| Mean (SD) | 6.09 (20.874) | 6.73 (18.556) | 5.37 (16.649) |
| Median | 0.00 | 0.00 | 0.00 |
| Min, max | −41.0, 93.0 | −46.0, 88.0 | −21.0, 82.0 |
| LSM (SE) | 5.965 (2.013) | 7.104 (1.770) | 5.005 (1.607) |
| Treatment difference (95% CI) | 0.959 (−4.121, 6.039) | −1.139 (−6.426, 4.147) | |
| P-value | 0.7100 | 0.6713 | |
| Day 2 4-hour Post dose | | | |
| N | 92 | 95 | 95 |
| Mean (SD) | 3.90 (11.749) | 5.24 (15.097) | 6.03 (13.640) |

TABLE 7j-continued

Analysis of Nausea Assessment Scores (Visual Analogue Scale [mm]) (ITT Population)

| Timepoint Statistic | DPI-386 Nasal Gel (N = 99) | TDS Patch (N = 98) | Placebo Nasal Gel (N = 100) |
|---|---|---|---|
| Median | 0.00 | 0.00 | 0.00 |
| Min, max | 0.0, 98.0 | 0.0, 98.0 | 0.0, 84.0 |
| Day 2 4-hour Post dose change from baseline | | | |
| N | 92 | 95 | 95 |
| Mean (SD) | 1.85 (13.119) | 2.79 (16.585) | 4.22 (13.964) |
| Median | 0.00 | 0.00 | 0.00 |
| Min, max | −43.0, 96.0 | −53.0, 92.0 | −22.0, 83.0 |
| LSM (SE) | 2.218 (1.256) | 3.123 (1.532) | 3.974 (1.401) |
| Treatment difference (95% CI) | −1.756 (−5.469, 1.957) | −0.905 (−4.813, 3.002) | |
| P-value | 0.3520 | 0.6481 | |
| Day 2 8-hour Post dose | | | |
| N | 92 | 95 | 95 |
| Mean (SD) | 1.93 (7.091) | 3.15 (9.514) | 4.26 (11.297) |
| Median | 0.00 | 0.00 | 0.00 |
| Min, max | 0.0, 59.0 | 0.0, 76.0 | 0.0, 69.0 |
| Day 2 8-hour Post dose change from baseline | | | |
| N | 92 | 95 | 95 |
| Mean (SD) | −0.12 (8.905) | 0.70 (12.206) | 2.45 (11.860) |
| Median | 0.00 | 0.00 | 0.00 |
| Min, max | −43.0, 57.0 | −55.0, 76.0 | −21.0, 69.0 |
| LSM (SE) | 0.051 (0.751) | 1.024 (0.975) | 2.259 (1.163) |
| Treatment difference (95% CI) | −2.208 (−4.942, 0.525) | −0.973 (−3.402, 1.455) | |
| P-value | 0.1126 | 0.4300 | |
| Day 3 4-hour Post dose | | | |
| N | 88 | 94 | 92 |
| Mean (SD) | 1.41 (3.861) | 2.93 (8.996) | 2.88 (8.555) |
| Median | 0.00 | 0.00 | 0.00 |
| Min, max | 0.0, 22.0 | 0.0, 68.0 | 0.0, 56.0 |
| Day 3 4-hour Post dose change from baseline | | | |
| N | 88 | 94 | 92 |
| Mean (SD) | −0.74 (6.380) | 0.46 (11.223) | 1.08 (8.808) |
| Median | 0.00 | 0.00 | 0.00 |
| Min, max | −43.0, 19.0 | −50.0, 68.0 | −14.0, 56.0 |
| LSM (SE) | −0.579 (0.412) | 0.780 (0.920) | 0.801 (0.871) |
| Treatment difference (95% CI) | −1.380 (−3.286, 0.525) | −1.360 (−3.353, 0.633) | |
| P-value | 0.1542 | 0.1795 | |
| Day 3 8-hour Post dose | | | |
| N | 88 | 93 | 93 |
| Mean (SD) | 0.91 (2.815) | 1.00 (2.255) | 2.15 (8.640) |
| Median | 0.00 | 0.00 | 0.00 |
| Min, max | 0.0, 21.0 | 0.0, 14.0 | 0.0, 62.0 |
| Day 3 8-hour Post dose change from baseline | | | |
| N | 88 | 93 | 93 |
| Mean (SD) | −1.24 (6.179) | −1.48 (7.761) | 0.37 (9.617) |
| Median | 0.00 | 0.00 | 0.00 |
| Min, max | −43.0, 19.0 | −56.0, 10.0 | −24.0, 62.0 |
| LSM (SE) | −1.065 (0.304) | −1.108 (0.233) | 0.115 (0.881) |
| Treatment difference (95% CI) | −1.181 (−3.026, 0.665) | 0.042 (−0.713, 0.798) | |
| P-value | 0.2077 | 0.9118 | |

CI = confidence interval; ITT = Intent-to-Treat; LSM = least squares mean; max = maximum; min = minimum; SD = standard deviation; SE = standard error.

Note:

Analysis was based on mixed model of repeated measure (MMRM) including fixed effects of treatment, visit, and interaction term of treatment by visit.

Baseline value was included as a covariate in the model.

Source: Table 14.2.4.1, Table 14.2.4.2, Table 14.2.4.3

6.4.2. Statistical/Analytical Issues 6.4.2.1. Adjustments for Covariates

Not applicable.

6.4.2.2. Handling of Dropouts or Missing Data

There were twenty-two (22) post-dose discontinuations/withdrawals during the conduct of the study.

Subject No. 102 discontinued from the study after dosing of Day 1 as she did not report on Day 2 or on Day 3. Subject No. 116 discontinued from the study after dosing of Day 1 as he did not return for Voyage remainder. Subject Nos. 167, 215, 224, 233, 249, 281, 283, 358, and 373 withdrew their consent after dosing of Day 1. Subject Nos. 205 and 246 were withdrawn from the study due to an AE after dosing of Day 1. Subject No. 290 was withdrawn from the study due to non-compliance after dosing of Day 1. Subject No. 395 discontinued from the study after dosing of Day 1 as he did not return on Day 2 and 3 due to family emergency.

Subject No. 115 withdrew from the remainder of the Voyage after dosing of Day 2. Subject No. 260 met an exclusion criterion that precluded further study participation after dosing of Day 2. Subject No. 264 withdrew his consent after dosing of Day 2. Subject Nos. 265 and 270 were withdrawn from the study due to non-compliance after dosing of Day 2. Subject No. 315 discontinued from the study after dosing of Day 2 as he did not return on Day 3. Subject No. 377 discontinued from the study after dosing of Day 2 as he did not return on Day 3 due to rain.

6.4.2.3. Interim Analysis and Data Monitoring

An interim analysis was not planned nor conducted. There was no plan to establish a data monitoring committee.

6.4.2.4. Multicenter Studies

This study was conducted at a single study site.

6.4.2.5. Multiple comparisons/Multiplicity

Not applicable.

6.4.2.6. Use of an "Efficacy Subset" of Subjects

The primary efficacy analysis is based on the ITT population. The PP population was used for additional analyses of efficacy endpoints and it excluded subjects with major protocol violations; one subject was excluded from the PP population.

6.4.2.7. Active-control Studies Intended to Show Equivalence

Not applicable.

6.4.2.8. Examination of Subgroups

Not applicable.

6.4.3. Tabulation of Individual Response Data

Individual listings of response data are provided in the appendices.

6.4.4. Drug dose, Drug Concentration and Relationships to Response Not applicable.

6.4.5. Drug-Drug and Drug-Disease Interactions

Not applicable.

6.4.6. By-Subject Displays

Not applicable.

6.4.7. Efficacy Conclusions

The analyses of the primary and secondary efficacy endpoints showed no statistically significant differences between the DPI-386 Nasal Gel arm and either of the control arms (TDS patch and Placebo Nasal Gel). The endpoints were the number (%) of subjects who developed motion sickness and requested further treatment (primary endpoint), time to use of rescue medication (secondary), MSAQ total score (secondary), and nausea assessment VAS scores (secondary).

7. Safety Evaluation 7.1 Extent of Exposure

Each subject received both a patch and nasal gel as per randomization to 1 of the following 3 arms: DPI-386 Nasal Gel+placebo patch [n=99], Placebo Nasal Gel+TDS patch [n=98], or Placebo Nasal Gel+placebo patch [n=100].

A summary of extent of exposure to study medication is provided. Compliance to study medication administration was >88% for both nasal gel and patch administration.

7.2. Adverse Events 7.2.1. Brief Summary of Adverse Events

The primary safety endpoint was the subject incidence of TEAEs while on study treatment.

An overall summary of TEAEs is provided in Table 7k.

A total of 558 TEAEs were reported by 212 (71.4%) subjects during the study (163 TEAEs in 57 subjects [57.6%] after administration of DPI-386 Nasal Gel, 191 TEAEs in 78 subjects [79.6%] after administration of TDS Patch, and 204 TEAEs in 77 subjects [77.0%] after administration of Placebo Nasal Gel).

The majority of TEAEs were mild (N=483) or moderate (N=71); 1 TEAE was severe. Mild TEAEs were reported in 54.5%, 77.6%, and 74.0% of subjects in the DPI-386 Nasal Gel arm, TDS patch arm, and the Placebo Nasal Gel arm, respectively. Moderate TEAEs were reported in 15.2%, 12.2%, and 17.0% of subjects in the DPI-386 Nasal Gel arm, TDS patch arm, and the Placebo Nasal Gel arm, respectively. The severe TEAE (diarrhea) occurred in a subject in the DPI-386 Nasal Gel arm.

The causality assessment was judged by the investigator as not related for 426 TEAEs and related for 132 TEAEs. Of the 426 unrelated TEAEs, 107 occurred in the DPI-386 Nasal Gel arm, 158 occurred in the TDS patch arm, and 161 occurred in the Placebo Nasal Gel arm. Of the 132 related TEAEs, 56 occurred in the DPI-386 Nasal Gel arm, 33 occurred in the TDS patch arm, and 43 occurred in the Placebo Nasal Gel arm.

TEAEs that were not related to treatment with study drug were reported in 50.5%, 74.5%, and 74.0% of subjects in the DPI-386 Nasal Gel arm, TDS patch arm, and the Placebo Nasal Gel arm, respectively. TEAEs that were related to treatment with study drug were reported in 28.3%, 23.5%, and 27.0% of subjects in the DPI-386 Nasal Gel arm, TDS patch arm, and the Placebo Nasal Gel arm, respectively.

No deaths occurred during the study. No subject discontinued treatment due to a TEAE.

Six SAEs were reported by 3 subjects during the study (dizziness×2 in the same subject, palpitations in 1 subject, and spinal fracture and amnesia×2 in 1 subject). Of the 6 SAEs, 4 were reported after administration of DPI-386 Nasal Gel and 2 (in the same subject) were reported after administration of TDS patch. Three SAEs were mild and the severity of 3 SAEs was not recorded. The causality assessment was judged as probably related for 1 SAE (dizziness), possibly related for 1 SAE (dizziness), possibly related for 1 SAE (palpitations), not related for 1 SAE (spinal fracture), and unable to determine for 2 SAEs (amnesia). Two subjects were followed until resolution of their SAEs; however, for Subject No. 373, his SAE of spinal fracture was ongoing and the outcome of other 2 SAEs of amnesia was not recorded.

Out of 558 TEAEs, 113 TEAEs were AESIs; 42 AESIs occurred in the DPI-386 Nasal Gel arm, 36 AESIs occurred in the TDS patch arm, and 35 AESIs occurred in the Placebo Nasal Gel arm. AESIs occurred in 31.3%, 29.6%, and 24.0% of subjects in the DPI-386 Nasal Gel arm, TDS patch arm, and the Placebo Nasal Gel arm, respectively.

Six SAEs were reported by 3 subjects during the study.

Of the 113 AESIs, 62 (blurred vision, dizziness, increased skin redness/flushing, photophobia, motion sickness, and palpitations) were "Significant, Non-serious" and 51 (dry mouth) were "Non-significant, Non-serious."

TABLE 7k

Summary of Treatment-Emergent Adverse Events (Safety Population)

| Parameter | DPI-386 Nasal Gel (N = 99) n (%) e | TDS Patch (N = 98) n (%) e | Placebo Nasal Gel (N = 100) n (%) e |
|---|---|---|---|
| All TEAEs (subjects with at least one TEAE) | 57 (57.6) 163 | 78 (79.6) 191 | 77 (77.0) 204 |
| Any Non-TEAEs (subjects with at least one non-TEAE) | 2 (2.0) 2 | 5 (5.1) 5 | 2 (2.0) 2 |
| Subjects with at least one TEAE leading to discontinuation from study drug | 0 | 0 | 0 |
| Relationship of TEAEs to IMP | | | |
| Not related | 50 (50.5) 107 | 73 (74.5) 158 | 74 (74.0) 161 |
| Related | 28 (28.3) 56 | 23 (23.5) 33 | 27 (27.0) 43 |
| Severity of TEAEs | | | |
| Mild | 54 (54.5) 137 | 76 (77.6) 172 | 74 (74.0) 174 |
| Moderate | 15 (15.2) 22 | 12 (12.2) 19 | 17 (17.0) 30 |
| Severe | 1 (1.0) 1 | 0 (0.0) 0 | 0 (0.0) 0 |
| Subjects with at least one SAE | 2 (2.0) 4 | 1 (1.0) 2 | 0 (0.0) 0 |
| Subjects with at least one AESI in TEAE | 31 (31.3) 42 | 29 (29.6) 36 | 24 (24.0) 35 |

AESI = adverse event of special interest;
e = number of events;
IMP = investigational medicinal product;
SAE = serious adverse event'
TEAE = treatment-emergent adverse event
Souce: Table 14.3.1.1

7.2.2. Display of Adverse Events

A summary of AEs by SOC and preferred term is provided in Table 71.

A total of 558 TEAEs were reported by 212 (71.4%) subjects during the study (163 TEAEs in 57 subjects [57.6%] after administration of DPI-386 Nasal Gel, 191 TEAEs in 78 subjects [79.6%] after administration of TDS Patch, and 204 TEAEs in 77 subjects [77.0%] after administration of Placebo Nasal Gel).

The most common TEAE was motion sickness (322 events in 170 subjects). Subjects in the DPI-386 Nasal Gel arm had the lowest incidence of motion sickness TEAEs (45.5% of subjects) and the lowest number of reported TEAEs (n=84). The incidence of motion sickness TEAEs in the TDS patch and Placebo Nasal Gel arms was 64.3% and 62.0%, respectively, and the number of reported motion sickness TEAEs in these 2 arms was 111 and 127, respectively.

The second most common TEAE was dry mouth (55 events in 43 subjects). Eighteen TEAEs of dry mouth were reported in 12 subjects (12.1%) in the DPI-386 Nasal Gel arm, 21 TEAEs of dry mouth were reported in 18 subjects (18.4%) in the TDS patch arm, and 16 TEAEs of dry mouth were reported in 13 subjects (13.0%) in the Placebo Nasal Gel arm.

The third most common TEAE was somnolence (36 events in 25 subjects). Fifteen TEAEs of somnolence were reported in 10 subjects (10.1%) in the DPI-386 Nasal Gel arm, 14 TEAEs of somnolence were reported in 10 subjects (10.2%) in the TDS patch arm, and 7 TEAEs of somnolence were reported in 5 subjects (5.0%) in the Placebo Nasal Gel arm.

Sixteen TEAEs of dizziness were reported in 14 subjects: 7 TEAEs in 7 subjects (7.1%) in the DPI-386 Nasal Gel arm, 5 TEAEs in 3 subjects (3.1%) in the TDS patch arm, and 4 TEAEs in 4 subjects (4.0%) in the Placebo Nasal Gel arm.

TABLE 7l

Summary of Adverse Events (Safety Population)

| System Organ Class Preferred Term | DPI-386 Nasal Gel (N = 99) n (%) e | TDS Patch (N = 98) n (%) e | Placebo Nasal Gel (N = 100) n (%) e |
|---|---|---|---|
| All TEAEs (subjects with at least one TEAE) | 57 (57.6) 163 | 78 (79.6) 191 | 77 (77.0) 204 |
| Cardiac disorders | 1 (1.0) 1 | 0 (0.0) 0 | 0 (0.0) 0 |
| Palpitations | 1 (1.0) 1 | 0 (0.0) 0 | 0 (0.0) 0 |
| Ear and labyrinth disorders | 45 (45.5) 84 | 63 (64.3) 111 | 62 (62.0) 127 |
| Motion sickness | 45 (45.5) 84 | 63 (64.3) 111 | 62 (62.0) 127 |
| Eye disorders | 2 (2.0) 2 | 3 (3.1) 3 | 4 (4.0) 5 |
| Eye irritation | 0 (0.0) 0 | 0 (0.0) 0 | 1 (1.0) 1 |
| Lacrimation increased | 0 (0.0) 0 | 0 (0.0) 0 | 1 (1.0) 1 |

TABLE 7l-continued

Summary of Adverse Events (Safety Population)

| System Organ Class<br>Preferred Term | DPI-386<br>Nasal Gel<br>(N = 99)<br>n (%) e | TDS Patch<br>(N = 98)<br>n (%) e | Placebo<br>Nasal Gel<br>(N = 100)<br>n (%) e |
|---|---|---|---|
| Photophobia | 2 (2.0) 2 | 3 (3.1) 3 | 3 (3.0) 3 |
| Gastrointestinal disorders | 15 (15.2) 22 | 21 (21.4) 26 | 20 (20.0) 26 |
| Abdominal distension | 0 (0.0) 0 | 0 (0.0) 0 | 1 (1.0) 1 |
| Constipation | 0 (0.0) 0 | 1 (1.0) 1 | 0 (0.0) 0 |
| Diarrhoea | 1 (1.0) 1 | 0 (0.0) 0 | 0 (0.0) 0 |
| Dry mouth | 12 (12.1) 18 | 18 (18.4) 21 | 13 (13.0) 16 |
| Dry throat | 0 (0.0) 0 | 0 (0.0) 0 | 1 (1.0) 1 |
| Dyspepsia | 0 (0.0) 0 | 0 (0.0) 0 | 1 (1.0) 1 |
| Lip swelling | 0 (0.0) 0 | 0 (0.0) 0 | 1 (1.0) 1 |
| Nausea | 3 (3.0) 3 | 2 (2.0) 3 | 6 (6.0) 6 |
| Vomiting | 0 (0.0) 0 | 1 (1.0) 1 | 0 (0.0) 0 |
| General disorders and administration site conditions | 5 (5.1) 7 | 6 (6.1) 14 | 8 (8.0) 12 |
| Fatigue | 1 (1.0) 2 | 5 (5.1) 10 | 7 (7.0) 10 |
| Hyperhidrosis | 0 (0.0) 0 | 1 (1.0) 1 | 0 (0.0) 0 |
| Hyperpyrexia | 2 (2.0) 2 | 0 (0.0) 0 | 2 (2.0) 2 |
| Irritability | 2 (2.0) 2 | 2 (2.0) 3 | 0 (0.0) 0 |
| Mucosal dryness | 1 (1.0) 1 | 0 (0.0) 0 | 0 (0.0) 0 |
| Injury, poisoning and procedural complications | 1 (1.0) 1 | 1 (1.0) 1 | 1 (1.0) 1 |
| Heat exhaustion | 0 (0.0) 0 | 0 (0.0) 0 | 1 (1.0) 1 |
| Skin abrasion | 0 (0.0) 0 | 1 (1.0) 1 | 0 (0.0) 0 |
| Spinal fracture | 1 (1.0) 1 | 0 (0.0) 0 | 0 (0.0) 0 |
| Musculoskeletal and connective tissue disorders | 0 (0.0) 0 | 0 (0.0) 0 | 1 (1.0) 1 |
| Joint injury | 0 (0.0) 0 | 0 (0.0) 0 | 1 (1.0) 1 |
| Nervous system disorders | 17 (17.2) 26 | 15 (15.3) 20 | 11 (11.0) 13 |
| Amnesia | 1 (1.0) 2 | 0 (0.0) 0 | 0 (0.0) 0 |
| Headache | 4 (4.0) 4 | 4 (4.1) 5 | 5 (5.0) 5 |
| Hypoaesthesia | 0 (0.0) 0 | 0 (0.0) 0 | 1 (1.0) 1 |
| Insomnia | 1 (1.0) 1 | 0 (0.0) 0 | 0 (0.0) 0 |
| Somnolence | 10 (10.1) 15 | 10 (10.2) 14 | 5 (5.0) 7 |
| Tremor | 1 (1.0) 1 | 0 (0.0) 0 | 0 (0.0) 0 |
| Vision blurred | 3 (3.0) 3 | 1 (1.0) 1 | 0 (0.0) 0 |
| Psychiatric disorders | 0 (0.0) 0 | 1 (1.0) 1 | 0 (0.0) 0 |
| Anxiety | 0 (0.0) 0 | 1 (1.0) 1 | 0 (0.0) 0 |
| Respiratory, thoracic and mediastinal disorders | 7 (7.1) 10 | 6 (6.1) 7 | 9 (9.0) 10 |
| Increased viscosity of upper respiratory secretion | 0 (0.0) 0 | 0 (0.0) 0 | 1 (1.0) 1 |
| Nasal congestion | 0 (0.0) 0 | 0 (0.0) 0 | 1 (1.0) 1 |
| Nasal discomfort | 5 (5.1) 6 | 3 (3.1) 3 | 5 (5.0) 5 |
| Nasal pruritus | 0 (0.0) 0 | 1 (1.0) 2 | 0 (0.0) 0 |
| Rhinorrhoea | 2 (2.0) 2 | 1 (1.0) 1 | 2 (2.0) 2 |
| Sneezing | 0 (0.0) 0 | 1 (1.0) 1 | 0 (0.0) 0 |
| Upper respiratory tract infection | 1 (1.0) 2 | 0 (0.0) 0 | 1 (1.0) 1 |
| Skin and subcutaneous tissue disorders | 3 (3.0) 3 | 2 (2.0) 2 | 3 (3.0) 3 |
| Flushing | 2 (2.0) 2 | 1 (1.0) 1 | 1 (1.0) 1 |
| Pruritus | 0 (0.0) 0 | 1 (1.0) 1 | 0 (0.0) 0 |
| Skin irritation | 0 (0.0) 0 | 0 (0.0) 0 | 1 (1.0) 1 |
| Sunburn | 1 (1.0) 1 | 0 (0.0) 0 | 1 (1.0) 1 |
| Vascular disorders | 7 (7.1) 7 | 3 (3.1) 5 | 4 (4.0) 4 |
| Dizziness | 7 (7.1) 7 | 3 (3.1) 5 | 4 (4.0) 4 |

N = Number of subjects in respective treatment population.

n = Number of subjects in respective categories.

e = Number of events.

Source: Table 14.3.1.2

TABLE 7m

Adverse Events of Special Interest (Safety Population)

| System Organ Class | Adverse Event (Preferred Term) | DPI-386 Nasal Gel (N = 99) n (%) e | TDS Patch (N = 98) n (%) e | Placebo Nasal Gel (N = 100) n (%) e |
|---|---|---|---|---|
| All TEAEs (Subjects with at least one TEAE) | | 31 (31.3) 42 | 29 (29.6) 36 | 24 (24.0) 35 |
| Cardiac disorders | Palpitations | 1 (1.0) 1 | 0 (0.0) 0 | 0 (0.0) 0 |
| Ear and labyrinth disorders | Motion sickness | 10 (10.1) 10 | 10 (10.0) 12 | 8 (8.2) 8 |
| Eye disorders | Photophobia | 2 (2.0) 2 | 3 (3.0) 3 | 3 (3.1) 3 |
| Gastrointestinal disorders | Dry mouth | 11 (11.1) 17 | 13 (13.0) 16 | 16 (16.3) 18 |
| Nervous system disorders | Vision blurred | 3 (3.0) 3 | 0 (0.0) 0 | 1 (1.0) 1 |
| Skin and subcutaneous tissue disorders | Flushing | 2 (2.0) 2 | 1 (1.0) 1 | 1 (1.0) 1 |
| Vascular disorders | Dizziness | 7 (7.1) 7 | 3 (3.0) 3 | 3 (3.1) 5 |

N = Number of subjects in respective treatment population.
n = Number of subjects in respective categories.
e = Number of events.
Source: Table 14.3.1.7

7.2.2. Analysis of Adverse Events

TEAEs are summarized by SOC and preferred term in Table 71.

TEAEs that occurred in >2 subjects in a treatment arm are summarized, by SOC and preferred term in Table 7n.

Motion sickness occurred less frequently in the DPI-386 Nasal Gel arm (45.5% of subjects) than in the TDS patch arm (64.3%) or the Placebo Nasal Gel arm (62.0%), likely due to a treatment effect of DPI-386 Nasal Gel (vs. Placebo Nasal Gel) and a more rapid onset of action than the TDS patch.

The incidence of dry mouth, a noted side effect of treatment with scopolamine, was similar in the DPI-386 Nasal Gel and Placebo Nasal Gel arms (12.1% and 13.0%, respectively) and lower than the incidence of dry mouth in the TDS patch arm (18.4%).

The incidence of somnolence, another noted side effect of treatment with scopolamine, was similar in the DPI-386 Nasal Gel and TDS patch arms (10.1% and 10.2%, respectively), and higher than the incidence of somnolence in the Placebo Nasal Gel arm (5.0%).

Dizziness occurred slightly more frequently in the DPI-386 Nasal Gel arm (7.1%) compared to the TDS patch arm (3.1%) and the Placebo Nasal Gel arm (4.0%).

All but one of the TEAEs that occurred in the study were mild or moderate in intensity. One TEAE was severe in intensity (diarrhea, DPI-386 Nasal Gel arm). A summary of moderate and severe TEAEs by SOC and preferred term is provided.

Compared to subjects in the TDS patch arm, slightly greater percentages of subjects in the DPI-386 Nasal Gel and Placebo Nasal Gel arms had TEAEs that were deemed to be related to treatment with study drug (23.5% in the TDS patch arm, 28.3% in the DPI-386 Nasal Gel arm, and 27.0% in the Placebo Nasal Gel arm). A summary of TEAEs that were related to the administration of study, by SOC and preferred term, is provided.

No deaths occurred during the study.

Two subjects (Subjects 205 and 246) discontinued the study due to an AE after dosing on Day 1; Subject 205 reported motion sickness (the event resolved) and Subject 246 reported palpitations (the event resolved). Subject 205 was in the TDS patch arm and Subject 246 was in the DPI-386 Nasal Gel arm.

TABLE 7n

Treatment-Emergent Adverse Events Occurring in >2 Subjects in a Treatment Arm, by System Organ Class and Preferred Term, Safety Population

| System Organ Class Preferred Term | DPI-386 Nasal Gel (N = 99) n (%) e | TDS Patch (N = 98) n (%) e | Placebo Nasal Gel (N = 100) n (%) e |
|---|---|---|---|
| Ear and labyrinth disorder | | | |
| Motion sickness | 45 (45.5) 84 | 63 (64.3) 111 | 62 (62.0) 127 |
| Eye disorders | | | |
| Photophobia | 2 (2.0) 2 | 3 (3.1) 3 | 3 (3.0) 3 |
| Gastrointestinal disorder | | | |
| Dry mouth | 12 (12.1) 18 | 18 (18.4) 21 | 13 (13.0) 16 |
| Nausea | 3 (3.0) 3 | 2 (2.0) 3 | 6 (6.0) 6 |
| General disorders and administration site conditions | | | |
| Fatigue | 1 (1.0) 2 | 5 (5.1) 10 | 7 (7.0) 10 |
| Nervous system disorders | | | |
| Headache | 4 (4.0) 4 | 4 (4.1) 5 | 5 (5.0) 5 |
| Somnolence | 10 (10.1) 15 | 10 (10.2) 14 | 5 (5.0) 7 |
| Vision blurred | 3 (3.0) 3 | 1 (1.0) 1 | 0 (0.0) 0 |
| Respiratory, thoracic and mediastinal disorders | | | |
| Nasal discomfort | 5 (5.1) 6 | 3 (3.1) 3 | 5 (5.0) 5 |
| Vascular disorders | | | |
| Dizziness | 7 (7.1) 7 | 3 (3.1) 5 | 4 (4.0) 4 |

N = Number of subjects in respective treatment population.
n = Number of subjects in respective categories.
e = Number of events.
Source: Adapted from Table 14.3.1.2

7.3. Deaths, Other Serious Adverse Events and Other Significant Adverse Events 7.3.1. Listing of Deaths, Other Serious Adverse Events and Other Significant Adverse Events 7.3.1.1. Deaths No deaths occurred during the study.

7.3.1.2. Other Serious Adverse Events

Six SAEs were reported by 3 subjects during the study:

Subject 133 (TDS patch arm) had 2 SAEs of dizziness (both mild, one probably related, one possibly related, both resolved). The events were SAEs because the investigator considered them to be an important medical events.

Subject 246 (DPI-386 Nasal Gel arm) had an SAE of palpitations (mild, possibly related, resolved). The event was an SAE because the investigator considered it to be an important medical event.

Subject 373 (DPI-386 Nasal Gel arm) had 3 SAEs: spinal fracture (intensity not reported, not related, ongoing), and 2 events of amnesia (intensity not reported, unable to determine causality, outcome not reported).

7.3.1.3. Other Significant Adverse Events

AEs of special interest are defined in Example 7, Section 4.5.1.4.2, as are the terms "Significant, Non-serious" and "Non-significant, Non-serious."

A total of 113 TEAEs were AEs of special interest, being expected anticholinergic effects of scopolamine. Of these, 62 (blurred vision, dizziness, increased skin redness/flushing, photophobia, motion sickness, and palpitations) were "Significant, Non-serious" and 51 (dry mouth) were "Non-significant, Non-serious."

A summary of AEs of special interest by SOC and preferred term is provided in Table 8q.

Two subjects (Subjects 205 and 246) discontinued the study after dosing on Day 1; Subject 205 reported motion sickness (the event resolved) and Subject 246 reported palpitations (the event resolved). Subject 205 was in the TDS patch arm and Subject 246 was in the DPI-386 Nasal Gel arm.

No other significant AEs were reported in the study.

7.3.2. Narratives of Deaths, Other Serious Adverse Events and Certain Other Significant Adverse Events No deaths or other significant AEs occurred during the study. Six SAEs in 3 subjects were reported during the study.

Detailed narratives of these events are provided in Section 14.3.1 (Narratives of deaths, other serious adverse events and certain other significant adverse events).

7.3.3. Analysis and Discussion of Deaths, Other Serious Adverse Events and Other Significant Adverse Events There were no deaths or significant AEs aside from the expected anticholinergic AESIs reported during the study. Two SAEs (both mild dizziness) were reported in a subject randomized to TDS patch; the Investigator considered one of the events as probably related to study drug and the other as probably related to study drug. One SAE of mild palpitations reported in a patient randomized to DPI-386 Nasal Gel was considered by the Investigator as possibly related to study drug. Each of the these SAEs, dizziness and palpitations, are known adverse events associated with scopolamine HBr.

7.4. Psychomotor Vigilance Test

The secondary safety endpoint was cognition as measured by the PVT. The PVT was administered twice a day, at 4 and 8 hours, for 3 consecutive days, resulting in 6 trials.

Twenty-one subjects were removed from the DPI-386 Nasal Gel group, 13 from the TDS patch group, and 16 from the Placebo Nasal Gel group. Removing response times below 150 ms is standard in all PVT data and only accounted for the removal of 1 subject. Two additional subjects were removed because their response times were consistently above 1000 ms. Thirteen removals were due to too many false starts, which is an anticipatory response (i.e., they responded before the task started). An additional 34 subjects were removed due to a combination of the 3 errors (<150 ms response times, >1000 ms response times, and false starts). Subjects who did not complete more than 3 trials were also removed—this accounted for 22 subjects. To fill in any gaps in the data (e.g., if a subject completed 4 trials but 5 and 6 were not completed), a type of bootstrapping was used where the overall average for that trial (all subjects) was substituted for the missing data. This left a complete dataset of 247 subjects.

To examine the possible effects of DPI-386 on reaction time on the PVT, Repeated Measures ANOVAs were performed. There was no effect of either the treatment (DPI-386 Nasal Gel, TDS patch, Placebo Nasal Gel) on reaction time. Also, response times did not vary based on age, sex, race, or motion sickness susceptibility.

7.5 Other Safety Endpoints 7.5.1. Karolinska Sleepiness Scale

Subjects were assessed at each visit and time point using the KSS. Descriptive statistics of the scores (n, mean, SD, median, minimum, maximum) at each time point and descriptive statistics of change from baseline values at each time point are presented by treatment arm in Table 14.3.5. In addition, between-group comparisons were performed at each time point and for the change from baseline using a logistic regression model that compares DPI-386 Nasal Gel to each control group and includes KSS as the response variable, a main effect for the treatment group, and the KSS score at screening as a covariate.

A higher score on the 10-point scale indicates a greater degree of sleepiness. For example, a score of 1 means 'extremely alert' and a score of 10 means 'extremely sleepy, can't keep awake.'

LS mean KSS scores at screening were similar among the treatment groups. At no time point either for raw scores or change from baseline scores were the differences between the DPI-386 Nasal Gel arm and either control arm statistically significant. At the Day 1 Hour 4 time point the difference between the DPI-386 Nasal Gel arm and the Placebo Nasal Gel arm approached statistical significance ($p=0.0554$), with the LS mean score being slightly higher in the Placebo Nasal Gel arm (4.1 vs. 3.5 in the DPI-386 Nasal Gel arm).

7.5.2. Anticholinergic Toxicity Screen

The most common ACTS AE reported by subjects in all treatment arms at screening and on Day 1, Day 2, and Day 3 was dry mouth (Table 70). Dizziness was the next most common ACTS AE at all time points in the DPI-386 Nasal Gel and TDS patch arms, and lightheadedness was the next most common ACTS AE in the Placebo Nasal Gel arm on Day 1 and Day 2. In the Placebo Nasal Gel arm on Day 3, dizziness and lightheadedness were reported by 13 subjects each (13.0%).

AEs that were reported on the ACTS and that were deemed related to treatment were considered to be AESIs. AESIs are summarized in Table 8q.

TABLE 7o

Summary of Anticholinergic Toxicity Screen (ACTS) Adverse Events (Safety Population)

| Visit | Adverse Event | DPI-386 Nasal (N = 99) n (%) | TDS Patch (N = 98) n (%) | Placebo Nasal Gel (N = 100) n (%) |
|---|---|---|---|---|
| Recuitment | Blurry vision | 3 (3.0) | 1 (1.0) | 0 (0.0) |
| and | Dizziness | 9 (9.1) | 5 (5.1) | 6 (6.0) |

TABLE 7o-continued

Summary of Anticholinergic Toxicity Screen (ACTS) Adverse Events (Safety Population)

| Visit | Adverse Event | DPI-386 Nasal (N = 99) n (%) | TDS Patch (N = 98) n (%) | Placebo Nasal Gel (N = 100) n (%) |
|---|---|---|---|---|
| screening | Dry mouth | 13 (13.1) | 16 (16.3) | 11 (11.0) |
| | Increased skin redness/ flushing | 1 (1.0) | 1 (1.0) | 1 (1.0) |
| | Light sensitivity | 1 (1.0) | 3 (3.1) | 3 (3.0) |
| | Light-headedness | 5 (5.1) | 3 (3.1) | 4 (4.0) |
| Treatment Day 1 | Blurry vision | 7 (7.1) | 6 (6.1) | 4 (4.0) |
| | Dizziness | 25 (25.3) | 13 (13.3) | 13 (13.0) |
| | Dry mouth | 47 (47.5) | 49 (50.0) | 37 (37.0) |
| | Increased skin redness/ flushing | 6 (6.1) | 2 (2.0) | 2 (2.0) |
| | Light sensitivity | 6 (6.1) | 8 (8.2) | 10 (10.0) |
| | Light-headedness | 11 (11.1) | 12 (12.2) | 18 (18.0) |
| | Palpitations | 4 (4.0) | 0 (0.0) | 0 (0.0) |
| Treatment Day 2 | Blurry vision | 4 (4.0) | 6 (6.1) | 2 (2.0) |
| | Dizziness | 24 (24.2) | 12 (12.2) | 11 (11.0) |
| | Dry mouth | 32 (32.3) | 41 (41.8) | 31 (31.0) |
| | Increased skin redness/ flushing | 2 (2.0) | 2 (2.0) | 2 (2.0) |
| | Light sensitivity | 6 (6.1) | 6 (6.1) | 7 (7.0) |
| | Light-headedness | 11 (11.1) | 6 (6.1) | 13 (13.0) |
| Treatment Day 3 | Blurry vision | 4 (4.0) | 6 (6.1) | 3 (3.0) |
| | Dizziness | 25 (25.3) | 10 (10.2) | 13 (13.0) |
| | Dry mouth | 33 (33.3) | 40 (40.8) | 28 (28.0) |
| | Increased skin redness/ flushing | 2 (2.0) | 2 (2.0) | 4 (4.0) |
| | Light sensitivity | 0 (0.0) | 8 (8.2) | 6 (6.0) |
| | Light-headedness | 9 (9.1) | 6 (6.1) | 13 (13.0) |
| Short-Term Follow-Up | Blurry vision | 2 (2.0) | 0 (0.0) | 0 (0.0) |
| | Dizziness | 9 (9.1) | 5 (5.1) | 7 (7.0) |
| | Dry mouth | 9 (9.1) | 18 (18.4) | 15 (15.0) |
| | Increased skin redness/ flushing | 3 (3.0) | 2 (2.0) | 1 (1.0) |
| | Light-headedness | 2 (2.0) | 3 (3.1) | 2 (2.0) |
| | Light sensitivity | 4 (4.0) | 3 (3.1) | 5 (5.0) |

Abbreviation:
ACTS = Anticholinergic Toxicity Screen
Source: Table 14.3.11

7.5.3. Performance Self-Assessment Questionnaire

Subjects completed the PSAQ at the post-treatment visit based on their experience over the 3 days of study treatment. Each of the 6 questions had 5 possible Likert-style responses, i.e., Strongly disagree, Disagree, Neither agree nor disagree, Agree, and Strongly agree. The number (%) of subjects who responded Agree or Strongly agree are provided below for the DPI-386 Nasal Gel, TDS patch, and Placebo Nasal Gel arms, respectively. Percentages are calculated based on the number of subjects who responded to each particular question.

The medication had no effect on my work performance: 41 (45.1%), 54 (57.4%), 51 (53.6%)

The medication had a positive effect on my work performance: 38 (41.8%), 42 (44.6%), 42 (44.2%)

The medication had a negative effect on my work performance: 10 (11.0%), 9 (9.6%), 10 (10.5%)

I experienced motion sickness: 29 (31.9%), 46 (48.9%), 49 (51.6%)

Motion sickness had no effect on my work performance: 38 (41.8%), 41 (43.6%), 42 (44.2%)

Motion sickness had a negative effect on my performance: 24 (26.4%), 25 (26.6%), 29 (30.5%)

The responses to the PSAQ, taken as a whole, were favorable in terms of the effect of study medication on work performance. Except for the statement "I experienced motion sickness," the percentages of subjects responding favorably were similar among the treatment arms. Fewer subjects in the DPI-386 Nasal Gel arm reported experiencing motion sickness than did subjects in the TDS patch and Placebo Nasal Gel arms.

7.6. Other Evaluations (Nasal Gel Device Ease-of-Use Questionnaire)

A summary of responses on the Nasal Gel EOUQ is provided. In general, the responses indicated that the nasal gel preparation was easy to use and administer.

7.7. Prior and Concomitant Medications

A summary of prior medications taken by subjects is provided. The number (%) of subjects who were taking medication prior to the study was 17 (17.2%), 9 (9.2%), and 18 (18.0%) in the DPI-386 Nasal Gel, TDS patch, and Placebo Nasal Gel treatment arms.

A summary of concomitant medications taken by subjects during the study is provided. The number (%) of subjects who took a non-study medication during the study was 4 (4.0%), 3 (3.1%), and 8 (8.0%) in the DPI-386 Nasal Gel, TDS patch, and Placebo Nasal Gel treatment arms.

7.8. Vital Signs, Physical Findings and Other Observations Related to Safety

Vital signs measurements and 12-lead ECG data were not collected in the study.

7.9. Clinical Laboratory Evaluation 7.9.1. Listing of Individual Laboratory Measurements by Subject and Each Abnormal Laboratory Value Laboratory measures were taken during screening. No laboratory measures were collected post-treatment.

7.9.2. Evaluation of Each Laboratory Parameter

Laboratory measures were taken during screening. No laboratory measures were collected post-treatment.

7.9.3. Laboratory Values Over Time

Not applicable.

7.9.4. Individual Subject Changes

Not applicable.

7.9.5. Individual Clinically Significant Abnormalities

None of the subjects had any clinically significant abnormalities during the study.

7.10. Safety Conclusions

A total of 558 TEAEs were reported by 212 (71.4%) subjects during the study. The incidence of subjects who had at least one TEAE was lower in the DPI-386 Nasal Gel arm (57.6%) compared to the TDS patch arm (79.6%) and the Placebo Nasal Gel arm (77.0%). All TEAEs except one were either mild or moderate in intensity. One TEAE of diarrhea was severe.

Motion sickness occurred less frequently in the DPI-386 Nasal Gel arm (45.5% of subjects) than in the TDS patch arm (64.3%) or the Placebo Nasal Gel arm (62.0%), likely due to a treatment effect of DPI-386 Nasal Gel (vs. Placebo Nasal Gel) and a more rapid onset of action than the TDS patch.

The incidence of dry mouth was similar in the DPI-386 Nasal Gel and Placebo Nasal Gel arms (12.1% and 13.0%, respectively) and lower than the incidence of dry mouth in the TDS patch arm (18.4%).

Dizziness occurred slightly more frequently in the DPI-386 Nasal Gel arm (7.1%) compared to the TDS patch arm (3.1%) and the Placebo Nasal Gel arm (4.0%).

No deaths or significant AEs aside from the expected anticholinergic AESIs occurred during the study.

Three subjects had 6 SAEs-3 were mild but were considered to be important medical events (2 events of dizziness in the same subject, and palpitations) and the intensity of the other 3 SAEs was not reported (spinal fracture and 2 events of amnesia in the same subject).

Two subjects withdrew from the study due to AEs (motion sickness [TDS patch arm] and palpitations [DPI-386 Nasal Gel arm]).

Two subjects discontinued the study after dosing on Day 1 (for TEAEs of motion sickness [TDS patch arm] and palpitations [DPI-386 Nasal Gel arm], respectively) Both events resolved.

Cognition, as measured by the PVT, was not impaired by the treatment that was administered in any of the treatment arms.

At no time point either for raw KSS scores or change from baseline scores were the differences between the DPI-386 Nasal Gel arm and either control arm statistically significant.

The most common ACTS AE reported by subjects in all treatment arms at screening and on Day 1, Day 2, and Day 3 was dry mouth. Dizziness was the next most common ACTS AE at all time points in the DPI-386 Nasal Gel and TDS patch arms, and lightheadedness was the next most common ACTS AE in the Placebo Nasal Gel arm on Day 1 and Day 2. In the Placebo Nasal Gel arm on Day 3, dizziness and motion sickness were reported by 13 subjects each (13.0%).

The responses to the PSAQ were favorable in terms of the effect of study medication on work performance. Except for the statement "I experienced motion sickness," the percentages of subjects responding favorably were similar among the treatment arms. Fewer subjects in the DPI-386 Nasal Gel arm reported experiencing motion sickness than did subjects in the TDS patch and Placebo Nasal Gel arms.

The responses reported on the Nasal Gel EOUQ indicated that the nasal gel preparation was easy to use and administer.

Both active study medications were generally well tolerated.

8. Discussion and Overall Conclusions 8.1. Discussion 8.1.1. Efficacy

This study failed to demonstrate any differences between DPI-386 Nasal Gel and the two control groups in the primary endpoint, which was the number (%) of subjects who developed motion sickness and requested further treatment with rescue medication, and in the secondary endpoints of time to use of rescue medication, MSAQ total score, and severity of nausea (VAS).

8.1.2. Safety

A total of 558 TEAEs were reported by 212 (71.4%) of the 297 subjects during the study.

The breakdown by treatment group is as follows:

163 TEAEs were reported by 57.6% (n=57) of 99 subjects who were administered DPI-386 Nasal Gel.

191 TEAEs were reported by 79.6% (n=78) of 98 subjects who were administered TDS patch.

204 TEAEs were reported by 77.0% (n=77) of 100 subjects who were administered Placebo Nasal Gel.

The causality assessment was judged by the investigator as not related for 426 TEAEs and related for 132 TEAEs. Compared to subjects in the TDS patch arm, slightly greater percentages of subjects in the DPI-386 Nasal Gel and Placebo Nasal Gel arms had TEAEs that were deemed to be related to treatment with study drug (23.5% in the TDS patch arm, 28.3% in the DPI-386 Nasal Gel arm, and 27.0% in the Placebo Nasal Gel arm).

The most common TEAE in all treatment arms was motion sickness, reported by 45.5%, 64.3%, and 62.0% of subjects in the DPI-386 Nasal Gel, TDS patch, and Placebo Nasal Gel arms, respectively.

Cognition was not impaired by the treatment administered in any of the treatment arms.

At no time point either for KSS raw scores or change from baseline scores were the differences between the DPI-386 Nasal Gel arm and either control arm statistically significant.

The most common ACTS AE reported by subjects in all treatment arms at screening and on Day 1, Day 2, and Day 3 was dry mouth. Dizziness was the next most common ACTS AE at all time points in the DPI-386 Nasal Gel and TDS patch arms, and motion sickness was the next most common ACTS AE in the Placebo Nasal Gel arm on Day 1 and Day 2. In the Placebo Nasal Gel arm on Day 3, dizziness and motion sickness were reported by 13 subjects each (13.0%).

The responses to the PSAQ were favorable in terms of the effect of study medication on work performance.

The responses reported on the Nasal Gel EOUQ indicated that the nasal gel preparation was easy to use and administer.

Upon conclusion of the clinical portion of the study, the results from all subjects, who completed post-study procedures, confirmed the absence of significant changes in the subjects' state of health.

8.2. Conclusions 8.2.1. Efficacy

The analyses of the primary and secondary efficacy endpoints showed no statistically significant differences between the DPI-386 Nasal Gel arm and either of the control arms (TDS patch and Placebo Nasal Gel). The endpoints were the number (%) of subjects who developed motion sickness and requested further treatment (primary endpoint), time to use of rescue medication (secondary), MSAQ total score (secondary), and nausea assessment VAS scores (secondary).

8.2.2. Safety

All study medications were well tolerated and no new safety signals for DPI-386 Nasal Gel were observed.

Example 8: Clinical Study MS-22-Safety and Efficacy of DPI-386 Nasal Gel

Clinical study MS-22 was a randomized, double-blind, placebo-controlled Phase 3 study of the safety and efficacy of DPI-386 nasal gel for the prevention of patient-reported motion sickness, using PT. The study consisted of a combination field and clinical site trial that was carried out on both an ocean-going vessel (Treatment Day 1) and at a clinical site (Treatment Days 2 and 3).

Title of Study: A randomized, double-blind, placebo-controlled Phase 3 study of the safety, efficacy, and pharmacokinetics of DPI-386 Nasal Gel for the prevention and treatment of nausea associated with motion sickness Study Site: This study was a combination field and clinical site trial that was carried out on both an ocean-going vessel (Treatment Day 1) and at a clinical site (Treatment Days 2 and 3).

Objectives:

Primary Objectives:

1. Determine the efficacy of DPI-386 Nasal Gel (0.2 mg scopolamine hydrobromide (HBr) per dose twice a day for one day) compared to the transdermal scopolamine (TDS) Patch and Placebo Nasal Gel in the prevention and treatment of nausea associated with motion sickness.

2. Determine the safety of DPI-386 Nasal Gel compared to the TDS patch and Placebo Nasal Gel with an emphasis on cognitive adverse events (AEs).

Secondary Objectives:

1. Determine the efficacy of DPI-386 Nasal Gel compared to the TDS patch and the Placebo Nasal Gel in severity of nausea.

2. Determine the efficacy of DPI-386 Nasal Gel compared to the TDS patch and the Placebo Nasal Gel in severity of motion sickness.

3. Determine the safety of DPI-386 Nasal Gel as compared to TDS patch and Placebo Nasal Gel in terms of cognition.

4. Describe the pharmacokinetic (PK) profile of a multi-dose schedule of DPI-386 Nasal Gel (0.2 mg twice a day for 3 consecutive days) as compared to the current standard of care (TDS).

Methodology:

This Phase 3 clinical trial was a randomized, double-blind, placebo-controlled study to identify the safety, efficacy, and PK of a repeated-dose regimen of DPI-386 Nasal Gel (intranasal scopolamine gel) for the prevention and treatment of nausea associated with motion sickness.

The study had 3 arms: DPI-386 Nasal Gel, Placebo Nasal Gel and TDS patch (1.5 mg/72 hours), the current standard of care for the treatment of motion sickness. The study included 34 subjects per arm, for a total of 102 subjects. A double-dummy design was used to mask the treatment assignment. All the subjects received both a patch and nasal gel randomized to one of the following 3 arms: DPI-386 Nasal Gel+placebo patch, Placebo Nasal Gel+placebo patch, or Placebo Nasal Gel+TDS patch.

Treatment Day 1 was conducted aboard an ocean-going vessel to obtain data in an operationally relevant real-world environment immediately followed by Treatment Days 2 and 3 at a clinical site.

On each Day 2 and 3, 12 blood samples, including one pre-dose blood sample, were collected from each subject except for the discontinued/withdrawn subjects to analyze the PK profile of DPI-386 Nasal Gel as compared to the current standard of care (TDS patch).

Statistical analysis was carried out using SAS® Version 9.4 (SAS Institute Inc., USA) to assess the efficacy and safety endpoints.

Number of Subjects (Planned and Analyzed):

Planned Enrollment:

As per the protocol, 102 subjects (34 in each of 3 treatment arms), between the ages of 18 and 59 (inclusive) were to be enrolled in the study. They were to be at least minimally susceptible to motion sickness, as determined by scoring at least 2 responses of 'Sometimes' or 'Frequently' on the Motion Sickness Susceptibility Questionnaire (MSSQ).

Actual Enrollment:

A total of 102 subjects (52 male and 50 female) were enrolled in the study.

Diagnosis and Main Criteria for Inclusion:

To be eligible to participate in this study, subjects must have met all of the following criteria:

1. Provision of a signed and dated informed consent form (ICF).

2. Stated willingness to comply with all study procedures and availability for the duration of the study.

3. Male or female, aged 18 to 59 (inclusive).

4. Minimally susceptible to provocative motion as evidenced by at least 2 responses on the MSSQ of "Sometimes" or "Frequently."

5. In good general health as evidenced by medical history with no recent history or current diagnosis of uncontrolled clinical problems as assessed by the Principal Investigator (PI) or qualified designee.

6. Ability to take intranasal medication and willingness to adhere to the study schedule and time constraints.

7. For females of child-bearing potential: willingness to provide a urine sample for the human chorionic gonadotropin (hCG) pregnancy test. The test must be negative within 7 days of Treatment Day 1.

Note: Women of non-childbearing potential are defined as those who are non-surgically sterile (i.e., without menses for at least 12 consecutive months) or surgically sterile (i.e., those who underwent a hysterectomy with or without oophorectomy, fallopian tube ligation, and endometrial ablation).

8. Agreement to adhere to the following lifestyle compliance considerations:

a. Refrain from consumption of grapefruit and any substance containing grapefruit for 7 days prior to, during, and for 7 days after the 3 treatment days.

b. Abstain from alcohol for 24 hours prior to first dose of study medication and during the 3 treatment days.

Note: there will be no restriction on caffeine or nicotine use during the study; however, the actual use of these substances will be recorded as part of the Confidential Exclusionary Behavior Questionnaire (CEBQ).

Investigational Medicinal Product:

DPI-386 Nasal Gel

- Active content: Scopolamine HBr
- Strength: Each 0.12 gram of the gel contains 0.2 mg of scopolamine HBr
- Dosage Regimen: 0.2 mg scopolamine HBr per dose (each 0.12 gram of the gel contains 0.2 mg of scopolamine HBr)—twice daily for 3 consecutive days
- Route of administration: Intranasal
- Storage: Store at 20° C. to 25° C., inclusive (68° F. to 77° F., inclusive), with brief temperature excursions permitted between 15° C. and 30° C., inclusive (59° F. and 86° F., inclusive).

Transderm Scop® [a Commercial TDS Patch]

- Strength: one patch of 1.5 mg reservoir of scopolamine can be delivered over a period of 72 hours
- Dosage Regimen: 1.5 mg reservoir of scopolamine delivered in a single day-One patch on Treatment Day 1 only
- Route of administration: applied behind the ear Placebo Nasal Gel Placebo Gel for DPI-386 Nasal Gel

- Storage: Store at 20° C. to 25° C., inclusive (68° F. to 77° F., inclusive), with brief temperature excursions permitted between 15° C. and 30° C., inclusive (59° F. and 86° F., inclusive).
- Route of administration: Intranasal Duration of Treatment:

For DPI-386 Nasal Gel (0.2 mg scopolamine HBr per dose) and Placebo Nasal Gel, 1 dose was delivered into one nostril twice daily over 3 consecutive treatment days (alternating nostrils). The 2 daily doses were separated by a minimum of 6 hours with no more than 2 doses, unless a third dose (rescue) was deemed necessary by the investigator (applicable for Treatment Day 1 only).

For the TDS patch and placebo patch, 1 patch was applied behind the ear on Treatment Day 1 only. The patch remained on until the end of Treatment Day 3, at which time it was removed by the research staff.

Criteria for Evaluation

Safety and Tolerability Evaluations:

Safety and tolerability assessments included demography, assessment of cognitive performance, assessment of alertness, assessment of anticholinergic toxicity symptoms, vital signs, electrocardiogram (ECG) recording, urine pregnancy test (for females of child-bearing potential), and recording of AEs and concomitant medications.

Study Endpoints

Primary Efficacy Endpoint:

The primary efficacy endpoint was the proportion of subjects who developed motion sickness and requested further treatment (i.e., subjects who received rescue medication).

The primary endpoint was evaluated for the following treatment comparisons and treatment intervals:

- A comparison of DPI-386 Nasal Gel to TDS patch within the first 4 hours on or after the first dose of study treatment on Treatment Day 1
- A comparison of DPI-386 Nasal Gel to TDS patch on or after the first dose of study treatment on Treatment Day 1
- A comparison of DPI-386 Nasal Gel to Placebo Nasal Gel within the first 4 hours on or after the first dose of study treatment on Treatment Day 1
- A comparison of DPI-386 Nasal Gel to Placebo Nasal Gel on or after the first dose of study treatment on Treatment Day 1

Secondary Efficacy Endpoints:

Nausea Assessment (Visual Analogue Scale)

A secondary efficacy endpoint was the severity of nausea as assessed on a visual analogue scale (VAS) over the treatment period. Subjects specified their degree of nausea by indicating a point along a continuous 10 cm line between 2 endpoints. The scale ranged from 0 (no nausea) to 10 (very severe nausea). Scoring was based on the length from the left edge of the scale to the point reported and a higher score indicated a more severe degree of nausea.

Mean VAS scores on Treatment Day 1 at Hour 4 and Hour 8 were assessed.

Motion Sickness Assessment Questionnaire Composite Score

A secondary efficacy endpoint was the severity of motion sickness as measured by the Motion Sickness Assessment Questionnaire (MSAQ). The MSAQ composite score was calculated as a percentage of total points scored from all 16 MSAQ symptoms: (sum of the points from all items/144)×100.

Mean MSAQ composite scores at Treatment Day 1 at Hour 4 and Hour 8 were assessed.

Other Efficacy Endpoint:

Another efficacy endpoint was time to first use of rescue medication during Treatment Day 1.

Primary Safety Endpoint:

The primary safety endpoint was the incidence of AEs.

Secondary Safety Endpoint:

A secondary endpoint was cognition as measured by the Automated Neuropsychological Assessment Metrics (ANAM).

Other Safety Endpoints:

- Symptoms of anticholinergic toxicity as recorded using the Anticholinergic Toxicity Screen (ACTS).
- Change from-60 minutes on Treatment Day 2 in vital sign and ECG measurements.
- Assessment of sleepiness using the Karolinska Sleepiness Scale (KSS).
- Assessment of performance of activities using the Performance Self-Assessment Questionnaire (PSAQ).

Pharmacokinetic Endpoints (Secondary Endpoint):

PK endpoints were maximum plasma concentration ($C_{max}$), time of maximum concentration ($t_{max}$), terminal half-life ($t_{1/2}$), and area under the curve (AUC).

Other Endpoint:

Another endpoint was the frequency of subject responses to the individual items of the Nasal Gel Device Ease-of-Use Questionnaire (EOUQ) at Post-Treatment Day 3.

Statistical Analysis:

Disposition of Subjects

Subject disposition was summarized for the safety, intent-to-treat (ITT), modified intent-to-treat (mITT), and per protocol (PP) populations by treatment group and over all subjects combined. The individual summaries included the number and percentage of subjects in each analysis population completing the study and discontinuing the study early by the primary reason for discontinuation.

Protocol Deviations

Major protocol violations were summarized by treatment group and over all subjects combined. Major protocol violations were protocol deviations captured on-study that were deemed by the Sponsor to potentially impact the efficacy or safety conclusions of the study.

Demographic and Other Baseline Characteristics

Demographic variables including age, sex, ethnicity, and race were summarized by treatment group and over all subjects combined for the ITT and PP populations.

Age was summarized using descriptive statistics. Sex, ethnicity, and race were summarized with the number and percentage of subjects.

Measurements of Treatment Compliance

Compliance with the study treatment regimen was summarized separately for the nasal gel application and patch application:

- Nasal Gel: The total number of doses administered as the full dose without dosing errors.
- Patch: The number of days the patch remained on the subject.

The number of nasal gel doses received were summarized with the number and percentage of subjects receiving 0, 1, 2, 3, 4, 5, or 6 complete doses without dosing errors by treatment group. The number of days with an administered patch were summarized with the number and percentage of subjects wearing the patch for 0, 1, 2, or 3 days during the treatment period by treatment group. Compliance with study treatment was summarized for the ITT population.

Extent of Exposure

Extent of exposure to study treatment was summarized for the Safety population by treatment group. The number of days with nasal gel administered and the number of days with a patch applied were summarized by counts and percentages of subjects in each category (i.e., 1, 2, or 3 days). The total nasal gel dose administered in grams was summarized with descriptive statistics. The total dose administered for each subject was derived as the number of full nasal gel doses given as reported on the Study Drug Dosing Log form×0.12 grams.

Primary Efficacy Endpoint Analysis Methods

The difference in proportions and p-value were from a logistic regression model based on the binomial distribution with an identity link function and compared DPI-386 Nasal Gel to each control group. The model included subject rescue medication use (yes/no) as the response variable, a main effect for the treatment group, and the raw MSSQ total score at screening as a covariate.

The analysis was performed on the ITT population.

Secondary Efficacy Endpoint Analysis Methods

Nausea Assessment (Visual Analogue Scale)

The least squares mean (LSM) VAS raw scores and change from baseline scores were analyzed at Treatment Day 1 Hour 4 and Hour 8. A regression model with change from baseline in VAS (mm) score and p-value were calculated from a logistic regression model that compared DPI-386 Nasal Gel to each control group and included VAS (mm) as the response variable, a main effect for the treatment group.

The analysis was performed on the ITT population.

Motion Sickness Assessment Questionnaire Composite Score

The LSM MSAQ composite raw scores and change from baseline scores were analyzed on Treatment Day 1 Hour 4 and Hour 8. A regression model with change from baseline in MSAQ for composite score and p-value were calculated from logistic regression model that compared DPI-386 Nasal Gel to each control group and included MSAQ as the response variable, a main effect for the treatment group, and the composite score at screening as a covariate.

The analysis was performed on the ITT population.

Other Efficacy Endpoint Analysis Methods

Time to First Use of Rescue Medication

Quartiles were derived from Kaplan-Meier product limit estimates. P-values were based on the log rank test for comparison between treatment groups.

Safety Analysis Methods

Safety analysis was carried out for the Safety population, which included all subjects who received at least one dose of study drug.

Adverse Events

Treatment-emergent adverse events (TEAEs) were defined as those AEs with onset after the first dose of study drug or existing events that worsened after the first dose during the study. TEAEs were summarized by treatment group.

Vital Signs

Vital sign parameter measurements were summarized by treatment group. Descriptive statistics were presented for observed measurements at each visit and timepoint, as well as the change in these measurements relative to the timepoint of-60 minutes on Treatment Day 2.

12-Lead Electrocardiogram

Twelve-Lead ECG interval parameters were summarized by treatment group. Descriptive statistics were presented for observed values at each visit and timepoint, as well as the change in these values relative to the timepoint of-60 minutes on Treatment Day 2.

Prolonged QTc intervals were summarized as QTc measurements (msec) that were >450 msec at each visit and timepoint where ECG was routinely collected per the clinical study protocol. Any other measured parameter that changed >30 msec relative to the value reported at −60 minutes on Treatment Day 2 was also reported by category. Summary results included the percentage of subjects within each category by treatment group.

Automated Neuropsychological Assessment Metrics (ANAM)

The ANAM subtest responses were summarized by treatment group. Descriptive statistics were presented for the observed values and changes from baseline to all post-baseline evaluations of cognition as measured by the throughput scores for each subtest.

Karolinska Sleepiness Scale

The KSS scores were summarized by treatment group. Descriptive statistics were presented for the observed values and changes from baseline to Treatment Day 1 Hour 4 and Hour 8.

A regression model with change from baseline in KSS for composite score and p-value were calculated from a logistic regression model that compared DPI-386 Nasal Gel to each control group and included KSS as the response variable, a main effect for the treatment group, and the composite score at screening as a covariate.

Anticholinergic Toxicity Screen

Subject incidence in reporting symptoms of anticholinergic toxicity using ACTS was presented by treatment group. The number and percentage of subjects who reported symptoms was summarized by symptom each visit and timepoint when the data was collected.

Performance Self-Assessment Questionnaire

The frequency of subject responses to the individual items of the PSAQ administered at Post-Treatment Day 3 was summarized by Treatment Group. The number and percentage of subjects who reported each of the possible responses for each item were summarized.

Nasal Gel Device Ease-of-Use Questionnaire

The frequency of subject responses to the individual items of the EOUQ administered at Post-Treatment Day 3 was summarized by Treatment Group. The number and percentage of subjects who reported each of the possible responses for each item were summarized.

Prior and Concomitant Medications

Prior and concomitant medications were summarized for each treatment.

Efficacy Results

Primary Efficacy Endpoint

In the ITT population, the difference between the DPI-386 Nasal Gel arm and the Placebo Nasal Gel arm in the proportion of subjects using rescue medication was statistically significant in favor of DPI-386 Nasal Gel at Hour 4 (p=0.0404) but was not statistically significant for all of Treatment Day 1 (p=0.0610). The difference between the DPI-386 Nasal Gel arm and the TDS patch arm was not statistically significant at either time point (Table 8a).

TABLE 8a

Analysis of Proportion of Subjects Using Rescue Medication (ITT Population)

| Parameter Statistic | DPI-386 Nasal Gel (N = 34) | TDS Patch (N = 34) | Placebo Nasal Gel (N = 34) |
|---|---|---|---|
| Subjects took rescue medication within 4 | | | |

TABLE 8a-continued

Analysis of Proportion of Subjects Using Rescue Medication (ITT Population)

| Parameter Statistic | DPI-386 Nasal Gel (N = 34) | TDS Patch (N = 34) | Placebo Nasal Gel (N = 34) |
|---|---|---|---|
| hours after first dose | | | |
| No | 33 (97.1) | 28 (82.4) | 27 (79.4) |
| Yes | 1 (2.9) | 6 (17.6) | 7 (20.6) |
| p-value[1] | | 0.0666 | 0.0404 |
| Difference in proportions (%) (95% CI) | | −2.05 (−4.2348; 0.1406) | −2.27 (−4.4492; −0.0992) |
| Subjects took rescue medication | | | |
| No | 31 (91.2) | 27 (79.4) | 25 (73.5) |
| Yes | 3 (8.8) | 7 (20.6) | 9 (26.5) |
| p-value[1] | | 0.1695 | 0.0610 |
| Difference in proportions (%) (95% CI) | | −1.02 (−2.4752; 0.4352) | −1.36 (−2.7826; 0.0627) |

CI = confidence interval; ITT = Intent-to-Treat; MSSQ = Motion Sickness Susceptibility Questionnaire.

[1]Difference in proportions and p-value are from a logistic regression model based on the binomial distribution with an identity link function and compares DPI-386 Nasal Gel to each control group. The model includes subject rescue medication use (yes/no) as the response variable, a main effect for the treatment group, and the raw MSSQ total score at screening as a covariate.

Source: Table 14.2.2.39

Secondary Efficacy Endpoints

In the ITT population, the differences between DPI-386 Nasal Gel and TDS patch in LSM nausea assessment VAS scores or LSM change from baseline scores at either time point were not statistically significant, and the differences between DPI-386 Nasal Gel and Placebo Nasal Gel at either time point were also not statistically significant.

In the ITT population, the differences between DPI-386 Nasal Gel and TDS patch in LS mean MSAQ composite scores change from baseline at either time point were not statistically significant, and the differences between DPI-386 Nasal Gel and Placebo Nasal Gel at either time point were also not statistically significant.

Other Efficacy Endpoint

In the ITT population, the difference between the DPI-386 Nasal Gel arm and each control arm in the time to first use of rescue medication was not statistically significant (p=0.0535 vs. Placebo Nasal Gel; p=0.1568 vs. TDS patch; log rank test) (Table 8b). The difference between the TDS patch arm and the Placebo Nasal Gel arm was not statistically significant (p=0.6629; log rank test).

TABLE 8b

Analysis of Time to First Use of Rescue Medication (ITT Population)

| Parameter | DPI-386 Nasal Gel (N = 34) | TDS Patch (N = 34) | Placebo Nasal Gel (N = 34) |
|---|---|---|---|
| Number (%) subjects censored | 31 (91.2) | 27 (26.5) | 25 (73.5) |
| Number (%) subjects who received rescue medication | 3 (8.8) | 7 (6.9) | 9 (26.5) |
| Quartiles (95% CI) | | | |
| $25^{th}$ percentile (95% CI) | NE | | 4.90 (3.08-.) |
| $50^{th}$ percentile (95% CI) | NE | NE | NE |

TABLE 8b-continued

Analysis of Time to First Use of Rescue Medication (ITT Population)

| Parameter | DPI-386 Nasal Gel (N = 34) | TDS Patch (N = 34) | Placebo Nasal Gel (N = 34) |
|---|---|---|---|
| $75^{th}$ percentile (95% CI) | NE | NE | NE |
| Log rank test p-value | 0.0535 | 0.6629 | 0.1568 |

CI = confidence interval; ITT = Intent-to-Treat; NE = not estimable.

Quartiles are derived from Kaplan-Meier product limit estimates. P-value is based on the Log-Rank Test for comparing between treatment groups.

P-value in DPI-386 Nasal Gel is for comparison between DPI-386 Nasal Gel and Placebo Nasal Gel.

P-value in TDS patch is for comparison between TDS patch and Placebo Nasal Gel.

P-value in Placebo Nasal Gel is for comparison between TDS patch and DPI-386 Nasal Gel.

Source: Table 14.2.2.37

Safety Results

A total of 150 TEAEs were reported by 79 (77.5%) of the 102 subjects during the study.

Of the 150 TEAEs, 50 AEs were reported by 34 subjects after administration of DPI-386 Nasal Gel, 57 AEs were reported by 29 subjects after administration of TDS patch, and 43 AEs were reported by 24 subjects after administration of Placebo Nasal Gel.

Of the 150 TEAEs, 123 AEs were mild, and 27 AEs were moderate. All of the subjects were followed up until resolution of their AEs except Subject Nos. 1023 and 1094. The outcome of 2 AEs of these subjects were unknown.

Motion sickness was the most frequently reported TEAE (81 events in 64 subjects). Subjects in the DPI-386 Nasal Gel arm had the lowest incidence of motion sickness TEAEs (52.9% of subjects) and the lowest number of reported motion sickness TEAEs (n=21). The incidence of motion sickness TEAEs in the TDS patch and Placebo Nasal Gel arms was 73.5% and 67.6%, respectively, and the number of reported motion sickness TEAEs was 30 in each arm.

The causality assessment was judged as not related for 100 TEAEs and as related for 50 TEAEs.

There were no deaths or SAEs.

Thirty-two TEAEs were reported as AESIs. Of these, 18 TEAEs (viz. asymptomatic hypotension, blurry vision, dizziness, increased skin redness/flushing and light sensitivity) were "Significant, Non-serious" and 14 TEAEs (dry mouth) were "Non-significant, Non-serious." The AEs are summarized by System Organ Class (SOC) and preferred term in Table 8c.

TABLE 8c

Display of Adverse Events (Safety Population)

| System Organ Class Preferred Term | DPI-386 Nasal Gel (N = 34) n (%) e | TDS patch (N = 34) n (%) e | Placebo Nasal Gel (N = 34) n (%) e |
|---|---|---|---|
| All TEAEs (Subjects with at least one TEAE) | 26 (76.5) 50 | 29 (85.3) 57 | 24 (70.6) 43 |
| Ear and labyrinth disorder | 18 (52.9) 21 | 25 (73.5) 30 | 23 (67.6) 30 |
| Motion sickness | 18 (52.9) 21 | 25 (73.5) 30 | 23 (67.6) 30 |
| Eye disorders | 2 (5.9) 2 | 2 (5.9) 2 | 1 (2.9) 1 |
| Photophobia | 2 (5.9) 2 | 2 (5.9) 2 | 1 (2.9) 1 |
| Gastrointestinal disorder | 8 (23.5) 8 | 6 (17.6) 7 | 5 (14.7) 5 |
| Diarrhoea | 0 (0.0) 0 | 0 (0.0) 0 | 1 (2.9) 1 |
| Dry mouth | 6 (17.6) 6 | 6 (17.6) 6 | 3 (8.8) 3 |
| Dyspepsia | 1 (2.9) 1 | 0 (0.0) 0 | 0 (0.0) 0 |
| Somnolence | 0 (0.0) 0 | 1 (2.9) 1 | 0 (0.0) 0 |
| Vomiting | 1 (2.9) 1 | 0 (0.0) 0 | 1 (2.9) 1 |
| General disorders and administration site conditions | 2 (5.9) 2 | 2 (5.9) 2 | 3 (8.8) 3 |
| Dysgeusia | 0 (0.0) 0 | 0 (0.0) 0 | 1 (2.9) 1 |
| Energy increased | 0 (0.0) 0 | 1 (2.9) 1 | 0 (0.0) 0 |
| Fatigue | 1 (2.9) 1 | 1 (2.9) 1 | 2 (5.9) 2 |
| Hyperhidrosis | 1 (2.9) 1 | 0 (0.0) 0 | 0 (0.0) 0 |
| Injury, poisoning and procedural complications | 1 (2.9) 1 | 0 (0.0) 0 | 0 (0.0) 0 |
| Heat exhaustion | 1 (2.9) 1 | 0 (0.0) 0 | 0 (0.0) 0 |
| Metabolism and nutrition disorders | 0 (0.0) 0 | 1 (2.9) 1 | 0 (0.0) 0 |
| Decreased appetite | 0 (0.0) 0 | 1 (2.9) 1 | 0 (0.0) 0 |
| Musculoskeletal and connective tissue disorders | 0 (0.0) 0 | 1 (2.9) 1 | 0 (0.0) 0 |
| Myalgia | 0 (0.0) 0 | 1 (2.9) 1 | 0 (0.0) 0 |
| Nervous system disorders | 5 (14.7) 5 | 6 (17.6) 7 | 1 (2.9) 1 |
| Headache | 1 (2.9) 1 | 1 (2.9) 1 | 0 (0.0) 0 |
| Hypoaesthesia | 1 (2.9) 1 | 0 (0.0) 0 | 0 (0.0) 0 |
| Somnolence | 2 (5.9) 2 | 1 (2.9) 1 | 0 (0.0) 0 |
| Vision blurred | 1 (2.9) 1 | 5 (14.7) 5 | 1 (2.9) 1 |
| Psychiatric disorders | 0 (0.0) 0 | 0 (0.0) 0 | 1 (2.9) 1 |
| Nightmare | 0 (0.0) 0 | 0 (0.0) 0 | 1 (2.9) 1 |
| Respiratory, thoracic and mediastinal disorders | 2 (5.9) 2 | 2 (5.9) 2 | 2 (5.9) 2 |
| Nasal discomfort | 1 (2.9) 1 | 1 (2.9) 1 | 1 (2.9) 1 |
| Nasal dryness | 0 (0.0) 0 | 1 (2.9) 1 | 1 (2.9) 1 |
| Throat irritation | 1 (2.9) 1 | 0 (0.0) 0 | 0 (0.0) 0 |
| Skin and subcutaneous tissue disorders | 5 (14.7) 5 | 1 (2.9) 1 | 0 (0.0) 0 |
| Flushing | 1 (2.9) 1 | 0 (0.0) 0 | 0 (0.0) 0 |
| Paraesthesia | 1 (2.9) 1 | 1 (2.9) 1 | 0 (0.0) 0 |
| Pruritus | 1 (2.9) 1 | 0 (0.0) 0 | 0 (0.0) 0 |
| Skin irritation | 2 (5.9) 2 | 0 (0.0) 0 | 0 (0.0) 0 |
| Vascular disorders | 4 (11.8) 4 | 4 (11.8) 4 | 0 (0.0) 0 |
| Dizziness | 2 (5.9) 2 | 2 (5.9) 2 | 0 (0.0) 0 |
| Epistaxis | 0 (0.0) 0 | 1 (2.9) 1 | 0 (0.0) 0 |
| Hypertension | 1 (2.9) 1 | 1 (2.9) 1 | 0 (0.0) 0 |
| Hypotension | 1 (2.9) 1 | 0 (0.0) 0 | 0 (0.0) 0 |

TDS = transdermal scopolamine; TEAE = treatment-emergent adverse event.
N = Number of subjects in respective treatment population.
n = Number of subjects in respective categories.
e = Number of events.
Source: Table 14.3.1.2

Efficacy Conclusions:

Subjects in the DPI-386 Nasal Gel arm had a statistically significantly lower incidence of rescue medication use than did subjects in the Placebo Nasal Gel arm at Treatment Day 1 Hour 4. There was no difference in severity of nausea as assessed by VAS or in MSAQ composite scores between the DPI-386 Nasal Gel arm and either control arm. There was no difference in time to use of rescue medication between the DPI-386 Nasal Gel arm and either control arm.

PK and PK/PD Conclusions:

As expected due to the differences in the formulations of the two products, the scopolamine AUC was lower for DPI-386 Nasal Gel compared with TDS patch because scopolamine concentrations decreased rapidly for DPI-386 Nasal Gel.

The PK of DPI-386 Nasal Gel were similar between men and women.

There was no apparent relationship between any PK parameter and the occurrence of ACTS events.

Running Memory Continuous Performance Throughput was the only ANAM test for which there appeared to be a relationship with scopolamine $C_{max}$, $AUC_{0-t}$, and $AUC_{0-6}$; higher scopolamine exposure was associated with lower performance.

Safety Conclusion:

All study medications were well tolerated and no new safety signals for DPI-386 Nasal Gel were observed.

No differences in changes in cognition were observed between treatment arms. Subjects in all treatment arms showed a slight increase in sleepiness on Day 1, the only day on which sleepiness was measured. There was no difference between treatment arms on the effects of study medication on performance. The nasal gel device was easy to use and administer.

2. Introduction

DPI-386 Nasal Gel is an intranasal formulation of the approved drug scopolamine hydrobromide (HBr), a naturally occurring belladonna alkaloid anticholinergic/antimuscarinic agent with antiemetic, antiparkinsonian and mydriatic effects. Scopolamine acts as a competitive inhibitor at postganglionic muscarinic receptor sites of the parasympathetic nervous system and smooth muscles that respond to acetylcholine but lack cholinergic innervation. Scopolamine generally exhibits the pharmacological actions associated with other antimuscarinics: it is more potent than atropine in its antimuscarinic action on the iris, ciliary body, and certain secretory (salivary, bronchial, sweat) glands, and less potent than atropine in its antimuscarinic action on the heart and on bronchial and intestinal smooth muscle.

Although the exact mechanism of action of scopolamine in the treatment of motion sickness is not fully understood, it has been suggested that scopolamine acts in the central nervous system by correcting a central imbalance between acetylcholine and norepinephrine by blocking cholinergic transmission from the vestibular nuclei to higher centers in the central nervous system and from the reticular formation to the vomiting center.

Scopolamine is absorbed from all mucous membranes as well as from subcutaneous and muscle tissue. At therapeutic dose levels, scopolamine can inhibit the secretion of saliva and sweat, decrease gastrointestinal secretions and motility, cause drowsiness, dilate the pupils, increase heart rate, and depress motor function. An overdose of scopolamine can cause disorientation, memory disturbances, dizziness, restlessness, hallucinations, confusion, or in cases of severe overdose, coma.

Scopolamine was initially available commercially in its hydrobromide form as an oral or parenteral (intramuscular and intravenous) drug. It is currently only available in the TDS patch form in the United States (US). The TDS patch is marketed for the prevention of nausea and vomiting associated with motion sickness, though it is also used in clinical management of post-operative nausea and vomiting.

2.1 Rationale and Aims

By comparison, a low-dose, rapidly acting nasal gel formulation of scopolamine could provide for the prevention and treatment of nausea associated with motion sickness, with a clinically meaningful reduced adverse events profile. Research into an intranasal formulation of scopolamine first occurred in a series of 1950s military studies, when a scopolamine nasal spray proved effective in reducing motion sickness but was abandoned due to the limitations of medication delivery devices at the time and an inability to deliver a properly metered dose (Chinn, Hyde, and Milch, 1955; Simmons, et al., 2010). However, modern intranasal drug formulations and medication delivery devices are vastly improved, making reliable, metered dosing possible.

This Phase 3 clinical trial was a randomized, double-blind, placebo-controlled study to identify the safety, efficacy, and pharmacokinetics of a repeated-dose regimen of DPI-386 Nasal Gel (intranasal scopolamine gel) for the prevention and treatment of nausea associated with motion sickness.

2.2. Target Population and Duration of the Study

As per the protocol, 102 subjects (34 in each of 3 treatment arms), between the ages of 18 and 59 (inclusive) were to be enrolled in the study. They were to be at least minimally susceptible to motion sickness, as determined by scoring at least two responses of ‘sometimes’ or ‘Frequently’ on the Motion Sickness Susceptibility Questionnaire (MSSQ).

For this study, a total of 102 subjects (52 male and 50 female) were enrolled in the study.

The actual duration of the clinical part of the study was 9 days [3 Jun. 2019 (First Subject First Visit-FSFV) to 11 Jun. 2019 (Last Subject Last Visit-LSLV)].

3. Study Objectives 3.1. Primary Objectives

Determine the efficacy of DPI-386 Nasal Gel (0.2 mg scopolamine HBr per dose twice a day for one day) compared to the TDS patch and Placebo Nasal Gel in the prevention and treatment of nausea associated with motion sickness.

Determine the safety of DPI-386 Nasal Gel compared to the TDS patch and Placebo Nasal Gel with an emphasis on cognitive adverse events (AEs).

3.2. Secondary Objectives

1 Determine the efficacy of DPI-386 Nasal Gel compared to the TDS patch and the Placebo Nasal Gel in severity of nausea.

2. Determine the efficacy of DPI-386 Nasal Gel compared to the TDS patch and the Placebo Nasal Gel in severity of motion sickness.

3. Determine the safety of DPI-386 Nasal Gel as compared to TDS patch and Placebo Nasal Gel in terms of cognition.

4. Describe the pharmacokinetic (PK) profile of a multi-dose schedule of DPI-386 Nasal Gel (0.2 mg twice a day for 3 consecutive days) as compared to the current standard of care (TDS).

4. Investigational Plan 4.1. Overall Study Design and Plan-Description

This Phase 3 clinical trial was a randomized, double-blind, placebo-controlled study to identify the safety, efficacy, and PK of a repeated-dose regimen of DPI-386 Nasal Gel (intranasal scopolamine gel) for the prevention and treatment of nausea associated with motion sickness.

The study had 3 arms: DPI-386 Nasal Gel, Placebo Nasal Gel, and TDS patch (1.5 mg/72 hours), the current standard of care for the treatment of motion sickness. The study included 34 subjects per arm, for a total of 102 subjects (n=102). A double-dummy design was used to mask the treatment assignment. All the subjects received both a patch and nasal gel randomized to one of the following three arms: DPI-386 Nasal Gel+placebo patch, Placebo Nasal Gel+placebo patch, or Placebo Nasal Gel+TDS patch.

Treatment Day 1 was conducted aboard an ocean-going vessel to obtain data in an operationally relevant real-world environment and was immediately followed by Treatment Days 2 and 3 at a clinical site.

There were 5 study periods during the study with acceptable windows: Recruitment and Screening; Treatment; Post-treatment Assessment; Short-term Follow-up; and Long-term Follow-up.

The Recruitment and Screening Period consisted of one visit during which research staff obtained informed consent, obtained self-reported medical history, and determined subject eligibility. If eligible, subjects were provided sufficient training to establish a baseline for Automated Neuropsychological Assessment Metrics (ANAM) cognitive tests. Subjects were also provided with training on study drug dosing and visit procedures.

The Treatment Period (Treatment Days 1 to 3) consisted of 3 visits in consecutive days of approximately 10-12 hours duration each day. Each Treatment Day visit included twice daily study drug dosing of nasal gel, patch application (Treatment Days 1 only), and cognitive testing and questionnaires (at specified time points described in below table of schedule of activities). Treatment Day 1 was carried out on an ocean-going vessel. Treatment Days 2-3 were carried out in a clinical study site.

The Post-Treatment Period (Treatment Day 3) consisted of one visit, at the end of the 8-hour controlled period on Treatment Day 3 to include safety questionnaires, performance self-assessment, ease-of-use questionnaire and debriefing and explanation of follow-up procedures.

The Short-term Follow-up Period (Day 10) consisted of research staff contacting the subject via phone or email at 1 week Post-Treatment Period to ask if they had experienced any new signs or symptoms, and to perform an anticholinergic toxicity screen (ACTS). The acceptable window was +3 days.

The Long-term Follow-up Period (Days 11 to 45, 2 weeks to 6 weeks post-Treatment Period) consisted of subjects having a standing obligation to contact research staff via telephone or e-mail at any time during this period and to report if they experienced any new signs or symptoms. There was no acceptable window requirement. Long-term Follow-up ended at the close of Day 45 (6 weeks).

The schedule of events is presented in Table 8d.

TABLE 8d

Schedule of Activities

| | Period | | | | | | |
|---|---|---|---|---|---|---|---|
| | Recruitment and Screening[1] | Treatment (Three Days Duration) | | | Post-treatment | Short-term Follow-up[2] | Long-term Follow-up[3] |
| | Visit | | | | | | |
| | 1 | 2 Boat | 3 Clinic | 4 Clinic | 5 | — | — |
| | Study Day | | | | | | |
| | Within 30 Days Prior to Day 1 | 1 | 2 | 3 | 3 | 10-13 | 11-45 |
| Informed consent form | X | | | | | | |
| Demographics[4] | X | | | | | | |
| MSSQ | X | | | | | | |
| CMQ | X | | | | | | |
| CEBQ[5] | X | X | X | X | | | |
| Inclusion/exclusion | X | | | | | | |
| Subject handout | X | X[6] | | X[6] | | | |
| Randomization | | X | | | | | |
| Pregnancy test[7] | X | | | | | | |
| Study drug dosing: TDS patch or Placebo patch[8] | | X[9] | X | X | | | |
| Study drug dosing: DPI-386 nasal gel or Placebo Nasal Gel[8] | | X[10] | X[11] | X[11] | | | |
| DPI-386 nasal gel rescue | | X[12] | | | | | |
| Vital signs[13] | | | X | X | | | |
| ECG14 | | | X | X | | | |
| ANAM CORE + CPT[15] | X | X | X | X | | | |
| ANAM CORE + CPT-CDD[16] | | X | X | X | | | |
| KSS[17] | X | X | | | | | |
| ACTS[17] | X | X | X | X | | X[2] | |
| MSAQ[17] | X | X | | | | | |
| VAS[17] | X | X | | | | | |
| PK blood draw | | | X[18] | X[18] | | | |
| Adverse events[19] | | X | X | X | X | X | X |
| IFU training | X | X | X | X | | | |
| Return of study materials[20] | | | | | X | | |
| Concomitant medication/ treatments[21] | | X | X | X | X | X | X |
| PSAQ[22] | | | | | X | | |
| Nasal gel device Ease-of-Use Questionnaire | | | | | X | | |
| Debriefing[23] | | | | | X | | |
| Record weather and sea state conditions[24] | | X | | | | | |

Abbreviations:

ACTS = Anticholinergic Toxicity Screen;

AE = adverse event;

ANAM = Automated Neuropsychological Assessment Metrics;

CDD = Code Substitution - Delayed;

CEBQ = Confidential Exclusionary Behavior Questionnaire;

CMQ = Confidential Medical Questionnaire;

CPT = Continuous Performance Test;

ECG = electrocardiogram;

IFU = Instructions for Use;

KSS = Karolinska Sleepiness Scale;

MSAQ = Motion Sickness Assessment Questionnaire;

MSSQ = Motion Sickness Susceptibility Questionnaire;

PK = pharmacokinetic;

PSAQ = Performance Self-Assessment Questionnaire;

TDS = transdermal scopolamine;

VAS = visual analogue scale.

[1]Screening occurred within 30 days prior to ship departure.

[2]The Short-term Follow-up Period (Day 10) consisted of research staff contacting the subject via phone or email at one week post-treatment period to ask if subjects had experienced any new signs or symptoms (including ACTS). The acceptable window was +3 days.

[3]Long-term Follow-up (Days 11 to 45, two weeks to six weeks post-treatment period) consisted of subjects having a standing obligation to contact research staff via phone or email at any time during this period to report any new signs or symptoms. There was no acceptable window requirement. Long-term Follow-up ended at the close of Day 45 (6 weeks). However, all AEs were followed until resolution.

[4]Date of birth, race, ethnicity, and gender.

[5]Subjects completed the CEBQ to confirm compliance with lifestyle compliance points listed under the inclusion criterion (i.e., no use of grapefruit and no use of alcohol) prior to dosing at the beginning of each visit.

[6]Re-explained the lifestyle adherence requirements (i.e., grapefruit, alcohol, etc.) of the treatment days listed in the IFU and Subject Handout.

[7]For females of child-bearing potential, a urine pregnancy test was performed and it was required to be negative within seven days of Treatment Day 1.

TABLE 8d-continued

Schedule of Activities

| Period | | | | | | |
|---|---|---|---|---|---|---|
| Recruitment and Screening[1] | Treatment (Three Days Duration) | | | Post-treatment | Short-term Follow-up[2] | Long-term Follow-up[3] |
| Visit | | | | | | |
| 1 | 2 Boat | 3 Clinic | 4 Clinic | 5 | — | — |
| Study Day | | | | | | |
| Within 30 Days Prior to Day 1 | 1 | 2 | 3 | 3 | 10-13 | 11-45 |

[8]For every administration of study drug, details were recorded in the Study Drug Accountability Log. With sufficient time prior to the investigator's notification of initial study drug dosing, the research staff trained all subjects on the proper administration and technique for priming the delivery device (using "DPI-386 Nasal Gel/Placebo Nasal Gel - INSTRUCTIONS FOR USE") and monitored the priming of the devices prior to the first dose. For all nasal gel administration, subjects self-administered 2 doses under supervision by research staff. No more than 2 doses of nasal gel were administered, with a minimum of 6 hours ± 15 minutes between doses, unless a third dose (rescue) was deemed necessary by the investigator (applicable for Treatment Day 1 only). Each nasal gel administration occurred in the presence of and was recorded by research staff. For all patch administration, an independent (unblinded) applicator applied the patches and bandage covers and confirmed that the patch administered on Treatment Day 1 remained appropriately applied on all Treatment Days.

[9]Subjects were randomized to receive a TDS patch or a placebo patch prior to getting on the ocean-going vessel.

[10]On Treatment Day 1, the investigator notified all the study subjects and independent (unblinded) applicators when to administer the first study drug doses (nasal gel and patch). This was the start of the controlled 8-hour period. A second treatment of nasal gel was self-administered 6 hours (±15 minutes) after the 1$^{st}$ dose administration time. The administration was supervised by the research staff.

[11]For Treatment Days 2 and 3, only DPI-386 Nasal Gel or placebo gel was administered twice per day with a minimum of 6 hours (±15 minutes) between doses.

[12]A rescue dose was only administered to subjects who requested further treatment for motion sickness.

[13]Vitals were taken at the clinical site as per the schedule: at pre-dose (within 60 minutes before dosing) and at 30, 60, 120, 180, 330, 390, 420, 480, and 600 minutes after 1$^{st}$ dosing.

[14]A resting ECG was recorded at the clinical site as per the schedule: at pre-dose (within 60 minutes before dosing) and at 120 minutes after 1$^{st}$ dosing.

[15]ANAM CORE + CPT was performed during screening, at 8 hours on Treatment Day 1 and at 420 minutes on Treatment Days 2-3.

[16]ANAM CORE + CPT-CDD was performed at 4 hours on Treatment Day 1 and at 60 minutes on Treatment Days 2-3.

[17]Safety Questionnaires and Tests including KSS, ACTS, MSAQ and VAS for nausea severity were completed by the subject at the following time points: Screening, twice on Treatment Day 1 at 4 and 8 hours and in the event a rescue dose was administered (ACTS, MSAQ, and VAS only). For Treatment Days 2-3, the ACTS was administered as per the schedule: at pre-dose (within 60 minutes before dosing) and at 180, 330, and 600 minutes after 1$^{st}$ dosing.

[18]PK blood draws were performed according to the schedule on Treatment Days 2-3: at pre-dose (within 60 minutes before dosing) and at 30, 60, 90, 120, 180, 330, 390, 420, 450, and 600 minutes after 1$^{st}$ dosing.

[19]AEs were assessed throughout screening and Treatment Days 1-3, including ACTS at specified time points for Treatment Day 1 and for Treatment Days 2-4. AEs were assessed by asking the subjects the following questions: How do you feel? Is this normal for you at this time of day?

[20]Research staff ensured the removal of the patch and discarded as per manufacturer instructions.

[21]All concomitant medications/treatments taken within 30 days of randomization through Treatment Day 3, in addition to any medications/treatments taken for reported AEs during follow-up, were recorded.

[22]PSAQ: Subjects completed the questionnaire.

[23]Research staff informed subjects of the follow-up periods (short and long term) procedures (timing, responsibilities, contact information) and reminded subjects to contact research staff if any new signs or symptoms arose.

[24]Research staff transcribed weather and sea state conditions from the ship's log into the source data for all entries made during the one day of treatment. Note: this was done one time at the end of each voyage, on one log, not per subject. The ship captain used the provided form.

Discussion of Study Design, Including the Choice of Control Groups

This study was designed as a randomized, double-blind trial of DPI-386 Nasal Gel that had both an active control (TDS patch) and a placebo control (Placebo Nasal Gel). Study medication was administered for 3 days. Efficacy and safety results with DPI-386 Nasal Gel were compared with those of TDS patch and Placebo Nasal Gel to establish the effectiveness of DPI-386 for prevention and treatment of nausea associated with motion sickness and the safety of DPI-386 when used in the study population.

TDS patch is the current standard of care for the treatment of motion sickness.

4.3. Selection of Study Population

Subjects were screened either by phone or email to determine initial eligibility: "Do you suffer from motion sickness on boats? Are you between the ages of 18 and 59?" Once initially screened, subjects were directed to meet the research staff for their Screening Visit. At the Screening Visit, the protocol was fully explained, including all potential risks known to both DPI-386 Nasal Gel and TDS patch. Any questions were answered by the PI or qualified designee. Once a person expressed interest in participation, the potential subject read and then signed the ICF, with the help of the researcher who consented the subject.

4.3.1. Inclusion Criteria

As per the protocol, inclusion criteria were as follows:

1. Provision of a signed and dated ICF.
2. Stated willingness to comply with all study procedures and availability for the duration of the study.
3. Male or female, aged 18 to 59 (inclusive).
4. Minimally susceptible to provocative motion as evidenced by at least two responses on the MSSQ of "Sometimes" or "Frequently."
5. In good general health as evidenced by medical history with no recent history or current diagnosis of uncontrolled clinical problems as assessed by the PI or qualified designee.
6. Ability to take intranasal medication and willingness to adhere to the study schedule and time constraints.
7. For females of child-bearing potential: willingness to provide a urine sample for the human chorionic gonadotropin (hCG) pregnancy test. The test must be negative within 7 days of Treatment Day 1.

Note: Women of non-childbearing potential are defined as those who are non-surgically sterile (i.e., without menses for at least 12 consecutive months) or surgically sterile (i.e., those who underwent a hysterectomy with or without oophorectomy, fallopian tube ligation, and endometrial ablation).

8. Agreement to adhere to the following lifestyle compliance considerations:

a. Refrain from consumption of grapefruit and any substance containing grapefruit for 7 days prior to, during, and for 7 days after the 3 treatment days.

b. Abstain from alcohol for 24 hours prior to first dose of study medication and during the three treatment days.

Note: there was no restriction on caffeine or nicotine use during the study; however, the actual use of these substances was recorded as part of the Confidential Exclusionary Behavior Questionnaire (CEBQ).

4.3.2. Exclusion Criteria

As per the protocol, exclusion criteria were as follows:

1. Pregnancy, lactation, or positive urine pregnancy test within 7 days of Treatment Day 1.

2. Known allergic reactions to scopolamine or other anticholinergics.

3. Currently prescribed any of the following medication types and used within the specified washout periods below:

any form of scopolamine (including Transderm Scop®) (washout 5 days), belladonna alkaloids (washout 2 weeks), antihistamines (including meclizine) (washout 2 weeks), tricyclic antidepressants (washout 2 weeks), muscle relaxants (washout 4 days) and nasal decongestants (washout 4 days).

4. Hospitalization or significant surgery requiring hospital admittance within the past 6 months.

5. Treatment with another investigational drug or other intervention within the past 30 days.

6. Having donated blood or plasma or suffered significant blood loss within the past 30 days.

7. Having any of the following medical conditions within the last 2 years or if any of the following medical conditions were experienced more than 2 years ago and are deemed clinically significant by the PI or qualified designee:

Significant gastrointestinal (GI) disorder, asthma, or seizure disorders.

History of cardiovascular disease.

History of vestibular disorders.

History of narrow-angle glaucoma.

History of urinary retention problems.

History of alcohol or drug abuse.

Nasal, nasal sinus, or nasal mucosa surgery.

All the enrolled subjects fulfilled all the above inclusion and no exclusion criteria.

4.3.3. Removal of Subject from Therapy or Assessment

As per the protocol, withdrawal criteria were as follows:

1. Subjects are free to withdraw from the study at any time upon request.

2. The PI or qualified designee must discontinue or withdraw any subject from the study for the following reasons:

Pregnancy.

Significant non-compliance to study requirements as listed in Inclusion and Exclusion Criteria.

If any serious adverse event (SAE) or other medical condition or situation occurs such that continued participation in the study would not be in the best interest of the subject.

Significant non-compliance with lifestyle study requirements as listed in Inclusion Criterion No. 8.

If any AE or other medical condition or situation occurs such that continued participation in the study would not be in the best interest of the subject.

If the subject meets an exclusion criterion (not previously recognized) that precludes further study participation.

If a subject deliberately removes the patch prior to the scheduled time.

If the subject fails to follow timeline requirements.

If the subject is disruptive, combative, or otherwise uncooperative with research staff.

4.4. Treatments 4.4.1. Treatments Administered

The initial study drug dosing on Treatment Day 1 for all the subjects in all treatment arms occurred at approximately the same time upon notification of the investigator and after the study drug dosing training was completed on the ship. On Treatment Days 2-3 at the clinic, subject treatment occurred according to the dosing schedule.

All the subjects received both a patch and nasal gel randomized to one of the following 3 arms: DPI-386 Nasal Gel+placebo patch, Placebo Nasal Gel+placebo patch, or Placebo Nasal Gel+TDS patch.

Nasal Gel Treatment Schedule

Subjects self-administered the first dose of DPI-386 Nasal Gel (0.2 mg/0.12 g) or Placebo Nasal Gel (0.12 g) into one nostril under research staff supervision upon notification by the investigator, and then self-administered a total of 5 additional doses over 3 treatment days always under research staff supervision, unless a rescue dose was administered on Treatment Day 1. There was a minimum of 6 hours±15 minutes separating any 2 doses. No more than 2 doses were applied, unless a third dose was deemed necessary by the investigator during Treatment Day 1 on the ship. After the initial dose on Treatment Day 1, all subsequent nasal gel doses occurred only during the subject's controlled 8-hour period.

Patch Treatment Schedule

An independent (unblinded) applicator administered a TDS patch or placebo patch placed behind either ear (subject's preference) upon notification by the investigator. The patch was removed and disposed of according to the manufacturer's instructions at the end of Treatment Day 3. The independent (unblinded) applicator applied a waterproof opaque bandage over the patch to ensure that the patch was not visible.

Procedure of Self-Administration of Nasal Gel

1. Before self-administration of the study drug, the subjects were required to clean their hands to prevent contamination.

2. Subjects were instructed to blow their nose into a clean tissue to clear both nostrils.

3. Subjects were handed the pump by research staff and told to remove the clip and cap and insert the gel unit tip approximately one cm into their nostril, pointing the tip toward the back of their nose.

4. Subjects closed their other nostril with their forefinger and tilted head slightly forward.

5. Subjects actuated the pump firmly by pushing down on the finger grips of the pump unit and against the thumb at the bottom of the device, devise delivering one dose of gel into the nostril.

6. Subjects removed the pump from their nose and placed the clip and cap back on the pump. Subjects then massaged their nostril for 3-5 seconds. The subjects returned the vial to the researcher after each dose administration for storage in the assigned kit at the secure storage location.

7. Subjects were instructed to avoid sniffing or sneezing and remained in an upright position for at least 30 minutes. Subjects did not need to stay with research staff during this time and only self-reported if sniffing and sneezing happened when they visited the research staff next.

8. Subjects were instructed to refrain from blowing their nose for at least 1 hour after dosing.

9. After self-administration of the study drug administration, subjects were required to clean their hands to prevent contamination.

4.4.2. Identity of Investigational Product

See Table for descriptions of the investigational products used in this study.

TABLE 8e

| Investigational Products | |
|---|---|
| DPI-386 Nasal Gel | |
| Active content | Scopolamine Hydrobromide |
| Strength | Each 0.12 gram of the gel contains 0.2 mg of scopolamine HBr |
| Storage condition | Store at 20° C. to 25° C., inclusive (68° F. to 77° F., inclusive), with brief temperature excursions permitted between 15° C. and 30° C., inclusive (59° F. and 86° F., inclusive). |
| Transderm Scop ® [a commercial transdermal scopolamine (TDS) patch] | |
| Strength | One patch of 1.5 mg reservoir of scopolamine can be delivered over a period of 72 hours |
| Lot No. | RDF0505 |
| Expiry Date | September 2021 |
| Placebo Nasal Gel (Placebo gel for DPI-386 Nasal Gel) | |
| Storage condition | Store at 20° C. to 25° C., inclusive (68° F. to 77° F., inclusive), with brief temperature excursions permitted between 15° C. and 30° C., inclusive (59° F. and 86° F., inclusive). |

TDS = transdermal scopolamine 4.4.3. Method of Assigning Subjects to Treatment Groups Each subject randomized on Treatment Day 1 of the voyage was assigned a subject number (starting with 1001, 1002, 1003, etc.) in consecutive order which randomized the subject to one of the 3 treatment arms: DPI-386 Nasal Gel, Placebo Nasal Gel, or TDS patch. The subject number was linked to a multi-digit random number (study drug kit number) different from the subject number. The nasal gel vial was labelled with the same study drug kit random number. The randomization scheme was secured with limited access to research staff delegated by the PI and was used to assign the patch treatment from a bulk supply. For all subjects, the link between each subject's number and that subject's study drug kit number with the actual treatment assignment was stored in individual secured envelopes. In a medical emergency, unblinding of a single double-blind subject at a time was permitted.

| | Patch | | Nasal Gel | |
|---|---|---|---|---|
| Treatment Arm | Active | Placebo | Active | Placebo |
| DPI-386 Nasal Gel | | X | X | |
| Placebo Nasal Gel | | X | | X |
| TDS patch | X | | | X |

4.4.4. Timing of Dose for Each Subject

One dose of DPI-386 Nasal Gel (0.2 mg scopolamine HBr per dose) or Placebo Nasal Gel was delivered into one nostril twice daily over 3 consecutive treatment days (alternating nostrils). The two daily doses were separated by a minimum of 6 hours with a maximum of 2 doses per day, unless a third dose (rescue) was deemed necessary by the investigator (applicable for Treatment Day 1 only).

For the TDS patch and placebo patch, one patch was applied behind the ear on Treatment Day 1 only. The patch remained on until the end of Treatment Day 3, at which time it was removed by the research staff.

4.4.5. Blinding

This study was double-blinded placebo-controlled for all treatment arms. All DPI-386 Nasal Gel and Placebo Nasal Gel vials were opaque and indistinguishable. The DPI-386 Nasal Gel and Placebo Nasal Gels were identical in color and viscosity, and without identifiable smell. Each placebo patch was similar in color and size as the TDS patch but did not deliver any medication or contain any excipients. A designated independent (unblinded) applicator administered all patch application and removal, including an opaque waterproof bandage cover over the patch, to further prevent unblinding.

To prevent bias, all research staff were trained to not make any leading or suggestive statements to subjects. All staff and subjects were instructed on proper administration of study drug and instructed to clean their hands thoroughly immediately after handling any study drug.

The sealed randomization scheme and individual unblinding envelopes were delivered to the vessel by the research staff with the accompanying study drugs on the morning of Treatment Day 1. The randomization scheme and individual unblinding envelopes were not kept in the same room as the clinical trial material aboard the vessel. Instead, the randomization scheme and individual unblinding envelopes were kept in a locked container in a separate room accessible by a designated research staff member.

The randomization scheme was opened only if the study had officially concluded all aspects of subject recruitment and data collection and the study Sponsor had been informed and agreed. A subject's unblinding envelope was opened only if a subject suffered an AE after self-administrating the blinded material, and medical providers needed to know whether the administered study drug was active medication or placebo in order to treat the subject. If a subject suffered an AE, the PI or qualified designee first tried to contact the medical monitor and/or Sponsor by email to obtain approval to unblind the subject. If email was not available and neither could be reached and/or the PI or qualified designee deemed it urgent to unblind without approval, then(s) he could proceed with unblinding the specific subject by opening the unblinding envelope. All actions related to unblinding were documented in writing by the PI or qualified designee to the medial monitor and Sponsor as soon as possible. The medical monitor and Sponsor determined the case's reportability and proceeded with additional reporting as per FDA regulations.

4.4.6. Prior and Concomitant Therapy

All concomitant medications/treatments taken within 30 days of randomization through Treatment Day 3, in addition to, any medications/treatments taken for reported AEs during follow-up were recorded.

Prohibited medications included any form of scopolamine, belladonna alkaloids, antihistamines (including meclizine), tricyclic antidepressants, muscle relaxants and nasal decongestants. The required washouts for these medications are listed below:

Any form of scopolamine (including Transderm Scop®)—washout 5 days prior to Treatment Day 1

Belladonna alkaloids—washout 2 weeks prior to Treatment Day 1

Antihistamines (including meclizine)—washout 2 weeks prior to Treatment Day 1

Tricyclic antidepressants—washout 2 weeks prior to Treatment Day 1

Muscle relaxants—washout 4 days prior to Treatment Day 1

Nasal decongestants—washouts 4 days prior to Treatment Day 1

For 30 days prior to, during Treatment Days 1-3, and 7 days after Treatment Day 3, the following restrictions were required:

Blood donation

Administration of another investigational drug

For 7 days prior to, during Treatment Days 1-3, and 7 days after Treatment Day 3, the following restrictions were required:

No product containing grapefruit or grapefruit juice should be consumed.

For 24 hours prior to Treatment Day 1 and during Treatment Days 1-3, the following restrictions were required:

No alcohol should be consumed.

No use of any motion sickness remedies (e.g., medications, wrist bands, pressure bands, herbals, etc. which state on the label for use in motion sickness) outside of the study protocol.

Permitted medications were determined by the medical PI or qualified designee.

4.4.7. Treatment Compliance

For Nasal Gel, the subjects self-administered each dose under research staff supervision as per the procedure mentioned in Example 8, Section 4.4.1 and as per the training given prior to the start of the dosing activity.

For the patch, an independent (unblinded) applicator performed the whole activity from placing the patch behind either ear (subject's preference) to removal of the same.

4.5. Efficacy, Safety, and Pharmacokinetic Variables 4.5.1. Efficacy Evaluations 4.5.1.1. Primary Efficacy Endpoint The primary efficacy endpoint was the incidence of subjects who developed motion sickness and requested further treatment (i.e., subjects who received rescue medication).

Results at Treatment Day 1 Hour 4 and at the end of Treatment Day 1 were assessed.

4.5.1.2. Secondary Efficacy Endpoints 4.5.1.2.1. Nausea Assessment (Visual Analogue Scale)

A secondary efficacy endpoint was the severity of nausea as assessed on a visual analogue scale (VAS). Subjects specified their degree of nausea by indicating a point along a continuous 10-cm line between 2 endpoints. The scale ranged from 0 (no nausea) to 10 (very severe nausea). Scoring was based on the length from the left edge of the scale to the point reported and a higher score indicated a more severe degree of nausea.

Mean VAS scores on Treatment Day 1 at Hour 4 and Hour 8 were assessed.

4.5.1.2.2. Motion Sickness Assessment Questionnaire Composite Score

A secondary efficacy endpoint was the mean MSAQ composite score. The MSAQ composite score was calculated as a percentage of total points scored from all 16 MSAQ symptoms: (sum of the points from all items/144)×100.

Mean MSAQ composite scores at Treatment Day 1 at Hour 4 and Hour 8 were assessed.

4.5.1.3. Other Efficacy Endpoint

Another efficacy endpoint was time to first use of rescue medication during Treatment Day 1. This was calculated in hours as the start time of administration of the first rescue medication dose minus the start time of the first dose of study drug. Subjects who did not receive any rescue medication were censored at the time of their last assessment on Treatment Day 1.

4.5.2. Safety Endpoints

Safety endpoints included AEs, vital signs, 12-lead electrocardiogram (ECG), ANAM, ACTS, KSS, PSAQ, EOUQ, and prior concomitant medications.

4.5.2.1. Primary Safety Endpoint

The primary safety endpoint was the incidence of AEs.

4.5.2.2. Secondary Safety Endpoint

The secondary safety endpoint was cognition as measured by ANAM test.

Multiple cognitive tests/questionnaires were administered during this study. The selected tests and questionnaires were chosen for their ability to measure broad functional domains that have been designated as important for the operation of motor vehicles and other operational tasks, including alertness, attention and processing speed, reaction time and psychomotor functions, sensory-perceptual functioning, and executive functions. The ANAM tests were self-administered by the subject using a tablet computer with ANAM software and took about 34 minutes. Two ANAM batteries were customized for this study:

ANAM CORE battery plus the Running Memory Continuous Performance Test (CPT). This battery has the following tests:

Sleepiness Scale
Symptoms Checklist
Mood Scale
Simple Reaction Time
Code Substitution-Learning (CDS)
Procedural Reaction Time
Mathematical Processing
Matching to Sample
Code Substitution-Delayed (CDD)
Simple Reaction time (repeated)
Go/No-Go
CPT ANAM CORE Battery with CPT added but CDD removed. This battery has the following tests:

Sleepiness Scale
Symptoms Checklist
Mood Scale
Simple Reaction Time
CDS
Procedural Reaction Time
Mathematical Processing
Matching to Sample
Simple Reaction time (repeated)
Go/No-Go
CPT Upon the ship's departure and during the subject's 8-hour controlled period of Treatment Day 1, ANAM was performed multiple times as follows:

4 hours post 1st dose: ANAM CORE+CPT-CDD 8 hours post 1st dose: ANAM CORE+CPT

During Treatment Days 2-3 at the study site, ANAM was performed multiple times as outlined in Appendix 15.3 of the study protocol.

4.5.2.3. Other Safety Endpoints 4.5.2.3.1. Symptoms of Anticholinergic Toxicity

Symptoms of anticholinergic toxicity were monitored and recorded using the ACTS, which was conducted by asking the subject the following questions: Have you experienced any of the following symptoms in the past 24 hours?

Dry mouth
Increased skin redness/flushing
Blurry vision
Light sensitivity
Difficulty urinating
Dizziness
Confusion
Hallucinations
Palpitations The questions were asked in ascending order of symptom severity. Subjects who responded "yes" to confusion, hallucinations, or palpitations were to be immediately disqualified, and emergency medical services were to be contacted immediately. If any subject responded "yes" to dizziness, increased skin redness/flushing, blurry vision, light sensitivity, or difficulty urinating, the PI or qualified designee and medical consultant were to be contacted immediately, and they were to determine whether these subjects should be disqualified or if they required medical care. If any subject responded "yes" to dry mouth, it was recorded as a non-significant non-serious AE, and the subject was allowed to continue in the study as long as he or she responded "no" to queries about all other symptoms.

4.5.2.3.2. Vital Sign and ECG Measurements

Vital signs were taken at the clinical site as per the schedule: at pre-dose (within 60 minutes before dosing) and at 30, 60, 120, 180, 330, 390, 420, 480, and 600 minutes after first dosing.

A resting ECG was recorded at the clinical site as per the schedule: at pre-dose (within 60 minutes before dosing) and at 120 minutes after first dosing.

Changes from −60 minutes on Treatment Day 2 in vital sign and ECG measurements were calculated.

4.5.2.3.3. Karolinska Sleepiness Scale

Sleepiness was assessed using the KSS.

The KSS measures sleepiness using a 9-point scale based on 5 states ranging from "extremely alert" to "extremely sleepy, fighting sleep." There are 4 intermediary states that are not designated with words. Higher scores indicated a greater degree of sleepiness. Previous research has found that the KSS is closely linked to the objective measures of encephalographic and oculographic signs of sleep onset (Akerstedt and Gillberg, 1990). Scores on the KSS were evaluated to determine the potential impact of the study medication on alertness.

4.5.2.3.4. Performance Self-Assessment Questionnaire

An assessment of performance of activities was done using the PSAQ, which is a brief questionnaire that was completed by subjects at the end of Treatment Day 3. Each statement had 5 possible Likert-style responses, i.e., Strongly disagree, Disagree, Neither agree nor disagree, Agree, and Strongly agree.

The questionnaire allowed subjects to subjectively identify any perceived performance decrements or enhancements due to medication use over the Treatment period. The 6 statements in the PSAQ to which subjects were asked to respond were:

Over the past three days the medication had no effect on my work performance.
Over the past three days the medication had a positive on my work performance.
Over the past three days the medication had a negative effect on my work performance.
I experienced motion sickness.
Motion sickness had no effect on my work performance.
Motion sickness had a negative effect on my performance.

4.5.2.3.5. Nasal Gel Device Ease-of-Use Questionnaire

Subjects evaluated the ease of use of the Nasal Gel device using the EOUQ. The EOUQ was a brief questionnaire completed by subjects at the end of Treatment Day 3. Each statement had 5 possible Likert-style responses, i.e., Strongly disagree, Disagree, Neither agree nor disagree, Agree, and Strongly agree.

The 7 statements in the EOUQ to which subjects were asked to respond were:

Over the past three days the medication was easy to use.
Over the past three days the instructions for using the medication were easy to understand.
Over the past three days I easily remembered how to use the medication.
Over the past three days I was able to use the medication successfully every time.
Over the past three days I didn't have any problems using the medication.
Over the past three days the medication device worked the way I wanted it to work.
Over the past three days the medication was effective in preventing motion sickness.

4.5.3. Pharmacokinetic Endpoints (Secondary)

Scopolamine PK parameters were:
Maximum plasma concentration ($C_{max}$)
Area under the curve from dose administration to last measurable concentration ($AUC_{(0-t)}$)
Area under the curve from dose administration to 6 hours ($AUC_{(0-6)}$)
Lag time ($t_{lag}$)
Time to maximum plasma concentration ($t_{max}$)
Terminal half-life ($t_{1/2}$)

Additionally, the following PK parameters were measured for both unbound scopolamine and fraction unbound scopolamine:

$C_{max,\ u}$, $C_{max,fu}$,
$AUC_{(0-t)u}$, $AUC_{(0-t),fu}$,
$AUC_{(0-6)u}$ and $AUC_{(0-6),u}$, 4.5.4. Assessment of Safety It was the responsibility of the investigator to ensure that adequate medical supervision and care was available for the study subjects during each visit to ensure the utmost safety and well-being of the study subjects.

The following measures were taken to monitor and assess the safety of the subjects during the study:

All standard ocean-going vessel safety practices and emergency procedures were followed to ensure maximum safety whether on the vessel or at the study site.
All research staff engaged in collecting subject data had cardio-pulmonary resuscitation (CPR) training to ensure the safety of all participants.
All the subjects were observed for symptoms related to study drug administration. Moreover, during each collection of vitals, subjects were evaluated for AEs. All abnormal responses were recorded as AEs.
Vital signs (blood pressure, heart rate, respiratory rate, and temperature) were taken at the clinical site on Treatment Days 2-3 as per the schedule: at pre-dose (within 60 minutes before dosing) and at 30, 60, 90, 120, 180, 330, 390, 420, 450, 480, and 600 minutes after first dosing.
All research personnel at the clinical site were trained in CPR and in the application of the ACTS based on known signs and symptoms of anticholinergic overdose. The ACTS was assessed each time the subject was seen during the three treatment days. On Treatment Day 1, the ACTS was performed at 4 and 8 hours post-dose of 1st dosing. For Treatment Days 2-3, the ACTS was performed as per the schedule: at pre-dose (within 60 minutes before dosing) and at 180, 330, and 600 minutes after first dosing.

All research staff involved in blood draws had received extensive training in minimizing subject discomfort had current CPR certifications, and blood borne pathogen training, and met the state requirements for blood withdrawal. All research staff routinely inspected sites of blood draws for any signs or symptoms of decreased clotting and/or infection, including redness and/or pain at needle insertion site, swelling, and increased/continuous bleeding.

At screening and prior to randomization, pregnancy tests were administered to subjects of child-bearing potential by research staff under the standing orders of the PI.

Cardiac safety was assessed by the administration of a resting 12-lead ECG on 6 different occasions across the Treatment Days 2-3. The first ECG applied on Treatment Day 2 occurred prior to the first medication dose and served as a baseline to compare subsequent ECGs. On Treatment Days 2-3, a resting ECG was recorded at the clinical site as per the schedule: at pre-dose (within 60 minutes before dosing) and at 90 and 450 minutes after first dosing.

Safety Questionnaires and Tests including KSS, ACTS, MSAQ, and VAS were completed by the subject at the following time points: Screening, twice on Treatment Day 1 at 4 and 8 hours and in the event a rescue dose was administered (ACTS, MSAQ, and VAS only).

Research staff transcribed weather and sea state conditions from the ship's log into the source data for all entries made during the one day of treatment. Note: this was done one time at the end of each voyage, on one log, not per subject. The ship captain used the provided form.

4.5.4.1. Adverse Events

All AEs that occurred during the study (whether treatment related or not) were recorded in the electronic case report form (eCRF) and followed as appropriate.

Criteria for assessing the adverse events:

The severity of the AEs was rated by the principal investigator as indicated below:

Mild—Events require minimal or no treatment and do not interfere with the subject's daily activities. Mild events require no action other than documentation.

Moderate—Events result in a low level of inconvenience or concern with the therapeutic measures. Moderate events may cause some interference with functioning.

Severe—Events interrupt a participant's usual daily activity and may require medical treatment. Severe events are usually potentially life-threatening or incapacitating.

AEs were additionally identified by temporal qualities in the following categories:

Continuous—The AE has a marked starting point and ending point, without recurrence.

Intermittent—The AE is sporadic in its effect, and recurring.

Causality assessment of the AE to the Investigational Medicinal Product (IMP) was done based on the following criteria:

Not related—The AE is completely independent of study drug administration, and/or evidence exists that the event is definitely related to another etiology. There must be an alternative definitive etiology documented by the medical monitor.

Related—This category includes (a) definitely related, (b) probably related, (c) possibly related, and (d) remotely related to study drug administration.

4.5.4.2. Adverse Events of Special Interest

AEs of special interest (AESIs) included all symptoms listed for the ACTS deemed "related" to the study drug by the PI. For monitoring and reporting purposes, these events of special interest were further divided into 2 categories:

1. Significant Non-Serious Adverse Events

Significant Non-Serious AEs included all symptoms on the ACTS symptoms list deemed "related" to the study drug by the PI (except for dry mouth) as well as any symptoms of light-headedness, asymptomatic hypotension, or symptomatic hypotension that were deemed "related" to the study drug by the PI. These AEs were reported using the same procedure for SAEs. All significant non-serious adverse events occurring within 30 days of the subject's last exposure to study medication were reported.

The Significant Non-Serious AEs included:

Increased skin redness/flushing

Blurry vision

Light sensitivity

Difficulty urinating

Dizziness

Light-headedness

Asymptomatic hypotension

Symptomatic hypotension

Confusion

Hallucinations

Palpitations

2. Non-significant Non-Serious Adverse Events

Dry mouth was the only event of special interest to be considered a Non-significant Non-Serious AE and was reported using the standard (non-expedited) AE reporting procedure.

4.5.5. Appropriateness of Measurements

Efficacy assessments were based on the need for rescue medication, nausea assessment (VAS), MSAQ, and time to administration of rescue medication.

Safety assessments were based on AEs, vital signs, 12-lead ECG, ANAM, KSS, ACTS, PSAQ, and EOUQ.

4.5.6. Drug Concentration Measurements

As per the protocol, a total of twelve (12) blood samples, on each Day 2 and 3 were to be collected from each subject in each period.

PK blood draws were performed according to the schedule on Treatment Days 2-3: at pre-dose (within 60 minutes before dosing) and at 30, 60, 90, 120, 180, 330, 390, 420, 450, and 600 minutes after first dosing.

Upon arrival at the study site on the Treatment Day, subjects received an indwelling 20- or 22-gauge catheter with an extension set in the antecubital vein of their non-dominant arm. Blood samples were collected, and the line was flushed with 0.9% saline after each draw. Prior to taking each sample, a 2 mL additive-free tube of blood was taken and discarded to clear the line of saline. If the indwelling catheter became compromised, the unit was either replaced or a direct stick via 21-gauge collection set were substituted. The maximum amount of blood that could be drawn from a subject was 300 mL over 11 hours.

PK blood draws were performed as close to the scheduled time point as possible.

Blood samples were centrifuged at 3000 rpm at 4° C. for 10 minutes for plasma separation. Plasma for each time point was divided equally into two cryovials via non-sterile pipettes to create two separate sets of plasma samples for each subject. Each cryovial received approximately 2.0 mL of plasma and was stored in a −80° C. freezer until transferred to the clinical laboratory for analysis.

4.6. Data Quality Assurance 4.6.1. Monitoring

Sponsor representatives were allowed to visit all study site locations to assess the data, quality, and study integrity in a manner consistent with applicable health authority regulations and the procedures adopted by sponsor. Prior to the start of the study, sponsor representatives reviewed the protocol, eCRF, regulatory obligations, and other material or equipment relevant to the conduct of the study with the Investigator and relevant study site personnel.

Monitoring visits and telephone consultations occurred as necessary and per the monitoring plan, in order to verify the following:

The rights and well-being of subjects were protected,

The conduct of the investigation was in compliance with the currently approved protocol/amendment, 21 Code of Federal Regulations Parts 50, 54, 56, and 812; 42 United States Code 282(j); ICH Good Clinical Practices (GCPs); and applicable local regulations, The integrity of the data, including adequate study documentation.

The facilities remained acceptable,

The Investigator and site personnel remained qualified and able to conduct the study, and Test article accountability.

4.6.2. Training

The investigator and team were trained in the ICH GCP guideline. Before the start of the study, the study team was trained on the protocol, informed consent procedures, eCRF completion and correction, source documentation, monitoring procedures, management of documents and timelines of subject recruitment and completion.

4.6.3. Quality Assurance

Compliance to the study requirements were observed as per GCP, Internal Standard Operating Procedures, Protocol, and applicable regulatory requirements.

4.6.4. Clinical Data Management

TAB Clinical was provided paper copies of the eCRFs and then entered the data into an electronic data capture (EDC) database with double-data entry per FDA guidance. TAB queried all incorrect, out-of-range, and missing data.

The ANAM datasets were reviewed by Vista Life-Sciences, Inc. to ensure proper organization and to identify missing data. In addition, test scores were reviewed to identify atypical observations or those that were indicative of invalid performance. This included a careful examination of individual test scores with accuracy ≤56%. Tests in the ANAM battery involve binary response options, thus ~50% accuracy reflects chance-level responding. Therefore, low accuracy scores are typically indicative of individuals who did not understand the test instructions or were not putting forth full effort. Low accuracy scores result from a combination of incorrect responses and/or failure to respond to stimulus in the allotted time.

Summaries of data exclusions/modifications, incomplete or missing data, data that indicated non-credible performance, and rescoring are provided in the ANAM Summary Analysis Report, Day 1, 2, and 3, which is provided in Appendix 16.5.

4.7. Statistical Methods Planned in the Protocol and Determination of Sample Size 4.7.1. Statistical and Analytical Plans Continuous data were summarized by reporting the number of subjects (n), mean, standard deviation (SD), median, minimum value, and maximum value.

Categorical data were summarized by reporting the frequency (count and percent) of subjects falling within each category of a given assessment. Unless specified otherwise for a particular assessment, the denominator for calculating a percentage was the total number of subjects in the analysis population for the subgroup being analyzed; for example, within study arm, the number of subjects within the study arm in the analysis population was the denominator. For overall summaries, the total number of subjects in the analysis population was used as the denominator.

Statistical tests and confidence intervals were provided. Among-group tests were performed. Tests comparing DPI-386 Nasal Gel to Placebo Nasal Gel, and DPI-386 Nasal Gel to TDS patch were performed with two-sided tests at the 5% significance level.

4.7.1.1. Analysis Populations

The analysis populations were defined as follows:

Intent-to-Treat (ITT): The ITT population included all randomized subjects.

Modified Intent-to-Treat (mITT): The mITT population included subjects randomized to treatment who received at least one dose of study treatment and who have at least one post-baseline assessment of at least one efficacy assessment (MSAQ or VAS).

Per-Protocol (PP): The PP population included all subjects randomized to treatment who received at least one dose of study treatment, who have at least one post-baseline assessment of at least one efficacy assessment (MSAQ or VAS), and who did not have any major protocol violations.

Safety: The Safety population included all subjects who received at least one dose of study treatment.

All safety analyses were done on the safety population and efficacy analyses were done on the ITT population using SAS® Version 9.4 (SAS Institute Inc., USA).

As the number of patients in the ITT and mITT populations were similar, no separate tables for the mITT population were generated.

4.7.1.2. Study Subjects 4.7.1.2.1. Disposition of Subjects

Subject disposition was summarized for the safety, ITT, and PP populations by treatment group and over all subjects combined. Summaries included the number and percentage of subjects in each analysis population, completing the study, and discontinuing the study early by the primary reason for discontinuation.

4.7.1.2.2. Protocol Deviations

Major protocol violations were summarized by treatment group and over all subjects combined. Major protocol violations were protocol deviations captured on-study that were deemed by the Sponsor to potentially impact the efficacy or safety conclusions of the study.

4.7.1.2.3. Measurements of Treatment Compliance

Compliance to the study treatment regimen were summarized separately for the nasal gel application and patch application:

Nasal Gel: The total number of doses administered as the full dose without dosing errors.

Patch: The number of days the patch remained on the subject.

The number of nasal gel doses received was summarized with the number and percentage of subjects receiving 0, 1, 2, 3, 4, 5, or 6 complete doses without dosing errors by treatment group. The number of days with an administered patch was summarized with the number and percentage of subjects wearing the patch for 0, 1, 2, or 3 days during the treatment period by treatment group. Compliance with study treatment was summarized for the ITT population.

4.7.1.2.4. Extent of Exposure

Extent of exposure to study treatment was summarized for the Safety population by treatment group. The number of days with nasal gel administered and the number of days with a patch applied were summarized by counts and percentages of subjects in each category (i.e., 1, 2, or 3 days). The total nasal gel dose administered in grams was summarized with descriptive statistics. The total dose administered for each subject was derived as the number of full nasal gel doses given as reported on the Study Drug Dosing Log form×0.12 grams.

4.7.1.3. Efficacy Evaluation 4.7.1.3.1. Demographic and Other Baseline Characteristics Demographic variables including age, sex, ethnicity, and race were summarized by treatment group and over all subjects combined for the ITT and PP populations.

Age was summarized using descriptive statistics. Sex, ethnicity, and race were summarized with the number and percentage of subjects.

4.7.1.3.2. Primary Efficacy Endpoint Analysis Methods

The primary efficacy endpoint was the proportion of subjects who developed motion sickness and requested further treatment.

The difference in proportions and p-value were from a logistic regression model based on the binomial distribution with an identity link function and compared DPI-386 Nasal Gel to each control group. The model included subject rescue medication use (yes/no) as the response variable, a main effect for the treatment group, and the raw MSSQ total score at screening as a covariate.

The analysis was performed on the ITT population.

4.7.1.3.3. Secondary Efficacy Endpoint Analysis Methods

Nausea Assessment (Visual Analogue Scale)

The least squares mean (LSM) VAS raw scores and change from baseline scores were analyzed at Treatment Day 1 Hour 4 and Hour 8. A regression model with change from baseline in VAS (mm) score and p-value were calculated from a logistic regression model that compared DPI-386 Nasal Gel to each control group and included VAS (mm) as the response variable, a main effect for the treatment group.

The analysis was performed on the ITT population.

Motion Sickness Questionnaire: Composite Score

The LSM MSAQ composite raw scores and change from baseline scores were analyzed on Treatment Day 1 Hour 4 and Hour 8. A regression model with change from baseline in MSAQ for composite score and p-value were calculated from logistic regression model that compared DPI-386 Nasal Gel to each control group and included MSAQ as the response variable, a main effect for the treatment group, and the composite score at screening as a covariate.

The analysis was performed on the ITT population.

4.7.1.3.4. Other Efficacy Endpoint, Analysis Methods

Time to first use of rescue medication was another efficacy endpoint.

Quartiles were derived from Kaplan-Meier product limit estimates. P-values were based on the log rank test for comparison between treatment groups.

4.7.1.4. Safety Evaluation

The safety analysis was performed on the Safety population and included all subjects who received at least one dose of study drug.

4.7.1.4.1. Primary Safety Endpoint: Adverse Events

Treatment-emergent adverse events (TEAEs) were defined as those AEs with onset after the first dose of study drug or existing events that worsened after the first dose during the study. TEAEs were summarized by treatment group.

Summaries that are displayed by Medical Dictionary for Regulatory Activities (MedDRA) System Organ Class (SOC) and preferred terms (PT) were ordered by descending incidence of SOC and by descending order of incidence by PT within each SOC. Summaries displayed by PT only were ordered by descending incidence of PT.

At each level of summarization (e.g., any AE, SOC, and PT), subjects experiencing more than one TEAE were counted only once. In the summary of TEAEs by severity grade, subjects were counted once at the highest severity reported at each level of summarization; in the summary of TEAEs by relationship, subjects were counted once at the closest relationship to study drug. Related events include those reported as having a “Possibly related,” “Probably related,” or “Definitely related” relationship to the study drug; events considered not related were those reported as “Remotely related” or “Unable to determine” with respect to the study drug. AE data were presented in data listings by subject, treatment group, and event.

4.7.1.4.2. Secondary Safety Endpoint: Cognition

The secondary safety endpoint was cognition as measured by the ANAM.

ANAM data were analyzed, and results reported by Vista LifeSciences.

Data from 2 time periods were analyzed: Day 1 only (the baseline session and the first 2 post-treatment sessions) and Day 1, 2, and 3 (all sessions).

Specific metrics were selected from each ANAM test and questionnaire to represent performance. The primary performance metric for most tests is Throughput. Throughput is reported as the number of correct responses per minute of available response time and is considered a measure of effectiveness or cognitive efficiency. Throughput is not an available metric for the Go/No-Go test, thus the sensitivity index, d', was used as the primary performance metric. Higher throughput and d' scores represent better performance.

The ANAM Sleepiness Scale score corresponds to the statement endorsed by the participant describing their level of alertness/sleepiness at the time of testing ranging from 1: ‘Feeling very alert, wide awake, and energetic’ to 7: ‘Very sleepy and cannot stay awake much longer.’ Higher values reflect increased levels of sleepiness.

The ANAM Mood Scale is a 42-item questionnaire used to assess current mood state. Participants rate a series of mood adjectives on a scale ranging from 0 (Not at all) to 6 (Very Much). The mood adjectives fall into seven subscales which include Vigor (high energy level), Happiness (positive disposition), Depression (dysphoria), Anger (negative disposition), Fatigue (low energy level), Restlessness (physical unease), and Anxiety (worry/apprehension). Data are presented as the percent of mood category which was computed as the average of the ratings across the adjectives for each category relative to the maximum possible rating. The resulting value represents the relative percent of each mood state reported by each participant. Higher values represent greater endorsement of the mood state.

The ANAM Symptoms Checklist assesses frequency and severity of subjective symptoms. The participant rates each of 21 symptoms on a scale from 0 (Not Present) to 6 (Severe). The percentage of symptoms endorsed and the percentage of the maximum symptom severity to the endorsed items are reported. Higher scores indicate more symptom endorsement and greater symptom severity.

In the analysis of the Day 1 only data, motion sickness symptoms were examined based on reports of such symptoms in the AE reports provided. Note that this symptom classification was independent of any symptoms reported on the ANAM Symptom, Mood, or Sleepiness questionnaires.

The ANAM subtest responses were summarized by treatment group. Descriptive statistics were presented for the observed values and changes from baseline to all post-baseline evaluations of cognition as measured by the throughput scores for each subtest.

4.7.1.4.3. Other Safety Endpoints

Anticholinergic Toxicity Screen

Subject incidence in reporting symptoms of anticholinergic toxicity using ACTS was presented by treatment group. The number and percentage of subjects who reported symptoms were summarized at each visit and time point where collected by symptom.

Vital Sign and ECG Measurements

Vital sign parameter measurements were summarized by treatment group. Descriptive statistics were presented for observed measurements and changes from −60 minutes on Treatment Day 2 to each visit and time point where parameters were scheduled to be collected.

Twelve-lead ECG interval parameters were summarized by treatment group. Descriptive statistics were presented for observed values and changes from −60 minutes on Treatment Day 2 to each visit and time point where parameters were scheduled to be collected.

Prolonged QTc intervals were summarized as QTc measurements that were >450 msec at each visit and time point where ECG was routinely collected per the clinical study protocol. Any other measured parameter that changed >30 msec relative to the value reported at −60 minutes on Treatment Day 2 was also reported by category. Summary results included the percentage of subjects within each category by treatment group.

Karolinska Sleepiness Scale

The KSS scores were summarized by treatment group. Descriptive statistics were presented for the observed values and changes from baseline to Treatment Day 1 Hour 4 and Hour 8.

A regression model with change from baseline in KSS for composite score and p-value were calculated from a logistic regression model that compared DPI-386 Nasal Gel to each control group and included KSS as the response variable, a main effect for the treatment group, and the composite score at screening as a covariate.

Performance Self-Assessment Questionnaire

The frequency of subject responses to the individual items of the PSAQ administered at Post-Treatment Day 3 were summarized by Treatment Group. The number and percentage of subjects who reported each of the possible responses for each item were summarized.

4.7.1.4.4. Pharmacokinetic Endpoint Analyses

The procedures for analyzing the PK data are presented in the PK Statistical Analysis Plan (SAP) (Appendix 16.1.9).

4.7.1.5. Other Evaluations 4.7.1.5.1. Nasal Gel Device Ease of Use

Subject responses to the individual items of the Nasal Gel Device Ease-of-Use Questionnaire (EOUQ) at Post-Treatment Day 3 were tabulated.

4.7.1.5.2. Prior and Concomitant Medications

Prior and concomitant medications were summarized for each treatment.

4.7.1.6. Pharmacokinetic Evaluation (Secondary Endpoint)

PK endpoints were $C_{max}$, $t_{max}$, $t_{1/2}$, and AUC.

4.7.1.7. Determination of Sample Size

The study sample size was 34 subjects per treatment arm and was not selected based on a power requirement for a specific parameter.

4.7.1.8. Changes in the Conduct of the Study or Planned Analyses

A SAP was not prepared for the analysis of the clinical data from the study. Results were analyzed as described in the study protocol. There were no changes to the study or planned analyses.

5. Study Subjects 5.1 Disposition of Subjects

A total of 102 subjects (52 male and 50 female) were enrolled and dosed in the study.

As per the protocol, all 102 subjects (Subject Nos. 1001-1102) were dosed on Treatment Day 1. A total of 95 subjects were dosed on Treatment Day 2 and 91 subjects were dosed on Treatment Day 3. In all, 91 subjects completed the clinical phase of the study.

Ten subjects discontinued from the study after dosing on Day 1 due to personal reasons (family emergency, unable/did not wish to return to clinic, and withdrawal of consent). One subject experienced an AE/medical condition/situation such that continued participation was not in the subject's best interest; the subject was withdrawn from the study.

A summary of the number (%) of subjects in each treatment arm who were present at each study visit is provided (ITT population) and (PP population).

A summary of subject disposition is presented in FIG. 8A.

5.2. Protocol Deviations

A total of 887 protocol deviations were reported in the trial. All 887 deviations were considered minor. Eleven subjects were excluded from the PP population due to protocol deviations.

6. Efficacy Evaluation 6.1. Data Sets Analyzed

A total of 102 subjects (52 male and 50 female) were enrolled and dosed in the study. Out of 102 dosed subjects, 91 subjects completed the clinical phase of the study. All enrolled 102 subjects were included in the Safety, ITT, and mITT populations. Ninety-one subjects were included in the PP population.

6.2 Demographic and Other Baseline Characteristics

The mean±standard deviation (SD) for age and details of gender are given in Table 8f.

TABLE 8f

| Demographic Data | | | | |
|---|---|---|---|---|
| Safety and ITT Population (N = 102) | | | | |
| Parameter (units) | DPI-386 Nasal Gel (N = 34) | TDS patch (N = 34) | Placebo Nasal Gel (N = 34) | Total (N = 102) |
| Age (years), mean ± SD | 34.7 ± 10.80 | 34.4 ± 11.97 | 32.7 ± 11.26 | 34.0 ± 11.28 |
| Gender (female), n (%) | 16 (47.1) | 18 (52.9) | 16 (47.1) | 50 (49.0) |
| Gender (male), n (%) | 18 (52.9) | 16 (47.1) | 18 (52.9) | 52 (51.0) |
| PP Population (N = 91) | | | | |
| Parameter (units) | DPI-386 Nasal Gel (N = 32) | TDS patch (N = 31) | Placebo Nasal Gel (N = 28) | Total (N = 91) |
| Age (years), mean ± SD | 35.4 ± 10.73 | 34.8 ± 12.05 | 31.7 ± 11.07 | 34.0 ± 11.29 |
| Gender (female), n (%) | 15 (46.9) | 17 (54.8) | 12 (42.9) | 44 (48.4) |
| Gender (male), n (%) | 17 (53.1) | 14 (45.2) | 16 (57.1) | 47 (51.6) |

ITT = intent-to-treat; PP = per protocol; SD = standard deviation; TDS = transdermal scopolamine.
Source: Table 14.1.1, Table 14.1.2

The demographic data of the subjects is summarized in Table 14.1.1 (ITT population) and Table 14.1.2 (PP population).

6.3. Measurements of Treatment Compliance

A summary of treatment compliance by number of doses of Nasal Gel received and number of days that the patch was applied is presented in Table 2g. In all treatment arms the number of subjects who received Nasal Gel and who used the patch decreased over time. The percentages of subjects in the DPI-386 Nasal Gel, TDS patch, and Placebo Nasal Gel arms who administered the gel at Dose 6 were 94.1%, 91.2%, and 82.4%, respectively. The percentages of subjects in the DPI-386 Nasal Gel, TDS patch, and Placebo Nasal Gel arms who were wearing a patch on Day 3 were 94.1%, 91.2%, and 82.4%, respectively.

TABLE 2g

| Treatment Compliance (Safety Population) | | | | |
|---|---|---|---|---|
| Parameter | Dose/ Patch | DPI-386 Nasal Gel (N = 34) n (%) | TDS Patch (N = 34) n (%) | Placebo Nasal Gel (N = 34) n (%) |
| Nasal gel application | | | | |
| Complete dose | 1 | 34 (100.0) | 34 (100.0) | 34 (100.0) |
| | 2 | 34 (100.0) | 33 (97.1) | 33 (97.1) |
| | 3 | 33 (97.1) | 31 (91.2) | 31 (91.2) |
| | 4 | 33 (97.1) | 31 (91.2) | 31 (91.2) |

TABLE 2g-continued

| Treatment Compliance (Safety Population) | | | | |
|---|---|---|---|---|
| Parameter | Dose/ Patch | DPI-386 Nasal Gel (N = 34) n (%) | TDS Patch (N = 34) n (%) | Placebo Nasal Gel (N = 34) n (%) |
| | 5 | 32 (94.1) | 31 (91.2) | 28 (82.4) |
| | 6 | 32 (94.1) | 31 (91.2) | 28 (82.4) |
| Patch application | | | | |
| Subject wearing patch for | Day 1 | 34 (100.0) | 34 (100.0) | 34 (100.0) |
| | Day 2 | 33 (97.1) | 31 (91.2) | 31 (91.2) |
| | Day 3 | 32 (94.1) | 31 (91.2) | 28 (82.4) |

Source: Table 14.3.17

6.4 Efficacy Results and Tabulations of Individual Subject Data 6.4.1. Analyses of Efficacy 6.4.1.1. Primary Efficacy Endpoint: Proportion of Subjects Who Received Rescue Medication The primary efficacy endpoint was the proportion of subjects who developed motion sickness and requested further treatment (ITT population). The difference between the DPI-386 Nasal Gel arm and the Placebo Nasal Gel arm in the proportion of subjects using rescue medication was statistically significant in favor of DPI-386 Nasal Gel at Hour 4 ($p=0.0404$) but was not statistically significant for all of Treatment Day 1 ($p=0.0610$). The difference between the DPI-386 Nasal Gel arm and the TDS patch arm was not statistically significant at either time point (Table 8h).

TABLE 8h

| Analysis of Proportion of Subjects Using Rescue Medication (ITT Population) | | | |
|---|---|---|---|
| Parameter Statistic | DPI-386 Nasal Gel (N = 34) | TDS Patch (N = 34) | Placebo Nasal Gel (N = 34) |
| Subjects took rescue medication within 4 hours after first dose | | | |
| No | 33 (97.1) | 28 (82.4) | 27 (79.4) |
| Yes | 1 (2.9) | 6 (17.6) | 7 (20.6) |

TABLE 8h-continued

Analysis of Proportion of Subjects Using Rescue Medication (ITT Population)

| Parameter Statistic | DPI-386 Nasal Gel (N = 34) | TDS Patch (N = 34) | Placebo Nasal Gel (N = 34) |
|---|---|---|---|
| p-value[1] | | 0.0666 | 0.0404 |
| Difference in proportions (%) (95% CI) | | −2.05 (−4.2348; 0.1406) | −2.27 (−4.4492; −0.0992) |
| Subjects took rescue medication | | | |
| No | 31 (91.2) | 27 (79.4) | 25 (73.5) |
| Yes | 3 (8.8) | 7 (20.6) | 9 (26.5) |
| p-value[1] | | 0.1695 | 0.0610 |
| Difference in proportions (%) (95% CI) | | −1.02 (−2.4752; 0.4352) | −1.36 (−2.7826; 0.0627) |

CI = confidence interval; ITT = Intent-to-Treat; MSSQ = Motion Sickness Susceptibility Questionnaire.

[1]Difference in proportions and p-value are from a logistic regression model based on the binomial distribution with an identity link function and compares DPI-386 Nasal Gel to each control group. The model includes subject rescue medication use (yes/no) as the response variable, a main effect for the treatment group, and the raw MSSQ total score at screening as a covariate.

Source: Table 14.2.2.39

6.4.1.2. Secondary Efficacy Endpoints 6.4.1.2.1. Nausea Assessment Score (Visual Analogue Scale)

In the ITT population, the differences between DPI-386 Nasal Gel and TDS patch in LSM nausea assessment VAS scores or LSM change from baseline scores at either time point were not statistically significant, and the differences between DPI-386 Nasal Gel and Placebo Nasal Gel at either time point were also not statistically significant (Table 8i).

TABLE 8i

Analysis of Nausea Visual Analog Scale Scores (ITT Population)

| Visit Statistic | DPI-386 Nasal Gel (N = 34) | TDS Patch (N = 34) | Placebo Nasal Gel (N = 34) |
|---|---|---|---|
| Baseline | | | |
| N | 34 | 34 | 34 |
| Mean | 0.300 | 0.359 | 0.189 |
| S | 0.6471 | 0.8272 | 0.3012 |
| Median | 0.000 | 0.000 | 0.000 |
| Min | 0.00 | 0.00 | 0.00 |
| Max | 3.00 | 3.80 | 1.00 |
| Day 1 Hour 4 | | | |
| N | 34 | 34 | 34 |
| Mean | 1.735 | 2.482 | 2.447 |
| SD | 2.5188 | 3.1491 | 2.9622 |
| Median | 0.800 | 0.750 | 0.900 |
| Min | 0.00 | 0.00 | 0.00 |
| Max | 8.50 | 9.50 | 9.70 |
| LS Mean (SE) | 1.7353 (0.4954) | 2.4824 (0.4954) | 2.4474 (0.4954) |
| Point estimate (SE) | | −0.7471 (0.7006) | −0.7121 (0.7006) |
| 95% CI | | (−2.1373, 0.6431) | (−2.1023, 0.6781) |
| p-value | | 0.2889 | 0.3120 |
| Day 1 Hour 4 change from baseline | | | |
| N | 34 | 34 | 34 |
| Mean | 1.435 | 2.124 | 2.258 |
| SD | 2.5323 | 2.8911 | 3.0123 |
| Median | 0.150 | 0.750 | 0.900 |
| Min | −1.00 | −0.70 | −1.00 |
| Max | 8.50 | 9.50 | 9.70 |
| LSM (SE) | 1.4353 (0.4835) | 2.1235 (0.4835) | 2.2579 (0.4835) |
| Point estimate (SE) | | −0.6882 (0.6838) | −0.8226 (0.6838) |
| P-value | | 0.3166 | 0.2318 |
| 95% CI | | (−2.0450, 0.6685) | (−2.1794, 0.5341) |
| Day 1 Hour 8 | | | |
| N | n | 34 | 34 |
| Mean | Mean | 0.729 | 0.571 |
| SD | SD | 1.6763 | 1.5581 |
| Median | Median | 0.000 | 0.000 |
| Min | 0.00 | 0.00 | 0.00 |

TABLE 8i-continued

Analysis of Nausea Visual Analog Scale Scores (ITT Population)

| Visit<br>Statistic | DPI-386<br>Nasal Gel<br>(N = 34) | TDS Patch<br>(N = 34) | Placebo<br>Nasal Gel<br>(N = 34) |
|---|---|---|---|
| Max | 7.10 | 7.80 | 9.70 |
| LS Mean (SE) | 0.7294 (0.2939) | 0.5706 (0.2939) | 0.7826 (0.2939) |
| Point estimate (SE) | | 0.1588 (0.4157) | −0.0532 (0.4157) |
| 95% CI | | (−0.6659, 0.9836) | (−0.8780, 0.7715) |
| p-value | | 0.7032 | 0.8983 |
| Day 1 Hour 8 change from baseline | | | |
| N | 34 | 34 | 34 |
| Mean | 0.429 | 0.212 | 0.593 |
| SD | 1.8112 | 1.6396 | 1.9125 |
| Median | 0.000 | 0.000 | 0.000 |
| Min | −3.00 | −3.70 | −1.00 |
| Max | 6.80 | 7.60 | 9.30 |
| LSM (SE) | 0.4294 (0.3072) | 0.2118 (0.3072) | 0.5932 (0.3072) |
| Point estimate (SE) | | 0.2176 (0.4345) | −0.1638 (0.4345) |
| P-value | | 0.6175 | 0.7069 |
| 95% CI | | (−0.6444, 1.0797) | (−1.0259, 0.6982) |

CI = confidence interval; ITT = Intent-to-Treat; LSM = least squares mean; max = maximum; min = minimum; SD = standard deviation; SE = standard error; TDS = transdermal scopolamine; VAS = visual analogue scale.
A regression model with change from baseline in VAS (mm) score and p-value are calculated from logistic regression model that compares DPI-386 Nasal Gel to each control group and includes VAS (mm) as the response variable, a main effect for the treatment group.
Source: Table 14.2.2.1

6.4.1.2.2. Motion Sickness Assessment Questionnaire, Composite Score

In the ITT population, the differences between DPI-386 Nasal Gel and TDS patch in LS mean MSAQ composite scores change from baseline at either time point were not statistically significant, and the differences between DPI-386 Nasal Gel and Placebo Nasal Gel at either time point were also not statistically significant (Table 8j).

TABLE 8j

Analysis of the MSAQ Composite Score (ITT Population)

| Visit<br>Statistic | DPI-386<br>Nasal Gel<br>(N = 34) | TDS Patch<br>(N = 34) | Placebo<br>Nasal Gel<br>(N = 34) |
|---|---|---|---|
| Baseline | | | |
| N | 34 | 34 | 34 |
| Mean | 1.000 | 1.088 | 1.029 |
| S | 0.0000 | 0.3788 | 0.1715 |
| Median | 1.000 | 1.000 | 1.000 |
| Min | 1.00 | 1.00 | 1.00 |
| Max | 1.00 | 3.00 | 2.00 |
| Day 1 Hour 4 | | | |
| N | 578 | 577 | 577 |
| Mean | 3.398 | 4.159 | 3.816 |
| SD | 8.4910 | 9.9229 | 8.9017 |
| Median | 1.000 | 1.000 | 1.000 |
| Min | 1.00 | 1.00 | 1.00 |
| Max | 130.00 | 108.00 | 106.00 |
| LS Mean (SE) | 3.3979 (0.3795) | 4.1594 (0.3799) | 3.8163 (0.3799) |
| Point estimate (SE) | | −0.7615 (0.5370) | −0.4184 (0.5370) |
| 95% CI | | (−1.8147, 0.2917) | (−1.4716, 0.6348) |
| p-value | | 0.1563 | 0.4360 |
| Day 1 Hour 4 change from baseline | | | |
| N | 578 | 577 | 577 |
| Mean | 2.398 | 3.071 | 2.787 |
| SD | 8.4910 | 9.8879 | 8.9066 |
| Median | 0.000 | 0.000 | 0.000 |
| Min | 0.00 | −2.00 | −1.00 |
| Max | 129.00 | 107.00 | 105.00 |
| LSM (SE) | 2.3979 (0.3791) | 3.0711 (0.3794) | 2.7868 (0.3794) |
| Point estimate (SE) | | −0.6731 (0.5363) | −0.3889 (0.5363) |
| P-value | | 0.2096 | 0.4685 |
| 95% CI | | (−1.7251, 0.3788) | (−1.4408, 0.6630) |

TABLE 8j-continued

Analysis of the MSAQ Composite Score (ITT Population)

| Visit<br>Statistic | DPI-386<br>Nasal Gel<br>(N = 34) | TDS Patch<br>(N = 34) | Placebo<br>Nasal Gel<br>(N = 34) |
|---|---|---|---|
| Day 1 Hour 8 | | | |
| N | 578 | 578 | 578 |
| Mean | 2.474 | 2.460 | 2.332 |
| SD | 5.3385 | 5.3808 | 4.9241 |
| Median | 1.000 | 1.000 | 1.000 |
| Min | 1.00 | 1.00 | 1.00 |
| Max | 64.00 | 62.00 | 58.00 |
| LS Mean (SE) | 2.4740 (0.2171) | 2.4602 (0.2171) | 2.3322 (0.2171) |
| Point estimate (SE) | | 0.0138 (0.3070) | 0.1419 (0.3070) |
| 95% CI | | (−0.5882, 0.6159) | (−0.4602, 0.7439) |
| p-value | | 0.9640 | 0.6440 |
| Day 1 Hour 8 change from baseline | | | |
| N | 578 | 578 | 578 |
| Mean | 1.474 | 1.372 | 1.303 |
| SD | 5.3385 | 5.4032 | 4.9283 |
| Median | 0.000 | 0.000 | 0.000 |
| Min | 0.00 | −2.00 | −1.00 |
| Max | 63.00 | 61.00 | 57.00 |
| LSM (SE) | 1.4740 (0.2174) | 1.3720 (0.2174) | 1.3028 (0.2174) |
| Point estimate (SE) | | 0.1021 (0.3075) | 0.1713 (0.3075) |
| P-value | | 0.7400 | 0.5776 |
| 95% CI | | (−0.5010, 0.7052) | (−0.4318, 0.7744) |

CI = confidence interval; ITT = Intent-to-Treat; MSAQ = Motion Sickness Assessment Questionnaire; LSM = least squares mean; max = maximum; min = minimum; SD = standard deviation; SE = standard error; TDS = transdermal scopolamine.

A regression model with change from baseline in MSAQ for composite score and p-value are calculated from logistic regression model that compares DPI-386 Nasal Gel to each control group and includes MSAQ as the response variable, a main effect for the treatment group, and the composite score at screening as a covariate.

Source: Table 14.2.2.7

6.4.1.3. Other Efficacy Endpoint: Time to Use of Rescue Medication

In the ITT population, the difference between the DPI-386 Nasal Gel arm and each control arm in the time to first use of rescue medication was not statistically significant (p=0.0535 vs. Placebo Nasal Gel; p=0.1568 vs. TDS patch; log rank test) (Table 8k). The difference between the TDS patch arm and the Placebo Nasal Gel arm was not statistically significant (p=0.6629; log rank test).

TABLE 8k

Analysis of Time to First Use of Rescue Medication (ITT Population)

| Parameter | DPI-386<br>Nasal Gel<br>(N = 34) | TDS Patch<br>(N = 34) | Placebo<br>Nasal Gel<br>(N = 34) |
|---|---|---|---|
| Number (%) subjects censored | 31 (91.2) | 27 (26.5) | 25 (73.5) |
| Number (%) subjects who received rescue medication | 3 (8.8) | 7 (6.9) | 9 (26.5) |
| Quartiles (95% CI) | | | |
| $25^{th}$ percentile (95% CI) | NE | | 4.90 (3.08-.) |
| $50^{th}$ percentile (95% CI) | NE | NE | NE |
| $75^{th}$ percentile (95% CI) | NE | NE | NE |
| Log rank test p-value | 0.0535 | 0.6629 | 0.1568 |

CI = confidence interval; ITT = Intent-to-Treat; NE = not estimable.

Quartiles are derived from Kaplan-Meier product limit estimates. P-value is based on the Log-Rank Test for comparing between treatment groups.

P-value in DPI-386 Nasal Gel is for comparison between DPI-386 Nasal Gel and Placebo Nasal Gel.

P-value in TDS patch is for comparison between TDS patch and Placebo Nasal Gel.

P-value in Placebo Nasal Gel is for comparison between TDS patch and DPI-386 Nasal Gel.

Source: Table 14.2.2.37

6.4.2. Statistical/Analytical Issues 6.4.2.1. Adjustments for Covariates

Not applicable.

6.4.2.2. Handling of Dropouts or Missing Data

Missing values in the safety database were not imputed.

6.4.2.3. Interim Analysis and Data Monitoring

No interim analyses were planned or performed, nor was there a plan to establish a data monitoring committee for this study.

6.4.2.4. Multicenter Studies

Not applicable.

6.4.2.5. Multiple Comparisons/Multiplicity

The efficacy assessment has been performed using a number of primary and key secondary endpoints with respect to two treatment-control comparisons based on:

DPI-386 Nasal Gel

TDS patch (active control)

Placebo Nasal Gel 6.4.2.6. Use of an "Efficacy Subset" of Subjects

The primary efficacy analysis is based on the ITT population; PP population has been utilized for additional analyses of efficacy endpoints. The PP population excluded subjects with major protocol violations. Other than the PP population, no efficacy subsets of subjects were analyzed.

6.4.2.7. Active-control Studies Intended to Show Equivalence

Not applicable.

6.4.2.8. Examination of Subgroups

Not applicable.

6.4.4.1. PK Accountability and Data Handling

Overall, 33 subjects receiving DPI-386 Nasal Gel underwent PK sampling. PK parameters were estimated for DPI-386 Nasal Gel; 30/33 subjects (91%) provided evaluable PK data following at least 3 of 4 doses (Table 8181). PK parameters were not calculated for 3 subjects (all doses) and for 2 subjects (1 dose each) because the majority of concentrations were below the quantifiable lower limit of quantitation. In addition, data from 4 subjects (1 dose each) were excluded from the PK summary because either PK sampling was limited (2 subjects) or the subject's unbound concentrations were higher than total concentrations at ≥1 time point during the profile (2 subjects).

Overall, 31 subjects receiving TDS patch underwent PK sampling. Concentrations were summarized by time. PK parameters were not estimated because PK samples were collected between approximately 24 and 58 hours after application of the patch.

TABLE 8l

Number of Subjects Included in the PK Population

| Treatment | PK Concentration Listing | PK Concentration Summary | PK Parameter Summary |
|---|---|---|---|
| DPI-386 Nasal Gel | 33 | 30[a] | 30[a] |
| TDS patch | 31 | 31 | Not applicable[b] |

Abbreviations: BLOQ = below limit of quantitation; PK = pharmacokinetic; FDS = transdermal scopolamine.
[a]Three subjects were excluded from the scopolamine concentration and PK parameter summaries for DPI-386 Nasal Gel because the majority (≥95%) of concentrations were BLOQ.
[b]Not applicable: PK parameters were not estimated for Transderm Scōp because PK sampling started approximately 24 hours and ended approximately 58 hours after application of the patch.

Figure 8B:
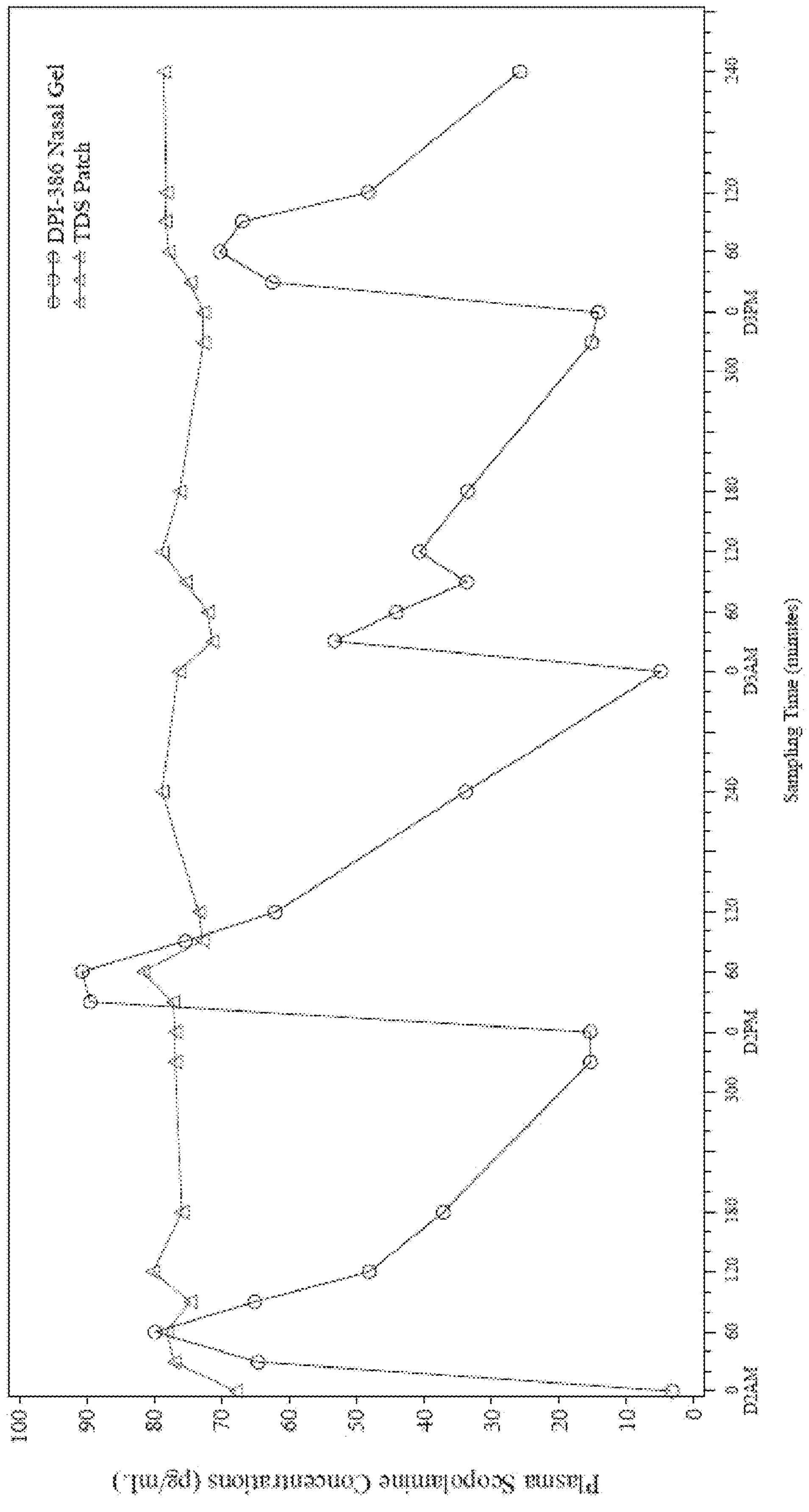
FIG. 8B is an illustration of median plasma scopolamine concentration-time profiles, Days 2 and 3. Doses of nasal gel were administered 6 hours apart on Days 1-3 and 18 hours apart between days. Scopolamine PK samples were collected relative to administration of nasal gel (DPI-386 or placebo) on Days 2 and 3. For subjects receiving TDS patch (+Placebo Nasal Gel), PK sampling started approximately 24 hours and ended approximately 58 hours after application of the patch.

6.4.4.2. Intranasal vs. Transdermal Scopolamine PK Profile 6.4.4.2.1. Plasma Total Scopolamine Scopolamine was rapidly absorbed following intranasal administration; concentrations were quantifiable at the first (30-minute) sampling time point and the median $t_{max}$ ranged from 31 to 60 minutes across doses (FIG. 8B, Table 8m). Following intranasal administration, peak scopolamine concentrations were within the range of steady-state concentrations achieved with TDS patch (FIG. 8B). After reaching $C_{max}$, scopolamine concentrations decreased rapidly for DPI-386 Nasal Gel (median $t_{1/2}$ values ranged from 116 to 122 minutes across doses); whereas concentrations were sustained near $C_{max}$ over the duration of PK sampling for TDS patch (FIG. 8B, Table 8m). Thus, the scopolamine $C_{max}$ was similar for DPI-386 Nasal Gel and TDS patch, but the AUC was lower for DPI-386 Nasal Gel compared with TDS patch as shown in FIG. 8B [Note: FIG. 8B shows PK profiles on Days 2 and 3].

TABLE 8m

Summary of Scopolamine PK Parameters for DPI-386 Nasal Gel (Overall N = 30)

| | GM (GM CV %) | | | Median (min, max) | | |
|---|---|---|---|---|---|---|
| Day and Dose | $AUC_{(0-t)}$[a] (min*pg/mL) | $AUC_{(0-6\ h)}$[b] (min*pg/mL) | $C_{max}$ (pg/mL) | $C_{330\ min}$ | $t_{1/2}$[b] (min) | $t_{max}$[c] (min) |
| Day 2 AM | 13,149 (96) [N = 27] | 16,123 (87) [N = 18] | 84.6 (136) [N = 27] | 15.4 (3.1, 57.7) [N = 27] | 116 (90.6, 312) [N = 18] | 60 (0, 125) [N = 27] |
| Day 2 PM | 14,089 (89) [N = 29] | — | 87.4 (104) [N = 30] | — | — | 31 (0, 251) [N = 30] |
| Day 3 AM | 11,496 (103) [N = 27] | 12,385 (122) [N = 19] | 65.7 (137) [N = 28] | 15.3 (BLOQ, 69.3) [N = 26] | 122 (72.5, 495) [N = 19] | 44 (0, 330) [N = 28] |
| Day 3 PM | 9038 (153) [N = 26] | — | 64.7 (172) [N = 26] | — | — | 60 (0, 203) [N = 26] |

Abbreviations:
AUC = area under the curve (time period specified);
$C_{330\ min}$ = concentration at 330 minutes;
$C_{max}$ = maximum concentration;
CV % = percent coefficient of variation;
GM = geometric mean; max = maximum;
min = minimum;
PK = pharmacokinetic;
$t_{1/2}$ = terminal half-life;
$t_{max}$ = time of maximum concentration.
Source: Table 14.2.3.1.1, Table 14.2.3.2.1
[a]$AUC_{(0-t)}$: PK Sampling Day 2 AM and Day 3 AM doses: pre-dose, 30, 60, 90, 120, 180, 330 minutes; PK Sampling Day 2 PM and Day 3 PM doses: pre-dose, 30, 60, 90, 120, 240 minutes
[b]$AUC_{(0-6\ h)}$ and $t_{1/2}$ were not estimated for Day 2 PM and Day 3 PM doses due to the limited PK sampling schedule.
[c]There were 6/111 (5.4%) instances where $t_{max}$ = 0. Three instances were for AM doses and three instances were for PM doses. For PM doses, the 330-minute PK sample collected after the AM dose was used as the pre-dose sample.

6.4.4.2.2. Plasma Unbound Scopolamine

Figure 8C:
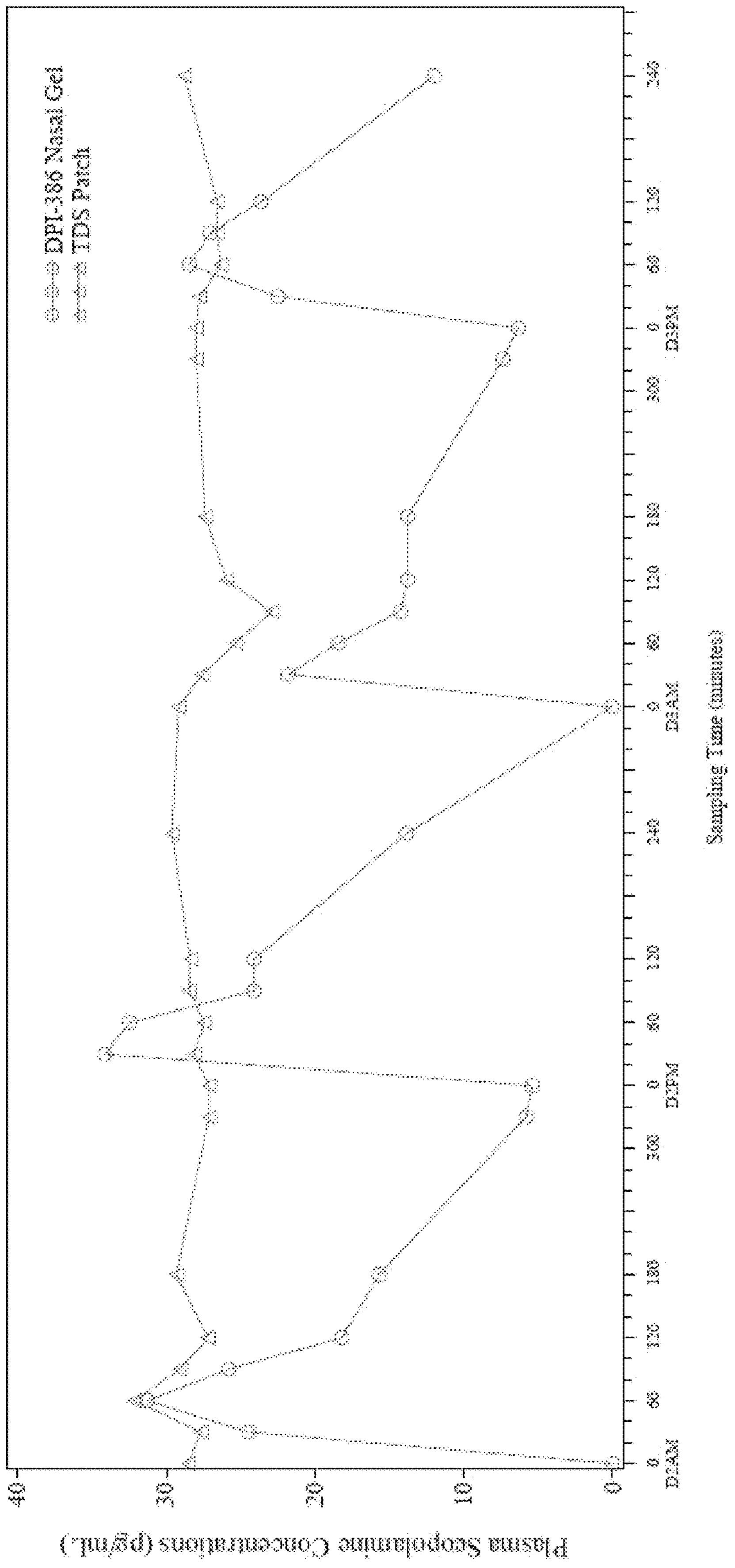
FIG. 8C is an illustration of median plasma unbound scopolamine concentration-time profiles. Doses of nasal gel were administered 6 hours apart on Days 1-3 and 18 hours apart between days. Scopolamine PK samples were collected relative to administration of nasal gel (DPI-386 or placebo) on Days 2 and 3. For subjects receiving TDS patch (+Placebo Nasal Gel), PK sampling started approximately 24 hours and ended approximately 58 hours after application of the patch.

Following intranasal administration, peak unbound scopolamine concentrations were within the range of steady-state unbound concentrations achieved with TDS patch (FIG. 8C). After reaching $C_{max}$, unbound scopolamine concentrations decreased rapidly for DPI-386 Nasal Gel; whereas unbound concentrations were sustained near $C_{max}$ over the duration of PK sampling for TDS patch (FIG. 8C, Table). Thus, the unbound scopolamine $C_{max}$ was similar for DPI-386 Nasal Gel and TDS patch, but the unbound AUC was lower for DPI-386 Nasal Gel compared with TDS patch as shown in FIG. 8C [Note: FIG. 8C shows PK profiles on Days 2 and 3]. Scopolamine was approximately 60% bound to plasma proteins (fraction unbound was approximately 40% [Table]).

TABLE 8n

Summary of Unbound Scopolamine PK Parameters for DPI-386 Nasal Gel (Overall N = 30)

| Day and Dose | Median (min, max) AUC$_{(0-t)}$ Fraction Unbound | Median (min, max) $C_{max}$ Fraction Unbound | GM (GM CV %) Unbound AUC$_{(0-t)}$[a] (min*pg/mL) | GM (GM CV %) Unbound $C_{max}$ (pg/mL) |
|---|---|---|---|---|
| Day 2 AM | 0.360 (0.15, 0.48) [N = 27] | 0.400 (0.23, 0.64) [N = 27] | 4750 (124) [N = 27] | 32.6 (143) [N = 27] |
| Day 2 PM | 0.390 (0.30, 0.50) [N = 28] | 0.375 (0.31, 0.60) [N = 30] | 5856 (78) [N = 28] | 34.1 (118) [N = 30] |
| Day 3 AM | 0.355 (0.12, 0.56) [N = 26] | 0.360 (0.25, 0.57) [N = 28] | 4312 (110) [N = 26] | 23.5 (141) [N = 28] |
| Day 3 PM | 0.370 (0.24, 0.52) [N = 23] | 0.400 (0.28, 0.58) [N = 25] | 4089 (125) [N = 23] | 28.3 (133) [N = 25] |

Abbreviations: AUC = area under the curve (time period specified); $C_{max}$ = maximum concentration; CV % = percent coefficient of variation; GM = geometric mean; max = maximum; min = minimum; PK = pharmacokinetic.
Source: Table 14.2.3.2.1, Table 14.2.3.2.2

[a]AUC$_{(0-t)}$: PK Sampling Day 2 AM and Day 3 AM doses: pre-dose, 30, 60, 90, 120, 180, 330 minutes; PK Sampling Day 2 PM and Day 3 PM doses: pre-dose, 30, 60, 90, 120, 240 minutes 6.4.4.3. Comparison of Scopolamine PK between Male and Female Subjects for DPI-386 Nasal Gel Following administration of DPI-386 Nasal Gel, scopolamine $C_{max}$, AUC$_{0-t}$, AUC$_{0-6}$, or $t_{1/2}$ were similar between male and female subjects. In contrast, following application of TDS patch, female subjects appeared to have higher scopolamine concentrations than male subjects.

6.4.4.4. Evaluation of Relationship between Scopolamine PK, ACTS, and ANAM for DPI-386 Nasal Gel For DPI-386 Nasal Gel, scopolamine PK parameters were summarized by ACTS event (Table 14.2.3.4) and ACTS events were plotted vs. scopolamine PK parameters. For the ACTS, 18 subjects reported no symptoms and 1, 1, and 9 subjects reported post-baseline ACTS events of dry mouth, blurry vision, and dizziness, respectively. There was no apparent relationship between scopolamine $C_{max}$, AUC$_{0-t}$, or AUC$_{0-6}$, and the occurrence of ACTS events.

For DPI-386 Nasal Gel, ANAM scores were plotted vs. scopolamine PK parameters. Running Memory CPT was the only ANAM test for which there appeared to be a relationship with scopolamine $C_{max}$, AUC$_{0-t}$, and AUC$_{0-6}$; higher scopolamine exposure was associated with lower performance.

6.4.4.5. PK and PK/PD Conclusions

Following administration of DPI-386 Nasal Gel, peak scopolamine concentrations were obtained approximately 30 to 60 minutes after dosing and the peak concentrations were within the range of steady-state concentrations achieved with TDS patch.

The scopolamine AUC was lower for DPI-386 Nasal Gel compared with TDS patch because scopolamine concentrations decreased rapidly for DPI-386 Nasal Gel (median $t_{1/2}$ of approximately 2 hours); whereas scopolamine concentrations were sustained near $C_{max}$ over the duration of PK sampling for TDS patch.

Scopolamine was approximately 60% bound to plasma proteins.

Following administration of DPI-386 Nasal Gel, scopolamine $C_{max}$, AUC$_{0-t}$, AUC$_{0-6}$, or $t_{1/2}$ were similar between men and women.

Following administration of DPI-386 Nasal Gel, there was no apparent relationship between scopolamine $C_{max}$, AUC$_{0-t}$, or AUC$_{0-6}$, and the occurrence of ACTS events.

Running Memory CPT was the only ANAM test for which there appeared to be a relationship with scopolamine $C_{max}$, AUC$_{0-t}$, and AUC$_{0-6}$; higher scopolamine exposure was associated with lower performance.

6.4.5. Drug-Drug and Drug-Disease Interactions

Not applicable.

6.4.6. By-Subject Displays

Not applicable.

6.4.7. Efficacy Conclusions

The analysis of the primary efficacy endpoint, the proportion of subjects who developed motion sickness and requested further treatment, showed a statistically significant difference in favor of the DPI-386 Nasal Gel arm between the DPI-386 Nasal Gel arm and the Placebo Nasal Gel arm at Treatment Day 1 Hour 4 (p=0.0404). The difference favored DPI-386 Nasal Gel at Hour 8 but was not statistically significant (p=0.0610). The difference between the DPI-386 Nasal Gel arm and the TDS patch arm was not statistically significantly different at Treatment Day 1 Hour 4 (p=0.0666) or at Hour 8 (p=0.1695).

In the secondary efficacy analyses, the differences between the DPI-386 Nasal Gel arm and the TDS patch arm and between the DPI-386 Nasal Gel arm and the Placebo Nasal Gel arm in severity of nausea (VAS) and in MSAQ composite score were not statistically significant at Treatment Day 1 Hour 4 or Treatment Day 1 Hour 8.

The difference between the DPI-386 Nasal Gel arm and the control arms in time to use of rescue medication was not statistically significant.

7.0. Safety Evaluation 7.1. Extent of Exposure

A summary of extent of exposure to study medication in the Safety Population is provided in Table 14.3.17. Compliance to study medication administration was >82% for both nasal gel and patch administration.

7.2. Adverse Events 7.2.1. Brief Summary of Adverse Events

The primary safety endpoint was the subject incidence of AEs.

An overall summary of AEs is provided in Table 80.

A total of 150 TEAEs were reported by 79 (77.5%) of the 102 subjects during the study.

Of the 150 TEAEs, 50 AEs were reported in the subjects after administration of DPI-386 Nasal Gel, 57 AEs were reported in the subjects after administration of TDS patch, and 43 AEs were reported in the subjects after administration of Placebo Nasal Gel.

Motion sickness was the most frequently reported TEAE (81 events in 64 subjects). Subjects in the DPI-386 Nasal Gel arm had the lowest incidence of motion sickness TEAEs (52.9% of subjects) and the lowest number of reported motion sickness TEAEs (n=21). The incidence of motion sickness TEAEs in the TDS patch and Placebo Nasal Gel arms was 73.5% and 67.6%, respectively, and the number of reported motion sickness TEAEs was 30 in each arm.

Of the 150 TEAEs, 123 AEs were mild, and 27 AEs were moderate. All of the subjects were followed up until resolution of their AEs except Subject Nos. 1023 and 1094. The outcome of 2 AEs of these subjects were unknown.

The causality assessment was judged as not related for 100 TEAEs and related for 50 TEAEs.

No deaths occurred and no SAEs were reported.

Out of 150 TEAEs, 32 AEs were reported as AESIs. Of these, 18 AEs (asymptomatic hypotension, blurry vision, dizziness, increased skin redness/flushing and light sensitivity) were "Significant, Non-serious" and 14 AEs (dry mouth) were "Non-significant, Non-serious."

TABLE 8o

Summary of Treatment Emergent Adverse Events (Safety Population)

| Parameter | DPI-386 Nasal Gel (N = 34) n (%) e | TDS Patch (N = 34) n (%) e | Placebo Nasal Gel (N = 34) n (%) e |
|---|---|---|---|
| All TEAEs (Subjects with at least one TEAE) | 26 (76.5) 50 | 29 (85.3) 57 | 24 (70.6) 43 |
| Relationship of TEAEs to IMP | | | |
| Not related | 23 (67.6) 33 | 26 (76.5) 33 | 24 (70.6) 34 |
| Related | 13 (38.2) 17 | 11 (32.4) 24 | 8 (23.5) 9 |
| Severity of TEAEs | | | |
| Mild | 25 (73.5) 44 | 26 (76.5) 51 | 20 (58.8) 28 |
| Moderate | 5 (14.7) 6 | 5 (14.7) 6 | 9 (26.5) 15 |
| Severe | 0 (0.0) 0 | 0 (0.0) 0 | 0 (0.0) 0 |
| TEAEs leading to rescue DPI-386 Nasal Gel | 3 (8.8) 5 | 7 (20.6) 11 | 8 (23.5) 11 |
| Subjects with at least one ACTS AESI in TEAE | 10 (29.4) 12 | 9 (26.5) 14 | 5 (14.7) 6 |
| Subjects with at least one SAE | 0 (0.0) 0 | 0 (0.0) 0 | 0 (0.0) 0 |

ACTS = Anticholinergic Toxicity Screen;
AESI = adverse event of special interest;
IMP = investigational product;
SAE = serious adverse event;
TEAE = treatment-emergent adverse event
N = Number of subjects in respective treatment population.
n = Number of subjects in respective categories.
e = Number of events.
Source: Table 14.3.1.1

7.2.2. Display of Adverse Events

A summary of AEs by SOC and PT is provided in Table 8p.

A summary of AESIs by SOC and PT is provided in Table 8q.

TABLE 8p

Summary of Treatment-Emergent Adverse Events (Safety Population)

| System Organ Class Preferred Term | DPI-386 Nasal Gel (N = 34) n (%) e | TDS patch (N = 34) n (%) e | Placebo Nasal Gel (N = 34) n (%) e |
|---|---|---|---|
| All TEAEs (Subjects with at least one TEAE) | 26 (76.5) 50 | 29 (85.3) 57 | 24 (70.6) 43 |
| Ear and labyrinth disorder | 18 (52.9) 21 | 25 (73.5) 30 | 23 (67.6) 30 |
| Motion sickness | 18 (52.9) 21 | 25 (73.5) 30 | 23 (67.6) 30 |
| Eye disorders | 2 (5.9) 2 | 2 (5.9) 2 | 1 (2.9) 1 |
| Photophobia | 2 (5.9) 2 | 2 (5.9) 2 | 1 (2.9) 1 |
| Gastrointestinal disorder | 8 (23.5) 8 | 6 (17.6) 7 | 5 (14.7) 5 |
| Diarrhoea | 0 (0.0) 0 | 0 (0.0) 0 | 1 (2.9) 1 |
| Dry mouth | 6 (17.6) 6 | 6 (17.6) 6 | 3 (8.8) 3 |
| Dyspepsia | 1 (2.9) 1 | 0 (0.0) 0 | 0 (0.0) 0 |
| Somnolence | 0 (0.0) 0 | 1 (2.9) 1 | 0 (0.0) 0 |
| Vomiting | 1 (2.9) 1 | 0 (0.0) 0 | 1 (2.9) 1 |
| General disorders and administration site conditions | 2 (5.9) 2 | 2 (5.9) 2 | 3 (8.8) 3 |
| Dysgeusia | 0 (0.0) 0 | 0 (0.0) 0 | 1 (2.9) 1 |
| Energy increased | 0 (0.0) 0 | 1 (2.9) 1 | 0 (0.0) 0 |
| Fatigue | 1 (2.9) 1 | 1 (2.9) 1 | 2 (5.9) 2 |
| Hyperhidrosis | 1 (2.9) 1 | 0 (0.0) 0 | 0 (0.0) 0 |
| Injury, poisoning and procedural complications | 1 (2.9) 1 | 0 (0.0) 0 | 0 (0.0) 0 |
| Heat exhaustion | 1 (2.9) 1 | 0 (0.0) 0 | 0 (0.0) 0 |
| Metabolism and nutrition disorders | 0 (0.0) 0 | 1 (2.9) 1 | 0 (0.0) 0 |
| Decreased appetite | 0 (0.0) 0 | 1 (2.9) 1 | 0 (0.0) 0 |
| Musculoskeletal and connective tissue disorders | 0 (0.0) 0 | 1 (2.9) 1 | 0 (0.0) 0 |
| Myalgia | 0 (0.0) 0 | 1 (2.9) 1 | 0 (0.0) 0 |
| Nervous system disorders | 5 (14.7) 5 | 6 (17.6) 7 | 1 (2.9) 1 |
| Headache | 1 (2.9) 1 | 1 (2.9) 1 | 0 (0.0) 0 |
| Hypoaesthesia | 1 (2.9) 1 | 0 (0.0) 0 | 0 (0.0) 0 |
| Somnolence | 2 (5.9) 2 | 1 (2.9) 1 | 0 (0.0) 0 |
| Vision blurred | 1 (2.9) 1 | 5 (14.7) 5 | 1 (2.9) 1 |
| Psychiatric disorders | 0 (0.0) 0 | 0 (0.0) 0 | 1 (2.9) 1 |
| Nightmare | 0 (0.0) 0 | 0 (0.0) 0 | 1 (2.9) 1 |
| Respiratory, thoracic and mediastinal disorders | 2 (5.9) 2 | 2 (5.9) 2 | 2 (5.9) 2 |
| Nasal discomfort | 1 (2.9) 1 | 1 (2.9) 1 | 1 (2.9) 1 |
| Nasal dryness | 0 (0.0) 0 | 1 (2.9) 1 | 1 (2.9) 1 |

TABLE 8p-continued

Summary of Treatment-Emergent Adverse Events (Safety Population)

| System Organ Class<br>Preferred Term | DPI-386<br>Nasal Gel<br>(N = 34)<br>n (%) e | TDS patch<br>(N = 34)<br>n (%) e | Placebo<br>Nasal Gel<br>(N = 34)<br>n (%) e |
|---|---|---|---|
| Throat irritation | 1 (2.9) 1 | 0 (0.0) 0 | 0 (0.0) 0 |
| Skin and subcutaneous tissue disorders | 5 (14.7) 5 | 1 (2.9) 1 | 0 (0.0) 0 |
| Flushing | 1 (2.9) 1 | 0 (0.0) 0 | 0 (0.0) 0 |
| Paraesthesia | 1 (2.9) 1 | 1 (2.9) 1 | 0 (0.0) 0 |
| Pruritus | 1 (2.9) 1 | 0 (0.0) 0 | 0 (0.0) 0 |
| Skin irritation | 2 (5.9) 2 | 0 (0.0) 0 | 0 (0.0) 0 |
| Vascular disorders | 4 (11.8) 4 | 4 (11.8) 4 | 0 (0.0) 0 |
| Dizziness | 2 (5.9) 2 | 2 (5.9) 2 | 0 (0.0) 0 |
| Epistaxis | 0 (0.0) 0 | 1 (2.9) 1 | 0 (0.0) 0 |
| Hypertension | 1 (2.9) 1 | 1 (2.9) 1 | 0 (0.0) 0 |
| Hypotension | 1 (2.9) 1 | 0 (0.0) 0 | 0 (0.0) 0 |

TDS = transdermal scopolamine; TEAE = treatment-emergent adverse event.
N = Number of subjects in respective treatment population.
n = Number of subjects in respective categories.
e = Number of events.
Source: Table 14.3.1.2

TABLE 8q

Adverse Events of Special Interest (Safety Population)

| System Organ Class<br>Preferred Term | DPI-386<br>Nasal Gel<br>(N = 34)<br>n (%) e | TDS patch<br>(N = 34)<br>n (%) e | Placebo<br>Nasal Gel<br>(N = 34)<br>n (%) e |
|---|---|---|---|
| All TEAEs (subjects with at least one ACTS AESI) | 10 (29.4) 12 | 9 (26.5) 14 | 5 (14.7) 6 |
| Ear and labyrinth disorders | 0 (0.0) 0 | 0 (0.0) 0 | 1 (2.9) 1 |
| Motion sickness | 0 (0.0) 0 | 0 (0.0) 0 | 1 (2.9) 1 |
| Eye disorders | 2 (5.9) 2 | 2 (5.9) 2 | 1 (2.9) 1 |
| Photophobia | 2 (5.9) 2 | 2 (5.9) 2 | 1 (2.9) 1 |
| Gastrointestinal disorders | 6 (17.6) 6 | 5 (14.7) 5 | 3 (8.8) 3 |
| Dry mouth | 6 (17.6) 6 | 5 (14.7) 5 | 3 (8.8) 3 |
| Nervous system disorders | 1 (2.9) 1 | 5 (14.7) 5 | 1 (2.9) 1 |
| Vision blurred | 1 (2.9) 1 | 5 (14.7) 5 | 1 (2.9) 1 |
| Skin and subcutaneous tissue disorders | 1 (2.9) 1 | 0 (0.0) 0 | 0 (0.0) 0 |
| Flushing | 1 (2.9) 1 | 0 (0.0) 0 | 0 (0.0) 0 |
| Vascular disorders | 2 (5.9) 2 | 2 (5.9) 2 | 0 (0.0) 0 |
| Dizziness | 1 (2.9) 1 | 2 (5.9) 2 | 0 (0.0) 0 |
| Hypotension | 1 (2.9) 1 | 0 (0.0) 0 | 0 (0.0) 0 |

ACTS = Anticholinergic Toxicity Screen; AESI = adverse event of special interest; TEAE = treatment-emergent adverse event.
N = Number of subjects in respective treatment population.
n = Number of subjects in respective categories.
e = Number of events.
Source: Table 14.3.1.2.1

7.2.3. Analysis of Adverse Events

AEs are summarized by SOC and PT in Table 8p.

Motion sickness was the most frequently reported TEAE (81 events in 66 subjects). Subjects in the DPI-386 Nasal Gel arm had the lowest incidence of motion sickness TEAEs (52.9% of subjects) and the lowest number of reported motion sickness TEAEs (n=21). The incidence of motion sickness TEAEs in the TDS patch and Placebo Nasal Gel arms was 73.5% and 67.6%, respectively, and the number of reported motion sickness TEAEs was 30 in each arm.

No subject was withdrawn from the study due to an AE.

AEs are summarized by relationship to study treatment and SOC and PT.

AEs are summarized by severity grade and SOC and PT.

7.3 Deaths, Other Serious Adverse Events and Other Significant Adverse Events 7.3.1. Listing of Deaths, Other Serious Adverse Events and Other Significant Adverse Events 7.3.1.1. Deaths There were no deaths in the study.

7.3.1.2. Other Serious Adverse Events

No SAEs were reported during the study.

7.3.1.3. Other Significant Adverse Events

Other significant AEs included the AESIs, which are defined in Example 8, Section 4.5.4.2, as are the terms "Significant, Non-serious" and "Non-significant, Non-serious."

Thirty-two AESIs in 24 subjects were reported. Of these, 18 AESIs (asymptomatic hypotension, blurry vision, dizziness, increased skin redness/flushing and light sensitivity) were "Significant, Non-serious" and 14 AESIs (dry mouth) were "Non-significant, Non-serious."

A summary of AESIs by SOC and PT is provided in Table 8q.

No subject was withdrawn from the study due to an AE.

No other significant AEs were reported in the study.

7.3.2. Narratives of Deaths, Other Serious Adverse Events and Certain Other Significant Adverse Events No deaths, SAEs, or other significant AEs occurred during the study.

7.3.3. Analysis and Discussion of Deaths, Other Serious Adverse Events and Other Significant Adverse Events Thirty-two AESIs were reported in 24 subjects during the study. All were AEs that have been associated with the administration of scopolamine.

7.4. Secondary Safety Endpoint: Automated Neuropsychological Assessment Metrics

The ANAM data were evaluated by Vista LifeSciences and the results are summarized here. Data from 2 time periods were analyzed: Day 1 only (the baseline session and the first 2 post-treatment sessions) and Day 1, 2, and 3 (all sessions). Complete reports of their findings are provided in Appendix 16.5. Refer to Section 4.5.2.2 for a description of the assessments.

CDD is a test that is subject to interference effects when given multiple times in a day. For this reason, 2 separate ANAM batteries were constructed to minimize interference. One battery included CDD (ANAM CORE+CPT) and the other did not (ANAM CORE+CPT-CDD). The battery with CDD was to be administered at screening and during the first session of each treatment day; the one without CDD was to be administered during the second session of each treatment day. However, a review of the data suggested that this was actually reversed. Specifically, no CDD data is available at screening. Further, only the second session of each treatment day (Sessions 3, 5, and 7) had CDD data. Due to the significant potential interference effects that can result when this test is repeatedly administered in a single day, it was recommended that this data not be evaluated for this study.

7.4.1. Results from Day 1

This analysis focused on Day 1 (sessions 1 [baseline], 2, and 3) cognitive performance. Multivariate repeated measures analysis of covariance (ANCOVA) was conducted to examine performance on each of the ANAM tests as a function of group (DPI-386 Nasal Gel, Placebo Nasal Gel, or TDS patch) and symptoms (motion sickness symptoms only) controlling for baseline performance. Mean reaction time, throughput, and accuracy scores served as dependent variables and were analyzed separately for each test. For the Go/No-Go test d' served as the outcome variable in lieu of throughput which is not an available metric for this test. The two- and three-way interactions were examined. Of particular interest was the Group×Symptoms×Session interaction which was examined to determine whether the pattern of performance over the 2 post-drug administration sessions differed according to group and symptom presence.

The number of subjects in each treatment group with and without motion sickness symptoms is summarized in Table 8r.

TABLE 8r

Frequency of Motion Sickness Symptoms in Treatment Groups

| Treatment Group | No Motion Sickness Symptoms | Motion Sickness Symptoms |
|---|---|---|
| DPI-386 Nasal Gel | 47 | 54 |
| TDS patch | 27 | 74 |
| Placebo Nasal Gel | 32 | 66 |

Few differences in cognitive performance were observed as a function of study treatment group and motion sickness symptom presence. In general, the pattern of performance at Sessions 2 and 3 on Treatment Day 1 were similar for the study treatment and symptom groups when controlling for baseline performance. Differences in the pattern of performance across the 2 post-drug sessions on Day 1 by study treatment and symptom groups (as measured by the 3-way session×group×symptoms interaction) were observed only for cognitive efficiency (as measured by throughput) on the Mathematical Processing test and speed of responding on the Go/No-Go test. Additionally, a significant session×symptom interaction was observed for cognitive efficiency and speed of responding on Procedural Reaction Time and accuracy of responding on Mathematical Processing. This interaction reflects a differential pattern of responding across the 2 post-drug administrations as a function of presence of motion sickness symptoms which was similar for each of the treatment groups.

7.4.2. Results from Day 1, 2, and 3

7.4.2.1. Group Comparisons of ANAM Scores at Screening

Group differences for each of the performance metrics were examined using the general linear model. No group differences were observed for any of the tests or questionnaires at the visit screening (all p>0.05) (ANAM Analysis Summary Report-Vista LifeSciences).

7.4.2.2. ANAM Performance as a Function of Treatment Group

Descriptive statistics for ANAM test and questionnaire scores at each of the non-screening study visits are presented. Individual multivariate repeated measures ANCOVA were conducted for each ANAM test to examine the effect of treatment group on performance across the test administrations during treatment sessions controlling for baseline performance. Specifically, the Group×Session interaction was examined to determine whether the pattern of performance over time differed between the treatment groups. Results of the analyses are shown in Table 8s.

Overall, some performance fluctuations were observed across the 6 treatment sessions that reached significance for Running Memory CPT, Matching to Sample, and both administrations of the Simple Reaction Time test (Session effect, Table 8s). However, the overall pattern of performance across the sessions was similar for each of the groups and did not reach significance for any of the tests (Group× Session effect, Table 8s).

TABLE 8s

Day 1, 2, and 3: Multivariate Repeated Measures Analysis of Covariance Results (Wilks' Lambda F and p-values) Over Time for ANAM Tests

| Scale | Session | p-Value | Group × Session | p-Value |
|---|---|---|---|---|
| Code Substitution - Learning | 1.42 | 0.23 | 0.81 | 0.61 |
| Running Memory CPT | 2.40 | 0.05 | 1.29 | 0.25 |
| Go/No-Go | 0.42 | 0.83 | 0.93 | 0.51 |
| Matching to Sample | 2.88 | 0.02 | 0.54 | 0.86 |
| Mathematical Processing | 0.56 | 0.73 | 1.09 | 0.37 |
| Procedural Reaction Time | 0.65 | 0.66 | 1.09 | 0.38 |
| Simple Reaction Time - repeated | 2.65 | 0.03 | 0.78 | 0.65 |
| Simple Reaction Time | 3.18 | 0.01 | 0.54 | 0.86 |

Abbreviations: ANAM = Automated Neuropsychological Assessment Metrics; CPT = Continuous Performance Test.
Source: Table 8a, ANAM Analysis Summary Report, Day 1, 2, and 3 (Appendix 16.5)

Since baseline performance did not differ between the groups, a multivariate repeated measures analysis of variance (ANOVA) was also conducted across the 7 study sessions with group serving as the independent variable. In this analysis, baseline scores served as one of the dependent variables and not as a covariate. As with the ANCOVA results, there were no significant Group×Session interactions which indicates that the pattern of performance across the seven study sessions (screening and treatment) was similar for the treatment groups.

Self-reported mood, sleepiness, and symptoms scores were examined for an effect of treatment group on reported scores controlling for baseline scores. Specifically, this analysis examined whether there were any differences in the patterns of scores reported across the sessions between the treatment groups. Results of these analyses are shown in Table 8t. As shown, depression, fatigue, restlessness, symptom frequency, and symptom severity scores fluctuated across the sessions (Session effect, Table 8t). However, the pattern of mood changes and symptom reports was similar for the treatment groups (Group×Session effect, Table 8t).

The mean (95% CI) ANAM scores for each of the tests and questionnaires across all test administrations are provided. The Screening visit is Session 1 and the non-screening visits are Sessions 2 through 7.

TABLE 8t

Day 1, 2, and 3: Multivariate Repeated Measures Analysis of Covariance Results (Wilks' Lambda F and p-values) Over Time for ANAM Questionnaires

| Questionnaires | Session | p-Value | Group × Session | p-Value |
|---|---|---|---|---|
| Mood Scale | | | | |
| Anger | 1.98 | 0.09 | 0.90 | 0.53 |
| Anxiety | 1.53 | 0.19 | 0.95 | 0.49 |
| Depression | 3.16 | 0.01 | 0.43 | 0.93 |
| Fatigue | 4.19 | 0.002 | 0.90 | 0.53 |
| Happiness | 0.84 | 0.53 | 0.90 | 0.54 |
| Restlessness | 2.67 | 0.03 | 0.63 | 0.79 |
| Vigor | 1.40 | 0.24 | 1.46 | 0.16 |
| Sleepiness Scale | 0.69 | 0.63 | 0.63 | 0.79 |
| Symptoms Scale | | | | |
| Frequency | 6.03 | <.0001 | 1.62 | 0.11 |
| Severity | 4.75 | 0.0008 | 0.80 | 0.63 |

Abbreviation: ANAM = Automated Neuropsychological Assessment Metrics.
Source: Table 8b, ANAM Analysis Summary Report, Day 1, 2, and 3

7.4.2.3. Change from Baseline

Descriptive statistics for change in Throughput scores from screening baseline to each of the post-screening session scores for each of the ANAM performance tests are presented in Table 14.3.7.9. Additionally, change scores for each of the questionnaires (Mood, Sleepiness, and Symptoms) are presented.

7.5. Other Safety Endpoints 7.5.1. Symptoms of Anticholinergic Toxicity

Symptoms of anticholinergic toxicity were recorded using the ACTS. See Example 8, Section 4.5.2.3.1 for a list of symptoms about which the subjects were queried.

The most common ACTS AE reported by subjects in all treatment arms on Treatment Day 1 Hour 4 and Treatment Day 1 Hour 8 was dizziness. At all later timepoints, the most common ACTS AE reported by subjects in all treatment arms was dry mouth. Subjects in the Placebo Nasal Gel arm reported very few ACTS AEs on Days 2 and 3.

The number (%) of subjects in each treatment arm who reported an AE on the ACTS at each timepoint is provided. In addition, the number (%) of subjects who reported specific ACTS AEs is tabulated.

AEs that were reported on the ACTS and that were deemed related to treatment were considered to be AESIs. AESIs are summarized in Table 8q.

7.5.2. Vital Signs and 12-lead ECG

Descriptive statistics of vital sign measurements at each timepoint on Treatment Days 2 and 3 are provided.

The mean changes from baseline at all timepoints in vital sign measurements were not clinically meaningful. Descriptive statistics of the change from baseline in vital sign measurements at each timepoint on Treatment Days 2 and 3 are provided.

Descriptive statistics of ECG parameters at each timepoint on Treatment Days 2 and 3 are provided.

The mean changes from baseline at all timepoints in ECG parameters were not clinically meaningful. Descriptive statistics of the change from baseline in ECG parameters at each timepoint on Treatment Days 2 and 3 are provided.

One subject (2.9%) in the DPI-386 Nasal Gel arm had a QTc interval >450 msec 90 minutes post-dosing on Day 3. One subject (2.9%) in the TDS patch arm had a QTc interval >450 msec 60 minutes prior to dosing on Day 2, and 2 subjects (5.9%) in the TDS patch arm had a QTc interval >450 msec 480 minutes post-dosing on Day 2. No subject in the Placebo Nasal Gel arm had a QTc interval >450 msec at any time.

One subject (2.9%) in the DPI-386 Nasal Gel arm and 3 subjects (8.8%) in the TDS patch arm had a QTc change from baseline >30 msec 60 minutes prior to dosing on Day 2 (Table 14.3.19). One subject (2.9%) in the TDS patch arm had a QTc change from baseline >30 msec 90 minutes post-dosing on Day 2. One subject (2.9%) in the DPI-386 Nasal Gel arm and 5 subjects (14.7%) in the TDS patch arm had a QTc change from baseline >30 msec 480 minutes post-dosing on Day 2. One subject (2.9%) in each treatment group had a QTc change from baseline >30 msec 480 minutes post-dosing on Day 3.

7.5.3. Karolinska Sleepiness Scale

Mean (SD) KSS scores at baseline were 2.1 (1.41), 2.6 (1.81), and 2.6 (1.88) for subjects in the DPI-386 Nasal Gel, TDS patch, and Placebo Nasal Gel treatment arms, respectively. Median (range) KSS scores at baseline were 1 (1 to 7), 2.5 (1 to 6), and 2.5 (1 to 7) for subjects in the DPI-386 Nasal Gel, TDS patch, and Placebo Nasal Gel treatment arms, respectively. Descriptive statistics of the scores at all timepoints (n, mean, SD, median, minimum, maximum) and of the changes from baseline at all post-baseline timepoints are presented by treatment arm.

Mean (SD) changes from baseline showed a slight increase in all treatment arms at both the Hour 4 and Hour 8 timepoints on Treatment Day 1. Mean (SD) changes from baseline at Hour 4 were 1.2 (2.13), 1.6 (1.89), and 1.5 (2.42) for subjects in the DPI-386 Nasal Gel, TDS patch, and Placebo Nasal Gel treatment arms, respectively (Table 14.3.9). Mean (SD) changes from baseline at Hour 8 were 1.2 (2.47), 0.8 (2.40), and 0.5 (1.97) for subjects in the DPI-386 Nasal Gel, TDS patch, and Placebo Nasal Gel treatment arms, respectively. The median scores at Hour 4 increased by 1.5 points from baseline in the DPI-386 Nasal Gel arm and by 2 points from baseline in the TDS patch and Placebo Nasal Gel treatment arms, while the median score change from baseline at Hour 8 was 0 in all treatment arms.

The differences between the DPI-386 Nasal Gel arm and the two control arms in raw KSS scores and in the change from baseline KSS scores were not statistically significant at any timepoint.

7.5.4. Performance Self-Assessment Questionnaire

Performance of activities was assessed using the PSAQ. See Example 8, Section 4.5.2.3.4 for a list of the statements to which the subjects were asked to respond. The number (%) of subjects who responded to each possible answer is provided.

Except for the statement "Over the past three days the medication had a positive effect on my work performance," the differences between the DPI-386 Nasal Gel arm and the Placebo Nasal Gel arm and the differences between the TDS patch arm and the Placebo Nasal Gel arm were not statistically significant. For the aforementioned statement, the difference in response distributions between the TDS patch arm and the Placebo Nasal Gel arm were statistically significant (p=0.0339) but not clinically meaningful, as the number of subjects who agreed or somewhat agreed with the statement were similar in the 2 treatment arms.

The responses to the PSAQ, taken as a whole, were favorable in terms of the effect of study medication on work performance.

7.6. Nasal Gel Device Ease of Use

Nasal Gel device ease of use data were collected using the EOUQ at Post-Treatment Day 3. See Example 8, Section 4.4.2.3.5 for a list of the statements to which the subjects were asked to respond.

A summary of responses on the Nasal Gel EOUQ is provided. In general, the responses indicated that the nasal gel device was easy to use and administer.

7.7. Prior and Concomitant Medications

A summary of prior medications taken by subjects is provided. The number (%) of subjects who were taking medication prior to the study was 1 subject (2.9%) in each treatment group.

A summary of concomitant medications taken by subjects during the study is provided in Table 14.3.14. The number (%) of subjects who took a non-study medication during the study was 1 (2.9%) in the DPI-386 Nasal Gel arm and 2 (5.9%) in the TDS patch arm.

7.8. Vital Signs, Physical Findings and Other Observations Related to Safety

The results of the evaluation of vital signs and 12-lead ECG data are presented in Example 8, Section 7.5.2.

7.9. Clinical Laboratory Evaluation

. No clinical laboratory tests were collected during the study.

7.9.1. Listing of Individual Laboratory Measurements by Subject and Each Abnormal Laboratory Value Not applicable.

7.9.2. Evaluation of Each Laboratory Parameter

Not applicable.

7.9.2.1. Laboratory Values Over Time Not applicable.

7.9.2.2. Individual Subject Changes

Not applicable.

7.9.2.3. Individual Clinically Significant Abnormalities

Not applicable.

7.10 Safety Conclusions

A total of 150 TEAEs were reported by 79 (77.5%) of the 102 subjects during the study. No deaths, SAEs, or other significant AEs were reported during the conduct of the study.

Overall, some performance fluctuations in ANAM testing (for cognition) were observed across the 6 treatment sessions that reached significance for Running Memory CPT, Matching to Sample, and both administrations of the Simple Reaction Time test (Session effect). However, the overall pattern of performance across the sessions was similar for each of the groups and did not reach significance for any of the tests (Group×Session effect).

The most common ACTS AE reported by subjects in all treatment arms on Treatment Day 1 Hour 4 and Treatment Day 1 Hour 8 was dizziness. At all later timepoints, the most common ACTS AE reported by subjects in all treatment arms was dry mouth. On Days 2 and 3, within each treatment arm there was little change from pre-dosing to any of the later timepoints in the numbers of subjects reporting ACTS AEs.

On the KSS sleepiness scale, mean (SD) changes from baseline showed a slight increase in all treatment arms at both the Hour 4 and Hour 8 timepoints on Treatment Day 1.

The responses to the PSAQ were favorable in terms of the effect of study medication on work performance.

Responses to the EOUQ indicated that the nasal gel preparation was easy to use and administer.

Data from this study demonstrated that all the products were well tolerated.

8. Discussion and Overall Conclusions 8.1. Discussion 8.1.1. Efficacy

The analysis of the primary efficacy endpoint, the proportion of subjects who developed motion sickness and requested further treatment, showed a statistically significant difference in favor of the DPI-386 arm between the DPI-386 Nasal Gel arm and the Placebo Nasal Gel arm at Treatment Day 1 Hour 4 (p=0.0471). The difference favored DPI-386 Nasal Gel at Hour 8 but was not statistically significant (p=0.0610). The difference between the DPI-386 Nasal Gel arm and the TDS patch arm was not statistically significantly different at Treatment Day 1 Hour 4 (p=0.0666) or at Hour 8 (p=0.1695).

In the secondary efficacy analyses, the differences between the DPI-386 Nasal Gel arm and the TDS patch arm and between the DPI-386 Nasal Gel arm and the Placebo Nasal Gel arm in severity of nausea (VAS) and in MSAQ composite score were not statistically significant at Treatment Day 1 Hour 4 or Treatment Day 1 Hour 8.

The difference between the DPI-386 Nasal Gel arm and the control arms in time to use of rescue medication was not statistically significant.

8.1.2. Safety

A total of 150 TEAEs were reported by 79 (77.5%) of the 102 subjects during the study.

The breakdown by treatment group is as follows:

50 TEAEs were reported by 76.5% (n=26) of 34 subjects who were administered DPI-386 Nasal Gel.

57 TEAEs were reported by 85.3% (n=29) of 34 subjects who were administered TDS patch.

43 TEAEs were reported by 70.6% (n=24) of 34 subjects who were administered Placebo Nasal Gel.

The causality assessment was judged as not related for 100 TEAEs and related for 50 TEAEs.

Cognition, as measured by ANAM, was not impaired by the treatment administered in any of the treatment arms. Some performance fluctuations were observed across the 6 treatment sessions that reached significance for Running Memory CPT, Matching to Sample, and both administrations of the Simple Reaction Time test (Session effect). However, the overall pattern of performance across the sessions was similar for each of the groups and did not reach significance for any of the tests (Group×Session effect).

In the KSS, mean (SD) changes from baseline in sleepiness scores showed a slight increase in all treatment arms at both the Hour 4 and Hour 8 timepoints on Treatment Day 1.

The most common ACTS AE reported by subjects in all treatment arms on Treatment Day 1 Hour 4 and Treatment Day 1 Hour 8 was dizziness. At all later timepoints, the most common ACTS AE reported by subjects in all treatment arms was dry mouth.

The responses to the PSAQ, taken as a whole, were favorable in terms of the effect of study medication on work performance.

The responses reported on the Nasal Gel EOUQ indicated that the nasal gel device was easy to use and administer.

Upon conclusion of the clinical portion of the study, the results from all subjects who completed post-study procedures confirmed the absence of significant changes in the subjects' state of health.

8.2. Conclusions 8.2.1. Efficacy

Subjects in the DPI-386 Nasal Gel arm had a statistically significantly lower incidence of rescue medication use than did subjects in the Placebo Nasal Gel arm at Treatment Day 1 Hour 4. There was no difference in severity of nausea as assessed by VAS or in MSAQ composite scores between the DPI-386 Nasal Gel arm and either control arm. There was no difference in time to use of rescue medication between the DPI-386 Nasal Gel arm and either control arm.

8.2.2. PK and PK/PD

Following administration of DPI-386 Nasal Gel, peak scopolamine concentrations were within the range of steady-state concentrations achieved with TDS patch; scopolamine concentrations decreased rapidly following administration of DPI-386 Nasal Gel (median $t_{1/2}$ of approximately 2 hours), whereas scopolamine concentrations were sustained near $C_{max}$ for TDS patch.

Following administration of DPI-386 Nasal Gel, scopolamine PK exposure was similar between men and women.

For DPI-386 Nasal Gel, there was no apparent relationship between scopolamine PK exposure and the occurrence of ACTS events.

For DPI-386 Nasal Gel, higher scopolamine PK exposure appeared to be associated with lower Running Memory CPT, which assesses attention, concentration, and working memory.

8.2.3. Safety

All study medications were well tolerated and no new safety signals for DPI-386 Nasal Gel were observed.

No differences in changes in cognition were observed between treatment arms. Subjects in all treatment arms showed a slight increase in sleepiness on Day 1, the only day on which sleepiness was measured. There was no difference between treatment arms on the effects of study medication on performance. The nasal gel device was easy to use and administer.

Example 9: Clinical Study DE-10-Safety in a Dose-Escalating Study

Clinical study DE-10 was an open-label, dose-escalating, non-randomized, single-center study to determine the safety of scopolamine in healthy volunteers. The primary objective was to describe the safety of scopolamine HBr in all cohorts.

This was an open-label, dose-escalating, non-randomized, single-center study to determine the safety of scopolamine in healthy volunteers. This study consisted of one screening visit, one treatment day visit, and one one-week post treatment day follow-up phone call. The study population consisted of healthy male and female subjects, aged 18 to 40 years (both inclusive). Screening evaluations were performed within 12 days before treatment day visit to determine health status of subjects.

Subjects were considered eligible for treatment phase upon the completion of screening evaluations, which included hematology, biochemistry, urinalysis, alcohol and drug screen, physical examination, including vital signs and electrocardiogram (ECG), and review of medical history by the Principal Investigator (PI) or qualified designee, serum pregnancy test (for female subjects).

Although 13 cohorts were proposed in the study protocol and cumulative amendments, the study was conducted in 100 subjects in 10 cohorts, each comprising 10 subjects. Several cohorts were not conducted for reasons described below. Cohort 5 received 4.0 ug/kg of scopolamine hydrobromide (HBr) by IV infusion, and the other cohorts received DPI-386 Nasal Gel with total scopolamine doses ranging from 0.2 to 1.2 mg. In 7 cohorts the dosage unit was 0.2 mg of scopolamine in 0.12 g of gel. This unit dose was administered 1, 2, 3 and 4 times (total doses 0.2, 0.4, 0.6 and 0.8 mg) for Cohorts 13, 1, 2 and 3, respectively, with <5 seconds between multiple applications. Furthermore Cohorts 5, 9 and 10 received 4, 5, and 6 applications of the 0.2 mg unit dose (total doses 0.8, 1.0, and 1.2 mg, respectively) with 20 minutes between applications. Cohort 6 received a single 0.8 mg dose of scopolamine, and Cohort 7 received a single 1.0 mg dose of scopolamine, both in 0.12 g of gel.

The study was planned to be conduct in 13 cohorts as per the protocol, however considering the results of other cohorts, the PI and Sponsor decided to skip Cohorts 8, 11, and 12, and not to complete Cohorts 14, 15, and 16.

A decision was made to put Cohort 8 (single 1.2 mg dose of scopolamine, in 0.12 g gel) on hold and move from Cohort 7 (1.0 mg single dose) to Cohort 9 (1.0 mg, five doses in alternating nostrils 20 minutes apart, for a total of 1.0 mg in one hour and 20 minutes).

As per Cohort 10 data evaluation by PI, 1.2 mg, six 0.2 mg doses, 20 minutes apart, in alternating nostrils, for a total of 1 hour and 40 minutes, was well tolerated by subjects in Cohort 10. The PI recommended to continue the study and to move to Cohort 13 (skipping Cohorts 11 and 12, in both of which DPI-386 nasal gel was to be delivered in a single and lower dose of 0.4 mg/0.12 g and 0.6 mg/0.12 g, respectively). Subjects in Cohort 13 received a lower single dose of 0.2 mg/0.12 g in one nostril.

Cohorts 1-4, 9-10, and 13: Each 0.12 g of the gel contains 0.2 mg of scopolamine HBr as the active ingredient along with the excipients sodium citrate, citric acid, sodium metabisulfite, glycerin, benzalkonium chloride, polyvinyl alcohol, and purified water.

Cohort 5: Scopolamine HBr Injection USP 0.4 mg/mL-1 mL vial, sterile. Each mL contains: scopolamine HBr 0.4 mg, methylparaben 0.18%, propylparaben 0.02%, water for Injection, pH adjusted with hydrobromic acid if necessary.

Cohort 6: Each 0.12 g of the gel contains 0.8 mg of scopolamine HBr as the active ingredient along with the excipients sodium citrate, citric acid, sodium metabisulfite, glycerin, benzalkonium chloride, polyvinyl alcohol, and purified water.

Cohort 7: Each 0.12 g of the gel contains 1.0 mg of scopolamine HBr as the active ingredient along with the excipients sodium citrate, citric acid, sodium metabisulfite, glycerin, benzalkonium chloride, polyvinyl alcohol, and purified water.

Approximately 60 minutes after arriving at the clinic on Treatment Day, subjects received either single or multiple doses of 0.2 mg or a single dose of 0.4 mg, 0.6 mg, 0.8 mg, 1.0 mg, or 1.2 mg of DPI-386 Nasal Gel or 0.4 mg/mL IV scopolamine per the assigned treatment cohort.

Subjects were self-administered DPI-386 Nasal Gel per the following cohort dosages (self-administration of the study drug was supervised by research staff): Cohort 1-0.4 mg (two 0.2 mg doses, one in each nostril); Cohort 2-0.6 mg (three 0.2 mg doses alternating nostrils); Cohort 3-0.8 mg (four 0.2 mg doses alternating nostrils); Cohort 4-0.8 mg (four 0.2 mg doses alternating nostrils, 20 minutes apart) for a total of 0.8 mg in one hour; Cohort 6-0.8 mg (one dose, one nostril); Cohort 7-1.0 mg (one dose, one nostril); Cohort 9-1.0 mg (five 0.2 mg doses alternating nostrils, 20 minutes apart) for a total of 1.0 mg in one hour and 20 minutes; Cohort 10-1.2 mg (six 0.2 mg doses alternating nostrils, 20 minutes apart) for a total of 1.2 mg in one hour and 40 minutes; and Cohort 13-0.2 mg (one dose, one nostril).

Subjects assigned to Cohort 5 were administered 4.0 g/kg of scopolamine HBr via a 15-minutes IV infusion by research staff. The dose of IV Scopolamine used in Cohort 5 was determined independently of enrolment into Cohorts 1-4, and 6-13, or the safety results for those cohorts. Dose escalation to Cohorts 2-4, 6-7, and 13 was based on safety events from the preceding DPI-386 Nasal Gel cohort and per gender. Dose escalation for Cohorts 9 and 10 was based on safety events from Cohort 4. Subjects were monitored for 8 hours after last dose. A follow-up call was done one-week post treatment visit.

Vital signs were performed during the study as follows: Cohorts 1-3, 6-7, and 13: Pre-dose (within 60 minutes prior to first dose), 5, 10, 15, 20, 30, 40, 50, 60, 75, 90, 120, 180, 240, 360, and 480 minutes after first dose; Cohort 4: Pre-dose (within 60 minutes prior to first dose), 5, 10, 15, 20, 30, 40, 50, 60, 75, 90, 120, 180, 240, 360, 480, and 540 minutes after first dose; Cohort 5: Pre-dose (within 60 minutes prior to first dose), 5, 10, 15 (end of infusion), 20, 30, 40, 50, 60, 75, 90, 120, 180, 240, 360, and 495 minutes after first dose; Cohort 9: Pre-dose (within 60 minutes prior to first dose), 5, 10, 15, 20, 30, 40, 50, 60, 75, 90, 120, 180, 240, 360, 480, 540, and 560 minutes after first dose; and Cohort 10: Pre-dose (within 60 minutes prior to first dose), 5, 10, 15, 20, 30, 40, 50, 60, 75, 90, 120, 180, 240, 360, 480, 540, and 580 minutes after first dose.

ECG was performed during the study as follows: Cohorts 1-3, 6-7, and 13: Pre-dose (within 60 minutes prior to first dose), 15, 30, 60, 90, 120, and 480 minutes after first dose; Cohorts 4: Pre-dose (within 60 minutes prior to first dose), 15, 30, 60, 90, 120, and 540 minutes after first dose; Cohorts 5: Pre-dose (within 60 minutes prior to first dose), 15, 30, 60, 90, 120, and 495 minutes after first dose; Cohorts 9: Pre-dose (within 60 minutes prior to first dose), 15, 30, 60, 90, 120, and 560 minutes after first dose; and Cohorts 10: Pre-dose (within 60 minutes prior to first dose), 15, 30, 60, 90, 120, and 580 minutes after first dose. The acceptable window for vital signs and ECG time points was −15 minutes to +5 minutes. Statistical analysis was carried out using SAS® Version 9.4 (SAS Institute Inc., USA) to assess the efficacy and safety end points.

Number of Subjects (Planned and Analyzed):

One hundred and thirty subjects in 13 cohorts (5 males/5 females in each cohort), between the ages of 18 and 40 (inclusive) were to be enrolled in the study. A total of 100 subjects in 10 cohorts-Cohorts 1, 2, 3, 4, 5, 6, 7, 9, 10, and 13 (5 males/5 females in each cohort) were actually enrolled in the study.

Diagnosis and Main Criteria for Inclusion

In order to be eligible to participate in this study, an individual met all of the following criteria: provision of a signed and dated informed consent form (ICF); stated willingness to comply with all study procedures and availability for the duration of the study; male or female, aged 18 to 40 (inclusive); males and females must agree to use highly effective contraception (e.g. double barrier method) for 4 weeks after receiving the last dose of treatment; have a body mass index (BMI) within a range of 18 to 30 inclusive; in good general health as evidenced by medical history with no recent history or current diagnosis of significant cardiovascular or respiratory problems as assessed by the PI or qualified designee; hematology, biochemistry, urinalysis and drug and alcohol laboratory test results that are determined by the PI or qualified designee to be not clinically significant; ability to take intranasal medication (for Cohorts 1-4, and 6-13 only) and willingness to adhere to the study schedule and time constraints; for females of childbearing potential: willingness to provide a sample for the pregnancy test upon every visit (test must be negative); and agreement to adhere to the following lifestyle compliance considerations: refrain from consumption of grapefruit and any substance containing grapefruit for seven days prior to, during, and for seven days after the treatment day; caffeine intake limited to 300 mg on treatment day (two 8-ounce cups); abstain from alcohol for 24 hours prior to first dose of study medication; and refrain from any type of nicotine within 30 days prior to the screening visit and through the completion of the treatment day.

Investigational Medicinal Product

DPI-386 Nasal Gel—Active content: Scopolamine HBr

Strength: Cohorts 1-4, 9-10, and 13: Each 0.12 g of the gel contains 0.2 mg of scopolamine HBr; Cohort 5: Scopolamine HBr Injection USP 0.4 mg/mL-1 mL vial, sterile Cohort 6: Each 0.12 g of the gel contains 0.8 mg of scopolamine HBr; and Cohort 7: Each 0.12 g of the gel contains 1.0 mg of scopolamine HBr.

Dosage Regimen: Cohort 1-0.4 mg (two 0.2 mg doses, one in each nostril); Cohort 2-0.6 mg (three 0.2 mg doses alternating nostrils); Cohort 3-0.8 mg (four 0.2 mg doses alternating nostrils); Cohort 4-0.8 mg (four 0.2 mg doses alternating nostrils, 20 minutes apart) for a total of 0.8 mg in 1 hour; Cohort 5-4.0 μg/kg of scopolamine HBr via a 15-minutes IV infusion; Cohort 6-0.8 mg (one dose, one nostril); Cohort 7-1.0 mg (one dose, one nostril); Cohort 9-1.0 mg (five 0.2 mg doses alternating nostrils, 20 minutes apart) for a total of 1.0 mg in 1 hour and 20 minutes; Cohort 10-1.2 mg (six 0.2 mg doses alternating nostrils, 20 minutes apart) for a total of 1.2 mg in 1 hour and 40 minutes; and Cohort 13-0.2 mg (one dose, one nostril).

Route of administration: Intranasal and IV infusion (Cohort 5)

Storage: DPI-386 Nasal Gel and IV Scopolamine HBr Injection USP 0.4 mg/mL, stored at 15° C. to 30° C., inclusive (59° F. to 86° F., inclusive).

Duration of Treatment

The total duration of the study consists of screening visit (within 12 days prior to treatment day visit), treatment day visit and one-week post treatment day follow-up phone call.

Criteria for Evaluation

Safety Evaluations

Safety assessments included ECGs and vital signs, which were monitored at regular intervals, including blood pressure, pulse rate, respirations and temperature and laboratory assessment and recording of adverse events (AEs). The 10 study also provided data on QT syndrome, where all cohorts were negative, thus supporting no QT prolongation.

Study Endpoints

Primary Safety Endpoint

Safety was evaluated in terms of AEs, including AEs of special interest (AESIs). AESIs included all symptoms listed for the Anticholinergic Toxicity Screen (ACTS). These AEs were considered significant because they are expected anticholinergic effects of scopolamine, and it was considered important that the PI and medical monitors assess their severity and relatedness in an expedited manner. The potential association of these events with clinically significant changes in heart rate or rhythm, blood pressure, and EKG parameters, were monitored. For that purpose, hypotension was added to the list.

Statistical Analysis

SAS® Version 9.4 (SAS Institute Inc., USA) was used to generate data displays. All study data were included in individual subject data listings and data were summarized and plotted.

Disposition of Subjects

Subject disposition was summarized by cohort and overall and included the number and percentage of subjects. Individual reasons for withdrawal and protocol deviations were presented in listings for all enrolled subjects.

Protocol Deviations

All protocol deviations were reviewed and finalized prior to database lock and were presented by in a data listing by cohort group and subject. All protocol deviations were listed by subject for all population.

Demographic and Other Baseline Characteristics

Demographic variables including age, sex, ethnicity, and race were summarized for the Safety populations. Age was summarized using descriptive statistics while race and ethnicity were summarized by counts and percentages, for the enrolled population.

Primary Safety Analysis

Safety analysis was carried out for the Safety population and included all subjects who received at least 1 dose of study drug.

Safety Results

Primary Safety Endpoints

A total of 6 pre-dose AEs were reported by 5 subjects during the study. All AEs were mild in nature and the subjects were followed up until resolution of their AEs. The causality assessment was judged as not related for all AEs.

Post-dose Adverse Events

A total of 106 treatment emergent adverse events (TEAEs) were reported by 53 (53.0%) of the 100 subjects during the study. There were: 2 AEs in Cohort 1; 4 AEs in Cohort 2; 3 AEs in Cohort 3; 11 AEs in Cohort 4; 25 AEs Cohort 5; 11 AEs in Cohort 6; 24 AEs in Cohort 7; 9 AEs in Cohort 9; and 13 AEs in Cohort 10.

Of the 106 TEAEs, 96 AEs were mild in nature and 10 AEs were moderate in nature. All the subjects were followed up until resolution of their AEs. The causality assessment was judged as definitely related for 1 AE, as possibly related for 16 AEs, as probably related for 88 AEs and as remotely related for 1 AE. There were no deaths or serious adverse events (SAEs) reported during the study. No subjects were discontinued from the study due to an adverse event.

Out of 106 TEAEs, 35 AEs were reported as AESIs. Of these 35 AEs, 17 AEs (viz. Dizziness), 3 AEs (viz. Hypotension), 2 AEs (viz. Vision blurred) and 1 AE (viz. Photophobia) were "Significant, Non-serious" and 12 AEs (viz. Dry mouth) were "Non-significant, Non-serious." The AEs are summarized by system organ class (SOC) and preferred term in Table 9a, below.

TABLE 9a

Safety Analysis: Treatment Emergent Adverse Events by System Organ Class and Preferred Term, Safety Population

| System Organ Class Preferred Term | Statistics | Total of All Cohorts (N = 100) |
|---|---|---|
| Eye Disorders | n (%) E | 6 (6.0) 7 |
| Asthenopia | n (%) E | 2 (2.0) 2 |
| Lacrimation Increased | n (%) E | 1 (1.0) 1 |
| Mydriasis | n (%) E | 3 (3.0) 3 |
| Photophobia | n (%) E | 1 (1.0) 1 |
| Gastrointestinal Disorders | n (%) E | 15 (15.0) 17 |
| Dry Mouth | n (%) E | 13 (13.0) 13 |
| Dry Throat | n (%) E | 1 (1.0) 1 |
| Taste Disorder | n (%) E | 3 (3.0) 3 |
| General Disorders and Administration Site Conditions | n (%) E | 11 (11.0) 12 |
| Asthenia | n (%) E | 1 (1.0) 1 |
| Fatigue | n (%) E | 7 (7.0) 7 |
| Gait Disturbance | n (%) E | 2 (2.0) 2 |
| Irritability | n (%) E | 1 (1.0) 1 |
| Lethargy | n (%) E | 1 (1.0) 1 |
| Investigations | n (%) E | 1 (1.0) 1 |
| Electrocardiogram Abnormal | n (%) E | 1 (1.0) 1 |
| Nervous System Disorders | n (%) E | 34 (34.0) 37 |
| Coordination Abnormal | n (%) E | 1 (1.0) 1 |
| Headache | n (%) E | 1 (1.0) 1 |
| Restlessness | n (%) E | 1 (1.0) 1 |
| Somnolence | n (%) E | 31 (31.0) 32 |
| Vision Blurred | n (%) E | 2 (2.0) 2 |
| Respiratory, Thoracic and Mediastinal Disorders | n (%) E | 10 (10.0) 11 |
| Choking Sensation | n (%) E | 1 (1.0) 1 |
| Nasal Discomfort | n (%) E | 2 (2.0) 2 |
| Nasal Dryness | n (%) E | 1 (1.0) 1 |
| Oropharyngeal Pain | n (%) E | 1 (1.0) 1 |
| Sneezing | n (%) E | 5 (5.0) 5 |
| Throat Irritation | n (%) E | 1 (1.0) 1 |
| Skin And Subcutaneous Tissue Disorders | n (%) E | 1 (1.0) 1 |
| Paraesthesia | n (%) E | 1 (1.0) 1 |
| Vascular Disorders | n (%) E | 18 (18.0) 20 |
| Dizziness | n (%) E | 17 (17.0) 17 |
| Hypotension | n (%) E | 3 (3.0) 3 |

E: Number of events; N: Number of subjects dosed; n: Number of subjects with adverse event with particular category; %: Calculated using the number of subjects treated with each treatment as the denominator (n/N)*100.

Safety Conclusions

A total of 106 TEAEs were reported by 53 (53.0%) of the 100 subjects during the study. There were no deaths or SAEs reported during conduct of the study. No subjects were discontinued from the study due to an adverse event. Data from this study demonstrated that the DPI-386 Nasal Gel of the present disclosure was well tolerated.

Unbound Scopolamine

Figure 9:
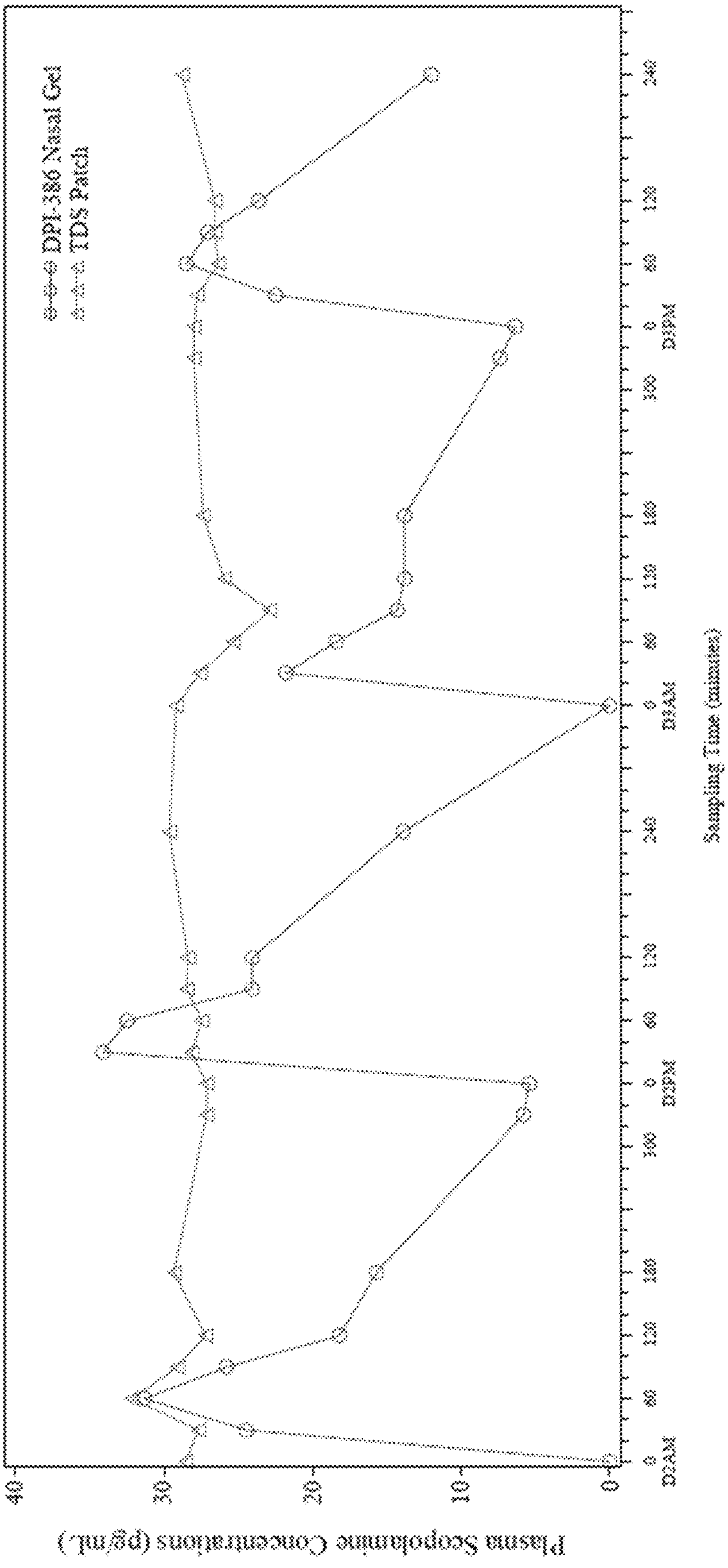
FIG. 9 is a graphic illustration of the profile for median plasma unbound scopolamine concentration vs time. Doses of nasal gel were administered 6 hours apart on Days 1-3 and 18 hours apart between days. Scopolamine PK samples were collected relative to administration of nasal gel (present DPI-386 or placebo) on Days 2 and 3. For subjects receiving TDS patch (+Placebo Nasal Gel), PK sampling started approximately 24 hours and ended approximately 58 hours after application of the patch.

FIG. 9 provides a graphic illustration of the median plasma unbound scopolamine concentration over time.

TABLE 9b

Summary of Total and Free Scopolamine PK Parameters and Calculated Free Fractions Following Single Doses of DPI-386 Gel (GLM and GLM % CV)

| | | Unbound PK Parameter | | Total PK Parameter | | Free Fraction PK Parameter | |
|---|---|---|---|---|---|---|---|
| Study | Dose (mg) | AUC(0-t) (min*pg/mL) | Cmax (pg/mL) | AUC(0-t) (min*pg/mL) | Cmax (pg/mL) | $AUC_{free}$ | $Cmax_{free}$ |
| DPI-386- | 0.2 | 6,143 | 39.1 | 15,400 | 92.3 | 0.398 | 0.425 |
| DE-10 | [9] | (68) | (75) | (68) | (71) | (6) | (12) |
| | 0.4 | 11,355 | 85.4 | 27,652 | 156 | 0.410 | 0.423 |
| | [10] | (80) | (96) | (83) | (100) | (7) | (10) |
| | 0..6 | 19,117 | 116 | 47,850 | 286 | 0.399 | 0.405 |
| | [10] | (45) | (45) | (46) | (46) | (7) | (11) |
| | 0.8 | 15,319 | 95.0 | 40,239 | 233 | 0.380 | 0.408 |
| | [10] | (77) | (111) | (70) | (107) | (6) | (9) |
| | 1.0 | 37,677 | 241 | 90,261 | 536 | 0.396 | 0.441 |
| | [10] | (87) | (108) | (83) | (99) | (9) | (11) |
| | 1.2 | 47,508 | 193 | 135,930 | 509 | 0.347 | 0.379 |
| | [9] | (123) | (114) | (123) | (116) | (46) | (32) |
| DPI-386- | 0.2 | 4,750 | 32.6 | 13,148 | 84.6 | 0.386 | 0.361 |
| MS-22 | [27] | (123) | (143) | (96) | (136) | (25) | (24) |

TABLE 9c

Summary of Plasma Unbound Scopolamine Concentrations; PK Parameter; Treatment: DPI-386 Nasal Gel

| AM/PM | Statistics | PRE-DOSE | 30 MINS | 60 MINS | 90 MINS | 120 MINS |
|---|---|---|---|---|---|---|
| D 2AM | N | 28 | 29 | 29 | 27 | 27 |
| | nBLQ | 19 | 2 | 0 | 0 | 0 |
| | Mean (SD) | 7.50 (25.556) | 38.49 (45.310) | 41.07 (33.123) | 30.17 (23.393) | 22.40 (15.969) |
| | CV (%) | 340.8 | 117.7 | 80.6 | 77.5 | 71.3 |
| | Median | 0.00 | 24.50 | 31.30 | 25.80 | 18.20 |
| | Min, Max | 0.0, 126.0 | 0.0, 184.0 | 2.5, 120.0 | 2.9, 91.0 | 2.7, 56.5 |
| D 2PM | N | 28 | 28 | 27 | 27 | 27 |
| | nBLQ | 3 | 1 | 1 | 1 | 2 |
| | Mean (SD) | 7.64 (5.833) | 41.71 (32.807) | 42.86 (35.138) | 35.97 (27.924) | 31.25 (25.705) |
| | CV (%) | 76.3 | 78.6 | 82.0 | 77.6 | 82.2 |
| | Median | 5.46 | 34.15 | 32.50 | 24.10 | 24.10 |
| | Min, Max | 0.0, 24.5 | 3.7, 127.0 | 4.6, 158.0 | 8.4, 123.0 | 7.7, 112.0 |
| D 3AM | N | 29 | 28 | 27 | 23 | 26 |
| | nBLQ | 17 | 3 | 2 | 2 | 1 |
| | Mean (SD) | 2.06 (3.218) | 29.27 (31.347) | 32.32 (32.051) | 23.19 (22.227) | 21.20 (20.663) |
| | CV (%) | 156.4 | 107.1 | 99.2 | 95.8 | 97.5 |
| | Median | 0.00 | 21.85 | 18.50 | 14.30 | 13.80 |
| | Min, Max | 0.0, 13.2 | 0.0, 141.0 | 2.9, 108.0 | 2.1, 87.8 | 3.0, 80.6 |
| D 3PM | N | 27 | 24 | 25 | 25 | 24 |
| | nBLQ | 2 | 2 | 1 | 1 | 1 |
| | Mean (SD) | 7.77 (6.524) | 28.47 (21.668) | 33.27 (28.431) | 32.59 (30.383) | 27.37 (25.525) |
| | CV (%) | 84.0 | 76.1 | 85.5 | 93.2 | 93.2 |
| | Median | 6.37 | 22.55 | 28.50 | 27.10 | 23.65 |
| | Min, Max | 0.0, 28.3 | 2.4, 88.2 | 2.9, 116.0 | 2.6, 124.0 | 3.3, 108.0 |

Note:

For the calculation of descriptive statistics, concentrations that are BLQ are set to 0 prior to the first measurable concentration and set to missing for the rest.

Note:

Doses of nasal gel were administered 6 hours apart on Days 1-3; doses were administered 18 hours apart between days.

Note:

Scopolamine PK samples were collected relative to administration of nasal gel (DPI-386 or placebo) on Days 2 and 3.

Note:

For subjects receiving TDS (+placebo nasal gel), PK sampling started approximately 24 hours and ended approximately 58 hours after application of the patch.

Note:

Subjects 1004 (all visits), 1044 (all visits), 1053 (all visits), 1067 (Day 2 AM dose), 1023 (Day 3 PM Dose), and 1073 (Day 3 PM dose) were excluded from concentration summaries because all or most (>86%) of the concentrations were BLOQ.

Table Generation: 28 Dec. 2021 22:34 Program source: t_adpc.sas

FIG. 9 is a graphic illustration of the profile for median plasma unbound scopolamine concentration vs time. Doses of nasal gel were administered 6 hours apart on Days 1-3 and 18 hours apart between days. Scopolamine PK samples were collected relative to administration of nasal gel (present DPI-386 or placebo) on Days 2 and 3. For subjects receiving TDS patch (+Placebo Nasal Gel), PK sampling started approximately 24 hours and ended approximately 58 hours after application of the patch.

Numbered Embodiments

The following numbered embodiments offer additional description of the present disclosure:

1. An intranasal pharmaceutical composition for the prevention of one or more of nausea and emesis related to motion, comprising a pharmaceutically acceptable salt of scopolamine, wherein administration of the composition to a human subject results in a Cmax (pg/mL) of free scopolamine that approximates a transdermal administration.
2. The intranasal pharmaceutical composition of embodiment 1, wherein the Cmax is measured with a 90% confidence interval which is 80% to 125% of a least squares geometric mean of between about 160 pg/mL to 60 pg/mL.
3. The intranasal pharmaceutical composition of embodiment 1 or 2, wherein the Cmax is measured with a 90% confidence interval which is 80% to 125% of a least squares geometric mean of between about 140 pg/mL to 80 pg/mL.
4. The intranasal pharmaceutical composition of any one of embodiments 1 to 3, wherein the Cmax is measured with a 90% confidence interval which is 80% to 125% of a least squares geometric mean of between about 120 pg/mL to 80 pg/mL.
5. The intranasal pharmaceutical composition of any one of embodiments 1 to 4, wherein the Cmax is measured with a 90% confidence interval which is 80% to 125% of a least squares geometric mean of between about 100 pg/mL to 80 pg/mL.
6. The intranasal pharmaceutical composition of any one of embodiments 1 to 5, wherein the Cmax is measured with a 90% confidence interval which is 80% to 125% of a least squares geometric mean of about 87 pg/mL.
7. The intranasal pharmaceutical composition of any one of embodiments 1 to 3, wherein the Cmax is measured with a 90% confidence interval which is 80% to 125% of a least squares geometric mean of about 137 pg/mL.
8. An intranasal pharmaceutical composition for the treatment of one or more symptoms associated with nausea or emesis related to motion, comprising a pharmaceutically acceptable salt of scopolamine, wherein administration of the composition to a human subject results in a Cmax (pg/mL) of free scopolamine that approximates a transdermal administration.
9. The intranasal pharmaceutical composition of embodiment 8, wherein the Cmax is measured with a 90% confidence interval which is 80% to 125% of a least squares geometric mean of between about 160 pg/mL to 60 pg/mL.
10. The intranasal pharmaceutical composition of embodiment 8 or 9, wherein the Cmax is measured with a 90% confidence interval which is 80% to 125% of a least squares geometric mean of between about 140 pg/mL to 80 pg/mL.
11. The intranasal pharmaceutical composition of any one of embodiments 8 to 10, wherein the Cmax is measured with a 90% confidence interval which is 80% to 125% of a least squares geometric mean of between about 120 pg/mL to 80 pg/mL.
12. The intranasal pharmaceutical composition of any one of embodiments 8 to 11, wherein the Cmax is measured with a 90% confidence interval which is 80% to 125% of a least squares geometric mean of between about 100 pg/mL to 80 pg/mL.
13. The intranasal pharmaceutical composition of any one of embodiments 8 to 12, wherein the Cmax is measured with a 90% confidence interval which is 80% to 125% of a least squares geometric mean of about 87 pg/mL.
14. The intranasal pharmaceutical composition of any one of embodiments 8 to 12, wherein the Cmax is measured with a 90% confidence interval which is 80% to 125% of a least squares geometric mean of about 137 pg/mL.
15. An intranasal pharmaceutical composition for the prevention of one or more of nausea and emesis related to motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean of between about 160 pg/mL to about 60 pg/mL.
16. The intranasal pharmaceutical composition of embodiment 15, wherein the least squares geometric mean is between about 140 pg/mL to 80 pg/mL.
17. The intranasal pharmaceutical composition of embodiment 15 or 16, wherein the least squares geometric mean is between about 137 pg/mL to about 87 pg/mL.
18. An intranasal pharmaceutical composition for the treatment of one or more of nausea and emesis related to motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean of between about 160 pg/mL to about 60 pg/mL.
19. The intranasal pharmaceutical composition of embodiment 18, wherein the least squares geometric mean is between about 140 pg/mL to 80 pg/mL.
20. The intranasal pharmaceutical composition of embodiment 18 or 19, wherein the least squares geometric mean is between about 137 pg/mL to about 87 pg/mL.
21. An intranasal pharmaceutical composition for the prevention of one or more of nausea and emesis related to motion, comprising a pharmaceutically acceptable salt of scopolamine, wherein administration of the composition to a human subject results in a Cmax of free scopolamine with a 90% confidence interval which is 80% to 125% of a least squares geometric mean of less than about 160 pg/mL following administration.
22. The intranasal pharmaceutical composition of embodiment 21, wherein the least squares geometric mean is greater than about 60 pg/mL.
23. The intranasal pharmaceutical composition of embodiment 21 or 22, wherein the least squares geometric mean is about 155, 150, 145, 140, 135, 130, 125, 120, 115, 110, 105, 100, 95, 90, 85, 80, 75, 70, 65, or 60 pg/mL.
24. An intranasal pharmaceutical composition for the treatment of one or more of nausea and emesis related to motion, comprising a pharmaceutically acceptable salt of scopolamine, wherein administration of the composition to a human subject results in a Cmax of free scopolamine with a 90% confidence interval which is 80% to 125% of a least squares geometric mean of less than about 160 pg/mL following administration.

25. The intranasal pharmaceutical composition of embodiment 24, wherein the least squares geometric mean is greater than about 60 pg/mL.

26. The intranasal pharmaceutical composition of embodiment 24 or 25, wherein the least squares geometric mean is about 155, 150, 145, 140, 135, 130, 125, 120, 115, 110, 105, 100, 95, 90, 85, 80, 75, 70, 65, or 60 pg/mL.

27. An intranasal pharmaceutical composition for the prevention of nausea and emesis related to motion, comprising a pharmaceutically acceptable salt of scopolamine, wherein administration of the composition to a human subject results in a least squares geometric mean Cmax of free scopolamine of from about 160 pg/mL to about 60 pg/mL.

28. The intranasal pharmaceutical composition of embodiment 27, wherein the least squares geometric mean Cmax of free scopolamine is of from about 150 pg/mL to about 70 pg/mL.

29. The intranasal pharmaceutical composition of embodiment 27 or 28, wherein the least squares geometric mean Cmax of free scopolamine is of from about 140 pg/mL to about 80 pg/mL.

30. The intranasal pharmaceutical composition of embodiment 29, wherein the least squares geometric mean Cmax of free scopolamine is of from about 137 pg/mL to about 87 pg/mL.

31. An intranasal pharmaceutical composition for the prevention of one or more of nausea and emesis related to motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean of from about 160 pg/mL to about 80 pg/mL.

32. The intranasal pharmaceutical composition of embodiment 31, wherein the least squares geometric mean is about 137 pg/mL.

33. The intranasal pharmaceutical composition of embodiment 31, wherein the least squares geometric mean is about 87 pg/mL.

34. An intranasal pharmaceutical composition for the treatment of one or more of nausea and emesis related to motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean of from about 160 pg/mL to about 90 pg/mL.

35. The intranasal pharmaceutical composition of embodiment 34, wherein the least squares geometric mean is about 137 pg/mL.

36. The intranasal pharmaceutical composition of embodiment 34, wherein the least squares geometric mean is about 87 pg/mL.

37. An intranasal pharmaceutical composition for the prevention of one or more of nausea and emesis related to motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean of about 137 pg/mL.

38. An intranasal pharmaceutical composition for the treatment of one or more of nausea and emesis related to motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean of about 137 pg/mL.

39. An intranasal pharmaceutical composition for the prevention of one or more of nausea and emesis related to motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean of about 87 pg/mL.

40. An intranasal pharmaceutical composition for the treatment of one or more of nausea and emesis related to motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean of about 87 pg/mL.

41. An intranasal pharmaceutical composition for the prevention of nausea and emesis related to motion, comprising a pharmaceutically acceptable salt of scopolamine, wherein administration of the composition to a human subject results in an AUC selected from one or more of AUC3d, AUCinf, AUCt, and AUCtau with a 90% confidence interval (CI) which is 80% to 125% of a least squares geometric mean that approximates a transdermal administration.

42. An intranasal pharmaceutical composition for the treatment of nausea and emesis related to motion, comprising a pharmaceutically acceptable salt of scopolamine, wherein administration of the composition to a human subject results in an AUC selected from one or more of AUC3d, AUCinf, AUCt, and AUCtau with a 90% confidence interval (CI) which is 80% to 125% of a least squares geometric mean that approximates a transdermal administration.

43. The intranasal pharmaceutical composition of embodiment 41 or 42, wherein the AUC is AUC3d and the least squares geometric mean is about 155,937 min*pg/mL.

44. The intranasal pharmaceutical composition of embodiment 41 or 42, wherein the AUC is AUCinf and the least squares geometric mean is about 26305 min*pg/mL.

45. The intranasal pharmaceutical composition of embodiment 41 or 42, wherein the AUC is AUCt and the least squares geometric mean is about 18545 min*pg/mL to about 26532 min*pg/mL.

46. The intranasal pharmaceutical composition of embodiment 41 or 42, wherein the AUC is AUCtau and the least squares geometric mean is about 18624 min*pg/mL to about 29120 min*pg/mL.

47. An intranasal pharmaceutical composition for the prevention of nausea and emesis related to motion, comprising a pharmaceutically acceptable salt of scopolamine, wherein administration of the composition to a human subject results in an AUC3d of free scopolamine with a 90% confidence interval (CI) which is 80% to 125% of a least squares geometric mean of about 155,937 min*pg/mL.

48. An intranasal pharmaceutical composition for the prevention of nausea and emesis related to motion, comprising a pharmaceutically acceptable salt of scopolamine, wherein administration of the composition to a human subject results in an AUC0-inf of free scopolamine with a 90% confidence interval (CI) which is 80% to 125% of a least squares geometric mean of about 26305 min*pg/mL following administration.

49. An intranasal pharmaceutical composition for the prevention of nausea and emesis related to motion, comprising a pharmaceutically acceptable salt of scopolamine, wherein administration of the composition to a human subject results in an AUCt of free scopolamine with a 90% confidence interval (CI) which is 80% to 125% of a least squares geometric mean of from about 18545 min*pg/mL to about 26532 min*pg/mL following administration.

50. An intranasal pharmaceutical composition for the prevention of nausea and emesis related to motion, comprising a pharmaceutically acceptable salt of scopolamine, wherein administration of the composition to a human subject results in an AUCtau of free scopolamine with a 90% confidence interval (CI) which is 80% to 125% of a least squares geometric mean of from about 18624 min*pg/mL to about 29120 min*pg/mL following administration.

51. An intranasal pharmaceutical composition for the treatment of nausea and emesis related to motion, comprising a pharmaceutically acceptable salt of scopolamine, wherein administration of the composition to a human subject results in an AUC3d of free scopolamine with a 90% confidence interval (CI) which is 80% to 125% of a least squares geometric mean of about 155,937 min*pg/mL.

52. An intranasal pharmaceutical composition for the treatment of nausea and emesis related to motion, comprising a pharmaceutically acceptable salt of scopolamine, wherein administration of the composition to a human subject results in an AUC0-inf of free scopolamine with a 90% confidence interval (CI) which is 80% to 125% of a least squares geometric mean of about 26305 min*pg/mL following administration.

53. An intranasal pharmaceutical composition for the treatment of nausea and emesis related to motion, comprising a pharmaceutically acceptable salt of scopolamine, wherein administration of the composition to a human subject results in an AUCt of free scopolamine with a 90% confidence interval (CI) which is 80% to 125% of a least squares geometric mean of from about 18545 min*pg/mL to about 26532 min*pg/mL following administration.

54. An intranasal pharmaceutical composition for the treatment of nausea and emesis related to motion, comprising a pharmaceutically acceptable salt of scopolamine, wherein administration of the composition to a human subject results in an AUCtau of free scopolamine with a 90% confidence interval (CI) which is 80% to 125% of a least squares geometric mean of from about 18624 min*pg/mL to about 29120 min*pg/mL following administration.

55. An intranasal pharmaceutical composition for the prevention of nausea and emesis related to motion, comprising a pharmaceutically acceptable salt of scopolamine, wherein administration of the composition to a human subject results in an AUC3d of free scopolamine with a 90% confidence interval which is 80% to 125% of a least squares geometric mean of less than about 182,116 min*pg/mL following administration.

56. An intranasal pharmaceutical composition for the prevention of nausea and emesis related to motion, comprising a pharmaceutically acceptable salt of scopolamine, wherein administration of the composition to a human subject results in an AUC3d of free scopolamine of from about 91,058 min*pg/mL to about 182,116 min*pg/mL following administration.

57. An intranasal pharmaceutical composition for the treatment of nausea and emesis related to motion, comprising a pharmaceutically acceptable salt of scopolamine, wherein administration of the composition to a human subject results in an AUC3d of free scopolamine with a 90% confidence interval which is 80% to 125% of a least squares geometric mean of less than about 182,116 min*pg/mL following administration.

58. An intranasal pharmaceutical composition for the treatment of nausea and emesis related to motion, comprising a pharmaceutically acceptable salt of scopolamine, wherein administration of the composition to a human subject results in an AUC3d of free scopolamine of from about 91,058 min*pg/mL to about 182,116 min*pg/mL following administration.

59. An intranasal pharmaceutical composition for the prevention of symptoms associated with motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean that approximates a transdermal administration.

60. An intranasal pharmaceutical composition for the treatment of symptoms associated with motion, comprising a pharmaceutically acceptable salt of scopolamine, wherein administration of the composition to a human subject results in a Cmax (pg/mL) of free scopolamine with a 90% confidence interval which is 80% to 125% of a least squares geometric mean that approximates a transdermal administration.

61. The intranasal pharmaceutical composition of embodiment 59 or 60, wherein the least squares geometric mean is less than about 160 pg/mL.

62. The intranasal pharmaceutical of any one of embodiments 59 to 61, wherein the least squares geometric mean is of from about 160 pg/mL to about 60 pg/mL.

63. The intranasal pharmaceutical composition of embodiment 62, wherein the least squares geometric mean is about 155, 150, 145, 140, 135, 130, 125, 120, 115, 110, 105, 100, 95, 90, 85, 80, 75, 70, 65, or 60 pg/mL.

64. An intranasal pharmaceutical composition for the prevention of symptoms associated with motion, comprising a pharmaceutically acceptable salt of scopolamine, wherein administration of the composition to human subject results in an AUC selected from one or more of AUC3d, AUCinf, AUCt, and AUCtau with a 90% confidence interval (CI) which is 80% to 125% of a least squares geometric mean that approximates a transdermal administration.

65. An intranasal pharmaceutical composition for the treatment of symptoms associated with motion, comprising a pharmaceutically acceptable salt of scopolamine, wherein administration of the composition to a human subject results in an AUC selected from one or more of AUC3d, AUCinf, AUCt, and AUCtau with a 90% confidence interval (CI) which is 80% to 125% of a least squares geometric mean that approximates a transdermal administration.

66. The intranasal pharmaceutical composition of embodiment 64 or 65, wherein the AUC is AUC3d and the least squares geometric mean is about 155,937 min*pg/mL.

67. The intranasal pharmaceutical composition of embodiment 64 or 65, wherein the AUC is AUCinf and the least squares geometric mean is about 26305 min*pg/mL.
68. The intranasal pharmaceutical composition of embodiment 64 or 65, wherein the AUC is AUCt and the least squares geometric mean is about 18545 min*pg/mL to about 26532 min*pg/mL.
69. The intranasal pharmaceutical composition of embodiment 64 or 65, wherein the AUC is AUCtau and the least squares geometric mean is about 18624 min*pg/mL to about 29120 min*pg/mL.
70. An intranasal pharmaceutical composition for the prevention of symptoms associated with motion, comprising a pharmaceutically acceptable salt of scopolamine, wherein administration of the composition to a human subject results in an AUC3d of free scopolamine with a 90% confidence interval (CI) which is 80% to 125% of a least squares geometric mean of about 155,937 min*pg/mL.
71. An intranasal pharmaceutical composition for the prevention of symptoms associated with motion, comprising a pharmaceutically acceptable salt of scopolamine, wherein administration of the composition to a human subject results in an AUC0-inf of free scopolamine with a 90% confidence interval (CI) which is 80% to 125% of a least squares geometric mean of about 26305 min*pg/mL following administration.
72. An intranasal pharmaceutical composition for the prevention of symptoms associated with motion, comprising a pharmaceutically acceptable salt of scopolamine, wherein administration of the composition to a human subject results in an AUCt of free scopolamine with a 90% confidence interval (CI) which is 80% to 125% of a least squares geometric mean of from about 18545 min*pg/mL to about 26532 min*pg/mL following administration.
73. An intranasal pharmaceutical composition for the prevention of symptoms associated with motion, comprising a pharmaceutically acceptable salt of scopolamine, wherein administration of the composition to a human subject results in an AUCtau of free scopolamine with a 90% confidence interval (CI) which is 80% to 125% of a least squares geometric mean of from about 18624 min*pg/mL to about 29120 min*pg/mL following administration.
74. An intranasal pharmaceutical composition for the treatment of symptoms associated with motion, comprising a pharmaceutically acceptable salt of scopolamine, wherein administration of the composition to a human subject results in an AUC3d of free scopolamine with a 90% confidence interval (CI) which is 80% to 125% of a least squares geometric mean of about 155,937 min*pg/mL.
75. An intranasal pharmaceutical composition for the treatment of symptoms associated with motion, comprising a pharmaceutically acceptable salt of scopolamine, wherein administration of the composition to a human subject results in an AUC0-inf of free scopolamine with a 90% confidence interval (CI) which is 80% to 125% of a least squares geometric mean of about 26305 min*pg/mL following administration.
76. An intranasal pharmaceutical composition for the treatment of symptoms associated with motion comprising a pharmaceutically acceptable salt of scopolamine, wherein administration of the composition to a human subject results in an AUCt of free scopolamine with a 90% confidence interval (CI) which is 80% to 125% of a least squares geometric mean of from about 18545 min*pg/mL to about 26532 min*pg/mL following administration.
77. An intranasal pharmaceutical composition for the treatment of symptoms associated with motion, comprising a pharmaceutically acceptable salt of scopolamine, wherein administration of the composition to a human subject results in an AUCtau of free scopolamine with a 90% confidence interval (CI) which is 80% to 125% of a least squares geometric mean of from about 18624 min*pg/mL to about 29120 min*pg/mL following administration.
78. An intranasal pharmaceutical composition for the of symptoms associated with motion, comprising a pharmaceutically acceptable salt of scopolamine, wherein administration of the composition to a human subject results in an AUC3d of free scopolamine with a 90% confidence interval which is 80% to 125% of a least squares geometric mean of less than about 182,116 min*pg/mL following administration.
79. An intranasal pharmaceutical composition for the prevention of symptoms associated with motion, comprising a pharmaceutically acceptable salt of scopolamine, wherein administration of the composition to a human subject results in an AUC3d of free scopolamine of from about 91,058 min*pg/mL to about 182,116 min*pg/mL following administration.
80. An intranasal pharmaceutical composition for the treatment of symptoms associated with motion, comprising a pharmaceutically acceptable salt of scopolamine, wherein administration of the composition to a human subject results in an AUC3d of free scopolamine with a 90% confidence interval which is 80% to 125% of a least squares geometric mean of less than about 182,116 min*pg/mL following administration.
81. An intranasal pharmaceutical composition for the treatment of symptoms associated with motion, comprising a pharmaceutically acceptable salt of scopolamine, wherein administration of the composition to a human subject results in an AUC3d of free scopolamine of from about 91,058 min*pg/mL to about 182,116 min*pg/mL following administration.
82. A method of one or more of treating, rescue therapy, and preventing one or more symptoms associated with one or more of nausea and emesis related to one or more of actual motion and virtual motion, the method comprising administering to a human subject in need thereof, the intranasal pharmaceutical composition of any one of embodiments 1 to 81.
83. An intranasal pharmaceutical composition comprising scopolamine or a pharmaceutically acceptable salt thereof, as a gel having a viscosity of about 1750 to 3500 centistokes.
84. The composition of embodiment 83, wherein the intranasal pharmaceutical composition is a gel comprising scopolamine or a pharmaceutically acceptable salt thereof, having a viscosity of about 1750 to 3500 centistokes.
85. The composition or method of any one of the preceding embodiments, wherein the intranasal pharmaceutical composition is a gel comprising scopolamine or a pharmaceutically acceptable salt thereof, having a viscosity of about 2000 to 3000 centistokes.
86. The composition or method of any one of the preceding embodiments, wherein the intranasal pharmaceutical composition is a gel comprising scopolamine or a pharmaceutically acceptable salt thereof, having a viscosity of about 2300 centistokes.

87. The composition or method of any one of the preceding embodiments, wherein the scopolamine is present at a concentration of from about 0.15% (w/w) to about 0.18% (w/w).
88. The composition or method of any one of the preceding embodiments, wherein the scopolamine is present at a concentration of about 0.167% (w/w).
89. The composition or method of any one of the preceding embodiments, wherein the scopolamine is scopolamine hydrobromide.
90. The composition or method of any one of the preceding embodiments, wherein the composition comprises polyvinyl alcohol.
91. The composition or method of any one of the preceding embodiments, wherein the polyvinyl alcohol is present at a concentration of from about 8% (w/w) to about 12% (w/w).
92. The composition or method of any one of the preceding embodiments, wherein the polyvinyl alcohol is present at a concentration of about 10% (w/w).
93. The composition or method of any one of the preceding embodiments, wherein the composition comprises sodium citrate.
94. The composition or method of any one of the preceding embodiments, wherein the sodium citrate is present at a concentration of from about 0.2% (w/w) to about 0.6% (w/w).
95. The composition or method of any one of the preceding embodiments, wherein the sodium citrate is present at a concentration of from about 0.3% (w/w) to about 0.4% (w/w).
96. The composition or method of any one of the preceding embodiments, wherein the sodium citrate is present at a concentration of about 0.35% (w/w).
97. The composition or method of any one of the preceding embodiments, wherein the composition comprises citric acid.
98. The composition or method of any one of the preceding embodiments, wherein the citric acid is present at a concentration of from about 0.5% (w/w) to about 1.3% (w/w).
99. The composition or method of any one of the preceding embodiments, wherein the citric acid is present at a concentration of from about 0.6% (w/w) to about 1.0% (w/w).
100. The composition or method of any one of the preceding embodiments, wherein the citric acid is present at a concentration of from about 0.7% (w/w) to about 0.8% (w/w).
101. The composition or method of any one of the preceding embodiments, wherein the citric acid is present at a concentration of about 0.74% (w/w).
102. The composition or method of one of the preceding embodiments, wherein the composition comprises sodium metabisulfite.
103. The composition or method of any one of the preceding embodiments, wherein the sodium metabisulfite is present at a concentration of from about 0.05% (w/w) to about 0.15% (w/w).
104. The composition or method of any one of the preceding embodiments, wherein the sodium metabisulfite is present at a concentration of about 0.1% (w/w).
105. The composition or method of any one of the preceding embodiments, wherein the composition comprises glycerin.
106. The composition or method of any one of the preceding embodiments, wherein the glycerin is present at a concentration of from about 3% (w/w) to about 7% (w/w).
107. The composition or method of any one of the preceding embodiments, wherein the glycerin is present at a concentration of about 5.00% (w/w).
108. The composition or method of any one of the preceding embodiments, wherein the composition comprises a solution of 50% benzalkonium chloride.
109. The composition or method of any one of the preceding embodiments, wherein the solution of 50% benzalkonium chloride is present at a concentration of from about 0.03% (w/w) to about 0.05% (w/w).
110. The composition or method of any one of the preceding embodiments, wherein the solution of 50% benzalkonium chloride is present at a concentration of about 0.04% (w/w).
111. The composition or method of any one of the preceding embodiments, wherein the composition is administered in an amount of from about 0.1 g to about 0.14 g.
112. The composition or method of any one of the preceding embodiments, wherein the composition is administered in an amount of 0.12 g of the composition per dose.
113. The composition or method of any one of the preceding embodiments, wherein the composition is administered in an amount which provides from about 0.15 mg to about 0.25 mg of scopolamine per dose.
114. The composition or method of any one of the preceding embodiments, wherein the composition is administered in an amount which provides about 0.2 mg per dose.
115. The composition or method of any one of the preceding embodiments, wherein the composition is administered to the subject twice daily in an amount of about 0.12 g of the composition.
116. The composition or method of any one of the preceding embodiments, wherein the composition is administered in a dose comprising 0.16 mg of scopolamine in a volume of about 120 mL.
117. The composition or method of any one of the preceding embodiments, wherein the composition is administered before the subject is exposed to a stimulus that may induce emesis, nausea, or symptoms associated with motion.
118. The composition or method of any one of the preceding embodiments, wherein the composition is administered after onset of emesis, nausea, or symptoms associated with motion.
119. The composition or method of any one of the preceding embodiments, wherein the human subject is from about 60 to about 80 years old.
120. The composition or method of any one of the preceding embodiments, wherein the human subject is geriatric.
121. The composition or method of any one of the preceding embodiments, wherein the human subject is over the age of about 60 years old.
122. The composition or method of any one of the preceding embodiments, wherein the human subject is over the age of about 65 years old.
123. The composition or method of any one of the preceding embodiments, wherein administration of the intranasal pharmaceutical composition results in substantially no anticholinergic side effects.
124. The composition or method of any one of the preceding embodiments, wherein the gel has a viscosity of about 2300 centistokes and is delivered by means of a pump.
125. The composition or method of any one of the preceding embodiments, wherein the subject is experiencing or is expecting to be exposed to one or more of microgravity, boating, air travel, vehicular travel, and combat activity.

126. The composition or method of any one of the preceding embodiments, wherein the subject is experiencing cybersickness or is expecting to be exposed to stimuli known to induce cybersickness.

127. The composition or method of any one of the preceding embodiments, wherein the subject is experiencing or is expecting to be exposed to microgravity.

128. The composition or method of any one of the preceding embodiments, wherein the subject is experiencing or expecting to be exposed to simulated motion during use of virtual reality equipment.

129. An intranasal pharmaceutical composition for the prevention or rescue from degradation of one or more of cognition, motor function, and mood due to motion, comprising a pharmaceutically acceptable salt of scopolamine, wherein administration of the composition to a human subject results in a Cmax of free scopolamine with a 90% confidence interval which is 80% to 125% of a least squares geometric mean of less than about 160 pg/mL, wherein motion sickness degradation of one or more of cognition, motor function, and mood is substantially prevented or eliminated.

130. An intranasal pharmaceutical composition for the prevention of one or more of nausea or emesis related to motion, comprising a pharmaceutically acceptable salt of scopolamine, wherein administration of the composition to a human subject results in a Cmax of free scopolamine that is from about 20% less to about 20% more than an average steady-state level resulting from application of a transdermal scopolamine having a total of 1.5 mg scopolamine and formulated for delivery of about 1 mg to a human subject over about three days.

131. A composition for the prevention of one or more of nausea or emesis related to motion, comprising a pharmaceutically acceptable salt of scopolamine, wherein administration of the composition to a human subject results in a Cmax of free scopolamine that is less than about 120% of an average steady-state level resulting from application of a transdermal scopolamine system having a total of 1.5 mg scopolamine and formulated for delivery of about 1 mg to a human subject over about three days.

132. The pharmaceutical composition of embodiments 130 or 131, wherein the Cmax of free scopolamine that is less than about 115% of an average steady-state level resulting from application of the transdermal scopolamine system.

133. The pharmaceutical composition of embodiments 130 or 131, wherein the Cmax of free scopolamine that less than about 110% of an average steady-state level resulting from application of the transdermal scopolamine system.

134. The pharmaceutical composition of any one of embodiments 130 to 133, wherein administration of the pharmaceutical composition twice daily for three days achieves a total dose of about 0.95 mg of free scopolamine in plasma of the human subject.

135. The pharmaceutical composition of any one of embodiments 130 to 134, wherein the transdermal scopolamine is a patch marketed as Transderm Scop®.

136. The composition or method of any one of the preceding embodiments, wherein the composition is delivered by a pump capable of delivering about 0.12 g of a composition having a viscosity of about 2000 centistokes or greater, wherein the volume of the composition delivered varies by no more than about 15%.

137. The composition or method of embodiment 136, wherein the volume of the composition delivered varies by no more than about 10%.

138. The composition or method of embodiment 136, wherein the volume of the composition delivered varies by no more than about 8%.

139. The composition or method of embodiment 136, wherein the volume of the composition delivered varies by no more than about 5%.

Any patents or publications mentioned in this specification are indicative of the levels of those skilled in the art to which the disclosure of the present invention pertains. These patents and publications are herein incorporated by reference for the indicated information to the same extent as if each individual publication was specifically and individually indicated to be incorporated by reference for such information. In case of conflict, the present specification, including definitions, will control.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An intranasal pharmaceutical composition for use in a human subject comprising a therapeutically effective amount of scopolamine or a pharmaceutically acceptable salt thereof, wherein the intranasal pharmaceutical composition is capable of the prevention of or rescue from one or more symptoms related to motion in a human subject, and wherein the composition has a viscosity of about 1750 to about 3500 centistokes.

2. The intranasal pharmaceutical composition of claim 1, wherein when the composition is administered to a subject, the composition is capable of exhibiting an AUC for unbound scopolamine or a pharmaceutically acceptable salt thereof that is approximately 40% of the unbound scopolamine or a pharmaceutically acceptable salt thereof for transdermal administration and wherein the composition is capable of an approximately equivalent Cmax for unbound scopolamine or a pharmaceutically acceptable salt thereof as compared to transdermal administration of scopolamine or a pharmaceutically acceptable salt thereof.

3. The intranasal pharmaceutical composition of claim 1, wherein the therapeutically effective amount comprises from about 0.15 to about 0.25 mg scopolamine or a pharmaceutically acceptable salt thereof.

4. The intranasal pharmaceutical composition of claim 3, wherein the composition comprises 0.2 mg scopolamine.

5. The intranasal pharmaceutical composition of claim 1, wherein the composition has a viscosity of about 2100 to 2700 centistokes.

6. The intranasal pharma composition of claim 1, wherein the composition comprises at least one buffer, gelling agent, antioxidant and humectant, and combinations thereof.

7. The intranasal pharmaceutical composition of claim 6, wherein the composition comprises at least one of citric acid, polyvinyl alcohol, benzalkonium chloride, sodium metabisulfite, sodium citrate dihydrate and glycerin, and combinations thereof.

8. The intranasal composition of claim 7, wherein:
a) the citric acid is present at a concentration of from about 0.7% (w/w) to about 0.8% (w/w);
b) the polyvinyl alcohol is present at a concentration of from about 8% (w/w) to about 12% (w/w);
c) the benzalkonium chloride is a solution of 50% benzalkonium chloride at a concentration of from about 0.03% (w/w) to about 0.05% (w/w);
d) the sodium metabisulfite is present at a concentration of from about 0.05% (w/w) to about 0.15% (w/w); and
e) glycerin is present at a concentration of from about 3% (w/w) to about 7% (w/w).

9. The intranasal composition of claim 6, wherein the composition has a pH of from about 3.2 to about 3.6.

10. The intranasal pharmaceutical composition of claim 1, wherein the composition is capable of providing absolute bioavailability of about 10-14% when administered to a subject.

11. An intranasal pharmaceutical composition for use in a human subject comprising a therapeutically effective amount of scopolamine or a pharmaceutically acceptable salt thereof at a concentration of from about 0.15% (w/w) to about 0.18% (w/w), wherein the composition is capable of prevention of, or rescue from, one or more of nausea or vomiting related to motion in a human subject, wherein when the composition is administered to a subject, the composition is capable of exhibiting an AUC for unbound scopolamine or a pharmaceutically acceptable salt thereof that is approximately 40% lower than unbound scopolamine or a pharmaceutically acceptable salt thereof for transdermal administration, wherein the composition is capable of an approximately equivalent Cmax for unbound scopolamine or a pharmaceutically acceptable salt thereof as compared to transdermal administration of scopolamine or a pharmaceutically acceptable salt thereof, and wherein the composition has a viscosity of at about 1750 to about 3500 centistokes.

12. The intranasal pharmaceutical composition of claim 11, wherein the composition is a gel having a viscosity of about 2000 to about 3000 centistokes.

13. The intranasal pharmaceutical composition of claim 12, wherein the composition has a viscosity of about 2100 to 2700 centistokes.

14. The intranasal pharmaceutical composition of claim 11, wherein the therapeutically effective amount comprises from about 0.15 to about 0.25 mg scopolamine or a pharmaceutically acceptable salt thereof.

15. The intranasal pharmaceutical composition of claim 14, wherein the composition comprises 0.2 mg scopolamine.

16. The intranasal pharmaceutical composition of claim 11, wherein the composition further comprises at least one buffer, gelling agent, antioxidant and humectant, and combinations thereof.

17. The intranasal composition of claim 16, wherein the composition comprises at least one of citric acid, polyvinyl alcohol, benzalkonium chloride, sodium metabisulfite, sodium citrate dihydrate and glycerin, and combinations thereof.

18. The intranasal composition of claim 17, wherein:
a) the citric acid is present at a concentration of from about 0.7% (w/w) to about 0.8% (w/w);
b) the polyvinyl alcohol is present at a concentration of from about 8% (w/w) to about 12% (w/w);
c) the benzalkonium chloride is a solution of 50% benzalkonium chloride at a concentration of from about 0.03% (w/w) to about 0.05% (w/w);
d) the sodium metabisulfite is present at a concentration of from about 0.05% (w/w) to about 0.15% (w/w); and
e) glycerin is present at a concentration of from about 3% (w/w) to about 7% (w/w).

19. The intranasal composition of claim 16, wherein the composition has a pH of from about 3.2 to about 3.6.

20. The intranasal pharmaceutical composition of claim 11, wherein the composition is capable of providing absolute bioavailability of about 10-14% when administered to a subject.

21. The intranasal pharmaceutical composition of claim 1 or 11, wherein the composition has a viscosity of about 1750 to about 2600 centistokes.

22. The intranasal pharmaceutical composition of claim 21, wherein the composition has a viscosity of about 1800 to 2600 centistokes.

23. The intranasal pharmaceutical composition of claim 21, wherein the composition has a viscosity of about 2000 to 2600 centistokes.

24. The intranasal pharmaceutical composition of claim 21, wherein the composition has a viscosity of about 2300 centistokes.

* * * * *